(12) United States Patent
Ikeura et al.

(10) Patent No.: US 8,470,816 B2
(45) Date of Patent: Jun. 25, 2013

(54) NITROGEN-CONTAINING HETEROCYCLIC COMPOUND AND USE THEREOF

(75) Inventors: Yoshinori Ikeura, Osaka (JP); Junya Shirai, Osaka (JP); Hideyuki Sugiyama, Osaka (JP); Yuji Nishikimi, Osaka (JP); Taku Kamei, Osaka (JP); Nobuki Sakauchi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1004 days.

(21) Appl. No.: 12/314,015

(22) Filed: Dec. 2, 2008

(65) Prior Publication Data

US 2009/0156572 A1 Jun. 18, 2009

Related U.S. Application Data

(60) Provisional application No. 60/996,734, filed on Dec. 3, 2007.

(51) Int. Cl.

| | |
|---|---|
| *A61K 31/5355* | (2006.01) |
| *A61K 31/445* | (2006.01) |
| *A61K 31/444* | (2006.01) |
| *A61K 31/40* | (2006.01) |
| *C07D 413/04* | (2006.01) |
| *C07D 401/04* | (2006.01) |
| *C07D 211/56* | (2006.01) |
| *C07D 207/14* | (2006.01) |

(52) U.S. Cl.
USPC ........ 514/231.5; 514/317; 514/336; 514/423; 544/124; 546/192; 546/268.1; 548/531

(58) Field of Classification Search
USPC .............. 548/517, 531; 514/422, 231.5, 317, 514/336, 423; 544/124; 546/192, 268.1
See application file for complete search history.

(56) References Cited

U.S. PATENT DOCUMENTS

| 5,288,725 A | 2/1994 | Witherup et al. |
| 2005/0256164 A1 | 11/2005 | O'Neill et al. |
| 2006/0167052 A1 | 7/2006 | Ikeura et al. |
| 2010/0056497 A1 | 3/2010 | Nakahira et al. |

FOREIGN PATENT DOCUMENTS

| EP | 1 553 084 A1 | 7/2005 |
| EP | 1 705 176 A1 | 9/2006 |
| WO | 97/31941 | 9/1997 |
| WO | 02/38547 | 5/2002 |
| WO | 02/38548 | 5/2002 |
| WO | 02/083663 | 10/2002 |
| WO | 02/083664 | 10/2002 |
| WO | 03/101964 | 12/2003 |
| WO | 2004/111000 | 12/2004 |
| WO | 2005/105802 | 11/2005 |
| WO | 2006/062478 | 6/2006 |
| WO | 2008/093737 | 8/2008 |
| WO | WO 2008/136457 A1 * | 11/2008 |

OTHER PUBLICATIONS

M. Otsuka et al., "Neurotransmitter Functions of Mammalian Tachykinins", Physiological Reviews, vol. 73, No. 2, pp. 229-308, Apr. 1993.

C. A. Maggi et al., "Tachykinin receptors and tachykinin receptor antagonists", Journal of Autonomic Pharmacology, vol. 13, pp. 23-93, 1993.

A. Kamel et al., "Metabolism, pharmacokinetics and excretion of a potent tachykinin NK1 receptor antagonist (CP-122,721) in rat: Characterization of a novel oxidative pathway", Xenobiotica, vol. 36, No. 2/3, pp. 235-258, Feb./Mar. 2006.

C. A. Maggi et al., "Competitive antagonists discriminate between $NK_2$ tachykinin receptor subtypes", Br. J. Pharmacol. vol. 100, pp. 588-592, 1990.

A. Bartolini et al.,"Role of Muscarinic receptor subtypes in central antinociception", Br. J. Pharmacol. vol. 105, pp. 77-82, 1992.

(Continued)

*Primary Examiner* — Joseph Kosack
(74) *Attorney, Agent, or Firm* — Wenderoth, Lind & Ponack, L.L.P.

(57) ABSTRACT

The present invention relates to a compound represented by the formula

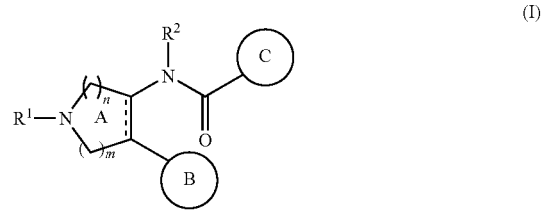

(I)

wherein ring A is a nitrogen-containing heterocycle optionally further having substituent(s), ring B is an aromatic ring optionally having substituent(s), ring C is a cyclic group optionally having substituent(s), $R^1$ is a hydrogen atom, a hydrocarbon group optionally having substituent(s), an acyl group, a heterocyclic group optionally having substituent(s) or an amino group optionally having substituent(s), $R^2$ is an optionally halogenated $C_{1-6}$ alkyl group, m and n are each an integer of 0 to 5, m+n is an integer of 2 to 5, and ----
is a single bond or a double bond, or a salt thereof and the like. Since the compound has a superior tachykinin receptor antagonistic action, and is useful as an agent for the prophylaxis or treatment of various diseases such as lower urinary tract diseases, gastrointestinal diseases, central nervous system diseases and the like.

36 Claims, No Drawings

OTHER PUBLICATIONS

A. W. J. Cooper et al., "GR159897 and Related Analogues as Highly Potent, Orally Active Non-Peptide Neurokinin $NK_2$ Receptor Antagonists", Bioorganic & Medicinal Chemistry Letters, vol. 4, No. 16, pp. 1951-1956, 1994.

R. M. Snider et al., "A Potent Nonpeptide Antagonist of the Substance P ($NK_1$) Receptor", Science, vol. 251, pp. 435-437, Jan. 25, 1991.

C. Garret et al., "Pharmacological properties of a potent and selective nonpeptide substance P antagonist", Proc. Natl. Acad. Sci., vol. 88, pp. 10208-10212, Nov. 1991.

Abstracts of Papers, Part 1, 214$^{th}$ National Meeting of the American Chemical Society, Las Vegas, NV, Sep. 7-11, 1997, MEDI, p. 264.

K. E. Frank et al., "Cyclizations of Substituted Benzylidene-3-alkenylamines: Synthesis of the Tricyclic Core of the Martinellines", J. Org. Chem., vol. 65, pp. 655-666, 2000.

D. Ma et al., "Aromatic Neuleophilic Substitution or CuI-Catalyzed Coupling Route to Martinellic Acid", J. Org. Chem., vol. 68, pp. 442-451, 2003.

D. Ma et al., "First Total Synthesis of Martinellic Acid, a Naturally Occurring Bradykinin Receptor Antagonist", Organic Letters, vol. 3, No. 14, pp. 2189-2191, 2001.

B. B. Snider et al., "Total Synthesis of (+)-Martinellic Acid", Organic Letters, vol. 3, No. 26, pp. 4217-4220, 2001.

M. Hadden et al., "Synthesis and reactivity of hexahydropyrroloquinolines", Tetrahedron, vol. 57, pp. 5615-5624, 2001.

M. Hadden et al., "Regioselective Synthesis of Pyrroloquinolines—Approaches to Martinelline", Tetrahedron Letters, vol. 40, pp. 1215-1218, 1999.

B. B. Snider et al., "Synthesis of the Tricyclic Triamine Core of Martinelline and Martinellic Acid", Tetrahedron Letters, vol. 40, pp. 3339-3342, 1999.

M. Nyerges, "Construction of Pyrrolo[3,2-c]Quinolines—Recent Advances in the Synthesis of the Martinelline Alkaloids", Heterocycles, vol. 63, No. 7, pp. 1685-1712, 2004.

N. Salome et al., "Selective blockade of NK2 or NK3 receptors produces anxiolytic- and antidepressant-like effects in gerbils", Pharmacology Biochemistry and Behavior, vol. 83, pp. 533-539, 2006.

W. Spooren et al., "$NK_3$ receptor antagonists: the next generation of antipsychotics", Nature Reviews, vol. 4, pp. 967-975, Dec. 2005.

* cited by examiner

NITROGEN-CONTAINING HETEROCYCLIC COMPOUND AND USE THEREOF

This application claims the benefit of U.S. provisional application Ser. No. 60/996,734 filed Dec. 3, 2007.

TECHNICAL FIELD

The present invention relates to a novel nitrogen-containing heterocyclic compound having excellent antagonistic action for a tachykinin receptor and use thereof.

BACKGROUND OF THE INVENTION

Tachykinin is a generic term for a group of neuropeptides. Substance P (SP), neurokinin A (NK-A) and neurokinin B (NK-B) are known in mammals, and these peptides are known to bind to the corresponding receptors (neurokinin-1 (NK-1), neurokinin-2 (NK-2) and neurokinin-3 (NK-3)) that exist in a living body and thereby to exhibit various biological activities.

Of such neuropeptides, SP has the longest history and has been studied in detail. In 1931, the existence of SP in the extract from equine intestines was confirmed, and in 1971, its structure was determined. SP is a peptide consisting of 11 amino acids.

SP is broadly distributed over the central and peripheral nervous systems, and has various physiological activities such as vasodilation, enhancement of vascular permeability, contraction of smooth muscles, excitation of neurons, salivation, enhancement of diuresis, immunological enhancement and the like, in addition to the function as a transmitter substance for primary sensory neurons. In particular, it is known that SP released from the terminal of the spinal (dorsal) horn due to a pain impulse transmits the information of pain to secondary neurons, and that SP released from the peripheral terminal induces an inflammatory response in the receptor thereof. Thus, it is considered that SP is involved in various disorders (e.g., pain, headache, particularly migraine, Alzheimer's disease, multiple sclerosis, cardiovascular modulation, chronic inflammatory diseases such as chronic rheumatic arthritis, respiratory diseases including asthma or allergic rhinitis, intestinal inflammatory diseases including ulcerative colitis and Crohn's disease, ocular damage and ocular inflammatory diseases, proliferative vitreous retinopathy, an irritable bowel syndrome, urinary frequency, psychosis, vomiting, etc.) [see, for example, Physiological Reviews, Vol. 73, pp. 229-308 (1993); Journal of Autonomic Pharmacology, Vol. 13, pp. 23-93 (1993)].

At present, the following compounds have been known as those having antagonistic action for SP receptors.

WO03/101964 describes a compound represented by the formula

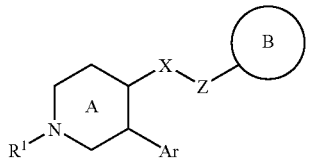

(I)

wherein Ar is an aryl group, an aralkyl group or an aromatic heterocyclic group, each of which may be substituted, $R^1$ is a hydrogen atom, an optionally substituted hydrocarbon group, an acyl group or an optionally substituted heterocyclic group, X is an oxygen atom or an optionally substituted imino group, Z is an optionally substituted methylene group, Ring A is a further optionally substituted piperidine ring, and Ring B is an optionally substituted aromatic ring, provided that when Z is a methylene group substituted with an oxo group, $R^1$ is not a methyl group, and when Z is a methylene group substituted with a methyl group, Ring B is a substituted aromatic ring, or a salt thereof.

In addition, US Patent Application Publication No. 2005/0256164 describes the following compound

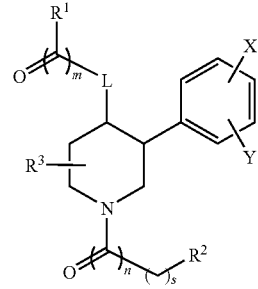

wherein m, n and s are each independently 0 or 1, L is —O— or —NR$^4$— ($R^4$ is hydrogen etc.), $R^1$ and $R^2$ are each independently hydrogen, aryl, heteroaryl, ($C_1$-$C_6$)alkyl, ($C_1$-$C_6$)alkyl-heteroaryl and the like, $R^3$ is hydrogen and the like, and X and Y are each independently hydrogen, ($C_1$-$C_6$)alkyl and the like, as a NK-1 and NK-3 receptor antagonist.

Xenobiotica (2006), 36 (2/3), 235-258, describes the following compound

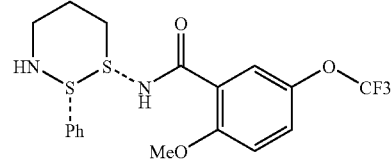

as a receptor antagonist for tachykinin, SP, NK-A or NK-B.

In addition, WO2004/111000 describes a compound represented by the following formula

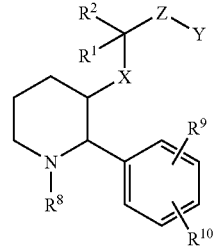

wherein
—X— is —NH— or —O—,
Y is

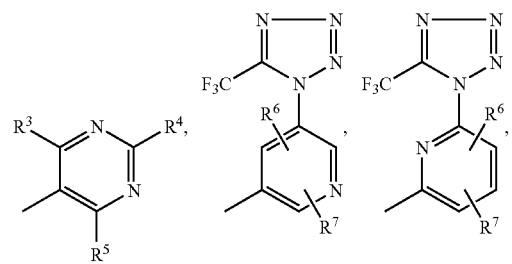

wherein $R^3$, $R^4$ and $R^5$ are independently hydrogen, lower alkyl, mono (or di or tri)halo(lower)alkyl and the like; and $R^6$ and $R^7$ are each independently hydrogen or lower alkoxy, and the like, —Z— is a bond or —CH($R^{11}$)— wherein $R^{11}$ is hydrogen or lower alkyl, $R^1$ and $R^2$ are independently hydrogen or lower alkyl, or in combination form oxo, $R^8$ is hydrogen, (5-oxo-4,5-dihydro-1H-1,2,4-triazol-3-yl) methyl or an amino protecting group, $R^9$ and $R^{10}$ are hydrogen, halogen and the like, or a salt thereof, as a compound having a tachykinin receptor antagonistic action.

In addition, a selective peptide antagonist of NK-2 receptor is known (Br. J. Pharmacol., 1990', vol. 100, pages 588-592 and WO97/31941). However, these known peptidic NK-2 antagonists have low activity and are metabolically unstable. Therefore, it is difficult to provide them as practical prophylactic drugs or therapeutic drugs.

As the selective non-peptide NK-2 receptor antagonists, SR 48968 (Brit. J. Pharmacol. 1992, vol. 105, page 77), GR-159897 (Bioorg. Med. Chem. Lett. 1994, vol. 4, page 1951), CP 96345 (Science, 1991, vol. 251, page 435), RP 67580 (Proc. Nat. Acad. Sci. 1991, vol. 88, page 10208), ZD 7944 (Abstracts of Papers, Part 1, 214th NATIONAL Meeting of the American Chemical Society, Las Vegas, Nev., Sep. 7-11, 1997, MEDI 264), WO02/38547, WO02/38548, WO02/083663, WO02/083664 and the like are known.

In addition, as the quinoline derivatives to be condensed with a nitrogen-containing heterocycle, the compounds described in J. Org. Chem., 2000, 65, 655-666; J. Org. Chem., 2003, 68, 442-451; Org. Lett., 2001, 3, 2189-2191; Org. Lett., 2001, 3, 4217-4220; Tetrahedron 57, 2001, 5615-5624; Tetrahedron Letters 40, 1999, 1215-1218; Tetrahedron Letters 40, 1999, 3339-3342; Heterocycles, 2004, 63, 1685-1712 and U.S. Pat. No. 5,288,725 and the like are known. Furthermore, WO05/105802 is known.

Moreover, the relationship between NK-3 receptor and central nervous system diseases, particularly depression, has been pointed out (Pharmacol. Biochem. Behav., 83 (2006), 533-539; Nature Rev. Drug Discov., 4, 967-975, 2005). Therefore, a compound showing an NK-3 receptor binding action is considered to be promising as a therapeutic drug for the central nervous system diseases.

DISCLOSURE OF THE INVENTION

An object of the present invention is to provide a nitrogen-containing heterocyclic compound having an antagonistic action for a tachykinin receptor, etc. and having a chemical structure different from that of known compounds including the above-mentioned compounds, a pharmaceutical agent comprising the compound, and the like.

The present inventors have made extensive studies in view of the above-mentioned situation and, as a result, have unexpectedly found that a nitrogen-containing heterocyclic compound represented by the following formula (I) (hereinafter sometimes to be simply referred to as compound (I)) or a salt thereof has, based on its specific chemical structure, an unexpectedly strong tachykinin receptor antagonistic action, particularly, an NK-1 receptor antagonistic action, an NK-2 receptor antagonistic action, an NK-3 receptor antagonistic action and the like, and is sufficiently satisfactory as a pharmaceutical agent. On the basis of these findings, the present inventors have completed the present invention.

Accordingly, the present invention relates to

[1] a compound represented by the formula

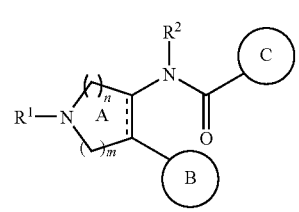

(I)

wherein ring A is a nitrogen-containing heterocycle optionally further having substituent(s), ring B is an aromatic ring optionally having substituent(s), ring C is a cyclic group optionally having substituent(s), $R^1$ is a hydrogen atom, a hydrocarbon group optionally having substituent(s), an acyl group, a heterocyclic group optionally having substituent(s) or an amino group optionally having substituent(s), $R^2$ is an optionally halogenated $C_{1-6}$ alkyl group, m and n are each an integer of 0 to 5, m+n is an integer of 2 to 5, and ---- is a single bond or a double bond (except N-[(rac.)-(3R,4R)-1-benzyl-4-phenylpiperidin-3-yl]-N-isopropyl-4-methoxy-3-(3-methoxypropoxy)benzamide, N-isopropyl-4-methoxy-3-(3-methoxypropoxy)-N-[(rac.)-(3R,4R)-4-phenylpiperidin-3-yl]benzamide, N-isopropyl-4-methoxy-3-(3-methoxypropoxy)-N-[(rac.)-(3R,4R)-4-(3-(methylsulfonyl)amino-phenyl)-piperidin-3-yl]benzamide, N-isopropyl-[(rac.)-(3R,4R)-4-[1,1'-biphenyl]-3-yl-3-piperidinyl]-4-methoxy-3-(3-methoxypropoxy) benzamide, N-ethyl-[(rac.)-(3R,4R)-4-[1,1'-biphenyl]-3-yl-3-piperidinyl]-4-methoxy-3-(3-methoxypropoxy) benzamide, N-propyl-[(rac.)-(3R,4R)-4-[1,1'-biphenyl]-3-yl-3-piperidinyl]-4-methoxy-3-(3-methoxypropoxy) benzamide, N-ethyl-[(rac.)-(3R,4R)-4-[3-[(3,5-dimethoxyphenyl)methoxy]phenyl]-3-piperidinyl]-4-methoxy-3-(3-methoxypropoxy)benzamide and 4-methoxy-3-(3-methoxypropoxy)-N-isopropyl-N-[(rac.)-4-(4-phenyl-2-oxazolyl)-3-piperidinyl]benzamide), or a salt thereof;

[2] the compound of the above-mentioned [1], wherein ring A is any of the rings represented by

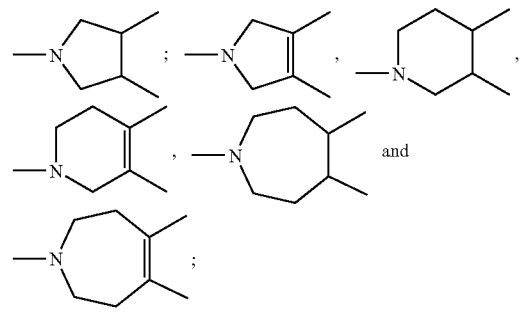

[3] the compound of the above-mentioned [1], wherein ring B is a phenyl group or a thienyl group each optionally having substituent(s);

[4] the compound of the above-mentioned [1], wherein ring C is an aromatic ring optionally having substituent(s);

[5] the compound of the above-mentioned [1], wherein ring C is a phenyl group, a pyrrolyl group, a thienyl group, a furyl group, a pyrazolyl group, an indolyl group, a benzimidazolyl group or a pyridyl group, each optionally having substituent(s);

[6] the compound of the above-mentioned [1], wherein ring C is a phenyl group, a pyridyl group, a benzothienyl group or a benzodioxolyl group, each optionally having substituent(s);

[7] the compound of the above-mentioned [1], wherein $R^1$ is a hydrogen atom, an acyl group, a piperidyl group optionally having substituent(s), a pyridyl group optionally having substituent(s), a pyrrolopyrimidinyl group optionally having substituent(s), an alkyl group optionally having substituent(s), a cycloalkenyl group optionally having substituent(s), an aryl group optionally having substituent(s) or an amino group optionally having substituent(s);

[8] the compound of the above-mentioned [1], wherein $R^2$ is a methyl group;

[9] N-[(3R,4R)-1-[(1-acetylpiperidin-4-yl)carbonyl]-3-(3,4-dichlorophenyl)piperidin-4-yl]-N-methyl-3,5-bis(trifluoromethyl)benzamide;

[10] N-[(3R,4R)-1-[(1-acetylpiperidin-4-yl)carbonyl]-3-(3,4-dichlorophenyl)piperidin-4-yl]-4-chloro-N-methylbenzamide;

[11] N-[(3R,4R)-1-[(1-acetylpiperidin-4-yl)carbonyl]-3-(3,4-dichlorophenyl)piperidin-4-yl]-4-methoxy-N-methylbenzamide;

[12] N-[(3R,4R)-1-[(1-acetylpiperidin-4-yl)carbonyl]-3-(3,4-dichlorophenyl)piperidin-4-yl]-N-methyl-4-(trifluoromethyl)benzamide;

[13] N-[(3R,4R)-1-[(1-acetylpiperidin-4-yl)carbonyl]-3-(3,4-dichlorophenyl)piperidin-4-yl]-N-methyl-4-morpholin-4-ylbenzamide or a salt thereof;

[14] N-[(3R,4R)-1-[(1-acetylpiperidin-4-yl)carbonyl]-3-(3,4-dichlorophenyl)piperidin-4-yl]-4-cyclopropyl-N-methylbenzamide;

[15] N-[(3R,4R)-1-[(1-acetylpiperidin-4-yl)carbonyl]-3-(3,4-dichlorophenyl)piperidin-4-yl]-5-bromo-N-methylpyridine-2-carboxamide;

[16] 4-chloro-N-[(3R,4R)-3-(3,4-dichlorophenyl)-1-{[1-(hydroxyacetyl)piperidin-4-yl]carbonyl}piperidin-4-yl]-N-methylbenzamide or a salt thereof;

[17] N-[(3R,4R)-1-[(1-acetylpiperidin-4-yl)methyl]-3-(3,4-dichlorophenyl)piperidin-4-yl]-4-chloro-N-methylbenzamide;

[18] N-[(3R,4R)-3-(3,4-dichlorophenyl)-1-({1-[(1-hydroxycyclopropyl)carbonyl]piperidin-4-yl}carbonyl)piperidin-4-yl]-N-methyl-4-morpholin-4-ylbenzamide or a salt thereof;

[19] N-[(3R,4R)-1-{[(3S,4S)-3-aminotetrahydro-2H-pyran-4-yl]carbonyl}-3-(3,4-dichlorophenyl)piperidin-4-yl]-N-methyl-4-morpholin-4-ylbenzamide or a salt thereof;

[20] N-[(3R,4R)-3-(3,4-dichlorophenyl)-1-{[1-(hydroxyacetyl)piperidin-4-yl]carbonyl}piperidin-4-yl]-N-methyl-4-(trifluoromethyl)benzamide or a salt thereof;

[21] 4-bromo-N-[(3R,4R)-3-(3,4-dichlorophenyl)-1-{[1-(hydroxyacetyl)piperidin-4-yl]carbonyl}piperidin-4-yl]-N-methylbenzamide or a salt thereof;

[22] N-[(3R,4R)-3-(3,4-dichlorophenyl)-1-{[1-(hydroxyacetyl)piperidin-4-yl]carbonyl}piperidin-4-yl]-N-methyl-5-(trifluoromethyl)pyridine-2-carboxamide or a salt thereof;

[23] a prodrug of the compound of the above-mentioned [1];

[24] a pharmaceutical agent comprising the compound of the above-mentioned [1] or a prodrug thereof;

[25] a tachykinin receptor antagonist agent comprising a compound represented by the formula

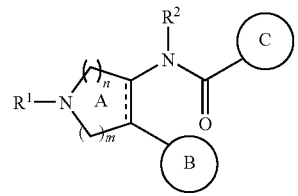

(I)

wherein ring A is a nitrogen-containing heterocycle optionally further having substituent(s), ring B is an aromatic ring optionally having substituent(s), ring C is a cyclic group optionally having substituent(s), $R^1$ is a hydrogen atom, a hydrocarbon group optionally having substituent(s), an acyl group, a heterocyclic group optionally having substituent(s) or an amino group optionally having substituent(s), $R^2$ is an optionally halogenated $C_{1-6}$ alkyl group, m and n are each an integer of 0 to 5, m+n is an integer of 2 to 5, and ---- is a single bond or a double bond,
or a salt thereof or a prodrug thereof;

[26] the agent of the above-mentioned [25], which is an NK-2 receptor antagonist;

[27] the agent of the above-mentioned [26], concurrently having an NK-1 receptor antagonistic action and/or an NK-3 receptor antagonistic action;

[28] the agent of the above-mentioned [25], which is an NK-1 receptor antagonist;

[29] the agent of the above-mentioned [28], concurrently having an NK-2 receptor antagonistic action and/or an NK-3 receptor antagonistic action;

[30] the agent of the above-mentioned [25], which is an agent for the prophylaxis or treatment of a lower urinary tract disease, a gastrointestinal disease or a central nervous system disease;

[31] a pharmaceutical agent which is an agent for the prophylaxis or treatment of overactive bladder, irritable bowel syndrome, functional dyspepsia, inflammatory bowel disease, gastroesophageal reflux disease, vomiting, nausea, depression, anxiety neurosis, anxiety symptom, pelvic visceral pain or interstitial cystitis, comprising a compound represented by the formula

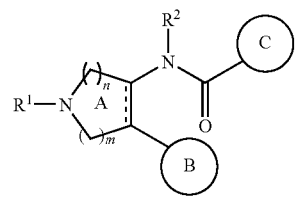

(I)

wherein ring A is a nitrogen-containing heterocycle optionally further having substituent(s), ring B is an aromatic ring optionally having substituent(s), ring C is a cyclic group optionally having substituent(s), $R^1$ is a hydrogen atom, a hydrocarbon group optionally having substituent(s), an acyl group, a heterocyclic group optionally having substituent(s) or an amino group optionally having substituent(s), $R^2$ is an optionally halogenated $C_{1-6}$ alkyl group, m and n are each an integer of 0 to 5, m+n is an integer of 2 to 5, and ---- is a single bond or a double bond,
or a salt thereof or a prodrug thereof;

[32] a method of preventing or treating a lower urinary tract disease, a gastrointestinal disease or a central nervous system disease, comprising administering, to a mammal, an effective amount of a compound represented by the formula

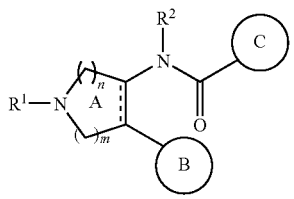
(I)

wherein ring A is a nitrogen-containing heterocycle optionally further having substituent(s), ring B is an aromatic ring optionally having substituent(s), ring C is a cyclic group optionally having substituent(s), $R^1$ is a hydrogen atom, a hydrocarbon group optionally having substituent(s), an acyl group, a heterocyclic group optionally having substituent(s) or an amino group optionally having substituent(s), $R^2$ is an optionally halogenated $C_{1-6}$ alkyl group, m and n are each an integer of 0 to 5, m+n is an integer of 2 to 5, and ----
is a single bond or a double bond,
or a salt thereof or a prodrug thereof;

[33] use of a compound represented by the formula

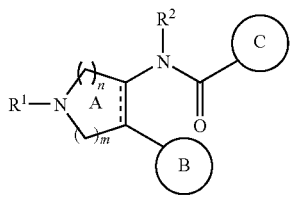
(I)

wherein ring A is a nitrogen-containing heterocycle optionally further having substituent(s), ring B is an aromatic ring optionally having substituent(s), ring C is a cyclic group optionally having substituent(s), $R^1$ is a hydrogen atom, a hydrocarbon group optionally having substituent(s), an acyl group, a heterocyclic group optionally having substituent(s) or an amino group optionally having substituent(s), $R^2$ is an optionally halogenated $C_{1-6}$ alkyl group, m and n are each an integer of 0 to 5, m+n is an integer of 2 to 5, and ----
is a single bond or a double bond,
or a salt thereof or a prodrug thereof, for the production of an agent for the prophylaxis or treatment of a lower urinary tract disease, a gastrointestinal disease or a central nervous system disease;
and the like.

Compound (I) or a salt thereof or a prodrug thereof of the present invention is superior in the tachykinin receptor antagonistic action, particularly, an NK-1 receptor antagonistic action, an NK-2 receptor antagonistic action, an NK-3 receptor antagonistic action and the like, and safe as a pharmaceutical agent due to low toxicity thereof. Accordingly, compound (I) or a salt thereof or a prodrug thereof of the present invention is useful as a pharmaceutical agent, for example, an agent for the prophylaxis or treatment of various diseases such as a lower urinary tract disease, a gastrointestinal disease or a central nervous system disease and the like.

The present invention is explained in detail in the following.

(Explanation of Ring A)
In the aforementioned formulas, ring A is a nitrogen-containing heterocycle optionally further having substituent(s), m and n are each an integer of 0 to 5, m+n is an integer of 2 to 5, and ----
is a single bond or a double bond. Namely, ring A is a 5- to 8-membered saturated or unsaturated nitrogen-containing heterocycle containing, as a ring-constituting atom, one nitrogen atom and 4 to 7 carbon atoms, and optionally having substituent(s) besides $R^1$, ring B and a partial structure:

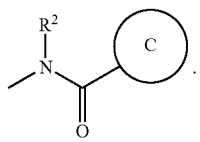

Examples of the substituent of ring A include 1 to 3 substituents selected from
(1) a halogen atom (e.g., fluorine, chlorine, bromine, iodine, etc.),
(2) a nitro group,
(3) a cyano group,
(4) a $C_{1-6}$ alkyl group optionally having 1 to 9 (preferably 1 to 5, more preferably 1 to 3) substituents selected from (i) a halogen atom, (ii) a 3- to 8-membered heterocyclic group (e.g., morpholinyl, 2-pyridyl), (iii) a hydroxy group and (iv) a $C_{1-6}$ alkyl-carbonyl group (e.g., acetyl) (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, morpholinylmethyl, —$C(CF_3)_3$, etc.), preferably a $C_{1-6}$ alkyl group optionally having 1 to 5 (more preferably 1 to 3) halogen atoms,
(5) a $C_{2-6}$ alkenyl group optionally having 1 to 3 halogen atoms (e.g., vinyl, allyl, isopropenyl, butenyl, isobutenyl, sec-butenyl, 3,3,3-trifluoro-1-propenyl, 4,4,4-trifluoro-1-butenyl, etc.),
(6) a $C_{2-6}$ alkynyl group optionally having 1 to 3 halogen atoms (e.g., ethynyl, propargyl, butynyl, 1-hexynyl, 3,3,3-trifluoro-1-propynyl, 4,4,4-trifluoro-1-butynyl, etc.),
(7) a $C_{3-8}$ cycloalkyl group optionally having 1 to 5 (preferably 1 to 3) halogen atoms (e.g., cyclopropyl, cyclobutyl, cyclopentyl, cyclohexyl, 4,4-dichlorocyclohexyl, 2,2,3,3-tetrafluorocyclopentyl, 4-chlorocyclohexyl, etc.),
(8) a $C_{6-14}$ aryl group optionally having 1 to 3 substituents selected from (i) a halogen atom, (ii) a cyano group, (iii) a $C_{1-6}$ alkyl group (e.g., methyl) optionally having 1 to 3 halogen atoms and (iv) a $C_{1-6}$ alkoxy group (e.g., methoxy) (e.g., phenyl, 1-naphthyl, 2-naphthyl, biphenylyl, 2-anthryl, chlorophenyl, bromophenyl, cyanophenyl, trifluoromethylphenyl etc.), preferably a $C_{6-14}$ aryl group,
(9) a $C_{7-16}$ aralkyl group (e.g., benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc.),
(10) a hydroxy group,
(11) a $C_{1-6}$ alkoxy group optionally having 1 to 3 halogen atoms (e.g., methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.),
(12) a $C_{6-14}$ aryloxy group (e.g., phenyloxy, naphthyloxy, etc.),
(13) a $C_{7-14}$ aralkyloxy group (e.g., benzyloxy),

(14) a mercapto group,
(15) a $C_{1-6}$ alkylthio group optionally having 1 to 3 halogen atoms (e.g., methylthio, difluoromethylthio, trifluoromethylthio, ethylthio, propylthio, isopropylthio, butylthio, 4,4,4-trifluorobutylthio, pentylthio, hexylthio, etc.),
(16) a $C_{6-14}$ arylthio group (e.g., phenylthio, naphthylthio, etc.),
(17) an amino group,
(18) a mono-$C_{1-6}$ alkylamino group (e.g., methylamino, ethylamino, etc.),
(19) a mono-$C_{6-14}$ arylamino group (e.g., phenylamino, 1-naphthylamino, 2-naphthylamino, etc.),
(20) a di-$C_{1-6}$ alkylamino group optionally having one substituent selected from (i) a $C_{1-6}$ alkoxy group (e.g., methoxy) and (ii) a heterocyclic group (e.g., isoxazolyl) optionally having a $C_{1-6}$ alkyl group (e.g., methyl) (e.g., dimethylamino, diethylamino, (2-methoxyethyl)-(methyl)amino, etc.), preferably a di-$C_{1-6}$ alkylamino group,
(21) a di-$C_{6-14}$ arylamino group (e.g., diphenylamino, etc.),
(22) a formyl group,
(23) a $C_{1-6}$ alkyl-carbonyl group (e.g., acetyl, propionyl, isobutyryl, butyryl, etc.) optionally having 1 to 3 substituents selected from (i) a cyano group, (ii) a hydroxy group and (iii) a halogen atom, preferably a $C_{1-6}$ alkyl-carbonyl group,
(24) $C_{3-6}$ cycloalkyl-carbonyl (e.g., cyclopropylcarbonyl) optionally having one hydroxy group,
(25) a $C_{6-14}$ aryl-carbonyl group (e.g., benzoyl, 1-naphthoyl, 2-naphthoyl, etc.) optionally having 1 to 3 substituents selected from (i) a $C_{1-6}$ alkoxy group (e.g., methoxy), (ii) a halogen atom, (iii) a cyano group and (iv) a. $C_{6-14}$ aryl group (e.g., phenyl), preferably a $C_{6-14}$ aryl-carbonyl group,
(26) a carboxy group,
(27) a $C_{1-6}$ alkoxy-carbonyl group (e.g., methoxycarbonyl, ethoxycarbonyl, propoxycarbonyl, tert-butoxycarbonyl, etc.),
(28) a $C_{6-14}$ aryloxy-carbonyl group (e.g., phenoxycarbonyl, etc.),
(29) a $C_{7-14}$ aralkyloxy-carbonyl group (e.g., benzyloxycarbonyl etc.),
(30) a carbamoyl-carbonyl group,
(31) a carbamoyl group,
(32) a thiocarbamoyl group,
(33) a mono-$C_{1-6}$ alkyl-carbamoyl group (e.g., methylcarbamoyl, ethylcarbamoyl, etc.),
(34) a di-$C_{1-6}$ alkyl-carbamoyl group (e.g., dimethylcarbamoyl, diethylcarbamoyl, ethylmethylcarbamoyl, etc.),
(35) a $C_{3-6}$ cycloalkyl-carbamoyl group (e.g., cyclopropylcarbamoyl),
(36) a $C_{6-14}$ aryl-carbamoyl group (e.g., phenylcarbamoyl, 1-naphthylcarbamoyl, 2-naphthylcarbamoyl, etc.),
(37) a $C_{1-6}$ alkylsulfonyl group (e.g., methylsulfonyl, ethylsulfonyl, etc.),
(38) a $C_{6-14}$ arylsulfonyl group (e.g., phenylsulfonyl, 1-naphthylsulfonyl, 2-naphthylsulfonyl, etc.),
(39) a $C_{1-6}$ alkylsulfinyl group (e.g., methylsulfinyl, ethylsulfinyl, etc.),
(40) a $C_{6-14}$ arylsulfinyl group (e.g., phenylsulfinyl, 1-naphthylsulfinyl, 2-naphthylsulfinyl, etc.),
(41) an aminosulfonyl group,
(42) a formylamino group,
(43) a $C_{1-6}$ alkyl-carbonylamino group (e.g., acetylamino, etc.),
(44) a $C_{6-14}$ aryl-carbonylamino group (e.g., benzoylamino, naphthoylamino, etc.),
(45) a $C_{1-6}$ alkoxy-carbonylamino group (e.g., methoxycarbonylamino, ethoxycarbonylamino, propoxycarbonylamino, butoxycarbonylamino, tert-butoxycarbonylamino, etc.),
(46) a $C_{1-6}$ alkylsulfonylamino group (e.g., methylsulfonylamino, ethylsulfonylamino, etc.),
(47) a $C_{6-14}$ arylsulfonylamino group (e.g., phenylsulfonylamino, 2-naphthylsulfonylamino, 1-naphthylsulfonylamino, etc.),
(48) a $C_{1-6}$ alkyl-carbonyloxy group (e.g., acetoxy, propionyloxy, etc.),
(49) a $C_{6-14}$ aryl-carbonyloxy group (e.g., benzoyloxy, naphthylcarbonyloxy, etc.),
(50) a $C_{1-6}$ alkoxy-carbonyloxy group (e.g., methoxycarbonyloxy, ethoxycarbonyloxy, propoxycarbonyloxy, butoxycarbonyloxy, etc.),
(51) a carbamoyloxy group,
(52) a mono-$C_{1-6}$ alkyl-carbamoyloxy group (e.g., methylcarbamoyloxy, ethylcarbamoyloxy, etc.),
(53) a di-$C_{1-6}$ alkyl-carbamoyloxy group (e.g., dimethylcarbamoyloxy, diethylcarbamoyloxy, etc.),
(54) a $C_{6-14}$ aryl-carbamoyloxy group (e.g., phenylcarbamoyloxy, naphthylcarbamoyloxy, etc.),
(55) a 3- to 14-membered (preferably a 5- to 10-membered) (monocyclic, bicyclic or tricyclic) heterocyclic group containing, besides carbon atoms, 1 to 5 hetero atoms of one to three kinds selected from a nitrogen atom (optionally N-oxidized), a sulfur atom and an oxygen atom, and optionally having 1 to 3 substituents selected from (i) a $C_{1-6}$ alkyl group optionally having 1 to 3 halogen atoms (e.g., methyl, trifluoromethyl), (ii) an oxo group, (iii) a halogen atom and (iv) a $C_{1-6}$ alkoxy-carbonyl group (e.g., tert-butoxycarbonyl) [e.g., aromatic heterocyclic groups such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl, 3-methyl-1-pyrazolyl), imidazolyl (e.g., 1-imidazolyl, 2-imidazolyl, 4-imidazolyl, 5-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl, 2-methyl-5-thiazolyl), triazolyl (e.g., 1,2,3-triazol-4-yl, 1,2,4-triazol-3-yl, 1,2,4-triazol-1-yl), oxadiazolyl (e.g., 1,2,4-oxadiazol-3-yl, 1,2,4-oxadiazol-5-yl, 1,3,4-oxadiazol-2-yl), thiadiazolyl (e.g., 1,2,4-thiadiazol-3-yl, 1,2,4-thiadiazol-5-yl, 1,3,4-thiadiazol-2-yl), tetrazolyl (e.g., 5-trifluoromethyl-tetrazol-1-yl), pyridyl (nitrogen atom is optionally N-oxidized) (e.g., 2-pyridyl, 3-pyridyl, 4-pyridyl, N-oxido-4-pyridyl), pyridazinyl (e.g., 3-pyridazinyl, 4-pyridazinyl), pyrimidinyl (e.g., 2-pyrimidinyl, 4-pyrimidinyl), pyrazinyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl) and the like; nonaromatic heterocyclic groups such as oxazolidinyl (e.g., 2-oxazolidinyl, 3-oxazolidinyl, 4-oxazolidinyl, 5-oxazolidinyl), imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl, 2-oxo-1-pyrrolidinyl), piperidinyl (e.g., 1-piperidinyl, 2-piperidinyl, 3-piperidinyl, 4-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl, 4-methyl-1,4-piperazin-1-yl), diazepanyl (e.g., 1,4-diazepan-1-yl, 1,4-diazepan-2-yl, 1,4-diazepan-5-yl, 1,4-diazepan-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), 4-morpholinyl, 4-thiomorpholinyl, 1,1-dioxidothiomorpholin-4-yl and the like; a heterocyclic group wherein the above-mentioned aromatic heterocyclic group is partially hydrogenated, such as indolinyl, dihydroquinolyl, tetrahydropyrazinyl and the like; a heterocyclic group wherein the above-mentioned nonaromatic heterocyclic group is partially dehydrogenated, such as dihydrofuryl and the like], preferably a 3- to 14-membered (monocyclic, bicyclic or tricyclic) heterocyclic group containing, besides carbon atoms, 1 to 5 hetero atoms of one to three kinds selected from a nitrogen atom, a sulfur atom and an oxygen atom,

(56) a 5- to 10-membered heterocyclyl-amino group (wherein the 5- to 10-membered heterocyclyl contains, besides carbon atoms, 1 to 4 hetero atoms of one or two kinds selected from a nitrogen atom, a sulfur atom and an oxygen atom) (e.g., morpholinylamino, 4-piperidylamino) optionally having one $C_{1-6}$ alkyl-carbonyl group (e.g., acetyl),

(57) a 5- to 10-membered heterocyclyl-carbonyl group (e.g., 2-furylcarbonyl, 4-pyridylcarbonyl, N-oxido-4-pyridylcarbonyl),

(58) a $C_{1-3}$ alkylenedioxy group (e.g., methylenedioxy, ethylenedioxy, etc.),

(59) an oxo group and the like.

One embodiment of the substituent of ring A is preferably 1 to 3 substituents selected from the above-mentioned (1)-(12), (14)-(23), (25)-(28), (31)-(34), (36)-(40), (42)-(50), (52)-(55), (58) and (59).

For example, ring A preferably has the following structure:

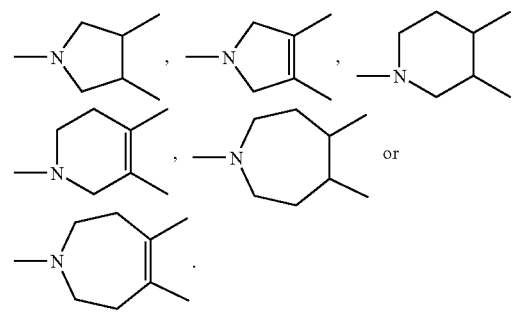

Of these, a ring having the above-mentioned structure and having substituents only for $R^1$, ring B and a partial structure:

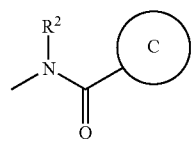

is preferable.

(Explanation of Ring B)

In the aforementioned formulas, ring B is an aromatic ring optionally having substituent(s).

Examples of the "aromatic ring" include an aryl group or an aromatic heterocyclic group.

As the "aryl group", for example, a $C_{6-14}$ aryl group (e.g., phenyl, naphthyl, anthryl, phenanthryl, etc.) and the like are used, with preference given to phenyl.

As the "aromatic heterocyclic group", for example, a 5- or 6-membered aromatic heterocyclic group containing, besides carbon atoms, 1 to 4 hetero atoms of one or two kinds selected from a nitrogen atom, an oxygen atom and a sulfur atom (e.g., furyl, thienyl, pyridyl, pyrrolyl, imidazolyl, pyrazolyl, thiazolyl, oxazolyl, thiadiazolyl, triazolyl, tetrazolyl, isoxazolyl, etc.), a bicyclic or tricyclic fused cyclic group containing, besides carbon atoms, 1 to 4 hetero atoms of one or two kinds selected from a nitrogen atom, an oxygen atom and a sulfur atom (preferably, a group formed by condensation of the above-mentioned 5- or 6-membered aromatic heterocycle with one or two 5- or 6-membered heterocycles containing, besides carbon atoms, 1 to 4 hetero atoms of one or two kinds selected from an oxygen atom, a sulfur atom and a nitrogen atom, or with a benzene ring; for example, indolyl, benzimidazolyl, benzothienyl, benzothiadiazolyl, quinolyl, triazolopyrimidinyl, pyrazolopyridyl, benzofuryl, benzoxazolyl, etc.) and the like are used.

As the substituent of the "aromatic ring" for ring B, for example, 1 to 5 (preferably 1 to 3) substituents similar to the substituents (1)-(59) exemplified as the substituents of the above-mentioned ring A and the like are used. Another preferable embodiment is 1 to 5 (preferably 1 to 3) substituents selected from (1)-(12), (14)-(23), (25)-(28), (31)-(34), (36)-(40), (42)-(50), (52)-(55), (58) and (59) exemplified as the substituents of the above-mentioned ring A.

As ring B, a phenyl group or a thienyl group each optionally having substituent(s) is preferable. Of these, a phenyl group optionally having substituent(s) is preferable. Preferable examples of ring B include (1) a phenyl group optionally having 1 to 3 substituents selected from (i) a $C_{1-6}$ alkyl group optionally having 1 to 3 halogen atoms, (ii) a halogen atom, (iii) a $C_{1-6}$ alkoxy group optionally having 1 to 3 halogen atoms, (iv) a $C_{1-6}$ alkoxy-carbonyl group, (v) a carboxy group, (vi) a $C_{6-14}$ aryl group and (vii) a $C_{3-8}$ cycloalkyl group optionally having 1 to 3 halogen atoms, and (2) a thienyl group optionally having a $C_{1-6}$ alkyl group optionally having 1 to 3 halogen atoms. Of these, a phenyl group optionally having 1 to 3 substituents selected from (1) a $C_{1-6}$ alkyl group optionally having 1 to 3 halogen atoms and (2) a halogen atom is still more preferable, and a phenyl group optionally having 1 or 2 substituents selected from (1) a $C_{1-6}$ alkyl group (e.g., methyl) and (2) a halogen atom (e.g., fluorine atom, chlorine atom) is more preferable. When ring B is a phenyl group optionally having substituent(s), a phenyl group having 1 or 2 substituents selected from a methyl group and a halogen atom at the 3-position and/or the 4-position is preferable.

(Explanation of Ring C)

In the aforementioned formulas, ring C is a cyclic group optionally having substituent(s). Examples of the "cyclic group" include unsaturated cyclic groups. The "unsaturated cyclic group" means a cyclic group having at least one double bond, for example, an aromatic ring and an unsaturated nonaromatic ring.

Examples of the "aromatic ring" include those similar to the aromatic rings exemplified as ring B.

Examples of the "unsaturated nonaromatic ring" include a nonaromatic group formed by condensation of a 5- or 6-membered heterocycle containing, besides carbon atoms, 1 to 4 hetero atoms of one or two kinds selected from a nitrogen atom, an oxygen atom and a sulfur atom with one or two 5- or 6-membered heterocycles containing, besides carbon atoms, 1 to 4 hetero atoms of one or two kinds selected from a nitrogen atom, an oxygen atom and a sulfur atom, or with a benzene ring; such as benzodioxolyl, 2,3-dihydrobenzofuryl, benzoxathiolyl, dihydrobenzoxazolyl, dihydro-1H-benzimidazolyl, dihydrobenzothiazolyl, dihydrobenzothiophenyl, dihydro-1H-indolyl, dihydrobenzisoxazolyl, dihydrobenzisothiazolyl, dihydro-2H-chromenyl, 2H-chromenyl, dihydro-1H-isochromenyl, 1H-isochromenyl, dihydro-2H-thiochromenyl, 2H-thiochromenyl, dihydro-1H-isothiochromenyl, 1H-isothiochromenyl, tetrahydroquinolinyl, dihydroquinolinyl, tetrahydroisoquinolinyl, dihydroisoquinolinyl, dihydro-2H-benzoxazinyl, dihydro-2H-benzothiazinyl, dihydrobenzodioxinyl, dihydrobenzoxathiinyl, dihydrobenzodithiinyl, tetrahydroquinoxalinyl, dihydroquinoxalinyl and the like.

Preferable examples of ring C include a phenyl group, a pyrrolyl group, a thienyl group, a furyl group, a pyrazolyl group, an indolyl group, a benzimidazolyl group, a pyridyl group, a benzothienyl group, an imidazolyl group, a benzothiadiazolyl group, a pyrazolopyridyl group, a benzofuryl group, a thiadiazolyl group, an oxazolyl group, an isoxazolyl group, a triazolopyrimidinyl group, a thiazolyl group, a quinolyl group, a benzodioxolyl group, a benzoxazolyl group, a 2,3-dihydrobenzofuryl group, each of which optionally has substituent(s). Of these, an optionally substituted aromatic ring is preferable, and a phenyl group, a pyrrolyl group, a thienyl group, a furyl group, a pyrazolyl group, an indolyl group, a benzimidazolyl group and a pyridyl group, each of which optionally has substituent(s), can be mentioned. In another embodiment, ring C is preferably a phenyl group, a pyridyl group, a benzothienyl group or a benzodioxolyl group, each optionally having substituent(s), more preferably a phenyl group, a pyridyl group or a benzothienyl group, each optionally having substituent(s).

As the substituent of the "cyclic group" for ring C, for example, 1 to 5 (preferably 1 to 3) substituents similar to the substituents (1)-(59) exemplified as the substituents of the above-mentioned ring A are used. In one preferable embodiment of the substituent of ring C is 1 to 5 (preferably 1 to 3) substituents selected from (1)-(12), (14)-(23), (25)-(28), (31)-(34), (36)-(40), (42)-(50), (52)-(55), (58) and (59) exemplified as the substituents of the above-mentioned ring A.

In another preferable embodiment, the substituent of ring C is 1 to 5 (preferably 1 to 3) substituents selected from (1) a $C_{1-6}$ alkyl group optionally having 1 to 9 (preferably 1 to 3) halogen atoms, (2) a halogen atom, (3) a $C_{1-6}$ alkoxy group optionally having 1 to 3 halogen atoms, (4) a cyano group, (5) a di-$C_{1-6}$ alkylamino group optionally having a $C_{1-6}$ alkoxy group, (6) a $C_{3-8}$ cycloalkyl group, (7) a $C_{6-14}$ aryl group optionally having 1 to 3 substituents selected from (i) a halogen atom, (ii) a cyano group, (iii) a $C_{1-6}$ alkyl group optionally having 1 to 3 halogen atoms and (iv) a $C_{1-6}$ alkoxy group, (8) a 5- to 10-membered heterocyclic group containing, besides carbon atoms, 1 to 4 hetero atoms of one or two kinds selected from a nitrogen atom, a sulfur atom and an oxygen atom, and optionally having 1 to 3 substituents selected from (i) a $C_{1-6}$ alkyl group optionally having 1 to 3 halogen atoms and (ii) an oxo group, (9) a $C_{7-14}$ aralkyloxy group,

(10) a $C_{1-6}$ alkoxy-carbonyl group,

(11) an aminosulfonyl group,

(12) a carbamoyl group,

(13) a $C_{1-6}$ alkyl-carbonylamino group,

(14) a 5- to 10-membered heterocyclyl-amino group (wherein the 5- to 10-membered heterocyclyl contains, besides carbon atoms, 1 to 4 hetero atoms of one or two kinds selected from a nitrogen atom, a sulfur atom and an oxygen atom),

(15) an oxo group and the like are preferable. Furthermore, 1 to 5 (preferably 1 to 3) substituents selected from (1) a $C_{1-6}$ alkyl group optionally having 1 to 3 halogen atoms, (2) a halogen atom, (3) a $C_{1-6}$ alkoxy group optionally having 1 to 3 halogen atoms, (4) a cyano group, (5) a di-$C_{1-6}$ alkylamino group, (6) a $C_{3-8}$ cycloalkyl group, (7) a $C_{6-14}$ aryl group optionally having a $C_{1-6}$ alkoxy group, (8) a 5- to 10-membered heterocyclic group containing, besides carbon atoms, 1 to 4 hetero atoms of one or two kinds selected from a nitrogen atom, a sulfur atom and an oxygen atom (preferably, an aromatic heterocyclic group or a morpholinyl group, more preferably an aromatic heterocyclic group), and optionally having a $C_{1-6}$ alkyl group, and the like are preferable. Preferably, 4-methoxy-3-(3-methoxypropoxy)phenyl group is excluded from ring C.

More preferable examples of ring C include

[1] a phenyl group optionally having 1 to 3 substituents selected from (1) a $C_{1-6}$ alkyl group optionally having 1 to 9 (preferably 1 to 3) halogen atoms (e.g., fluorine) (e.g., methyl, isopropyl, tert-butyl, trifluoromethyl), (2) a halogen atom (e.g., fluorine, chlorine, bromine), (3) a $C_{1-6}$ alkoxy group (e.g., methoxy) optionally having 1 to 3 halogen atoms (e.g., fluorine), (4) a cyano group, (5) a di-$C_{1-6}$ alkylamino group optionally having a $C_{1-6}$ alkoxy group (e.g., dimethylamino, (2-methoxyethyl)-(methyl)amino), (6) a $C_{3-8}$ cycloalkyl group (e.g., cyclopropyl, cyclopentyl, cyclohexyl),
(7) a $C_{6-14}$ aryl group (e.g., phenyl) optionally having 1 to 3 substituents selected from (i) a halogen atom, (ii) a cyano group and (iii) a $C_{1-6}$ alkyl group optionally having 1 to 3 halogen atoms,
(8) a 5- to 10-membered heterocyclic group (e.g., pyrazolyl, morpholinyl tetrazolyl, triazolyl, pyridyl, piperidinyl, pyrrolidinyl, tetrahydropyrazinyl, thiazolyl etc.) containing, besides carbon atoms, 1 to 4 hetero atoms of one or two kinds selected from a nitrogen atom, a sulfur atom and an oxygen atom, and optionally having 1 to 3 substituents selected from (i) a $C_{1-6}$ alkyl group (e.g., methyl) optionally having 1 to 3 halogen atoms and (ii) an oxo group,
(9) a $C_{1-6}$ alkyl-carbonylamino group (e.g., acetylamino),
(10) a 5- to 10-membered heterocyclyl-amino group (e.g., morpholinylamino),
(11) a $C_{1-6}$ alkoxy-carbonyl group,
(12) an aminosulfonyl group,
(13) a $C_{7-14}$ aralkyloxy group, and
(14) a carbamoyl group, or
[2] a pyrrolyl group, a thienyl group, a furyl group, a pyrazolyl group, an indolyl group, a benzimidazolyl group, a benzothienyl group, a pyridyl group, an imidazolyl group, a benzothiazolyl group, a pyrazolopyridyl group, a benzofuryl group, a triazolopyrimidinyl group, a thiadiazolyl group, a thiazolyl group, an oxazolyl group, a quinolyl group, an isoxazolyl group or a benzoxazolyl group, each optionally having 1 to 5 (preferably 1 to 3) substituents selected from
(1) a $C_{6-14}$ aryl group (e.g., phenyl) optionally having 1 to 3 substituents selected from (i) a halogen atom (e.g., chlorine, bromine, fluorine) and (ii) a $C_{1-6}$ alkoxy group (e.g., methoxy),
(2) a $C_{1-6}$ alkyl group optionally having 1 to 3 halogen atoms (e.g., fluorine) (e.g., methyl, trifluoromethyl),
(3) a 5- to 10-membered heterocyclic group (e.g., pyridyl, morpholinyl) containing, besides carbon atoms, 1 to 4 hetero atoms of one or two kinds selected from a nitrogen atom, a sulfur atom and an oxygen atom,
(4) a $C_{1-6}$ alkoxy group (e.g., methoxy),
(5) an oxo group,
(6) a halogen atom,
(7) a cyano group,
(8) a di-$C_{1-6}$ alkylamino group,
(9) a $C_{1-6}$ alkyl-carbonylamino group and
(10) a 5- to 10-membered heterocyclyl-amino group, more preferably substituents are selected from the above-mentioned (1)-(6), or
[3] a benzodioxolyl group or a 2,3-dihydrobenzofuryl group, each optionally having 1 to 5 (preferably 1 to 3) substituents selected from (1)-(10) as shown in the above-mentioned [2] (preferably (1)-(6), more preferably (2) and (6)).
More preferably, ring C is
[1] a phenyl group optionally having 1 to 3 substituents selected from
(1) a $C_{1-6}$ alkyl group optionally having 1 to 3 halogen atoms (e.g., fluorine) (e.g., methyl, isopropyl, tert-butyl, trifluoromethyl),
(2) a halogen atom (e.g., fluorine, chlorine, bromine),
(3) a $C_{1-6}$ alkoxy group (e.g., methoxy) optionally having 1 to 3 halogen atoms (e.g., fluorine),
(4) a cyano group,
(5) a di-$C_{1-6}$ alkylamino group (e.g., dimethylamino),
(6) a $C_{3-8}$ cycloalkyl group (e.g., cyclopentyl, cyclohexyl),
(7) a $C_{6-14}$ aryl group (e.g., phenyl), and
(8) a 5- to 10-membered heterocyclic group (e.g., pyrazolyl, morpholinyl, tetrazolyl) (preferably an aromatic heterocyclic group) containing, besides carbon atoms, 1 to 4 hetero atoms of one or two kinds selected from a nitrogen atom, a sulfur atom and an oxygen atom, and optionally having a $C_{1-6}$ alkyl group (e.g., methyl), or
[2] a pyrrolyl group, a thienyl group, a furyl group, a pyrazolyl group, an indolyl group, a benzimidazolyl group or a pyridyl group, each optionally having a $C_{6-14}$ aryl group (e.g., phenyl) optionally having a $C_{1-6}$ alkoxy group (e.g., methoxy).
When ring C is a phenyl group optionally having substituent(s) and having two substituents, a 3,5- or 2,5-disubstituted phenyl is preferable. Particularly, a 3,5-bis(trifluoromethyl)phenyl group, a 3-halo-5-trifluoromethylphenyl group, a 2-methoxy-5-(5-(trifluoromethyl)-1H-tetrazol-1-yl)phenyl group and the like are preferable.
In addition, when ring C is a phenyl group, a pyridyl group or a benzothienyl group, each optionally having substituent(s), one having a substituent at the para-position is preferable. Preferable examples of the substituent include a halogen atom, a trifluoromethyl group, a cyano group, a methoxy group, a dimethylamino group, a (2-methoxyethyl)-(methyl)amino group, an acetylamino group, a morpholinylamino group, a morpholinyl group optionally having a benzyl group and the like.

(Explanation of $R^1$)

In the aforementioned formulas, $R^1$ is a hydrogen atom, a hydrocarbon group optionally having substituent(s), an acyl group, a heterocyclic group optionally having substituent(s) or an amino group optionally having substituent(s) (preferably, a hydrogen atom, a hydrocarbon group optionally having substituent(s), an acyl group or a heterocyclic group optionally having substituent(s)). Preferably, in the aforementioned formula, when n=1, $R^1$ is not a hydrogen atom.

Examples of the "hydrocarbon group" of the "hydrocarbon group optionally having substituent(s)" for $R^1$ include an aliphatic hydrocarbon group, a monocyclic saturated hydrocarbon group, an aromatic hydrocarbon group and the like, with preference given to one having 1 to 16 carbon atoms. Specifically, for example, an alkyl group, an alkenyl group, an alkynyl group, a cycloalkyl group, a cycloalkenyl group, an alkylidene group, an aryl group, an aralkyl group and the like (preferably, an alkyl group, an alkenyl group, an alkynyl group, a cycloalkyl group, an aryl group, an aralkyl group etc.) are used.

As the "alkyl group", for example, a $C_{1-6}$ alkyl group (e.g., methyl, ethyl, propyl, isopropyl, butyl, isobutyl, sec-butyl, tert-butyl, pentyl, hexyl, etc.) and the like are preferable, and $C_{1-4}$ alkyl is more preferable.

As the "alkenyl group", for example, a $C_{2-6}$ alkenyl group (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like are preferable.

As the "alkynyl group", for example, a $C_{2-6}$ alkynyl group (e.g., ethynyl, propargyl, 1-butynyl, 2-butynyl, 3-butynyl, 1-hexynyl, etc.) and the like are preferable.

As the "cycloalkyl group", for example, a $C_{3-10}$ cycloalkyl group (e.g., cyclopropyl, cyclobutyl, cyclopentyl, cyclohexyl, tricyclodecyl (e.g., adamantyl), etc.) and the like are preferable, a $C_{3-8}$ cycloalkyl group is more preferable, and a $C_{3-6}$ cycloalkyl group is still more preferable.

As the "cycloalkenyl group", for example, a $C_{5-8}$ cycloalkenyl group (e.g., cyclopentenyl, cyclohexenyl, etc.) and the like are preferable.

As the "alkylidene group", for example, a $C_{1-6}$ alkylidene group (e.g., methylidene) and the like are preferable.

As the "aryl group", for example, a $C_{6-14}$ aryl group (e.g., phenyl, 1-naphthyl, 2-naphthyl, 2-biphenylyl, 3-biphenylyl, 4-biphenylyl, 2-anthryl, etc.) and the like are preferable.

As the "aralkyl group", for example, a $C_{7-16}$ aralkyl group (e.g., benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like are preferable.

Examples of the substituent of the "hydrocarbon group" include 1 to 3 substituents selected from
(1) a halogen atom (e.g., fluorine, chlorine, bromine, iodine etc.),
(2) a nitro group,
(3) a cyano group,
(4) a $C_{1-6}$ alkyl group optionally having 1 to 3 halogen atoms (e.g., methyl, trifluoromethyl),
(5) a $C_{3-8}$ cycloalkyl group optionally having 1 to 5 (preferably 1 to 3) halogen atoms (e.g., cyclopropyl, cyclobutyl, cyclopentyl, cyclohexyl, 4,4-dichlorocyclohexyl, 2,2,3,3-tetrafluorocyclopentyl, 4-chlorocyclohexyl etc.),
(6) a $C_{6-14}$ aryl group (e.g., phenyl, 1-naphthyl, 2-naphthyl, biphenylyl, 2-anthryl etc.) optionally having a $C_{1-6}$ alkyl group optionally having 1 to 3 halogen atoms (e.g., methyl, trifluoromethyl), preferably a $C_{6-14}$ aryl group,
(7) a hydroxy group,
(8) a $C_{1-6}$ alkoxy group optionally having 1 to 3 halogen atoms (e.g., methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy etc.),
(9) a $C_{6-14}$ aryloxy group (e.g., phenyloxy, naphthyloxy etc.) optionally having a $C_{1-6}$ alkyl-carbonylamino group (e.g., acetylamino), preferably a $C_{6-14}$ aryloxy group,
(10) a mercapto group,
(11) a $C_{1-6}$ alkylthio group optionally having 1 to 3 halogen atoms (e.g., methylthio, difluoromethylthio, trifluoromethylthio, ethylthio, propylthio, isopropylthio, butylthio, 4,4,4-trifluorobutylthio, pentylthio, hexylthio etc.),
(12) a $C_{6-14}$ arylthio group (e.g., phenylthio, naphthylthio etc.),
(13) an amino group,
(14) a mono-$C_{1-6}$ alkylamino group (e.g., methylamino, ethylamino etc.),
(15) a mono-$C_{6-14}$ arylamino group (e.g., phenylamino, 1-naphthylamino, 2-naphthylamino etc.),
(16) a di-$C_{1-6}$ alkylamino group (e.g., dimethylamino, diethylamino etc.),
(17) a di-$C_{6-14}$ arylamino group (e.g., diphenylamino etc.),
(18) a ($C_{1-6}$ alkyl)-($C_{1-6}$ alkyl-carbonyl)amino group (e.g., (acetyl)-(methyl)amino),
(19) a formyl group,
(20) a $C_{1-6}$ alkyl-carbonyl group (e.g., acetyl, propionyl etc.),
(21) a $C_{6-14}$ aryl-carbonyl group (e.g., benzoyl, 1-naphthoyl, 2-naphthoyl etc.),
(22) a carboxy group,
(23) a $C_{1-6}$ alkoxy-carbonyl group (e.g., methoxycarbonyl, ethoxycarbonyl, propoxycarbonyl, tert-butoxycarbonyl etc.),
(24) a $C_{6-14}$ aryloxy-carbonyl group (e.g., phenoxycarbonyl etc.),
(25) a carbamoyl group,
(26) a thiocarbamoyl group,
(27) a mono-$C_{1-6}$ alkyl-carbamoyl group (e.g., methylcarbamoyl, ethylcarbamoyl etc.),
(28) a di-$C_{1-6}$ alkyl-carbamoyl group (e.g., dimethylcarbamoyl, diethylcarbamoyl, ethylmethylcarbamoyl etc.),
(29) a $C_{6-14}$ aryl-carbamoyl group (e.g., phenylcarbamoyl, 1-naphthylcarbamoyl, 2-naphthylcarbamoyl etc.),
(30) a $C_{1-6}$ alkylsulfonyl group (e.g., methylsulfonyl, ethylsulfonyl etc.),
(31) a $C_{6-14}$ arylsulfonyl group (e.g., phenylsulfonyl, 1-naphthylsulfonyl, 2-naphthylsulfonyl etc.),
(32) an aminosulfonyl group,
(33) a $C_{1-6}$ alkylsulfinyl group (e.g., methylsulfinyl, ethylsulfinyl etc.),
(34) a $C_{6-14}$ arylsulfinyl group (e.g., phenylsulfinyl, 1-naphthylsulfinyl, 2-naphthylsulfinyl etc.),
(35) a formylamino group,
(36) a carbamoylamino group,
(37) a $C_{1-6}$ alkyl-carbonylamino group (e.g., acetylamino etc.),
(38) a $C_{6-14}$ aryl-carbonylamino group (e.g., benzoylamino, naphthoylamino etc.),
(39) a $C_{1-6}$ alkoxy-carbonylamino group (e.g., methoxycarbonylamino, ethoxycarbonylamino, propoxycarbonylamino, butoxycarbonylamino, tert-butoxycarbonylamino etc.),
(40) a $C_{1-6}$ alkylsulfonylamino group (e.g., methylsulfonylamino, ethylsulfonylamino etc.),
(41) a $C_{6-14}$ arylsulfonylamino group (e.g., phenylsulfonylamino, 2-naphthylsulfonylamino, 1-naphthylsulfonylamino etc.),
(42) a $C_{1-6}$ alkyl-carbonyloxy group (e.g., acetoxy, propionyloxy etc.),
(43) a $C_{6-14}$ aryl-carbonyloxy group (e.g., benzoyloxy, naphthylcarbonyloxy etc.),
(44) a $C_{1-6}$ alkoxy-carbonyloxy group (e.g., methoxycarbonyloxy, ethoxycarbonyloxy, propoxycarbonyloxy, butoxycarbonyloxy etc.),
(45) a mono-$C_{1-6}$ alkyl-carbamoyloxy group (e.g., methylcarbamoyloxy, ethylcarbamoyloxy etc.),
(46) a di-$C_{1-6}$ alkyl-carbamoyloxy group (e.g., dimethylcarbamoyloxy, diethylcarbamoyloxy etc.),
(47) a $C_{6-14}$ aryl-carbamoyloxy group (e.g., phenylcarbamoyloxy, naphthylcarbamoyloxy etc.),
(48) a 3- to 14-membered (monocyclic, bicyclic or tricyclic) heterocyclic group containing, besides carbon atoms, 1 to 5 hetero atoms of one to three kinds selected from a nitrogen atom, a sulfur atom and an oxygen atom, and optionally having 1 to 5 substituents selected from (i) an oxo group, (ii) a $C_{1-6}$ alkyl-carbonyl group (e.g., acetyl) optionally having 1 to 3 halogen atoms, (iii) a $C_{1-6}$ alkoxy-carbonyl group (e.g., tert-butoxycarbonyl), (iv) a $C_{1-6}$ alkyl group (e.g., methyl) (preferably a $C_{1-3}$ alkyl group) and (v) a $C_{6-14}$ aryl group (e.g., phenyl) [for example, aromatic heterocyclic group such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl (e.g., 1,2,3,4-tetrazol-1-yl), pyridyl (e.g., 2-pyridyl, 3-pyridyl, 4-pyridyl), pyridazinyl (e.g., 3-pyridazinyl, 4-pyridazinyl), pyrimidinyl (e.g., 1-pyrimidinyl, 2-pyrimidinyl, 4-pyrimidinyl), pyrazinyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]

furanyl, 5-benzo[c]furanyl), benzo[b]thienyl, (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl) and the like; for example, nonaromatic heterocyclic group such as oxazolidinyl (e.g., 2-oxazolidinyl, 3-oxazolidinyl, 4-oxazolidinyl, 5-oxazolidinyl), imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl, 4-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepanyl (e.g., 1,4-diazepan-1-yl, 1,4-diazepan-2-yl, 1,4-diazepan-5-yl, 1,4-diazepan-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), 4-morpholinyl, 4-thiomorpholinyl, 2-azaspiro[4.5]decan-2-yl and the like; a heterocyclic group wherein the above-mentioned aromatic heterocyclic group is partially hydrogenated, for example, indolinyl, dihydroquinolyl, dihydroquinoxalinyl, dihydrooxazolyl and the like; a heterocyclic group wherein the above-mentioned nonaromatic heterocyclic group is partially dehydrogenated, for example, dihydrofuryl and the like], preferably a 3- to 14-membered (monocyclic, bicyclic or tricyclic) heterocyclic group containing, besides carbon atoms, 1 to 5 hetero atoms of one to three kinds selected from a nitrogen atom, a sulfur atom and an oxygen atom,

(49) a 3- to 14-membered heterocyclyl-oxy group optionally having a $C_{6-14}$ aryl-carbonyl group (e.g., benzoyl) (e.g., piperidin-4-yloxy, 1-benzoyl-piperidin-4-yloxy),

(50) a 3- to 14-membered heterocyclyl-amino group (e.g., 4-piperidylamino) optionally having a $C_{1-6}$ alkyl-carbonyl group (e.g., acetyl),

(51) a $C_{1-3}$ alkylenedioxy group (e.g., methylenedioxy, ethylenedioxy etc.),

(52) an oxo group,

(53) a hydrazino group optionally having one $C_{1-6}$ alkoxy-carbonyl group (e.g., tert-butoxycarbonyl)

and the like, and preferred is 1 to 3 substituents selected from the above-mentioned (1)-(3), (5)-(17), (19)-(31), (33)-(35), (37)-(48), (51) and (52).

Examples of the "heterocyclic group" of the "heterocyclic group optionally having substituent(s)" for $R^1$ include a 4- to 14-membered (preferably 5- to 14-membered, more preferably 5- to 10-membered) monocyclic, bicyclic or tricyclic (preferably monocyclic or bicyclic) aromatic or nonaromatic heterocyclic group containing, besides carbon atoms, 1 to 4 (preferably 1 to 3) hetero atoms of one or two kinds selected from a nitrogen atom (optionally N-oxidized), an oxygen atom and a sulfur atom, and the like. For example, a 4-membered ring group containing, besides carbon atoms, 1 to 3 hetero atoms selected from an oxygen atom, a sulfur atom and a nitrogen atom such as 3-azetidinyl and the like; a 5-membered ring group containing, besides carbon atoms, 1 to 4 hetero atoms selected from an oxygen atom, a sulfur atom and a nitrogen atom such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1-, 2- or 4-imidazolidinyl, 1,2,3-triazolyl, 1,2,4-triazolyl, 1H- or 2H-tetrazolyl, tetrahydrofuryl and the like; a 6-membered ring group containing, besides carbon atoms, 1 to 4 hetero atoms selected from an oxygen atom, a sulfur atom and a nitrogen atom (optionally N-oxidized) such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl (e.g., 3-morpholinyl), piperidino, 2-, 3- or 4-piperidyl, thiopyranyl, 1,4-oxazinyl, 1,4-thiazinyl, 1,3-thiazinyl, piperazinyl, triazinyl, 3- or 4-pyridazinyl, pyrazinyl, tetrahydropyridyl, tetrahydropyrimidinyl, dihydropyrimidinyl, N-oxido-3- or 4-pyridazinyl, tetrahydro-2H-pyran-4-yl and the like; a bicyclic or tricyclic fused cyclic group containing, besides carbon atoms, 1 to 4 hetero atoms selected from an oxygen atom, a sulfur atom and a nitrogen atom such as indolyl, benzo[b]furyl, benzo[c]furyl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuryl, carbazolyl, acridinyl, phenanthridinyl, chromanyl, phenothiazinyl, phenoxazinyl, imidazopyridinyl, tetrahydrotriazolopyrazinyl, hexahydropyrazolopyridyl, tetrahydroindolyl, benzotriazolyl, pyrrolopyrimidinyl and the like (preferably, a group formed by condensation of the above-mentioned 5- or 6-membered ring with one or two 5- or 6-membered ring groups containing, besides carbon atoms, 1 to 4 hetero atoms selected from an oxygen atom, a sulfur atom and a nitrogen atom, or with a benzene ring) and the like are used. Of these, a 5- to 7-membered (preferably 5- or 6-membered) aromatic or non-aromatic heterocyclic group containing, besides carbon atoms, 1 to 4 hetero atoms selected from an oxygen atom, a sulfur atom and a nitrogen atom is preferable.

As the "substituent" of the "heterocyclic group", 1 to 3 substituents similar to the substituents (1)-(59) exemplified as the substituents of the above-mentioned ring A are used. One preferable embodiment is 1 to 3 substituents selected from (1)-(12), (14)-(23), (25)-(28), (31)-(34), (36)-(40), (42)-(50), (52)-(55), (58) and (59) exemplified as the substituents of the above-mentioned ring A.

Examples of the "acyl group" for $R^1$ include an acyl group represented by the formula: —(C=O)—$R^3$, —(C=O)—

$OR^3$, —(C=O)—$NR^3R^4$, —(C=S)—$NHR^3$ or —$SO_2$—$R^5$ wherein $R^3$ is a hydrogen atom, a hydrocarbon group optionally having substituent(s) or a heterocyclic group optionally having substituent(s), $R^4$ is a hydrogen atom or a $C_{1-6}$ alkyl group, $R^5$ is a hydrocarbon group optionally having substituent(s) or a heterocyclic group optionally having substituent(s).

As the "hydrocarbon group optionally having substituent(s)" and "heterocyclic group optionally having substituent(s)" for $R^3$ or $R^5$, those similar to the "hydrocarbon group optionally having substituent(s)" or "heterocyclic group optionally having substituent(s)" for $R^1$ are used.

Examples of the "$C_{1-6}$ alkyl group" for $R^4$ include methyl, ethyl, propyl, isopropyl, butyl, isobutyl, sec-butyl, tert-butyl, pentyl, hexyl and the like.

Examples of the "substituent" of the "amino group optionally having substituent(s)" for $R^1$ include 1 or 2 substituents selected from (1) a $C_{1-6}$ alkyl group (e.g., methyl) optionally having 1 to 3 halogen atoms,
(2) a 3- to 14-membered heterocyclic group (e.g., piperidinyl, pyridyl) optionally having a $C_{1-6}$ alkyl-carbonyl group (e.g., acetyl) or a halogen atom,
(3) an oxo group,
(4) a $C_{1-6}$ alkyl-carbonyl-heterocyclyl-carbonyl group (e.g., acetylpiperidylcarbonyl),
(5) a $C_{1-6}$ alkylidene group (e.g., methylidene) optionally having a 3- to 14-membered heterocyclic group (e.g., imidazolyl) optionally having a $C_{1-6}$ alkyl group (e.g., methyl), and the like.

$R^1$ is preferably a hydrogen atom, an acyl group or a piperidyl group optionally having substituent(s). Of these, preferred is (1) a hydrogen atom,
(2) a 5- to 7-membered aromatic or nonaromatic heterocyclic group (e.g., piperidyl) containing, besides carbon atoms, 1 to 4 hetero atoms selected from an oxygen atom, a sulfur atom and a nitrogen atom and optionally having 1 to 3 substituents selected from a $C_{1-6}$ alkyl-carbonyl group (e.g., acetyl) and a $C_{1-6}$ alkoxy-carbonyl group (e.g., tert-butoxycarbonyl), or
(3) an acyl group represented by the formula: —(C=O)—$R^{3'}$ wherein $R^{3'}$ is
(a) a $C_{1-6}$ alkoxy group (e.g., tert-butoxy),
(b) a $C_{1-6}$ alkyl group (e.g., methyl) optionally having substituent(s) selected from a $C_{1-6}$ alkoxy group (e.g., methoxy) and a $C_{1-6}$ alkyl-carbonylamino group (e.g., acetylamino),
(c) a 5- to 7-membered aromatic or nonaromatic heterocyclic group (e.g., piperidyl) containing, besides carbon atoms, 1 to 4 hetero atoms selected from an oxygen atom, a sulfur atom and a nitrogen atom, and optionally having 1 to 3 substituents selected from an oxo group, a $C_{1-6}$ alkyl-carbonyl group (e.g., acetyl) and a $C_{1-6}$ alkoxy-carbonyl group (e.g., tert-butoxycarbonyl), or
(d) a $C_{3-8}$ cycloalkyl group (e.g., cyclohexyl) optionally having a $C_{1-6}$ alkyl-carbonylamino group (e.g., acetylamino).

Particularly preferably, $R^1$ is an acyl group represented by the formula: —(C=O)—$R^{3''}$
wherein $R^{3''}$ is a 5- to 7-membered aromatic or nonaromatic heterocyclic group (e.g., piperidyl) containing, besides carbon atoms, 1 to 4 hetero atoms selected from an oxygen atom, a sulfur atom and a nitrogen atom, and optionally having 1 to 3 substituents selected from an oxo group, a $C_{1-6}$ alkyl-carbonyl group (e.g., acetyl) and a $C_{1-6}$ alkoxy-carbonyl group (e.g., tert-butoxycarbonyl).

In another embodiment, $R^1$ is preferably a hydrogen atom, an acyl group, an alkyl group optionally having substituent(s), a cycloalkenyl group optionally having substituent(s), an aryl group optionally having substituent(s), an amino group optionally having substituent(s), a piperidyl group optionally having substituent(s), a pyridyl group optionally having substituent(s) or a pyrrolopyrimidinyl group optionally having substituent(s). Of these, $R^1$ is particularly preferably (1) a hydrogen atom,
(2) a $C_{1-6}$ alkyl group optionally having 1 to 3 substituents selected from (i) a heterocyclic group (e.g., piperidyl) optionally having 1 to 3 substituents selected from (a) an oxo group, (b) a $C_{1-6}$ alkoxy-carbonyl group and (c) a $C_{1-6}$ alkyl-carbonyl group, (ii) a $C_{6-14}$ aryl group and (iii) a halogen atom,
(3) a $C_{3-6}$ cycloalkenyl group optionally having an oxo group or a methyl group,
(4) a $C_{6-14}$ aryl group optionally having a $C_{1-6}$ alkoxy-carbonyl group,
(5) an amino group optionally having 1 or 2 substituents selected from (i) a $C_{1-6}$ alkyl group, (ii) a heterocyclic group (e.g., piperidyl, pyridyl) optionally having a $C_{1-6}$ alkyl-carbonyl group or a halogen atom, (iii) an oxo group, (iv) a $C_{1-6}$ alkyl-carbonyl-heterocyclyl-carbonyl group (e.g., acetylpiperidylcarbonyl) and (v) a $C_{1-6}$ alkylidene group optionally having a heterocyclic group (e.g., imidazolyl) optionally having a $C_{1-6}$ alkyl group,
(6) a 5- to 7-membered aromatic or nonaromatic heterocyclic group (e.g., piperidyl, pyridyl, pyrrolopyrimidinyl) containing, besides carbon atoms, 1 to 4 hetero atoms selected from an oxygen atom, a sulfur atom and a nitrogen atom, and optionally having 1 to 3 substituents selected from (i) a $C_{1-6}$ alkyl-carbonyl group (e.g., acetyl), (ii) a $C_{1-6}$ alkoxy-carbonyl group (e.g., methoxycarbonyl, ethoxycarbonyl, tert-butoxycarbonyl), (iii) a $C_{1-6}$ alkyl group optionally having 1 to 3 halogen atoms (e.g., methyl, trifluoromethyl), (iv) a carboxy group, (v) a carbamoyl group, (vi) a cyano group and (vii) a halogen atom,
(7) an acyl group represented by the formula: —(C=O)—$R^{3''''}$ wherein $R^{3''''}$ is
(A) a $C_{1-6}$ alkyl group optionally having 1 to 3 substituents selected from
(a) a $C_{1-6}$ alkyl-carbonylamino group (e.g., acetylamino),
(b) a 5- to 7-membered aromatic or nonaromatic heterocyclic group (e.g., piperidyl, tetrazolyl, morpholinyl, imidazolyl etc.) containing, besides carbon atoms, 1 to 4 hetero atoms selected from an oxygen atom, a sulfur atom and a nitrogen atom, and optionally having 1 to 3 substituents selected from (i) an oxo group, (ii) a $C_{6-14}$ aryl group (e.g., phenyl) and (iii) a $C_{1-6}$ alkyl group (e.g., methyl),
(c) a hydroxy group,
(d) a $C_{1-6}$ alkoxy group (e.g., methoxy),
(e) a $C_{6-14}$ aryl-carbonylamino group (e.g., benzoylamino),
(f) a carbamoylamino group,
(g) a carbamoyl group,
(h) a di-$C_{1-6}$ alkylamino group (e.g., dimethylamino),
(i) a ($C_{1-6}$ alkyl)-($C_{1-6}$ alkyl-carbonyl)amino group (e.g., (acetyl)-(methyl)amino),
(j) a $C_{6-14}$ aryloxy group (e.g., phenoxy) optionally having a $C_{1-6}$ alkyl-carbonylamino group (e.g., acetylamino),
(k) a heterocyclyl-oxy group (e.g., piperidinyloxy) optionally having a $C_{6-14}$ aryl-carbonyl group (e.g., benzoyl), and
(l) a $C_{1-6}$ alkylsulfonyl group (e.g., methylsulfonyl),
(B) a $C_{3-10}$ cycloalkyl group (e.g., cyclopropyl, cyclohexyl, tricyclodecyl) optionally having 1 to 3 substituents selected from
(a) a halogen atom,
(b) a $C_{1-6}$ alkyl-carbonylamino group (e.g., acetylamino),
(c) a $C_{6-14}$ aryl-carbonylamino group (e.g., benzoylamino),
(d) a $C_{1-6}$ alkyl-carbonyl group (e.g., acetyl), (e) a $C_{1-6}$ alkoxy-carbonylamino group (e.g., tert-butoxycarbonylamino),
(f) an amino group,
(g) a carbamoyl group,
(h) a $C_{1-6}$ alkoxy-carbonyl group (e.g., tert-butoxycarbonyl), and
(i) a $C_{1-6}$ alkyl group,
(C) a heterocyclic group (e.g., pyrrolyl, morpholinyl, piperidinyl, piperazinyl, pyrrolidinyl etc.) optionally having 1 to 3 substituents selected from
(a) a $C_{7-14}$ aralkyl group (e.g., benzyl),
(b) an oxo group,
(c) a $C_{1-6}$ alkyl-carbonyl group (e.g., propionyl, isobutyryl, acetyl etc.) optionally having 1 to 3 substituents selected from
(i) a hydroxy group, (ii) a cyano group and (iii) a halogen atom,
(d) an amino group,
(e) a $C_{1-6}$ alkyl-carbonylamino group (e.g., acetylamino),
(f) a di-$C_{1-6}$ alkylamino group (e.g., dimethylamino) optionally having a heterocyclic group (e.g., isoxazolyl) optionally having 1 to 3 $C_{1-6}$ alkyl groups (e.g., ethyl),
(g) a $C_{1-6}$ alkyl group (e.g., methyl) optionally having 1 to 3 substituents selected from (i) a hydroxy group, (ii) a heterocyclic group (e.g., 2-pyridyl), (iii) a $C_{1-6}$ alkyl-carbonyl group (e.g., acetyl) and (iv) a halogen atom,
(h) a $C_{3-10}$ cycloalkyl group (e.g., cyclopropyl),
(i) a carbamoyl group,
(j) a mono-$C_{1-6}$ alkyl-carbamoyl group,
(k) a $C_{3-6}$ cycloalkyl-carbamoyl group,
(l) a carbamoyl-carbonyl group,
(m) a $C_{1-6}$ alkoxy-carbonyl group (e.g., methoxycarbonyl),
(n) a heterocyclic group (e.g., pyrimidinyl, piperidinyl) optionally having (i) a halogen atom or (ii) a $C_{1-6}$ alkyl group (e.g., methyl),
(o) a $C_{6-14}$ aryl group (e.g., phenyl) optionally having a $C_{1-6}$ alkyl group (e.g., methyl),
(p) a $C_{6-14}$ aryl-carbonyl group (e.g., benzoyl) optionally having 1 to 3 substituents selected from (i) a $C_{1-6}$ alkoxy group (e.g., methoxy), (ii) a cyano group, (iii) a $C_{6-14}$ aryl group and (iv) a halogen atom,
(q) a $C_{6-14}$ aryl-carbonylamino group,
(r) a heterocyclyl-amino group (e.g., piperidinylamino) optionally having a $C_{1-6}$ alkyl-carbonyl group (e.g., acetyl),
(s) a heterocyclyl-carbonyl group (e.g., pyridylcarbonyl, N-oxidopyridylcarbonyl),
(t) a formyl group,
(u) a $C_{3-6}$ cycloalkyl-carbonyl group (e.g., cyclopropylcarbonyl) optionally having a hydroxy group, and
(v) a $C_{1-6}$ alkyl-sulfonyl group (e.g., methylsulfonyl), or
(D) a $C_{1-6}$ alkylidene group (e.g., methylidene) optionally having a heterocyclic group (e.g., piperidinyl) optionally having a $C_{1-6}$ alkoxy-carbonyl group (e.g., tert-butoxycarbonyl), or
(8) an acyl group represented by the formula: —(C=O)—OR$^{3''''}$ wherein R$^{3''''}$ is a $C_{1-6}$ alkyl group (e.g., tert-butyl).
(Explanation of $R^2$)
In the aforementioned formula (I), $R^2$ is an optionally halogenated $C_{1-6}$ alkyl group.
Examples of the "optionally halogenated $C_{1-6}$ alkyl group" for $R^2$ include a $C_{1-6}$ alkyl group optionally having 1 to 5 (preferably 1 to 3) halogen atoms (e.g., fluorine, chlorine, bromine, iodine etc.) (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl etc.) and the like.

$R^2$ is preferably a $C_{1-6}$ alkyl group, more preferably a $C_{1-4}$ alkyl group, and particularly preferably a methyl group.
When $R^2$ is a $C_{1-6}$ alkyl group, a compound having a high NK-1 receptor antagonistic activity, NK-2 receptor antagonistic activity, NK-3 receptor antagonistic activity, NK-1 receptor and NK-2 receptor antagonistic activity, NK-1 receptor and NK-3 receptor antagonistic activity, NK-2 receptor and NK-3 receptor antagonistic activity, or NK-1 receptor and NK-2 receptor and NK-3 receptor antagonistic activity is obtained.

As compound (I), the following compounds are preferably used.
[Compound (I)-1]
Compound (I) wherein ring A is any of the rings represented by

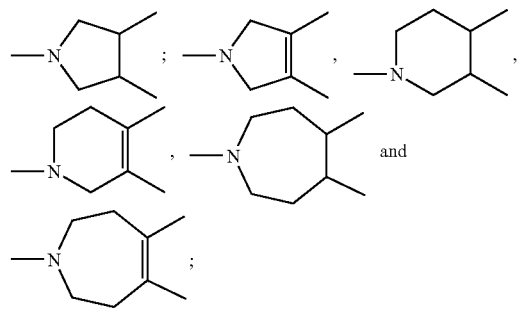

ring B is a phenyl group optionally having 1 to 3 substituents selected from a $C_{1-6}$ alkyl group (e.g., methyl) optionally having 1 to 3 halogen atoms and a halogen atom (e.g., fluorine, chlorine), more preferably a phenyl group optionally substituted by the above-mentioned substituent(s) at the 3-position and/or the 4-position,
ring C is a phenyl group, a pyrrolyl group, a thienyl group, a furyl group, a pyrazolyl group, an indolyl group, a benzimidazolyl group or a pyridyl group, each optionally having 1 to 3 substituents selected from
(1) a $C_{1-6}$ alkyl group optionally having 1 to 3 halogen atoms (e.g., fluorine) (e.g., methyl, isopropyl, tert-butyl, trifluoromethyl),
(2) a halogen atom (e.g., fluorine, chlorine, bromine),
(3) a $C_{1-6}$ alkoxy group (e.g., methoxy) optionally having 1 to 3 halogen atoms (e.g., fluorine),
(4) a cyano group,
(5) a di-$C_{1-6}$ alkylamino group (e.g., dimethylamino),
(6) a $C_{3-8}$ cycloalkyl group (e.g., cyclopentyl, cyclohexyl) optionally having 1 to 3 halogen atoms,
(7) a $C_{6-14}$ aryl group (e.g., phenyl) optionally having a $C_{1-6}$ alkoxy group (e.g., methoxy),
(8) a 5- to 10-membered aromatic heterocyclic group (e.g., pyrazolyl) containing, besides carbon atoms, 1 to 4 hetero atoms of one or two kinds selected from a nitrogen atom, a sulfur atom and an oxygen atom, and optionally having a $C_{1-6}$ alkyl group (e.g., methyl),
$R^1$ is
(1) a hydrogen atom,
(2) a 5- to 7-membered aromatic or nonaromatic heterocyclic group (e.g., piperidyl) containing, besides carbon atoms, 1 to 4 hetero atoms selected from an oxygen atom, a sulfur atom and a nitrogen atom, and optionally having 1 to 3 substituents selected from a $C_{1-6}$ alkyl-carbonyl group (e.g., acetyl) and a $C_{1-6}$ alkoxy-carbonyl group (e.g., tert-butoxycarbonyl), or (3) an acyl group represented by the formula: —(C=O)—R³'
wherein R³' is
(a) a $C_{1-6}$ alkoxy group (e.g., tert-butoxy),
(b) a $C_{1-6}$ alkyl group (e.g., methyl) optionally having substituent(s) selected from a $C_{1-6}$ alkoxy group (e.g., methoxy) and a $C_{1-6}$ alkyl-carbonylamino group (e.g., acetylamino),
(c) a 5- to 7-membered aromatic or nonaromatic heterocyclic group (e.g., piperidyl) containing, besides carbon atoms, 1 to 4 hetero atoms selected from an oxygen atom, a sulfur atom and a nitrogen atom, and optionally having 1 to 3 substituents selected from an oxo group, a $C_{1-6}$ alkyl-carbonyl group (e.g., acetyl) and a $C_{1-6}$ alkoxy-carbonyl group (e.g., tert-butoxycarbonyl), or
(d) a $C_{3-8}$ cycloalkyl group (e.g., cyclohexyl) optionally having a $C_{1-6}$ alkyl-carbonylamino group (e.g., acetylamino), and
$R^2$ is a $C_{1-6}$ alkyl group (e.g., methyl).

[Compound (I)-2]
Compound (I) wherein
ring A is a ring represented by

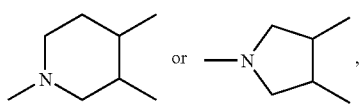

ring B is a phenyl group optionally having 1 to 3 substituents selected from a $C_{1-6}$ alkyl group (e.g., methyl) optionally having 1 to 3 halogen atoms and a halogen atom (e.g., fluorine, chlorine), more preferably a phenyl group optionally substituted by the above-mentioned substituent(s) at the 3-position and/or the 4-position,
ring C is a phenyl group optionally having substituent(s) selected from
(1) $C_{1-6}$ alkyl group optionally having 1 to 3 halogen atoms (e.g., fluorine) (e.g., methyl, isopropyl, tert-butyl, trifluoromethyl),
(2) a halogen atom (e.g., fluorine, chlorine, bromine),
(3) a $C_{1-6}$ alkoxy group (e.g., methoxy) optionally having 1 to 3 halogen atoms (e.g., fluorine),
(4) a cyano group,
(5) a di-$C_{1-6}$ alkylamino group (e.g., dimethylamino),
(6) a $C_{3-8}$ cycloalkyl group (e.g., cyclopentyl, cyclohexyl),
(7) a $C_{6-14}$ aryl group (e.g., phenyl), and
(8) a 5-10-membered aromatic heterocyclic group (e.g., pyrazolyl) containing, besides carbon atoms, 1 to 4 hetero atoms of one or two kinds selected from a nitrogen atom, a sulfur atom and an oxygen atom, and optionally having a $C_{1-6}$ alkyl group (e.g., methyl),
$R^1$ is an acyl group represented by the formula: —(C=O)—R³'' wherein R³'' is a 5- to 7-membered aromatic or nonaromatic heterocyclic group (e.g., piperidyl) containing, besides carbon atoms, 1 to 4 hetero atoms selected from an oxygen atom, a sulfur atom and a nitrogen atom, and optionally having 1 to 3 substituents selected from an oxo group, a $C_{1-6}$ alkyl-carbonyl group (e.g., acetyl) and a $C_{1-6}$ alkoxy-carbonyl group (e.g., tert-butoxycarbonyl), and
$R^2$ is a $C_{1-6}$ alkyl group (e.g., methyl).

[Compound (I)-3]
Compound (I) wherein
ring A is a ring represented by

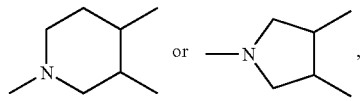

ring B is a phenyl group optionally having 1 to 3 substituents selected from a $C_{1-6}$ alkyl group (e.g., methyl) optionally having 1 to 3 halogen atoms and a halogen atom (e.g., fluorine, chlorine), more preferably a phenyl group optionally substituted by the above-mentioned substituent(s) at the 3-position and/or the 4-position,
ring C is a phenyl group optionally having 1 to 3 substituents selected from
(1) a $C_{1-6}$ alkyl group optionally having 1 to 3 halogen atoms (e.g., fluorine) (e.g., trifluoromethyl),
(2) a halogen atom (e.g., fluorine, chlorine, bromine),
(3) a $C_{1-6}$ alkoxy group (e.g., methoxy) optionally having 1 to 3 halogen atoms (e.g., fluorine),
(4) a cyano group,
(5) a di-$C_{1-6}$ alkylamino group (e.g., dimethylamino) optionally having a $C_{1-6}$ alkoxy group,
(6) an amino group optionally having a $C_{1-6}$ alkyl-carbonyl group or a heterocyclic group (e.g., morpholinyl), and
(7) a 5-10-membered heterocyclic group (e.g., pyrazolyl, morpholinyl, tetrazolyl, pyrrolidinyl, tetrahydropyrazinyl) containing, besides carbon atoms, 1 to 4 hetero atoms of one or two kinds selected from a nitrogen atom, a sulfur atom and an oxygen atom, and optionally having 1 to 3 substituents selected from (i) a $C_{1-6}$ alkyl group optionally having 1 to 3 halogen atoms (e.g., trifluoromethyl) and (ii) a $C_{1-6}$ alkoxy group (e.g., methoxy),
and more preferably, when one substituent selected from the above-mentioned substituents is present, it is a 4-substituted phenyl, and when two substituents selected from the above-mentioned substituents are present, it is a 3,5- or 2,5-disubstituted phenyl group,
$R^1$ is an acyl group represented by the formula: —(C=O)—R³'''' wherein R³'''' is a 5- to 7-membered aromatic or nonaromatic heterocyclic group (e.g., piperidyl, tetrahydropyranyl) containing, besides carbon atoms, 1 to 4 hetero atoms selected from an oxygen atom, a sulfur atom and a nitrogen atom, and optionally having 1 to 3 substituents selected from (i) a $C_{1-6}$ alkyl-carbonyl group (e.g., acetyl) optionally having a hydroxy group, (ii) a $C_{3-6}$ cycloalkyl-carbonyl group optionally having a hydroxy group, (iii) a $C_{1-6}$ alkoxy-carbonyl group (e.g., tert-butoxycarbonyl) and (iv) an amino group, and
$R^2$ is a $C_{1-6}$ alkyl group (e.g., methyl).

[Compound (I)-4]
Compound (I) wherein
ring A is a ring represented by

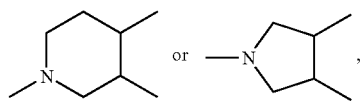

ring B is a phenyl group optionally having 1 to 3 substituents selected from
(1) a $C_{1-6}$ alkyl group optionally having 1 to 3 halogen atoms,
(2) a halogen atom,
(3) a $C_{1-6}$ alkoxy group optionally having 1 to 3 halogen atoms,
(4) a $C_{1-6}$ alkoxy-carbonyl group, (5) a carboxy group,
(6) a $C_{6-14}$ aryl group and
(7) a $C_{3-8}$ cycloalkyl group optionally having 1 to 3 halogen atoms,
ring C is
(1) a 3,5-bis(trifluoromethyl)phenyl group,
(2) a 3-halo-5-trifluoromethylphenyl group,
(3) a 2-methoxy-5-(5-(trifluoromethyl)-1H-tetrazol-1-yl)phenyl group or
(4) a phenyl group,
$R^1$ is a hydrogen atom, an acyl group, an alkyl group optionally having substituent(s), a cycloalkenyl group optionally having substituent(s), an aryl group optionally having substituent(s), an amino group optionally having substituent(s), a piperidyl group optionally having substituent(s), a pyridyl group optionally having substituent(s) or a pyrrolopyrimidinyl group optionally having substituent(s), and
$R^2$ is a $C_{1-6}$ alkyl group (e.g., methyl).

Compound (I)-4 shows a good NK-1 receptor antagonistic activity.

[Compound (I)-5]
Compound (I) wherein
ring A is a ring represented by

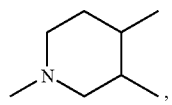

ring B is a phenyl group optionally having 1 to 3 substituents selected from a $C_{1-6}$ alkyl group (e.g., methyl) optionally having 1 to 3 halogen atoms and a halogen atom (e.g., fluorine, chlorine), more preferably a phenyl group optionally substituted by the above-mentioned substituent(s) at the 3-position and/or the 4-position,
ring C is a phenyl group, a pyridyl group or a benzothienyl group, each optionally having 1 to 3 substituents selected from
(1) a $C_{1-6}$ alkyl group optionally having 1 to 3 substituents selected from (i) a halogen atom (e.g., fluorine) or (ii) a 3- to 14-membered heterocyclic group (e.g., trifluoromethyl, tert-butyl, ethyl, morpholinomethyl), preferably a $C_{1-6}$ alkyl group optionally having 1 to 3 halogen atoms (e.g., fluorine),
(2) a halogen atom (e.g., fluorine, chlorine, bromine),
(3) a $C_{1-6}$ alkoxy group optionally having 1 to 3 halogen atoms (e.g., fluorine) (e.g., methoxy, difluoromethoxy),
(4) a cyano group,
(5) a di-$C_{1-6}$ alkylamino group (e.g., dimethylamino) optionally having a $C_{1-6}$ alkoxy group,
(6) a $C_{3-8}$ cycloalkyl group (e.g., cyclohexyl),
(7) an amino group optionally having a $C_{1-6}$ alkyl-carbonyl group (e.g., acetyl) or a heterocyclic group (e.g., morpholinyl, piperazinyl, pyrrolidinyl, dioxothiomorpholinyl, piperidinyl, oxopyrrolidinyl),
(8) a 5- to 10-membered heterocyclic group (e.g., pyrazolyl, morpholinyl, tetrazolyl, pyrrolidinyl, tetrahydropyrazinyl, piperazinyl, dioxothiomorpholinyl, piperidinyl, oxopyrrolidinyl) containing, besides carbon atoms, 1 to 4 hetero atoms of one or two kinds selected from a nitrogen atom, a sulfur atom and an oxygen atom, and optionally having 1 to 3 substituents selected from (i) a $C_{1-6}$ alkyl group optionally having 1 to 3 halogen atoms (e.g., trifluoromethyl), (ii) a $C_{1-6}$ alkoxy group (e.g., methoxy) and (iii) an oxo group,
(9) a carbamoyl group, and
(10) a mono-$C_{1-6}$ alkyl-carbamoyl group (e.g., methylcarbamoyl, ethylcarbamoyl),
(11) a di-$C_{1-6}$ alkyl-carbamoyl group (e.g., dimethylcarbamoyl, diethylcarbamoyl, ethylmethylcarbamoyl), and
(12) a $C_{1-6}$ alkyl-carbonyl group (e.g., acetyl), (preferably above-mentioned (1)-(9)), particularly, ring C is a phenyl group, and, when one substituent selected from the above-mentioned substituents is present, it is a 4-substituted phenyl, when ring C is a phenyl group and has two substituents selected from the above-mentioned substituents, it is a 3,5- or 2,5-disubstituted phenyl group,
$R^1$ is a hydrogen atom, an acyl group, an alkyl group optionally having substituent(s), a cycloalkenyl group optionally having substituent(s), an aryl group optionally having substituent(s), an amino group optionally having substituent(s), a piperidyl group optionally having substituent(s), a pyridyl group optionally having substituent(s) or a pyrrolopyrimidinyl group optionally having substituent(s), and
$R^2$ is a $C_{1-6}$ alkyl group (e.g., methyl).

Compound (I)-5 shows a good NK-2 receptor antagonistic activity.

In compound (I)-4 and compound (I)-5, $R^1$ is preferably
(1) a hydrogen atom,
(2) a $C_{1-6}$ alkyl group optionally having 1 to 3 substituents selected from (i) a heterocyclic group (e.g., piperidyl) optionally having 1 to 3 substituents selected from (a) an oxo group, (b) a $C_{1-6}$ alkoxy-carbonyl group and (c) a $C_{1-6}$ alkyl-carbonyl group, (ii) a $C_{6-14}$ aryl group and (iii) a halogen atom,
(3) a $C_{3-6}$ cycloalkenyl group optionally having an oxo group or a methyl group,
(4) a $C_{6-14}$ aryl group optionally having a $C_{1-6}$ alkoxy-carbonyl group,
(5) an amino group optionally having 1 or 2 substituents selected from (i) a $C_{1-6}$ alkyl group, (ii) a heterocyclic group (e.g., piperidyl, pyridyl) optionally having a $C_{1-6}$ alkyl-carbonyl group or a halogen atom, (iii) an oxo group, (iv) a $C_{1-6}$ alkyl-carbonyl-heterocyclyl-carbonyl group (e.g., acetylpiperidylcarbonyl) and (v) a $C_{1-6}$ alkylidene group optionally having a heterocyclic group (e.g., imidazolyl) optionally having a $C_{1-6}$ alkyl group,
(6) a piperidyl group, a pyridyl group or a pyrrolopyrimidinyl group each optionally having 1 to 3 substituents selected from (i) a $C_{1-6}$ alkyl-carbonyl group (e.g., acetyl), (ii) a $C_{1-6}$ alkoxy-carbonyl group (e.g., methoxycarbonyl, ethoxycarbonyl, tert-butoxycarbonyl), (iii) a $C_{1-6}$ alkyl group optionally having 1 to 3 halogen atoms (e.g., methyl, trifluoromethyl), (iv) a carboxy group, (v) a carbamoyl group, (vi) a cyano group and (vii) a halogen atom,
(7) an acyl group represented by the formula: —(C=O)—$R^{3'''}$ wherein $R^{3'''}$ is
(A) a $C_{1-6}$ alkyl group optionally having 1 to 3 substituents selected from
(a) a $C_{1-6}$ alkyl-carbonylamino group (e.g., acetylamino),
(b) a 5- to 7-membered aromatic or nonaromatic heterocyclic group (e.g., piperidyl, tetrazolyl, morpholinyl, imidazolyl etc.) containing, besides carbon atoms, 1 to 4 hetero atoms selected from an oxygen atom, a sulfur atom and a nitrogen atom, and optionally having 1 to 3 substituents selected from (i) an oxo group, (ii) a $C_{6-14}$ aryl group (e.g., phenyl) and (iii) a $C_{1-6}$ alkyl group (e.g., methyl),
(c) a hydroxy group,
(d) a $C_{1-6}$ alkoxy group (e.g., methoxy),
(e) a $C_{6-14}$ aryl-carbonylamino group (e.g., benzoylamino),
(f) a carbamoylamino group,
(g) a carbamoyl group,
(h) a di-$C_{1-6}$ alkylamino group (e.g., dimethylamino), (i) a ($C_{1-6}$ alkyl)-($C_{1-6}$ alkyl-carbonyl)amino group (e.g., (acetyl)-(methyl)amino),
(j) a $C_{6-14}$ aryloxy group (e.g., phenoxy) optionally having a $C_{1-6}$ alkyl-carbonylamino group (e.g., acetylamino),
(k) a heterocyclyl-oxy group (e.g., piperidinyloxy) optionally having a $C_{6-14}$ aryl-carbonyl group (e.g., benzoyl), and
(l) a $C_{1-6}$ alkylsulfonyl group (e.g., methylsulfonyl),
(B) a $C_{3-10}$ cycloalkyl group (e.g., cyclopropyl, cyclohexyl, tricyclodecyl) optionally having 1 to 3 substituents selected from
(a) a halogen atom,
(b) a $C_{1-6}$ alkyl-carbonylamino group (e.g., acetylamino),
(c) a $C_{6-14}$ aryl-carbonylamino group (e.g., benzoylamino),
(d) a $C_{1-6}$ alkyl-carbonyl group (e.g., acetyl),
(e) a $C_{1-6}$ alkoxy-carbonylamino group (e.g., tert-butoxycarbonylamino),
(f) an amino group,
(g) a carbamoyl group,
(h) a $C_{1-6}$ alkoxy-carbonyl group (e.g., tert-butoxycarbonyl), and
(i) a $C_{1-6}$ alkyl group,
(C) a heterocyclic group (e.g., pyrrolyl, morpholinyl, piperidinyl, piperazinyl, pyrrolidinyl etc.) optionally having 1 to 3 substituents selected from
(a) a $C_{7-14}$ aralkyl group (e.g., benzyl),
(b) an oxo group,
(c) a $C_{1-6}$ alkyl-carbonyl group (e.g., propionyl, isobutyryl, acetyl etc.) optionally having 1 to 3 substituents selected from (i) a hydroxy group, (ii) a cyano group and (iii) a halogen atom,
(d) an amino group,
(e) a $C_{1-6}$ alkyl-carbonylamino group (e.g., acetylamino),
(f) a di-$C_{1-6}$ alkylamino group (e.g., dimethylamino) optionally having a heterocyclic group (e.g., isoxazolyl) optionally having 1 to 3 $C_{1-6}$ alkyl groups (e.g., ethyl),
(g) a $C_{1-6}$ alkyl group (e.g., methyl) optionally having 1 to 3 substituents selected from (i) a hydroxy group, (ii) a heterocyclic group (e.g., 2-pyridyl), (iii) a $C_{1-6}$ alkyl-carbonyl group (e.g., acetyl) and (iv) a halogen atom,
(h) a $C_{3-10}$ cycloalkyl group (e.g., cyclopropyl),
(i) a carbamoyl group,
(j) a mono-$C_{1-6}$ alkyl-carbamoyl group,
(k) a $C_{3-6}$ cycloalkyl-carbamoyl group,
(l) a carbamoyl-carbonyl group,
(m) a $C_{1-6}$ alkoxy-carbonyl group (e.g., methoxycarbonyl),
(n) a heterocyclic group (e.g., pyrimidinyl, piperidinyl) optionally having (i) a halogen atom or (ii) a $C_{1-6}$ alkyl group (e.g., methyl),
(o) a $C_{6-14}$ aryl group (e.g., phenyl) optionally having a $C_{1-6}$ alkyl group (e.g., methyl),
(p) a $C_{6-14}$ aryl-carbonyl group (e.g., benzoyl) optionally having 1 to 3 substituents selected from (i) a $C_{1-6}$ alkoxy group (e.g., methoxy), (ii) cyano group, (iii) a $C_{6-14}$ aryl group and (iv) a halogen atom,
(q) a $C_{6-14}$ aryl-carbonylamino group,
(r) a heterocyclyl-amino group (e.g., piperidinylamino) optionally having a $C_{1-6}$ alkyl-carbonyl group (e.g., acetyl),
(s) a heterocyclyl-carbonyl group (e.g., pyridylcarbonyl, N-oxidopyridylcarbonyl),
(t) a formyl group,
(u) a $C_{3-6}$ cycloalkyl-carbonyl group (e.g., cyclopropylcarbonyl) optionally having a hydroxy group, and
(v) a $C_{1-6}$ alkyl-sulfonyl group (e.g., methylsulfonyl), or
(D) a $C_{1-6}$ alkylidene group (e.g., methylidene) optionally having a heterocyclic group (e.g., piperidinyl) optionally having a $C_{1-6}$ alkoxy-carbonyl group (e.g., tert-butoxycarbonyl), or (8) an acyl group represented by the formula: —(C=O)—$OR^{3''''}$ wherein $R^{3''''}$ is a $C_{1-6}$ alkyl group (e.g., tert-butyl).

As compound (I), for example, the following compounds are particularly preferable:

N-[(3R,4R)-1-[(1-acetylpiperidin-4-yl)carbonyl]-3-(3,4-dichlorophenyl)piperidin-4-yl]-N-methyl-3,5-bis(trifluoromethyl)benzamide;

N-[(3R,4R)-1-[(1-acetylpiperidin-4-yl)carbonyl]-3-(3,4-dichlorophenyl)piperidin-4-yl]-4-chloro-N-methylbenzamide;

N-[(3R,4R)-1-[(1-acetylpiperidin-4-yl)carbonyl]-3-(3,4-dichlorophenyl)piperidin-4-yl]-4-methoxy-N-methylbenzamide;

N-[(3R,4R)-1-[(1-acetylpiperidin-4-yl)carbonyl]-3-(3,4-dichlorophenyl)piperidin-4-yl]-N-methyl-4-(trifluoromethyl)benzamide;

N-[(3R,4R)-1-[(1-acetylpiperidin-4-yl)carbonyl]-3-(3,4-dichlorophenyl)piperidin-4-yl]-N-methyl-4-morpholin-4-ylbenzamide or a salt thereof;

N-[(3R,4R)-1-[(1-acetylpiperidin-4-yl)carbonyl]-3-(3,4-dichlorophenyl)piperidin-4-yl]-4-cyclopropyl-N-methylbenzamide;

N-[(3R,4R)-1-[(1-acetylpiperidin-4-yl)carbonyl]-3-(3,4-dichlorophenyl)piperidin-4-yl]-5-bromo-N-methylpyridine-2-carboxamide;

4-chloro-N-[(3R,4R)-3-(3,4-dichlorophenyl)-1-{[1-(hydroxyacetyl)piperidin-4-yl]carbonyl}piperidin-4-yl]-N-methylbenzamide or a salt thereof;

N-[(3R,4R)-1-[(1-acetylpiperidin-4-yl)methyl]-3-(3,4-dichlorophenyl)piperidin-4-yl]-4-chloro-N-methylbenzamide;

N-[(3R,4R)-3-(3,4-dichlorophenyl)-1-({1-[(1-hydroxycyclopropyl)carbonyl]piperidin-4-yl}carbonyl)piperidin-4-yl]-N-methyl-4-morpholin-4-ylbenzamide or a salt thereof;

N-[(3R,4R)-1-{[(3S,4S)-3-aminotetrahydro-2H-pyran-4-yl]carbonyl}-3-(3,4-dichlorophenyl)piperidin-4-yl]-N-methyl-4-morpholin-4-ylbenzamide or a salt thereof;

N-[(3R,4R)-3-(3,4-dichlorophenyl)-1-{[1-(hydroxyacetyl)piperidin-4-yl]carbonyl}piperidin-4-yl]-N-methyl-4-(trifluoromethyl)benzamide or a salt thereof;

4-bromo-N-[(3R,4R)-3-(3,4-dichlorophenyl)-1-{[1-(hydroxyacetyl)piperidin-4-yl]carbonyl}piperidin-4-yl]-N-methylbenzamide or a salt thereof;

N-[(3R,4R)-3-(3,4-dichlorophenyl)-1-{[1-(hydroxyacetyl)piperidin-4-yl]carbonyl}piperidin-4-yl]-N-methyl-5-(trifluoromethyl)pyridine-2-carboxamide or a salt thereof.

A salt of compound (I) includes, for example, a metal salt, an ammonium salt, a salt with an organic base, a salt with an inorganic acid, a salt with an organic acid, a salt with basic or acidic amino acid, etc. Suitable examples of the metal salt include an alkali metal salt such as a sodium salt, a potassium salt, etc.; an alkaline earth metal salt such as a calcium salt, a magnesium salt, a barium salt, etc.; an aluminum salt, etc. Suitable examples of the salts with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Suitable examples of the salts with an inorganic acid include salts with hydrochloric acid, hydrobromic acid, nitric acid, sulfuric acid, phosphoric acid, etc. Suitable examples of the salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Suitable examples of the salts with basic amino acid include salts with arginine, lysine, ornithine, etc. Suitable examples of the salts with acidic amino acid include salts with aspartic acid and glutamic acid, etc.

Among these, pharmaceutically acceptable salts are preferred. For example, if the compound has acidic functional group, preferred are inorganic salts such as an alkali metal salt (e.g., sodium salt, potassium salt, etc.), an alkaline earth metal salt (e.g., calcium salt, magnesium salt, barium salt, etc.), an ammonium salt, etc. If the compound has a basic functional group, preferred are salts with an inorganic acid such as hydrochloric acid, hydrobromic acid, nitric acid, sulfuric acid, phosphoric acid, etc., or salts with an organic acid such as acetic acid, phthalic acid, fumaric acid, oxalic acid, tartaric acid, maleic acid, citric acid, succinic acid, methanesulfonic acid, p-toluenesulfonic acid, etc.

The prodrug of compound (I) or a salt thereof of the present invention means a compound which is converted to compound (I) of the present invention under the physiological condition in the living body by a reaction with an enzyme, a gastric acid, or the like, that is, by enzymatic oxidation, reduction, hydrolysis, etc.; by hydrolysis with gastric acid, etc.

The prodrug of compound (I) of the present invention includes a compound wherein an amino group of compound (I) is modified with acyl, alkyl or phosphoryl (e.g., a compound wherein an amino group of compound (I) of the present invention is modified with eicosanoyl, alanyl, pentylaminocarbonyl, (5-methyl-2-oxo-1,3-dioxolen-4-yl)methoxycarbonyl, tetrahydrofuryl, pyrrolidylmethyl, pivaloyloxymethyl or t-butyl, etc.); a compound wherein a hydroxyl group of compound (I) of the present invention is modified with acyl, alkyl, phosphoric acid or boric acid (e.g., a compound wherein a hydroxyl group of compound (I) is modified with acetyl, palmitoyl, propanoyl, pivaloyl, succinyl, fumaryl, alanyl or dimethylaminomethylcarbonyl, etc.); a compound wherein a carboxy group of compound (I) of the present invention is modified to ester or amide (e.g., a compound wherein a carboxy group of compound (I) of the present invention is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These prodrugs can be produced from compound (I) of the present invention by a method known per se.

In addition, the prodrug of compound (I) of the present invention may be a compound, which is converted into compound (I) of the present invention under the physiological conditions, as described in "Pharmaceutical Research and Development", Vol. 7 (Drug Design), pp. 163-198 (1990), published by Hirokawa Publishing Co.

The present invention encompasses a solvate (e.g., hydrate) of compound (I) or a salt thereof. Compound (I) may be labeled with an isotope (e.g., $^3H$, $^{14}C$, $^{35}S$, $^{125}I$, etc.) and the like. Compound (I) may also be a deuterated compound.

When compound (I) has chiral center, isomers such as an enantiomer or a diastereomer may exist. Such isomers and a mixture thereof are all included in the scope of the present invention. In addition, there can be instances where the isomers by conformation are generated in cases, but such isomers or a mixture thereof are also included in compound (I) or a salt thereof.

For the NK receptor antagonistic activity of compound (I), an optically active compound represented by the formula

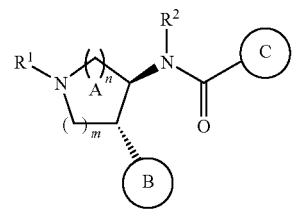

wherein each symbol is as defined above, is preferable.

Compound (I) wherein m=1 and n=2 is preferably an optically active compound of the above-mentioned [1] represented by the formula

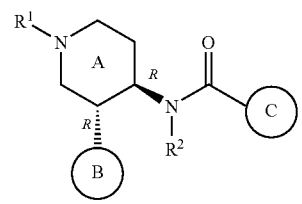

wherein each symbol is as defined above.

Compound (I) wherein m=1 and n=1 is preferably an optically active compound of the above-mentioned [1] represented by the formula

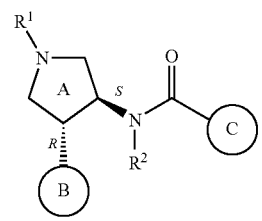

wherein each symbol is as defined above.

The production method of compound (I) or a salt thereof of the present invention is explained in the following.

The intermediates produced in the following production methods may be isolated and purified by column chromatography, recrystallization, distillation and the like, or may be used as they are for the next step without isolation. In the following explanation of the production methods, a compound represented by the formula (II) is referred to as, for example, compound (II).

Compound (I) or a salt thereof of the present invention can be produced according to the following Method A or Method B.

[Method A]

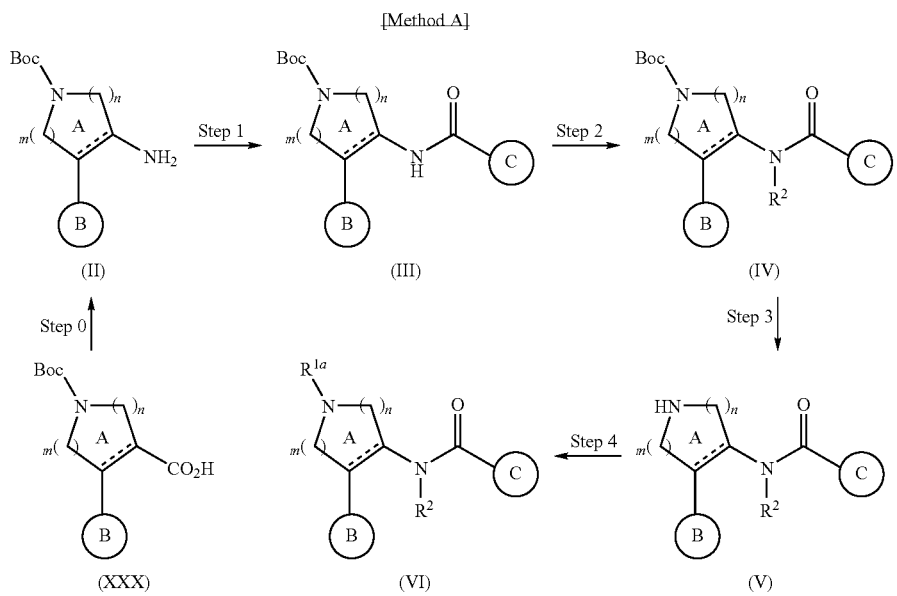

wherein $R^{1a}$ is a hydrocarbon group optionally having substituent(s), an acyl group (excluding tert-butoxycarbonyl group) or a heterocyclic group optionally having substituent(s), Boc is a tert-butoxycarbonyl group, and the other symbols are as defined above.

(Step 0)

This step is a step of subjecting compound (XXX) to rearrangement reaction (Step 0-1), and then hydrolysis (Step 0-2) to convert compound (XXX) to compound (II).

(Step 0-1)

This step can be performed according to a method known per se (e.g., the methods described in "4th Ed. Jikken Kagaku Koza (Courses in Experimental Chemistry) 20, Organic Synthesis II", The Chemical Society of Japan Ed., 1991 and the like, or a method analogous thereto).

Examples of the rearrangement reaction include Hofmann rearrangement reaction, Schmidt rearrangement reaction, Curtius rearrangement reaction and the like. While the rearrangement reaction varies depending on compound (XXX), generally, it is preferably the Curtius rearrangement reaction.

The Curtius rearrangement reaction is generally carried out by reacting compound (XXX) with an azidating agent in a solvent that does not adversely influence the reaction in the presence of a base, and heating.

Examples of the base include inorganic bases (alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate and the like; alkoxides such as sodium methoxide, sodium ethoxide and the like, and the like), organic bases (amines such as trimethylamine, triethylamine, diisopropylethylamine and the like; aromatic amines such as pyridine, 4-dimethylaminopyridine and the like; and the like) and the like. Of these, organic bases (triethylamine, diisopropylethylamine and the like) and the like are preferable. While the amount of the base to be used varies depending on the kind of the solvent and the other reaction conditions, it is generally about 1 to 10 molar equivalents, preferably about 1 to 5 molar equivalents, per 1 mol of compound (XXX).

Preferable examples of the azidating agent include diphenylphosphoryl azide (DPPA).

Examples of the solvent that does not adversely influence the reaction include hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), amides (N,N-dimethylformamide, N,N-dimethylacetamide and the like), sulfoxides (dimethyl sulfoxide and the like) and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (XXX), the reaction temperature and the like, it is, for example, about 0.5 to 24 hr, preferably about 0.5 to 2 hr.

(Step 0-2)

The hydrolysis can be carried out according to a method known per se, for example, in the presence of a base, as necessary in a solvent that does not adversely influence the reaction.

Examples of the base include inorganic bases (alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate and the like; alkoxides such as sodium methoxide, sodium ethoxide and the like, and the like), organic bases (amines such as trimethylamine, triethylamine, diisopropylethylamine and the like; aromatic amines such as pyridine, 4-dimethylaminopyridine and the like; and the like) and the like. Of these, lithium hydroxide, sodium hydroxide, potassium hydroxide and the like are preferable. While the amount of the base to be used varies depending on the kind of the solvent and the other reaction conditions, it is generally about 1 to 100 molar equivalents, preferably about 1 to 20 molar equivalents, per 1 mol of compound (XXX).

Examples of the solvent that does not adversely influence the reaction include hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), amides (N,N-dimethylformamide, N,N-dimethylacetamide and the like), sulfoxides (dimethyl sulfoxide and the like), water and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (XXX), the reaction temperature and the like, it is, for example, about 0.5 to 24 hr, preferably about 0.5 to 2 hr.
(Step 1)

This step is a step of reacting compound (II) or a salt thereof with a compound represented by the formula:

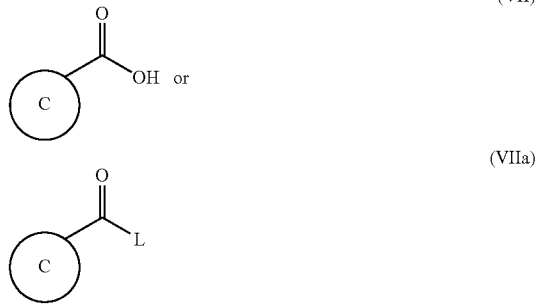

wherein L is a leaving group, and the other symbols are as defined above, or a salt thereof to produce compound (III) or a salt thereof. Examples of the leaving group for L include halogen atoms (a chlorine atom, a bromine atom, an iodine atom and the like), substituted sulfonyloxy groups ($C_{1-6}$ alkylsulfonyloxy groups such as methanesulfonyloxy, ethanesulfonyloxy and the like; $C_{6-14}$ arylsulfonyloxy groups such as benzenesulfonyloxy, p-toluenesulfonyloxy and the like; $C_{7-16}$ aralkylsulfonyloxy groups such as benzylsulfonyloxy group and the like; and the like), acyloxy groups (acetoxy, benzoyloxy and the like), hydroxy groups substituted by a heterocyclic group or an aryl group optionally having substituent(s) (succinimide, benzotriazole, quinoline, 4-nitrophenyl and the like), heterocyclic groups (imidazole and the like) and the like.

Compound (II) or a salt thereof can be produced according to the below-mentioned method or a known method. Compound (VII) or compound (VIIa) or a salt thereof may be a commercially available product, or can be produced according to a known method. The amount of compound (VII) or compound (VIIa) or a salt thereof to be used is about 1 to 10 molar equivalents, preferably about 1 to 2 molar equivalents, per 1 mol of compound (II).

This reaction can be carried out according to a method known per se (e.g., the methods described in "4th Ed. Jikken Kagaku Koza (Courses in Experimental Chemistry) 22, Organic Synthesis IV", The Chemical Society of Japan Ed., 1991 and the like, or a method analogous thereto). Examples thereof include a method using a condensing agent, a method via a reactive derivative, and the like.

Examples of the condensing agent used for the "method using a condensing agent" include dicyclohexylcarbodiimide, diisopropylcarbodiimide, N-ethyl-N'-3-dimethylaminopropylcarbodiimide and a hydrochloride thereof, benzotriazol-1-yl-tris(dimethylamino)phosphonium hexafluorophosphate, diphenylphosphoryl azide and the like. These may be used alone, or in combination with an additive (e.g., N-hydroxysuccinimide, 1-hydroxybenzotriazole or 3-hydroxy-4-oxo-3,4-dihydro-1,2,3-benzotriazine and the like). The amount of the condensing agent to be used is about 1 to 10 molar equivalents, preferably about 1 to 2 molar equivalents, per 1 mol of compound (II). The amount of the additive to be used is about 1 to 10 molar equivalents, preferably about 1 to 2 molar equivalents, per 1 mol of compound (II).

The above-mentioned reaction is generally carried out in a solvent that does not adversely influence the reaction, and may be promoted using a base. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), organic amines (pyridine and the like), water and the like. Such solvent may be used in a mixture of two or more at a suitable ratio. Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine and the like), organic amines (pyridine, picoline, N,N-dimethylaniline and the like) and the like. The amount of the base to be used is generally about 1 to 100 molar equivalents, preferably about 1 to 5 molar equivalents, per 1 mol of compound (II). The reaction temperature is generally about −80° C. to 150° C., preferably about 0° C. to 50° C. The reaction time is generally about 0.5 to 48 hr, preferably 0.5 to 16 hr.

The reactive derivative of the "method via a reactive derivative" is a compound represented by the formula (VIIa), and examples thereof include acid halides, acid anhydrides, mixed acid anhydrides, activated esters and the like. The conversion of compound (VII) to the reactive derivative (compound (VIIa)) can be carried out according to a method known per se. Examples of the conversion to an acid halide include a method using a halogenating agent (e.g., thionyl chloride, oxalyl chloride and the like), a method using a halide of phosphorus or phosphoric acid (e.g., phosphorus trichloride, phosphorus pentachloride and the like), and the like. While the above-mentioned reaction using a reactive derivative varied depending on the kind of the reactive derivative or compound (II), it is generally carried out in a solvent that does not adversely influence the reaction, and may be promoted using a base. The kind and amount of the solvent and base, the reaction temperature and the reaction time to be used for the reaction are the same as those described in the above-mentioned "method using a condensing agent".
(Step 2)

This step is a step of reacting compound (III) or a salt thereof with a compound represented by the formula:

wherein each symbol is as defined above, to produce compound (IV) or a salt thereof.

The amount of compound (VIII) to be used is, for example, about 1 to 5 molar equivalents, preferably about 1 to 3 molar equivalents, per 1 mol of compound (III).

This reaction can be generally carried out by reacting compound (VIII) in a solvent in the presence of a base. Examples of the solvent include ethers (dimethoxyethane, dioxane, tetrahydrofuran and the like), nitrites (acetonitrile and the like), amides (N,N-dimethylformamide and the like), sulfoxides (dimethyl sulfoxide and the like) and the like. Such solvent may be used in a mixture of two or more at a suitable ratio. Examples of the base include organic bases (trimethylamine, triethylamine, N-methylmorpholine, pyridine, picoline, N,N-dimethylaniline and the like), inorganic bases (sodium hydride, potassium hydride, potassium carbonate, sodium carbonate, potassium hydroxide, sodium hydroxide and the like) and the like. The amount of the base to be used is, for example, about 1 to 100 molar equivalents, preferably about 1 to 10 molar equivalents, per 1 mol of compound (III).

The reaction may be promoted using an additive as necessary. Examples of the additive include iodide salts (sodium iodide, potassium iodide and the like) and the like. The amount thereof is about 0.1 to 10 molar equivalents, preferably about 0.1 to 5 molar equivalents, per 1 mol of compound (VIII).

The reaction temperature is generally −10° C. to 200° C., preferably about 0° C. to 110° C. The reaction time is generally 0.5 to 48 hr, preferably 0.5 to 16 hr.

(Step 3)

This step is a step of subjecting compound (IV) or a salt thereof to deprotection to produce compound (V) or a salt thereof.

The deprotection can be carried out according to a known method (e.g., "Protective Groups in Organic Synthesis, 3$^{rd}$ Ed." by Theodora W. Greene, Peter G. M. Wuts, published by Wiley-Interscience, 1999). While the deprotection varies depending on, for example, the kind of compound (IV), it is generally in the presence of an acid, as necessary in a solvent that does not adversely influence the reaction.

Examples of the acid include mineral acids (hydrochloric acid, hydrobromic acid, sulfuric acid, hydrogen chloride etc.), carboxylic acids (acetic acid, trifluoroacetic acid, trichloroacetic acid, etc.), sulfonic acids (methanesulfonic acid, toluenesulfonic acid, etc.), Lewis acids (aluminum chloride, tin chloride, zinc bromide, etc.) and the like. If necessary, it may be used in a mixture of two or more. While the amount of the acid to be used varies depending on the kinds of the solvent and other reaction conditions, it is usually about 0.1 molar equivalents or more, per 1 mol of compound (IV), and it can be used as a solvent.

The solvent that does not adversely influence the reaction includes alcohols (methanol, ethanol, propanol, 2-propanol, butanol, isobutanol, t-butanol, etc.), aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), carboxylic acids (acetic acid, etc.), amides (N,N-dimethylformamide, etc.), sulfoxides (dimethyl sulfoxide, etc.), water and the like. Such solvent may be used in a mixture of two or more at a suitable ratio.

The reaction temperature is, for example, about −50° C. to 200° C., preferably about 0° C. to 100° C. While the reaction time varies depending on the kinds of compound (IV) or a salt thereof, the reaction temperature and the like, it is, for example, about 0.5 to 100 hr, preferably about 0.5 to 24 hr.

(Step 4)

This step is a step of subjecting compound (V) or a salt thereof to an "alkylation reaction", "acylation reaction", "arylation reaction", "enamine/imine formation reaction" or "amination reaction", or these reactions combined with "deprotection" or "hydrolysis", to produce compound (VI) or a salt thereof.

The above-mentioned "alkylation reaction" or "acylation reaction" is a step of (a) by subjecting compound (V) or a salt thereof and a compound represented by the formula:

$$R^{1a}\text{—OH} \tag{IX}$$

$$\text{or } R^{1a}\text{-L} \tag{IXa}$$

wherein each symbol is as defined above, or a salt thereof to an alkylation reaction or acylation reaction, (b) by reacting compound (V) or a salt thereof with an aldehyde or a ketone, and then subjecting the resulting imine or iminium ion to a reduction reaction, (c) by reacting compound (V) or a salt thereof with an isocyanic acid, or (d) by reacting a reactive derivative of compound (V) or a salt thereof with a compound represented by the formula:

$$R^{1a}\text{—H} \tag{IXc}$$

wherein each symbol is as defined above, or a salt thereof, to produce compound (VI) or a salt thereof.

This reaction can be carried out according to a method known per se. For example, the alkyl reaction can be generally carried out by reacting compound (V) or a salt thereof with compound (IXa) or a salt thereof in a solvent in the presence of a base, in the same manner as in the method described in Step 2 of Method A.

The acylation reaction can be generally carried out by reacting compound (V) or a salt thereof with compound (IX) or compound (IXa) or a salt thereof in a solvent in the presence of a base, in the same manner as in the method described in Step 1 of Method A.

When compound (V) or a salt thereof is reacted with an aldehyde or a ketone, the formation reaction of imine or iminium ion is carried out generally in a solvent that does not adversely influence the reaction. Examples of the solvent include aromatic hydrocarbons (toluene, xylene and the like), aliphatic hydrocarbons (heptane, hexane and the like), halogenated hydrocarbons (chloroform, dichloromethane and the like), ethers (diethyl ether, tetrahydrofuran, dioxane and the like), alcohols (methanol, ethanol, 2-propanol, butanol, benzyl alcohol and the like), nitriles (acetonitrile and the like), amides (N,N-dimethylformamide and the like), sulfoxides (dimethyl sulfoxide and the like) and the like. Such solvent may be used in a mixture of two or more at a suitable ratio. Examples of the aldehyde include formalin, aliphatic aldehydes (acetaldehyde and the like) optionally having substituent(s), aromatic aldehydes (benzaldehyde and the like) optionally having substituent(s) and the like. Examples of the ketone include aliphatic ketones (acetone, cyclohexanone, piperidone and the like) optionally having substituent(s), aromatic ketones (acetophenone, benzophenone and the like) optionally having substituent(s) and the like. The amount thereof is, for example, about 1 to 100 molar equivalents, preferably about 1 to 5 molar equivalents, per 1 mol of compound (V).

Where necessary, the reaction may be advantageously promoted using a catalyst. Examples of the catalyst include mineral acids (hydrochloric acid, hydrobromic acid, sulfuric acid and the like), carboxylic acids (formic acid, acetic acid, propionic acid, trifluoroacetic acid and the like), sulfonic acids (methanesulfonic acid, p-toluenesulfonic acid and the like), Lewis acids (aluminum chloride, zinc chloride, zinc bromide, boron trifluoride, titanium chloride and the like), acetates (sodium acetate, potassium acetate and the like), molecular sieves (molecular sieves 3A, 4A, 5A and the like) and the like. The amount of the catalyst to be used is, for example, about 0.01 to 50 molar equivalents, preferably about 0.1 to 10 molar equivalents, per 1 mol of compound (V).

The reaction temperature is generally about 0° C. to 200° C., preferably about 20° C. to 150° C. The reaction time is generally 0.5 to 48 hr, preferably 0.5 to 24 hr.

The reduction reaction of imine or iminium ion, can be carried out according to a method known per se, for example, a method using a metal hydride and a method by catalytic hydrogenation reaction.

Examples of the metal hydride as a reducing agent include metal hydrides (sodium borohydride, lithium borohydride, zinc borohydride, sodium cyanoborohydride, sodium triacetoxyborohydride, lithium cyanoborohydride, diisobutylaluminum hydride, aluminum hydride, lithium aluminum hydride and the like), borane complexes (borane-tetrahydrofuran complex, catecholborane and the like) and the like. Sodium borohydride, sodium cyanoborohydride, sodium triacetoxyborohydride and the like are preferable. The amount of the reducing agent to be used is, for example, about 1 to 50 molar equivalents, preferably about 1 to 10 molar equivalents, per 1 mol of compound (V). Examples of the solvent include aromatic hydrocarbons (toluene, xylene and the like), aliphatic hydrocarbons (heptane, hexane and the like), halogenated hydrocarbons (chloroform, dichloromethane and the like), ethers (diethyl ether, tetrahydrofuran, dioxane and the like), alcohols (methanol, ethanol, 2-propanol, butanol, benzyl alcohol and the like), nitriles (acetonitrile and the like), amides (N,N-dimethylformamide and the like), sulfoxides (dimethyl sulfoxide and the like) and the like. Such solvent may be used in a mixture of two or more at a suitable ratio. The reaction temperature is generally about –80° C. to 80° C., preferably about –40° C. to 40° C. The reaction time is generally 5 min to 48 hr, preferably 1 to 24 hr.

The catalytic hydrogenation reaction can be carried out in the presence of a catalyst under a hydrogen atmosphere. Examples of the catalyst include palladium compounds (palladium carbon, palladium hydroxide, palladium oxide, etc.), nickel compounds (Raney-nickel, etc.), platinum compounds (platinum oxide, platinum carbon, etc.), rhodium compounds (rhodium acetate, etc.) and the like. The amount thereof is about 0.001 to 1 equivalent, preferably about 0.01 to 0.5 equivalent, per 1 mol of compound (V).

The catalytic hydrogenation reaction can be generally carried out in a solvent inert to the reaction. Examples of the solvent include alcohols (methanol, ethanol, propanol, butanol, etc.), hydrocarbons (benzene, toluene, xylene, etc.), halogenated hydrocarbons (dichloromethane, chloroform, etc.), ethers (diethyl ether, dioxane, tetrahydrofuran, etc.), esters (ethyl acetate, etc.), amides (N,N-dimethylformamide, etc.), carboxylic acids (acetic acid, etc.), water and a mixture thereof. The hydrogen pressure at which the reaction is carried out is generally about 1 to 50 atm, preferably about 1 to 10 atm. The reaction temperature is generally about 0° C. to 150° C., preferably about 20° C. to 100° C., and the reaction time is generally about 5 min to 72 hr, preferably about 0.5 to 40 hr.

In this reaction, the above-mentioned formation reaction and reduction reaction of the imine or iminium ion are simultaneously carried our without isolation to directly give compound (VI) or a salt thereof from compound (V) or a salt thereof. In this case, the pH of the reaction mixture is preferably about 4 to 5.

When compound (V) or a salt thereof is reacted with an isocyanic acid, the reaction can be generally carried out in a solvent that does not adversely influence the reaction in the presence of a base. This reaction can be carried out in the same manner as in the method described in Step 1 of Method A.

Examples of the reactive derivative of compound (V) or a salt thereof include a compound represented by a compound represented by the formula:

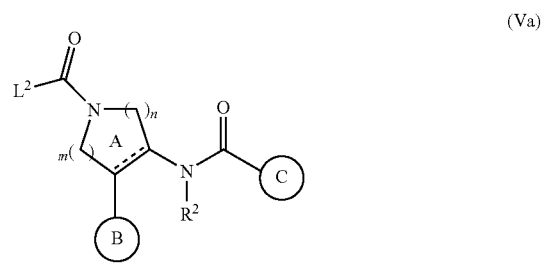

(Va)

wherein $L^2$ is a leaving group, and the other symbols are as defined above, or a salt thereof.

Examples of the leaving group for $L^2$ include those similar to the aforementioned leaving group for L, particularly acyloxy groups (e.g., trichloroacetoxy group), heterocyclic groups (e.g., imidazole group), aryloxy groups (e.g., 4-nitrophenoxy group) and the like.

When compound (IXc) or a salt thereof is reacted with compound (Va) or a salt thereof, the reaction can be generally carried out in a solvent that does not adversely influence the reaction in the presence of a base. This reaction can be carried out in the same manner as in the method described in Step 1 of Method A.

The above-mentioned "arylation reaction" is a step of reacting compound (V) or a salt thereof with a compound represented by the formula:

$$R^{1a}-X \qquad (IXb)$$

wherein X is a leaving group, and the other symbols are as defined above, or a salt thereof to produce compound (VI) or a salt thereof.

Examples of the leaving group for X include those similar to the aforementioned leaving group for L. Of these, a halogen atom (e.g., a fluorine atom, a chlorine atom, a bromine atom, iodine atom and the like), a substituted sulfinyl group (e.g., methylsulfinyl and the like), a substituted sulfonyloxy group (e.g., trifluoromethanesulfonyloxy and the like) and the like are preferable.

This reaction can be carried out according to a method known per se, for example, in the same manner as in the method described in Step 2 of Method A.

The above-mentioned "enamine/imine formation reaction" is a step of subjecting compound (V) or a salt thereof to dehydrating condensation with a ketone or an aldehyde to produce compound (VI) or a salt thereof which is an enamine compound or imine compound, and it can be carried out in the same manner as in the method described in the aforementioned "reacting compound (V) or a salt thereof with an aldehyde or a ketone".

The above-mentioned "amination reaction" is a step of subjecting compound (V) or a salt thereof to N-nitrosation, and reducing the resulting N-nitroso compound to produce compound (VI) or a salt thereof.

The N-nitrosation reaction can be carried out according to a method known per se, for example, the methods described in "4th Ed. Jikken Kagaku Koza (Courses in Experimental Chemistry) 20, Organic Synthesis II", The Chemical Society of Japan Ed. 1991 and the like, or a method analogous thereto.

Examples of the method include a method using tert-butyl nitrite or sodium nitrite. The amount thereof is about 1 equivalent to 20 equivalents, preferably about 1 equivalent to 5 equivalents, per 1 mol of compound (V). The reaction is generally carried out in a solvent that does not adversely influence the reaction. The reaction may be promoted using an acid. Examples of the solvent include hydrocarbons (benzene, toluene, xylene and the like), halogenated hydrocarbons (dichloromethane, chloroform and the like), ethers (diethyl ether, dioxane, tetrahydrofuran and the like), carboxylic acids (acetic acid and the like), water and a mixture thereof. Examples of the acid include hydrochloric acid, nitric acid and the like. The reaction temperature is generally about 0° C. to 150° C., preferably about 0° C. to 100° C. The reaction time is generally 5 min to 72 hr, preferably 0.5 to 40 hr.

The reduction reaction of N-nitroso compound can be carried out according to a method known per se, for example, using a metal or a metal salt or a metal hydride. Examples of the metal or metal salt include alkali metals (lithium, sodium, potassium and the like), alkaline earth metals (magnesium, calcium and the like), other metals (zinc, chrome, titanium, iron, samarium, selenium and the like), alloys (zinc-amalgam, zinc-copper alloy, aluminum-amalgam and the like), metal salts (sodium hydrosulfite and the like) and the like. Examples of the metal hydride include lithium aluminum hydride. The amount of the reducing agent to be used is about 1 to 50 molar equivalents, preferably about 1 to 5 molar equivalents, per 1 mol of compound (V).

Examples of the solvent include alcohols (methanol, ethanol, 2-propanol, t-butanol, benzyl alcohol and the like), amines (liquid ammonia, methylamine, ethylamine, ethylenediamine and the like), ethers (diethyl ether, tetrahydrofuran, dioxane, dimethoxyethane and the like), mineral acids (hydrochloric acid, hydrobromic acid, sulfuric acid and the like), carboxylic acids (acetic acid and the like), amides (hexamethylphosphoramide), water and the like. Such solvent may be used in a mixture of two or more at a suitable ratio.

The reaction temperature is generally about −80° C. to 150° C., preferably about −80° C. to 100° C. The reaction time is generally 5 min to 48 hr, preferably 1 to 24 hr.

The above-mentioned "deprotection" can be carried out according to a known method (e.g., "Protective Groups in Organic Synthesis, 3$^{rd}$ Ed." by Theodora W. Greene, Peter G. M. Wuts, published by Wiley-Interscience, 1999).

The above-mentioned "hydrolysis" can be carried out in the same manner as in the method described in Step 8 of the below-mentioned Method C.

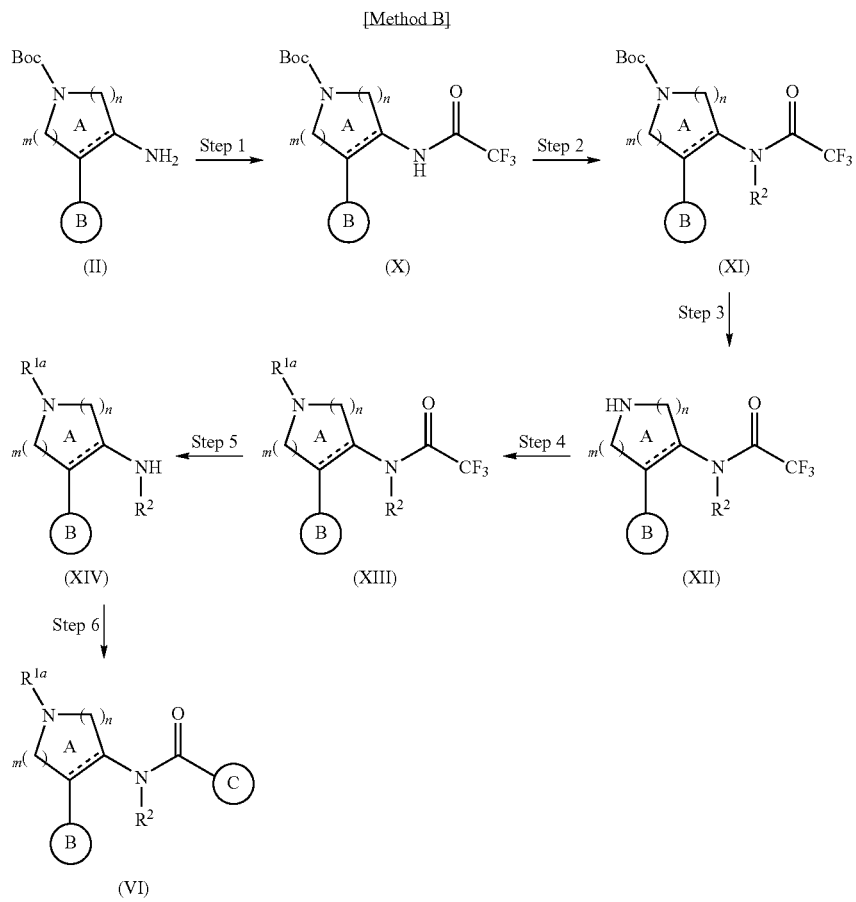

[Method B]

wherein each symbol is as defined above.

(Step 1)

This step is a step of subjecting compound (II) or a salt thereof to trifluoroacetylation reaction to produce compound (X) or a salt thereof.

This reaction can be carried out according to a known method (e.g., "Protective Groups in Organic Synthesis, 3$^{rd}$ Ed." by Theodora W. Greene, Peter G. M. Wuts, published by Wiley-Interscience, 1999). This reaction can be generally carried out by reacting compound (II) or a salt thereof with a trifluoroacetylating agent in a solvent that does not adversely influence the reaction, as necessary in the presence of a base.

Examples of the trifluoroacetylating agent include trifluoroacetates (ethyl trifluoroacetate and the like), trifluoroacetic anhydrides, succinimidyl trifluoroacetate and the like. The amount of the trifluoroacetylating agent to be used is generally about 1 to 100 molar equivalents, preferably about 1 to 10 molar equivalents, per 1 mol of compound (II).

Examples of the solvent include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), carboxylic acids (acetic acid and the like), amides (N,N-dimethylformamide and the like), sulfoxides (dimethyl sulfoxide and the like) and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (II) or a salt thereof, the reaction temperature and the like, it is, for example, about 0.5 to 100 hr, preferably about 0.5 to 24 hr.

Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), organic amines (trimethylamine, triethylamine, N-methylmorpholine, pyridine, picoline, N,N-dimethylaniline and the like) and the like. The amount of the base to be used is generally about 1 to 100 molar equivalents, preferably about 1 to 10 molar equivalents, per 1 mol of compound (II).

(Step 2)

This step is a step of reacting compound (X) or a salt thereof with a compound represented by the formula:

R²-L  (VIII)

wherein each symbol is as defined above, a salt thereof to produce compound (XI) or a salt thereof.

This step can be performed in the same manner as in the method described in Step 2 of Method A.

(Step 3)

This step is a step of subjecting compound (XI) or a salt thereof to deprotection to produce compound (XII) or a salt thereof. This step can be performed in the same manner as in the method described in Step 3 of Method A.

(Step 4)

This step is a step of subjecting compound (XII) or a salt thereof to an "alkylation reaction", "acylation reaction", "arylation reaction", "enamine/imine formation reaction" or "amination reaction", or these reactions combined with "deprotection" or "hydrolysis", to produce compound (XIII) or a salt thereof.

This step can be performed in the same manner as in the method described in Step 4 of Method A.

(Step 5)

This step is a step of subjecting compound (XIII) or a salt thereof to deprotection to produce compound (XIV) or a salt thereof.

This reaction can be carried out according to a known method (e.g., "Protective Groups in Organic Synthesis, 3rd Ed." by Theodora W. Greene, Peter G. M. Wuts, published by Wiley-Interscience, 1999). For example, while the reaction varies depending on the kind of compound (XIII), it is generally in the presence of a base, as necessary in a solvent that does not adversely influence the reaction.

Examples of the base include alkali metal hydroxides (sodium hydroxide, potassium hydroxide and the like), alkaline earth metal hydroxides (barium hydroxide and the like), hydrogen carbonates (sodium hydrogen carbonate, potassium hydrogen carbonate and the like), carbonates (sodium carbonate, potassium carbonate and the like), ammonium salts (benzyltriethylammonium hydroxide and the like), amines (ammonia and the like) and the like. The amount of the base to be used is generally about 1 to 100 molar equivalents, preferably about 1 to 10 molar equivalents, per 1 mol of compound (XIII).

Examples of the solvent that does not adversely influence the reaction include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitrites (acetonitrile and the like), carboxylic acids (acetic acid and the like), amides (N,N-dimethylformamide and the like), sulfoxides (dimethyl sulfoxide and the like), water and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (XIII) or a salt thereof, the reaction temperature and the like, it is, for example, about 0.5 to 400 hr, preferably about 0.5 to 120 hr.

(Step 6)

This step is a step of reacting compound (XIV) or a salt thereof with a compound represented by the formula:

(VII)

(VIIa)

wherein each symbol is as defined above, or a salt thereof to produce compound (VI) or a salt thereof. This step can be performed in the same manner as in the method described in Step 1 of Method A.

Compound (XXX) or a salt thereof used for Method A can be produced according to a known method (e.g., WO2005/068427, WO2006/004195, Bioorganic & Medicinal Chemistry Letters 13 (2003) 4431-4435 and the like).

Compound (II) or a salt thereof used for Method A or Method B can be produced according to the below-mentioned Method C or Method E (a compound represented by the formula (IIa)), Method D (a compound represented by the formula (IIb)) or Method F.

[Method C]

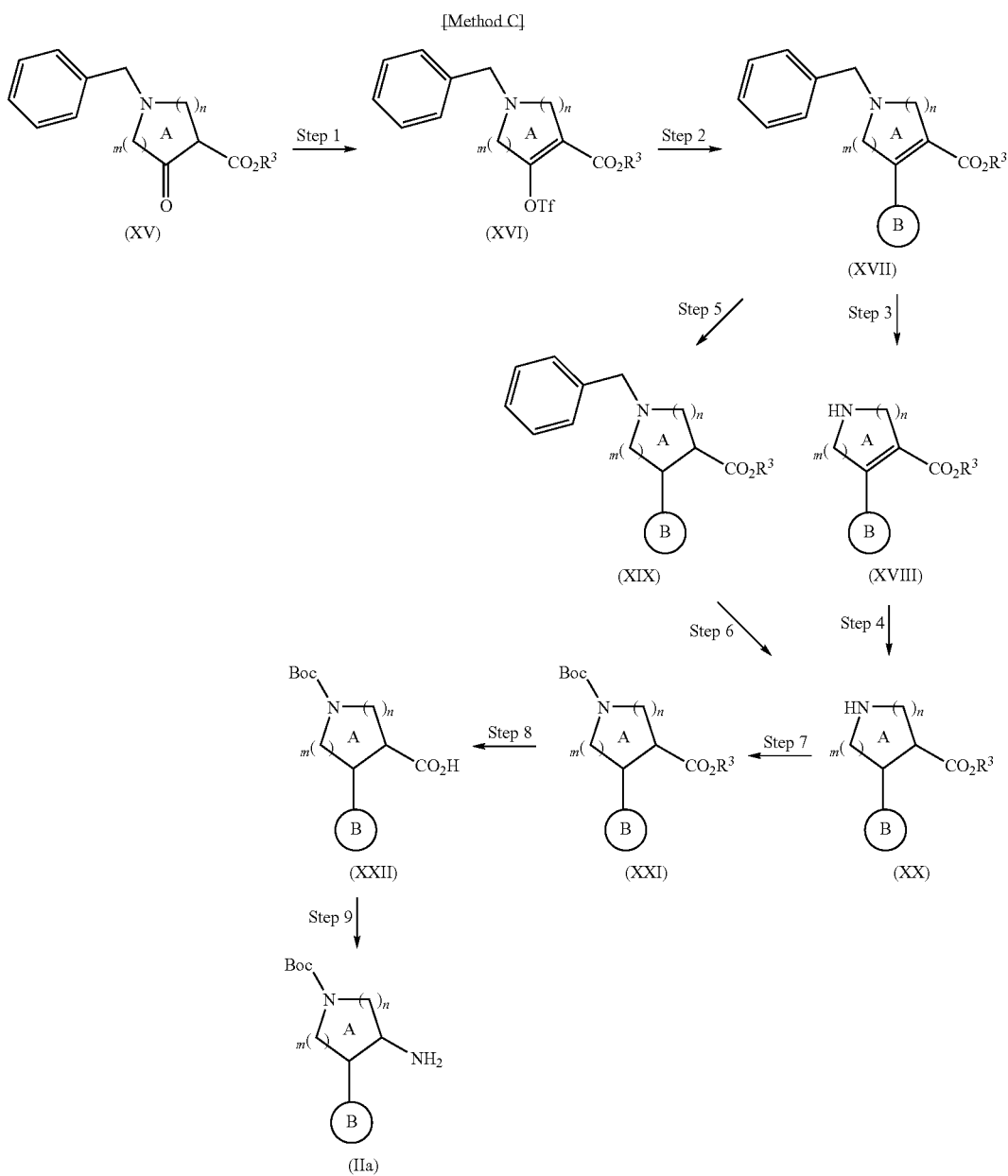

wherein $R^3$ is a hydrocarbon group optionally having substituent(s), Tf is a trifluoromethanesulfonyl group, and the other symbols are as defined above. Examples of the "hydrocarbon group optionally having substituent(s)" for $R^3$ include those similar to the above-mentioned "hydrocarbon group optionally having substituent(s)" for $R^1$.

(Step 1)

This step is a step of triflating compound (XV) or a salt thereof to produce compound (XVI) or a salt thereof.

Compound (XV) or a salt thereof which is a starting material may be commercially available, or can be produced according to a known method [e.g., Heterocycles, Vol. 11, pp. 267-273 (1978) etc.].

This step can be performed according to a method known per se, for example, the methods described in "4th Ed. Jikken Kagaku Koza (Courses in Experimental Chemistry) 24, Organic Synthesis VI", The Chemical Society of Japan Ed. 1991 and the like, or a method analogous thereto. For example, the step can be performed by reacting compound (XV) or a salt with a triflating agent in the presence of a base in a solvent that does not adversely influence the reaction.

Examples of the base include organic amines (trimethylamine, triethylamine, diisopropylamine, N-methylmorpholine, 1,8-diazabicyclo[5.4.0]undec-7-ene, pyridine, N,N-dimethylaniline, etc.), alkali metal salts (sodium hydrogen carbonate, potassium hydrogen carbonate, sodium carbonate, potassium carbonate, cesium carbonate, sodium hydroxide, potassium hydroxide, etc.), metal hydrides (potassium hydride, sodium hydride, etc.) and the like. Of these, organic amines such as triethylamine, diisopropylamine, etc.; metal hydrides such as sodium hydride, etc.; and the like are preferable. The amount of the base to be used is about 0.1 to 10 molar equivalents, preferably about 1 to 5 molar equivalents, per 1 mol of compound (XV).

The solvent may be any as long as it does not adversely influence the reaction, and examples thereof include hydrocarbons (benzene, toluene, xylene, etc.), halogenated hydrocarbons (chloroform, 1,2-dichloroethane, etc.), esters (ethyl acetate, etc.), nitrites (acetonitrile, etc.), ethers (dimethoxyethane, tetrahydrofuran), aprotic polar solvents (N,N-dimethylformamide, dimethyl sulfoxide, hexamethylphosphoramide, etc.) and a mixture thereof.

Examples of the triflating agent include sulfonic acid anhydrides (e.g., trifluoromethanesulfonic anhydride, etc.), sulfonyl halides (e.g., trifluoromethanesulfonyl chloride, etc.), sulfonimides (e.g., N-phenyl-bis(trifluoromethanesulfonimide), etc.), sulfonates (e.g., ethyl trifluoromethanesulfonate, etc.) and the like. Of these, sulfonic acid anhydrides such as trifluoromethanesulfonic anhydride and the like, sulfonimides such as N-phenyl-bis(trifluoromethanesulfonimide) and the like are preferable. The amount of the triflating agent to be used is about 0.1 to 10 molar equivalents, preferably about 1 to 5 molar equivalents, per 1 mol of compound (XV).

The reaction temperature is generally about −80° C. to 100° C., preferably about −80° C. to 20° C., and the reaction time is generally about 5 min to 48 hr, preferably about 5 min to 8 hr.

(Step 2)

This step is a step of subjecting compound (XVI) or a salt thereof to a coupling reaction with a compound represented by the formula:

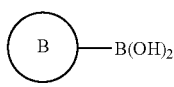

(XXIII)

wherein each symbol is as defined above, or a salt thereof to produce compound (XVII) or a salt thereof.

This step can be performed according to a method known per se [e.g., Chemical Reviews, Vol. 95, p. 2457 (1995) etc.] and, for example, it can be performed in the presence of a transition metal catalyst and a base in a solvent that does not adversely influence the reaction.

Examples of the transition metal catalyst include palladium catalysts (palladium acetate, palladium chloride, tetrakis(triphenylphosphine)palladium, etc.), nickel catalysts (nickel chloride, etc.) and the like. Where necessary, a ligand (triphenylphosphine, tri-t-butylphosphine, etc.) may be added, or a metal oxide (copper oxide, silver oxide, etc.) and the like may be used as a cocatalyst. While the amount of the catalyst to be used varies depending on the kind of the catalyst, it is generally about 0.0001 to 1 molar equivalents, preferably about 0.01 to 0.5 molar equivalents, per 1 mol of compound (XVI). The amount of the ligand to be used is generally about 0.0001 to 4 molar equivalents, preferably about 0.01 to 2 molar equivalents, per 1 mol of compound (XVI), and the amount of the cocatalyst to be used is about 0.0001 to 4 molar equivalents, preferably about 0.01 to 2 molar equivalents, per 1 mol of compound (XVI).

Examples of the base include organic amines (trimethylamine, triethylamine, diisopropylamine, N-methylmorpholine, 1,8-diazabicyclo[5.4.0]undec-7-ene, pyridine, N,N-dimethylaniline, etc.), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide, etc.), metal hydrides (potassium hydride, sodium hydride, etc.), alkali metal alkoxides (sodium methoxide, sodium ethoxide, sodium t-butoxide, potassium t-butoxide, etc.), alkali disilazides (lithium disilazide, sodium disilazide, potassium disilazide, etc.) and the like. Of these, alkali metal salts such as potassium carbonate, cesium carbonate, sodium phosphate, potassium phosphate and the like; alkali metal alkoxides such as sodium t-butoxide, potassium t-butoxide and the like; organic amines such as triethylamine, diisopropylamine and the like; and the like are preferable. The amount of the base to be used is about 0.1 to 10 molar equivalents, preferably about 1 to 5 molar equivalents, per 1 mol of compound (XVI).

The solvent to be used may be any as long as it does not adversely influence the reaction, and examples thereof include hydrocarbons (benzene, toluene, xylene, etc.), halogenated hydrocarbons (chloroform, 1,2-dichloroethane, etc.), nitrites (acetonitrile, etc.), ethers (dimethoxyethane, tetrahydrofuran, etc.), alcohols (methanol, ethanol, etc.), aprotic polar solvent (N,N-dimethylformamide, dimethyl sulfoxide, hexamethylphosphoramide, etc.), water and a mixture thereof.

The reaction temperature is generally about −10° C. to 200° C., preferably about 0° C. to 150° C., and the reaction time is generally about 0.5 to 48 hr, preferably about 0.5 to 16 hr.

(Step 3)

This step is a step of subjecting compound (XVII) or a salt thereof to deprotection to produce compound (XVIII) or a salt thereof.

This deprotection can be carried out according to a known method (e.g., the method described in "Protective Groups in Organic Synthesis, 3$^{rd}$ Ed." by Theodora W. Greene, Peter G. M. Wuts, published by Wiley-Interscience, 1999), or a method analogous thereto. For example, the deprotection can be carried out by a treatment with an acid, a base, ultraviolet rays, a transition metal catalyst and the like, or an oxidation reaction, a reduction reaction, an acylation reaction followed by hydrolysis, and the like, or by a combination of these methods.

(Step 4)

This step is a step of subjecting compound (XVIII) or a salt thereof to a reduction reaction to convert the compound to compound (XX) or a salt thereof. This reaction can be carried out according to a method known per se, for example, by reduction with a metal or a metal salt, by reduction with a metal hydride, by catalytic hydrogenation with a transition metal catalyst, to produce compound (XX) or a salt thereof.

Preferable examples of the metal and metal salt used for the "reduction with a metal or a metal salt" include alkali metals (lithium, sodium, potassium and the like), alkaline earth metals (magnesium, calcium and the like), other metals (zinc, chrome, titanium, iron, samarium, selenium and the like), alloys (zinc-amalgam, zinc-copper alloy, aluminum-amalgam), metal salts (sodium hydrosulfite and the like) and the like. The amount of the reducing agent to be used is, for example, about 1 to 50 molar equivalents, preferably about 1 to 5 molar equivalents, per 1 mol of compound (XVIII).

Examples of the solvent used for reaction include alcohols (methanol, ethanol, 2-propanol, t-butanol, benzyl alcohol and the like), amines (liquid ammonia, methylamine, ethylamine, ethylenediamine and the like), ethers (diethyl ether, tetrahydrofuran, dioxane, dimethoxyethane and the like), mineral acids (hydrochloric acid, hydrobromic acid, sulfuric acid and the like), carboxylic acids (acetic acid and the like), amides (hexamethylphosphoramide), water and the like. Such solvent may be used in a mixture of two or more at a suitable ratio.

The reaction temperature is generally about −80° C. to 150° C., preferably about −80° C. to 100° C. The reaction time is generally 5 min to 48 hr, preferably 1 to 24 hr. Examples of the metal hydride used for the "reduction with a metal hydride" include NaHFe(CO)$_8$, NaHTe, sodium borohydride, sodium bis(2-methoxyethoxy)aluminum hydride (SMEAH)-copper(I) bromide, trimethoxyaluminum hydride-copper(I) bromide and the like. The amount of the reducing agent to be used is, for example, about 1 to 50 molar equivalents, preferably about 1 to 5 molar equivalents, per 1 mol of compound (XVIII).

The solvent to be used may be any as long as it does not adversely influence the reaction, and examples thereof include alcohols (methanol, ethanol, 2-propanol, t-butanol, benzyl alcohol and the like), amines (pyridine and the like), ethers (diethyl ether, tetrahydrofuran, dioxane, dimethoxyethane and the like), carboxylic acids (acetic acid and the like), carboxylic acids (acetic acid and the like), amides (hexamethylphosphoramide) and the like. Such solvent may be used in a mixture of two or more at a suitable ratio.

The reaction temperature is generally about −80° C. to 150° C., preferably about −80° C. to 100° C. The reaction time is generally 5 min to 48 hr, preferably 1 to 24 hr.

Examples of the transition metal catalyst used for the "catalytic hydrogenation with a transition metal catalyst" include palladium compounds (palladium carbon, palladium hydroxide, palladium oxide and the like), nickel compounds (Raney-nickel and the like), platinum compounds (platinum oxide, platinum carbon and the like), rhodium compounds (rhodium acetate, rhodium carbon and the like) and the like. The amount thereof is about 0.001 to 1 equivalent, preferably about 0.01 to 0.5 equivalents, per 1 mol of compound (XVIII). The catalyst hydrogenation reaction is carried out generally in a solvent inert to the reaction. Examples of the solvent include alcohols (methanol, ethanol, propanol, butanol and the like), hydrocarbons (benzene, toluene, xylene and the like), halogenated hydrocarbons (dichloromethane, chloroform and the like), ethers (diethyl ether, dioxane, tetrahydrofuran and the like), esters (ethyl acetate and the like), amides (N,N-dimethylformamide and the like), carboxylic acids (acetic acid and the like), water and mixture thereof. Hydrogen pressure for the reaction is generally about 1 to 500 atm, preferably about 1 to 100 atm. In addition, as a hydrogen source, cyclohexene, hydrazine, formic acid, amine salts of formic acid (ammonium formate, triethylammonium formate and the like), salts of phosphinic acid (sodium phosphinate and the like) and the like may be used instead of hydrogen gas.

The reaction temperature is generally about 0° C. to 150° C., preferably about 20° C. to 100° C. The reaction time is generally 5 min to 72 hr, preferably 0.5 to 40 hr.

(Step 5)

This step is a step of subjecting compound (XVII) or a salt thereof to reduction reaction to convert the compound to compound (XIX) or a salt thereof, and can be carried out in the same manner as in the method described in Step 4 of Method C.

(Step 6)

This step is a step of subjecting compound (XIX) or a salt thereof to deprotection to produce compound (XX) or a salt thereof, and can be carried out in the same manner as in the method described in Step 3 of Method C.

(Step 7)

This step is a step of subjecting compound (XX) or a salt thereof to tert-butoxycarbonylation reaction to produce compound (XXI) or a salt thereof.

This reaction can be carried out according to a known method (e.g., "Protective Groups in Organic Synthesis, 3$^{rd}$ Ed." by Theodora W. Greene, Peter G. M. Wuts, published by Wiley-Interscience, 1999). For example, while the reaction varies depending on the kind of compound (XX), it is generally carried out by reacting compound (XX) or a salt thereof with a tert-butoxycarbonylating agent in a solvent that does not adversely influence the reaction, as necessary in the presence of a base.

Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine and the like), organic amines (pyridine, picoline, N,N-dimethylaniline and the like) and the like. The amount of the base to be used is generally about 1 to 10 molar equivalents, preferably about 1 to 2 molar equivalents, per 1 mol of compound (XX).

Examples of the tert-butoxycarbonylating agent include di-tert-butyl bicarbonate and the like. The amount thereof is about 1 to 10 molar equivalents, preferably about 1 to 2 molar equivalents, per 1 mol of compound (XX).

Examples of the solvent that does not adversely influence the reaction include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitrites (acetonitrile and the like), esters (ethyl acetate and the like), carboxylic acids (acetic acid and the like), amides (N,N-dimethylformamide and the like), sulfoxides (dimethyl sulfoxide and the like), water and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (XX) or a salt thereof, the reaction temperature and the like, it is, for example, about 0.5 to 100 hr, preferably about 0.5 to 24 hr.

(Step 8)

This step is a step of subjecting compound (XXI) or a salt thereof to hydrolysis to convert the compound to compound (XXII) or a salt thereof. This reaction can be carried out according to a method known per se, in the presence of a base, as necessary in a solvent that does not adversely influence the reaction.

Preferable examples of the base include inorganic bases (alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate and the like; alkoxides such as sodium methoxide, sodium ethoxide and the like; and the like), organic bases (amines such as trimethylamine, triethylamine, diisopropylethylamine and the like; cyclic amines such as pyridine, 4-dimethylaminopyridine and the like; and the like) and the like. Of these, lithium hydroxide, sodium hydroxide, potassium hydroxide, sodium ethoxide and the like are preferable. While the amount of the base to be used varies depending on the kind of the solvent and the other reaction conditions, it is generally about 0.1 to 50 molar equivalents, preferably about 0.1 to 10 molar equivalents, per 1 mol of compound (XXI).

Examples of the solvent that does not adversely influence the reaction include alcohols (methanol, ethanol, propanol, 2-propanol, butanol, isobutanol, t-butanol and the like), hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), carboxylic acids (acetic acid and the like), amides (N,N-dimethylformamide, N,N-dimethylacetamide and the like), sulfoxides (dimethyl sulfoxide and the like), water and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (XXI) or a salt thereof, the reaction temperature and the like, it is, for example, about 0.5 to 100 hr, preferably about 0.5 to 24 hr.

(Step 9)

This step is a step of subjecting compound (XXII) or a salt thereof to a rearrangement reaction and then hydrolysis to convert the compound to compound (IIa) or a salt thereof, and can be carried out in the same manner as in the method described in Step 0 of Method A.

[Method D]

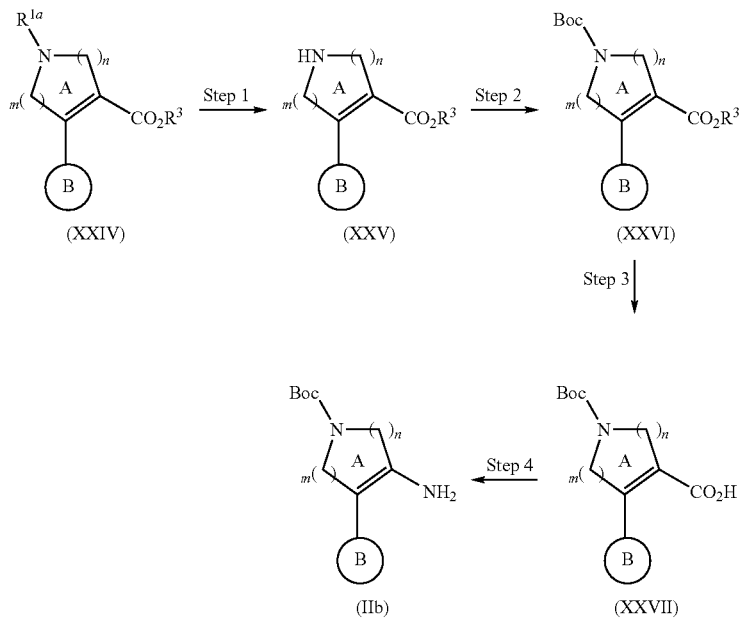

wherein each symbol is as defined above.

(Step 1)

This step is a step of subjecting compound (XXIV) or a salt thereof to deprotection to produce compound (XXV) or a salt thereof, and can be carried out in the same manner as in the method described in Step 3 of Method C.

(Step 2)

This step is a step of subjecting compound (XXV) or a salt thereof to tert-butoxycarbonylation reaction to produce compound (XXVI) or a salt thereof, and can be carried out in the same manner as in the method described in Step 7 of Method C.

(Step 3)

This step is a step of subjecting compound (XXVI) or a salt thereof to hydrolysis to convert the compound to compound (XXVII) or a salt thereof, and can be carried out in the same manner as in the method described in Step 8 of Method C.

(Step 4)

This step is a step of subjecting compound (XXVII) or a salt thereof to a rearrangement reaction and then hydrolysis to convert the compound to compound (IIb) or a salt thereof, and can be carried out in the same manner as in the method described in Step 0 of Method A.

[Method E]

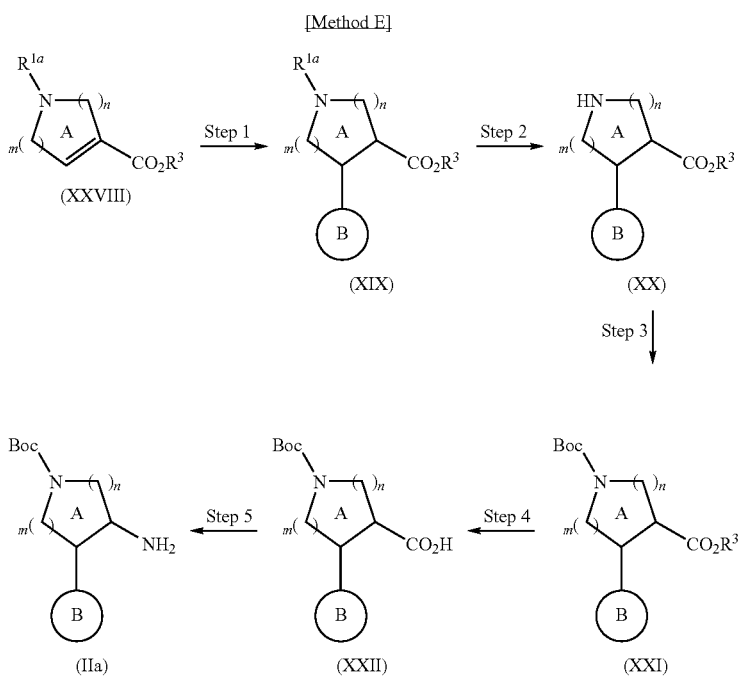

wherein each symbol is as defined above.

(Step 1)

This step is a step of reacting compound (XXVIII) or a salt thereof with a compound represented by the formula:

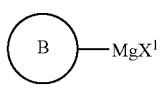

(XXXII)

wherein $X^1$ is a halogen atom, and the other symbols are as defined above, or a salt thereof to produce compound (XIX) or a salt thereof.

Compound (XXVIII) or a salt thereof which is a starting material may be commercially available product, or can be produced according to a method known per se (e.g., Journal of the Chemical Society, Perkin Transactions 1: Organic and Bio-Organic Chemistry, 1981, Vol. 6, page 1754-1762).

The Grignard reagent represented by the formula (XXXII) may be a commercially available product, or can be prepared according to a method known per se, for example, the methods described in "4th Ed. Jikken Kagaku Koza (Courses in Experimental Chemistry) 24, Organic Synthesis VI", The Chemical Society of Japan Ed. 1991 and the like, or a method analogous thereto.

This step may be advantageously promoted using an additive as necessary. Examples of the additive include copper salts (e.g., copper chloride, copper bromide, copper iodide, copper cyanide and the like), lithium salts (e.g., lithium chloride, lithium bromide, lithium iodide and the like), Lewis acids (e.g., boron trifluoride, trimethylsilyl chloride, aluminum chloride and the like), Lewis bases (e.g., tributylphosphine, triphenylphosphine, dimethylethylenediamine and the like), a mixture thereof and the like. Of these, copper bromide, copper iodide, copper cyanide and the like are preferable. The amount of the additive to be used is about 0.001 to 10 molar equivalents, preferably about 0.1 to 2 molar equivalents, per 1 mol of the Grignard reagent represented by the formula (XXXII).

This step is performed in a solvent inert to the reaction. Examples of the solvent include hydrocarbons (hexane, benzene, toluene, xylene and the like), halogenated hydrocarbons (dichloromethane, chloroform and the like), ethers (diethyl ether, dioxane, tetrahydrofuran and the like) and a mixture thereof.

The reaction temperature is generally about −80° C. to 50° C., preferably about −35° C. to 0° C. The reaction time is generally 5 min to 48 hr, preferably 1 to 24 hr.

(Step 2)

This step is a step of subjecting compound (XIX) or a salt thereof to deprotection to produce compound (XX) or a salt thereof, and can be carried out in the same manner as in the method described in Step 3 of Method C.

(Step 3)

This step is a step of subjecting compound (XX) or a salt thereof to tert-butoxycarbonylation reaction to produce compound (XXII) or a salt thereof, and can be carried out in the same manner as in the method described in Step 7 of Method C.

(Step 4)

This step is a step of subjecting compound (XXI) or a salt thereof to hydrolysis to produce compound (XXII) or a salt thereof, and can be carried out in the same manner as in the method described in Step 8 of Method C.

(Step 5)

This step is a step of subjecting compound (XXII) or a salt thereof to rearrangement reaction and then hydrolysis to convert the compound to compound (IIa) or a salt thereof, and can be carried out in the same manner as in the method described in Step 0 of Method A.

[Method F]

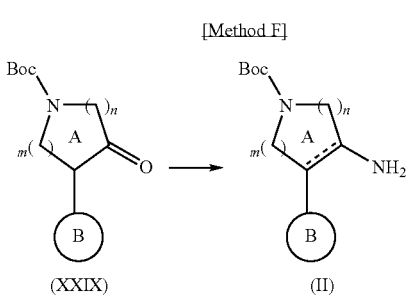

This step is a step of converting compound (XXIX) or a salt thereof to an imine or an oxime, and, as necessary, subjecting the resulting compound to a reduction reaction to convert compound (XXIX) or a salt thereof to compound (II) or a salt thereof.

The conversion of compound (XXIX) to an imine or an oxime can be carried out according to a known method, for example, with a suitable amine in a solvent inert to the reaction.

Examples of the amine include ammonias (e.g., aqueous ammonia, ammonium chloride, ammonium acetate and the like), hydroxylamines (e.g., hydroxylamine, O-methylhydroxylamine, O-benzylhydroxylamine and the like), organic amines (e.g., benzylamine, aminodiphenylmethane, 1-phenylethylamine and the like) and the like. These may be used in the form of a salt thereof (e.g., hydrochloride, a sulfate and the like), or an aqueous solution thereof. The amount of the amine to be used is, for example, about 1 to about 50 mol, preferably about 1 to about 10 mol, per 1 mol of compound (XXIX).

Examples of the solvent inert to the reaction include aromatic hydrocarbons (e.g., toluene, xylene and the like), aliphatic hydrocarbons (e.g., heptane, hexane and the like), halogenated hydrocarbons (e.g., chloroform, dichloromethane and the like), ethers (diethyl ether, tetrahydrofuran, dioxane and the like), alcohols (e.g., methanol, ethanol, 2-propanol, butanol, benzyl alcohol and the like), nitriles (e.g., acetonitrile and the like), amides (e.g., N,N-dimethylformamide and the like), sulfoxides (e.g., dimethyl sulfoxide and the like), water and the like. Such solvent may be used in a mixture of two or more at a suitable ratio.

The reaction may be advantageously promoted using a catalyst as necessary. Examples of the catalyst include mineral acids (e.g., hydrochloric acid, hydrobromic acid, sulfuric acid etc.), carboxylic acids (e.g., formic acid, acetic acid, propionic acid, trifluoroacetic acid etc.), sulfonic acids (e.g., methanesulfonic acid, p-toluenesulfonic acid etc.), Lewis acids (e.g., aluminum chloride, zinc chloride, zinc bromide, boron trifluoride, titanium chloride etc.), acetates (e.g., sodium acetate, potassium acetate etc.), molecular sieves (e.g., molecular sieves 3A, 4A, 5A etc.), dehydrating agents (e.g., magnesium sulfate etc.) and the like. The amount of the catalyst to be used is, for example, about 0.01 to about 50 mol, preferably about 0.1 to about 10 mol, per 1 mol of compound (XXIX).

The reaction temperature is generally about 0° C. to about 200° C., preferably about 20° C. to about 150° C. The reaction time is generally about 0.5 hr to about 48 hr, preferably about 0.5 hr to about 24 hr.

The reduction reaction of the imine or oxime can be carried out in a solvent inert to the reaction. This reduction reaction can be carried out according to a method known per se, for example, using a metal hydride or by catalytic hydrogenation reaction.

Examples of the metal hydride include sodium borohydride, lithium borohydride, zinc borohydride, sodium cyanoborohydride, sodium triacetoxyborohydride, lithium cyanoborohydride, diisobutylaluminum hydride, aluminum hydride, lithium aluminum hydride, borane complex (borane-THF complex, catecholborane etc.) and the like. Of these, sodium borohydride, sodium cyanoborohydride, sodium triacetoxyborohydride and the like are preferable. The amount of the metal hydride to be used is, for example, about 1 to about 50 mol, preferably about 1 to about 10 mol, per 1 mol of the imine or oxime.

The reduction reaction with a metal hydride can be generally carried out in a solvent inert to the reaction. Examples of the solvent include aromatic hydrocarbons (e.g., toluene, xylene and the like), aliphatic hydrocarbons (e.g., heptane, hexane and the like), halogenated hydrocarbons (e.g., chloroform, dichloromethane and the like), ethers (diethyl ether, tetrahydrofuran, dioxane and the like), alcohols (e.g., methanol, ethanol, 2-propanol, butanol, benzyl alcohol and the like), nitriles (e.g., acetonitrile and the like), amides (e.g., N,N-dimethylformamide and the like), sulfoxides (e.g., dimethyl sulfoxide and the like) and the like. Such solvent may be used in a mixture of two or more at a suitable ratio. In addition, this reaction may be carried out with azeotropic dehydration as necessary.

The reaction temperature is generally about −80° C. to about 80° C., preferably about −40° C. to about 40° C. The reaction time is generally about 5 min to about 48 hr, preferably about 1 hr to about 24 hr.

The catalytic hydrogenation reaction can be carried out in the presence of a catalyst under a hydrogen atmosphere. Examples of the catalyst include palladium compounds such as palladium carbon, palladium hydroxide carbon, palladium oxide and the like; nickel compounds such as Raney-nickel catalyst and the like; platinum compounds such as platinum oxide, platinum carbon and the like; rhodium compounds such as rhodium carbon and the like; and the like. The amount thereof is about 0.001 to about 1 mol, preferably about 0.01 to about 0.5 mol, per 1 mol of the imine or oxime.

The catalytic hydrogenation reaction can be generally carried out in a solvent inert to the reaction. Examples of the solvent include alcohols (e.g., methanol, ethanol, propanol, butanol and the like), hydrocarbons (e.g., heptane, hexane, benzene, toluene, xylene and the like), halogenated hydrocarbons (e.g., dichloromethane, chloroform and the like), ethers (diethyl ether, dioxane, tetrahydrofuran and the like), esters (e.g., ethyl acetate and the like), amides (e.g., N,N-dimethylformamide and the like), carboxylic acids (e.g., acetic acid, trifluoroacetic acid and the like), water and a mixture thereof.

The hydrogen pressure for the reaction is generally about 1 to about 50 atm, preferably about 1 to about 10 atm. The reaction temperature is generally about 0° C. to about 150° C., preferably about 20° C. to about 100° C. The reaction time is generally about 5 min to about 72 hr, preferably about 0.5 hr to about 40 hr.

In this step, the imine or oxime which is an intermediate may be subjected to the next reduction reaction without isolation to produced directly amine form (II) from compound (XXIX). In this case, the pH of the reaction mixture is preferably about 4 to about 5.

Compound (XXII) produced in the above-mentioned Method C and Method E can also be produced according to a known method (e.g., WO2005/068427, WO2006/004195, Bioorganic & Medicinal Chemistry Letters 13 (2003) 4431-4435, Bioorganic & Medicinal Chemistry Letters 15 (2005) 4023-4028, Bioorganic & Medicinal Chemistry Letters 17 (2007) 5310-5315 and the like).

In each of the reactions for the synthesis of the objective compounds and the starting materials, when the starting compounds have an amino group, a carboxyl group or a hydroxyl group as a substituent, such groups may be protected with the protecting groups which are generally used in peptide chemistry, etc. In such case, if necessary, such protecting groups can be removed to obtain the objective compounds after the reactions.

Such protecting group includes, for example, protecting groups described in "Protective Groups in Organic Synthesis, $3^{rd}$ Ed." by Theodora W. Greene, Peter G. M. Wuts, published by Wiley-Interscience, 1999.

The protecting group for the amino group includes, for example, a formyl group, a $C_{1-6}$ alkyl-carbonyl group (an acetyl group, a propionyl group, etc.), a phenylcarbonyl group, a $C_{1-6}$ alkyl-oxycarbonyl group (a methoxycarbonyl group, an ethoxycarbonyl group, etc.), a $C_{6-14}$ aryloxycarbonyl group (a phenyloxycarbonyl group, etc.), a $C_{7-10}$ aralkyl-carbonyl group (a benzyloxycarbonyl group, etc.), a benzyl group, a benzhydryl group, a trityl group, a phthaloyl, etc., each of which may be substituted. Such substituent includes, for example, a halogen atom (a fluorine atom, a chlorine atom, a bromine atom, an iodine atom, etc.), a $C_{1-6}$ alkyl-carbonyl group (an acetyl group, a propionyl group, a butyl-carbonyl group, etc.), a nitro group and the like. The number of substituent is in the order of 1 to 3.

A protecting group for the carboxyl group includes, for example, a $C_{1-6}$ alkyl group (a methyl group, an ethyl group, an n-propyl group, an isopropyl group, an n-butyl group, a tert-butyl group, etc.), a phenyl group, a trityl group, a silyl group and the like, each of which may be substituted. Such substituent includes, for example, a halogen atom (a fluorine atom, a chlorine atom, a bromine atom, an iodine atom, etc.), a formyl group, a $C_{1-6}$ alkyl-carbonyl group (an acetyl group, a propionyl group, a butylcarbonyl group, etc.), a nitro group and the like. The number of substituent is in the order of 1 to 3.

The protecting group for the hydroxyl group includes, for example, a $C_{1-6}$ alkyl group (a methyl group, an ethyl group, an n-propyl group, an isopropyl group, an n-butyl group, a tert-butyl group, etc.), a phenyl group, a $C_{7-10}$ aralkyl group (a benzyl group, etc.), a formyl group, a $C_{1-6}$ alkyl-carbonyl group (an acetyl group, a propionyl group, etc.), a $C_{6-14}$ aryloxycarbonyl group (a phenyloxycarbonyl group, etc.), a $C_{7-10}$ aralkyl-carbonyl group (a benzyloxycarbonyl group, etc.), a pyranyl group, a furyl group, a silyl group and the like, each of which may be substituted. Such substituent includes, for example, a halogen atom (a fluorine atom, a chlorine atom, a bromine atom, an iodine atom, etc.), a $C_{1-6}$ alkyl group, a phenyl group, a $C_{7-10}$ aralkyl group, a nitro group and the like. The number of substituent is in the order of 1 to 4.

Such protecting groups can be removed by a known deprotection method or the method described in "Protective Groups in Organic Synthesis, $3^{rd}$ Ed." by Theodora W. Greene, Peter G. M. Wuts, published by Wiley-Interscience, 1999, or an analogous method thereto. For example, treatment with an acid, a base, reduction, ultraviolet radiation, hydrazine, phenylhydrazine, sodium N-methyldithiocarbamate, tetrabutylammonium fluoride, palladium acetate or the like, can be used.

When compound (I) is obtained as a free compound in the above-mentioned method, a salt with for example, inorganic acids (hydrochloric acid, sulfuric acid, hydrobromic acid, etc.), organic acids (methanesulfonic acid, benzenesulfonic acid, p-toluenesulfonic acid, oxalic acid, fumaric acid, maleic acid, tartaric acid, etc.), inorganic bases (alkali metals such as sodium, potassium, etc., alkaline earth metals such as calcium, magnesium, etc., aluminum, ammonium, etc.), or organic bases (trimethylamine, triethylamine, pyridine, picoline, ethanolamine, diethanolamine, triethanolamine, dicyclohexylamine, N,N'-dibenzylethylenediamine, etc.) and the like can be produced in a routine manner. When compound (I) is obtained in the form of a salt, the compound can be converted to a free compound or another salt in a routine manner.

In addition, when the starting compound forms a salt in each of the above-mentioned reactions, the compound may be used as a salt. Such salt includes, for example, those exemplified as a salt of compound (I).

Compound (I) of the present invention thus produced by such method, can be isolated and purified by a typical separation means such as recrystallization, distillation, chromatography, etc.

When compound (I) contains an optical isomer, a stereoisomer, a regioisomer or a rotamer, these are also encompassed in compound (I), and can be obtained as a single product according to synthesis and separation methods known per se (concentration, solvent extraction, column chromatography, recrystallization, etc.). For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (phosphate buffer, etc.) and organic solvents (ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (a fractional recrystallization method, a chromatography method, etc.) and the like, and is subjected to a chemical treatment such as hydrolysis and the like to separate an optically active reagent moiety, whereby an optical isomer is obtained. For example, when compound (I) contains hydroxy, or primary or secondary amino in a molecule, the compound and an optically active organic acid (MTPA [α-methoxy-α-(trifluoromethyl)phenylacetic acid], (−)-menthoxyacetic acid, etc.) and the like are subjected to condensation reaction to give diastereomers in the ester form or in the amide form, respectively. When compound (I) has a carboxylic acid group, this compound and an optically active amine or an alcohol reagent are subjected to condensation reaction to give diastereomers in the amide form or in the ester form, respectively. The separated diastereomer is converted to an optical isomer of the original compound by acid hydrolysis or base hydrolysis.

Compound (I) or a salt thereof may be in the form of a crystal.

The crystal of compound (I) or a salt thereof (hereinafter, it may be referred to as crystal of the present invention) can be produced by crystallization of compound (I) or a salt thereof by a crystallization method known per se.

Examples of the crystallization method include a method of crystallization from a solution, a method of crystallization from vapor, a method of crystallization from the melts and the like.

The "crystallization from a solution" is typically a method of shifting a non-saturated state to supersaturated state by varying factors involved in solubility of compounds (solvent composition, pH, temperature, ionic strength, redox state, etc.) or the amount of solvent. To be specific, for example, a concentration method, a cooling method, a reaction method (a diffusion method, an electrolysis method), a hydrothermal growth method, a flux method and the like can be mentioned. Examples of the solvent to be used include aromatic hydrocarbons (benzene, toluene, xylene, etc.), halogenated hydrocarbons (dichloromethane, chloroform, etc.), saturated hydrocarbons (hexane, heptane, cyclohexane, etc.), ethers (diethyl ether, diisopropyl ether, tetrahydrofuran, dioxane, etc.), nitrites (acetonitrile, etc.), ketones (acetone, etc.), sulfoxides (dimethyl sulfoxide, etc.), amides (N,N-dimethylformamide, etc.), esters (ethyl-acetate, etc.), alcohols (methanol, ethanol, isopropyl alcohol, etc.), water and the like. These solvents are used alone or in a combination of two or more at a suitable ratio (e.g., 1:1 to 1:100 (a volume ratio)).

The "crystallization from vapor" is, for example, a vaporization method (a sealed tube method, a gas stream method), a gas phase reaction method, a chemical transportation method and the like.

The "crystallization from the melts" is, for example, a normal freezing method (a Czockralski method, a temperature gradient method and a Bridgman method, etc.), a zone melting method (a zone leveling method and a floating zone method, etc.), a special growth method (a VLS method and a liquid phase epitaxy method, etc.) and the like.

Preferable examples of the crystallization method include a method of dissolving compound (I) or a salt thereof in a suitable solvent (e.g., alcohols such as methanol, ethanol, etc., etc.) at a temperature of 20 to 120° C., and cooling the resulting solution to a temperature not higher than the temperature of dissolution (e.g., 0 to 50° C., preferably 0 to 20° C.) and the like.

The thus obtained crystals of the present invention can be isolated, for example, by filtration and the like.

In the present specification, the melting point means that measured using, for example, a micro melting point apparatus (Yanako, MP-500D) or a DSC (differential scanning calorimetry) device (SEIKO, EXSTAR6000) and the like.

In the present specification, the peak by a powder X-ray diffraction means that measured using, for example, RINT2100 (Rigaku Corporation), etc. with a Cu—Kα1 ray (tube voltage: 40 KV; tube current: 50 mA) as a ray source.

In the present specification, moreover, the specific rotation ($[\alpha]_D$) means, for example, a specific rotation measured using a polarimeter (JASCO, P-1030 polarimeter (No. AP-2)) and the like.

In general, the melting points and the peak by a powder X-ray diffraction vary depending on the measurement apparatuses, the measurement conditions and the like. The crystal in the present specification may show different values from the melting point described in the present specification or the peak by a powder X-ray diffraction vary depending on the measurement apparatuses, as long as they are within each of a general error range.

The crystal of the present invention is superior in physicochemical properties (melting point, solubility, stability, etc.) and biological properties (pharmacokinetics (absorption, distribution, metabolism, excretion), efficacy expression, etc.), and thus it is extremely useful as a medicament.

Compound (I) or a salt thereof or a prodrug thereof of the present invention (hereinafter sometimes to be abbreviated as the compound of the present invention) has a suppressive action on the promotion of tracheal vascular permeability induced by capsaicin, as well as a superior tachykinin receptor antagonistic action, for example, an SP receptor antagonistic action, an NK-1, NK-2 and NK-3 receptor antagonistic action and the like. It may concurrently have an NK-1 receptor antagonistic action and an NK-3 receptor antagonistic action, or an NK-2 receptor antagonistic action and an NK-3 receptor antagonistic action. The compound of the present invention is superior in an NK-1 and NK-2 receptor antagonistic action, particularly an NK-2 receptor antagonistic action. Such compound of the present invention has low toxicity and is safe.

Accordingly, the compound of the present invention having the above-mentioned superior action can be used for mammals (e.g., mouse, rat, hamster, rabbit, cat, dog, bovine, sheep, monkey, human etc.) as a safe prophylactic or therapeutic drug for the SP-associated diseases indicated below.

(1) Lower urinary tract diseases (including lower urinary tract dysfunction, lower urinary tract symptom and the like) [for example, overactive bladder, benign prostatic hyperplasia, interstitial cystitis, chronic prostatitis, storage symptom (diurnal urinary frequency, nocturnal urinary frequency, urinary urgency, urinary incontinence, stress urinary incontinence, urge urinary incontinence, mixed urinary incontinence, enuresis, nocturnal enuresis, continuous urinary incontinence, other urinary incontinence, enhanced, decreased or missing bladder sensation etc.), voiding symptom (weak urinary stream (or slow stream), split urinary stream (or splitting stream), spraying stream, intermittent urinary stream (or intermittent stream), voiding postponement (or hesitancy), straining at urination (or straining), terminal dribbling (or terminal dribble) etc.), post-micturition symptom (sense of residual urine, post-micturition dribble etc.), symptom due to sexual intercourse (coital pain, vaginal dryness, urinary incontinence etc.), pelvic visceral pain, symptom due to pelvic organ prolapse (foreign body sensation, lumbago etc.), genital organ pain or lower urinary tract pain (cystalgia, urethral pain, pudendalgia, vaginodynia, scrotal pain, perineal pain, pelvic pain etc.), genital organ or urinary tract pain syndrome (cystalgia syndrome, urethral pain syndrome, pudendalgia syndrome, vaginal syndrome, scrotal pain syndrome, perineal pain syndrome, pelvic pain syndrome etc.), symptom syndrome suggesting lower urinary tract dysfunction (overactive bladder syndrome, lower urinary tract symptom suggesting bladder outlet obstruction etc.), polyuria, urolithiasis (urinary duct, urethra) and the like]

(2) Gastrointestinal diseases (e.g., functional gastrointestinal disease, irritable bowel syndrome, functional dyspepsia, gastroesophageal reflux disease, dyschezia, constipation, diarrhea, malabsorption, dyspepsia, gastritis, duodenitis, reflux esophagitis, inflammatory bowel disease (ulcerative colitis, Crohn's disease etc.), gastric ulcer, peptic ulcer, gastrointestinal diseases caused by *H. pylori* infection), vomiting, nausea, pain (e.g., visceral pain, abdominal pain, gastric pain, heartburn)

(3) Inflammatory or allergic diseases [for example, inflammatory bowel disease, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitidis, inflammatory ophthalmic diseases, etc.]

(4) Osteoarthropathy diseases [for example, rheumatoid arthritis (chronic rheumatoid arthritis), arthritis deformans, rheumatoid myelitis, osteoporosis, abnormal growth of cells, bone fracture, bone refracture, osteomalacia, osteopenia, Peget's disease of bone, rigid myelitis, articular tissue destruction by gonarthrosis deformans and similar diseases thereto, etc.]

(5) Respiratory diseases [for example, cold syndrome, pneumonia, asthma, pulmonary hypertension, pulmonary thrombi/pulmonary embolism, pulmonary sarcoidosis, pulmonary tuberculosis, interstitial pneumonia, silicosis, adult respiratory distress syndrome, chronic obstructive pulmonary diseases, cough, etc.]

(6) Infectious diseases [for example, HIV infectious diseases, virus infectious diseases due to cytomegalo virus, influenza virus, herpes virus and the like, *rickettsia* infectious diseases, bacterial infectious diseases, sexually-transmitted diseases, carinii pneumonia, *H. pylori* infectious disease, systemic fungal infectious diseases, tuberculosis, invasive staphylococcal infectious diseases, acute viral encephalitis, acute bacterial meningitidis, AIDS encephalitis, septicemia, sepsis, sepsis gravis, septic shock, endotoxin shock, toxic shock syndromes, etc.]

(7) Cancers [for example, primary, metastatic or recurrent breast cancer, prostatic cancer, pancreatic cancer, gastric cancer, lung cancer, colorectal cancer (colon cancer, rectal cancer, anal cancer), esophagus cancer, duodenal cancer, head and neck cancer (cancer of the tongue, pharynx cancer, laryngeal cancer), brain tumor, schwannoma, non-small cell lung cancer, small cell lung cancer, liver cancer, kidney cancer, cancer of the bile duct, uterine cancer (endometrial cancer, cancer of the uterine cervix), ovarian cancer, urinary bladder cancer, skin cancer, hemangioma, malignant lymphoma, malignant melanoma, thyroid cancer, bone tumor, vascular fibroma, retinosarcoma, penile cancer, solid cancer in childhood, Kaposi's sarcoma, Kaposi's sarcoma caused by acquired immunodeficiency syndrome (AIDS), maxillary tumor, fibrous histiocytoma, leiomyosarcoma, rhabdomyosarcoma, liposarcoma, fibroid tumors of the uterus, osteoblastoma, osteosarcoma, chondrosarcoma, cancerous mesothelioma, tumors such as leukemia, Hodgkin's disease, etc.]

(8) Central nervous system diseases [for example, neurodegenerative diseases (e.g., Alzheimer's disease, Down's disease, Parkinson's disease, Creutzfeldt-Jakob's disease, amyotrophic lateral sclerosis (ALS), Huntington chorea, diabetic neuropathy, multiple sclerosis, etc.), mental diseases (e.g., schizophrenia, depression, mania, anxiety neurosis, obsessive-compulsive neurosis, panic disorder, epilepsy, alcohol dependence, an anxiety symptom, anxious mental state, etc.), central and peripheral nerve disorders (e.g., head trauma, spinal cord injury, brain edema, disorders of sensory function, abnormality of sensory function, disorders of autonomic nervous function and abnormality of autonomic nervous function, whiplash injury, etc.), memory disorders (e.g., senile dementia, amnesia, cerebrovascular dementia, etc.), cerebrovascular disorders (e.g., disorders and aftereffect and/or complication from intracerebral hemorrhage, brain infarction, etc., asymptomatic cerebro-vascular accident, transient cerebral ischemic attack, hypertensive encephalopathia, blood-brain barrier disorder, etc.), recurrence and aftereffect of cerebro-vascular accident (neural symptoms, mental symptoms, subjective symptoms, disorders of daily living activities, etc.), post-cerebrovascular occlusion central hypofunction, disorder or abnormality of autoregulation of cerebral circulation and/or renal circulation]

(9) Circulatory diseases [for example, acute coronary artery syndromes (e.g., acute myocardial infarction, unstable angina, etc.), peripheral arterial obstruction, Raynaud's disease, Buerger disease, restenosis after coronary-artery intervention (percutaneous transluminal coronary angioplasty (PTCA), directional coronary atherectomy (DCA), stenting, etc.), restenosis after coronary-artery bypass operation, restenosis after intervention (angioplasty, atherectomy, stenting, etc.) or bypass operation in other peripheral artery, ischemic cardiac diseases (e.g., myocardial infarction, angina, etc.), myocarditis, intermittent claudication, lacunar infarction, arteriosclerosis (e.g., atherosclerosis, etc.), cardiac failure (acute cardiac failure, chronic cardiac failure including congestive cardiac failure), arrhythmia, progress of atherosclerotic plaque, thrombosis, hypertension, hypertensive tinnitus, hypotension, etc.]

(10) Pains [e.g., migraine, neuralgia, somatic pain, neuropathic pain, etc.]

(11) Autoimmune diseases [for example, collagen disease, systemic lupus erythematosus, scleroderma, polyarteritis, myasthenia gravis, multiple sclerosis, Sjogren's syndrome, Behcet's disease, etc.]

(12) Hepatic diseases [e.g., hepatitis (including chronic hepatitis), cirrhosis, interstitial hepatic diseases, etc.]

(13) Pancreatic diseases [e.g., pancreatitis (including chronic pancreatitis), etc.]

(14) Renal diseases [e.g., nephritis, glomerulonephritis, glomerulosclerosis, renal failure, thrombotic microangiopathy, dialysis complications, organ disorders including nephropathia by radiation, diabetic nephropathy, etc.]

(15) Metabolic diseases [e.g., diabetic diseases (insulin-dependent diabetes, diabetic complications, diabetic retinopathy, diabetic microangiopathy, diabetic neuropathy, etc.), impaired glucose tolerance, obesity, benign prostatic hyperplasia, sexual dysfunction, etc.]

(16) Endocrine diseases [e.g., Addison's disease, Cushing's syndrome, melanocytoma, primary aldosteronism, etc.]

(17) Other Diseases (i) Transplant rejection [e.g., posttransplantational rejection, posttransplantational polycythemia, hypertension, organ disorder and/or vascular hypertrophy, graft-versus-host disease, etc.]

(ii) Abnormality in characteristic of blood and/or blood components [e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy, etc.]

(iii) Gynecologic diseases [e.g., climacteric disorder, gestational toxicosis, endometriosis, hysteromyoma, ovarian disease, mammary disease, etc.]

(iv) Dermatic diseases [e.g., keloid, hemangioma, psoriasis, pruritus, etc.]
(v) Ophthalmic diseases [e.g., glaucoma, ocular hypertension disease, etc.]
(vi) Otolaryngological diseases [e.g., Menuel syndrome, tinnitus, gustation disorder, dizziness, disequilibrium, dysphagia, etc.]
(vii) Diseases due to environmental and/or occupational factors (e.g., radiation disorder, disorders by ultraviolet ray•infrared ray•laser ray, altitude sickness, etc.)
(viii) Ataxia
(ix) Chronic fatigue syndrome The compound of the present invention is useful as a tachykinin receptor antagonist, particularly, as an agent for the prophylaxis or treatment of the above-mentioned lower urinary tract diseases, gastrointestinal diseases, central nervous system diseases and the like.

A pharmaceutical preparation containing the compound of the present invention may be in the form of a solid preparation such as powder, granule, tablet, capsule, suppository, orally disintegrable film and the like or a liquid such as syrup, emulsion, injection, suspension and the like.

The pharmaceutical preparations of the present invention can be produced by any conventional methods, for example, blending, kneading, granulation, tabletting, coating, sterilization, emulsification, etc., in accordance with the forms of the preparations to be produced. For the production of such pharmaceutical preparations, for example, each of the items in General Rules for Preparations in the Japanese Pharmacopoeia, can be made reference to. In addition, the pharmaceutical preparations of the present invention may be formulated into a sustained release preparation containing active ingredients and biodegradable polymer compounds. The sustained release preparation can be produced according to the method described in JP-A-9-263545.

In the pharmaceutical preparations of the present invention, the content of the compound of the present invention or a salt thereof varies depending on the forms of the preparations, but is generally in the order of about 0.01 to 100% by weight, preferably about 0.1 to 50% by weight, more preferably 0.5 to 20% by weight, relative to the total weight of each preparation.

When the compound of the present invention is used in the above-mentioned pharmaceutical preparations, it may be used alone, or in admixture with a suitable, pharmaceutically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by ordinary methods. It can be formulated into the solid preparations such as powders, fine granules, granules, tablets, capsules, orally disintegrable films, etc., or into the liquid preparations such as injections, etc., and can be administered non-parenterally or parenterally.

The dose of the pharmaceutical preparation of the present invention varies depending on the kinds of the compound of the present invention or a pharmaceutically acceptable salt thereof, the administration route, the condition and the age of patients, etc. For example, the dose for oral administration of the pharmaceutical preparation to an adult patient suffering from abnormal micturition is generally from about 0.005 to 50 mg/kg body/day, preferably from about 0.05 to 10 mg/kg body/day, more preferably from about 0.2 to 4 mg/kg body/day, in terms of the compound of the present invention, which may be administered once a day or in two or three divided portions a day.

The dose of the pharmaceutical composition of the present invention in the form of a sustained release preparation varies depending on the kinds and the content of compound (I) or a salt thereof, the formulation, the duration time of drug release, the animals to be administered (e.g., mammals such as humans, rats, mice, cats, dogs, rabbits, bovines, pigs, etc.), and the purpose of administration. For example, when it is applied by parenteral administration, preferably about 0.1 to about 100 mg of compound (I) or a salt thereof is released from the preparation for 1 week.

The compound of the present invention can be used in a mixture or combination with other pharmaceutically active ingredients at a suitable ratio.

Combination of the compound of the present invention with other pharmaceutically active ingredients can give the following excellent effects:

(1) a dose can be reduced as compared with separate administration of the compound of the present invention or other pharmaceutically active ingredients. More specifically, when the compound of the present invention is combined with anticholinergic agents or NK-2 receptor antagonists, the dose can be reduced as compared with separate administration of anticholinergic agents or NK-2 receptor antagonists, and therefore, side effects such as dry mouth can be reduced;

(2) according to symptoms of patient (mild symptoms, severe symptoms, etc.), a drug to be combined with the compound of the present invention can be selected;

(3) by choosing other pharmaceutically active ingredients which have different mechanism of action from that of the compound of the present invention, the therapeutic period can be designed longer;

(4) by choosing other pharmaceutically active ingredients which have different mechanism of action from that of the compound of the present invention, continuation of therapeutic effects can be obtained; and (5) by combining the compound of the present invention and other pharmaceutically active ingredients, excellent effects such as synergic effects can be obtained.

A drug which is mixed or combined with the compound of the present invention (hereinafter, briefly referred to as combination drugs) includes the following:

(1) Agent for Treating Diabetes

Insulin preparations (e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1, etc.), insulin sensitizers (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., sitagliptin, vildagliptin, saxagliptin, alogliptin etc.), $\beta_3$ agonists (e.g., CL-316243, SR-58611-A, UL-TG-307, AJ-9677, AZ40140, YM178 etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.) and the like.

(2) Agent for Treating Diabetic Complications

Aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapride, etc.) and the like.

(3) Antihyperlipidemic Agent

Statin compounds inhibiting cholesterol synthesis (e.g., pravastatin, simvastatin, lovastatin, atorvastatin, fluvastatin, cerivastatin or their salt (e.g., sodium salt, etc.), etc.), squalene synthase inhibitors or fibrate compounds having triglyceride lowering action (e.g., bezafibrate, clofibrate, simfibrate, clinofibrate, etc.) and the like.

(4) Hypotensive Agent

Angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine, and the like.

(5) Antiobesity Agent

Antiobesity drugs acting on the central nervous system (e.g., dexfenfluramine, fenfluramine, phentermine, sibutramine, anfepramone, dexamphetamine, mazindol, phenylpropanolamine, clobenzorex, etc.), pancreatic lipase inhibitors (e.g., orlistat, etc.), β3 agonists (e.g., CL-316243, SR-58611-A, UL-TG-307, AJ-9677, AZ40140, etc.), anorectic peptides (e.g., leptin, CNTF (Ciliary Neurotrophic Factor), etc.), cholecystokinin agonists (e.g., lintitript, FPL-15849, etc.).

(6) Diuretic Agent

Xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide, etc.

(7) Chemotherapeutic Agent

Alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as Furtulon and Neo-Furtulon are preferred.

(8) Immunotherapeutic Agent

Microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating factors (e.g., granulocyte colony stimulating factor, erythropoietin, etc.) and the like. Among these, IL-1, IL-2, IL-12, etc. are preferred.

(9) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above references are applied to both), fat metabolism ameliorating agents (e.g., eicosapentanoic acid) [British Journal of Cancer, vol. 68, pp. 314-318, 1993], growth hormones, IGF-1, and antibodies to the cachexia-inducing factors such as TNF-α, LIF, IL-6 and oncostatin M.

(10) Antiinflammatory Agent

Steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.) and the like.

(11) Miscellaneous

Glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), opioid receptor complete agonist (e.g., pentazocine), opioid receptor partial agonist (e.g., buprenorphine, axomadol, TRK-130), γ-aminobutyric acid (GABA) receptor agonists, GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), serotonin noradrenaline uptake inhibitors (e.g., duloxetine, venlafaxine), hypnotics (e.g., triazolam, zolpidem), anticholinergic agents, $\alpha_1$ receptor blocking agents (e.g., tamsulosin, naftopidil, silodosin), muscle relaxants (e.g., baclofen, etc.), potassium channel openers (e.g., nicorandil), calcium channel blocking agents (e.g., nifedipine, gabapentin), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast), etc.

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin chloride, tolterodine tartrate, etc.), preferably, oxybutynin, propiverine, darifenacin, tolterodine, temiverine, trospium chloride or a salt thereof (e.g., oxybutynin chloride, tolterodine tartrate, etc.). In addition, acetylcholinesterase inhibitors (e.g., distigmine, etc.) and the like can be used.

NK-2 receptor antagonists include, for example, a piperidine derivative such as GR159897, GR149861, SR48968 (saredutant), SR144190, YM35375, YM38336, ZD7944, L-743986, MDL105212A, ZD6021, MDL105172A, SCH205528, SCH62373, R-113281, etc., a perhydroisoindole derivative such as RPR-106145, etc., a quinoline derivative such as SB-414240, etc., a pyrrolopyrimidine derivative such as ZM-253270, etc., a pseudopeptide derivative such as MEN11420 (nepadutant), SCH217048, L-659877, PD-147714 (CAM-2291), MEN10376, S16474, etc., and others such as GR100679, DNK333, GR94800, UK-224671, MEN10376, MEN10627, or a salt thereof, and the like.

The pharmaceutical composition comprising a mixture or combination of the compound of the present invention and the combination drugs may be formulated into
(1) a single formulation as a pharmaceutical composition containing the compound of the present invention and the combination drugs, or
(2) a formulation comprising the compound of the present invention and the combination drugs which are separately formulated. Hereinafter, it is generally briefly referred to as the combination preparation of the present invention.

The combination preparation of the present invention can be formulated by mixing the compound of the present invention and active ingredients of the combination drugs separately or at the same time as itself or with pharmaceutically acceptable carriers in the same manner as in the method of producing the pharmaceutical preparation comprising the compound of the present invention.

A daily dose of the combination preparation of the present invention varies depending on severity of the symptoms, age, sex, weight and sensitivity of the subject to be administered, time and interval of administration, property, formulation and kinds of pharmaceutical preparation, kinds of active ingredients, etc., and is not particularly limited. The dose in terms of the compound of the present invention is not particularly limited if it causes no problems of side effects. In the case of oral administration, a daily dosage is usually in a range of about 0.005 to 100 mg, preferably about 0.05 to 50 mg, and more preferably about 0.2 to 30 mg, per 1 kg body weight of mammals, which may be administered once a day or in two or three divided portions a day.

The dose of the compound or the combination preparation of the present invention may be set within the range such that it causes no problems of side effects. The daily dose as the compound or the combination preparation of the present invention varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of active ingredients is usually in the order of about 0.001 to 2000 mg, preferably about 0.01 to 500 mg, and more preferably about 0.1 to 100 mg, per 1 kg body weight of mammals, which may be administered once a day or in two to four divided portions a day.

In administering the combination preparation of the present invention, the compound of the present invention and the combination drugs may be administered at the same time or, the combination drugs may be administered before administering the compound of the present invention, and vice versa. In case of staggered administration, the time interval varies depending on the active ingredients to be administered, a formulation and an administration route. For example, if the combination drugs are administered first, the compound of the present invention may be administered 1 minute to 3 days, preferably 10 minutes to 1 day, more preferably 15 minutes to 1 hour after administering the combination drugs. If the compound of the present invention is administered first, the combination drugs may be administered 1 minute to 1 day, preferably 10 minutes to 6 hours, more preferably 15 minutes to 1 hour after administering the compound of the present invention.

In a preferred administration method, about 0.001 to 200 mg/kg of the combination drugs formulated as an oral preparation is administered orally and then after about 15 minutes, about 0.005 to 100 mg/kg of the compound of the present invention formulated as an oral preparation is administered orally as a daily dose.

In the combination preparation of the present invention, the content of the compound of the present invention varies depending on the forms of the preparation, but usually in the order of 0.01 to 100 wt %, preferably 0.1 to 50 wt %, and further preferably 0.5 to 20 wt %, relative to the total preparation.

EXAMPLES

The present invention is further described in detail with reference to Reference Examples, Examples, Preparative Examples and Experimental Example, which are not intended to restrict the invention and may be modified without departing from the scope of the invention.

Elution in the column chromatography in the following Reference Examples and Examples was conducted under observation by TLC (thin layer chromatography), unless otherwise indicated. In the TLC observation, 60F254, TLC plates, produced by Merck & Co., Inc. was used, and the solvent employed as an elution solvent in the column chromatography was used as an eluent. For the detection, a UV detector was used. As silica gel for the column chromatography, Silica Gel 60 (70 to 230 mesh) produced by Merck & Co., Inc. was used. The "room temperature" here means a temperature of generally from about 10° C. to 35° C. For drying extracts, sodium sulfate or magnesium sulfate was used.

The abbreviations used in the following Examples and Reference Examples mean the following:
LC: liquid chromatography
MS: mass spectrum
ESI: electrospray ionization
NMR: nuclear magnetic resonance
Hz: hertz
J: coupling constant
m: multiplet
q: quartet
t: triplet
d: doublet
s: singlet
br: broad
$^t$Bu: tert-butyl group, t-butyl group
Boc: tert-butyloxycarbonyl
Rf: retardation factor
Rt: retention time
N: normal concentration
MPa: mega pascal
wt %: percent by weight
DMF: N,N-dimethylformamide
THF: tetrahydrofuran
DMSO: dimethyl sulfoxide
p-TsOH: p-toluenesulfonic acid IPE: diisopropyl ether
HOBt: 1-hydroxybenzotriazole hydrate
WSC.HCl: 1-ethyl-3-(dimethylaminopropyl)carbodiimide hydrochloride
Boc$_2$O: di-tert-butyl dicarbonate
DPPA: diphenylphosphoryl azide
TFA: trifluoroacetic acid
DEPC: diethyl phosphorocyanidate
EtOAc: ethyl acetate
de: diastereomer excess LC-MS in Examples and Reference Examples was measured under the following conditions.
Analysis by LC-MS
Measurement instrument: LC-MS system, Waters Corporation
HPLC part: HP1100, Agilent Technologies, Inc.
MS part: Micromass ZMD
HPLC Conditions
Column: CAPCELL PAK C18UG120, S-3 µm, 1.5×35 mm (Shiseido Co., Ltd.)
Solvent: Solution A; 0.05% trifluoroacetic acid-containing water, Solution B; 0.05% trifluoroacetic acid-containing acetonitrile
Gradient cycle: 0.00 minute (Solution A/Solution B=90/10), 2.00 minutes (Solution A/Solution B=5/95), 2.75 minutes (Solution A/Solution B=5/95), 2.76 minutes (Solution A/Solution B=90/10), 3.60 minutes (Solution A/Solution B=90/10)
Injection volume: 2 µL, Flow rate: 0.5 mL/min,
Detection method: UV 220 nm
MS Conditions
Ionization method: ESI
In the description of the mass spectrometry of the compounds exemplified in the following, the molecular weight of the corresponding compound is indicated as M.
Analysis by LC
Measurement instrument: CLASS-VP system, Shimadzu Corporation
HPLC Conditions
Column: Inertsil ODS-2, CAPCELL PAK C18UG120, 5 µm, 4.6×150 mm (GL Sciences Inc.)
Solvent: Solution A; 0.1% trifluoroacetic acid-containing water, Solution B; 0.1% trifluoroacetic acid-containing acetonitrile
Gradient cycle: 0.00 minute (Solution A/Solution B=70/30), 15.00 minutes (Solution A/Solution B=15/85), 15.01 minutes (Solution A/Solution B=5/95), 20.00 minutes (Solution A/Solution B=5/95), 20.01 minutes (Solution A/Solution B=70/30), 25.00 minutes (Solution A/Solution B=70/30)
Injection volume: 10 µL, Flow rate: 1.0 mL/min, Detection method: UV 220 nm
Purification by preparative HPLC in Examples and Reference Examples was carried out under the following conditions.
Instrument: High Throughput Purification System, Gilson Company, Inc.
Column: YMC CombiPrep ODS-A S-5 µm, 50×20 mm
Solvent: Solution A; 0.1% trifluoroacetic acid-containing water, Solution B; 0.1% trifluoroacetic acid-containing acetonitrile
Gradient cycle: 0.00 minute (Solution A/Solution B=95/5), 1.00 minutes (Solution A/Solution B=95/5), 4.60 minutes (Solution A/Solution B=5/95), 6.40 minutes (Solution A/Solution B=5/95), 6.50 minutes (Solution A/Solution B=95/5), 6.60 minutes (Solution A/Solution B=95/5)
Flow rate: 20 mL/min, Detection method: UV 220 nm In the following, "*" in the steric configuration of the compound names shows the relative configuration, and unless specifically indicated, it means a racemic mixture.

Reference Example 1 tert-butyl (3R*,4R*)-4-({[3,5-bis(trifluoromethyl)phenyl]carbonyl}amino)-3-(3,4-dichlorophenyl)piperidine-1-carboxylate (Step 1)
To a solution of ethyl isonicotinate (151 g) in ethyl acetate (1000 mL) was added methyl iodide (126 mL), and the mixture was stirred at 80° C. for 3 hr. The reaction mixture was cooled, and the orange precipitate was collected by filtration. The precipitate was suspended in ethanol (1000 mL), sodium borohydride (37.8 g) was added with cooling at −40° C., and the mixture was stirred at room temperature for 2 hr. The reaction mixture was poured into water, and ethanol was evaporated under reduced pressure. The resultant product was extracted with ethyl acetate-tetrahydrofuran, the organic layer was dried, and the solvent was evaporated under reduced pressure. The residue was distilled under reduced pressure to give ethyl 1-methyl-1,2,3,6-tetrahydropyridine-4-carboxylate (85.8 g, 51%) as a pale yellow oil.
Boiling point: 64-77° C. (1 mmHg)
$^1$H-NMR (CDCl$_3$) δ 1.29 (3H, t, J=7.2 Hz), 2.37 (3H, s), 2.40-2.50 (2H, m), 2.54 (2H, t, J=3.3 Hz), 3.09 (2H, q, J=3.0 Hz), 4.20 (2H, q, J=7.2 Hz), 6.86-6.91 (1H, m)

(Step 2)
To a suspension of magnesium (10.76 g) in diethyl ether (110 mL) was added a trace amount of iodine. About one-tenth of a solution of 3,4-dichlorobromobenzene (100 g) in diethyl ether (110 mL) was added slowly at 35-40° C., and the mixture was vigorously stirred until the reaction started. When the reaction started, the rest of the 3,4-dichlorobromobenzene/diethyl ether solution was added slowly while cooling the reaction mixture to 35-40° C. When all was added, the mixture was stirred at 40° C. for 1 hr, and then cooled to 0° C. To the reaction mixture was added copper(I) iodide (12.6 g), and the compound (56.2 g) obtained in step 1 was slowly added dropwise at 0° C. The reaction mixture was stirred at 0° C. for 1 hr, and at room temperature for 1 hr. The reaction mixture was poured into water (40 mL), diethyl ether (500 mL) was added, and the precipitate was removed by decantation. The reaction mixture was washed with aqueous ammonium chloride solution and brine and dried, and the solvent was evaporated under reduced pressure. The obtained residue was purified by silica gel column chromatography (solvent gradient; 20% ethyl acetate/hexane→2.5% aqueous ammonia/17.5% methanol/ethyl acetate) to give crude ethyl 3-(3,4-dichlorophenyl)-1-methylpiperidine-4-carboxylate (cis/trans mixture) (75.5 g) as a brown oil.

(Step 3)
To a solution of the compound (75.1 g) obtained in step 2 in acetonitrile (200 mL) was added α-chloroethyl chloroformate (ACE-Cl) (38.4 g), and the mixture was stirred at 90° C. for 1 hr. The reaction mixture was cooled, and the solvent was evaporated under reduced pressure. Methanol (300 mL) was added to the residue, and the mixture was stirred at 80° C. for 1 hr. The reaction mixture was cooled, and the solvent was evaporated under reduced pressure. The residue was suspended in acetonitrile (400 mL), and triethylamine (36.4 mL) was added. A solution of Boc$_2$O (57.0 g) in acetonitrile (28 mL) was added slowly, and the mixture was stirred at room temperature for 14 hr. The reaction mixture was poured into water, and the resultant product was extracted with ethyl acetate. The organic layer was washed with aqueous ammonium chloride solution and brine and dried, and the solvent was evaporated under reduced pressure. The obtained residue was purified by silica gel column chromatography (solvent gradient; 5→20% ethyl acetate/hexane) to give a pale yellow oil (73.7 g). The obtained oil (70.0 g) was dissolved in ethanol (348 mL). 1M sodium ethoxide/ethanol solution (348 mL) was added, and the mixture was stirred at 90° C. for 2 hr. The reaction mixture was cooled, 8N aqueous sodium hydroxide solution (70 mL) and water (478 mL) were added, and the mixture was stirred at 90° C. for 2 hr. The reaction mixture was cooled, and citric acid (173 g) was added. Ethanol was evaporated under reduced pressure, and the mixture was extracted with ethyl acetate (500 mL) with heating. Furthermore, the mixture was extracted with ethyl acetate (200 mL×2) with heating. The organic layer was washed with water and dried, and the solvent was evaporated under reduced pressure to give a pale yellow powder. The obtained pale yellow powder was recrystallized from THF-IPE to give (3R*,4R*)-1-(tert-butoxycarbonyl)-3-(3,4-dichlorophenyl)piperidine-4-carboxylic acid (58.6 g, 47%) as a white powder.

$^1$H-NMR (CDCl$_3$) δ 1.46 (9H, s), 1.65-1.80 (1H, m), 2.00-2.10 (1H, m), 2.60-2.95 (4H, m), 4.00-4.35 (2H, m), 7.05 (1H, dd, J=8.1, 2.1 Hz), 7.30 (1H, d, J=2.1 Hz), 7.36 (1H, d, J=8.1 Hz)

(Step 4)

To a solution of the compound (2.0 g) obtained in step 3 in toluene (13.6 mL) were added DPPA (1.62 g) and triethylamine (0.82 mL) at room temperature, and the mixture was stirred at 100° C. for 30 min. The reaction mixture was cooled, 8N aqueous sodium hydroxide solution (6.8 mL) and water (478 mL) were added, and the mixture was stirred at room temperature for 2 hr. The reaction mixture was poured into water, and the resultant product was extracted with ethyl acetate. The organic layer was washed with water and brine and dried, and the solvent was evaporated under reduced pressure. The obtained residue was dissolved in ethyl acetate (20 mL) and methanol (0.5 mL), and p-toluenesulfonic acid monohydrate (0.62 g) was added. The precipitate was collected by filtration to give tert-butyl (3R*,4R*)-4-amino-3-(3,4-dichlorophenyl)piperidine-1-carboxylate p-toluenesulfonate (1.58 g, 57%) as a white powder.

$^1$H-NMR (CDCl$_3$+DMSO-d$_6$) δ 1.45 (9H, s), 1.60-1.80 (1H, m), 2.20-2.30 (1H, m), 2.37 (3H, s), 2.60-2.95 (4H, m), 3.28-3.38 (1H, m), 3.95-4.30 (2H, br), 7.10-7.20 (3H, m), 7.36 (1H, d, J=8.4 Hz), 7.38 (1H, d, J=1.8 Hz), 7.69 (2H, d, J=6.6 Hz), 7.90-8.20 (2H, br)

(Step 5)

To a solution of the compound (1.48 g) obtained in step 4, 3,5-bis(trifluoromethyl)benzoic acid (1.10 g) and Et$_3$N (0.40 mL) in acetonitrile (15 mL) were added WSC.HCl (1.10 g) and HOBt (0.88 g), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 10→33% ethyl acetate/hexane) to give the title compound (1.65 g, 98%) as a white powder.

$^1$H-NMR (CDCl$_3$) δ 1.48 (9H, s), 1.50-1.70 (1H, m), 2.20-2.30 (1H, m), 2.70-3.10 (3H, m), 4.20-4.60 (3H, m), 5.93 (1H, d, J=8.7 Hz), 7.13 (1H, dd, J=8.1, 2.1 Hz), 7.34-7.30 (2H, m), 7.95 (3H, s)

MS (ESI+): 529 (M-$^t$Bu+2H)

Reference Example 2 tert-butyl 4-({[3,5-bis(trifluoromethyl)phenyl]carbonyl}amino)-3-(3,4-dichlorophenyl)piperidine-1-carboxylate (cis/trans mixture)

(Step 1)

To a solution of sodium hydride (60% in oil, 6.56 g) in m-xylene (100 mL) was slowly added ethanol (15.7 mL) at 0° C. and then diethyl oxalate (32.0 g) was added. Furthermore, a solution of ethyl 3,4-dichlorophenylacetate (51.0 g) in m-xylene (30 mL) was added at 0° C., and the mixture was stirred at room temperature for 14 hr. To the reaction mixture was added 37% aqueous formalin solution (140 mL) at room temperature, and the mixture was stirred at room temperature for 1 hr. Furthermore, potassium carbonate (115 g) was added at room temperature, and the mixture was stirred at room temperature for 1 hr. The insoluble material was filtered off, and the filtrate was partitioned between ethyl acetate (500 mL) and water (500 mL). The organic layer was separated, washed with brine and dried, and the solvent was evaporated under reduced pressure. The obtained residue was purified by silica gel column chromatography (solvent; 5% ethyl acetate/hexane) to give crude ethyl 2-(3,4-dichlorophenyl)acrylate (38.1 g, 44%) as a colorless oil.

$^1$H-NMR (CDCl$_3$): δ 1.34 (3H, t, J=7.2 Hz), 4.29 (2H, q, J=7.2 Hz), 5.92 (1H, d, J=1.0 Hz), 6.12 (1H, d, J=1.0 Hz), 7.26 (1H, dd, J=8.4, 2.2 Hz), 7.43 (1H, d, J=8.4 Hz), 7.54 (1H, d, J=2.2 Hz)

(Step 2)

To a solution of the compound (38.1 g) obtained in step 1 in triethylamine (20.4 mL) was added β-alanine ethyl ester monohydrochloride (22.5 g), and the mixture was stirred at room temperature for 14 hr. The reaction mixture was poured into water, and the resultant product was extracted with diethyl ether. The organic layer was washed with brine and dried, and the solvent was evaporated under reduced pressure to give N-[2-(3,4-dichlorophenyl)-3-ethoxy-3-oxopropyl]-β-alanine ethyl ester (27.8 g, 78%) as a colorless oil.

$^1$H-NMR (CDCl$_3$): δ 1.22 (3H, t, J=7.4 Hz), 1.24 (3H, t, J=7.4 Hz), 2.46 (2H, t, J=6.6 Hz), 2.89 (2H, td, J=6.6 Hz), 2.89 (1H, dd, J=12.2, 6.6 Hz), 3.23 (1H, dd, J=12.2, 8.4 Hz), 3.72 (1H, dd, J=8.4, 6.6 Hz), 4.06-4.24 (4H, m), 7.15 (1H, dd, J=8.4, 2.2 Hz), 7.40 (1H, d, J=8.4 Hz), 7.41 (1H, d, J=2.2 Hz)

(Step 3)

To a solution of the compound (27.8 g) obtained in step 2 and sodium carbonate (16.3 g) in acetonitrile (132 mL) was added benzyl bromide (14.4 g) at room temperature, and the mixture was stirred at 75° C. for 2 hr. The reaction mixture was poured into water, and the resultant product was extracted with ethyl acetate. The organic layer was washed with brine and dried, and the solvent was evaporated under reduced pressure. The obtained residue was purified by silica gel column chromatography (solvent gradient; 5→20% ethyl acetate/hexane) to give N-benzyl-N-[2-(3,4-dichlorophenyl)-3-ethoxy-3-oxopropyl]-β-alanine ethyl ester (34.6 g, 99%) as a colorless oil.

$^1$H-NMR (CDCl$_3$): δ 1.22 (3H, t, J=7.0 Hz), 1.23 (3H, t, J=7.0 Hz), 2.38-2.47 (2H, m), 2.66-2.90 (3H, m), 3.13 (1H, dd, J=13.2, 8.4 Hz), 3.60 (2H, s), 3.72 (1H, dd, J=8.4, 6.6 Hz), 4.00-4.22 (4H, m), 7.05 (1H, dd, J=8.4, 2.2 Hz), 7.11-7.17 (2H, m), 7.20-7.28 (3H, m), 7.29-7.35 (2H, m)

(Step 4)

To a solution of sodium hydride (60% in oil, 4.85 g) in toluene (109 mL) was added a solution of the compound (34.6 g) obtained in step 3 in ethanol (25.1 mL), and the mixture was stirred at 75° C. for 2 hr. The reaction mixture was poured into water, and the resultant product was extracted with ethyl acetate. The organic layer was washed with brine and dried, and the solvent was evaporated under reduced pressure. A solution of the obtained residue (30.3 g) in concentrated hydrochloric acid (100 mL) and acetic acid (34 mL) was stirred at 140° C. for 5 hr. The reaction mixture was concentrated under reduced pressure, and the obtained residue was made basic with aqueous sodium hydroxide solution. The resultant product was extracted with ethyl acetate, and the organic layer was washed with brine and dried, and the solvent was evaporated under reduced pressure. The obtained residue was purified by silica gel column chromatography (solvent gradient; 10→50% ethyl acetate/hexane) to give 1-benzyl-3-(3,4-dichlorophenyl)-4-piperidinone (18.2 g, 73%) as a colorless oil.

$^1$H-NMR (CDCl$_3$): δ 2.45-2.82 (4H, m), 2.98-3.20 (2H, m), 3.66 (2H, s), 3.75 (1H, dd, J=9.2, 4.8 Hz), 7.05 (1H, dd, J=8.2, 1.8 Hz), 7.26-7.40 (7H, m)

(Step 5)

To a solution of the compound (18.0 g) obtained in step 4 in acetonitrile (100 mL) was added α-chloroethyl chloroformate (11.6 g), and the mixture was stirred at 100° C. for 2 hr. The reaction mixture was cooled, and the solvent was evaporated under reduced pressure. Methanol (100 mL) was added to the residue, and the mixture was stirred at 80° C. for 1 hr. The reaction mixture was cooled, and the solvent was evaporated under reduced pressure. The residue was suspended in acetonitrile (100 mL), and triethylamine (9.03 mL) was added. Boc$_2$O (14.1 g) was added slowly, and the mixture was stirred at room temperature for 14 hr. The reaction mixture was poured into water, and the resultant product was extracted with ethyl acetate. The organic layer was washed with aqueous ammonium chloride solution and brine and dried, and the solvent was evaporated under reduced pressure. The obtained residue was purified by silica gel column chromatography (solvent gradient; 10→50% ethyl acetate/hexane) to give tert-butyl 4-oxo-3-(3,4-dichlorophenyl)piperidine-1-carboxylate (4.17 g, 22%) as a white powder.

$^1$H-NMR (CDCl$_3$): δ 1.51 (9H, s), 2.54 (1H, d, J=6.0 Hz), 2.58 (1H, t, J=3.4 Hz), 3.41-3.60 (2H, m), 3.63-3.71 (1H, m), 4.07-4.40 (2H, m), 7.02 (1H, dd, J=8.2, 2.2 Hz), 7.31 (1H, d, =8.2 Hz), 7.42 (1H, d, J=8.2 Hz)

(Step 6)

A solution of the compound (4.00 g) obtained in step 5, hydroxylamine hydrochloride (1.45 g) and sodium acetate (1.44 g) in ethanol (20 mL) and water (10 mL) was stirred at 75° C. for 2 hr. The reaction mixture was poured into water, and the resultant product was extracted with ethyl acetate. The organic layer was washed with saturated aqueous ammonium chloride solution and brine and dried, and the solvent was evaporated under reduced pressure to give a pale yellow oil (2.83 g). A mixture of the thus-obtained oil and Raney-nickel (about 8 g) in ethanol (30 mL) was stirred under a hydrogen atmosphere (5 atm) at 40° C. for 4 hr. The catalyst was filtered off, and the filtrate was evaporated under reduced pressure. The obtained residue was purified by silica gel column chromatography (solvent gradient; 20% ethyl acetate/hexane→1% aqueous ammonia/1% methanol/ethyl acetate) to give crude tert-butyl 4-amino-3-(3,4-dichlorophenyl)piperidine-1-carboxylate (cis/trans mixture) (2.83 g, 70%) as a pale yellow oil.

MS (ESI+): 289 (M-$^t$Bu+2H)

(Step 7)

To a solution of the compound (2.81 g) obtained in step 6 and triethylamine (1.2 mL) in acetonitrile (20 mL) was added 3,5-bis(trifluoromethyl)benzoyl chloride (1.10 g) at 0° C., and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 10→33% ethyl acetate/hexane) to give the title compound (4.67 g, 98%) as a white powder.

MS (ESI+): 529 (M-$^t$Bu+2H)

Reference Example 3 tert-butyl (3R*,4R*)-3-(3,4-dichlorophenyl)piperidine-4-[(phenylcarbonyl)amino]-1-carboxylate Using the compound obtained in Reference Example 1, step 4 and benzoyl chloride, and by the reaction and purification in the same manner as in Reference Example 2, step 7, the title compound was obtained.

MS (ESI+): 393 (M-$^t$Bu+2H)

Reference Example 4 tert-butyl (3R*,4R*)-4-{[(4-bromophenyl)carbonyl]amino}-3-(3,4-dichlorophenyl)piperidine-1-carboxylate Using the compound obtained in Reference Example 1, step 4 and 4-bromobenzoyl chloride, and by the reaction and purification in the same manner as in Reference Example 2, step 7, the title compound was obtained.

MS (ESI+): 471 (M-$^t$Bu+2H)

Reference Example 5 tert-butyl (3R*,4R*)-3-(3,4-dichlorophenyl)-4-{[(4-methoxyphenyl)carbonyl]amino}piperidine-1-carboxylate Using the compound obtained in Reference Example 1, step 4 and 4-methoxybenzoyl chloride, and by the reaction and purification in the same manner as in Reference Example 2, step 7, the title compound was obtained.

MS (ESI+): 423 (M-$^t$Bu+2H)

Reference Example 6 tert-butyl (3R*,4R*)-3-(3,4-dichlorophenyl)-4-{[(4-methylphenyl)carbonyl]amino}piperidine-1-carboxylate Using the compound obtained in Reference Example 1, step 4 and 4-methylbenzoyl chloride, and by the reaction and purification in the same manner as in Reference Example 2, step 7, the title compound was obtained.

MS (ESI+): 407 (M-$^t$Bu+2H)

Reference Example 7 tert-butyl (3R*,4R*)-3-(3,4-dichlorophenyl)-4-[(4-fluorobenzoyl)amino]piperidine-1-carboxylate Using the compound obtained in Reference Example 1, step 4 and 4-fluorobenzoyl chloride, and by the reaction and purification in the same manner as in Reference Example 2, step 7, the title compound was obtained.

MS (ESI+): 411 (M-$^t$Bu+2H)

Reference Example 8 tert-butyl (3R*,4R*)-3-(3,4-dichlorophenyl)-4-{[(4-chlorophenyl)carbonyl]amino}piperidine-1-carboxylate Using the compound obtained in Reference Example 1, step 4 and 4-chlorobenzoic acid, and by the reaction and purification in the same manner as in Reference Example 1, step 5, the title compound was obtained.

MS (ESI+): 427 (M-$^t$Bu+2H)

Reference Example 9 tert-butyl (3R*,4R*)-4-({[3,5-bis(trifluoromethyl)phenyl]carbonyl}amino)-3-(4-fluoro-2-methylphenyl)piperidine-1-carboxylate (Step 1)

To a solution of (3R*,4R*)-1-(tert-butoxycarbonyl)-3-(4-fluoro-2-methylphenyl)piperidine-4-carboxylic acid (4.33 g) synthesized by a known method (WO2006/004195) in toluene (24 mL) were added DPPA (5.30 g) and triethylamine (2.7 mL) at room temperature, and the mixture was stirred at 100° C. for 1 hr. The reaction mixture was cooled, 8N aqueous sodium hydroxide solution (16 mL) was added, and the mixture was stirred at room temperature for 3 hr. The reaction mixture was poured into water, and the resultant product was extracted with ethyl acetate. The organic layer was washed with water and brine and dried, and the solvent was evaporated under reduced pressure. The obtained residue was purified by silica gel column chromatography (NH Chromatorex) (solvent gradient; 30→70% ethyl acetate/hexane) to give tert-butyl (3R*,4R*)-4-amino-3-(4-fluoro-2-methylphenyl)piperidine-1-carboxylic acid (3.79 g, 96%) as a pale yellow oil.

MS (ESI+): 253 (M-$^t$Bu+2H)

(Step 2)

sing the compound obtained in step 1 and 3,5-(bistrifluoromethyl)benzoic acid, and by the reaction and purification in the same manner as in Reference Example 1, step 5, the title compound was obtained.

MS (ESI+): 493 (M-$^t$Bu+2H)

Reference Example 10 tert-butyl (3R*,4R*)-4-{[(4-bromophenyl)carbonyl]amino}-3-(4-fluoro-2-methylphenyl)piperidine-1-carboxylate Using the compound obtained in Reference Example 9, step 1 and 4-bromobenzoic acid, and by the reaction and purification in the same manner as in Reference Example 1, step 5, the title compound was obtained.

MS (ESI+): 435 (M-$^t$Bu+2H)

Reference Example 11 tert-butyl (3R*,4R*)-4-{[(4-chlorophenyl)carbonyl]amino}-3-phenylpiperidine-1-carboxylate (Step 1)

To a solution of sodium hydride (60% in oil, 6.36 g) in DMF (100 mL) was added ethyl 1-benzyl-3-oxopiperidine-4-carboxylate monohydrochloride (19.0 g) at 0° C., and the mixture was stirred for 5 min. N-phenylbis(trifluoromethanesulfonimide) (25.0 g) was added, and the mixture was stirred at 0° C. for 1 hr. The reaction mixture was poured into ice water, and the resultant product was extracted with ethyl acetate. The organic layer was washed with water and brine and dried, and the solvent was evaporated under reduced pressure. To a mixture of the obtained residue in toluene (125 mL) and water (7.5 mL) were added dihydroxyphenylborane (5.82 g), potassium carbonate (4.40 g) and tetrakis(triphenylphosphine)palladium(0) (3.67 g), and the mixture was stirred under an argon atmosphere at 100° C. for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 10→20% ethyl acetate/hexane) to give ethyl 1-benzyl-5-phenyl-1,2,3,6-tetrahydropyridine-4-carboxylate (10.2 g) as a pale yellow oil.

$^1$H-NMR (CDCl$_3$): δ 0.83 (3H, t, J=7.2 Hz), 2.54-2.62 (2H, m), 2.70 (2H, t, J=5.7 Hz), 3.26 (2H, t, J=2.9 Hz), 3.67 (2H, s), 3.87 (2H, q, J=7.2 Hz), 7.08-7.14 (2H, m), 7.20-7.40 (8H, m)

(Step 2)

A solution of the compound (10.5 g) obtained in step 1 in 20% palladium hydroxide on carbon (50% wet, 2.63 g) in ethanol (250 mL) was stirred under a hydrogen atmosphere (1 atm) at room temperature for 14 hr. The catalyst was filtered off, and the filtrate was concentrated under reduced pressure. To a solution of the obtained residue in acetonitrile (50 mL) were added triethylamine (4.6 mL) and Boc$_2$O (7.14 g), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was separated and purified by silica gel column chromatography (solvent gradient; 10→20% ethyl acetate/hexane) to give 4-ethyl 1-tert-butyl (3R*,4S*)-3-phenylpiperidine-1,4-dicarboxylate (8.31 g, 76%) as a colorless oil.

$^1$H-NMR (CDCl$_3$): δ 1.01 (3H, t, J=7.7 Hz), 1.43 (9H, s), 1.80-2.05 (2H, m), 2.93-3.00 (1H, m), 3.10-3.20 (1H, m), 3.50-4.10 (6H, m), 7.05-7.30 (5H, m)

(Step 3)

To a solution of the compound (6.3 g) obtained in step 2 in ethanol (60 mL) was added $^t$BuONa (3.63 g), and the mixture was stirred at 90° C. for 1 hr. The reaction mixture was cooled, 8N aqueous sodium hydroxide solution (60 mL) and water (60 mL) were added, and the mixture was stirred at 85° C. for 2 hr. The reaction mixture was cooled, and citric acid (51 g) was added. Ethanol was evaporated under reduced pressure, and the residue was extracted with ethyl acetate (200 mL). The organic layer was washed with water and dried, and the solvent was evaporated under reduced pressure. The residue was crystallized from ethyl acetate-IPE-hexane to give (3R*,4R*)-1-(tert-butoxycarbonyl)-3-phenylpiperidine-4-carboxylic acid (5.26 g, 91%) as a white powder.

$^1$H-NMR (CDCl$_3$): δ 1.45 (9H, s), 1.65-1.75 (1H, m), 1.98-2.05 (1H, m), 2.65-3.00 (4H, m), 4.00-4.40 (2H, m), 7.17-7.32 (5H, m)

(Step 4)

To a solution of the compound (4.06 g) obtained in step 3 in toluene (33 mL) were added DPPA (5.50 g) and triethylamine (2.8 mL) at room temperature, and the mixture was stirred at 100° C. for 60 min. The reaction mixture was cooled, 8N aqueous sodium hydroxide solution (15.7 mL) was added, and the mixture was stirred at room temperature for 2 hr. The reaction mixture was poured into water, and the resultant product was extracted with ethyl acetate. The organic layer was washed with water and brine and dried, and the solvent was evaporated under reduced pressure. The obtained residue was dissolved in ethyl acetate (20 mL) and methanol (0.5 mL), and p-toluenesulfonic acid monohydrate (2.51 g) was added. The precipitate was collected by filtration to give tert-butyl (3R*,4R*)-4-amino-3-phenylpiperidine-1-carboxylate p-toluenesulfonate (2.87 g, 48%) as a white powder.

$^1$H-NMR (CDCl$_3$) δ 1.45 (9H, s), 1.65-1.80 (1H, m), 2.20-2.30 (1H, m), 2.36 (3H, s), 2.70-2.95 (3H, m), 3.30-3.48 (1H, m), 4.00-4.30 (2H, m), 7.15 (2H, d, J=8.4 Hz), 7.24-7.40 (4H, m), 7.49 (1H, s), 7.69 (2H, d, J=6.6 Hz), 7.91 (3H, br)

(Step 5)

To a solution of the compound (0.50 g) obtained in step 4, 4-chlorobenzoic acid (0.35 g) and triethylamine (0.16 mL) in acetonitrile (15 mL) were added WSC.HCl (0.43 g) and HOBt (0.34 g), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent; 33% ethyl acetate/hexane) to give the title compound (0.42 g, 91%) as a white powder.

MS (ESI+): 359 (M-$^t$Bu+2H)

Reference Example 12 tert-butyl (3R*,4R*)-4-({[3,5-bis(trifluoromethyl)phenyl]carbonyl}amino)-3-(3,4-difluorophenyl)piperidine-1-carboxylate (Step 1)

Using 3,4-difluorophenylboronic acid, and by the reaction and purification in the same manner as in Reference Example 11, steps 1 to 4, tert-butyl (3R*,4R*)-4-amino-3-(3,4-difluorophenyl)piperidine-1-carboxylate p-toluenesulfonate was obtained.

$^1$H-NMR (CDCl$_3$) δ 1.44 (9H, s), 1.60-1.80 (1H, m), 2.20-2.30 (1H, m), 2.37 (3H, s), 2.70-2.95 (3H, m), 3.25-3.38 (1H, m), 4.00-4.25 (2H, m), 7.04-7.15 (3H, m), 7.15 (2H, d, J=8.4 Hz), 7.68 (2H, d, J=8.4 Hz), 7.97 (3H, br)

(Step 2)

sing the compound obtained in step 1 and 3,5-bis(trifluoromethyl)benzoic acid, and by the reaction and purification in the same manner as in Reference Example 1, step 5, the title compound was obtained.

MS (ESI+): 497 (M-$^t$Bu+2H)

Reference Example 13 tert-butyl (3R*,4R*)-4-{[(4-chlorophenyl)carbonyl]amino}-3-(3,4-difluorophenyl)piperidine-1-carboxylate Using the compound obtained in Reference Example 12, step 1 and 4-chlorobenzoic acid, and by the reaction and purification in the same manner as in Reference Example 1, step 5, the title compound was obtained.

MS (ESI+): 395 (M-$^t$Bu+2H)

Reference Example 14 tert-butyl (3R*,4R*)-3-(3-chloro-4-fluorophenyl)-4-{[(4-chlorophenyl)carbonyl]amino}piperidine-1-carboxylate (Step 1)

Using 3-chloro-4-fluorophenylboronic acid, and by the reaction and purification in the same manner as in Reference Example 11, steps 1 to 4, tert-butyl (3R*,4R*)-4-amino-3-(3-chloro-4-fluorophenyl)piperidine-1-carboxylate p-toluenesulfonate was obtained.

$^1$H-NMR (CDCl$_3$) δ 1.44 (9H, s), 1.60-1.80 (1H, m), 2.18-2.30 (1H, m), 2.37 (3H, s), 2.65-2.95 (3H, m), 3.25-3.40 (1H, m), 4.00-4.30 (2H, m), 7.01 (1H, d, J=7.8 Hz), 7.09 (1H, d, J=10.2 Hz), 7.17 (2H, d, J=8.4 Hz), 7.28 (1H, t, J=8.1 Hz), 7.65 (2H, d, J=8.4 Hz), 7.99 (3H, br)

(Step 2)

sing the compound obtained in step 1 and 4-chlorobenzoic acid, and by the reaction and purification in the same manner as in Reference Example 1, step 5, the title compound was obtained.

MS (ESI+): 411 (M-$^t$Bu+2H)

Reference Example 15 tert-butyl (3R*,4R*)-4-({[3,5-bis(trifluoromethyl)phenyl]carbonyl}amino)-3-(4-chloro-3-fluorophenyl)piperidine-1-carboxylate (Step 1)

Using 4-chloro-3-fluorophenylboronic acid, and by the reaction and purification in the same manner as in Reference Example 11, steps 1 to 4, tert-butyl (3R*,4R*)-4-amino-3-(4-chloro-3-fluorophenyl)piperidine-1-carboxylate p-toluenesulfonate was obtained.

$^1$H-NMR (CDCl$_3$) δ 1.45 (9H, s), 1.60-1.80 (1H, m), 2.20-2.30 (1H, m), 2.36 (3H, s), 2.70-2.95 (3H, m), 3.24-3.40 (1H, m), 4.00-4.30 (2H, m), 7.07 (1H, d, J=8.7 Hz), 7.16 (2H, d, J=8.1 Hz), 7.33 (1H, d, J=5.1 Hz), 7.44 (1H, s), 7.68 (2H, d, J=8.1 Hz), 8.03 (3H, br)

(Step 2)

Using the compound obtained in step 1 and 3,5-bis(trifluoromethyl)benzoic acid, and by the reaction and purification in the same manner as in Reference Example 1, step 5, the title compound was obtained.

MS (ESI+): 495 (M-$^t$BuO)

Reference Example 16 tert-butyl (3R*,4R*)-4-[(4-chlorobenzoyl)amino]-3-(4-chloro-3-fluorophenyl)piperidine-1-carboxylate Using the compound obtained in Reference Example 15, step 1 and 4-chlorobenzoic acid, and by the reaction and purification in the same manner as in Reference Example 1, step 5, the title compound was obtained.

MS (ESI+): 411 (M-$^t$Bu+2H)

Reference Example 17 tert-butyl (3R*,4R*)-4-({[3,5-bis(trifluoromethyl)phenyl]carbonyl}amino)-3-(3-chloro-4-methylphenyl)piperidine-1-carboxylate (Step 1)

Using 3-chloro-4-methylbromobenzene, and by the reaction and purification in the same manner as in Reference Example 1, steps 2 to 4, tert-butyl (3R*,4R*)-4-amino-3-(3-chloro-4-methylphenyl)piperidine-1-carboxylate p-toluenesulfonate was obtained.

MS (ESI+): 269 (M-p-TsOH-$^t$Bu+2H)

(Step 2)

Using the compound obtained in step 1 and 3,5-bis(trifluoromethyl)benzoic acid, and by the reaction and purification in the same manner as in Reference Example 1, step 5, the title compound was obtained.

MS (ESI+): 509 (M-$^t$Bu+2H)

Reference Example 18 tert-butyl (3R*,4R*)-4-({[3,5-bis(trifluoromethyl) phenyl]carbonyl}amino)-3-(4-chloro-3-methylphenyl)piperidine-1-carboxylate (Step 1)

Using 4-chloro-3-methylbromobenzene, and by the reaction and purification in the same manner as in Reference Example 1, steps 2 to 4, tert-butyl (3R*,4R*)-4-amino-3-(4-chloro-3-methylphenyl)piperidine-1-carboxylate p-toluenesulfonate was obtained.

MS (ESI+): 269 (M-p-TsOH-$^t$Bu+2H)

(Step 2)

Using the compound obtained in step 1 and 3,5-bis(trifluoromethyl)benzoic acid, and by the reaction and purification in the same manner as in Reference Example 1, step 5, the title compound was obtained.

MS (ESI+) 509 (M-$^t$Bu+2H)

Reference Example 19 tert-butyl (3R*,4R*)-4-({[3,5-bis(trifluoromethyl) phenyl]carbonyl}amino)-3-(2-methylphenyl)piperidine-1-carboxylate (Step 1)

Using 2-methylphenylboronic acid, and by the reaction and purification in the same manner as in Reference Example 11, steps 1 to 4, tert-butyl (3R*,4R*)-4-amino-3-(2-methylphenyl)piperidine-1-carboxylate p-toluenesulfonate was obtained.

MS (ESI+): 235 (M-p-TsOH-$^t$Bu+2H)

(Step 2)

Using the compound obtained in step 1 and 3,5-bis(trifluoromethyl)benzoic acid, and by the reaction and purification in the same manner as in Reference Example 1, step 5, the title compound was obtained.

MS (ESI+): 457 (M-$^t$BuO)

Reference Example 20 tert-butyl (3R*,4R*)-4-({[3,5-bis(trifluoromethyl) phenyl]amino}-3-phenylpiperidine-1-carboxylate Using the compound obtained in Reference Example 11, step 4 and 3,5-bis(trifluoromethyl)benzoic acid, and by the reaction and purification in the same manner as in Reference Example 1, step 5, the title compound was obtained.

MS (ESI+): 461 (M-$^t$Bu+2H)

Reference Example 21 tert-butyl (3R*,4R*)-4-({[3,5-bis(trifluoromethyl) phenyl}amino)-3-(3-chloro-4-fluorophenyl)piperidine-1-carboxylate Using the compound obtained in Reference Example 14, step 1 and 3,5-bis(trifluoromethyl)benzoic acid, and by the reaction and purification in the same manner as in Reference Example 1, step 5, the title compound was obtained.

MS (ESI+): 513 (M-$^t$Bu+2H)

Reference Example 22 tert-butyl (3R*,4S*)-3-({[3,5-bis(trifluoromethyl) phenyl]carbonyl}amino)-4-(3,4-dichlorophenyl)pyrrolidine-1-carboxylate (Step 1)

To a solution of 3,4-dichlorocinnamic acid (21.7 g) and cesium carbonate (22.8 g) in DMF (200 mL) was added methyl iodide (7.47 mL) at 0° C., and the mixture was stirred at room temperature for 12 hr. The reaction mixture was poured into water, and the resultant product was extracted with ethyl acetate. The organic layer was washed with saturated aqueous sodium hydrogen carbonate solution, water, 1M KHSO$_4$ solution and brine and dried, and the solvent was evaporated under reduced pressure to give methyl 3,4-dichlorocinnamate (22.4 g, 97%) as a white powder.

$^1$H-NMR (CDCl$_3$) δ 3.81 (3H, s), 6.42 (1H, d, J=16.2 Hz), 7.35 (1H, d, J=8.3 Hz), 7.47 (1H, d, J=8.3 Hz), 7.56-7.61 (2H, m)

(Step 2)

To a solution of the compound (20.4 g) obtained in step 1 and N-(methoxymethyl)-N-(trimethylsilylmethyl)benzylamine (22.0 g) in toluene (180 mL) was added a solution of trifluoroacetic acid (1.31 mL) in toluene (18 mL) at 0° C., and the mixture was stirred at room temperature for 14 hr. To the reaction mixture was added ethyl acetate (300 mL), and the mixture was washed with saturated aqueous sodium hydrogen carbonate solution, water and brine and dried, and the solvent was evaporated under reduced pressure. The obtained residue was purified by silica gel column chromatography (solvent gradient; 10→25% ethyl acetate/hexane) to give methyl (3R*,4S*)-1-benzyl-4-(3,4-dichlorophenyl)pyrrolidine-3-carboxylate (33.4 g, 100%) as a pale yellow oil.

MS (ESI+): 364 (M+H)

(Step 3)

To a solution of the compound (33.4 g) obtained in step 2 in acetonitrile (250 mL) was added ACE-Cl (13.9 g) at room temperature, and the mixture was stirred at 90° C. for 2 hr. The reaction mixture was cooled, and the solvent was evaporated under reduced pressure. Methanol (250 mL) was added to the residue, and the mixture was stirred at 80° C. for 2 hr. The reaction mixture was cooled, and the solvent was evaporated under reduced pressure to give methyl (3R*,4S*)-4-(3,4-dichlorophenyl)pyrrolidine-3-carboxylate monohydrochloride (26.9 g, 98%) as a pale yellow powder.

MS (ESI+): 274 (M−HCl+H)

(Step 4)

To a solution of the compound (26.4 g) obtained in step 3 and triethylamine (13.0 mL) in acetonitrile (260 mL) was added Boc$_2$O (20.4 g) at 0° C., and the mixture was stirred at room temperature for 5 hr. The reaction mixture was poured into water, and the resultant product was extracted with ethyl acetate. The organic layer was washed with 1N hydrochloric acid and brine and dried, and the solvent was evaporated under reduced pressure. The obtained residue was purified by silica gel column chromatography (solvent gradient; 10→25% ethyl acetate/hexane) to give 3-methyl 1-tert-butyl (3R*,4S*)-4-(3,4-dichlorophenyl)pyrrolidine-1,3-dicarboxylate (31.2 g, 98%) as a pale yellow oil.

MS (ESI+): 318 (M-$^t$Bu+2H)

(Step 5)

To a mixture of the compound (31.2 g) obtained in step 4 in ethanol (160 mL), THF (30 mL) and water (31.3 mL) was added 8N aqueous sodium hydroxide solution (31.3 mL), and the mixture was heated under reflux for 2 hr. The reaction mixture was cooled to 0° C., and the reaction mixture was made slightly acidic with 1N hydrochloric acid solution (270 mL). The organic solvent was evaporated under reduced pressure, and the resultant product was extracted with ethyl acetate. The organic layer was washed with water and brine and dried, and the solvent was evaporated under reduced pressure. The obtained residue was crystallized from ethyl acetate-hexane to give (3R*,4S*)-1-(tert-butoxycarbonyl)-4-(3,4-dichlorophenyl)pyrrolidine-3-carboxylic acid (19.2 g, 64%) as a white powder.

$^1$H-NMR (CDCl$_3$) δ 1.47 (9H, s), 3.17 (1H, dd, J=9.1, 17.0 Hz), 3.36 (1H, q, J=10.3 Hz), 3.61 (2H, t, J=9.4 Hz), 3.80-3.90 (2H, br), 7.10 (1H, dd, J=2.3, 8.3 Hz), 7.35 (1H, d, J=2.2 Hz), 7.41 (1H, d, J=8.3 Hz)

(Step 6)

To a solution of the compound (14.4 g) obtained in step 5 in toluene (120 mL) were added DPPA (16.5 g) and triethylamine (8.36 mL) at room temperature, and the mixture was stirred at 100° C. for 2 hr. The reaction mixture was cooled, 8N aqueous sodium hydroxide solution (50 mL) was added, and the mixture was stirred at room temperature for 14 hr. The reaction mixture was poured into water, and the resultant product was extracted with ethyl acetate. The organic layer was washed with saturated aqueous ammonium chloride solution and brine and dried, and the solvent was evaporated under reduced pressure to give crude tert-butyl (3R*,4S*)-3-amino-4-(3,4-dichlorophenyl)pyrrolidine-1-carboxylate (13.3 g, 100%) as a brown oil.

MS (ESI+): 258 (M-$^t$BuO+H)

(Step 7)

To a solution of the compound (4.07 g) obtained in step 6 and 3,5-bis(trifluoromethyl)benzoic acid (4.78 g) in acetonitrile (60 mL) were added WSC.HCl (3.55 g) and HOBt (1.88 g), and the mixture was stirred at room temperature for 14 hr. The reaction mixture was poured into water, and the resultant product was extracted with ethyl acetate. The organic layer was washed with saturated aqueous sodium hydrogen carbonate solution, water, 1N hydrochloric acid and brine and dried, and the solvent was evaporated under reduced pressure. The obtained residue was purified by silica gel column chromatography (solvent gradient; 0→33% ethyl acetate/hexane) to give the title compound (3.45 g, 49%) as a white powder.

MS (ESI+): 515 (M-$^t$Bu+2H)

Reference Example 23 tert-butyl (3R,4R)-4-({[3,5-bis(trifluoromethyl)phenyl]carbonyl}amino)-3-(3,4-dichlorophenyl)piperidine-1-carboxylate (Step 1)

To a solution of the compound (22.0 g) obtained in Reference Example 1, step 3 in acetonitrile (100 mL) were added potassium carbonate (8.13 g) and ethyl iodide (47 mL), and the mixture was stirred at 60° C. for 14 hr. The insoluble material was filtered off, and ethyl acetate (300 mL) was added to the filtrate. The solution was washed with 10% aqueous citric acid solution (100 mL), water and brine and dried, and the solvent was evaporated under reduced pressure. The obtained residue was purified by silica gel column chromatography (solvent; 15% ethyl acetate/hexane) to give 4-ethyl 1-tert-butyl (3R*,4R*)-3-(3,4-dichlorophenyl)piperidine-1,4-dicarboxylate (22.2 g, 93%) as white crystals.

$^1$H-NMR (CDCl$_3$) δ 1.05 (3H, t, J=7.2 Hz), 1.47 (9H, s), 1.65-1.80 (1H, m), 1.95-2.05 (1H, m), 2.60-3.00 (4H, m), 3.96 (2H, q, J=7.2 Hz), 4.00-4.40 (2H, br), 7.06 (1H, dd, J=8.4, 2.4 Hz), 7.31 (1H, d, J=2.4 Hz), 7.36 (1H, d, J=8.4 Hz)

(Step 2)

The compound (4.4 g) obtained in step 1 was optically resolved by chiral column chromatography. The collected fraction with a short retention time was concentrated to give 4-ethyl 1-tert-butyl (3S,4S)-3-(3,4-dichlorophenyl)piperidine-1,4-dicarboxylate (2.14 g), and the collected fraction with a long retention time was concentrated to give 4-ethyl 1-tert-butyl (3R,4R)-3-(3,4-dichlorophenyl)piperidine-1,4-dicarboxylate (1.57 g), each as a colorless oil.

Purification Conditions by Chiral Column Chromatography
    Column: CHIRALPAK AD 50 mmID×500 mL
    Solvent: hexane/2-propanol=950/50 (v/v)
    Flow rate: 80 mL/min
    Temperature: 30° C.
    Detection method: UV 220 nm
    4-ethyl 1-tert-butyl (3S,4S)-3-(3,4-dichlorophenyl)piperidine-1,4-dicarboxylate (compound with short retention time)
    MS (ESI+): 328 (M-$^t$BuO)
    $[α]_D^{25}$ −13.7° (c 0.25, MeOH)
    4-ethyl 1-tert-butyl (3R,4R)-3-(3,4-dichlorophenyl)piperidine-1,4-dicarboxylate (compound with long retention time)
    MS (ESI+): 328 (M-$^t$BuO)
    $[α]_D^{25}$ +13.8° (c 0.25, MeOH)

(Step 3a)

To a solution of the compound (1.50 g) obtained in step 2 and having a long retention time in ethanol (10 mL) was added 8N aqueous sodium hydroxide solution (2.3 mL), and the mixture was stirred at 90° C. for 1 hr. The reaction mixture was cooled, and the reaction mixture was made slightly acidic with aqueous citric acid solution. The resultant product was extracted with ethyl acetate, and the organic layer was washed with water and dried, and the solvent was evaporated under reduced pressure to give (3R,4R)-1-(tert-butoxycarbonyl)-3-(3,4-dichlorophenyl)piperidine-4-carboxylic acid (1.19 g, 85%) as a white powder.

$[α]_D^{25}$ +22.7° (c 0.26, MeOH)

(Step 3b)

A solution of the compound (71.7 g) obtained in Reference Example 1, step 3 in DMF (576 mL) was heated to 60° C., and a mixture of (R)-(−)-1-phenylethylamine (11.6 g) in DMF (192 mL) and water (76.8 mL) was added dropwise. The mixture was stirred at room temperature for 24 hr, and the precipitate was collected by filtration, and washed with DMF and water to give a white powder (29.3 g, 31%, 99.0% de). The obtained white powder (4.76 g) and citric acid (2.23 g) were dissolved in water (19 mL) and THF (19 mL), and the mixture was extracted with ethyl acetate. The organic layer was washed with water and brine and dried, and the solvent was evaporated under reduced pressure to give (3R,4R)-1-(tert-butoxycarbonyl)-3-(3,4-dichlorophenyl)piperidine-4-carboxylic acid (3.41 g, 95%) as a white powder.

(Step 4)

To a solution of the compound (1.30 g) obtained in step 3a or step 3b in toluene (7 mL) were added DPPA (1.18 g) and triethylamine (0.60 mL) at room temperature, and the mixture was stirred at 100° C. for 2 hr. The reaction mixture was cooled, 8N aqueous sodium hydroxide solution (3.4 mL) was added, and the mixture was stirred at room temperature for 2 hr. The reaction mixture was poured into water, and the resultant product was extracted with ethyl acetate. The organic layer was washed with saturated aqueous ammonium chloride solution and brine and dried, and the solvent was evaporated under reduced pressure. To the obtained residue was added p-toluenesulfonic acid monohydrate (0.55 g), and the mixture was crystallized from ethyl acetate to give tert-butyl (3R,4R)-4-amino-3-(3,4-dichlorophenyl)piperidine-1-carboxylate p-toluenesulfonate (1.12 g, 75%) as a white powder.

$[\alpha]_D^{25}$ +14.3° (c 0.25, MeOH)

(Step 5)

To a solution of the compound (1.06 g) obtained in step 4, 3,5-bis(trifluoromethyl)benzoic acid (0.79 g) and triethylamine (0.28 mL) in acetonitrile (15 mL) were added WSC.HCl (0.78 g) and HOBt (0.62 g), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 10→33% ethyl acetate/hexane) to give the title compound (1.15 g, 96%) as a white powder.

$[\alpha]_D^{25}$ −20.7° (c 0.26, MeOH)

Reference Example 24 tert-butyl (3S,4S)-4-({[3,5-bis(trifluoromethyl)phenyl]carbonyl}amino)-3-(3,4-dichlorophenyl)piperidine-1-carboxylate (Step 1)

To a solution of the compound (2.0 g) obtained in Reference Example 23, step 2 and having a short retention time in ethanol (10 mL) was added 8N aqueous sodium hydroxide solution (3.1 mL), and the mixture was stirred at 90° C. for 1 hr. The reaction mixture was cooled, and the reaction mixture was made slightly acidic with aqueous citric acid solution. The resultant product was extracted with ethyl acetate, and the organic layer was washed with water and dried, and the solvent was evaporated under reduced pressure to give (3S,4S)-1-(tert-butoxycarbonyl)-3-(3,4-dichlorophenyl)piperidine-4-carboxylic acid (1.66 g, 89%) as a white powder.

$[\alpha]_D^{25}$ −25.5° (c 0.26, MeOH)

(Step 2)

To a solution of the compound (1.30 g) obtained in step 1 in toluene (8 mL) were added DPPA (1.43 g) and triethylamine (0.73 mL) at room temperature, and the mixture was stirred at 100° C. for 2 hr. The reaction mixture was cooled, 8N aqueous sodium hydroxide solution (4.4 mL) was added, and the mixture was stirred at room temperature for 2 hr. The reaction mixture was poured into water, and the resultant product was extracted with ethyl acetate. The organic layer was washed with saturated aqueous ammonium chloride solution and brine and dried, and the solvent was evaporated under reduced pressure. To the obtained residue was added p-toluenesulfonic acid monohydrate (0.66 g), and the mixture was crystallized from ethyl acetate to give tert-butyl (3S,4S)-4-amino-3-(3,4-dichlorophenyl)piperidine-1-carboxylate p-toluenesulfonate (1.57 g, 87%) as a white powder.

$[\alpha]_D^{25}$ −20.0° (c 0.25, MeOH)

(Step 3)

To a solution of the compound (1.48 g) obtained in step 2, 3,5-bis(trifluoromethyl)benzoic acid (1.10 g) and triethylamine (0.40 mL) in acetonitrile (15 mL) were added WSC.HCl (1.10 g) and HOBt (0.88 g), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 10→33% ethyl acetate/hexane) to give the title compound (1.65 g, 98%) as a white powder.

$[\alpha]_D^{25}$ +14.3° (c 0.25, MeOH)

Reference Example 25

(3R*,4R*)-1-[(1-acetylpiperidin-4-yl)carbonyl]-3-(3,4-dichlorophenyl)-N-methylpiperidin-4-amine (Step 1)

To a solution of the compound (1.03 g) obtained in Reference Example 1 and pyridine (0.40 mL) in THF (10 mL) was added trifluoroacetic anhydride (0.35 mL) at 0° C., and the mixture was stirred at 0° C. for 3 hr. To the reaction mixture was added aqueous sodium hydrogen carbonate solution, and the resultant product was extracted with ethyl acetate. The organic layer was washed with water, 1N hydrochloric acid and brine and dried, and the solvent was evaporated under reduced pressure. The obtained residue was purified by silica gel column chromatography (solvent gradient; 10→40% ethyl acetate/hexane) to give tert-butyl (3R*,4R*)-3-(3,4-dichlorophenyl)-4-[(trifluoroacetyl)amino]piperidine-1-carboxylate (0.84 g, 95%) as a white powder.

MS (ESI+): 367 (M−$^t$BuO)

(Step 2)

To a solution of the compound (0.80 g) obtained in step 1 in DMF (8 mL) was added sodium hydride (60% in oil, 0.094 g) at 0° C., and the mixture was stirred at 0° C. for 15 min. Furthermore, methyl iodide (0.17 mL) was added at 0° C., and the mixture was stirred at room temperature for 4 hr. The reaction mixture was poured into water, and the resultant product was extracted with ethyl acetate. The organic layer was washed with 1M KHSO$_4$ aqueous solution and brine and dried, and the solvent was evaporated under reduced pressure. The obtained residue was purified by silica gel column chromatography (solvent gradient; 5→40% ethyl acetate/hexane) to give tert-butyl (3R*,4R*)-3-(3,4-dichlorophenyl)-4-[methyl(trifluoroacetyl)amino]piperidine-1-carboxylate (0.72 g, 89%) as a pale yellow powder.

MS (ESI+): 381 (M−$^t$BuO)

(Step 3)

To a solution of the compound (0.69 g) obtained in step 2 in ethyl acetate (6 mL) was added 4N hydrogen chloride/ethyl acetate (3 mL) at room temperature, and the mixture was stirred at room temperature for 4 hr. The reaction mixture was evaporated under reduced pressure to give N-[(3R*,4R*)-3-(3,4-dichlorophenyl)piperidin-4-yl]-2,2,2-trifluoro-N-methylacetamide monohydrochloride (0.51 g, 85%) as a white powder.

MS (ESI+): 355 (M−HCl+H)

(Step 4)

To a solution of the compound (0.49 g) obtained in step 3, 1-acetylpiperidine-4-carboxylic acid (0.33 g) and triethylamine (0.53 mL) in DMF (5 mL) was added DEPC (0.29 mL), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 0→9% methanol/ethyl acetate) to give N-[(3R*,4R*)-1-[(1-acetylpiperidin-4-yl)carbonyl]-3-(3,4-dichlorophenyl)piperidin-4-yl]-2,2,2-trifluoro-N-methylacetamide (0.66 g, 100%) as a white powder.

MS (ESI+): 508 (M+H)

(Step 5)

To a mixture of the compound (0.66 g) obtained in step 4 in methanol (6.5 mL) and water (1.3 mL) was added potassium carbonate (0.35 g) at room temperature, and the mixture was stirred at 50° C. for 24 hr. Furthermore, potassium carbonate (1.70 g) was added, and the mixture was stirred at 50° C. for 6 days. The organic solvent was evaporated under reduced pressure, and the residue was poured into saturated aqueous sodium hydrogen carbonate solution and ethyl acetate. The organic layer was washed with brine and dried, and the solvent was evaporated under reduced pressure. The obtained residue was purified by silica gel column chromatography (NH Chromatorex) (solvent gradient; 0→9% methanol/ethyl acetate) to give the title compound (0.30 g, 58%) as a white powder.

MS (ESI+): 412 (M+H)

The compounds described in Reference Examples 1-25 are as follows (Tables 1-4).

TABLE 1

| Ref. Ex. No. | chemical formula |
|---|---|
| 1 | (structure) |
| 2 | (structure, cis/trans) |
| 3 | (structure) |
| 4 | (structure) |
| 5 | (structure) |
| 6 | (structure) |
| 7 | (structure) |

TABLE 1-continued
Ref. Ex. No. | chemical formula
---|---
8 | 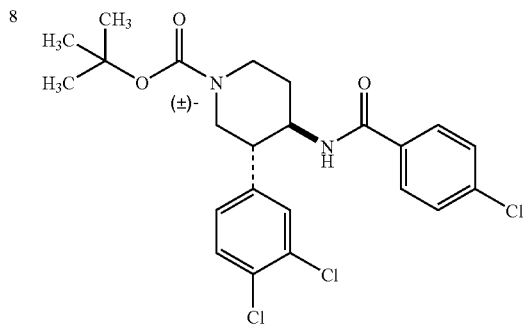
 | 
TABLE 2
Ref. Ex. No. | chemical formula
---|---
9 | 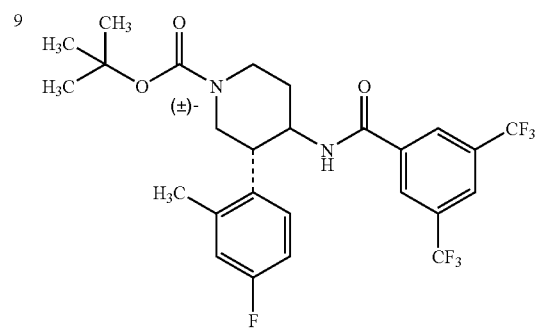
10 | 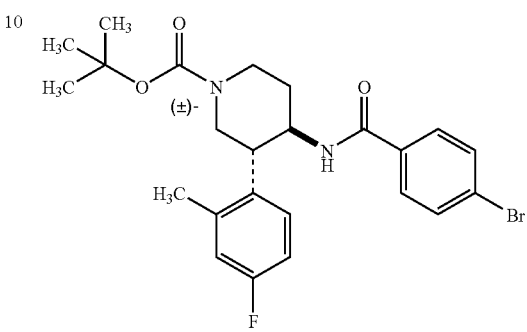
11 | 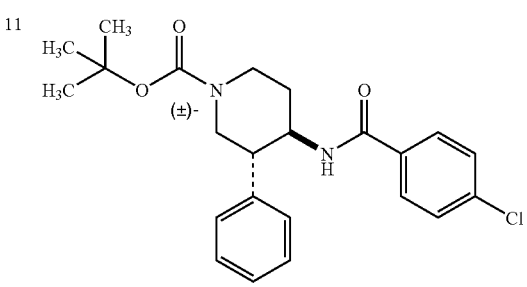
TABLE 2-continued
Ref. Ex. No. | chemical formula
---|---
12 | 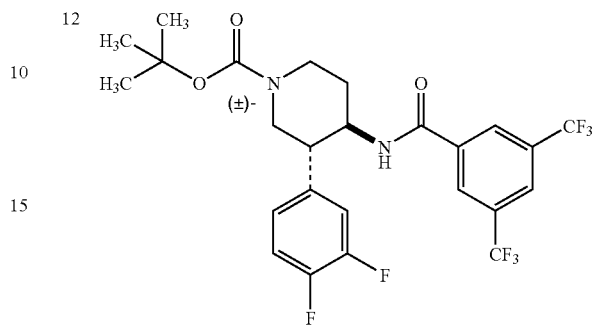
13 | 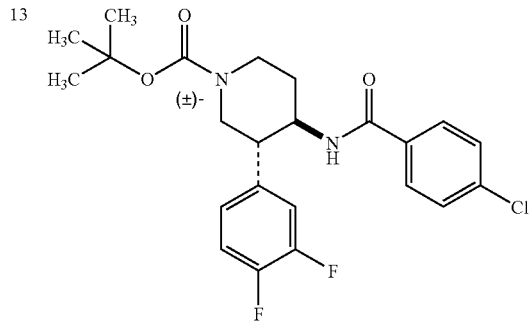
14 | 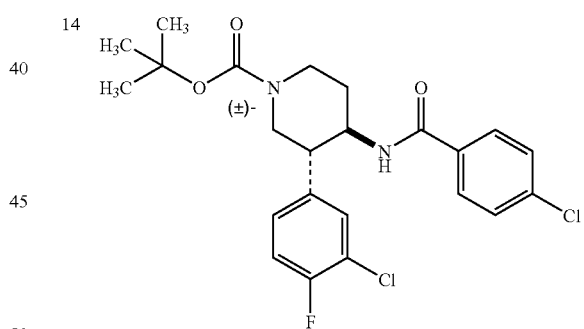
15 | 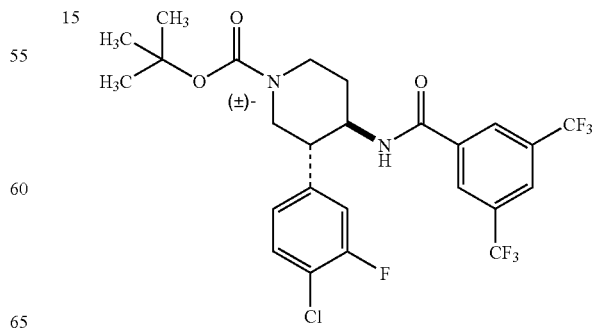

TABLE 2-continued

| Ref. Ex. No. | chemical formula |
|---|---|
| 16 | tert-butyl (±)-3-(3,4-dichloro... 4-chlorobenzamide piperidine-1-carboxylate (structure with 4-chlorobenzamide and 3-chloro-4-fluorophenyl) |

TABLE 3

| Ref. Ex. No. | chemical formula |
|---|---|
| 17 | tert-butyl (±) piperidine carboxylate with 3-chloro-4-methylphenyl and 3,5-bis(trifluoromethyl)benzamide |
| 18 | tert-butyl (±) piperidine carboxylate with 4-chloro-3-methylphenyl and 3,5-bis(trifluoromethyl)benzamide |
| 19 | tert-butyl (±) piperidine carboxylate with 2-methylphenyl and 3,5-bis(trifluoromethyl)benzamide |

TABLE 3-continued

| Ref. Ex. No. | chemical formula |
|---|---|
| 20 | tert-butyl (±) piperidine carboxylate with phenyl and 3,5-bis(trifluoromethyl)benzamide |
| 21 | tert-butyl (±) piperidine carboxylate with 3-chloro-4-fluorophenyl and 3,5-bis(trifluoromethyl)benzamide |
| 22 | tert-butyl (±) pyrrolidine carboxylate with 3,4-dichlorophenyl and 3,5-bis(trifluoromethyl)benzamide |
| 23 | tert-butyl (3R,4R) piperidine carboxylate with 3,4-dichlorophenyl and 3,5-bis(trifluoromethyl)benzamide |

TABLE 3-continued

| Ref. Ex. No. | chemical formula |
|---|---|
| 24 | (structure: tert-butyl piperidine-1-carboxylate with 3-(3,4-dichlorophenyl) and 4-[N-methyl-N-(3,5-bis(trifluoromethyl)benzoyl)amino], (S,S) configuration) |

TABLE 4

| Ref. Ex. No. | chemical formula |
|---|---|
| 25 | (±)- (structure: 1-acetyl-piperidine-4-carbonyl linked to 3-(3,4-dichlorophenyl)-4-(methylamino)piperidine) |

Example 1 tert-butyl (3R*,4R*)-4-[{[3,5-bis(trifluoromethyl)phenyl]carbonyl}(methyl)amino]-3-(3,4-dichlorophenyl)piperidine-1-carboxylate To a solution of the compound (2.34 g) obtained in Reference Example 1 in DMF (15 mL) was added sodium hydride (60% in oil, 0.32 g) at 0° C., and the mixture was stirred at 0° C. for 30 min. Furthermore, methyl iodide (1.25 mL) was added at 0° C., and the mixture was stirred at room temperature for 2 hr or longer. The reaction mixture was poured into water, and the resultant product was extracted with ethyl acetate. The organic layer was washed with aqueous ammonium chloride solution and brine and dried, and the solvent was evaporated under reduced pressure. The obtained residue was purified by silica gel column chromatography (solvent gradient; 50→100% ethyl acetate/hexane) to give the title compound (1.74 g, 73%) as a white powder.
MS (ESI+): 543 (M-$^t$Bu+2H)

Example 2

N-[(3R*,4R*)-3-(3,4-dichlorophenyl)piperidin-4-yl]-N-methyl-3,5-bis(trifluoromethyl)benzamide monohydrochloride To a solution of the compound (1.70 g) obtained in Example 1 in ethyl acetate (5 mL) was added 4N hydrogen chloride/ethyl acetate solution (5 mL), and the mixture was stirred at 50° C. for 2 hr with heating. The reaction mixture was concentrated under reduced pressure, ethyl acetate was added to the residue, and the mixture was made basic with aqueous sodium hydrogen carbonate solution. The organic layer was separated, washed with water, and the solvent was evaporated under reduced pressure. The obtained residue was treated with 1 equivalent of 4N hydrogen chloride/ethyl acetate to give the title compound (1.52 g, 100%) as a white powder.
MS (ESI+): 499 (M−HCl+H)

Example 3

N-[(3R*,4R*)-1-[(1-acetylpiperidin-4-yl)carbonyl-3-(3,4-dichlorophenyl)piperidin-4-yl]-N-methyl-3,5-bis(trifluoromethyl)benzamide To a solution of the compound (250 mg) obtained in Example 2, 1-acetylpiperidine-4-carboxylic acid (120 mg) and triethylamine (66 μL) in acetonitrile (10 mL) were added WSC.HCl (180 mg) and HOBt (110 mg), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (NH Chromatorex) (solvent gradient; 50→100% ethyl acetate/hexane) to give the title compound (180 mg, 61%) as a white powder.
MS (ESI+): 652 (M+H)

Example 4

N-[(3R*,4R*)-1-acetyl-3-(3,4-dichlorophenyl)piperidin-4-yl]-N-methyl-3,5-bis(trifluoromethyl)benzamide Using the compound obtained in Example 2 and acetic acid, and by the reaction and purification in the same manner as in Example 3, the title compound was obtained.
MS (ESI+): 541 (M+H)

Example 5 tert-butyl 4-{[(3R*,4R*)-4-[{[3,5-bis(trifluoromethyl)phenyl]carbonyl}(methyl)amino]-3-(3,4-dichlorophenyl)piperidin-1-yl]carbonyl}piperidine-1-carboxylate A mixture of N-[(3R*,4R*)-3-(3,4-dichlorophenyl)piperidin-4-yl]-N-methyl-3,5-bis(trifluoromethyl)benzamide monohydrochloride (0.90 g) obtained in Example 2, N-Boc-isonipecotic acid (1.52 g), WSC.HCl (0.82 mg) and HOBt (0.65 mg) was stirred at room temperature for 2 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 50→100% ethyl acetate/hexane, then 0→10% methanol/ethyl acetate) to give the title compound (1.19 g, 59%) as a white powder.
MS (ESI+): 610 (M-Boc+2H)

Example 6

N-[(3R*,4R*)-3-(3,4-dichlorophenyl)-1-(piperidin-4-ylcarbonyl)piperidin-4-yl]-N-methyl-3,5-bis(trifluoromethyl)benzamide monohydrochloride Using the compound obtained in Example 5, and by the reaction and purification in the same manner as in Example 2, the title compound was obtained.
MS (ESI+): 610 (M−HCl+H)

Example 7

N-[(3R*,4R*)-1-{[trans-4-(acetylamino)cyclohexyl]carbonyl}-3-(3,4-dichlorophenyl)piperidin-4-yl]-N-methyl-3,5-bis(trifluoromethyl)benzamide Using the compound obtained in Example 2 and trans-4-(acetylamino)cyclohexylcarboxylic acid, and by the reaction and purification in the same manner as in Example 3, the title compound was obtained.
MS (ESI+): 666 (M+H)

Example 8

N-{(3R*,4R*)-3-(3,4-dichlorophenyl)-1-[(2,6-dioxopiperidin-4-yl)carbonyl]piperidin-4-yl}-N-methyl-3,5-bis(trifluoromethyl)benzamide Using the compound obtained in Example 2 and (2,6-dioxopiperidin-4-yl)carboxylic acid, and by the reaction and purification in the same manner as in Example 3, the title compound was obtained.
MS (ESI+): 638 (M+H)

Example 9 tert-butyl (3R*,4S*)-4-[{[3,5-bis(trifluoromethyl)phenyl]carbonyl}(methyl)amino]-3-(3,4-dichlorophenyl)piperidine-1-carboxylate To a solution of the compound (4.57 g) obtained in Reference Example 2 in DMF (50 mL) was added sodium hydride (60% in oil, 0.47 g) at 0° C., and the mixture was stirred at 0° C. for 30 min. Furthermore, methyl iodide (2.43 mL) was added at 0° C., and the mixture was stirred at room temperature for 2 hr or longer. The reaction mixture was poured into water, and the resultant product was extracted with ethyl acetate. The organic layer was washed with aqueous ammonium chloride solution and brine and dried, and the solvent was evaporated under reduced pressure. The obtained residue was purified by silica gel column chromatography (solvent; 25% ethyl acetate/hexane) to give the title compound (2.40 g, 51%) as a white powder from less polar fractions.
MS (ESI+): 543 (M−$^t$Bu+2H)

Example 10

N-[(3R*,4S*)-3-(3,4-dichlorophenyl)piperidin-4-yl]-N-methyl-3,5-bis(trifluoromethyl)benzamide monohydrochloride Using the compound obtained in Example 9, and by the reaction and purification in the same manner as in Example 2, the title compound was obtained.
MS (ESI+): 499 (M−HCl+H)

Example 11

N-[(3R*,4S*)-1-acetyl-3-(3,4-dichlorophenyl)piperidin-4-yl]-N-methyl-3,5-bis(trifluoromethyl)benzamide Using the compound obtained in Example 10 and acetic acid, and by the reaction and purification in the same manner as in Example 3, the title compound was obtained.
MS (ESI+): 541 (M+H)

Example 12

N-[(3R*,4S*)-1-[(1-acetylpiperidin-4-yl)carbonyl]-3-(3,4-dichlorophenyl)piperidin-4-yl]-N-methyl-3,5-bis(trifluoromethyl)benzamide Using the compound obtained in Example 10 and 1-acetylpiperidine-4-carboxylic acid, and by the reaction and purification in the same manner as in Example 3, the title compound was obtained.
MS (ESI+): 652 (M+H)

Example 13 tert-butyl (3R*,4R*)-3-(3,4-dichlorophenyl)-4-[methyl(phenylcarbonyl)amino]piperidine-1-carboxylate Using the compound obtained in Reference Example 3, and by the reaction and purification in the same manner as in Example 1, the title compound was obtained.
MS (ESI+): 463 (M+H)

Example 14

N-[(3R*,4R*)-3-(3,4-dichlorophenyl)piperidin-4-yl]-N-methylbenzamide

To a solution of the compound (0.455 g) obtained in Example 13 in ethyl acetate (3 mL) was added 4N hydrogen chloride/ethyl acetate solution (3 mL), and the mixture was stirred at room temperature for 24 hr with heating. The reaction mixture was concentrated under reduced pressure, ethyl acetate was added to the residue, and the mixture was made basic with 2N aqueous sodium hydroxide solution. The organic layer was separated, washed with water, and the solvent was evaporated under reduced pressure to give the title compound (0.27 g, 75%) as a white powder.
MS (ESI+): 363 (M+H)

Example 15

N-[(3R*,4R*)-1-[(1-acetylpiperidin-4-yl)carbonyl]-3-(3,4-dichlorophenyl)piperidin-4-yl]-N-methylbenzamide Using the compound obtained in Example 14 and 1-acetylpiperidine-4-carboxylic acid, and by the reaction and purification in the same manner as in Example 3, the title compound was obtained.
MS (ESI+): 516 (M+H)

Example 16 tert-butyl (3R*,4R*)-4-{[(4-bromophenyl)carbonyl](methyl)amino}-3-(3,4-dichlorophenyl)piperidine-1-carboxylate Using the compound obtained in Reference Example 4, and by the reaction and purification in the same manner as in Example 1, the title compound was obtained.
MS (ESI+): 541 (M+H)

Example 17

4-bromo-N-[(3R*,4R*)-3-(3,4-dichlorophenyl)piperidin-4-yl]-N-methylbenzamide monohydrochloride Using the compound obtained in Example 16, and by the reaction and purification in the same manner as in Example 2, the title compound was obtained.
MS (ESI+): 441 (M−HCl+H)

Example 18

N-[(3R*,4R*)-1-[(1-acetylpiperidin-4-yl)carbonyl]-3-(3,4-dichlorophenyl)piperidin-4-yl]-4-bromo-N-methylbenzamide Using the compound obtained in Example 17 and 1-acetylpiperidine-4-carboxylic acid, and by the reaction and purification in the same manner as in Example 3, the title compound was obtained.
MS (ESI+): 594 (M+H)

Example 19 tert-butyl (3R*,4R*)-3-(3,4-dichlorophenyl)-4-{[(4-methoxyphenyl)carbonyl(methyl)amino}piperidine-1-carboxylate Using the compound obtained in Reference Example 5, and by the reaction and purification in the same manner as in Example 1, the title compound was obtained.
MS (ESI+): 493 (M+H)

Example 20

N-[(3R*,4R*)-3-(3,4-dichlorophenyl)piperidin-4-yl]-4-methoxy-N-methylbenzamide monohydrochloride Using the compound obtained in Example 19, and by the reaction and purification in the same manner as in Example 2, the title compound was obtained.
MS (ESI+): 393 (M−HCl+H)

Example 21

N-[(3R*,4R*)-1-[(1-acetylpiperidin-4-yl)carbonyl]-3-(3,4-dichlorophenyl)piperidin-4-yl]-4-methoxy-N-methylbenzamide Using the compound obtained in Example 20 and 1-acetylpiperidine-4-carboxylic acid, and by the reaction and purification in the same manner as in Example 3, the title compound was obtained.
MS (ESI+): 546 (M+H)

Example 22 tert-butyl (3R*,4R*)-3-(3,4-dichlorophenyl)-4-{methyl[(4-methylphenyl)carbonyl]amino]piperidine-1-carboxylate Using the compound obtained in Reference Example 6, and by the reaction and purification in the same manner as in Example 1, the title compound was obtained.
MS (ESI+): 477 (M+H)

Example 23

N-[(3R*,4R*)-3-(3,4-dichlorophenyl)piperidin-4-yl]-N,4-dimethylbenzamide

Using the compound obtained in Example 22, and by the reaction and purification in the same manner as in Example 14, the title compound was obtained.
MS (ESI+): 377 (M+H)

Example 24

N-[(3R*,4R*)-1-[(1-acetylpiperidin-4-yl)carbonyl]-3-(3,4-dichlorophenyl)piperidin-4-yl]-N,4-dimethylbenzamide Using the compound obtained in Example 23 and 1-acetylpiperidine-4-carboxylic acid, and by the reaction and purification in the same manner as in Example 3, the title compound was obtained.
MS (ESI+): 530 (M+H)

Example 25 tert-butyl (3R*,4R*)-3-(3,4-dichlorophenyl)-4-{[(4-fluorophenyl)carbonyl](methyl)amino}piperidine-1-carboxylate Using the compound obtained in Reference Example 7, and by the reaction and purification in the same manner as in Example 1, the title compound was obtained.
MS (ESI+): 425 (M-$^t$Bu+2H)

Example 26

N-[(3R*,4R*)-3-(3,4-dichlorophenyl)piperidin-4-yl]-4-fluoro-N-methylbenzamide

Using the compound obtained in Example 25, and by the reaction and purification in the same manner as in Example 14, the title compound was obtained.
MS (ESI+): 381 (M+H)

Example 27

N-[(3R*,4R*)-1-[(1-acetylpiperidin-4-yl)carbonyl]-3-(3,4-dichlorophenyl)piperidin-4-yl]-4-fluoro-N-methylbenzamide Using the compound obtained in Example 26 and 1-acetylpiperidine-4-carboxylic acid, and by the reaction and purification in the same manner as in Example 3, the title compound was obtained.
MS (ESI+): 534 (M+H)

Example 28 tert-butyl (3R*,4R*)-4-{[(4-chlorophenyl)carbonyl](methyl)amino}-3-(3,4-dichlorophenyl)piperidine-1-carboxylate Using the compound obtained in Reference Example 8, and by the reaction and purification in the same manner as in Example 1, the title compound was obtained.
MS (ESI+): 441 (M-$^t$Bu+2H)

Example 29

4-chloro-N-[(3R*,4R*)-3-(3,4-dichlorophenyl)piperidin-4-yl]-N-methylbenzamide monohydrochloride Using the compound obtained in Example 28, and by the reaction and purification in the same manner as in Example 2, the title compound was obtained.
MS (ESI+): 397 (M−HCl+H)

Example 30

N-[(3R*,4R*)-1-[(1-acetylpiperidin-4-yl)carbonyl]-3-(3,4-dichlorophenyl)piperidin-4-yl]-4-chloro-N-methylbenzamide Using the compound obtained in Example 29 and 1-acetylpiperidine-4-carboxylic acid, and by the reaction and purification in the same manner as in Example 3, the title compound was obtained.
MS (ESI+): 550 (M+H)

Example 31

N-[(3R*,4R*)-1-[(1-acetylpiperidin-4-yl)carbonyl]-3-(3,4-dichlorophenyl)piperidin-4-yl]-N-methylbiphenyl-4-carboxamide To a mixture of the compound obtained in Example 18 (0.20 g) in toluene (10 mL) and water (0.5 mL) were added phenylboronic acid (0.083 g), tetrakis(triphenylphosphine)palladium(0) (0.039 g) and potassium carbonate (0.047 g), and the mixture was stirred under an argon atmosphere at 100° C. for 14 hr. The reaction mixture was poured into water, and the resultant product was extracted with ethyl acetate. The organic layer was washed with aqueous ammonium chloride solution and brine and dried, and the solvent was evaporated under reduced pressure. The obtained residue was purified by silica gel column chromatography (NH Chromatorex) (solvent gradient; 75→100% ethyl acetate/hexane) to give the title compound (0.14 g, 69%) as a white powder.
MS (ESI+): 592 (M+H)

Example 32 tert-butyl (3R*,4R*)-4-[{[3,5-bis(trifluoromethyl)phenyl]carbonyl(methyl)amino]-3-(4-fluoro-2-methylphenyl)piperidine-1-carboxylate Using the compound obtained in Reference Example 9, and by the reaction and purification in the same manner as in Example 1, the title compound was obtained.
MS (ESI+): 507 (M-$^t$Bu+2H)

Example 33

N-[(3R*,4R*)-3-(4-fluoro-2-methylphenyl)piperidin-4-yl]-N-methyl-3,5-bis(trifluoromethyl)benzamide monohydrochloride Using the compound obtained in Example 32, and by the reaction and purification in the same manner as in Example 2, the title compound was obtained.
MS (ESI+): 463 (M−HCl+H)

Example 34

N-[(3R*,4R*)-1-[(1-acetylpiperidin-4-yl)carbonyl]-3-(4-fluoro-2-methylphenyl)piperidin-4-yl]-N-methyl-3,5-bis(trifluoromethyl)benzamide Using the compound obtained in Example 33 and 1-acetylpiperidine-4-carboxylic acid, and by the reaction and purification in the same manner as in Example 3, the title compound was obtained.
MS (ESI+): 616 (M+H)

Example 35

N-[(3R*,4R*)-1-(N-acetylglycyl)-3-(4-fluoro-2-methylphenyl)piperidin-4-yl]-N-methyl-3,5-bis(trifluoromethyl)benzamide Using the compound obtained in Example 33 and N-acetylglycine, and by the reaction and purification in the same manner as in Example 3, the title compound was obtained.
MS (ESI+): 562 (M+H)

Example 36

N-[(3R*,4R*)-3-(4-fluoro-2-methylphenyl)-1-(methoxyacetyl)piperidin-4-yl]-N-methyl-3,5-bis(trifluoromethyl)benzamide Using the compound obtained in Example 33 and methoxyacetic acid, and by the reaction and purification in the same manner as in Example 3, the title compound was obtained.
MS (ESI+): 535 (M+H)

Example 37 tert-butyl (3R*,4R*)-4-[{[3,5-bis(trifluoromethyl)phenyl]carbonyl}(methyl)amino]-3-(4-fluoro-2-methylphenyl)-1,4'-bipiperidine-1'-carboxylate To a solution of the compound (0.25 g) obtained in Example 33 and N-Boc-piperidone (0.99 g) in ethyl acetate (7.5 mL) was added triethylamine (0.080 mL), and the mixture was stirred at room temperature for 2 hr. Then, acetic acid (0.5 mL) and sodium triacetoxyborohydride (0.53 g) were added, and the mixture was stirred at room temperature for 14 hr. The reaction mixture was poured into water, the mixture was made basic with 2N aqueous sodium hydroxide solution, and the resultant product was extracted with ethyl acetate. The organic layer was washed with aqueous sodium hydrogen carbonate solution and brine and dried, and the solvent was evaporated under reduced pressure. The obtained residue was purified by silica gel column chromatography (solvent gradient; 15→50% ethyl acetate/hexane, then 5% methanol/ethyl acetate) to give the title compound (0.30 g, 92%) as a white powder.
MS (ESI+): 646 (M+H)

Example 38

N-[(3R*,4R*)-3-(4-fluoro-2-methylphenyl)-1,4'-bipiperidin-4-yl]-N-methyl-3,5-bis(trifluoromethyl)benzamide dihydrochloride Using the compound obtained in Example 37, and by the reaction and purification in the same manner as in Example 2, the title compound was obtained.
MS (ESI+): 546 (M-2HCl+H)

Example 39

N-[(3R*,4R*)-1'-acetyl-3-(4-fluoro-2-methylphenyl)-1,4'-bipiperidin-4-yl]-N-methyl-3,5-bis(trifluoromethyl)benzamide monohydrochloride To a solution of the compound obtained (0.13 g) in Example 38 and triethylamine (0.12 mL) in acetonitrile (5 mL) was added acetyl chloride (0.030 mL) at 0° C., and the mixture was stirred at room temperature for 14 hr. The reaction mixture was poured into water, the mixture was made basic with 2N aqueous sodium hydroxide solution, and the resultant product was extracted with ethyl acetate. The organic layer was washed with aqueous sodium hydrogen carbonate solution and brine and dried, and the solvent was evaporated under reduced pressure. The obtained residue was purified by silica gel column chromatography (NH Chromatorex) (solvent gradient; 50→100% ethyl acetate/hexane). The obtained residue was treated with 1 equivalent of 4N hydrogen chloride/ethyl acetate to give the title compound (0.072 g, 54%) as a white powder.
MS (ESI+): 588 (M−HCl+H)

Example 40 tert-butyl (3R*,4R*)-4-{[(4-bromophenyl)carbonyl](methyl)amino}-3-(4-fluoro-2-methylphenyl)-1,4'-bipiperidine-1'-carboxylate Using the compound obtained in Reference Example 10, and by the reaction and purification in the same manner as in Example 1, the title compound was obtained.
MS (ESI+): 449 (M-$^t$Bu+2H)

Example 41

4-bromo-N-[(3R*,4R*)-3-(4-fluoro-2-methylphenyl)piperidin-4-yl]-N-methylbenzamide Using the compound obtained in Example 40, and by the reaction and purification in the same manner as in Example 14, the title compound was obtained.
MS (ESI+): 405 (M+H)

Example 42

N-[(3R*,4R*)-1-[(1-acetylpiperidin-4-yl)carbonyl]-3-(4-fluoro-2-methylphenyl)piperidin-4-yl]-4-bromo-N-methylbenzamide Using the compound obtained in Example 41 and 1-acetylpiperidine-4-carboxylic acid, and by the reaction and purification in the same manner as in Example 3, the title compound was obtained.
MS (ESI+): 558 (M+H)

Example 43 tert-butyl (3R*,4R*)-4-{[(4-chlorophenyl)carbonyl](methyl)amino}-3-phenylpiperidine-1-carboxylate Using the compound obtained in Reference Example 11, and by the reaction and purification in the same manner as in Example 1, the title compound was obtained.
MS (ESI+): 429 (M+H)

Example 44

4-chloro-N-methyl-N-[(3R*,4R*)-3-phenylpiperidin-4-yl]benzamide monohydrochloride Using the compound obtained in Example 43, and by the reaction and purification in the same manner as in Example 2, the title compound was obtained.
MS (ESI+): 329 (M−HCl+H)

Example 45

N-{(3R*,4R*)-1-[(1-acetylpiperidin-4-yl)carbonyl]-3-phenylpiperidin-4-yl}-4-chloro-N-methylbenzamide Using the compound obtained in Example 44 and 1-acetylpiperidine-4-carboxylic acid, and by the reaction and purification in the same manner as in Example 3, the title compound was obtained.
MS (ESI+): 482 (M+H)

Example 46 tert-butyl (3R*,4R*)-4-[{[3,5-bis(trifluoromethyl)phenyl]carbonyl}(methyl)amino]-3-(3,4-difluorophenyl)piperidine-1-carboxylate Using the compound obtained in Reference Example 12, and by the reaction and purification in the same manner as in Example 1, the title compound was obtained.
MS (ESI+): 511 (M-$^t$Bu+2H)

Example 47

N-[(3R*,4R*)-3-(3,4-difluorophenyl)piperidin-4-yl]-N-methyl-3,5-bis(trifluoromethyl)benzamide monohydrochloride Using the compound obtained in Example 46, and by the reaction and purification in the same manner as in Example 2, the title compound was obtained.
MS (ESI+): 467 (M−HCl+H)

Example 48

N-[(3R*,4R*)-1-[(1-acetylpiperidin-4-yl)carbonyl]-3-(3,4-difluorophenyl)piperidin-4-yl]-N-methyl-3,5-bis(trifluoromethyl)benzamide Using the compound obtained in Example 47 and 1-acetylpiperidine-4-carboxylic acid, and by the reaction and purification in the same manner as in Example 3, the title compound was obtained.
MS (ESI+): 620 (M+H)

Example 49 tert-butyl (3R*,4R*)-4-{[(4-chlorophenyl)carbonyl
(methyl)amino}-3-(3,4-difluorophenyl)piperidine-1-
carboxylate Using the compound obtained in Reference Example 13,
and by the reaction and purification in the same manner as in
Example 1, the title compound was obtained.
MS (ESI+): 409 (M-$^t$Bu+2H)

Example 50

4-chloro-N-[(3R*,4R*)-3-(3,4-difluorophenyl)pip-
eridin-4-yl]-N-methylbenzamide monohydrochloride Using the compound obtained in Example 49, and by the
reaction and purification in the same manner as in Example 2,
the title compound was obtained.
MS (ESI+): 365 (M−HCl+H)

Example 51

N-[(3R*,4R*)-1-[(1-acetylpiperidin-4-yl)carbonyl]-
3-(3,4-difluorophenyl)piperidin-4-yl]-4-chloro-N-
methylbenzamide Using the compound obtained in Example 50 and
1-acetylpiperidine-4-carboxylic acid, and by the reaction and
purification in the same manner as in Example 3, the title
compound was obtained.
MS (ESI+): 518 (M+H)

Example 52 tert-butyl (3R*,4R*)-3-(3-chloro-4-fluorophenyl)-4-
{[(4-chlorophenyl)carbonyl](methyl)
amino}piperidine-1-carboxylate Using the compound obtained in Reference Example 14,
and by the reaction and purification in the same manner as in
Example 1, the title compound was obtained.
MS (ESI+): 425 (M-$^t$Bu+2H)

Example 53

4-chloro-N-[(3R*,4R*)-3-(3-chloro-4-fluorophenyl)
piperidin-4-yl]-N-methylbenzamide monohydrochlo-
ride Using the compound obtained in Example 52, and by the
reaction and purification in the same manner as in Example 2,
the title compound was obtained.
MS (ESI+): 381 (M−HCl+H)

Example 54

N-[(3R*,4R*)-1-[(1-acetylpiperidin-4-yl)carbonyl]-
3-(3-chloro-4-fluorophenyl)piperidin-4-yl]-4-chloro-
N-methylbenzamide Using the compound obtained in Example 78 and
1-acetylpiperidine-4-carboxylic acid, and by the reaction and
purification in the same manner as in Example 3, the title
compound was obtained.
MS (ESI+): 534 (M+H)

Example 55 tert-butyl (3R*,4R*)-4-[{[3,5-bis(trifluoromethyl)
phenyl]carbonyl}(methyl)amino]-3-(3-chloro-4-fluo-
rophenyl)-1,4'-bipiperidine-1'-carboxylate Using the compound obtained in Example 53 and N-Boc-
piperidone, and by the reaction and purification in the same
manner as in Example 37, the title compound was obtained.
MS (ESI+): 666 (M+H)

Example 56 tert-butyl (3R*,4R*)-4-[{[3,5-bis(trifluoromethyl)
phenyl]carbonyl}(methyl)amino]-3-(4-chloro-3-fluo-
rophenyl)piperidine-1-carboxylate Using the compound obtained in Reference Example 15,
and by the reaction and purification in the same manner as in
Example 1, the title compound was obtained.
MS (ESI+): 527 (M-$^t$Bu+2H)

Example 57

N-[(3R*,4R*)-3-(4-chloro-3-fluorophenyl)piperidin-
4-yl]-N-methyl-3,5-bis(trifluoromethyl)benzamide
monohydrochloride Using the compound obtained in Example 56, and by the
reaction and purification in the same manner as in Example 2,
the title compound was obtained.
MS (ESI+): 483 (M−HCl+H)

Example 58

N-[(3R*,4R*)-1-[(1-acetylpiperidin-4-yl)carbonyl]-
3-(4-chloro-3-fluorophenyl)piperidin-4-yl]-N-me-
thyl-3,5-bis(trifluoromethyl)benzamide Using the compound obtained in Example 57 and
1-acetylpiperidine-4-carboxylic acid, and by the reaction and
purification in the same manner as in Example 3, the title
compound was obtained.
MS (ESI+): 636 (M+H)

Example 59 tert-butyl (3R*,4R*)-3-(4-chloro-3-fluorophenyl)-4-
{[(4-chlorophenyl)carbonyl](methyl)
amino}piperidine-1-carboxylate Using the compound obtained in Reference Example 16,
and by the reaction and purification in the same manner as in
Example 1, the title compound was obtained.
MS (ESI+): 425 (M-$^t$Bu+2H)

Example 60

4-chloro-N-[(3R*,4R*)-3-(4-chloro-3-fluorophenyl)
piperidin-4-yl]-N-methylbenzamide monohydrochlo-
ride Using the compound obtained in Example 59, and by the
reaction and purification in the same manner as in Example 2,
the title compound was obtained.
MS (ESI+): 381 (M−HCl+H)

Example 61

N-[(3R*,4R*)-1-[(1-acetylpiperidin-4-yl)carbonyl]-3-(4-chloro-3-fluorophenyl)piperidin-4-yl]-4-chloro-N-methylbenzamide Using the compound obtained in Example 60 and 1-acetylpiperidine-4-carboxylic acid, and by the reaction and purification in the same manner as in Example 3, the title compound was obtained.
MS (ESI+): 534 (M+H)

Example 62 tert-butyl (3R*,4R*)-4-[{[3,5-bis(trifluoromethyl)phenyl]carbonyl(methyl)amino}-3-(3-chloro-4-methylphenyl)piperidine-1-carboxylate Using the compound obtained in Reference Example 17, and by the reaction and purification in the same manner as in Example 1, the title compound was obtained.
MS (ESI+): 523 (M-$^t$Bu+2H)

Example 63

N-[(3R*,4R*)-3-(3-chloro-4-methylphenyl)piperidin-4-yl]-N-methyl-3,5-bis(trifluoromethyl)benzamide p-toluenesulfonate Using the compound obtained in Example 62, and by the reaction and purification in the same manner as in Example 2, the title compound was obtained.
MS (ESI+): 479 (M-p-TsOH+H)

Example 64

N-[(3R*,4R*)-1-[(1-acetylpiperidin-4-yl)carbonyl]-3-(3-chloro-4-methylphenyl)piperidin-4-yl]-N-methyl-3,5-bis(trifluoromethyl)benzamide Using the compound obtained in Example 63 and 1-acetylpiperidine-4-carboxylic acid, and by the reaction and purification in the same manner as in Example 3, the title compound was obtained.
MS (ESI+): 632 (M+H)

Example 65

N-[(3R*,4R*)-3-(3-chloro-4-methylphenyl)-1,4'-bipiperidin-4-yl]-N-methyl-3,5-bis(trifluoromethyl)benzamide dihydrochloride (Step 1)
Using the compound obtained in Example 63 and N-Boc-piperidone, and by the reaction and purification in the same manner as in Example 37, N-[(3R*,4R*)-3-(3-chloro-4-methylphenyl)-1,4'-bipiperidin-4-yl]-N-methyl-3,5-bis(trifluoromethyl)benzamide was obtained.
MS (ESI+): 662 (M+H)
(Step 2)
Using the compound obtained in step 1, and by the reaction and purification in the same manner as in Example 2, the title compound was obtained.
MS (ESI+): 562 (M-2HCl+H)

Example 66

N-[(3R*,4R*)-1'-acetyl-3-(3-chloro-4-methylphenyl)-1,4'-bipiperidin-4-yl]-N-methyl-3,5-bis(trifluoromethyl)benzamide monohydrochloride Using the compound obtained in Example 65, and by the reaction and purification in the same manner as in Example 39, the title compound was obtained.
MS (ESI+): 604 (M-HCl+H)

Example 67 tert-butyl (3R*,4R*)-4-[{[3,5-bis(trifluoromethyl)phenyl]carbonyl}(methyl)amino]-3-(4-chloro-3-methylphenyl)piperidine-1-carboxylate Using the compound obtained in Reference Example 18, and by the reaction and purification in the same manner as in Example 1, the title compound was obtained.
MS (ESI+): 523 (M-$^t$Bu+2H)

Example 68

N-[(3R*,4R*)-3-(4-chloro-3-methylphenyl)piperidin-4-yl]-N-methyl-3,5-bis(trifluoromethyl)benzamide monohydrochloride Using the compound obtained in Example 67, and by the reaction and purification in the same manner as in Example 2, the title compound was obtained.
MS (ESI+): 479 (M-HCl+H)

Example 69

N-[(3R*,4R*)-1-[(1-acetylpiperidin-4-yl)carbonyl]-3-(4-chloro-3-methylphenyl)piperidin-4-yl]-N-methyl-3,5-bis(trifluoromethyl)benzamide Using the compound obtained in Example 68 and 1-acetylpiperidine-4-carboxylic acid, and by the reaction and purification in the same manner as in Example 3, the title compound was obtained.
MS (ESI+): 632 (M+H)

Example 70 tert-butyl (3R*,4R*)-4-[{[3,5-bis(trifluoromethyl)phenyl]carbonyl}(methyl)amino]-3-(2-methylphenyl)piperidine-1-carboxylate Using the compound obtained in Reference Example 19, and by the reaction and purification in the same manner as in Example 1, the title compound was obtained.
MS (ESI+): 489 (M-$^t$Bu+2H)

Example 71

N-methyl-N-[(3R*,4R*)-3-(2-methylphenyl)piperidin-4-yl]-3,5-bis(trifluoromethyl)benzamide monohydrochloride Using the compound obtained in Example 60, and by the reaction and purification in the same manner as in Example 2, the title compound was obtained.
MS (ESI+): 445 (M-HCl+H)

Example 72

N-[(3R*,4R*)-1-[(1-acetylpiperidin-4-yl)carbonyl]-
3-(2-methylphenyl)piperidin-4-yl]-N-methyl-3,5-bis
(trifluoromethyl)benzamide Using the compound obtained in Example 71 and
1-acetylpiperidine-4-carboxylic acid, and by the reaction and
purification in the same manner as in Example 3, the title
compound was obtained.
MS (ESI+): 598 (M+H)

Example 73 tert-butyl (3R*,4R*)-4-[{[3,5-bis(trifluoromethyl)
phenyl]carbonyl}(methyl)amino]-3-phenylpiperi-
dine-1-carboxylate Using the compound obtained in Reference Example 20,
and by the reaction and purification in the same manner as in
Example 1, the title compound was obtained.
MS (ESI+): 475 (M-$^t$Bu+2H)

Example 74

N-methyl-N-[(3R*,4R*)-3-phenylpiperidin-4-yl]-3,
5-bis(trifluoromethyl)benzamide monohydrochloride Using the compound obtained in Example 73, and by the
reaction and purification in the same manner as in Example 2,
the title compound was obtained.
MS (ESI+): 431 (M−HCl+H)

Example 75

N-{(3R*,4R*)-1-[(1-acetylpiperidin-4-yl)carbonyl]-
3-phenylpiperidin-4-yl}-N-methyl-3,5-bis(trifluo-
romethyl)benzamide Using the compound obtained in Example 74 and
1-acetylpiperidine-4-carboxylic acid, and by the reaction and
purification in the same manner as in Example 3, the title
compound was obtained.
MS (ESI+): 584 (M+H)

Example 76 tert-butyl (3R*,4R*)-4-[{[3,5-bis(trifluoromethyl)
phenyl]carbonyl}(methyl)amino]-3-phenyl-1,4'-bipi-
peridine-1'-carboxylate Using the compound obtained in Example 74 and N-Boc-
piperidone, and by the reaction and purification in the same
manner as in Example 37, the title compound was obtained.
MS (ESI+): 614 (M+H)

Example 77 tert-butyl (3R*,4R*)-4-[{[3,5-bis(trifluoromethyl)
phenyl]carbonyl}(methyl)amino]-3-(3-chloro-4-fluo-
rophenyl)piperidine-1-carboxylate Using the compound obtained in Reference Example 21,
and by the reaction and purification in the same manner as in
Example 1, the title compound was obtained.
MS (ESI+): 527 (M-$^t$Bu+2H)

Example 78

N-[(3R*,4R*)-3-(3-chloro-4-fluorophenyl)piperidin-
4-yl]-N-methyl-3,5-bis(trifluoromethyl)benzamide
monohydrochloride Using the compound obtained in Example 77, and by the
reaction and purification in the same manner as in Example 2,
the title compound was obtained.
MS (ESI+): 483 (M−HCl+H)

Example 79

N-[(3R*,4R*)-1-[(1-acetylpiperidin-4-yl)carbonyl]-
3-(3-chloro-4-fluorophenyl)piperidin-4-yl]-N-me-
thyl-3,5-bis(trifluoromethyl)benzamide Using the compound obtained in Example 78 and
1-acetylpiperidine-4-carboxylic acid, and by the reaction and
purification in the same manner as in Example 3, the title
compound was obtained.
MS (ESI+): 636 (M+H)

Example 80 tert-butyl (3S*,4R*)-3-[{[3,5-bis(trifluoromethyl)
phenyl]carbonyl}(methyl)amino]-4-(3,4-dichlo-
rophenyl)pyrrolidine-1-carboxylate Using the compound obtained in Reference Example 22,
and by the reaction and purification in the same manner as in
Example 1, the title compound was obtained.
MS (ESI+): 529 (M-$^t$Bu+2H)

Example 81

N-[(3S*,4R*)-4-(3,4-dichlorophenyl)pyrrolidin-3-
yl]-N-methyl-3,5-bis(trifluoromethyl)benzamide
monohydrochloride Using the compound obtained in Example 80, and by the
reaction and purification in the same manner as in Example 2,
the title compound was obtained.
MS (ESI+): 485 (M−HCl+H)

Example 82

N-[(3S*,4R*)-1-[(1-acetylpiperidin-4-yl)carbonyl]-
4-(3,4-dichlorophenyl)pyrrolidin-3-yl]-N-methyl-3,
5-bis(trifluoromethyl)benzamide Using the compound obtained in Example 81 and
1-acetylpiperidine-4-carboxylic acid, and by the reaction and
purification in the same manner as in Example 3, the title
compound was obtained.
MS (ESI+): 638 (M+H)

Example 83

N-[(3S*,4R*)-4-(3,4-dichlorophenyl)-1-piperidin-4-
ylpyrrolidin-3-yl]-N-methyl-3,5-bis(trifluoromethyl)
benzamide dihydrochloride (Step 1)
Using the compound obtained in Example 81 and N-Boc-
piperidone, and by the reaction and purification in the same
manner as in Example 37, tert-butyl 4-[(3S*,4R*)-3-[{[3,5- bis(trifluoromethyl)phenyl]carbonyl}(methyl)amino]-4-(3,4-dichlorophenyl)pyrrolidin-1-yl]piperidine-1-carboxylate was obtained.
MS (ESI+): 668 (M+H)
(Step 2)
Using the compound obtained in step 1, and by the reaction and purification in the same manner as in Example 2, the title compound was obtained.
MS (ESI+): 568 (M−2HCl+H)

Example 84

N-[(3S*,4R*)-1-(1-acetylpiperidin-4-yl)-4'-(3,4-dichlorophenyl)pyrrolidin-3-yl]-N-methyl-3,5-bis(trifluoromethyl)benzamide monohydrochloride Using the compound obtained in Example 83, and by the reaction and purification in the same manner as in Example 39, the title compound was obtained.
MS (ESI+): 610 (M−HCl+H)

Example 85

(+)-N-[((3S*,4R*)-1-[(1-acetylpiperidin-4-yl)carbonyl]-3-(3,4-dichlorophenyl)piperidin-4-yl]-N-methyl-3,5-bis(trifluoromethyl)benzamide Example 86

(−)-N-[(3S*,4R*)-1-[(1-acetylpiperidin-4-yl)carbonyl]-3-(3,4-dichlorophenyl)piperidin-4-yl]-N-methyl-3,5-bis(trifluoromethyl)benzamide The compound obtained in Example 12 (1.40 g) was optically resolved by chiral column chromatography. The collected fraction with a short retention time was concentrated to give the compound (0.66 g) of Example 85, and the collected fraction with a long retention time was concentrated to give the compound (0.66 g) of Example 86, each as a white powder.
Purification Conditions by Chiral Column Chromatography
 Column: CHIRALPAK AD 50 mmID×500 mL
 Solvent: hexane/2-propanol=500/500 (v/v)
 Flow rate: 80 mL/min
 Temperature: 30° C.
 Detection method: UV 220 nm
 Compound of Example 85
 MS (ESI+): 652 (M+H)
 $[\alpha]_D^{25}$ +102.2° (c 0.25, MeOH)
 Compound of Example 86
 MS (ESI+): 652 (M+H)
 $[\alpha]_D^{25}$ −103.2° (c 0.25, MeOH)

Example 87 tert-butyl 4-{[(3R,4R)-4-[{[3,5-bis(trifluoromethyl)phenyl]carbonyl}(methyl)amino]-3-(3,4-dichlorophenyl)piperidin-1-yl]carbonyl}piperidine-1-carboxylate Example 88 tert-butyl 4-{[(3S,4S)-4-[{[3,5-bis(trifluoromethyl)phenyl]carbonyl}(methyl)amino]-3-(3,4-dichlorophenyl)piperidin-1-yl]carbonyl}piperidine-1-carboxylate The compound (1.28 g) obtained in Example 5 was optically resolved by chiral column chromatography. The collected fraction with a short retention time was concentrated to give the compound (0.58 g) of Example 87, and the collected fraction with a long retention time was concentrated to give the compound (0.58 g) of Example 88, each as a white powder.
Purification Conditions by Chiral Column Chromatography
 Column: CHIRALPAK AD 50 mmID×500 mL
 Solvent: hexane/2-propanol=900/100 (v/v)
 Flow rate: 80 mL/min
 Temperature: 30° C.
 Detection method: UV 220 nm
 Compound of Example 87
 MS (ESI+): 610 (M−Boc+2H)
 $[\alpha]_D^{25}$ +28.9° (c 0.26, MeOH)
 Compound of Example 88
 MS (ESI+): 610 (M−Boc+2H)
 $[\alpha]_D^{25}$ −28.3° (c 0.26, MeOH)

Example 89

N-[(3R,4R)-3-(3,4-dichlorophenyl)-1-(piperidin-4-ylcarbonyl)piperidin-4-yl]-N-methyl-3,5-bis(trifluoromethyl)benzamide monohydrochloride To a solution of tert-butyl 4-{[(3R,4R)-4-[{[3,5-bis(trifluoromethyl)phenyl]carbonyl}(methyl)amino]-3-(3,4-dichlorophenyl)piperidin-1-yl]carbonyl}piperidine-1-carboxylate (0.502 g) obtained in Example 87 in ethyl acetate (5 mL) was added 4N hydrogen chloride/ethyl acetate (4 mL), and the mixture was stirred at 50° C. for 2 hr. The reaction mixture was concentrated under reduced pressure and the residue was dissolved in ethyl acetate. This was washed with 1N aqueous sodium hydroxide solution and dried, and the solvent was evaporated under reduced pressure. The obtained residue was treated with 1 equivalent of 4N hydrogen chloride/ethyl acetate to give the title compound (0.405 g, 89%) as a white powder.
MS (ESI+): 610 (M−HCl+H)
$[\alpha]_D^{25}$ +14.9° (c 0.26, MeOH)

Example 90

N-[(3S,4S)-3-(3,4-dichlorophenyl)-1-(piperidin-4-ylcarbonyl)piperidin-4-yl]-N-methyl-3,5-bis(trifluoromethyl)benzamide monohydrochloride Using the compound obtained in Example 88, and by the reaction and purification in the same manner as in Example 2, the title compound was obtained.
MS (ESI+): 610 (M−HCl+H)
$[\alpha]_D^{25}$ −10.6° (c 0.25, MeOH)

Example 91

N-[(3R,4R)-1-[(1-acetylpiperidin-4-yl)carbonyl]-3-(3,4-dichlorophenyl)piperidin-4-yl]-N-methyl-3,5-bis(trifluoromethyl)benzamide 0.5 hydrate To a solution of N-[(3R,4R)-3-(3,4-dichlorophenyl)-1-(piperidin-4-ylcarbonyl)piperidin-4-yl]-N-methyl-3,5-bis(trifluoromethyl)benzamide monohydrochloride (0.35 g) obtained in Example 89 and triethylamine (0.24 mL) in acetonitrile (10 mL) was added acetyl chloride (0.080 mL) at 0° C., and the mixture was stirred at room temperature for 14 hr. The reaction mixture was poured into water, the mixture was made basic with 2N aqueous sodium hydroxide solution, and the resultant product was extracted with ethyl acetate. The organic layer was washed with aqueous sodium hydrogen carbonate solution and brine and dried, and the solvent was evaporated under reduced pressure. The obtained residue was purified by silica gel column chromatography (NH Chromatorex) (solvent gradient; 75→100% ethyl acetate/hexane) to give the title compound (0.25 g, 71%) as a white crystal powder.

MS (ESI+): 652 (M+H)

$^1$H-NMR (CDCl$_3$) δ 1.60-2.20 (9H, m), 2.60-5.20 (14H, m), 6.73-7.99 (6H, m)

Elemental analysis: $C_{29}H_{29}Cl_2F_6N_3O_3 \cdot 0.5H_2O$

Found C, 52.72; H, 4.50; N, 6.44

Calcd. C, 52.66; H, 4.57; N, 6.35

Melting point: 177-179° C.

$[\alpha]_D^{25}$ +32.4° (c 0.26, MeOH)

Example 92

N-[(3S,4S)-1-[(1-acetylpiperidin-4-yl)carbonyl]-3-(3,4-dichlorophenyl)piperidin-4-yl]-N-methyl-3,5-bis(trifluoromethyl)benzamide Using the compound obtained in Example 90, and by the reaction and purification in the same manner as in Example 91, the title compound was obtained.

MS (ESI+): 652 (M+H)

$[\alpha]_D^{25}$ −29.5° (c 0.26, MeOH)

Example 93 tert-butyl (3R,4R)-4-[{[3,5-bis(trifluoromethyl)phenyl]carbonyl}(methyl)amino]-3-(3,4-dichlorophenyl)piperidine-1-carboxylate Using the compound obtained in Reference Example 23, and by the reaction and purification in the same manner as in Example 1, the title compound was obtained.

MS (ESI+): 543 (M-$^t$Bu+2H)

$[\alpha]_D^{25}$ +23.1° (c 0.25, MeOH)

Example 94 tert-butyl (3S,4S)-4-[{[3,5-bis(trifluoromethyl)phenyl]carbonyl}(methyl)amino]-3-(3,4-dichlorophenyl)piperidine-1-carboxylate Using the compound obtained in Reference Example 24, and by the reaction and purification in the same manner as in Example 1, the title compound was obtained.

MS (ESI+): 543 (M-$^t$Bu+2H)

$[\alpha]_D^{25}$ −26.5° (c 0.25, MeOH)

Example 95

N-[(3R,4R)-3-(3,4-dichlorophenyl)piperidin-4-yl]-N-methyl-3,5-bis(trifluoromethyl)benzamide monohydrochloride Using the compound obtained in Example 93, and by the reaction and purification in the same manner as in Example 2, the title compound was obtained.

MS (ESI+): 499 (M−HCl+H)

Example 96

N-[(3S,4S)-3-(3,4-dichlorophenyl)piperidin-4-yl]-N-methyl-3,5-bis(trifluoromethyl)benzamide monohydrochloride Using the compound obtained in Example 94, and by the reaction and purification in the same manner as in Example 2, the title compound was obtained.

MS (ESI+): 499 (M−HCl+H)

Example 97

N-[(3R*,4R*)-1-[(1-acetylpiperidin-4-yl)carbonyl]-3-(3,4-dichlorophenyl)piperidin-4-yl]-N-methyl-4-(3-methyl-1H-pyrazol-1-yl)benzamide To a solution of the compound (0.082 g) obtained in Reference Example 25, 4-(3-methyl-1H-pyrazol-1-yl)benzoic acid (0.061 g) and triethylamine (55 µL) in acetonitrile (3 mL) were added WSC.HCl (0.077 mg) and HOBt (0.061 mg), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (NH Chromatorex) (solvent gradient; 50→100% ethyl acetate/hexane) to give the title compound (0.026 g, 21%) as a white powder.

MS (ESI+): 596 (M+H)

Example 98

N-[(3R*,4R*)-1-[(1-acetylpiperidin-4-yl)carbonyl]-3-(3,4-dichlorophenyl)piperidin-4-yl]-3-methoxy-N-methylbenzamide To a solution of the compound (0.088 g) obtained in Reference Example 25 and triethylamine (59 µL) in acetonitrile (3 mL) was added 3-methoxybenzoyl chloride (0.055 g) at 0° C., and the mixture was stirred at room temperature for 14 hr. The reaction mixture was poured into water, and the resultant product was extracted with ethyl acetate. The organic layer was washed with aqueous sodium hydrogen carbonate solution and brine and dried, and the solvent was evaporated under reduced pressure. The obtained residue was purified by silica gel column chromatography (NH Chromatorex) (solvent gradient; 75→100% ethyl acetate/hexane) to give the title compound (0.097 g, 83%) as a white powder.

MS (ESI+): 546 (M+H)

Example 99

N-[(3R*,4R*)-1-[(1-acetylpiperidin-4-yl)carbonyl]-3-(3,4-dichlorophenyl)piperidin-4-yl]-2-methoxy-N-methylbenzamide Using the compound obtained in Reference Example 25 and 2-methoxybenzoyl chloride, and by the reaction and purification in the same manner as in Example 98, the title compound was obtained.

MS (ESI+): 546 (M+H)

Example 100

N-[(3R*,4R*)-1-[(1-acetylpiperidin-4-yl)carbonyl]-3-(3,4-dichlorophenyl)piperidin-4-yl]-N-methylthiophene-2-carboxamide Using the compound obtained in Reference Example 25 and thiophene-2-carbonyl chloride, and by the reaction and purification in the same manner as in Example 98, the title compound was obtained.

MS (ESI+): 522 (M+H)

Example 101

N-[(3R*,4R*)-1-[(1-acetylpiperidin-4-yl)carbonyl]-3-(3,4-dichlorophenyl)piperidin-4-yl]-3-chloro-N-methylbenzamide Using the compound obtained in Reference Example 25 and 3-chlorobenzoyl chloride, and by the reaction and purification in the same manner as in Example 98, the title compound was obtained.

MS (ESI+): 550 (M+H)

Example 102

N-[(3R*,4R*)-1-[(1-acetylpiperidin-4-yl)carbonyl]-3-(3,4-dichlorophenyl)piperidin-4-yl]-2-chloro-N-methylbenzamide Using the compound obtained in Reference Example 25 and 2-chlorobenzoyl chloride, and by the reaction and purification in the same manner as in Example 98, the title compound was obtained.

MS (ESI+): 550 (M+H)

The compounds described in Examples 1-102 are as follows (Tables 5-13).

TABLE 5

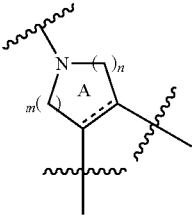

| Ex. No. | A | B | C | R$^1$ | R$^2$ | salt/additive |
|---|---|---|---|---|---|---|
| 1 | 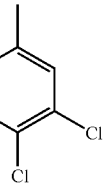 | 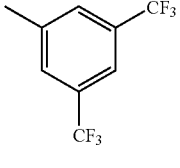 | 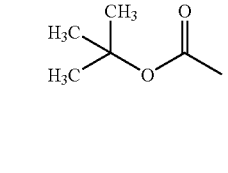 | 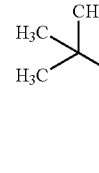 | CH$_3$ | CH$_3$ |
| 2 | 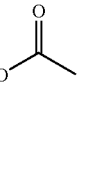 |  |  | H | CH$_3$ | HCl |
| 3 |  |  | | | CH$_3$ | |

TABLE 5-continued

| Ex. No. | A | B | C | R¹ | R² | salt/additive |
|---|---|---|---|---|---|---|
| 4 | (±)- 1-methyl-3,4-dimethylpiperidine | 3,4-dichlorophenyl | 3,5-bis(trifluoromethyl)phenyl | acetyl (H₃C-C(=O)-) | CH₃ | |
| 5 | (±)- 1-methyl-3,4-dimethylpiperidine | 3,4-dichlorophenyl | 3,5-bis(trifluoromethyl)phenyl | 1-Boc-piperidin-4-yl carbonyl | CH₃ | |
| 6 | (±)- 1-methyl-3,4-dimethylpiperidine | 3,4-dichlorophenyl | 3,5-bis(trifluoromethyl)phenyl | piperidin-4-yl carbonyl | CH₃ | HCl |
| 7 | (±)- 1-methyl-3,4-dimethylpiperidine | 3,4-dichlorophenyl | 3,5-bis(trifluoromethyl)phenyl | trans-4-acetamidocyclohexyl carbonyl | CH₃ | |

TABLE 5-continued

| Ex. No. | B | C | R¹ | R² | salt/additive |
|---|---|---|---|---|---|
| 8 | 3,4-Cl₂-phenyl (±)-N-methyl-piperidin-3,4-diyl | 3,5-(CF₃)₂-phenyl | 2,6-dioxopiperidin-4-yl-carbonyl | CH₃ | |
| 9 | 3,4-Cl₂-phenyl (±)-N-methyl-piperidin-3,4-diyl | 3,5-(CF₃)₂-phenyl | tert-butoxycarbonyl | CH₃ | |
| 10 | 3,4-Cl₂-phenyl (±)-N-methyl-piperidin-3,4-diyl | 3,5-(CF₃)₂-phenyl | H | CH₃ | HCl |
| 11 | 3,4-Cl₂-phenyl (±)-N-methyl-piperidin-3,4-diyl | 3,5-(CF₃)₂-phenyl | acetyl | CH₃ | |

TABLE 6

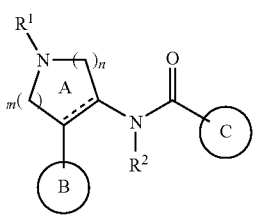

| Ex. No. |  | B | C | R¹ | R² | salt/ additive |
|---|---|---|---|---|---|---|
| 12 | (±)- N-methyl-3,4-dimethylpiperidine | 3,4-dichlorophenyl | 3,5-bis(trifluoromethyl)phenyl | 1-acetylpiperidin-4-yl | CH₃ | |
| 13 | (±)- N-methyl-3,4-dimethylpiperidine | 3,4-dichlorophenyl | phenyl | tert-butyl acetate | CH₃ | |
| 14 | (±)- N-methyl-3,4-dimethylpiperidine | 3,4-dichlorophenyl | phenyl | H | CH₃ | |
| 15 | (±)- N-methyl-3,4-dimethylpiperidine | 3,4-dichlorophenyl | phenyl | 1-acetylpiperidin-4-yl | CH₃ | |
| 16 | (±)- N-methyl-3,4-dimethylpiperidine | 3,4-dichlorophenyl | 4-bromophenyl | tert-butyl acetate | CH₃ | |

TABLE 6-continued

| Ex. No. | A | B | C | R¹ | R² | salt/additive |
|---|---|---|---|---|---|---|
| 17 | (±)- N-methylpiperidine | 3,4-dichlorophenyl | 4-bromophenyl | H | CH₃ | HCl |
| 18 | (±)- N-methylpiperidine | 3,4-dichlorophenyl | 4-bromophenyl | 1-acetylpiperidin-4-yl-carbonyl | CH₃ | |
| 19 | (±)- N-methylpiperidine | 3,4-dichlorophenyl | 4-methoxyphenyl | tert-butyl acetate | CH₃ | |
| 20 | (±)- N-methylpiperidine | 3,4-dichlorophenyl | 4-methoxyphenyl | H | CH₃ | HCl |
| 21 | (±)- N-methylpiperidine | 3,4-dichlorophenyl | 4-methoxyphenyl | 1-acetylpiperidin-4-yl-carbonyl | CH₃ | |

TABLE 6-continued
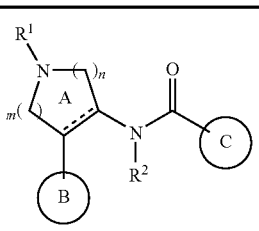
| Ex. No. | 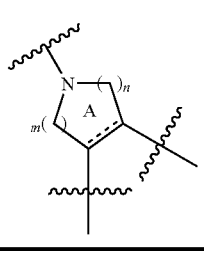 | B | C | R¹ | R² | salt/additive |
|---|---|---|---|---|---|---|
| 22 |  (±)- |  |  |  | CH₃ | |
| 23 |  (±)- |  |  | H | CH₃ | |
TABLE 7
| Ex. No. |  | B | C | R¹ | R² | salt/additive |
|---|---|---|---|---|---|---|
| 24 | 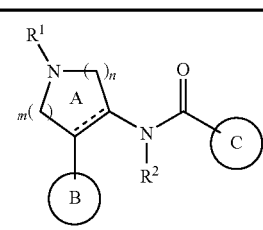 (±)- | 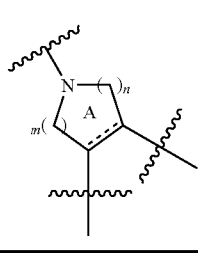 | 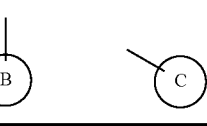 | 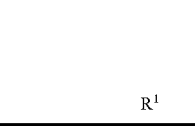 | CH₃ | |

TABLE 7-continued

| Ex. No. | B | C | R¹ | R² | salt/additive |
|---|---|---|---|---|---|
| 25 | (±)- N-methylpiperidin-4-yl, 3,4-dichlorophenyl | 4-fluorophenyl | tert-butyl acetate (OC(CH₃)₃ with acetyl) | CH₃ | |
| 26 | (±)- N-methylpiperidin-4-yl, 3,4-dichlorophenyl | 4-fluorophenyl | H | CH₃ | |
| 27 | (±)- N-methylpiperidin-4-yl, 3,4-dichlorophenyl | 4-fluorophenyl | 1-acetylpiperidin-4-yl | CH₃ | |
| 28 | (±)- N-methylpiperidin-4-yl, 3,4-dichlorophenyl | 4-chlorophenyl | tert-butyl acetate | CH₃ | |
| 29 | (±)- N-methylpiperidin-4-yl, 3,4-dichlorophenyl | 4-chlorophenyl | H | CH₃ | HCl |
| 30 | (±)- N-methylpiperidin-4-yl, 3,4-dichlorophenyl | 4-chlorophenyl | 1-acetylpiperidin-4-yl | CH₃ | |

TABLE 7-continued
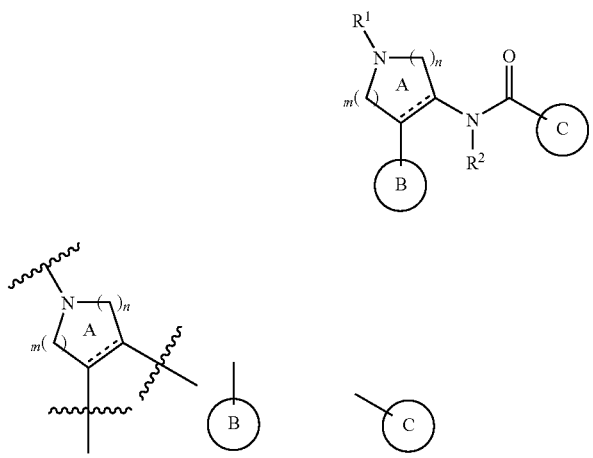
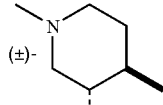
| Ex. No. | [A] | [B] | [C] | R[1] | R[2] | salt/additive |
|---|---|---|---|---|---|---|
| 31 | 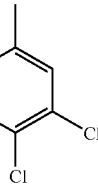 | 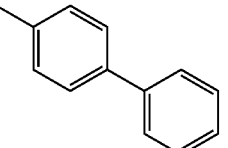 | 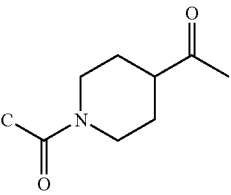 | 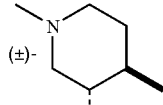 | CH₃ | |
| 32 | 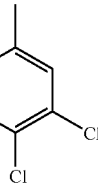 | 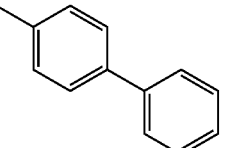 |  | 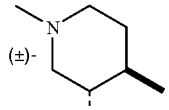 | CH₃ | |
| 33 | 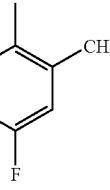 |  | 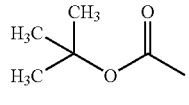 | H | CH₃ | HCl |
| 34 | 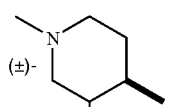 |  | 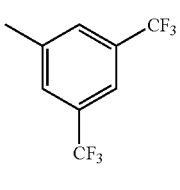 | 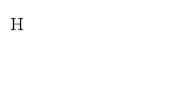 | CH₃ | |

TABLE 8

| Ex. No. | A | B | C | R¹ | R² | salt/additive |
|---|---|---|---|---|---|---|
| 35 | (±)- 1-methyl-4-methylpiperidin-3-yl | 4-fluoro-2-methylphenyl | 3,5-bis(trifluoromethyl)phenyl | H₃C-C(=O)-NH-CH₂-C(=O)- | CH₃ | |
| 36 | (±)- 1-methyl-4-methylpiperidin-3-yl | 4-fluoro-2-methylphenyl | 3,5-bis(trifluoromethyl)phenyl | CH₃O-CH₂-C(=O)- | CH₃ | |
| 37 | (±)- 1-methyl-4-methylpiperidin-3-yl | 4-fluoro-2-methylphenyl | 3,5-bis(trifluoromethyl)phenyl | tert-butyl 4-methylpiperidine-1-carboxylate | CH₃ | |
| 38 | (±)- 1-methyl-4-methylpiperidin-3-yl | 4-fluoro-2-methylphenyl | 3,5-bis(trifluoromethyl)phenyl | 4-methylpiperidinyl | CH₃ | 2HCl |
| 39 | (±)- 1-methyl-4-methylpiperidin-3-yl | 4-fluoro-2-methylphenyl | 3,5-bis(trifluoromethyl)phenyl | 1-acetyl-4-methylpiperidinyl | CH₃ | HCl |
| 40 | (±)- 1-methyl-4-methylpiperidin-3-yl | 4-fluoro-2-methylphenyl | 4-bromophenyl | tert-butyl acetate | CH₃ | |

TABLE 8-continued
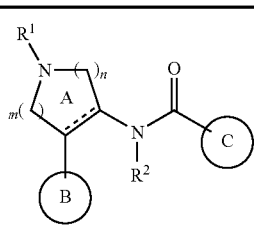
| Ex. No. | B | C | R¹ | R² | salt/additive |
|---|---|---|---|---|---|
| 41 | 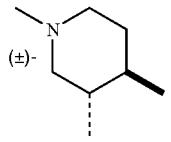 |  |  | H | CH₃ |  |
| 42 | 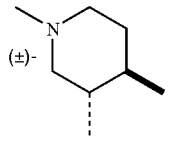 | 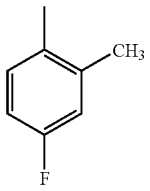 | 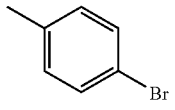 | 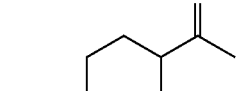 | CH₃ |  |
| 43 | 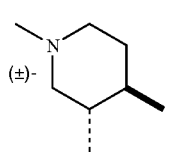 |  | 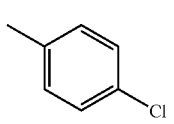 | 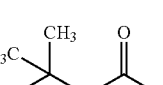 | CH₃ |  |
| 44 | 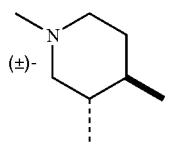 |  | 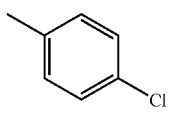 | H | CH₃ | HCl |
| 45 | 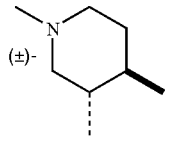 |  | 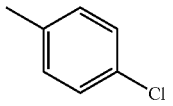 | 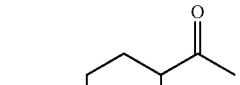 | CH₃ |  |
| 46 | 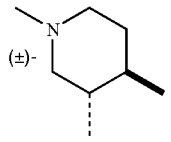 |  | 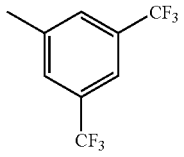 | 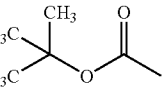 | CH₃ |  |

TABLE 9

| Ex. No. | A (ring) | B | C | R¹ | R² | salt/additive |
|---|---|---|---|---|---|---|
| 47 | (±)-1-methylpiperidin-3,4-diyl | 3,4-difluorophenyl | 3,5-bis(trifluoromethyl)phenyl | H | CH₃ | HCl |
| 48 | (±)-1-methylpiperidin-3,4-diyl | 3,4-difluorophenyl | 3,5-bis(trifluoromethyl)phenyl | 1-acetyl-4-acetylpiperidin-4-yl | CH₃ | |
| 49 | (±)-1-methylpiperidin-3,4-diyl | 3,4-difluorophenyl | 4-chlorophenyl | tert-butoxycarbonylmethyl (OC(CH₃)₃-CH₂-C(O)-) | CH₃ | |
| 50 | (±)-1-methylpiperidin-3,4-diyl | 3,4-difluorophenyl | 4-chlorophenyl | H | CH₃ | HCl |
| 51 | (±)-1-methylpiperidin-3,4-diyl | 3,4-difluorophenyl | 4-chlorophenyl | 1-acetyl-4-acetylpiperidin-4-yl | CH₃ | |

TABLE 9-continued

| Ex. No. | A | B | C | R¹ | R² | salt/additive |
|---|---|---|---|---|---|---|
| 52 | (±)- N-methylpiperidine | 3-Cl-4-F-phenyl | 4-Cl-phenyl | C(CH₃)₂-O-C(O)-CH₃ (tert-butyl acetate) | CH₃ | |
| 53 | (±)- N-methylpiperidine | 3-Cl-4-F-phenyl | 4-Cl-phenyl | H | CH₃ | HCl |
| 54 | (±)- N-methylpiperidine | 3-Cl-4-F-phenyl | 4-Cl-phenyl | 1-acetyl-4-acetylpiperidine | CH₃ | |
| 55 | (±)- N-methylpiperidine | 3-Cl-4-F-phenyl | 3,5-bis(CF₃)-phenyl | tert-butyl 4-methylpiperidine-1-carboxylate | CH₃ | |
| 56 | (±)- N-methylpiperidine | 3-F-4-Cl-phenyl | 3,5-bis(CF₃)-phenyl | C(CH₃)₂-O-C(O)-CH₃ | CH₃ | |
| 57 | (±)- N-methylpiperidine | 3-F-4-Cl-phenyl | 3,5-bis(CF₃)-phenyl | H | CH₃ | HCl |

TABLE 9-continued

| Ex. No. | A | B | C | R¹ | R² | salt/additive |
|---|---|---|---|---|---|---|
| 58 | (±)- N-methyl-3,4-dimethylpiperidine | 4-Cl, 3-F phenyl | 3,5-bis(CF₃) phenyl | 1-acetyl-piperidin-4-yl C(=O)CH₃ | CH₃ | |

TABLE 10

| Ex. No. | A | B | C | R¹ | R² | salt/additive |
|---|---|---|---|---|---|---|
| 59 | (±)- N-methyl-3,4-dimethylpiperidine | 4-Cl, 3-F phenyl | 4-Cl phenyl | (CH₃)₂C(OC(=O)CH₃) | CH₃ | |
| 60 | (±)- N-methyl-3,4-dimethylpiperidine | 4-Cl, 3-F phenyl | 4-Cl phenyl | H | CH₃ | HCl |

TABLE 10-continued
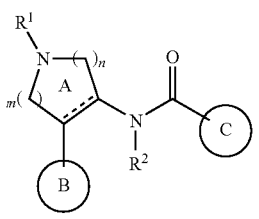

TABLE 10-continued

| Ex. No. | A | B | C | R¹ | R² | salt/additive |
|---|---|---|---|---|---|---|
| 66 | (±)- 1-methyl-3,4-dimethylpiperidine | 2-chloro-3-methylphenyl (4-Me, 3-Cl arrangement) | 3,5-bis(trifluoromethyl)phenyl | 1-acetyl-4-methylpiperidine | CH₃ | HCl |
| 67 | (±)- 1-methyl-3,4-dimethylpiperidine | 2-chloro-3-methylphenyl | 3,5-bis(trifluoromethyl)phenyl | 2-methylpropan-2-yl acetate (tert-butyl acetate moiety) | CH₃ | |
| 68 | (±)- 1-methyl-3,4-dimethylpiperidine | 2-chloro-3-methylphenyl | 3,5-bis(trifluoromethyl)phenyl | H | CH₃ | HCl |
| 69 | (±)- 1-methyl-3,4-dimethylpiperidine | 2-chloro-3-methylphenyl | 3,5-bis(trifluoromethyl)phenyl | 1-acetyl-4-acetylpiperidine | CH₃ | |
| 70 | (±)- 1-methyl-3,4-dimethylpiperidine | 2-methylphenyl | 3,5-bis(trifluoromethyl)phenyl | 2-methylpropan-2-yl acetate | CH₃ | |

TABLE 11
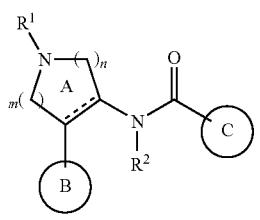
| Ex. No. | B | C | R¹ | R² | salt/additive |
|---|---|---|---|---|---|
| 71 | 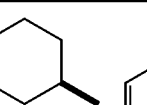 (±)- |  | 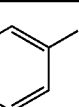 | CH₃ | HCl |
| 72 | 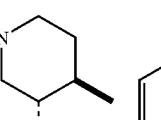 (±)- | 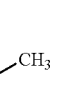 |  | CH₃ | |
| 73 | 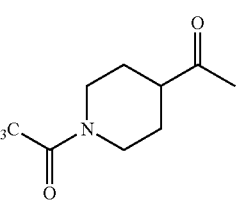 (±)- | 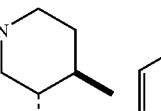 | 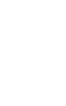 | CH₃ | |
| 74 |  (±)- | 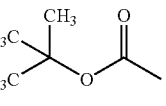 | 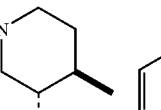 | CH₃ | HCl |
| 75 |  (±)- |  | 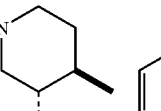 | CH₃ | |
| 76 | 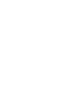 (±)- | 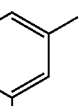 |  | CH₃ | |

TABLE 11-continued

| Ex. No. | A (B position) | B | C | R[1] | R[2] | salt/additive |
|---|---|---|---|---|---|---|
| 77 | (±)-1-methyl-piperidine (3,4) | 3-Cl-4-F-phenyl | 3,5-bis(CF₃)-phenyl | C(CH₃)₂-OC(O)CH₃ | CH₃ | |
| 78 | (±)-1-methyl-piperidine (3,4) | 3-Cl-4-F-phenyl | 3,5-bis(CF₃)-phenyl | H | CH₃ | HCl |
| 79 | (±)-1-methyl-piperidine (3,4) | 3-Cl-4-F-phenyl | 3,5-bis(CF₃)-phenyl | 1-acetyl-piperidin-4-yl | CH₃ | |
| 80 | (±)-1-methyl-pyrrolidine | 3,4-diCl-phenyl | 3,5-bis(CF₃)-phenyl | C(CH₃)₂-OC(O)CH₃ | CH₃ | |
| 81 | (±)-1-methyl-pyrrolidine | 3,4-diCl-phenyl | 3,5-bis(CF₃)-phenyl | H | CH₃ | HCl |

TABLE 11-continued
| Ex. No. | 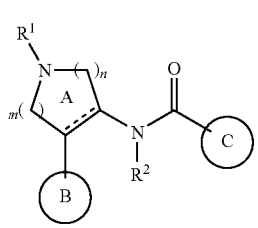 | B | C | R¹ | R² | salt/ additive |
|---|---|---|---|---|---|---|
| 82 | 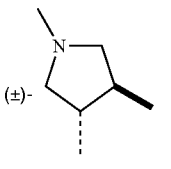 (±)- | 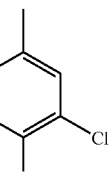 | 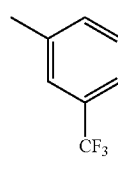 | 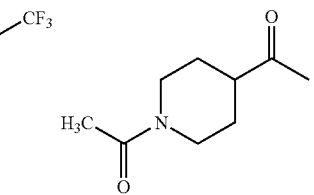 | CH₃ | |
TABLE 12
| Ex. No. | 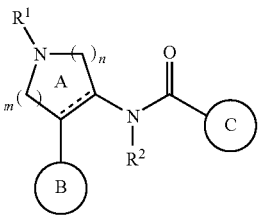 | B | C | R¹ | R² | salt/ additive |
|---|---|---|---|---|---|---|
| 83 | 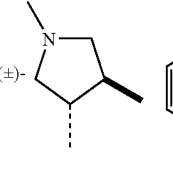 (±)- | 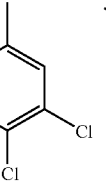 | 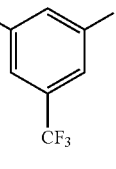 | 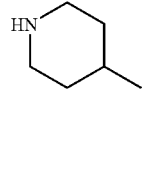 | CH₃ | 2HCl |
| 84 | 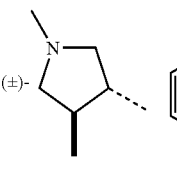 (±)- | 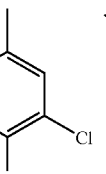 | 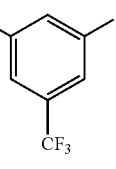 | 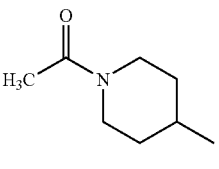 | CH₃ | HCl |

TABLE 12-continued

| Ex. No. | A (ring) | B | C | R¹ | R² | salt/additive |
|---|---|---|---|---|---|---|
| 85 | (+)- 1-methylpiperidine (3,4-dimethyl) | 3,4-dichlorophenyl | 3,5-bis(CF₃)phenyl | 1-acetylpiperidin-4-yl-carbonyl | CH₃ | |
| 86 | (+)- 1-methylpiperidine (3,4-dimethyl) | 3,4-dichlorophenyl | 3,5-bis(CF₃)phenyl | 1-acetylpiperidin-4-yl-carbonyl | CH₃ | |
| 87 | 1-methylpiperidine (3R,4R-dimethyl) | 3,4-dichlorophenyl | 3,5-bis(CF₃)phenyl | 1-Boc-piperidin-4-yl-carbonyl | CH₃ | |
| 88 | 1-methylpiperidine (3S,4S-dimethyl) | 3,4-dichlorophenyl | 3,5-bis(CF₃)phenyl | 1-Boc-piperidin-4-yl-carbonyl | CH₃ | |
| 89 | 1-methylpiperidine (3R,4R-dimethyl) | 3,4-dichlorophenyl | 3,5-bis(CF₃)phenyl | piperidin-4-yl-carbonyl | CH₃ | HCl |
| 90 | 1-methylpiperidine (3S,4S-dimethyl) | 3,4-dichlorophenyl | 3,5-bis(CF₃)phenyl | piperidin-4-yl-carbonyl | CH₃ | HCl |

TABLE 12-continued

| Ex. No. | A | B | C | R¹ | R² | salt/additive |
|---|---|---|---|---|---|---|
| 91 | N-methylpiperidine (R,R) | 3,4-dichlorophenyl | 3,5-bis(CF₃)phenyl | 1-acetylpiperidin-4-yl | CH₃ | 0.5H₂O |
| 92 | N-methylpiperidine (S,S) | 3,4-dichlorophenyl | 3,5-bis(CF₃)phenyl | 1-acetylpiperidin-4-yl | CH₃ | |
| 93 | N-methylpiperidine (R,R) | 3,4-dichlorophenyl | 3,5-bis(CF₃)phenyl | 2-(acetyloxy)propan-2-yl (tert-butyl acetate) | CH₃ | |
| 94 | N-methylpiperidine (S,S) | 3,4-dichlorophenyl | 3,5-bis(CF₃)phenyl | 2-(acetyloxy)propan-2-yl (tert-butyl acetate) | CH₃ | |

TABLE 13
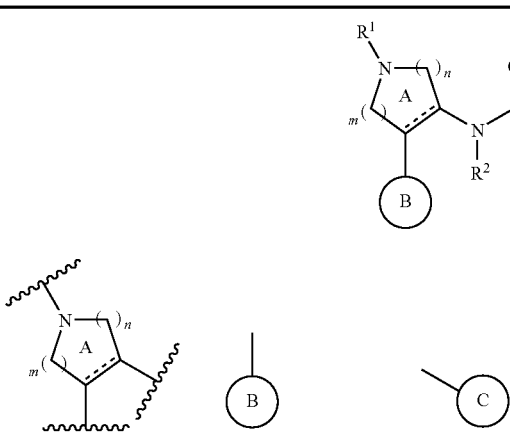
| Ex. No. | 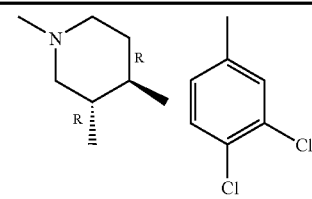 | B | C | R¹ | R² | salt/additive |
|---|---|---|---|---|---|---|
| 95 | 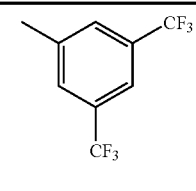 | 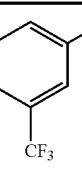 | 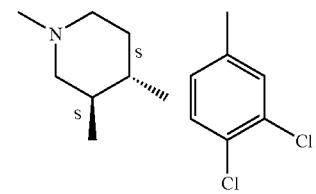 | H | CH₃ | HCl |
| 96 | 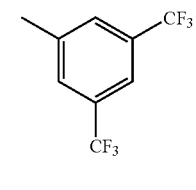 | 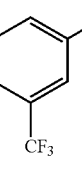 | 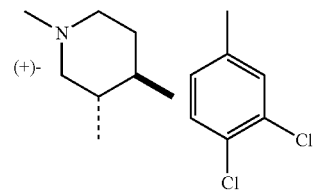 | H | CH₃ | HCl |
| 97 | 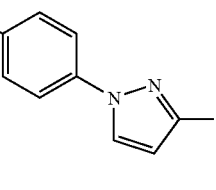 | 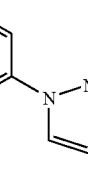 | 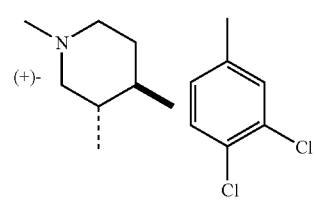 | 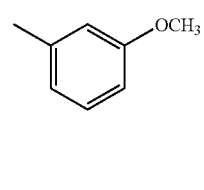 | CH₃ | |
| 98 | 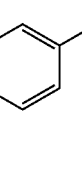 | | 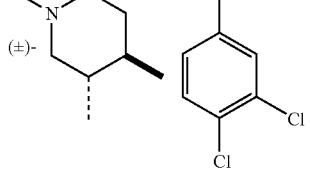 | 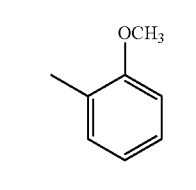 | CH₃ | |
| 99 | 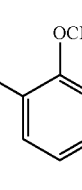 | | 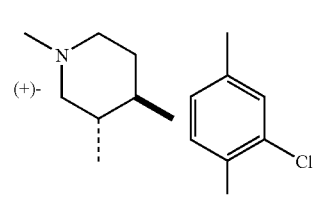 | 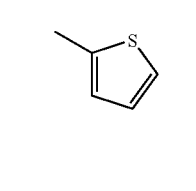 | CH₃ | |
| 100 | 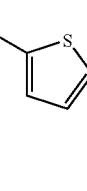 | | | | CH₃ | |

TABLE 13-continued

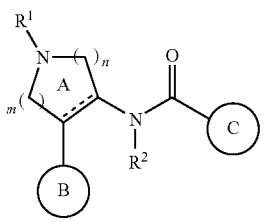

| Ex. No. | | B | C | R¹ | R² | salt/ additive |
|---|---|---|---|---|---|---|
| 101 | 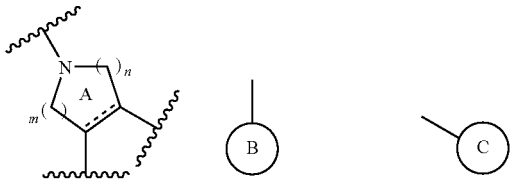 (+)- | | | | | |
| 102 |  (+)- | | | | | |

Reference Example 26 tert-butyl (3R*,4R*)-4-({[3-bromo-5-(trifluoromethyl)phenyl]carbonyl}amino)-3-(3,4-dichlorophenyl)piperidine-1-carboxylate Using the compound obtained in Reference Example 1, step 4 and 3-bromo-5-trifluoromethylbenzoic acid, and by the reaction and purification in the same manner as in Reference Example 1, step 5, the title compound was obtained.
MS (ESI+): 495 (M-Boc+2H)

Reference Example 27a tert-butyl (3R*,4R*)-4-({[3-bromo-5-(trifluoromethyl)phenyl]carbonyl}amino)-3-(3-fluoro-4-methylphenyl)piperidine-1-carboxylate (Step 1)
Using 3-fluoro-4-methylphenylboronic acid, and by the reaction and purification in the same manner as in Reference Example 11, steps 1 to 4, tert-butyl (3R*,4R*)-4-amino-3-(3-fluoro-4-methylphenyl)piperidine-1-carboxylate p-toluenesulfonate was obtained.
MS (ESI+): 253 (M-p-TsOH-ᵗBu+2H)
(Step 2)
Using the compound obtained in step 1 and 3-bromo-5-trifluoromethylbenzoic acid, and by the reaction and purification in the same manner as in Reference Example 1, step 5, the title compound was obtained.
MS (ESI+): 459 (M-Boc+2H)

Reference Example 27b tert-butyl (3R*,4R*)-4-({[3,5-bis(trifluoromethyl)phenyl]carbonyl}amino)-3-(3-fluoro-4-methylphenyl)piperidine-1-carboxylate Using the compound obtained in Reference Example 27a, step 1 and 3,5-bis(trifluoromethyl)benzoic acid, and by the reaction and purification in the same manner as in Reference Example 1, step 5, the title compound was obtained.
MS (ESI+): 449 (M-Boc+2H)

Reference Example 28a tert-butyl (3R*,4R*)-4-({[3-bromo-5-(trifluoromethyl)phenyl]carbonyl}amino)-3-(4-fluoro-3-methylphenyl)piperidine-1-carboxylate (Step 1)
Using 4-fluoro-3-methylphenylboronic acid, and by the reaction and purification in the same manner as in Reference Example 11, steps 1 to 4, tert-butyl (3R*,4R*)-4-amino-3-(4-fluoro-3-methylphenyl)piperidine-1-carboxylate p-toluenesulfonate was obtained.
MS (ESI+): 253 (M-p-TsOH-ᵗBu+2H)
(Step 2)
Using the compound obtained in step 1 and 3-bromo-5-trifluoromethylbenzoic acid, and by the reaction and purification in the same manner as in Reference Example 1, step 5, the title compound was obtained.
MS (ESI+): 459 (M-Boc+2H)

Reference Example 28b tert-butyl (3R*,4R*)-4-({[3,5-bis(trifluoromethyl) phenyl]carbonyl}amino)-3-(4-fluoro-3-methylphenyl)piperidine-1-carboxylate Using the compound obtained in Reference Example 28a and 3,5-bis(trifluoromethyl)benzoic acid, and by the reaction and purification in the same manner as in Reference Example 1, step 5, the title compound was obtained.
MS (ESI+): 449 (M-Boc+2H)

Reference Example 29 tert-butyl (3R*,4R*)-4-({[3,5-bis(trifluoromethyl) phenyl]carbonyl}amino)-3-(4-fluorophenyl)piperidine-1-carboxylate (Step 1)
Using 4-fluorophenylboronic acid, and by the reaction and purification in the same manner as in Reference Example 11, steps 1 to 4, tert-butyl (3R*,4R*)-4-amino-3-(4-fluorophenyl)piperidine-1-carboxylate p-toluenesulfonate was obtained.
MS (ESI+): 239 (M-p-TsOH-$^t$Bu+2H)
(Step 2)
Using the compound obtained in step 1 and 3,5-bis(trifluoromethyl)benzoic acid, and by the reaction and purification in the same manner as in Reference Example 1, step 5, the title compound was obtained.
MS (ESI+): 435 (M-Boc+2H)

Reference Example 30 tert-butyl (3R*,4R*)-4-({[3-bromo-5-(trifluoromethyl)phenyl]carbonyl}amino)-3-(4-fluorophenyl) piperidine-1-carboxylate Using the compound obtained in Reference Example 29, step 1 and 3-bromo-5-trifluoromethylbenzoic acid, and by the reaction and purification in the same manner as in Reference Example 1, step 5, the title compound was obtained.
MS (ESI+): 445 (M-Boc+2H)

Reference Example 31 tert-butyl (3R*,4R*)-4-({[3-bromo-5-(trifluoromethyl)phenyl]carbonyl}amino)-3-(4-methoxyphenyl) piperidine-1-carboxylate (Step 1)
Using 4-methoxyphenylboronic acid, and by the reaction and purification in the same manner as in Reference Example 11, steps 1 to 4, tert-butyl (3R*,4R*)-4-amino-3-(4-methoxyphenyl)piperidine-1-carboxylate p-toluenesulfonate was obtained.
MS (ESI+): 251 (M-p-TsOH-$^t$Bu+2H)
(Step 2)
Using the compound obtained in step 1 and 3-bromo-5-trifluoromethylbenzoic acid, and by the reaction and purification in the same manner as in Reference Example 1, step 5, the title compound was obtained.
MS (ESI+): 457 (M-Boc+2H)

Reference Example 32 tert-butyl (3R*,4R*)-4-({[3,5-bis(trifluoromethyl) phenyl]carbonyl}amino)-3-(4-methoxyphenyl)piperidine-1-carboxylate Using the compound obtained in Reference Example 31, step 1 and 3,5-bis(trifluoromethyl)benzoic acid, and by the reaction and purification in the same manner as in Reference Example 1, step 5, the title compound was obtained.
MS (ESI+): 447 (M-Boc+2H)

Reference Example 33 tert-butyl (3R*,4R*)-4-({[3,5-bis(trifluoromethyl) phenyl]carbonyl}amino)-3-(4-methylphenyl)piperidine-1-carboxylate (Step 1)
Using 4-methylphenylboronic acid, and by the reaction and purification in the same manner as in Reference Example 11, steps 1 to 4, tert-butyl (3R*,4R*)-4-amino-3-(4-methylphenyl)piperidine-1-carboxylate p-toluenesulfonate was obtained.
MS (ESI+): 235 (M-p-TsOH-$^t$Bu+2H)
(Step 2)
Using the compound obtained in step 1 and 3,5-bis(trifluoromethyl)benzoic acid, and by the reaction and purification in the same manner as in Reference Example 1, step 5, the title compound was obtained.
MS (ESI+): 431 (M-Boc+2H)

Reference Example 34 tert-butyl (3R*,4R*)-4-({[3,5-bis(trifluoromethyl) phenyl]carbonyl}amino)-3-(4-chlorophenyl)piperidine-1-carboxylate (Step 1)
Using the compound obtained in Reference Example 1, step 1 and 4-bromochlorobenzene, and by the reaction and purification in the same manner as in Reference Example 1, steps 2 to 4, tert-butyl (3R*,4R*)-4-amino-3-(4-chlorophenyl)piperidine-1-carboxylate p-toluenesulfonate was obtained.
MS (ESI+): 255 (M-p-TsOH-$^t$Bu+2H)
(Step 2)
Using the compound obtained in step 1 and 3,5-bis(trifluoromethyl)benzoic acid, and by the reaction and purification in the same manner as in Reference Example 1, step 5, the title compound was obtained.
MS (ESI+): 451 (M-Boc+2H)

Reference Example 35 tert-butyl (3R*,4R*)-4-({[3-bromo-5-(trifluoromethyl)phenyl]carbonyl}amino)-3-(4-methylphenyl) piperidine-1-carboxylate Using the compound obtained in Reference Example 33, step 1 and 3-bromo-5-trifluoromethylbenzoic acid, and by the reaction and purification in the same manner as in Reference Example 1, step 5, the title compound was obtained.
MS (ESI+): 441 (M-Boc+2H)

Reference Example 36 tert-butyl (3R*,4R*)-4-({[3-bromo-5-(trifluoromethyl)phenyl]carbonyl}amino)-3-(4-chlorophenyl)piperidine-1-carboxylate Using the compound obtained in Reference Example 34, step 1 and 3-bromo-5-trifluoromethylbenzoic acid, and by the reaction and purification in the same manner as in Reference Example 1, step 5, the title compound was obtained.
MS (ESI+): 461 (M-Boc+2H)

Reference Example 37 tert-butyl (3R*,4R*)-4-({[3,5-bis(trifluoromethyl)phenyl]carbonyl}amino)-3-(3,5-dichlorophenyl)piperidine-1-carboxylate (Step 1)
Using 1-bromo-3,5-dichlorobenzene, and by the reaction and purification in the same manner as in Reference Example 1, steps 2 and 3, (3R*,4R*)-1-(tert-butoxycarbonyl)-3-(3,5-dichlorophenyl)piperidine-4-carboxylic acid was obtained.
MS (ESI+): 266 (M-$^t$BuO)

(Step 2)
To a solution of the compound (9.1 g) obtained in step 1 in toluene (60 mL) were added DPPA (10.0 g) and triethylamine (5.0 mL) at room temperature, and the mixture was stirred at 100° C. for 1 hr. The reaction mixture was cooled, 8N aqueous sodium hydroxide solution (24 mL) was added, and the mixture was stirred at room temperature for 2 hr. The reaction mixture was poured into water, and the resultant product was extracted with ethyl acetate. The organic layer was washed with water and brine and dried, and the solvent was evaporated under reduced pressure to give tert-butyl (3R*,4R*)-4-amino-3-(3,5-dichlorophenyl)piperidine-1-carboxylate (4.78 g, 57%) as a white powder.
MS (ESI+): 289 (M-$^t$Bu+2H)

(Step 3)
Using the compound obtained in step 2 and 3,5-bis(trifluoromethyl)benzoic acid, and by the reaction and purification in the same manner as in Reference Example 44, the title compound was obtained.
MS (ESI+): 529 (M-$^t$Bu+2H)

Reference Example 38 tert-butyl (3R*,4R*)-3-phenyl-4-[(thiophen-2-ylcarbonyl)amino]piperidine-1-carboxylate Using the compound obtained in Reference Example 11, step 4 and thiophene-2-carbonyl chloride, and by the reaction and purification in the same manner as in Example 39, the title compound was obtained.
MS (ESI+): 287 (M-Boc+2H)

Reference Example 39 tert-butyl (3R*,4R*)-3-(3-chloro-4-methylphenyl)-4-{[(4-chlorophenyl)carbonyl]amino}piperidine-1-carboxylate Using the compound obtained in Reference Example 17, step 1 and 4-chlorobenzoyl chloride, and by the reaction and purification in the same manner as in Example 39, the title compound was obtained.
MS (ESI+): 463 (M+H)

Reference Example 40 tert-butyl (3R*,4R*)-3-(4-chloro-3-methylphenyl)-4-{[(4-chlorophenyl)carbonyl]amino}piperidine-1-carboxylate Using the compound obtained in Reference Example 18, step 1 and 4-chlorobenzoyl chloride, and by the reaction and purification in the same manner as in Example 39, the title compound was obtained.
MS (ESI+): 463 (M+H)

Reference Example 41 tert-butyl (3R*,4R*)-4-{[(4-chlorophenyl)carbonyl]amino}-3-(2-methylphenyl)piperidine-1-carboxylate Using the compound obtained in Reference Example 19, step 1 and 4-chlorobenzoyl chloride, and by the reaction and purification in the same manner as in Example 39, the title compound was obtained.
MS (ESI+): 427 (M+H)

Reference Example 42 tert-butyl (3R*,4R*)-4-{[(4-chlorophenyl)carbonyl]amino}-3-(4-fluoro-2-methylphenyl)piperidine-1-carboxylate Using the compound obtained in Reference Example 9, step 1 and 4-chlorobenzoyl chloride, and by the reaction and purification in the same manner as in Example 39, the title compound was obtained.
MS (ESI+): 447 (M+H)

Reference Example 43 tert-butyl (3R,4R)-4-{[(4-chlorophenyl)carbonyl]amino}-3-(3,4-dichlorophenyl)piperidine-1-carboxylate To a solution of the compound (1.0 g) obtained in Reference Example 23, step 4 and triethylamine (400 µL) in acetonitrile (10 mL) was added 4-chlorobenzoyl chloride (296 µL) at 0° C., and the mixture was stirred at room temperature for 14 hr. The reaction mixture was poured into water, and the resultant product was extracted with ethyl acetate. The organic layer was washed with aqueous sodium hydrogen carbonate solution and brine and dried, and the solvent was evaporated under reduced pressure. The obtained residue was purified by silica gel column chromatography (solvent gradient; 10→50% ethyl acetate/hexane) to give the title compound (0.80 g, 85%) as a white powder.
MS (ESI+): 429 (M-$^t$Bu+2H)

Reference Example 44 tert-butyl (3R,4R)-3-(3,4-dichlorophenyl)-4-{[(4-methoxyphenyl)carbonyl]amino}piperidine-1-carboxylate To a solution of tert-butyl (3R,4R)-4-amino-3-(3,4-dichlorophenyl)piperidine-1-carboxylate p-toluenesulfonate (1.0 g) obtained in Reference Example 23, step 4 and triethylamine (400 µL) in acetonitrile (10 mL) was added 4-methoxybenzoyl chloride (312 µL) at 0° C., and the mixture was stirred at room temperature for 14 hr. The reaction mixture was poured into water, and the resultant product was extracted with ethyl acetate. The organic layer was washed with aqueous sodium hydrogen carbonate solution and brine and dried, and the solvent was evaporated under reduced pressure. The obtained residue was purified by silica gel column chromatography (solvent gradient; 10→50% ethyl acetate/hexane) to give the title compound (0.80 g, 86%) as a white powder.

MS (ESI+): 479 (M+H)

Reference Example 45 tert-butyl (3R,4R)-3-(3,4-dichlorophenyl)-4-({[4-(3-methyl-1H-pyrazol-1-yl)phenyl]carbonyl}amino)piperidine-1-carboxylate To a solution of the compound (1.0 g) obtained in Reference Example 23, step 4, 4-(3-methyl-1H-pyrazol-1-yl)benzoic acid (0.59 g) and triethylamine (534 μL) in acetonitrile (15 mL) were added WSC.HCL (739 mg) and HOBt (591 mg), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 50→100% ethyl acetate/hexane) to give the title compound (0.87 g, 85%) as a white powder.

MS (ESI+): 529 (M+H)

Reference Example 46 tert-butyl (3R*,4R*)-3-(4-bromophenyl)-4-{[(4-methoxyphenyl)carbonyl]amino}piperidine-1-carboxylate (Step 1)
Using 1,4-dibromobenzene, and by the reaction and purification in the same manner as in Reference Example 1, steps 2 to 4, tert-butyl (3R*,4R*)-4-amino-3-(4-bromophenyl)piperidine-1-carboxylate p-toluenesulfonate was obtained.

$^1$H-NMR (CDCl$_3$) δ 1.33-1.67 (10H, m), 1.77-1.91 (1H, m), 2.18 (1H, s), 2.43 (3H, s), 2.49-2.79 (3H, m), 3.14 (1H, dd, J=7.2, 4.9 Hz), 3.87-4.22 (2H, m), 6.97 (2H, d, J=8.1 Hz), 7.22 (4H, d, J=8.5 Hz), 7.46 (2H, d, J=8.1 Hz), 7.57 (2H, s)

(Step 2)
Using the compound obtained in step 1, and by the reaction and purification in the same manner as in Reference Example 44, the title compound was obtained.

MS (ESI+): 433 (M-$^t$Bu+2H)

Reference Example 47 tert-butyl (3R*,4R*)-4-({[3,5-bis(trifluoromethyl)phenyl]carbonyl}amino)-3-(4-bromophenyl)piperidine-1-carboxylate (Step 1)
Using the compound obtained in Reference Example 1, step 1 and 1,4-dibromobenzene, and by the reaction and purification in the same manner as in Reference Example 1, steps 2 to 4, tert-butyl (3R*,4R*)-4-amino-3-(4-bromophenyl)piperidine-1-carboxylate p-toluenesulfonate was obtained.

MS (ESI+): 300 (M-p-TsOH-$^t$Bu+2H)

(Step 2)
Using the compound obtained in step 1 and 3,5-bis(trifluoromethyl)benzoic acid, and by the reaction and purification in the same manner as in Reference Example 1, step 5, the title compound was obtained.

MS (ESI+): 495 (M-Boc+2H)

Reference Example 48 tert-butyl (3R*,4R*)-3-(4-bromophenyl)-4-({[3-bromo-5-(trifluoromethyl)phenyl]carbonyl}amino)piperidine-1-carboxylate Using the compound obtained in Reference Example 47, step 1 and 3-bromo-5-trifluoromethylbenzoic acid, and by the reaction and purification in the same manner as in Reference Example 1, step 5, the title compound was obtained.

MS (ESI+): 505 (M-Boc+2H)

Reference Example 49 tert-butyl (3R*,4R*)-4-({[3,5-bis(trifluoromethyl)phenyl]carbonyl}amino)-3-(3-chlorophenyl)piperidine-1-carboxylate (Step 1)
Using 1,3-bromochlorobenzene, and by the reaction and purification in the same manner as in Reference Example 1, steps 2 to 4, tert-butyl (3R*,4R*)-4-amino-3-(3-chlorophenyl)piperidine-1-carboxylate p-toluenesulfonate was obtained.

$^1$H-NMR (CDCl$_3$) δ 1.44 (9H, s), 1.60-1.80 (1H, m), 2.20-2.32 (1H, m), 2.37 (3H, s), 2.60-3.00 (3H, m), 3.30-3.37 (1H, m), 4.00-4.30 (2H, m), 7.15-7.18 (3H, m), 7.23-7.25 (3H, m), 7.68 (2H, d, J=8.1 Hz), 7.97 (3H, br)

(Step 2)
Using the compound obtained in step 1 and 3,5-bis(trifluoromethyl)benzoic acid, and by the reaction and purification in the same manner as in Reference Example 44, the title compound was obtained.

MS (ESI+): 495 (M-$^t$Bu+2H)

Reference Example 50 tert-butyl (3R*,4R*)-4-({[3-bromo-5-(trifluoromethyl)phenyl]carbonyl}amino)-3-phenylpiperidine-1-carboxylate Using the compound obtained in Reference Example 11, step 4 and 3-bromo-5-trifluoromethylbenzoic acid, and by the reaction and purification in the same manner as in Reference Example 1, step 5, the title compound was obtained.

MS (ESI+): 427 (M-Boc+2H)

Reference Example 51 tert-butyl (3R*,4R*)-4-({[3-bromo-5-(trifluoromethyl)phenyl]carbonyl}amino)-3-(4-chloro-3-methylphenyl)piperidine-1-carboxylate Using the compound obtained in Reference Example 18, step 1 and 3-bromo-5-trifluoromethylbenzoic acid, and by the reaction and purification in the same manner as in Reference Example 1, step 5, the title compound was obtained.

MS (ESI+): 475 (M-Boc+2H)

Reference Example 52 tert-butyl (3R*,4R*)-3-(4-fluorophenyl)-4-({[4-fluoro-3-(trifluoromethyl)phenyl]carbonyl}amino) piperidine-1-carboxylate Using the compound obtained in Reference Example 29, step 1 and 4-fluoro-3-trifluoromethylbenzoic acid, and by the reaction and purification in the same manner as in Reference Example 1, step 5, the title compound was obtained.
MS (ESI+): 385 (M-Boc+2H)

Reference Example 53 tert-butyl (3R*,4R*)-3-(4-chlorophenyl)-4-({[4-fluoro-3-(trifluoromethyl)phenyl]carbonyl}amino) piperidine-1-carboxylate Using the compound obtained in Reference Example 34, step 1 and 4-fluoro-3-trifluoromethylbenzoic acid, and by the reaction and purification in the same manner as in Reference Example 1, step 5, the title compound was obtained.
MS (ESI+): 401 (M-Boc+2H)

Reference Example 54 tert-butyl (3R*,4R*)-3-(4-chlorophenyl)-4-({[4-chloro-3-(trifluoromethyl)phenyl]carbonyl}amino) piperidine-1-carboxylate Using the compound obtained in Reference Example 34, step 1 and 4-chloro-3-trifluoromethylbenzoic acid, and by the reaction and purification in the same manner as in Reference Example 1, step 5, the title compound was obtained.
MS (ESI+): 417 (M-Boc+2H)

Reference Example 55 tert-butyl (3R*,4R*)-4-({[4-chloro-3-(trifluoromethyl)phenyl]carbonyl}amino)-3-(4-fluorophenyl) piperidine-1-carboxylate Using the compound obtained in Reference Example 29, step 1 and 4-chloro-3-trifluoromethylbenzoic acid, and by the reaction and purification in the same manner as in Reference Example 1, step 5, the title compound was obtained.
MS (ESI+): 401 (M-Boc+2H)

Reference Example 56 tert-butyl (3R,4R)-4-({[3,5-bis(trifluoromethyl)phenyl]carbonyl}amino)-3-phenylpiperidine-1-carboxylate (Step 1)
To a solution of sodium hydride (60% in oil, 6.36 g) in DMF (100 mL) was added ethyl 1-benzyl-3-oxopiperidine-4-carboxylate monohydrochloride (19.0 g) at 0° C., and the mixture was stirred for 5 min. N-phenylbis(trifluoromethanesulfonimide) (25.0 g) was added, and the mixture was stirred at 0° C. for 1 hr. The reaction mixture was poured into ice water, and the resultant product was extracted with ethyl acetate. The organic layer was washed with water and brine and dried, and the solvent was evaporated under reduced pressure. To a mixture of the obtained residue in a mixed solvent of toluene (125 mL) and water (7.5 mL) were added dihydroxyphenylborane (5.82 g), potassium carbonate (4.40 g) and tetrakis(triphenylphosphine)palladium(0) (3.67 g), and the mixture was stirred under an argon atmosphere at 100° C. for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 10→20% ethyl acetate/hexane) to give ethyl 1-benzyl-5-phenyl-1,2,3,6-tetrahydropyridine-4-carboxylate (10.2 g) as a pale yellow oil.
$^1$H-NMR (CDCl$_3$): δ 0.83 (3H, t, J=7.2 Hz), 2.54-2.62 (2H, m), 2.70 (2H, t, J=5.7 Hz), 3.26 (2H, t, J=2.9 Hz), 3.67 (2H, s), 3.87 (2H, q, J=7.2 Hz), 7.08-7.14 (2H, m), 7.20-7.40 (8H, m)
(Step 2)
A solution of the compound (10.5 g) obtained in step 1 and 20% palladium hydroxide on carbon (50% wet, 2.63 g) in ethanol (250 mL) was stirred under a hydrogen atmosphere (1 atm) at room temperature for 14 hr. The catalyst was filtered off, and the filtrate was concentrated under reduced pressure. To a solution of the obtained residue in acetonitrile (50 mL) were added triethylamine (4.6 mL) and Boc$_2$O (7.14 g), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 10→20% ethyl acetate/hexane) to give 4-ethyl 1-tert-butyl (3R*,4S*)-3-phenylpiperidine-1,4-dicarboxylate (8.31 g, 76%) as a colorless oil.
$^1$H-NMR (CDCl$_3$): δ 1.01 (3H, t, J=7.7 Hz), 1.43 (9H, s), 1.80-2.05 (2H, m), 2.93-3.00 (1H, q like), 3.10-3.20 (1H, q like), 3.50-4.10 (6H, m), 7.05-7.30 (5H, m)
(Step 3)
To a solution of the compound (6.3 g) obtained in step 2 in ethanol (60 mL) was added $^t$BuONa (3.63 g), and the mixture was stirred at 90° C. for 1 hr. The reaction mixture was cooled, 8N aqueous sodium hydroxide solution (60 mL) and water (60 mL) were added, and the mixture was stirred at 85° C. for 2 hr. The reaction mixture was cooled, and citric acid (51 g) was added. Ethanol was evaporated under reduced pressure, and the mixture was extracted with ethyl acetate (200 mL). The organic layer was washed with water and dried, and the solvent was evaporated under reduced pressure. The residue was crystallized from ethyl acetate-IPE-hexane to give (3R*, 4R*)-1-(tert-butoxycarbonyl)-3-phenylpiperidine-4-carboxylic acid (5.26 g, 91%) as a white powder.
$^1$H-NMR (CDCl$_3$): δ 1.45 (9H, s), 1.65-1.75 (1H, m), 1.98-2.05 (1H, m), 2.65-3.00 (4H, m), 4.00-4.40 (2H, m), 7.17-7.32 (5H, m)
(Step 4)
A solution of the compound (30.5 g) obtained in step 3 in THF (200 mL) was heated to 55° C., and a solution of (R)-(−)-1-phenylethylamine (6.06 g) in THF (99 mL) and water (30.0 mL) were added dropwise. The reaction mixture was stirred at room temperature for 24 hr, and the precipitate was collected by filtration and washed with THF and hexane to give a white powder (14.9 g, 35%, 98.9% de). The obtained white powder (14.9 g (98.9% de)) and citric acid (8.07 g) were dissolved in a mixed solvent of water, THF and ethyl acetate, and the organic layer was separated. The organic layer was washed with water and brine and dried, and the solvent was evaporated under reduced pressure to give (3R,4R)-1-(tert-butoxycarbonyl)-3-phenylpiperidine-4-carboxylic acid (10.1 g, 95%) as a white powder.
MS (ESI+): 232 (M-$^t$BuO)

(Step 5)

Using the compound obtained in step 4, and by the reaction and purification in the same manner as in Reference Example 1, step 4, tert-butyl (3R,4R)-4-amino-3-phenylpiperidine-1-carboxylate p-toluenesulfonate was obtained.

MS (ESI+): 221 (M-p-TsOH-$^t$Bu+2H)

(Step 6)

Using the compound obtained in step 5 and 3,5-bis(trifluoromethyl)benzoic acid, and by the reaction and purification in the same manner as in Reference Example 1, step 5, the title compound was obtained.

MS (ESI+): 417 (M-Boc+2H)

Reference Example 57 tert-butyl (3R,4R)-4-({[3-bromo-5-(trifluoromethyl)phenyl]carbonyl}amino)-3-phenylpiperidine-1-carboxylate Using the compound obtained in Reference Example 56, step 5 and 3-bromo-5-trifluoromethylbenzoic acid, and by the reaction and purification in the same manner as in Reference Example 1, step 5, the title compound was obtained.

MS (ESI+): 427 (M-Boc+2H)

Reference Example 59

4-chloro-N-[(3R,4R)-3-(3,4-dichlorophenyl)piperidin-4-yl]benzamide monohydrochloride The compound obtained in Reference Example 43 (0.48 g) was dissolved in 10M hydrogen chloride-methanol solution (30 mL), and the mixture was stirred at room temperature for 24 hr. The reaction mixture was concentrated under reduced pressure to give the title compound (0.42 g) as a white powder.

MS (ESI+): 383 (M−HCl+H)

Reference Example 61

N-[(3R,4R)-1-[(1-acetylpiperidin-4-yl)carbonyl]-3-(3,4-dichlorophenyl)piperidin-4-yl]-4-chlorobenzamide Using the compound obtained in Reference Example 59, and by the reaction and purification in the same manner as in Example 339, the title compound was obtained.

MS (ESI+): 536 (M+H)

Reference Example 62 tert-butyl (3R*,4S*)-4-{[(4-chlorophenyl)carbonyl]amino}-3-(3,4-dichlorophenyl)piperidine-1-carboxylate (Step 1)

A solution of methyl 3-iodopyridine-4-carboxylate (20 g), 3,4-dichlorophenylboronic acid (16.0 g), palladium acetate (Pd(OAc)$_2$) (0.85 g) and triphenylphosphine (PPh$_3$) (2.0 g) in DMF (200 mL) was degassed with argon gas, and cesium carbonate (27.3 g) was added. The reaction mixture was stirred under an argon atmosphere at 100° C. for 6 hr, and cooled to room temperature. The reaction mixture was poured into water, and the resultant product was extracted with ethyl acetate. The organic layer was washed with brine and dried, and the solvent was evaporated under reduced pressure. The obtained residue was purified by silica gel column chromatography (NH Chromatorex) (solvent gradient; 25% ethyl acetate/hexane) and treated with 1 equivalent of 4N hydrogen chloride/ethyl acetate to give methyl 3-(3,4-dichlorophenyl)pyridine-4-carboxylate monohydrochloride (18.1 g, 75%) as a white powder.

(Step 2)

To a solution of the compound (18.1 g) obtained in step 1 in acetic acid (181 mL) was added platinum oxide (PtO$_2$) (1.29 g), and the mixture was stirred overnight under a hydrogen atmosphere (5 atm) at room temperature. The catalyst was filtered off, and the filtrate was concentrated under reduced pressure to give methyl (3R*,4S*)-3-(3,4-dichlorophenyl)piperidine-4-carboxylate monohydrochloride (14.04 g, 76%) as a white powder.

(Step 3)

To a solution of the compound (1.8 g) obtained in step 2 in acetonitrile (10 mL) were added Boc$_2$O (2.62 g) and triethylamine (1.66 mL), and the mixture was stirred at room temperature for 14 hr. The reaction mixture was poured into water, and the resultant product was extracted with ethyl acetate. The organic layer was washed with brine and dried, and the solvent was evaporated under reduced pressure. The obtained residue was purified by silica gel column chromatography (solvent gradient; 5→45% ethyl acetate/hexane) to give 1-tert-butyl 4-methyl (3R*,4S*)-3-(3,4-dichlorophenyl)piperidine-1,4-dicarboxylate (0.62 g, 27%) as a colorless oil.

$^1$H-NMR (CDCl$_3$) δ 1.19-1.49 (9H, m), 1.70-1.86 (2H, m), 2.69-3.28 (3H, m), 3.40-4.09 (3H, m), 7.22 (1H, dd, J=8.5, 2.1 Hz), 7.48 (1H, d, J=2.1 Hz), 7.55 (1H, d, J=8.3 Hz), 12.33 (1H, s)

(Step 4)

To a solution of the compound (0.55 g) obtained in step 3 in toluene (3 mL) were added DPPA (0.46 g) and triethylamine (229 μL) at room temperature, and the mixture was stirred at 100° C. for 1 hr. The reaction mixture was cooled, 8N aqueous sodium hydroxide solution (1.4 mL) was added, and the mixture was stirred at room temperature for 2 hr. The reaction mixture was poured into water, and the resultant product was extracted with ethyl acetate. The organic layer was washed with saturated aqueous ammonium chloride solution and brine and dried, and the solvent was evaporated under reduced pressure. To the obtained residue was added p-toluenesulfonic acid monohydrate (0.21 g), and the residue was crystallized from ethyl acetate to give tert-butyl (3R*,4S*)-4-amino-3-(3,4-dichlorophenyl)piperidine-1-carboxylate p-toluenesulfonate (0.63 g, 82%) as a white powder.

$^1$H-NMR (DMSO-d$_6$) δ 1.27-1.29 (10H, m), 1.78 (2H, s), 2.29 (3H, s), 3.14-3.29 (1H, m), 3.54 (2H, dd, J=13.8, 4.0 Hz), 3.64 (2H, s), 3.81-3.93 (1H, m), 7.11 (2H, d, J=7.7 Hz), 7.28 (1H, dd, J=8.4, 2.0 Hz), 7.47 (2H, d, J=8.1 Hz), 7.54 (1H, d, J=2.1 Hz), 7.67 (1H, d, J=8.3 Hz), 7.72-7.82 (2H, m)

(Step 5)

To a solution of the compound (0.55 g) obtained in step 4 and triethylamine (439 μL) in acetonitrile (5 mL) was added 4-chlorobenzoyl chloride (177 μL) at 0° C., and the mixture was stirred at room temperature for 14 hr. The reaction mixture was poured into water, and the resultant product was extracted with ethyl acetate. The organic layer was washed with aqueous sodium hydrogen carbonate solution and brine and dried, and the solvent was evaporated under reduced pressure. The obtained residue was purified by silica gel column chromatography (solvent gradient; 25→50% ethyl acetate/hexane) to give the title compound (0.51 g, 99%) as a white powder.

MS (ESI+): 383 (M-Boc+2H)

Reference Example 63

4-chloro-N-[(3R*,4S*)-3-(3,4-dichlorophenyl)piperidin-4-yl]benzamide monohydrochloride Using the compound obtained in Reference Example 62, and by the reaction and purification in the same manner as in Example 2, the title compound was obtained.
MS (ESI+): 383 (M−HCl+H)

Reference Example 64

N-[(3R*,4S*)-1-[(1-acetylpiperidin-4-yl)carbonyl]-3-(3,4-dichlorophenyl)piperidin-4-yl]-4-chlorobenzamide Using the compound obtained in Reference Example 63, and by the reaction and purification in the same manner as in Example 3, the title compound was obtained.
MS (ESI+): 536 (M+H)

Reference Example 65 tert-butyl (3R*,4R*)-4-{[(4-chlorophenyl)carbonyl]amino}-3-[4-(trifluoromethyl)phenyl]piperidine-1-carboxylate (Step 1)
Using 4-(trifluoromethyl)phenylboronic acid, and by the reaction and purification in the same manner as in Reference Example 11, steps 1 to 4, tert-butyl (3R*,4R*)-4-amino-3-[4-(trifluoromethyl)phenyl]piperidine-1-carboxylate p-toluenesulfonate was obtained.
$^1$H-NMR (DMSO-$d_6$) δ 1.33-1.60 (10H, m), 1.95-2.15 (1H, m), 2.29 (3H, s), 2.71-2.88 (2H, m), 2.99 (2H, s), 3.53-3.74 (1H, m), 3.80-3.94 (1H, m), 3.97-4.13 (1H, m), 7.12 (2H, d, J=8.0 Hz), 7.48 (2H, d, J=8.0 Hz), 7.59 (2H, d, J=8.0 Hz), 7.66-7.83 (4H, m)
(Step 2)
Using the compound obtained in step 1, and by the reaction and purification in the same manner as in Reference Example 62, step 5, the title compound was obtained.
MS (ESI+): 383 (M-Boc+2H)

Reference Example 66 tert-butyl (3R*,4R*)-3-[4-(trifluoromethyl)phenyl]-4-({[4-(trifluoromethyl)phenyl]carbonyl}amino)piperidine-1-carboxylate Using the compound obtained in Reference Example 65, step 1 and 4-(trifluoromethyl)benzoyl chloride, and by the reaction and purification in the same manner as in Reference Example 62, step 5, the title compound was obtained.
MS (ESI+): 417 (M-Boc+2H)

Reference Example 67 tert-butyl (3R*,4R*)-4-{[(4-morpholin-4-ylphenyl)carbonyl]amino}-3-[4-(trifluoromethyl)phenyl]piperidine-1-carboxylate Using the compound obtained in Reference Example 65, step 1 and 4-morpholin-4-ylbenzoic acid, and by the reaction and purification in the same manner as in Example 3, the title compound was obtained.
MS (ESI+): 478 (M-$^t$Bu+2H)

Reference Example 68 tert-butyl (3S*,4R*)-3-{[(4-chlorophenyl)carbonyl]amino}-4-(3,4-dichlorophenyl)pyrrolidine-1-carboxylate Using the compound obtained in Reference Example 22, step 6, and by the reaction and purification in the same manner as in Reference Example 62, step 5, the title compound was obtained.
MS (ESI+): 369 (M-Boc+2H)

Reference Example 69

4-chloro-N-[(3S*,4R*)-4-(3,4-dichlorophenyl)pyrrolidin-3-yl]benzamide monohydrochloride Using the compound obtained in Reference Example 68, and by the reaction and purification in the same manner as in Example 2, the title compound was obtained.
MS (ESI+): 369 (M−HCl+H)

Reference Example 70

N-[(3S*,4R*)-1-[(1-acetylpiperidin-4-yl)carbonyl]-4-(3,4-dichlorophenyl)pyrrolidin-3-yl]-4-chlorobenzamide Using the compound obtained in Reference Example 69, and by the reaction and purification in the same manner as in Example 3, the title compound was obtained.
MS (ESI+): 522 (M+H)

Reference Example 74

N-[(3R*,4R*)-3-(3,5-dichlorophenyl)piperidin-4-yl]-3,5-bis(trifluoromethyl)benzamide monohydrochloride (Step 1)
Using 3,4-dichlorobromobenzene, and by the reaction and purification in the same manner as in Reference Example 1, steps 2 and 3, (3R*,4R*)-1-(tert-butoxycarbonyl)-3-(3,5-dichlorophenyl)piperidine-4-carboxylic acid as a white powder.
MS (ESI+): 300 (M-$^t$BuO)
(Step 2)
To a solution of the compound (9.1 g) obtained in step 1 in toluene (60 mL) were added DPPA (10.0 g) and triethylamine (5.0 mL) at room temperature, and the mixture was stirred at 100° C. for 1 hr. The reaction mixture was cooled, 8N aqueous sodium hydroxide solution (24 mL) was added, and the mixture was stirred at room temperature for 2 hr. The reaction mixture was poured into water, and the resultant product was extracted with ethyl acetate. The organic layer was washed with water and brine and dried, and the solvent was evaporated under reduced pressure. The obtained residue was purified by silica gel column chromatography (NH Chromatorex) (solvent gradient; 30→50% ethyl acetate/hexane) to give tert-butyl (3R*,4R*)-4-amino-3-(3,5-dichlorophenyl)piperidine-1-carboxylate (4.78 g, 57%) as a white powder.
$^1$H-NMR (CDCl$_3$) δ 1.35-1.50 (1H, m), 1.46 (9H, s), 1.90-2.00 (1H, m), 2.30-2.39 (1H, m), 2.60-3.05 (3H, m), 4.00-4.40 (2H, m), 7.13 (2H, d, J=1.8 Hz), 7.25-7.28 (1H, m) (NH$_2$ peak was not observed)

(Step 3)

Using the compound obtained in step 2, and by the reaction and purification in the same manner as in Reference Example 1, step 5, tert-butyl (3R*,4R*)-4-({[3,5-bis(trifluoromethyl)phenyl]carbonyl}amino)-3-(3,5-dichlorophenyl)piperidine-1-carboxylate was obtained.

MS (ESI+): 529 (M-$^t$Bu+2H)

(Step 4)

Using the compound obtained in step 3, and by the reaction and purification in the same manner as in Example 2, the title compound was obtained.

MS (ESI+): 485 (M−HCl+H)

Reference Example 75

N-[(3R*,4R*)-1-[(1-acetylpiperidin-4-yl)carbonyl]-3-(3,5-dichlorophenyl)piperidin-4-yl]-3,5-bis(trifluoromethyl)benzamide Using the compound obtained in Reference Example 74, and by the reaction and purification in the same manner as in Example 3, the title compound was obtained.

MS (ESI+): 638 (M+H)

Reference Example 76

N-[(3R,4R)-3-(3,4-dichlorophenyl)piperidin-4-yl]-2,2,2-trifluoro-N-methylacetamide monohydrochloride (Step 1)

To a solution of the compound obtained in Reference Example 23, step 4 (8.29 g) in THF (80 mL) was added pyridine (3.88 mL) at 0° C., and the mixture was stirred for 10 min. Then, trifluoroacetic anhydride (3.33 mL) was added, and the mixture was stirred overnight at room temperature. The reaction mixture was poured into saturated aqueous sodium hydrogen carbonate solution, and the resultant product was extracted with ethyl acetate. The organic layer was washed with saturated aqueous ammonium chloride solution and brine and dried, and the solvent was evaporated under reduced pressure. The obtained residue was purified by silica gel column chromatography (solvent gradient; 10→40% ethyl acetate/hexane) to give tert-butyl (3R,4R)-3-(3,4-dichlorophenyl)-4-[(trifluoroacetyl)amino]piperidine-1-carboxylate (7.23 g, 100%) as a white powder.

MS (ESI+): 367 (M-$^t$BuO)

(Step 2)

To a solution of the compound (7.23 g) obtained in step 1 in DMF (70 mL) was added sodium hydride (60% in oil, 0.96 g) at 0° C., and the mixture was stirred at 0° C. for 10 min. Furthermore, methyl iodide (2.0 mL) was added at 0° C., and the mixture was stirred at room temperature for 3 hr. The reaction mixture was poured into water, and the resultant product was extracted with ethyl acetate. The organic layer was washed with water and brine and dried, and the solvent was evaporated under reduced pressure. The obtained residue was purified by silica gel column chromatography (solvent; 5→40% ethyl acetate/hexane) to give tert-butyl (3R,4R)-3-(3,4-dichlorophenyl)-4-[methyl(trifluoroacetyl)amino]piperidine-1-carboxylate (6.00 g, 82%) as a white powder.

MS (ESI+): 401 (M-$^t$Bu+2H)

(Step 3)

To a solution of the compound (6.00 g) obtained in step 2 in ethyl acetate (50 mL) was added 4N hydrogen chloride/ethyl acetate (25 mL) at room temperature, and the mixture was stirred at room temperature for 4 hr. The reaction mixture was evaporated under reduced pressure to give the title compound (4.97 g, 96%) as a white powder.

MS (ESI+): 355 (M−HCl+2H)

Reference Example 77

N-[(3R,4R)-1-[(1-acetylpiperidin-4-yl)carbonyl]-3-(3,4-dichlorophenyl)piperidin-4-yl]-2,2,2-trifluoro-N-methylacetamide To a solution of the compound (4.97 g) obtained in Reference Example 76, 1-acetylpiperidine-4-carboxylic acid (3.25 g) and triethylamine (5.25 mL) in DMF (55 mL) was added DEPC (3.2 mL), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure to give the title compound (6.76 g, 100%) as a white powder.

MS (ESI+): 508 (M+H)

Reference Example 78

(3R,4R)-1-[(1-acetylpiperidin-4-yl)carbonyl]-3-(3,4-dichlorophenyl)-N-methylpiperidin-4-amine To a solution of the compound obtained in Reference Example 77 (6.76 g) in a mixed solvent of methanol (64 mL) and water (13 mL) was added potassium carbonate (17.5 g), and the mixture was stirred at 55° C. for 60 hr. The reaction mixture was concentrated under reduced pressure, saturated aqueous sodium hydrogen carbonate solution was added to the residue, and the resultant product was extracted with ethyl acetate. The organic layer was washed with brine and dried, and the solvent was evaporated under reduced pressure to give the title compound (4.11 g, 78%) as a white powder.

MS (ESI+): 412 (M+H)

Reference Example 79 tert-butyl (3R*,4R*)-4-({[3,5-bis(trifluoromethyl)phenyl]carbonyl}amino)-3-(3-methylthiophen-2-yl)piperidine-1-carboxylate (Step 1)

Using (3-methylthiophen-2-yl)boronic acid, and by the reaction and purification in the same manner as in Reference Example 11, steps 1 to 4, tert-butyl (3R*,4R*)-4-amino-3-(3-methylthiophen-2-yl)piperidine-1-carboxylate p-toluenesulfonate was obtained.

$^1$H-NMR (CDCl$_3$) δ 1.43 (9H, s), 1.65-2.20 (5H, m), 2.38 (3H, s), 2.60-2.80 (2H, m), 2.95-3.30 (2H, m), 4.00-4.30 (2H, m), 6.63 (1H, d, J=5.1 Hz), 7.00 (1H, d, J=5.1 Hz), 7.13 (2H, d, J=8.1 Hz), 7.57 (2H, d, J=8.1 Hz), 7.70 (3H, s)

(Step 2)

Using the compound obtained in step 1, and by the reaction and purification in the same manner as in Reference Example 62, step 5, the title compound was obtained.

MS (ESI+): 481 (M-$^t$Bu+2H)

Reference Example 80 tert-butyl (3S,4R)-3-{[(4-chlorophenyl)carbonyl]amino}-4-(3,4-dichlorophenyl)pyrrolidine-1-carboxylate (Step 1)

To a solution of (2E)-3-(3,4-dichlorophenyl)prop-2-enoic acid (5.0 g) and DMF (178 μL) in THF (115 mL) was added oxalyl chloride (3.98 mL) at room temperature, and the mixture was stirred for 45 min. The reaction mixture was concentrated under reduced pressure, and the residue was dissolved in THF (13.8 mL). The THF solution was added dropwise to a solution of (4R)-4-benzyl-1,3-oxazolidin-2-one (4.48 g), triethylamine (15.9 mL) and LiCl (4.87 g) in THF (115 mL) at 0° C., and the mixture was stirred overnight at room temperature. The reaction mixture was poured into water, and the resultant product was extracted with ethyl acetate. The organic layer was washed with water and brine and dried, and the solvent was evaporated under reduced pressure to give (4R)-4-benzyl-3-[(2E)-3-(3,4-dichlorophenyl)prop-2-enoyl]-1,3-oxazolidin-2-one (4.22 g, 49%) as a white powder.

(Step 2)

To a suspension of the compound (15.0 g) obtained in step 1 and N-benzyl-1-methoxy-N-[(trimethylsilyl)methyl]methanamine (11.3 mL) in toluene (25 mL) was added a solution of trifluoroacetic acid (0.59 mL) in toluene (6 mL) at 0° C., and the mixture was stirred at room temperature for 10 hr. The reaction mixture was poured into water, and the resultant product was extracted with ethyl acetate. The organic layer was washed with saturated aqueous sodium hydrogen carbonate solution and dried, and the solvent was evaporated under reduced pressure. The obtained residue was purified by silica gel column chromatography (solvent; 20→50% ethyl acetate/hexane) to give (4R)-4-benzyl-3-{[(3S,4R)-1-benzyl-4-(3,4-dichlorophenyl)pyrrolidin-3-yl]carbonyl}dihydrofuran-2(3H)-one (9.15 g, 45%) as a white powder.

(Step 3)

To a solution of the compound (9.0 g) obtained in step 2 in acetonitrile (45 mL) was added ACE-Cl (2.86 mL) at room temperature, and the mixture was stirred at 80° C. for 1.5 hr. ACE-Cl (2.86 mL) was added again, and the mixture was stirred at 90° C. for 1 hr. The reaction mixture was cooled, triethylamine (7.33 mL) was added, and the mixture was stirred at 90° C. for 4 hr. The precipitate was filtered off, and the filtrate was concentrated under reduced pressure. Methanol (25 mL) was added to the residue, and the mixture was stirred at 80° C. for 1.5 hr. After the reaction mixture being cooled, acetonitrile (25 mL) and triethylamine (3.66 mL) were added, and then Boc$_2$O (5.77 g) was added. The reaction mixture was stirred at room temperature for 14 hr, and the reaction mixture was poured into water. The resultant product was extracted with ethyl acetate, and the organic layer was washed with aqueous citric acid solution, saturated aqueous sodium hydrogen carbonate solution and brine and dried, and the solvent was evaporated under reduced pressure. The obtained residue was purified by silica gel column chromatography (solvent; 0→40% ethyl acetate/hexane) to give tert-butyl (3S,4R)-3-{[(4R)-4-benzyl-2-oxo-1,3-oxazolidin-3-yl]carbonyl}-4-(3,4-dichlorophenyl)pyrrolidine-1-carboxylate (2.77 g, 30%) as a white powder.

(Step 4)

To a solution of the compound (2.5 g) obtained in step 3 in THF (27 mL) was added 4N aqueous lithium hydroxide solution (3.6 mL) at room temperature, and the mixture was stirred for 60 hr. The reaction mixture was made slightly acidic with aqueous citric acid solution, and the resultant product was extracted with ethyl acetate. The organic layer was washed with water and dried, and the solvent was evaporated under reduced pressure. The obtained residue was purified by silica gel column chromatography (solvent; 0→70% ethyl acetate/hexane) to give (3S,4R)-1-(tert-butoxycarbonyl)-4-(3,4-dichlorophenyl)pyrrolidine-3-carboxylic acid (1.41 g, 81%) as a white powder.

$^1$H-NMR (DMSO-d$_6$) δ 1.41 (9H, s), 3.11-3.26 (1H, m), 3.36-3.45 (2H, m), 3.47-3.62 (1H, m), 3.63-3.83 (2H, m), 7.36 (1H, dd, J=8.3, 1.9 Hz), 7.58 (1H, d, J=8.3 Hz), 7.65 (1H, s), 12.59 (1H, s)

(Step 5)

To a solution of the compound (1.2 g) obtained in step 4 in toluene (9 mL) were added DPPA (1.06 mL) and triethylamine (0.68 mL) at room temperature, and the mixture was stirred at 100° C. for 1 hr. The reaction mixture was cooled, 8N aqueous sodium hydroxide solution (4.2 mL) was added, and the mixture was stirred at room temperature for 1 hr. The reaction mixture was poured into water, and the resultant product was extracted with ethyl acetate. The organic layer was washed with water and brine and dried, and the solvent was evaporated under reduced pressure to give tert-butyl (3S,4R)-3-amino-4-(3,4-dichlorophenyl)pyrrolidine-1-carboxylate (1.06 g, 96%) as a colorless oil.

$^1$H-NMR (CDCl$_3$) δ 1.47 (9H, s), 1.92-2.30 (2H, m), 2.78-3.57 (4H, m), 3.64-4.01 (2H, m), 7.09 (1H, d, J=8.3 Hz), 7.30-7.48 (2H, m)

(Step 6)

To a solution of the compound (0.92 g) obtained in step 5 in ethyl acetate (8 mL) was added p-toluenesulfonic acid monohydrate (0.53 g), and then hexane (1.5 mL) was added. The precipitate was collected by filtration to give tert-butyl (3S,4R)-3-amino-4-(3,4-dichlorophenyl)pyrrolidine-1-carboxylate p-toluenesulfonate (1.24 g, 77%).

(Step 7)

To a solution of the compound (1.1 g) obtained in step 6 and triethylamine (664 μL) in acetonitrile (10 mL) was added 4-chlorobenzoyl chloride (308 μL) at 0° C., and the mixture was stirred at room temperature for 14 hr. The reaction mixture was poured into water, and the resultant product was extracted with ethyl acetate. The organic layer was washed with aqueous sodium hydrogen carbonate solution and brine and dried, and the solvent was evaporated under reduced pressure. The obtained residue was purified by silica gel column chromatography (solvent gradient; 10→40% ethyl acetate/hexane) to give the title compound (0.80 g, 78%) as a white powder.

$^1$H-NMR (CDCl$_3$) δ 1.42-1.58 (9H, m), 3.13-3.58 (3H, m), 3.75-4.07 (2H, m), 4.50-4.76 (1H, m), 6.20-6.58 (1H, m), 7.16 (1H, d, J=7.3 Hz), 7.31-7.47 (4H, m), 7.65 (2H, d, J=8.3 Hz)

The compounds described in Reference Examples 26-80 are as follows (Tables 14-19).

TABLE 14

| Ref. Ex. No. | chemical formula | salt/formula |
|---|---|---|
| 26 | (±)- tert-butyl 4-[(3-bromo-5-trifluoromethylbenzoyl)amino]-3-(3,4-dichlorophenyl)piperidine-1-carboxylate | |
| 27a | (±)- tert-butyl 4-[(3-bromo-5-trifluoromethylbenzoyl)amino]-3-(3-fluoro-4-methylphenyl)piperidine-1-carboxylate | |
| 27b | (±)- tert-butyl 4-[(3,5-bis(trifluoromethyl)benzoyl)amino]-3-(3-fluoro-4-methylphenyl)piperidine-1-carboxylate | |
| 28a | (±)- tert-butyl 4-[(3-bromo-5-trifluoromethylbenzoyl)amino]-3-(4-fluoro-3-methylphenyl)piperidine-1-carboxylate | |

TABLE 14-continued

| Ref. Ex. No. | chemical formula | salt/formula |
|---|---|---|
| 28b | (±)- tert-butyl 4-[(3,5-bis(trifluoromethyl)benzoyl)amino]-3-(4-fluoro-3-methylphenyl)piperidine-1-carboxylate | |
| 29 | (±)- tert-butyl 4-[(3,5-bis(trifluoromethyl)benzoyl)amino]-3-(4-fluorophenyl)piperidine-1-carboxylate | |
| 30 | (±)- tert-butyl 4-[(3-bromo-5-(trifluoromethyl)benzoyl)amino]-3-(4-fluorophenyl)piperidine-1-carboxylate | |
| 31 | (±)- tert-butyl 4-[(3-bromo-5-(trifluoromethyl)benzoyl)amino]-3-(4-methoxyphenyl)piperidine-1-carboxylate | |

TABLE 14-continued

| Ref. Ex. No. | chemical formula | salt/formula |
|---|---|---|
| 32 | (±)- tert-butyl 4-[(3,5-bis(trifluoromethyl)benzoyl)amino]-3-(4-methoxyphenyl)piperidine-1-carboxylate | |
| 33 | (±)- tert-butyl 4-[(3,5-bis(trifluoromethyl)benzoyl)amino]-3-(4-methylphenyl)piperidine-1-carboxylate | |

TABLE 15

| Ref. Ex. No. | chemical formula | salt/additive |
|---|---|---|
| 34 | (±)- tert-butyl 4-[(3,5-bis(trifluoromethyl)benzoyl)amino]-3-(4-chlorophenyl)piperidine-1-carboxylate | |
| 35 | (±)- tert-butyl 4-[(3-bromo-5-(trifluoromethyl)benzoyl)amino]-3-(4-methylphenyl)piperidine-1-carboxylate | |

TABLE 15-continued
| Ref. Ex. No. | chemical formula | salt/additive |
|---|---|---|
| 36 | 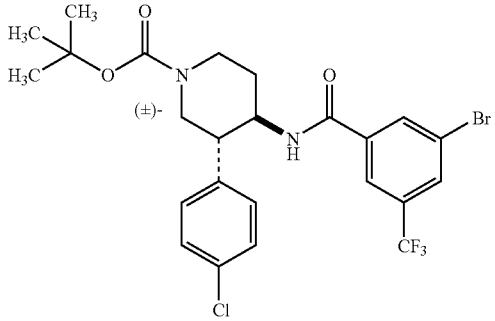 | |
| 37 | 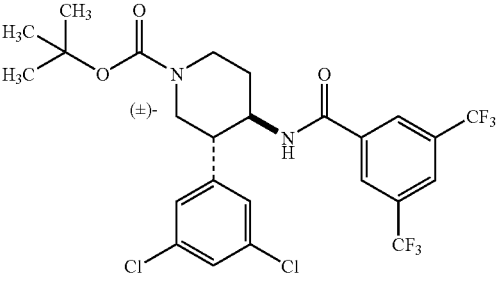 | |
| 38 | 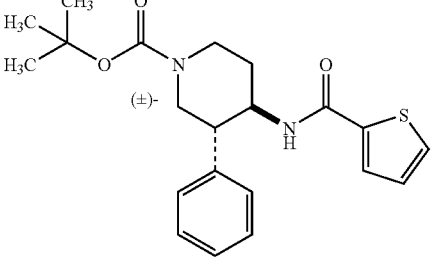 | |
| 39 | 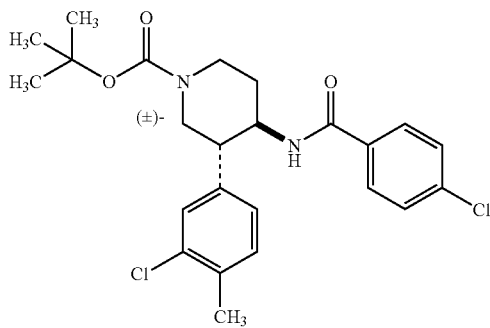 | |
| 40 | 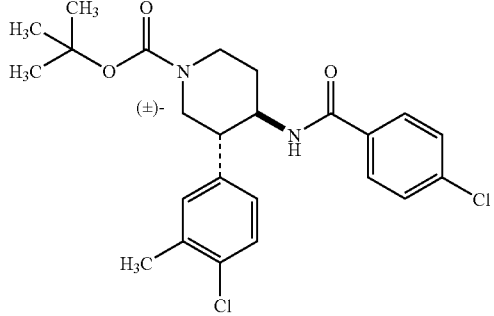 | |

TABLE 15-continued

| Ref. Ex. No. | chemical formula | salt/additive |
|---|---|---|
| 41 | tert-butyl (±)-3-(2-methylphenyl)-4-[(4-chlorobenzoyl)amino]piperidine-1-carboxylate | |
| 42 | tert-butyl (±)-3-(4-fluoro-2-methylphenyl)-4-[(4-chlorobenzoyl)amino]piperidine-1-carboxylate | |
| 43 | tert-butyl (3R,4R)-3-(3,4-dichlorophenyl)-4-[(4-chlorobenzoyl)amino]piperidine-1-carboxylate | |

TABLE 16

| Ref. Ex. No. | chemical formula | salt/additive |
|---|---|---|
| 44 | tert-butyl (3R,4R)-3-(3,4-dichlorophenyl)-4-[(4-methoxybenzoyl)amino]piperidine-1-carboxylate | |

TABLE 16-continued
| Ref. Ex. No. | chemical formula | salt/additive |
|---|---|---|
| 45 | 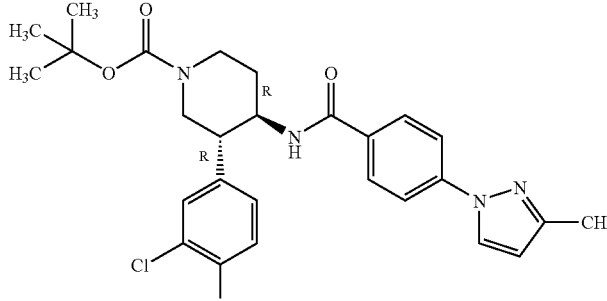 | |
| 46 | 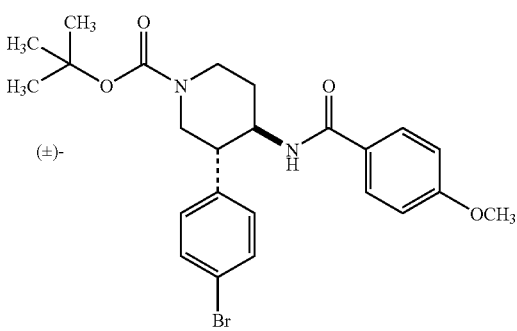 | |
| 47 | 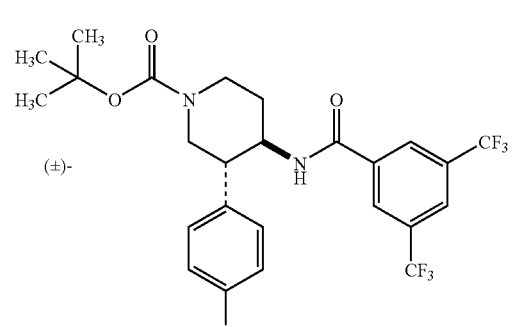 | |
| 48 | 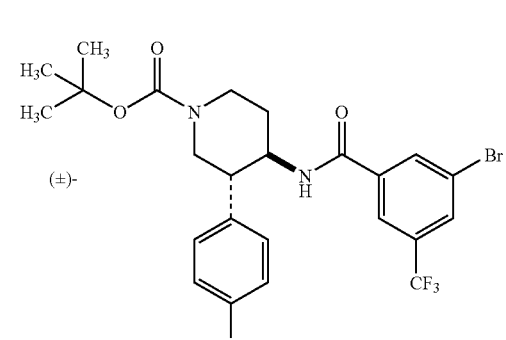 | |

TABLE 16-continued
| Ref. Ex. No. | chemical formula | salt/additive |
|---|---|---|
| 49 | 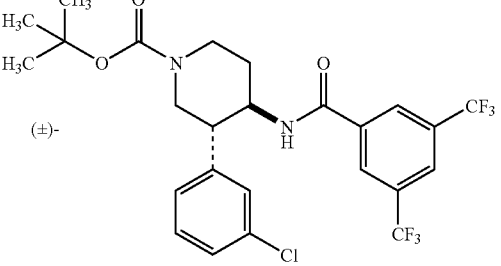 | |
| 50 | 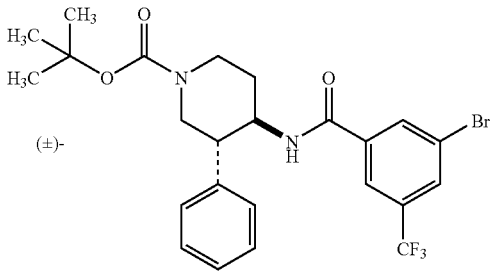 | |
| 51 | 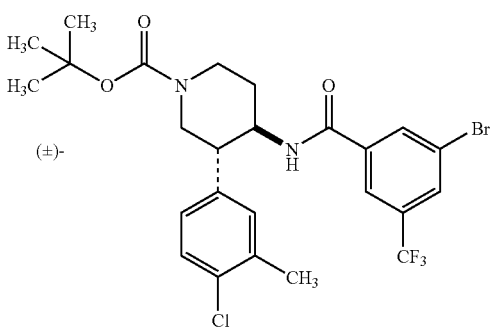 | |
| 52 | 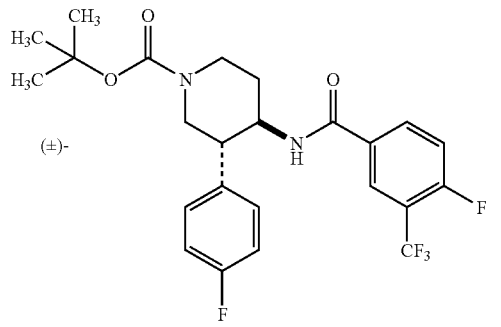 | |
| 53 | 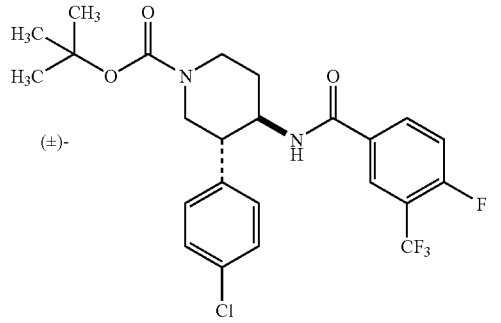 | |

TABLE 17
| Ref. Ex. No. | chemical formula | salt/additive |
|---|---|---|
| 54 | 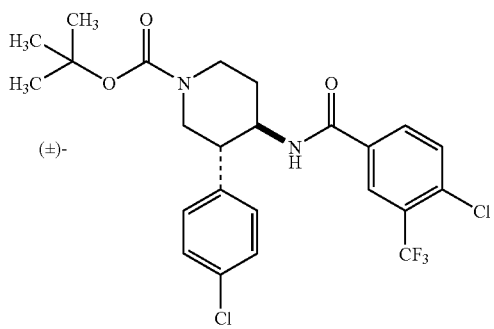 | |
| 55 | 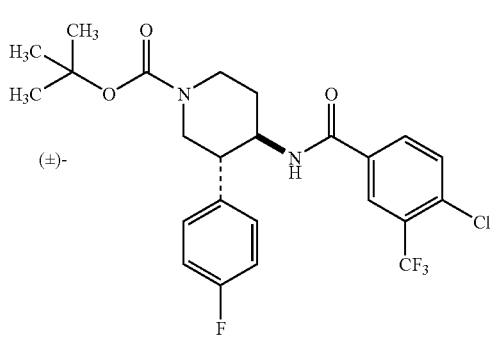 | |
| 56 | 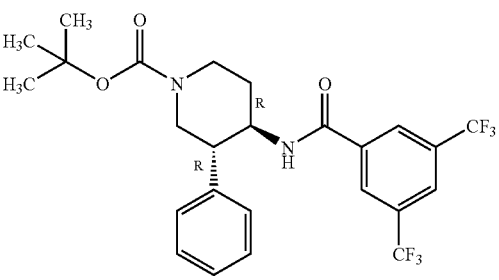 [SMILES: CC(C)(C)OC(=O)N1CC[C@@H](NC(=O)c2cc(C(F)(F)F)cc(C(F)(F)F)c2)[C@H](c2ccccc2)C1] | |
| 57 | 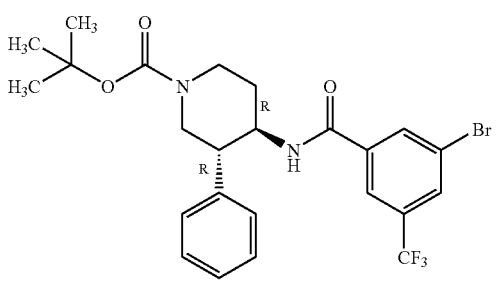 [SMILES: CC(C)(C)OC(=O)N1CC[C@@H](NC(=O)c2cc(Br)cc(C(F)(F)F)c2)[C@H](c2ccccc2)C1] | |
| 59 | 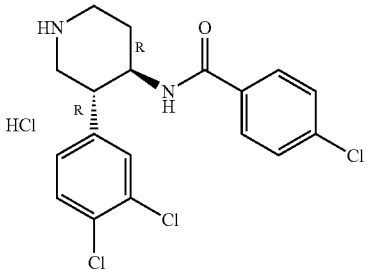 [SMILES: Cl ; O=C(N[C@@H]1CCNC[C@H]1c1ccc(Cl)c(Cl)c1)c1ccc(Cl)cc1] | HCl |

TABLE 17-continued
| Ref. Ex. No. | chemical formula | salt/additive |
|---|---|---|
| 61 | 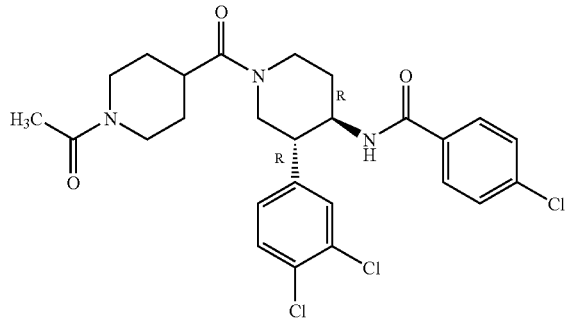 [SMILES: CC(=O)N1CCC(C(=O)N2CC[C@@H](NC(=O)c3ccc(Cl)cc3)[C@H](c3ccc(Cl)c(Cl)c3)C2)CC1] | |
| 62 | 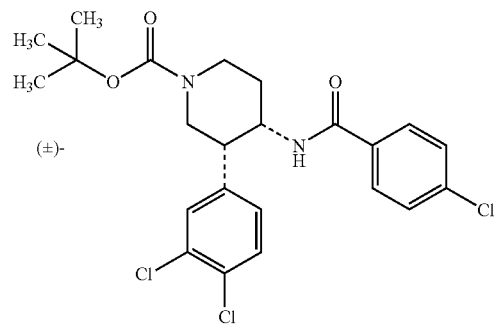 | |
| 63 | 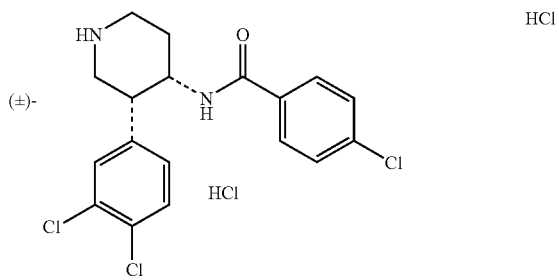 | HCl |
| 64 | 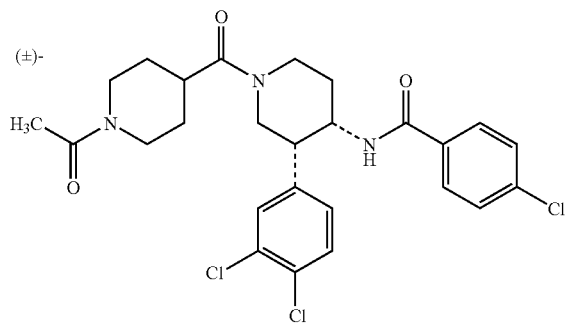 | |

TABLE 17-continued

| Ref. Ex. No. | chemical formula | salt/additive |
|---|---|---|
| 65 | *[structure: tert-butyl piperidine-1-carboxylate with 3-(4-trifluoromethylphenyl) and 4-(4-chlorobenzamido) substituents]* | |

TABLE 18

| Ref. Ex. No. | chemical formula | salt/additive |
|---|---|---|
| 66 | *[structure: tert-butyl piperidine-1-carboxylate with 3-(4-trifluoromethylphenyl) and 4-(4-trifluoromethylbenzamido) substituents]* | |
| 67 | *[structure: tert-butyl piperidine-1-carboxylate with 3-(4-trifluoromethylphenyl) and 4-(4-morpholinobenzamido) substituents]* | |
| 68 | *[structure: (±)-tert-butyl pyrrolidine-1-carboxylate with 3-(3,4-dichlorophenyl) and 4-(4-chlorobenzamido) substituents]* | |

TABLE 18-continued

| Ref. Ex. No. | chemical formula | salt/additive |
| --- | --- | --- |
| 69 | | HCl |
| 70 | | |
| 74 | | HCl |
| 75 | | |
| 76 | | HCl |

TABLE 18-continued

| Ref. Ex. No. | chemical formula | salt/additive |
|---|---|---|
| 77 | | |
| 78 | | |

TABLE 19

| Ref. Ex. No. | chemical formula | salt/additive |
|---|---|---|
| 79 | | |
| 80 | | |

Example 103

N-[(3R*,4R*)-3-(3-fluoro-4-methylphenyl)piperidin-4-yl]-N-methyl-3,5-bis(trifluoromethyl)benzamide monohydrochloride Using the compound obtained in Example 141, and by the reaction and purification in the same manner as in Example 2, the title compound was obtained.
MS (ESI+): 463 (M–HCl+H)

Example 104

N-[(3R*,4R*)-3-(4-fluoro-3-methylphenyl)piperidin-4-yl]-N-methyl-3,5-bis(trifluoromethyl)benzamide monohydrochloride Using the compound obtained in Example 142, and by the reaction and purification in the same manner as in Example 2, the title compound was obtained.
MS (ESI+): 463 (M–HCl+H)

Example 105

N-[(3R*,4R*)-3-(4-fluorophenyl)piperidin-4-yl]-N-methyl-3,5-bis(trifluoromethyl)benzamide monohydrochloride Using the compound obtained in Example 143, and by the reaction and purification in the same manner as in Example 2, the title compound was obtained.
MS (ESI+): 449 (M–HCl+H)

Example 106

3-bromo-N-[(3R*,4R*)-3-(4-fluorophenyl)piperidin-4-yl]-N-methyl-5-(trifluoromethyl)benzamide monohydrochloride Using the compound obtained in Example 144, and by the reaction and purification in the same manner as in Example 2, the title compound was obtained.
MS (ESI+): 459 (M–HCl+H)

Example 107

3-bromo-N-[(3R*,4R*)-3-(4-methoxyphenyl)piperidin-4-yl]-N-methyl-5-(trifluoromethyl)benzamide monohydrochloride Using the compound obtained in Example 145, and by the reaction and purification in the same manner as in Example 2, the title compound was obtained.
MS (ESI+): 471 (M–HCl+H)

Example 108

N-[(3R*,4R*)-3-(4-methoxyphenyl)piperidin-4-yl]-N-methyl-3,5-bis(trifluoromethyl)benzamide monohydrochloride Using the compound obtained in Example 146, and by the reaction and purification in the same manner as in Example 2, the title compound was obtained.
MS (ESI+): 461 (M–HCl+H)

Example 109

4-chloro-N-[(3R*,4R*)-3-(3-chloro-4-methylphenyl)piperidin-4-yl]-N-methylbenzamide monohydrochloride Using the compound obtained in Example 155, and by the reaction and purification in the same manner as in Example 2, the title compound was obtained.
MS (ESI+): 377 (M–HCl+H)

Example 110

4-chloro-N-[(3R*,4R*)-3-(4-chloro-3-methylphenyl)piperidin-4-yl]-N-methylbenzamide monohydrochloride Using the compound obtained in Example 156, and by the reaction and purification in the same manner as in Example 2, the title compound was obtained.
MS (ESI+): 377 (M–HCl+H)

Example 111

4-chloro-N-methyl-N-[(3R*,4R*)-3-(2-methylphenyl)piperidin-4-yl]benzamide monohydrochloride Using the compound obtained in Example 157, and by the reaction and purification in the same manner as in Example 2, the title compound was obtained.
MS (ESI+): 343 (M–HCl+H)

Example 112

4-chloro-N-[(3R*,4R*)-3-(4-fluoro-2-methylphenyl)piperidin-4-yl]-N-methylbenzamide monohydrochloride Using the compound obtained in Example 158, and by the reaction and purification in the same manner as in Example 2, the title compound was obtained.
MS (ESI+): 361 (M–HCl+H)

Example 113

4-chloro-N-[(3S*,4R*)-4-(3,4-dichlorophenyl)pyrrolidin-3-yl]-N-methylbenzamide monohydrochloride Using the compound obtained in Example 176a, and by the reaction and purification in the same manner as in Example 2, the title compound was obtained.
MS (ESI+): 383 (M–HCl+H)

Example 114

4-chloro-N-[(3S,4R)-4-(3,4-dichlorophenyl)pyrrolidin-3-yl]-N-methylbenzamide monohydrochloride Using the compound obtained in Example 177, and by the reaction and purification in the same manner as in Example 2, the title compound was obtained.
MS (ESI+): 383 (M–HCl+H)

Example 115

N-methyl-N-[(3R*,4R*)-3-phenylpiperidin-4-yl]
thiophene-2-carboxamide monohydrochloride Using the compound obtained in Example 154, and by the reaction and purification in the same manner as in Example 2, the title compound was obtained.
MS (ESI+): 301 (M−HCl+H)

Example 116

N-methyl-N-[(3R*,4R*)-3-(4-methylphenyl)piperidin-4-yl]-3,5-bis(trifluoromethyl)benzamide monohydrochloride Using the compound obtained in Example 147, and by the reaction and purification in the same manner as in Example 2, the title compound was obtained.
MS (ESI+): 445 (M−HCl+H)

Example 117

3-bromo-N-methyl-N-[(3R*,4R*)-3-(4-methylphenyl)piperidin-4-yl]-5-(trifluoromethyl)benzamide
monohydrochloride Using the compound obtained in Example 148, and by the reaction and purification in the same manner as in Example 2, the title compound was obtained.
MS (ESI+): 455 (M−HCl+H)

Example 118

N-[(3R*,4R*)-3-(3,5-dichlorophenyl)piperidin-4-yl]-N-methyl-3,5-bis(trifluoromethyl)benzamide monohydrochloride Using the compound obtained in Example 149, and by the reaction and purification in the same manner as in Example 2, the title compound was obtained.
MS (ESI+): 499 (M−HCl+H)

Example 119

N-[(3R*,4R*)-3-(4-bromophenyl)piperidin-4-yl]-4-methoxy-N-methylbenzamide monohydrochloride Using the compound obtained in Example 159, and by the reaction and purification in the same manner as in Example 2, the title compound was obtained.
MS (ESI+): 403 (M−HCl+H)

Example 120

N-[(3R*,4R*)-3-(4-chlorophenyl)piperidin-4-yl]-N-methyl-3,5-bis(trifluoromethyl)benzamide monohydrochloride Using the compound obtained in Example 15.0, and by the reaction and purification in the same manner as in Example 2, the title compound was obtained.
MS (ESI+): 465 (M−HCl+H)

Example 121

3-bromo-N-[(3R*,4R*)-3-(4-chlorophenyl)piperidin-4-yl]-N-methyl-5-(trifluoromethyl)benzamide monohydrochloride Using the compound obtained in Example 153b, and by the reaction and purification in the same manner as in Example 2, the title compound was obtained.
MS (ESI+): 475 (M−HCl+H)

Example 122

N-[(3R*,4R*)-3-(3-chlorophenyl)piperidin-4-yl]-N-methyl-3,5-bis(trifluoromethyl)benzamide monohydrochloride Using the compound obtained in Example 151, and by the reaction and purification in the same manner as in Example 2, the title compound was obtained.
MS (ESI+): 465 (M−HCl+H)

Example 123

N-[(3R*,4R*)-3-(4-bromophenyl)piperidin-4-yl]-N-methyl-3,5-bis(trifluoromethyl)benzamide monohydrochloride Using the compound obtained in Example 152, and by the reaction and purification in the same manner as in Example 2, the title compound was obtained.
MS (ESI+): 509 (M−HCl+H)

Example 124

3-bromo-N-[(3R*,4R*)-3-(4-bromophenyl)piperidin-4-yl]-N-methyl-5-(trifluoromethyl)benzamide
monohydrochloride Using the compound obtained in Example 153a, and by the reaction and purification in the same manner as in Example 2, the title compound was obtained.
MS (ESI+): 520 (M−HCl+H)

Example 125

3-bromo-N-methyl-N-[(3R*,4R*)-3-phenylpiperidin-4-yl]-5-(trifluoromethyl)benzamide monohydrochloride Using the compound obtained in Example 160, and by the reaction and purification in the same manner as in Example 2, the title compound was obtained.
MS (ESI+): 441 (M−HCl+H)

Example 126a 3-bromo-N-[(3R*,4R*)-3-(4-chloro-3-methylphenyl)piperidin-4-yl]-N-methyl-5-(trifluoromethyl)benzamide monohydrochloride Using the compound obtained in Example 171, and by the reaction and purification in the same manner as in Example 2, the title compound was obtained.
MS (ESI+): 489 (M−HCl+H)

Example 126b 3-bromo-N-[(3R*,4R*)-3-(3,4-dichlorophenyl)piperidin-4-yl]-N-methyl-5-(trifluoromethyl)benzamide monohydrochloride Using the compound obtained in Example 138, and by the reaction and purification in the same manner as in Example 2, the title compound was obtained.
MS (ESI+): 510 (M−HCl+H)

Example 126c 3-bromo-N-[(3R*,4R*)-3-(3-fluoro-4-methylphenyl)piperidin-4-yl]-N-methyl-5-(trifluoromethyl)benzamide monohydrochloride Using the compound obtained in Example 139, and by the reaction and purification in the same manner as in Example 2, the title compound was obtained.
MS (ESI+): 473 (M−HCl+H)

Example 126d 3-bromo-N-[(3R*,4R*)-3-(4-fluoro-3-methylphenyl)piperidin-4-yl]-N-methyl-5-(trifluoromethyl)benzamide monohydrochloride Using the compound obtained in Example 140, and by the reaction and purification in the same manner as in Example 2, the title compound was obtained.
MS (ESI+): 473 (M−HCl+H)

Example 127

4-fluoro-N-[(3R*,4R*)-3-(4-fluorophenyl)piperidin-4-yl]-N-methyl-3-(trifluoromethyl)benzamide monohydrochloride Using the compound obtained in Example 172, and by the reaction and purification in the same manner as in Example 2, the title compound was obtained.
MS (ESI+): 399 (M−HCl+H)

Example 128

N-[(3R*,4R*)-3-(4-chlorophenyl)piperidin-4-yl]-4-fluoro-N-methyl-3-(trifluoromethyl)benzamide monohydrochloride Using the compound obtained in Example 161, and by the reaction and purification in the same manner as in Example 2, the title compound was obtained.
MS (ESI+): 415 (M−HCl+H)

Example 129

4-chloro-N-[(3R*,4R*)-3-(4-chlorophenyl)piperidin-4-yl]-N-methyl-3-(trifluoromethyl)benzamide monohydrochloride Using the compound obtained in Example 162, and by the reaction and purification in the same manner as in Example 2, the title compound was obtained.
MS (ESI+): 431 (M−HCl+H)

Example 130

4-chloro-N-[(3R*,4R*)-3-(4-fluorophenyl)piperidin-4-yl]-N-methyl-3-(trifluoromethyl)benzamide monohydrochloride Using the compound obtained in Example 163, and by the reaction and purification in the same manner as in Example 2, the title compound was obtained.
MS (ESI+): 415 (M−HCl+H)

Example 131

N-methyl-N-[(3R*,4R*)-3-(3-methylthiophen-2-yl)piperidin-4-yl]-3,5-bis(trifluoromethyl)benzamide monohydrochloride Using the compound obtained in Example 164, and by the reaction and purification in the same manner as in Example 2, the title compound was obtained.
MS (ESI+): 451 (M−HCl+H)

Example 132

4-chloro-N-methyl-N-{(3R*,4R*)-3-[4-(trifluoromethyl)phenyl]piperidin-4-yl}benzamide monohydrochloride Using the compound obtained in Example 165, and by the reaction and purification in the same manner as in Example 2, the title compound was obtained.
MS (ESI+): 397 (M−HCl+H)

Example 133

N-methyl-4-(trifluoromethyl)-N-{(3R*,4R*)-3-[4-(trifluoromethyl)phenyl]piperidin-4-yl}benzamide monohydrochloride Using the compound obtained in Example 166, and by the reaction and purification in the same manner as in Example 2, the title compound was obtained.
MS (ESI+): 431 (M−HCl+H)

Example 134

N-methyl-4-morpholin-4-yl-N-{(3R*,4R*)-3-[4-(trifluoromethyl)phenyl]piperidin-4-yl}benzamide monohydrochloride Using the compound obtained in Example 167, and by the reaction and purification in the same manner as in Example 2, the title compound was obtained.
MS (ESI+): 448 (M−HCl+H)

Example 135

N-methyl-N-[(3R,4R)-3-phenylpiperidin-4-yl]-3,5-bis(trifluoromethyl)benzamide monohydrochloride Using the compound obtained in Example 173, and by the reaction and purification in the same manner as in Example 2, the title compound was obtained.
MS (ESI+): 431 (M−HCl+H)

Example 136

3-bromo-N-methyl-N-[(3R,4R)-3-phenylpiperidin-4-yl]-5-(trifluoromethyl)benzamide monohydrochloride Using the compound obtained in Example 174, and by the reaction and purification in the same manner as in Example 2, the title compound was obtained.
MS (ESI+): 441 (M−HCl+H)

Example 137a 4-chloro-N-[(3R,4R)-3-(3,4-dichlorophenyl)piperidin-4-yl]-N-methylbenzamide monohydrochloride To a solution of tert-butyl (3R,4R)-4-{[(4-chlorophenyl)carbonyl](methyl)amino}-3-(3,4-dichlorophenyl)piperidine-1-carboxylate (700 mg) obtained in Example 168 in ethyl acetate (5 mL) was added 4N hydrogen chloride/ethyl acetate solution (5 mL), and the mixture was stirred at 50° C. for 4 hr. The reaction mixture was concentrated under reduced pressure, and the precipitate was collected by filtration to give the title compound.
MS (ESI+): 397 (M−HCl+H)

Example 137b 4-chloro-N-[(3R,4R)-3-(3,4-dichlorophenyl)piperidin-4-yl]-N-ethylbenzamide monohydrochloride Using the compound obtained in Example 175, and by the reaction and purification in the same manner as in Reference Example 59, the title compound was obtained.
MS (ESI+): 411 (M−HCl+H)

Example 138 tert-butyl (3R*,4R*)-4-[{[3-bromo-5-(trifluoromethyl)phenyl]carbonyl}(methyl)amino]-3-(3,4-dichlorophenyl)piperidine-1-carboxylate Using the compound obtained in Reference Example 26, and by the reaction and purification in the same manner as in Example 1, the title compound was obtained.
MS (ESI+): 553 (M-$^t$Bu+2H)

Example 139 tert-butyl (3R*,4R*)-4-[{[3-bromo-5-(trifluoromethyl)phenyl]carbonyl}(methyl)amino]-3-(3-fluoro-4-methylphenyl)piperidine-1-carboxylate Using the compound obtained in Reference Example 27a, and by the reaction and purification in the same manner as in Example 1, the title compound was obtained.
MS (ESI+): 517 (M-$^t$Bu+2H)

Example 140 tert-butyl (3R*,4R*)-4-[{[3-bromo-5-(trifluoromethyl)phenyl]carbonyl}(methyl)amino]-3-(4-fluoro-3-methylphenyl)piperidine-1-carboxylate Using the compound obtained in Reference Example 28a, and by the reaction and purification in the same manner as in Example 1, the title compound was obtained.
MS (ESI+): 517 (M-$^t$Bu+2H)

Example 141 tert-butyl (3R*,4R*)-4-[{[3,5-bis(trifluoromethyl)phenyl]carbonyl}(methyl)amino]-3-(3-fluoro-4-methylphenyl)piperidine-1-carboxylate Using the compound obtained in Reference Example 27b, and by the reaction and purification in the same manner as in Example 1, the title compound was obtained.
MS (ESI+): 507 (M-$^t$Bu+2H)

Example 142 tert-butyl (3R*,4R*)-4-[{[3,5-bis(trifluoromethyl)phenyl]carbonyl}(methyl)amino]-3-(4-fluoro-3-methylphenyl)piperidine-1-carboxylate Using the compound obtained in Reference Example 28b, and by the reaction and purification in the same manner as in Example 1, the title compound was obtained.
MS (ESI+): 507 (M-$^t$Bu+2H)

Example 143 tert-butyl (3R*,4R*)-4-[{[3,5-bis(trifluoromethyl)phenyl]carbonyl}(methyl)amino]-3-(4-fluorophenyl)piperidine-1-carboxylate Using the compound obtained in Reference Example 29, and by the reaction and purification in the same manner as in Example 1, the title compound was obtained.
MS (ESI+): 493 (M-$^t$Bu+2H)

Example 144 tert-butyl (3R*,4R*)-4-[{[3-bromo-5-(trifluoromethyl)phenyl]carbonyl}(methyl)amino]-3-(4-fluorophenyl)piperidine-1-carboxylate Using the compound obtained in Reference Example 30, and by the reaction and purification in the same manner as in Example 1, the title compound was obtained.
MS (ESI+): 459 (M-Boc+2H)

Example 145 tert-butyl (3R*,4R*)-4-[{[3-bromo-5-(trifluoromethyl)phenyl]carbonyl}(methyl)amino]-3-(4-methoxyphenyl)piperidine-1-carboxylate Using the compound obtained in Reference Example 31, and by the reaction and purification in the same manner as in Example 1, the title compound was obtained.
MS (ESI+): 471 (M-Boc+2H)

Example 146 tert-butyl (3R*,4R*)-4-[{[3,5-bis(trifluoromethyl)phenyl]carbonyl}(methyl)amino]-3-(4-methoxyphenyl)piperidine-1-carboxylate Using the compound obtained in Reference Example 32, and by the reaction and purification in the same manner as in Example 1, the title compound was obtained.
MS (ESI+): 461 (M-Boc+2H)

Example 147 tert-butyl (3R*,4R*)-4-[{[3,5-bis(trifluoromethyl)phenyl]carbonyl}(methyl)amino]-3-(4-methylphenyl)piperidine-1-carboxylate Using the compound obtained in Reference Example 33, and by the reaction and purification in the same manner as in Example 1, the title compound was obtained.
MS (ESI+): 445 (M-Boc+2H)

Example 148 tert-butyl (3R*,4R*)-4-[{[3-bromo-5-(trifluoromethyl)phenyl]carbonyl}(methyl)amino]-3-(4-methylphenyl)piperidine-1-carboxylate Using the compound obtained in Reference Example 35, and by the reaction and purification in the same manner as in Example 1, the title compound was obtained.
MS (ESI+): 455 (M-Boc+2H)

Example 149 tert-butyl (3R*,4R*)-4-[{[3,5-bis(trifluoromethyl)phenyl]carbonyl}(methyl)amino]-3-(3,5-dichlorophenyl)piperidine-1-carboxylate Using the compound obtained in Reference Example 37, and by the reaction and purification in the same manner as in Example 1, the title compound was obtained.
MS (ESI+): 543 (M-$^t$Bu+2H)

Example 150 tert-butyl (3R*,4R*)-4-[{[3,5-bis(trifluoromethyl)phenyl]carbonyl}(methyl)amino]-3-(4-chlorophenyl)piperidine-1-carboxylate Using the compound obtained in Reference Example 34, and by the reaction and purification in the same manner as in Example 1, the title compound was obtained.
MS (ESI+): 465 (M-Boc+2H)

Example 151 tert-butyl (3R*,4R*)-4-[{[3,5-bis(trifluoromethyl)phenyl]carbonyl}(methyl)amino]-3-(3-chlorophenyl)piperidine-1-carboxylate Using the compound obtained in Reference Example 49, and by the reaction and purification in the same manner as in Example 1, the title compound was obtained.
MS (ESI+): 509 (M-$^t$Bu+2H)

Example 152 tert-butyl (3R*,4R*)-4-[{[3,5-bis(trifluoromethyl)phenyl]carbonyl}(methyl)amino]-3-(4-bromophenyl)piperidine-1-carboxylate Using the compound obtained in Reference Example 47, and by the reaction and purification in the same manner as in Example 1, the title compound was obtained.
MS (ESI+): 509 (M-Boc+2H)

Example 153a tert-butyl (3R*,4R*)-3-(4-bromophenyl)-4-[{[3-bromo-5-(trifluoromethyl)phenyl]carbonyl}(methyl)amino]piperidine-1-carboxylate Using the compound obtained in Reference Example 48, and by the reaction and purification in the same manner as in Example 1, the title compound was obtained.
MS (ESI+): 519 (M-Boc+2H)

Example 153b tert-butyl (3R*,4R*)-4-[{[3-bromo-5-(trifluoromethyl)phenyl]carbonyl}(methyl)amino]-3-(4-chlorophenyl)piperidine-1-carboxylate Using the compound obtained in Reference Example 36, and by the reaction and purification in the same manner as in Example 1, the title compound was obtained.
MS (ESI+): 475 (M-Boc+2H)

Example 154 tert-butyl (3R*,4R*)-4-[methyl(thiophen-2-ylcarbonyl)amino]-3-phenylpiperidine-1-carboxylate Using the compound obtained in Reference Example 38, and by the reaction and purification in the same manner as in Example 1, the title compound was obtained.
MS (ESI+): 301 (M-Boc+2H)

Example 155 tert-butyl (3R*,4R*)-3-(3-chloro-4-methylphenyl)-4-{[(4-chlorophenyl)carbonyl](methyl)amino}piperidine-1-carboxylate Using the compound obtained in Reference Example 39, and by the reaction and purification in the same manner as in Example 1, the title compound was obtained.
MS (ESI+): 421 (M-$^t$Bu+2H)

Example 156 tert-butyl (3R*,4R*)-3-(4-chloro-3-methylphenyl)-4-{[(4-chlorophenyl)carbonyl](methyl)amino}piperidine-1-carboxylate Using the compound obtained in Reference Example 40, and by the reaction and purification in the same manner as in Example 1, the title compound was obtained.
MS (ESI+): 421 (M-$^t$Bu+2H)

Example 157 tert-butyl (3R*,4R*)-4-{[(4-chlorophenyl)carbonyl](methyl)amino}-3-(2-methylphenyl)piperidine-1-carboxylate Using the compound obtained in Reference Example 41, and by the reaction and purification in the same manner as in Example 1, the title compound was obtained.
MS (ESI+): 387 (M-$^t$Bu+2H)

Example 158 tert-butyl (3R*,4R*)-4-{[(4-chlorophenyl)carbonyl](methyl)amino}-3-(4-fluoro-2-methylphenyl)piperidine-1-carboxylate Using the compound obtained in Reference Example 42, and by the reaction and purification in the same manner as in Example 1, the title compound was obtained.
MS (ESI+): 405 (M-$^t$Bu+2H)

Example 159 tert-butyl (3R*,4R*)-3-(4-bromophenyl)-4-{[(4-methoxyphenyl)carbonyl](methyl)amino}piperidine-1-carboxylate Using the compound obtained in Reference Example 46, and by the reaction and purification in the same manner as in Example 1, the title compound was obtained.
MS (ESI+): 447 (M-$^t$Bu+2H)

Example 160 tert-butyl (3R*,4R*)-4-[{[3-bromo-5-(trifluoromethyl)phenyl]carbonyl}(methyl)amino]-3-phenylpiperidine-1-carboxylate Using the compound obtained in Reference Example 50, and by the reaction and purification in the same manner as in Example 1, the title compound was obtained.
MS (ESI+): 441 (M-Boc+2H)

Example 161 tert-butyl (3R*,4R*)-3-(4-chlorophenyl)-4-[{[4-fluoro-3-(trifluoromethyl)phenyl]carbonyl}(methyl)amino]piperidine-1-carboxylate Using the compound obtained in Reference Example 53, and by the reaction and purification in the same manner as in Example 1, the title compound was obtained.
MS (ESI+): 415 (M-Boc+2H)

Example 162 tert-butyl (3R*,4R*)-3-(4-chlorophenyl)-4-[{[4-chloro-3-(trifluoromethyl)phenyl]carbonyl}(methyl)amino]piperidine-1-carboxylate Using the compound obtained in Reference Example 54, and by the reaction and purification in the same manner as in Example 1, the title compound was obtained.
MS (ESI+): 431 (M-Boc+2H)

Example 163 tert-butyl (3R*,4R*)-4-[{[4-chloro-3-(trifluoromethyl)phenyl]carbonyl}(methyl)amino]-3-(4-fluorophenyl)piperidine-1-carboxylate Using the compound obtained in Reference Example 55, and by the reaction and purification in the same manner as in Example 1, the title compound was obtained.
MS (ESI+): 415 (M-Boc+2H)

Example 164 tert-butyl (3R*,4R*)-4-[{[3,5-bis(trifluoromethyl)phenyl]carbonyl}(methyl)amino]-3-(3-methylthiophen-2-yl)piperidine-1-carboxylate Using the compound obtained in Reference Example 79, and by the reaction and purification in the same manner as in Example 1, the title compound was obtained.
MS (ESI+): 495 (M-$^t$Bu+2H)

Example 165 tert-butyl (3R*,4R*)-4-{[(4-chlorophenyl)carbonyl](methyl)amino}-3-[4-(trifluoromethyl)phenyl]piperidine-1-carboxylate Using the compound obtained in Reference Example 65, and by the reaction and purification in the same manner as in Example 1, the title compound was obtained.
MS (ESI+): 441 (M-$^t$Bu+2H)

Example 166 tert-butyl (3R*,4R*)-4-(methyl{[4-(trifluoromethyl)phenyl]carbonyl}amino)-3-[4-(trifluoromethyl)phenyl]piperidine-1-carboxylate Using the compound obtained in Reference Example 66, and by the reaction and purification in the same manner as in Example 1, the title compound was obtained.
MS (ESI+): 475 (M-$^t$Bu+2H)

Example 167 tert-butyl (3R*,4R*)-4-{methyl[(4-morpholin-4-ylphenyl)carbonyl]amino}-3-[4-(trifluoromethyl)phenyl]piperidine-1-carboxylate Using the compound obtained in Reference Example 67, and by the reaction and purification in the same manner as in Example 1, the title compound was obtained.
MS (ESI+): 492 (M-$^t$Bu+2H)

Example 168 tert-butyl (3R,4R)-4-{[(4-chlorophenyl)carbonyl](methyl)amino}-3-(3,4-dichlorophenyl)piperidine-1-carboxylate To a solution of tert-butyl (3R,4R)-4-{[(4-chlorophenyl)carbonyl]amino}-3-(3,4-dichlorophenyl)piperidine-1-carboxylate (700 mg) obtained in Reference Example 43 in DMF (5 mL) was added sodium hydride (60% in oil, 115 mg) at 0° C., and the mixture was stirred for 15 min. Then, methyl iodide (450 μL) was added, and the mixture was stirred at room temperature for 14 hr. To the reaction mixture was added water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography to give the title compound (777 mg, 100%) as a white powder.
MS (ESI+): 441 (M-$^t$Bu+2H)

Example 169 tert-butyl (3R,4R)-3-(3,4-dichlorophenyl)-4-{[(4-methoxyphenyl)carbonyl](methyl)amino}piperidine-1-carboxylate To a solution of tert-butyl (3R,4R)-3-(3,4-dichlorophenyl)-4-{[(4-methoxyphenyl)carbonyl]amino}piperidine-1-carboxylate (700 mg) obtained in Reference Example 44 in DMF (5 mL) was added sodium hydride (60% in oil, 116 mg) at 0° C., and the mixture was stirred for 5 min. Then, methyl iodide (454 μL) was added, and the mixture was stirred at room temperature for 2 hr. To the reaction mixture was added water, and the resultant product was extracted with ethyl acetate. The organic layer was washed with water and brine and dried, and the solvent was evaporated under reduced pressure. The obtained residue was purified by silica gel column chromatography to give the title compound (777 mg, 100%) as a white powder.
MS (ESI+): 437 (M-$^t$Bu+2H)

Example 170 tert-butyl (3R,4R)-3-(3,4-dichlorophenyl)-4-(methyl{[4-(3-methyl-1H-pyrazol-1-yl)phenyl]carbonyl}amino)piperidine-1-carboxylate Using the compound obtained in Reference Example 45, and by the reaction and purification in the same manner as in Example 1, the title compound was obtained.
MS (ESI+): 487 (M-$^t$Bu+2H)

Example 171 tert-butyl (3R*,4R*)-4-[{[3-bromo-5-(trifluoromethyl)phenyl]carbonyl}(methyl)amino]-3-(4-chloro-3-methylphenyl)piperidine-1-carboxylate Using the compound obtained in Reference Example 51, and by the reaction and purification in the same manner as in Example 1, the title compound was obtained.
MS (ESI+): 489 (M-Boc+2H)

Example 172 tert-butyl (3R*,4R*)-3-(4-fluorophenyl)-4-[{[4-fluoro-3-(trifluoromethyl)phenyl]carbonyl}(methyl)amino]piperidine-1-carboxylate Using the compound obtained in Reference Example 52, and by the reaction and purification in the same manner as in Example 1, the title compound was obtained.
MS (ESI+): 399 (M-Boc+2H)

Example 173 tert-butyl (3R,4R)-4-[{[3,5-bis(trifluoromethyl)phenyl]carbonyl}(methyl)amino]-3-phenylpiperidine-1-carboxylate Using the compound obtained in Reference Example 56, and by the reaction and purification in the same manner as in Example 1, the title compound was obtained.
MS (ESI+): 431 (M-Boc+2H)

Example 174 tert-butyl (3R,4R)-4-[{[3-bromo-5-(trifluoromethyl)phenyl]carbonyl}(methyl)amino]-3-phenylpiperidine-1-carboxylate Using the compound obtained in Reference Example 57, and by the reaction and purification in the same manner as in Example 1, the title compound was obtained.
MS (ESI+): 441 (M-Boc+2H)

Example 175 tert-butyl (3R,4R)-4-{[(4-chlorophenyl)carbonyl](ethyl)amino}-3-(3,4-dichlorophenyl)piperidine-1-carboxylate Using the compound obtained in Reference Example 43 and iodoethane, and by the reaction and purification in the same manner as in Example 1, the title compound was obtained.
MS (ESI+): 511 (M+H)

Example 176 tert-butyl (3S*,4R*)-3-{[(4-chlorophenyl)carbonyl](methyl)amino}-4-(3,4-dichlorophenyl)pyrrolidine-1-carboxylate Using the compound obtained in Reference Example 68, and by the reaction and purification in the same manner as in Example 1, the title compound was obtained.
MS (ESI+): 427 (M-$^t$Bu+2H)

Example 177 tert-butyl (3S,4R)-3-{[(4-chlorophenyl)carbonyl](methyl)amino}-4-(3,4-dichlorophenyl)pyrrolidine-1-carboxylate Using the compound obtained in Reference Example 80, and by the reaction and purification in the same manner as in Example 1, the title compound was obtained.
MS (ESI+): 427 (M-$^t$Bu+2H)

Example 178

N-[(3R*,4R*)-1-[(1-acetylpiperidin-4-yl)carbonyl]-3-(3,4-dichlorophenyl)piperidin-4-yl]-N-methylfuran-2-carboxamide To a solution of the compound (24.7 mg) obtained in Reference Example 25, 2-furoic acid (6.7 mg) and triethylamine (8.3 μL) in DMF (1.5 mL) were added WSC.HCl (13.7 mg) and HOBt (9.8 mg, 72 μmol), and the mixture was stirred at room temperature for 16 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by preparative HPLC, and the eluate was concentrated to give the title compound (19.7 mg).
MS (ESI+): 506 (M+H)

Example 179

N-[(3R*,4R*)-1-[(1-acetylpiperidin-4-yl)carbonyl]-3-(3,4-dichlorophenyl)piperidin-4-yl]-N-methylthiophene-3-carboxamide Using the compound obtained in Reference Example 25 and thiophene-3-carboxylic acid, and by the reaction and purification in the same manner as in Example 178, the title compound was obtained.
MS (ESI+): 522 (M+H)

Example 180

N-[(3R*,4R*)-1-[(1-acetylpiperidin-4-yl)carbonyl]-3-(3,4-dichlorophenyl)piperidin-4-yl]-3-fluoro-N-methylbenzamide Using the compound obtained in Reference Example 25 and 3-fluorobenzoic acid, and by the reaction and purification in the same manner as in Example 178, the title compound was obtained.
MS (ESI+): 534 (M+H)

Example 181

N-[(3R*,4R*)-1-[(1-acetylpiperidin-4-yl)carbonyl]-3-(3,4-dichlorophenyl)piperidin-4-yl]-4-cyano-N-methylbenzamide Using the compound obtained in Reference Example 25 and 4-cyanobenzoic acid, and by the reaction and purification in the same manner as in Example 178, the title compound was obtained.
MS (ESI+): 541 (M+H)

Example 182

N-[(3R*,4R*)-1-[(1-acetylpiperidin-4-yl)carbonyl]-3-(3,4-dichlorophenyl)piperidin-4-yl]-2-cyano-N-methylbenzamide Using the compound obtained in Reference Example 25 and 2-cyanobenzoic acid, and by the reaction and purification in the same manner as in Example 178, the title compound was obtained.
MS (ESI+): 541 (M+H)

Example 183

N-[(3R*,4R*)-1-[(1-acetylpiperidin-4-yl)carbonyl]-3-(3,4-dichlorophenyl)piperidin-4-yl]-N-methyl-1H-indole-5-carboxamide Using the compound obtained in Reference Example 25 and 1H-indole-5-carboxylic acid, and by the reaction and purification in the same manner as in Example 178, the title compound was obtained.
MS (ESI+): 555 (M+H)

Example 184

N-[(3R*,4R*)-1-[(1-acetylpiperidin-4-yl)carbonyl]-3-(3,4-dichlorophenyl)piperidin-4-yl]-N-methyl-1H-indole-2-carboxamide Using the compound obtained in Reference Example 25 and 1H-indole-2-carboxylic acid, and by the reaction and purification in the same manner as in Example 178, the title compound was obtained.
MS (ESI+): 555 (M+H)

Example 185

N-[(3R*,4R*)-1-[(1-acetylpiperidin-4-yl)carbonyl]-3-(3,4-dichlorophenyl)piperidin-4-yl]-N-methyl-1H-indole-3-carboxamide Using the compound obtained in Reference Example 25 and 1H-indole-3-carboxylic acid, and by the reaction and purification in the same manner as in Example 178, the title compound was obtained.
MS (ESI+): 555 (M+H)

Example 186

N-[(3R*,4R*)-1-[(1-acetylpiperidin-4-yl)carbonyl]-3-(3,4-dichlorophenyl)piperidin-4-yl]-4-tert-butyl-N-methylbenzamide Using the compound obtained in Reference Example 25 and 4-tert-butylbenzoic acid, and by the reaction and purification in the same manner as in Example 178, the title compound was obtained.
MS (ESI+): 572 (M+H)

Example 187

4-(acetylamino)-N-[(3R*,4R*)-1-[(1-acetylpiperidin-4-yl)carbonyl]-3-(3,4-dichlorophenyl)piperidin-4-yl]-N-methylbenzamide Using the compound obtained in Reference Example 25 and 4-acetamidebenzoic acid, and by the reaction and purification in the same manner as in Example 178, the title compound was obtained.
MS (ESI+): 573 (M+H)

Example 188 methyl 4-{[(3R*,4R*)-1-[(1-acetylpiperidin-4-yl)carbonyl]-3-(3,4-dichlorophenyl)piperidin-4-yl](methyl)carbamoyl}benzoate Using the compound obtained in Reference Example 25 and mono-methyl terephthalate, and by the reaction and purification in the same manner as in Example 178, the title compound was obtained.
MS (ESI+): 574 (M+H)

Example 189

N-[(3R*,4R*)-1-[(1-acetylpiperidin-4-yl)carbonyl]-3-(3,4-dichlorophenyl)piperidin-4-yl]-2,5-dimethoxy-N-methylbenzamide Using the compound obtained in Reference Example 25 and 2,5-dimethoxybenzoic acid, and by the reaction and purification in the same manner as in Example 178, the title compound was obtained.
MS (ESI+): 576 (M+H)

Example 190

N-[(3R*,4R*)-1-[(1-acetylpiperidin-4-yl)carbonyl]-3-(3,4-dichlorophenyl)piperidin-4-yl]-3,5-dichloro-N-methylbenzamide Using the compound obtained in Reference Example 25 and 3,5-dichlorobenzoic acid, and by the reaction and purification in the same manner as in Example 178, the title compound was obtained.
MS (ESI+): 584 (M+H)

Example 191

N-[(3R*,4R*)-1-[(1-acetylpiperidin-4-yl)carbonyl]-3-(3,4-dichlorophenyl)piperidin-4-yl]-N-methyl-4-sulfamoylbenzamide Using the compound obtained in Reference Example 25 and 4-carboxybenzenesulfonamide, and by the reaction and purification in the same manner as in Example 178, the title compound was obtained.
MS (ESI+): 595 (M+H)

Example 192

N-[(3R*,4R*)-1-[(1-acetylpiperidin-4-yl)carbonyl]-3-(3,4-dichlorophenyl)piperidin-4-yl]-N-methyl-4-(trifluoromethoxy)benzamide Using the compound obtained in Reference Example 25 and 4-(trifluoromethoxy)benzoic acid, and by the reaction and purification in the same manner as in Example 178, the title compound was obtained.
MS (ESI+): 600 (M+H)

Example 193

N-[(3R*,4R*)-1-[(1-acetylpiperidin-4-yl)carbonyl]-3-(3,4-dichlorophenyl)piperidin-4-yl]-3,4,5-trimethoxy-N-methylbenzamide Using the compound obtained in Reference Example 25 and 3,4,5-trimethoxybenzoic acid, and by the reaction and purification in the same manner as in Example 178, the title compound was obtained.
MS (ESI+): 606 (M+H)

Example 194

N-[(3R*,4R*)-1-[(1-acetylpiperidin-4-yl)carbonyl]-3-(3,4-dichlorophenyl)piperidin-4-yl]-2-fluoro-N methylbenzamide Using the compound obtained in Reference Example 25 and 2-fluorobenzoic acid, and by the reaction and purification in the same manner as in Example 178, the title compound was obtained.
MS (ESI+): 534 (M+H)

Example 195

N-[(3R*,4R*)-1-[(1-acetylpiperidin-4-yl)carbonyl]-3-(3,4-dichlorophenyl)piperidin-4-yl]-3-cyano-N-methylbenzamide Using the compound obtained in Reference Example 25 and 3-cyanobenzoic acid, and by the reaction and purification in the same manner as in Example 178, the title compound was obtained.
MS (ESI+): 541 (M+H)

Example 196

N-[(3R*,4R*)-1-[(1-acetylpiperidin-4-yl)carbonyl]-3-(3,4-dichlorophenyl)piperidin-4-yl]-N-methylfuran-3-carboxamide Using the compound obtained in Reference Example 25 and 3-furoic acid, and by the reaction and purification in the same manner as in Example 178, the title compound was obtained.
MS (ESI+): 506 (M+H)

Example 197

N-[(3R*,4R*)-1-[(1-acetylpiperidin-4-yl)carbonyl]-3-(3,4-dichlorophenyl)piperidin-4-yl]-N,2-dimethylbenzamide Using the compound obtained in Reference Example 25 and o-toluic acid, and by the reaction and purification in the same manner as in Example 178, the title compound was obtained.
MS (ESI+): 530 (M+H)

Example 198

N-[(3R*,4R*)-1-[(1-acetylpiperidin-4-yl)carbonyl]-3-(3,4-dichlorophenyl)piperidin-4-yl]-N,3-dimethylbenzamide Using the compound obtained in Reference Example 25 and m-toluic acid, and by the reaction and purification in the same manner as in Example 178, the title compound was obtained.
MS (ESI+): 530 (M+H)

Example 199

N-[(3R*,4R*)-1-[(1-acetylpiperidin-4-yl)carbonyl]-3-(3,4-dichlorophenyl)piperidin-4-yl]-N-methyl-1H-imidazole-4-carboxamide trifluoroacetate Using the compound obtained in Reference Example 25 and imidazole-4-carboxylic acid, and by the reaction and purification in the same manner as in Example 178, the title compound was obtained.
MS (ESI+): 506 (M-TFA+H)

Example 200

N-[(3R*,4R*)-1-[(1-acetylpiperidin-4-yl)carbonyl]-3-(3,4-dichlorophenyl)piperidin-4-yl]-N-methylpyridine-3-carboxamide trifluoroacetate Using the compound obtained in Reference Example 25 and nicotinic acid, and by the reaction and purification in the same manner as in Example 178, the title compound was obtained.
MS (ESI+): 517 (M-TFA+H)

Example 201

N-[(3R*,4R*)-1-[(1-acetylpiperidin-4-yl)carbonyl]-
3-(3,4-dichlorophenyl)piperidin-4-yl]-N-methylpyridine-2-carboxamide trifluoroacetate Using the compound obtained in Reference Example 25 and picoline acid, and by the reaction and purification in the same manner as in Example 178, the title compound was obtained.
MS (ESI+): 517 (M-TFA+H)

Example 202

N-[(3R*,4R*)-1-[(1-acetylpiperidin-4-yl)carbonyl]-
3-(3,4-dichlorophenyl)piperidin-4-yl]-N-methylpyridine-4-carboxamide trifluoroacetate Using the compound obtained in Reference Example 25 and isonicotinic acid, and by the reaction and purification in the same manner as in Example 178, the title compound was obtained.
MS (ESI+): 517 (M-TFA+H)

Example 203

N-[(3R*,4R*)-1-[(1-acetylpiperidin-4-yl)carbonyl]-
3-(3,4-dichlorophenyl)piperidin-4-yl]-6-chloro-N-methylpyridine-3-carboxamide trifluoroacetate Using the compound obtained in Reference Example 25 and 6-chloronicotinic acid, and by the reaction and purification in the same manner as in Example 178, the title compound was obtained.
MS (ESI+): 551 (M-TFA+H)

Example 204

N-[(3R*,4R*)-1-[(1-acetylpiperidin-4-yl)carbonyl]-
3-(3,4-dichlorophenyl)piperidin-4-yl]-4-(dimethylamino)-N-methylbenzamide trifluoroacetate Using the compound obtained in Reference Example 25 and 4-dimethylaminobenzoic acid, and by the reaction and purification in the same manner as in Example 178, the title compound was obtained.
MS (ESI+): 559 (M-TFA+H)

Example 205

N-[(3R*,4R*)-1-[(1-acetylpiperidin-4-yl)carbonyl]-
3-(3,4-dichlorophenyl)piperidin-4-yl]-5-chloro-N-methylpyridine-2-carboxamide trifluoroacetate Using the compound obtained in Reference Example 25 and 5-chloropyridine-2-carboxylic acid, and by the reaction and purification in the same manner as in Example 178, the title compound was obtained.
MS (ESI+): 551 (M-TFA+H)

Example 206

N-[(3R*,4R*)-1-[(1-acetylpiperidin-4-yl)carbonyl]-
3-(3,4-dichlorophenyl)piperidin-4-yl]-3-cyano-5-fluoro-N-methylbenzamide Using the compound obtained in Reference Example 25 and 3-cyano-5-fluorobenzoic acid, and by the reaction and purification in the same manner as in Example 178, the title compound was obtained.
MS (ESI+): 559 (M+H)

Example 207

N-[(3R*,4R*)-1-[(1-acetylpiperidin-4-yl)carbonyl]-
3-(3,4-dichlorophenyl)piperidin-4-yl]-3-chloro-N-methyl-5-(trifluoromethyl)benzamide Using the compound obtained in Reference Example 25 and 3-chloro-5-(trifluoromethyl)benzoic acid, and by the reaction and purification in the same manner as in Example 178, the title compound was obtained.
MS (ESI+): 618 (M+H)

Example 208

N-[(3R*,4R*)-1-[(1-acetylpiperidin-4-yl)carbonyl]-
3-(3,4-dichlorophenyl)piperidin-4-yl]-5,6-dichloro-N-methylpyridine-3-carboxamide trifluoroacetate Using the compound obtained in Reference Example 25 and 5,6-dichloronicotinic acid, and by the reaction and purification in the same manner as in Example 178, the title compound was obtained.
MS (ESI+): 584 (M-TFA+H)

Example 209

N-[(3R*,4R*)-1-[(1-acetylpiperidin-4-yl)carbonyl]-
3-(3,4-dichlorophenyl)piperidin-4-yl]-2,6-dichloro-N-methylpyridine-3-carboxamide trifluoroacetate Using the compound obtained in Reference Example 25 and 2,6-dichloronicotinic acid, and by the reaction and purification in the same manner as in Example 178, the title compound was obtained.
MS (ESI+): 584 (M-TFA+H)

Example 210

N-[(3R*,4R*)-1-[(1-acetylpiperidin-4-yl)carbonyl]-
3-(3,4-dichlorophenyl)piperidin-4-yl]-3,5-difluoro-N-methylpyridine-2-carboxamide trifluoroacetate Using the compound obtained in Reference Example 25 and 3,5-difluoropyridine-2-carboxylic acid, and by the reaction and purification in the same manner as in Example 178, the title compound was obtained.
MS (ESI+): 553 (M-TFA+H)

Example 211

N-[(3R*,4R*)-1-[(1-acetylpiperidin-4-yl)carbonyl]-
3-(3,4-dichlorophenyl)piperidin-4-yl]-N,6-dimethylpyridine-3-carboxamide trifluoroacetate Using the compound obtained in Reference Example 25 and 6-methylnicotinic acid, and by the reaction and purification in the same manner as in Example 178, the title compound was obtained.
MS (ESI+): 531 (M-TFA+H)

Example 212

N-[(3R*,4R*)-1-[(1-acetylpiperidin-4-yl)carbonyl]-
3-(3,4-dichlorophenyl)piperidin-4-yl]-4-cyclohexyl-
N-methylbenzamide Using the compound obtained in Reference Example 25 and 4-cyclohexylbenzoic acid, and by the reaction and purification in the same manner as in Example 178, the title compound was obtained.
MS (ESI+): 598 (M+H)

Example 213

N-[(3R*,4R*)-1-[(1-acetylpiperidin-4-yl)carbonyl]-
3-(3,4-dichlorophenyl)piperidin-4-yl]-4-ethyl-N-
methylbenzamide Using the compound obtained in Reference Example 25 and 4-ethylbenzoic acid, and by the reaction and purification in the same manner as in Example 178, the title compound was obtained.
MS (ESI+): 544 (M+H)

Example 214

N-[(3R*,4R*)-1-[(1-acetylpiperidin-4-yl)carbonyl]-
3-(3,4-dichlorophenyl)piperidin-4-yl]-3,4-dichloro-
N-methylbenzamide Using the compound obtained in Reference Example 25 and 3,4-dichlorobenzoic acid, and by the reaction and purification in the same manner as in Example 178, the title compound was obtained.
MS (ESI+): 584 (M+H)

Example 215

N-[(3R*,4R*)-1-[(1-acetylpiperidin-4-yl)carbonyl]-
3-(3,4-dichlorophenyl)piperidin-4-yl]-N,3,5-trimeth-
ylbenzamide Using the compound obtained in Reference Example 25 and 3,5-dimethylbenzoic acid, and by the reaction and purification in the same manner as in Example 178, the title compound was obtained.
MS (ESI+): 544 (M+H)

Example 216

N-[(3R*,4R*)-1-[(1-acetylpiperidin-4-yl)carbonyl]-
3-(3,4-dichlorophenyl)piperidin-4-yl]-N-methyl-1H-
pyrrole-2-carboxamide Using the compound obtained in Reference Example 25 and pyrrole-2-carboxylic acid, and by the reaction and purification in the same manner as in Example 178, the title compound was obtained.
MS (ESI+): 505 (M+H)

Example 217

N-[(3R*,4R*)-1-[(1-acetylpiperidin-4-yl)carbonyl]-
3-(3,4-dichlorophenyl)piperidin-4-yl]-N-methylbi-
phenyl-3-carboxamide Using the compound obtained in Reference Example 25 and 3-biphenylcarboxylic acid, and by the reaction and purification in the same manner as in Example 178, the title compound was obtained.
MS (ESI+): 592 (M+H)

Example 218

N-[(3R*,4R*)-1-[(1-acetylpiperidin-4-yl)carbonyl]-
3-(3,4-dichlorophenyl)piperidin-4-yl]-N,2-dimethyl-
1H-benzimidazole-5-carboxamide trifluoroacetate Using the compound obtained in Reference Example 25 and 2-methyl-1H-benzimidazole-5-carboxylic acid, and by the reaction and purification in the same manner as in Example 178, the title compound was obtained.
MS (ESI+): 570 (M-TFA+H)

Example 219

N-[(3R*,4R*)-1-[(1-acetylpiperidin-4-yl)carbonyl]-
3-(3,4-dichlorophenyl)piperidin-4-yl]-4-(difluo-
romethoxy)-N-methylbenzamide Using the compound obtained in Reference Example 25 and 4-(difluoromethoxy)benzoic acid, and by the reaction and purification in the same manner as in Example 178, the title compound was obtained.
MS (ESI+): 582 (M+H)

Example 220

N-[(3R*,4R*)-1-[(1-acetylpiperidin-4-yl)carbonyl]-
3-(3,4-dichlorophenyl)piperidin-4-yl]-N-methylben-
zene-1,4-dicarboxamide Using the compound obtained in Reference Example 25 and terephthalic acid monoamide, and by the reaction and purification in the same manner as in Example 178, the title compound was obtained.
MS (ESI+): 559 (M+H)

Example 221

N-[(3R*,4R*)-1-[(1-acetylpiperidin-4-yl)carbonyl]-
3-(3,4-dichlorophenyl)piperidin-4-yl]-N-methyl-1H-
pyrazole-4-carboxamide trifluoroacetate Using the compound obtained in Reference Example 25 and 1H-pyrazole-4-carboxylic acid, and by the reaction and purification in the same manner as in Example 178, the title compound was obtained.
MS (ESI+): 506 (M-TFA+H)

Example 222

N-[(3R*,4R*)-1-[(1-acetylpiperidin-4-yl)carbonyl]-
3-(3,4-dichlorophenyl)piperidin-4-yl]-N-methyl-1H-
pyrrole-3-carboxamide Using the compound obtained in Reference Example 25 and 1H-pyrrole-3-carboxylic acid, and by the reaction and purification in the same manner as in Example 178, the title compound was obtained.
MS (ESI+): 505 (M+H)

Example 223

N-[(3R*,4R*)-1-[(1-acetylpiperidin-4-yl)carbonyl]-
3-(3,4-dichlorophenyl)piperidin-4-yl]-N-methyl-2,1,
3-benzothiadiazole-4-carboxamide Using the compound obtained in Reference Example 25 and 2,1,3-benzothiadiazole-4-carboxylic acid, and by the reaction and purification in the same manner as in Example 178, the title compound was obtained.

MS (ESI+): 574 (M+H)

Example 224

N-[(3R*,4R*)-1-[(1-acetylpiperidin-4-yl)carbonyl]-3-(3,4-dichlorophenyl)piperidin-4-yl]-5-chloro-N-methyl-1H-benzimidazole-2-carboxamide Using the compound obtained in Reference Example 25 and 5-chloro-1H-benzimidazole-2-carboxylic acid, and by the reaction and purification in the same manner as in Example 178, the title compound was obtained.
MS (ESI+): 590 (M+H)

Example 225

N-[(3R*,4R*)-1-[(1-acetylpiperidin-4-yl)carbonyl]-3-(3,4-dichlorophenyl)piperidin-4-yl]-3-bromo-N-methyl-5-(trifluoromethyl)benzamide Using the compound obtained in Reference Example 25 and 3-bromo-5-(trifluoromethyl)benzoic acid, and by the reaction and purification in the same manner as in Example 178, the title compound was obtained.
MS (ESI+): 662 (M+H)

Example 226

N-[(3R*,4R*)-1-[(1-acetylpiperidin-4-yl)carbonyl]-3-(3,4-dichlorophenyl)piperidin-4-yl]-5-(benzyloxy)-2-methoxy-N-methylbenzamide Using the compound obtained in Reference Example 25 and 5-(benzyloxy)-2-methoxybenzoic acid, and by the reaction and purification in the same manner as in Example 178, the title compound was obtained.
MS (ESI+): 652 (M+H)

Example 227

N-[(3R*,4R*)-1-[(1-acetylpiperidin-4-yl)carbonyl]-3-(3,4-dichlorophenyl)piperidin-4-yl]-5-(4-chlorophenyl)-N-methyl-1H-pyrazole-3-carboxamide trifluoroacetate Using the compound obtained in Reference Example 25 and 5-(4-chlorophenyl)-1H-pyrazole-3-carboxylic acid, and by the reaction and purification in the same manner as in Example 178, the title compound was obtained.
MS (ESI+): 616 (M-TFA+H)

Example 228

N-[(3R*,4R*)-1-[(1-acetylpiperidin-4-yl)carbonyl]-3-(3,4-dichlorophenyl)piperidin-4-yl]-2-methoxy-N-methyl-5-[5-(trifluoromethyl)-1H-tetrazol-1-yl]benzamide Using the compound obtained in Reference Example 25 and 2-methoxy-5-[5-(trifluoromethyl)-1H-tetrazol-1-yl]benzoic acid, and by the reaction and purification in the same manner as in Example 178, the title compound was obtained.
MS (ESI+): 682 (M+H)

Example 229

N-[(3R*,4R*)-1-[(1-acetylpiperidin-4-yl)carbonyl]-3-(3,4-dichlorophenyl)piperidin-4-yl]-N,4-dimethyl-1,2,3-thiadiazole-5-carboxamide Using the compound obtained in Reference Example 25 and 4-methyl-1,2,3-thiadiazole-5-carboxylic acid, and by the reaction and purification in the same manner as in Example 178, the title compound was obtained.
MS (ESI+): 538 (M+H)

Example 230

N-[(3R*,4R*)-1-[(1-acetylpiperidin-4-yl)carbonyl]-3-(3,4-dichlorophenyl)piperidin-4-yl]-N-methyl[1,2,4]triazolo[1,5-a]pyrimidine-2-carboxamide trifluoroacetate Using the compound obtained in Reference Example 25 and [1,2,4]triazolo[1,5-a]pyrimidine-2-carboxylic acid, and by the reaction and purification in the same manner as in Example 178, the title compound was obtained.
MS (ESI+): 558 (M-TFA+H)

Example 231

N-[(3R*,4R*)-1-[(1-acetylpiperidin-4-yl)carbonyl]-3-(3,4-dichlorophenyl)piperidin-4-yl]-N-methylbiphenyl-2-carboxamide To a solution of the compound (0.052 g) obtained in Reference Example 25, 2-biphenylcarboxylic acid (0.050 g) and DEPC (38 μL) in DMF (3 mL) was added triethylamine (42 μL) at 0° C., and the mixture was stirred overnight at room temperature. The reaction mixture was poured into water, and the resultant product was extracted with ethyl acetate. The organic layer was washed with saturated aqueous sodium hydrogen carbonate solution, water, 1M $KHSO_4$ aqueous solution and brine and dried, and the solvent was evaporated under reduced pressure. The obtained residue was purified by silica gel column chromatography (NH Chromatorex) (solvent; 50→100% ethyl acetate/hexane) to give the title compound (0.052 g, 70%) as a white powder.
MS (ESI+): 592 (M+H)

Example 232

N-[(3R*,4R*)-1-[(1-acetylpiperidin-4-yl)carbonyl]-3-(3-chloro-4-methylphenyl)piperidin-4-yl]-4-chloro-N-methylbenzamide Using the compound obtained in Example 10.9, and by the reaction and purification in the same manner as in Example 3, the title compound was obtained.
MS (ESI+): 530 (M+H)

Example 233

N-[(3R*,4R*)-1-[(1-acetylpiperidin-4-yl)carbonyl]-3-(4-chloro-3-methylphenyl)piperidin-4-yl]-4-chloro-N-methylbenzamide Using the compound obtained in Example 110, and by the reaction and purification in the same manner as in Example 3, the title compound was obtained.
MS (ESI+): 530 (M+H)

(reaction and purification in the same manner as in Example 178, the title compound was obtained.
MS (ESI+): 574 (M+H))

Example 234

N-[((3R*,4R*)-1-[(1-acetylpiperidin-4-yl)carbonyl]-3-(2-methylphenyl)piperidin-4-yl]-4-chloro-N-methylbenzamide Using the compound obtained in Example 111, and by the reaction and purification in the same manner as in Example 3, the title compound was obtained.
MS (ESI+): 495 (M+H)

Example 235

N-[(3R*,4R*)-1-[(1-acetylpiperidin-4-yl)carbonyl]-3-(4-fluoro-2-methylphenyl)piperidin-4-yl]-4-chloro-N-methylbenzamide Using the compound obtained in Example 112, and by the reaction and purification in the same manner as in Example 3, the title compound was obtained.
MS (ESI+): 514 (M+H)

Example 236

N-[(3R*,4R*)-1-[(1-acetylpiperidin-4-yl)carbonyl]-3-(4-fluorophenyl)piperidin-4-yl]-3-bromo-N-methyl-5-(trifluoromethyl)benzamide Using the compound obtained in Example 106 and 1-acetylpiperidinecarboxylic acid, and by the reaction and purification in the same manner as in Example 3, the title compound was obtained.
MS (ESI+): 612 (M+H)

Example 237

N-[(3R*,4R*)-1-[(1-acetylpiperidin-4-yl)carbonyl]-3-(4-methoxyphenyl)piperidin-4-yl]-3-bromo-N-methyl-5-(trifluoromethyl)benzamide Using the compound obtained in Example 107 and 1-acetylpiperidinecarboxylic acid, and by the reaction and purification in the same manner as in Example 3, the title compound was obtained.
MS (ESI+): 624 (M+H)

Example 238

N-[(3R*,4R*)-1-[(1-acetylpiperidin-4-yl)carbonyl]-3-(4-methoxyphenyl)piperidin-4-yl]-N-methyl-3,5-bis(trifluoromethyl)benzamide Using the compound obtained in Example 108 and 1-acetylpiperidinecarboxylic acid, and by the reaction and purification in the same manner as in Example 3, the title compound was obtained.
MS (ESI+): 614 (M+H)

Example 239

N-[(3R*,4R*)-1-[(1-acetylpiperidin-4-yl)carbonyl]-3-(4-bromophenyl)piperidin-4-yl]-4-methoxy-N-methylbenzamide Using the compound obtained in Example 119, and by the reaction and purification in the same manner as in Example 3, the title compound was obtained.
MS (ESI+): 556 (M+H)

Example 240 methyl 4-[(3R*,4R*)-1-[(1-acetylpiperidin-4-yl)carbonyl]-4-{[(4-methoxyphenyl)carbonyl](methyl)amino}piperidin-3-yl]benzoate A mixture of the compound (0.50 g) obtained in Example 239, bis(diphenylphosphino)ferrocene (dppf) (0.099 g), Pd(OAc)$_2$ (0.040 g) and triethylamine (248 µL) in methanol (10 mL) and DMF (10 mL) was stirred under a carbon monoxide atmosphere (10 atm) at 80° C. for 12 hr. The reaction mixture was poured into water, and the resultant product was extracted with ethyl acetate. The organic layer was washed with saturated aqueous ammonium chloride solution and brine and concentrated. The residue was purified by silica gel column chromatography (NH Chromatorex) (solvent gradient; 10→33% ethyl acetate/hexane) to give the title compound (0.31 g, 63%) as a white powder.
MS (ESI+): 536 (M+H)

Example 241

4-[(3R*,4R*)-1-[(1-acetylpiperidin-4-yl)carbonyl]-4-{[(4-methoxyphenyl)carbonyl](methyl)amino}piperidin-3-yl]benzoic acid To a solution of the compound (0.20 g) obtained in Example 240 in methanol (3 mL) was added 1N aqueous sodium hydroxide solution (3 mL), and the mixture was stirred at 50° C. for 2 hr. Methanol was evaporated under reduced pressure, and the residue was extracted with ethyl acetate. The organic layer was washed with water and concentrated to give the title compound (0.092 g, 47%) as a white powder.
MS (ESI+): 522 (M+H)

Example 242

N-{(3R*,4R*)-1-[(1-acetylpiperidin-4-yl)carbonyl]-3-biphenyl-4-ylpiperidin-4-yl}-4-methoxy-N-methylbenzamide A mixture of the compound obtained in Example 239 (0.20 g), phenylboronic acid (0.066 g), dppf (0.040 g), Pd(OAc)$_2$ (0.008 g) and potassium carbonate (0.050 g) in toluene (3 mL), water (0.3 mL) and DMF (1 mL) was stirred under an argon atmosphere at 100° C. for 10 hr. The reaction mixture was poured into water, and the resultant product was extracted with ethyl acetate. The organic layer was washed with saturated aqueous sodium hydrogen carbonate solution and brine, and concentrated. The residue was purified by silica gel column chromatography (NH Chromatorex) (solvent gradient; 65→95% ethyl acetate/hexane) to give the title compound (0.12 g, 61%) as a white powder.
MS (ESI+): 554 (M+H)

Example 243

N-[(3R*,4R*)-1-[(1-acetylpiperidin-4-yl)carbonyl]-3-(4-cyclopropylphenyl)piperidin-4-yl]-4-methoxy-N-methylbenzamide Using the compound obtained in Example 239 and cyclopropylboronic acid (0.066 g), and by the reaction and purification in the same manner as in Example 242, the title compound was obtained.
MS (ESI+): 518 (M+H)

Example 244

N-[(3R*,4R*)-1-[(1-acetylpiperidin-4-yl) carbonyl]-3-(4-bromophenyl)piperidin-4-yl]-N-methyl-3,5-bis(trifluoromethyl)benzamide Using the compound obtained in Example 123 and 1-acetylpiperidinecarboxylic acid, and by the reaction and purification in the same manner as in Example 3, the title compound was obtained.
MS (ESI+): 662 (M+H)

Example 245

N-[(3R*,4R*)-1-[(1-acetylpiperidin-4-yl)carbonyl]-3-(4-bromophenyl)piperidin-4-yl]-3-bromo-N-methyl-5-(trifluoromethyl)benzamide Using the compound obtained in Example 124 and 1-acetylpiperidinecarboxylic acid, and by the reaction and purification in the same manner as in Example 3, the title compound was obtained.
MS (ESI+): 672 (M+H)

Example 246

N-[(3R*,4R*)-1-[(1-acetylpiperidin-4-yl)carbonyl]-3-(3-methylthiophen-2-yl)piperidin-4-yl]-N-methyl-3,5-bis(trifluoromethyl)benzamide Using the compound obtained in Example 131, and by the reaction and purification in the same manner as in Example 3, the title compound was obtained.
MS (ESI+): 604 (M+H)

Example 247

N-{(3R*,4R*)-1-[(1-acetylpiperidin-4-yl)carbonyl]-3-[4-(trifluoromethyl)phenyl]piperidin-4-yl}-4-chloro-N-methylbenzamide Using the compound obtained in Example 132, and by the reaction and purification in the same manner as in Example 3, the title compound was obtained.
MS (ESI+): 550 (M+H)

Example 248

N-{(3R*,4R*)-1-[(1-acetylpiperidin-4-yl)carbonyl]-3-[4-(trifluoromethyl)phenyl]piperidin-4-yl}-N-methyl-4-(trifluoromethyl)benzamide Using the compound obtained in Example 133, and by the reaction and purification in the same manner as in Example 3, the title compound was obtained.
MS (ESI+): 584 (M+H)

Example 249

N-{(3R*,4R*)-1-[(1-acetylpiperidin-4-yl)carbonyl]-3-[4-(trifluoromethyl)phenyl]piperidin-4-yl}-N-methyl-4-morpholin-4-ylbenzamide Using the compound obtained in Example 134, and by the reaction and purification in the same manner as in Example 3, the title compound was obtained.
MS (ESI+): 601 (M+H)

Example 250

N-[(3S*,4R*)-1-[(1-acetylpiperidin-4-yl)carbonyl]-4-(3,4-dichlorophenyl)pyrrolidin-3-yl]-4-chloro-N-methylbenzamide Using the compound obtained in Example 113, and by the reaction and purification in the same manner as in Example 3, the title compound was obtained.
MS (ESI+): 536 (M+H)

Example 251a

N-[(3R,4R)-1-[(1-acetylpiperidin-4-yl)carbonyl]-3-(3,4-dichlorophenyl)piperidin-4-yl]-4-chloro-N-methylbenzamide To a solution of 4-chloro-N-[(3R,4R)-3-(3,4-dichlorophenyl)piperidin-4-yl]-N-methylbenzamide monohydrochloride (200 mg) obtained in Example 137a, 1-acetylpiperidine-4-carboxylic acid (118 mg) and triethylamine (127 μL) in acetonitrile (5 mL) were added WSC.HCl (176 mg) and HOBt (140 mg), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (NH Chromatorex) (solvent gradient; 15→100% ethyl acetate/hexane) to give the title compound (113 mg, 44%) as a white powder.
MS (ESI+): 550 (M+H)
$^1$H-NMR (CDCl$_3$) δ 1.49-2.20 (10H, m), 2.51-3.38 (9H, m), 3.74-4.27 (2H, m), 4.47-5.21 (2H, m), 6.70-7.55 (7H, m)
Elemental analysis: $C_{27}H_{30}Cl_3N_3O_3$
Found C, 58.59; H, 5.70; N, 7.51
Calcd. C, 58.86; H, 5.49; N, 7.63
$[α]_D^{25}$ +60.9° (c 0.26, MeOH)

Example 251b

N-[(3R,4R)-1-[(1-acetylpiperidin-4-yl)carbonyl]-3-(3,4-dichlorophenyl)piperidin-4-yl]-4-chloro-N-methylbenzamide 0.5 hydrate To a solution of the compound (0.96 g) obtained in Example 251a in ethyl acetate (10 mL) was added hexane (10 mL), and the mixture was stirred at room temperature for 2 days or longer. The precipitate was collected by filtration to give the title compound (0.83 g, 86%) as a white crystal powder.
Elemental analysis: $C_{27}H_{30}Cl_3N_3O_3$ 0.5H$_2$O
Found C, 58.12; H, 5.71; N, 7.54
Calcd. C, 57.92; H, 5.58; N, 7.50
Melting point: 126-127° C.

Example 251c

N-[(3R,4R)-1-[(1-acetylpiperidin-4-yl)carbonyl]-3-(3,4-dichlorophenyl)piperidin-4-yl]-4-chloro-N-methylbenzamide monohydrate To a solution of the compound (0.30 g) obtained in Example 251a in ethyl acetate (3 mL) was added hexane (2 mL), and the mixture was stirred at room temperature for 60 hr. The precipitate was collected by filtration to give the title compound (0.25 g, 83%) as a white crystal powder.
Elemental analysis: $C_{27}H_{30}Cl_3N_3O_3 \cdot H_2O$
Found C, 57.16; H, 5.69; N, 7.41
Calcd. C, 57.00; H, 5.67; N, 7.39
Melting point: 113-115° C.

Example 252

N-[(3R,4R)-1-[(1-acetylpiperidin-4-yl)carbonyl]-3-(3,4-dichlorophenyl)piperidin-4-yl]-4-methoxy-N-methylbenzamide (Step 1)
To a solution of tert-butyl (3R,4R)-3-(3,4-dichlorophenyl)-4-{[(4-methoxyphenyl)carbonyl](methyl)amino}piperidine-1-carboxylate (700 mg) obtained in Example 169 in ethyl acetate (5 mL) was added 4N hydrogen chloride/ethyl acetate (5 mL), and the mixture was stirred at 50° C. for 4 hr. The reaction mixture was concentrated under reduced pressure to give (3R,4R)-3-(3,4-dichlorophenyl)-4-{[(4-methoxyphenyl)carbonyl](methyl)amino}piperidine monohydrochloride (608 mg, 99%) as a white powder.
MS (ESI+): 393 (M−HCl+H)

(Step 2)
To a solution of the compound (200 mg) obtained in step 1, 1-acetylpiperidine-4-carboxylic acid (119 mg) and triethylamine (128 μL) in acetonitrile (5 mL) were added WSC.HCl (178 mg) and HOBt (142 mg), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (NH Chromatorex) (solvent gradient; 10→100% ethyl acetate/hexane) to give the title compound (118 mg, 46%) as a white crystal powder.
MS (ESI+): 546 (M+H)
$^1$H-NMR (CDCl$_3$) δ 1.63 (3H, s), 1.70-1.96 (5H, m), 2.11 (3H, s), 2.44-3.48 (8H, m), 3.80 (5H, m), 4.62 (2H, m), 6.73-7.59 (7H, m)
Elemental analysis: $C_{28}H_{33}Cl_2N_3O_3$
Found C, 61.51; H, 6.43; N, 7.46
Calcd. C, 61.54; H, 6.09; N, 7.69
$[\alpha]_D^{25}$ +56.0° (c 0.25, MeOH)
Melting point: 134-136° C.

Example 253

N-[(3R,4R)-1-[(1-acetylpiperidin-4-yl)carbonyl]-3-(3,4-dichlorophenyl)piperidin-4-yl]-N-methyl-4-(3-methyl-1H-pyrazol-1-yl)benzamide (Step 1)
Using the compound obtained in Example 170, and by the reaction and purification in the same manner as in Example 1, (3R,4R)-3-(3,4-dichlorophenyl)-4-(methyl{[4-(3-methyl-1H-pyrazol-1-yl)phenyl]carbonyl}amino)piperidine monohydrochloride as a white powder.
MS (ESI+): 443 (M−HCl+H)
(Step 2)
Using the compound obtained in step 1, and by the reaction and purification in the same manner as in Example 3, the title compound was obtained.
MS (ESI+): 596 (M+H)

Example 254

N-[(3R,4R)-1-[(1-acetylpiperidin-4-yl)carbonyl]-3-(3,4-dichlorophenyl)piperidin-4-yl]-4-fluoro-N-methylbenzamide Using the compound obtained in Reference Example 78 and 4-fluorobenzoyl chloride, and by the reaction and purification in the same manner as in Example 39, the title compound was obtained.
MS (ESI+): 534 (M+H)

Example 255

N-[(3R,4R)-1-[(1-acetylpiperidin-4-yl)carbonyl]-3-(3,4-dichlorophenyl)piperidin-4-yl]-4-bromo-N-methylbenzamide Using the compound obtained in Reference Example 78 and 4-bromobenzoyl chloride, and by the reaction and purification in the same manner as in Example 39, the title compound was obtained.
MS (ESI+): 595 (M+H)

Example 256

N-[(3R,4R)-1-[(1-acetylpiperidin-4-yl)carbonyl]-3-(3,4-dichlorophenyl)piperidin-4-yl]-N-methylbiphenyl-4-carboxamide Using the compound obtained in Reference Example 78 and 4-biphenylcarbonyl chloride, and by the reaction and purification in the same manner as in Example 39, the title compound was obtained.
MS (ESI+): 592 (M+H)

Example 257

N-[(3R,4R)-1-[(1-acetylpiperidin-4-yl)carbonyl]-3-(3,4-dichlorophenyl)piperidin-4-yl]-4'-cyano-4-methoxy-N-methylbiphenyl-3-carboxamide Using the compound obtained in Reference Example 78 and 4'-cyano-4-methoxybiphenyl-3-carboxylic acid, and by the reaction and purification in the same manner as in Example 3, the title compound was obtained.
MS (ESI+): 647 (M+H)

Example 258

N-[(3R,4R)-1-[(1-acetylpiperidin-4-yl)carbonyl]-3-(3,4-dichlorophenyl)piperidin-4-yl]-2-methoxy-N-methyl-5-(trifluoromethoxy)benzamide Using the compound obtained in Reference Example 78 and 2-methoxy-5-(trifluoromethoxy)benzoic acid, and by the reaction and purification in the same manner as in Example 3, the title compound was obtained.
MS (ESI+): 630 (M+H)

Example 259

N-[(3R,4R)-1-[(1-acetylpiperidin-4-yl)carbonyl]-3-(3,4-dichlorophenyl)piperidin-4-yl]-4'-cyano-N-methyl-5-(trifluoromethyl)biphenyl-3-carboxamide Using the compound obtained in Reference Example 78 and 4'-cyano-5-(trifluoromethyl)biphenyl-3-carboxylic acid, and by the reaction and purification in the same manner as in Example 3, the title compound was obtained.
MS (ESI+): 685 (M+H)

Example 260

N-[(3R,4R)-1-[(1-acetylpiperidin-4-yl)carbonyl]-3-(3,4-dichlorophenyl)piperidin-4-yl]-1-(4-bromophenyl)-3-methoxy-N-methyl-1H-pyrazole-4-carboxamide Using the compound obtained in Reference Example 78 and 1-(4-bromophenyl)-3-methoxy-1H-pyrazole-4-carboxylic acid, and by the reaction and purification in the same manner as in Example 3, the title compound was obtained.
MS (ESI+): 690 (M+H)

Example 261

N-[(3R,4R)-1-[(1-acetylpiperidin-4-yl)carbonyl]-3-(3,4-dichlorophenyl)piperidin-4-yl]-N-methyl-3-(3-methyl-1H-pyrazol-1-yl)benzamide Using the compound obtained in Reference Example 78 and 3-(3-methyl-1H-pyrazol-1-yl)benzoic acid, and by the reaction and purification in the same manner as in Example 3, the title compound was obtained.
MS (ESI+): 596 (M+H)

Example 262

N-[(3R,4R)-1-[(1-acetylpiperidin-4-yl)carbonyl]-3-(3,4-dichlorophenyl)piperidin-4-yl]-6-bromo-N-methyl-2-oxo-1,2-dihydroquinoline-3-carboxamide Using the compound obtained in Reference Example 78 and 6-bromo-2-oxo-1,2-dihydroquinoline-3-carboxylic acid, and by the reaction and purification in the same manner as in Example 3, the title compound was obtained.
MS (ESI+): 661 (M+H)

Example 263

N-[(3R,4R)-1-[(1-acetylpiperidin-4-yl)carbonyl]-3-(3,4-dichlorophenyl)piperidin-4-yl]-4-cyano-N-methylbenzamide Using the compound obtained in Reference Example 78 and 4-cyanobenzoyl chloride, and by the reaction and purification in the same manner as in Example 39, the title compound was obtained.
MS (ESI+): 541 (M+H)

Example 264

N-[(3R,4R)-1-[(1-acetylpiperidin-4-yl)carbonyl]-3-(3,4-dichlorophenyl)piperidin-4-yl]-4-(dimethylamino)-N-methylbenzamide Using the compound obtained in Reference Example 78 and 4-(dimethylamino)benzoic acid, and by the reaction and purification in the same manner as in Example 3, the title compound was obtained.
MS (ESI+): 559 (M+H)

Example 265

N-[(3R,4R)-1-[(1-acetylpiperidin-4-yl)carbonyl]-3-(3,4-dichlorophenyl)piperidin-4-yl]-N-methyl-4-(trifluoromethyl)benzamide 0.5 hydrate To a solution of (3R,4R)-1-[(1-acetylpiperidin-4-yl)carbonyl]-3-(3,4-dichlorophenyl)-N-methylpiperidin-4-amine (0.150 g) obtained in Reference Example 78 and 4-trifluoromethylbenzoic acid (0.083 g) in acetonitrile (3 mL) was added DEPC (0.066 mL) at 0° C., and the mixture was stirred at room temperature for 10 hr. To the reaction mixture was added water, and the resultant product was extracted with ethyl acetate. The organic layer was washed with brine and dried, and the solvent was evaporated under reduced pressure. The obtained residue was purified by silica gel column chromatography (NH Chromatorex) (solvent gradient; 30→70% ethyl acetate/hexane) to give N-[(3R,4R)-1-[(1-acetylpiperidin-4-yl)carbonyl]-3-(3,4-dichlorophenyl)piperidin-4-yl]-N-methyl-4-(trifluoromethyl)benzamide (0.103 g, 49%) as a white powder.
$^1$H-NMR (CDCl$_3$) δ 1.25-2.11 (9H, m), 2.57-3.50 & 3.70-4.20 & 4.50-5.00 (total 14H, m), 6.86-7.73 (7H, m)
The obtained compound (0.32 g) was crystallized from a mixture of diethyl ether (10 mL)/ethyl acetate (1 mL)/water (0.1 mL) to give the title compound (0.27 g, 85%) as a white crystal powder.
MS (ESI+): 584 (M-0.5H$_2$O+H)
Melting point: 122° C.
Elemental analysis: C$_{28}$H$_{30}$Cl$_2$F$_3$N$_3$O$_3$ 0.5H$_2$O
Found C, 56.61; H, 5.10; N, 7.09
Calcd. C, 56.67; H, 5.27; N, 7.08
$[α]_D^{25}$ +47.3° (c 0.25, MeOH)

Example 266

N-[(3R,4R)-1-[(1-acetylpiperidin-4-yl)carbonyl]-3-(3,4-dichlorophenyl)piperidin-4-yl]-N-methyl-4-(2-oxopyrrolidin-1-yl)benzamide Using the compound obtained in Reference Example 78 and 4-(2-oxopyrrolidin-1-yl)benzoic acid, and by the reaction and purification in the same manner as in Example 265, the title compound was obtained.
MS (ESI+): 599 (M+H)

Example 267

N-[(3R,4R)-1-[(1-acetylpiperidin-4-yl)carbonyl]-3-(3,4-dichlorophenyl)piperidin-4-yl]-N,4-dimethyl-3,4-dihydro-2H-1,4-benzoxazin-7-carboxamide Using the compound obtained in Reference Example 78 and 4-methyl-3,4-dihydro-2H-1,4-benzoxazin-7-carboxylic acid, and by the reaction and purification in the same manner as in Example 265, the title compound was obtained.
MS (ESI+): 587 (M+H)

Example 268

N-[(3R,4R)-1-[(1-acetylpiperidin-4-yl)carbonyl]-3-(3,4-dichlorophenyl)piperidin-4-yl]-N-methyl-4-morpholin-4-ylbenzamide monohydrate To a solution of (3R,4R)-1-[(1-acetylpiperidin-4-yl)carbonyl]-3-(3,4-dichlorophenyl)-N-methylpiperidin-4-amine (180 mg) obtained in Reference Example 78, 4-morpholin- 4-ylbenzoic acid (0.135 mg) and triethylamine (179 μL) in DMF (5 mL) was added DEPC (110 μL) at 0° C., and the mixture was stirred at room temperature for 10 hr. To the reaction mixture was added water, and the resultant product was extracted with ethyl acetate. The organic layer was washed with brine and dried, and the solvent was evaporated under reduced pressure. The obtained residue was purified by silica gel column chromatography to give the title compound as a white crystal powder.

MS (ESI+): 601 (M−H$_2$O+H)

$^1$H-NMR (CDCl$_3$) δ 1.15-1.37 (5H, m), 1.57-2.24 (14H, m), 2.57-3.38 (8H, m), 3.85 (4H, m), 6.58-7.56 (7H, m)

Elemental analysis: C$_{31}$H$_{38}$Cl$_2$N$_4$O$_4$.H$_2$O

Found C, 59.88; H, 6.47; N, 8.79

Calcd. C, 60.09; H, 6.51; N, 9.04

Melting point: 136-139° C.

[α]$_D^{25}$ +59.5° (c 0.25, MeOH)

Example 269

N-[(3R,4R)-1-[(1-acetylpiperidin-4-yl)carbonyl]-3-(3,4-dichlorophenyl)piperidin-4-yl]-N-methyl-1H-indole-2-carboxamide Using the compound obtained in Reference Example 78 and 1H-indole-2-carboxylic acid, and by the reaction and purification in the same manner as in Example 3, the title compound was obtained.

MS (ESI+): 555 (M+H)

Example 270

N-[(3R,4R)-1-[(1-acetylpiperidin-4-yl)carbonyl]-3-(3,4-dichlorophenyl)piperidin-4-yl]-N-methyl-1-benzothiophene-2-carboxamide Using the compound obtained in Reference Example 78 and 1-benzothiophene-2-carboxylic acid, and by the reaction and purification in the same manner as in Example 3, the title compound was obtained.

MS (ESI+): 572 (M+H)

Example 271

N-[(3R,4R)-1-[(1-acetylpiperidin-4-yl)carbonyl]-3-(3,4-dichlorophenyl)piperidin-4-yl]-N-methyl-4-(4-methylpiperazin-1-yl)benzamide Using the compound obtained in Reference Example 78 and 4-(4-methylpiperazin-1-yl)benzoic acid, and by the reaction and purification in the same manner as in Example 3, the title compound was obtained.

MS (ESI+): 614 (M+H)

Example 272

N-[(3R,4R)-1-[(1-acetylpiperidin-4-yl)carbonyl]-3-(3,4-dichlorophenyl)piperidin-4-yl]-4-cyclohexyl-N-methylbenzamide Using the compound obtained in Reference Example 78 and 4-cyclohexylbenzoic acid, and by the reaction and purification in the same manner as in Example 231, the title compound was obtained.

MS (ESI+): 598 (M+H)

Example 273

N-[(3R,4R)-1-[(1-acetylpiperidin-4-yl)carbonyl]-3-(3,4-dichlorophenyl)piperidin-4-yl]-4-(difluoromethoxy)-N-methylbenzamide Using the compound obtained in Reference Example 78 and 4-(difluoromethoxy)benzoic acid, and by the reaction and purification in the same manner as in Example 231, the title compound was obtained.

MS (ESI+): 582 (M+H)

Example 274

N-[(3R,4R)-1-[(1-acetylpiperidin-4-yl)carbonyl]-3-(3,4-dichlorophenyl)piperidin-4-yl]-N-methyl-5-phenylthiophene-2-carboxamide Using the compound obtained in Reference Example 78 and 5-phenylthiophene-2-carboxylic acid, and by the reaction and purification in the same manner as in Example 3, the title compound was obtained.

MS (ESI+): 598 (M+H)

Example 275

N-[(3R,4R)-1-[(1-acetylpiperidin-4-yl)carbonyl]-3-(3,4-dichlorophenyl)piperidin-4-yl]-4'-chloro-N-methyl-4-(trifluoromethoxy)biphenyl-3-carboxamide Using the compound obtained in Reference Example 78 and 4'-chloro-4-(trifluoromethoxy)biphenyl-3-carboxylic acid, and by the reaction and purification in the same manner as in Example 3, the title compound was obtained.

MS (ESI+): 710 (M+H)

Example 276

N-[(3R,4R)-1-[(1-acetylpiperidin-4-yl)carbonyl]-3-(3,4-dichlorophenyl)piperidin-4-yl]-2-methoxy-N-methyl-5-[5-(trifluoromethyl)-1H-tetrazol-1-yl]benzamide Using the compound obtained in Reference Example 78 and 2-methoxy-5-[5-(trifluoromethyl)-1H-tetrazol-1-yl]benzoic acid, and by the reaction and purification in the same manner as in Example 3, the title compound was obtained.

MS (ESI+): 682 (M+H)

Example 277

N-[(3R,4R)-1-[(1-acetylpiperidin-4-yl)carbonyl]-3-(3,4-dichlorophenyl)piperidin-4-yl]-3-bromo-N-methyl-5-(trifluoromethyl)benzamide Using the compound obtained in Reference Example 78 and 3-bromo-5-trifluoromethylbenzoic acid, and by the reaction and purification in the same manner as in Example 3, the title compound was obtained.

MS (ESI+): 662 (M+H)

Example 278

N-[(3R,4R)-1-[(1-acetylpiperidin-4-yl)carbonyl]-3-(3,4-dichlorophenyl)piperidin-4-yl]-N-methyl-6-morpholin-4-ylpyridine-3-carboxamide Using the compound obtained in Reference Example 78 and 6-morpholin-4-ylpyridine-3-carboxylic acid, and by the reaction and purification in the same manner as in Example 265, the title compound was obtained.
MS (ESI+): 602 (M+H)

Example 279

N-[(3R,4R)-1-[(1-acetylpiperidin-4-yl)carbonyl]-3-(3,4-dichlorophenyl)piperidin-4-yl]-3-cyano-4-methoxy-N-methylbenzamide Using the compound obtained in Reference Example 78 and 3-cyano-4-methoxybenzoic acid, and by the reaction and purification in the same manner as in Example 265, the title compound was obtained.
MS (ESI+): 571 (M+H)

Example 280

N-[(3R,4R)-1-[(1-acetylpiperidin-4-yl)carbonyl]-3-(3,4-dichlorophenyl)piperidin-4-yl]-N-methyl-4-(2-methyl-1,3-thiazole-4-yl)benzamide Using the compound obtained in Reference Example 78 and 4-(2-methyl-1,3-thiazole-4-yl)benzoic acid, and by the reaction and purification in the same manner as in Example 265, the title compound was obtained.
MS (ESI+): 613 (M+H)

Example 281

N-[(3R,4R)-1-[(1-acetylpiperidin-4-yl)carbonyl]-3-(3,4-dichlorophenyl)piperidin-4-yl]-N-methyl-4-(1H-1,2,4-triazol-1-yl)benzamide Using the compound obtained in Reference Example 78 and 4-(1H-1,2,4-triazol-1-yl)benzoic acid, and by the reaction and purification in the same manner as in Example 265, the title compound was obtained.
MS (ESI+): 583 (M+H)

Example 282

N-[(3R,4R)-1-[(1-acetylpiperidin-4-yl)carbonyl]-3-(3,4-dichlorophenyl)piperidin-4-yl]-N-methylpyrazolo[1,5-a]pyridine-2-carboxamide Using the compound obtained in Reference Example 78 and pyrazolo[1,5-a]pyridine-2-carboxylic acid, and by the reaction and purification in the same manner as in Example 265, the title compound was obtained.
MS (ESI+): 556 (M+H)

Example 283

N-[(3R,4R)-1-[(1-acetylpiperidin-4-yl)carbonyl]-3-(3,4-dichlorophenyl)piperidin-4-yl]-N-methyl-2,3-dihydro-1-benzofuran-5-carboxamide Using the compound obtained in Reference Example 78 and 2,3-dihydro-1-benzofuran-5-carboxylic acid, and by the reaction and purification in the same manner as in Example 3, the title compound was obtained.
MS (ESI+): 558 (M+H)

Example 284

N-[(3R,4R)-1-[(1-acetylpiperidin-4-yl)carbonyl]-3-(3,4-dichlorophenyl)piperidin-4-yl]-5-chloro-N-methyl-1H-indole-2-carboxamide Using the compound obtained in Reference Example 78 and 5-chloro-1H-indole-2-carboxylic acid, and by the reaction and purification in the same manner as in Example 231, the title compound was obtained.
MS (ESI+): 589 (M+H)

Example 285

N-[(3R,4R)-1-[(1-acetylpiperidin-4-yl)carbonyl]-3-(3,4-dichlorophenyl)piperidin-4-yl]-6-chloro-N-methyl-1H-indole-2-carboxamide Using the compound obtained in Reference Example 78 and 6-chloro-1H-indole-2-carboxylic acid, and by the reaction and purification in the same manner as in Example 231, the title compound was obtained.
MS (ESI+): 589 (M+H)

Example 286

N-[(3R,4R)-1-[(1-acetylpiperidin-4-yl)carbonyl]-3-(3,4-dichlorophenyl)piperidin-4-yl]-N,5-dimethyl-1H-indole-2-carboxamide Using the compound obtained in Reference Example 78, 6-chloro-1H-indole-2-carboxylic acid and 5-methyl-1H-indole-2-carboxylic acid, and by the reaction and purification in the same manner as in Example 231, the title compound was obtained.
MS (ESI+): 569 (M+H)

Example 287

N-[(3R,4R)-1-[(1-acetylpiperidin-4-yl)carbonyl]-3-(3,4-dichlorophenyl)piperidin-4-yl]-N,1-dimethyl-1H-indole-2-carboxamide Using the compound obtained in Reference Example 78 and 1-methyl-1H-indole-2-carboxylic acid, and by the reaction and purification in the same manner as in Example 231, the title compound was obtained.
MS (ESI+): 569 (M+H)

Example 288

4-acetyl-N-[(3R,4R)-1-[(1-acetylpiperidin-4-yl)carbonyl]-3-(3,4-dichlorophenyl)piperidin-4-yl]-N-methylbenzamide To a solution of the compound (150 mg) obtained in Reference Example 78, 4-acetylbenzoic acid (72 mg) and triethylamine (0.254 mL) in DMF (3 mL) was added DEPC (59 mg), and the mixture was stirred at room temperature for 18 hr. To the reaction mixture was added saturated aqueous sodium hydrogen carbonate solution, and the mixture was extracted with ethyl acetate. The organic layer was washed with brine and dried, and the solvent was evaporated under reduced pressure. The obtained residue was purified by silica gel column chromatography (solvent gradient; 10→20% methanol/ethyl acetate) to give the title compound (53 mg, 26%) as a white powder.
MS (ESI+): 558 (M+H)

Example 289

N-[(3R,4R)-1-[(1-acetylpiperidin-4-yl)carbonyl]-3-(3,4-dichlorophenyl)piperidin-4-yl]-5-methoxy-N-methyl-1-benzofuran-2-carboxamide Using the compound obtained in Reference Example 78 and 5-methoxy-1-benzofuran-2-carboxylic acid, and by the reaction and purification in the same manner as in Example 3, the title compound was obtained.
MS (ESI+): 586 (M+H)

Example 290

N-[(3R,4R)-1-[(1-acetylpiperidin-4-yl)carbonyl]-3-(3,4-dichlorophenyl)piperidin-4-yl]-N-methyl-1-benzofuran-2-carboxamide Using the compound obtained in Reference Example 78 and 1-benzofuran-2-carboxylic acid, and by the reaction and purification in the same manner as in Example 3, the title compound was obtained.
MS (ESI+): 556 (M+H)

Example 291

N-[(3R,4R)-1-[(1-acetylpiperidin-4-yl)carbonyl]-3-(3,4-dichlorophenyl)piperidin-4-yl]-5-chloro-N,1-dimethyl-1H-indole-2-carboxamide Using the compound obtained in Reference Example 78 and 5-chloro-1-methyl-1H-indole-2-carboxylic acid, and by the reaction and purification in the same manner as in Example 3, the title compound was obtained.
MS (ESI+): 603 (M+H)

Example 292

N-[(3R,4R)-1-[(1-acetylpiperidin-4-yl)carbonyl]-3-(3,4-dichlorophenyl)piperidin-4-yl]-4-cyclopropyl-N-methylbenzamide 0.5 ethyl acetate To a solution of (3R,4R)-1-[(1-acetylpiperidin-4-yl)carbonyl]-3-(3,4-dichlorophenyl)-N-methylpiperidin-4-amine (200 mg) obtained in Reference Example 78, 4-cyclopropylbenzoic acid (118 mg) and triethylamine (134 μL) in acetonitrile (5 mL) were added WSC.HCl (0.185 g) and HOBt (0.148 g), and the mixture was stirred at room temperature for 14 hr. To the reaction mixture was added water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography to give the title compound (205 mg, 76%) as a white crystal powder.
MS (ESI+): 556 (M-0.5EtOAc+H)
$^1$H-NMR (CDCl$_3$) δ 0.56-1.15 (4H, m), 1.45-1.99 (8H, m), 2.03-2.18 (3H, m), 2.44-3.46 (8H, m), 3.68-4.08 (2H, m), 4.37-5.22 (3H, m), 6.22-7.67 (7H, m)
Elemental analysis: $C_{30}H_{35}Cl_2N_3O_3 \cdot 0.5EtOAc$
Found C, 63.79; H, 6.76; N, 7.09
Calcd. C, 64.00; H, 6.55; N, 7.00
Melting point: 129-133° C.
$[\alpha]_D^{25}$ +61.9° (c 0.25, MeOH)

Example 293

N-[(3R,4R)-1-[(1-acetylpiperidin-4-yl)carbonyl]-3-(3,4-dichlorophenyl)piperidin-4-yl]-N-methyl-6-(trifluoromethyl)pyridine-3-carboxamide Using the compound obtained in Reference Example 78 and 6-(trifluoromethyl)pyridine-3-carboxylic acid, and by the reaction and purification in the same manner as in Example 265, the title compound was obtained.
MS (ESI+): 585 (M+H)

Example 294

N-[(3R,4R)-1-[(1-acetylpiperidin-4-yl)carbonyl]-3-(3,4-dichlorophenyl)piperidin-4-yl]-4-fluoro-N-methyl-3-(trifluoromethyl)benzamide Using the compound obtained in Example 78 and 4-fluoro-3-trifluoromethylbenzoic acid, and by the reaction and purification in the same manner as in Example 3, the title compound was obtained.
MS (ESI+): 602 (M+H)

Example 295

N-[(3R,4R)-1-[(1-acetylpiperidin-4-yl)carbonyl]-3-(3,4-dichlorophenyl)piperidin-4-yl]-4-chloro-N-methyl-3-(trifluoromethyl)benzamide Using the compound obtained in Example 78 and 4-chloro-3-trifluoromethylbenzoic acid, and by the reaction and purification in the same manner as in Example 3, the title compound was obtained.
MS (ESI+): 618 (M+H)

Example 296

N-[(3R,4R)-1-[(1-acetylpiperidin-4-yl)carbonyl]-3-(3,4-dichlorophenyl)piperidin-4-yl]-N,3-dimethyl-5-(trifluoromethyl)benzamide Using the compound obtained in Example 78 and 3-methyl-5-trifluoromethylbenzoic acid, and by the reaction and purification in the same manner as in Example 3, the title compound was obtained.
MS (ESI+): 598 (M+H)

Example 297

N-[(3R,4R)-1-[(1-acetylpiperidin-4-yl)carbonyl]-3-(3,4-dichlorophenyl)piperidin-4-yl]-6-methoxy-N,1-dimethyl-2-oxo-1,2,3,4-tetrahydroquinoline-7-carboxamide (Step 1)
To a mixture of 6-methoxy-1-methyl-2-oxo-1,2,3,4-tetrahydroquinoline-7-carbaldehyde (2.0 g) synthesized by a known method (WO2001/077100), sodium dihydrogen phosphate (1.63 g) and 2-methyl-2-butene (4.3 ml) in tert-butanol (52 mL) and water (8 mL) was slowly added sodium chlorite (2.89 g) at 0° C., and the mixture was stirred at room temperature for 2 hr. After cooling to 0° C., the reaction was quenched with 6N hydrochloric acid, and the mixture was extracted twice with ethyl acetate. The organic layer was washed with brine and dried, and the solvent was evaporated under reduced pressure. The obtained crystals were collected by filtration, and washed with hexane to give 6-methoxy-1-methyl-2-oxo-1,2,3,4-tetrahydroquinoline-7-carboxylic acid (0.72 g, 34%) as white crystals.
MS (ESI+): 236 (M+H)
(Step 2)
Using the compound obtained in step 1 and the compound obtained in Example 78, and by the reaction and purification in the same manner as in Example 3, the title compound was obtained.
MS (ESI+): 629 (M+H)

Example 298

N-[(3R,4R)-1-[(1-acetylpiperidin-4-yl)carbonyl]-3-(3,4-dichlorophenyl)piperidin-4-yl]-N-methyl-4-phenyl-5-(trifluoromethyl)thiophene-2-carboxamide Using the compound obtained in Example 78 and 4-phenyl-5-(trifluoromethyl)thiophene-2-carboxylic acid, and by the reaction and purification in the same manner as in Example 3, the title compound was obtained.
MS (ESI+): 666 (M+H)

Example 299

N-[(3R,4R)-1-[(1-acetylpiperidin-4-yl)carbonyl]-3-(3,4-dichlorophenyl)piperidin-4-yl]-N-methyl-1-[2-(trifluoromethyl)phenyl]-1H-imidazole-2-carboxamide Using the compound obtained in Example 78 and 1-[2-(trifluoromethyl)phenyl]-1H-imidazole-2-carboxylic acid, and by the reaction and purification in the same manner as in Example 3, the title compound was obtained.
MS (ESI+): 650 (M+H)

Example 300

N-[(3R,4R)-1-[(1-acetylpiperidin-4-yl)carbonyl]-3-(3,4-dichlorophenyl)piperidin-4-yl]-6-methoxy-N,3-dimethyl-2-oxo-1a,2,3,7b-tetrahydro-1H-cyclopropa[c]quinoline-5-carboxamide (Step 1)
Using 6-methoxy-3-methyl-2-oxo-1a,2,3,7b-tetrahydro-1H-cyclopropa[c]quinoline-5-carbaldehyde synthesized by a known method (WO2001/077100), and by the reaction and purification in the same manner as in Example 297, step 1,6-methoxy-3-methyl-2-oxo-1a,2,3,7b-tetrahydro-1H-cyclopropa[c]quinoline-5-carboxylic acid was obtained.
MS (ESI+): 248 (M+H)
(Step 2)
Using the compound obtained in step 1 and the compound obtained in Example 78, and by the reaction and purification in the same manner as in Example 3, the title compound was obtained.
MS (ESI+): 641 (M+H)

Example 301

N-[(3R,4R)-1-[(1-acetylpiperidin-4-yl)carbonyl]-3-(3,4-dichlorophenyl)piperidin-4-yl]-N-methylbenzamide Using the compound obtained in Reference Example 78 and benzoyl chloride, and by the reaction and purification in the same manner as in Example 39, the title compound was obtained.
MS (ESI+): 516 (M+H)

Example 302

N-[(3R,4R)-1-[(1-acetylpiperidin-4-yl)carbonyl]-3-(3,4-dichlorophenyl)piperidin-4-yl]-N,4-dimethylbenzamide Using the compound obtained in Reference Example 78 and 4-methylbenzoyl chloride, and by the reaction and purification in the same manner as in Example 39, the title compound was obtained.
MS (ESI+): 530 (M+H)

Example 303

N-[(3R,4R)-1-[(1-acetylpiperidin-4-yl)carbonyl]-3-(3,4-dichlorophenyl)piperidin-4-yl]-N-methyl-4-(trifluoromethoxy)benzamide Using the compound obtained in Reference Example 78 and 4-(trifluoromethoxy)benzoyl chloride, and by the reaction and purification in the same manner as in Example 39, the title compound was obtained.
MS (ESI+): 600 (M+H)

Example 304

N-[(3R,4R)-1-[(1-acetylpiperidin-4-yl)carbonyl]-3-(3,4-dichlorophenyl)piperidin-4-yl]-4-ethyl-N-methylbenzamide Using the compound obtained in Reference Example 78 and 4-ethylbenzoyl chloride, and by the reaction and purification in the same manner as in Example 39, the title compound was obtained.
MS (ESI+): 544 (M+H)

Example 305

N-[(3R,4R)-1-[(1-acetylpiperidin-4-yl)carbonyl]-3-(3,4-dichlorophenyl)piperidin-4-yl]-N,1-dimethyl-1H-indole-5-carboxamide Using the compound obtained in Reference Example 78 and 1-methyl-1H-indole-2-carboxylic acid, and by the reaction and purification in the same manner as in Example 3, the title compound was obtained.
MS (ESI+): 569 (M+H)

Example 306

N-[(3R,4R)-1-[(1-acetylpiperidin-4-yl)carbonyl]-3-(3,4-dichlorophenyl)piperidin-4-yl]-3-fluoro-N-methyl-4-(trifluoromethyl)benzamide Using the compound obtained in Reference Example 78 and 3-fluoro-4-(trifluoromethyl)benzoic acid, and by the reaction and purification in the same manner as in Example 265, the title compound was obtained.
MS (ESI+): 602 (M+H)

Example 307

N-[(3R,4R)-1-[(1-acetylpiperidin-4-yl)carbonyl]-3-(3,4-dichlorophenyl)piperidin-4-yl]-N-methyl-5-(trifluoromethyl)pyridine-2-carboxamide Using the compound obtained in Reference Example 78 and 5-(trifluoromethyl)pyridine-2-carboxylic acid, and by the reaction and purification in the same manner as in Example 265, the title compound was obtained.

MS (ESI+): 585 (M+H)

Example 308

N-[(3R,4R)-1-[(1-acetylpiperidin-4-yl)carbonyl]-3-(3,4-dichlorophenyl)piperidin-4-yl]-4-chloro-3-fluoro-N-methylbenzamide Using the compound obtained in Reference Example 78 and 4-chloro-3-fluorobenzoic acid, and by the reaction and purification in the same manner as in Example 265, the title compound was obtained.

MS (ESI+): 568 (M+H)

Example 309

N-[(3R,4R)-1-[(1-acetylpiperidin-4-yl)carbonyl]-3-(3,4-dichlorophenyl)piperidin-4-yl]-3-methoxy-N-methylbiphenyl-2-carboxamide Using the compound obtained in Reference Example 78 and 3-methoxybiphenyl-2-carboxylic acid, and by the reaction and purification in the same manner as in Example 231, the title compound was obtained.

MS (ESI+): 622 (M+H)

Example 310

N-[(3R,4R)-1-[(1-acetylpiperidin-4-yl)carbonyl]-3-(3,4-dichlorophenyl)piperidin-4-yl]-4'-cyano-3-methoxy-N-methylbiphenyl-2-carboxamide Using the compound obtained in Reference Example 78 and 4'-cyano-3-methoxybiphenyl-2-carboxylic acid, and by the reaction and purification in the same manner as in Example 3, the title compound was obtained.

MS (ESI+): 647 (M+H)

Example 311

N-[(3R,4R)-1-[(1-acetylpiperidin-4-yl)carbonyl]-3-(3,4-dichlorophenyl)piperidin-4-yl]-N-methyl-5-phenyl-1,3-oxazole-4-carboxamide Using the compound obtained in Example 78 and 5-phenyl-1,3-oxazole-4-carboxylic acid, and by the reaction and purification in the same manner as in Example 3, the title compound was obtained.

MS (ESI+): 583 (M+H)

Example 312a

N-[(3R,4R)-1-[(1-acetylpiperidin-4-yl)carbonyl]-3-(3,4-dichlorophenyl)piperidin-4-yl]-N-methyl-5-phenylisoxazole-3-carboxamide Using the compound obtained in Example 78 and 5-phenylisoxazole-3-carboxylic acid, and by the reaction and purification in the same manner as in Example 3, the title compound was obtained.

MS (ESI+): 583 (M+H)

Example 312b

N-[(3R,4R)-1-[(1-acetylpiperidin-4-yl)carbonyl]-3-(3,4-dichlorophenyl)piperidin-4-yl]-N-methyl-3-phenylisoxazole-5-carboxamide Using the compound obtained in Example 78 and 3-phenylisoxazole-5-carboxylic acid, and by the reaction and purification in the same manner as in Example 3, the title compound was obtained.

MS (ESI+): 583 (M+H)

Example 313

N-[(3R,4R)-1-[(1-acetylpiperidin-4-yl)carbonyl]-3-(3,4-dichlorophenyl)piperidin-4-yl]-4-methoxy-N-methyl-2-phenyl-1,3-thiazole-5-carboxamide (Step 1)

To a solution (10 mL) of ethyl 4-methoxy-2-phenyl-1,3-thiazole-5-carboxylate (1.37 g) synthesized by a known method (WO2007/089031) in methanol was added 2N aqueous sodium hydroxide solution (3 mL) at room temperature, and the mixture was stirred at 50° C. for 4 hr. The reaction was quenched with 6N hydrochloric acid (1 mL), and the obtained crystals were collected by filtration. The obtained crystals were recrystallized from methanol and diisopropyl ether to give 4-methoxy-2-phenyl-1,3-thiazole-5-carboxylic acid (1.25 g, 100%) as white crystals.

MS (ESI+): 236 (M+H)

(Step 2)

Using the compound obtained in step 1 and the compound obtained in Example 78, and by the reaction and purification in the same manner as in Example 3, the title compound was obtained.

MS (ESI+): 629 (M+H)

Example 314

N-[(3R,4R)-1-[(1-acetylpiperidin-4-yl)carbonyl]-3-(3,4-dichlorophenyl)piperidin-4-yl]-N,1-dimethyl-1H-indole-3-carboxamide Using the compound obtained in Reference Example 78 and 1-methyl-1H-indole-3-carboxylic acid, and by the reaction and purification in the same manner as in Example 3, the title compound was obtained.

MS (ESI+): 569 (M+H)

Example 315

N-[(3R,4R)-1-[(1-acetylpiperidin-4-yl)carbonyl]-3-(3,4-dichlorophenyl)piperidin-4-yl]-N,5-dimethyl-2-phenyl-1,3-thiazole-4-carboxamide Using the compound obtained in Example 78 and 5-methyl-2-phenyl-1,3-thiazole-4-carboxylic acid, and by the reaction and purification in the same manner as in Example 3, the title compound was obtained.

MS (ESI+): 613 (M+H)

Example 316

N-[(3R,4R)-1-[(1-acetylpiperidin-4-yl)carbonyl]-3-(3,4-dichlorophenyl)piperidin-4-yl]-4-methoxy-N-methylbiphenyl-3-carboxamide Using the compound obtained in Example 78 and 4-methoxybiphenyl-3-carboxylic acid, and by the reaction and purification in the same manner as in Example 3, the title compound was obtained.
MS (ESI+): 622 (M+H)

Example 317

N-[(3R,4R)-1-[(1-acetylpiperidin-4-yl)carbonyl]-3-(3,4-dichlorophenyl)piperidin-4-yl]-5-chloro-N-methylpyridine-2-carboxamide Using the compound obtained in Reference Example 78 and 5-chloropyridine-2-carboxylic acid, and by the reaction and purification in the same manner as in Example 3, the title compound was obtained.
MS (ESI+): 551 (M+H)

Example 318

N-[(3R,4R)-1-[(1-acetylpiperidin-4-yl)carbonyl]-3-(3,4-dichlorophenyl)piperidin-4-yl]-5-bromo-N-methylpyridine-2-carboxamide To a solution of obtained in Reference Example 78 (3R,4R)-1-[(1-acetylpiperidin-4-yl)carbonyl]-3-(3,4-dichlorophenyl)-N-methylpiperidin-4-amine (170 mg), 5-bromopyridine-2-carboxylic acid (124 mg) and triethylamine (114 µL) in acetonitrile (3 mL) were added WSC.HCl (0.158 g) and HOBt (0.126 g), and the mixture was stirred at room temperature for 14 hr. To the reaction mixture was added water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography to give the title compound (171 mg, 70%) as a white crystal powder.
MS (ESI+): 595 (M+H)
$^1$H-NMR (CDCl$_3$) δ 1.47-2.48 (12H, m), 2.53-3.60 (8H, m), 3.60-4.33 (2H, m), 4.36-5.10 (1H, m), 6.74-7.63 (4H, m), 7.68-8.17 (1H, m), 8.30-8.86 (1H, m)
Elemental analysis: C$_{26}$H$_{29}$BrCl$_2$N$_4$O$_3$
Found C, 52.43; H, 5.13; N, 9.07
Calcd. C, 52.37; H, 4.90; N, 9.40
Melting point: 128-130° C.
$[α]_D^{25}$ +103.1° (c 0.25, MeOH)

Example 319

N-[(3R,4R)-1-[(1-acetylpiperidin-4-yl)carbonyl]-3-(3,4-dichlorophenyl)piperidin-4-yl]-N,6-dimethylpyridine-3-carboxamide Using the compound obtained in Reference Example 78 and 6-methylpyridine-3-carboxylic acid, and by the reaction and purification in the same manner as in Example 3, the title compound was obtained.
MS (ESI+): 531 (M+H)

Example 320

N-[(3R,4R)-1-[(1-acetylpiperidin-4-yl)carbonyl]-3-(3,4-dichlorophenyl)piperidin-4-yl]-N-methyl-5-phenylpyridine-2-carboxamide Using the compound obtained in Reference Example 78 and 5-phenylpyridine-2-carboxylic acid, and by the reaction and purification in the same manner as in Example 3, the title compound was obtained.
MS (ESI+): 593 (M+H)

Example 321

N-[(3R,4R)-1-[(1-acetylpiperidin-4-yl)carbonyl]-3-(3,4-dichlorophenyl)piperidin-4-yl]-N,5-dimethylpyridine-2-carboxamide Using the compound obtained in Reference Example 78 and 5-methylpyridine-2-carboxylic acid sodium salt, and by the reaction and purification in the same manner as in Example 3, the title compound was obtained.
MS (ESI+): 531 (M+H)

Example 322

4-cyano-N-[(3R,4R)-1-{[1-(cyclopropylcarbonyl)piperidin-4-yl]carbonyl}-3-(3,4-dichlorophenyl)piperidin-4-yl]-2-fluoro-N-methylbenzamide (Step 1)
To a solution of the compound (1.5 g) obtained in Reference Example 23, step 4,4-cyano-2-fluorobenzoic acid (0.62 g) and triethylamine (0.529 mL) in acetonitrile (15 mL) were added WSC.HCl (0.72 g) and HOBt (0.508 g), and the mixture was stirred at room temperature for 14 hr. To the reaction mixture was added water, and the resultant product was extracted with ethyl acetate. The organic layer was washed with 1N hydrochloric acid, saturated aqueous sodium hydrogen carbonate solution and brine and dried, and the solvent was evaporated under reduced pressure. The obtained residue was purified by silica gel column chromatography (solvent gradient; 30→80% ethyl acetate/hexane) to give tert-butyl (3R,4R)-4-{[(4-cyano-2-fluorophenyl)carbonyl]amino}-3-(3,4-dichlorophenyl)piperidine-1-carboxylate (1.44 g, 100%) as a white powder.
MS (ESI+): 392 (M-Boc+2H)
(Step 2)
To a solution of the compound (1.44 g) obtained in step 1 in DMF (15 mL) was added sodium hydride (60% in oil, 0.240 g) at 0° C., and the mixture was stirred for 20 min. Furthermore, methyl iodide (0.97 mL) was added, and the mixture was stirred at room temperature for 4 hr. The reaction mixture was poured into water, and the resultant product was extracted with ethyl acetate. The organic layer was washed with 1M aqueous KHSO$_4$ solution and brine and dried, and the solvent was evaporated under reduced pressure. The obtained residue was purified by silica gel column chromatography (solvent gradient; 5→40% ethyl acetate/hexane) to give tert-butyl (3R,4R)-4-{[(4-cyano-2-fluorophenyl)carbonyl](methyl)amino}-3-(3,4-dichlorophenyl)piperidine-1-carboxylate (1.35 g, 92%) as a pale yellow powder.
MS (ESI+): 406 (M-Boc+2H)
(Step 3)
To a solution of the compound (1.38 g) obtained in step 2 in 2-propanol (4 mL) was added 4N hydrogen chloride/ethyl acetate (8 mL) at room temperature, and the mixture was stirred at 50° C. for 2 hr. The reaction mixture was evaporated under reduced pressure, ethyl acetate was added to the obtained residue, and the mixture was neutralized with 1N aqueous sodium hydroxide solution. The resultant product was extracted with ethyl acetate. The organic layer was washed with brine and dried, and the solvent was evaporated under reduced pressure to give 4-cyano-N-[3-(3,4-dichlorophenyl)piperidin-4-yl]-2-fluoro-N-methylbenzamide (1.06 g, 100%).

MS (ESI+): 406 (M+H)

(Step 4)

To a solution of ethyl piperidine-4-carboxylate (5 g) and triethylamine (5.3 mL) in THF (100 mL) was added cyclopropylcarbonyl chloride (3.99 g) at 0° C., and the mixture was stirred overnight at room temperature. The reaction mixture was poured into water, and the resultant product was extracted with ethyl acetate. The organic layer was washed with 1N hydrochloric acid, saturated aqueous sodium hydrogen carbonate solution and brine and dried, and the solvent was evaporated under reduced pressure to give ethyl 1-(cyclopropylcarbonyl)piperidine-4-carboxylate (6.32 g, 81%) as a pale yellow oil.

MS (ESI+): 226 (M+H)

(Step 5)

To a solution of the compound (6.3 g) obtained in step 4 in ethanol (30 mL) was added 4N aqueous sodium hydroxide solution (35 mL), and the mixture was stirred at room temperature for 22 hr. The reaction mixture was concentrated under reduced pressure, and made acidic with 6N hydrochloric acid. The resultant product was extracted with ethyl acetate, the organic layer was washed with brine and dried, and the solvent was evaporated under reduced pressure to give 1-(cyclopropylcarbonyl)piperidine-4-carboxylic acid (5.21 g, 95%) as a pale yellow powder.

MS (ESI+): 198 (M+H)

(Step 6)

Using the compounds obtained in step 3 and step 5, and by the reaction and purification in the same manner as in Example 97, the title compound was obtained.

MS (ESI+): 585 (M+H)

Example 323

N-[(3R,4R)-1-[(1-acetylpiperidin-4-yl)carbonyl]-3-(3,4-dichlorophenyl)piperidin-4-yl]-4-[(2-methoxyethyl)(methyl)amino]-N-methylbenzamide Using the compound obtained in Reference Example 78 and 4-[(2-methoxyethyl)(methyl)amino]benzoic acid, and by the reaction and purification in the same manner as in Example 97, the title compound was obtained.

MS (ESI+): 603 (M+H)

Example 324

N-[(3R,4R)-1-[(1-acetylpiperidin-4-yl)carbonyl]-3-(3,4-dichlorophenyl)piperidin-4-yl]-N-methyl-4-pyrrolidin-1-ylbenzamide Using the compound obtained in Reference Example 78 and 4-pyrrolidin-1-ylbenzoic acid, and by the reaction and purification in the same manner as in Example 97, the title compound was obtained.

MS (ESI+): 585 (M+H)

Example 325

N-[(3R,4R)-1-[(1-acetylpiperidin-4-yl)carbonyl]-3-(3,4-dichlorophenyl)piperidin-4-yl]-N-methyl-4-(morpholin-4-ylamino)benzamide Using the compound obtained in Reference Example 78 and 4-(morpholin-4-ylamino)benzoic acid, and by the reaction and purification in the same manner as in Example 3, the title compound was obtained.

MS (ESI+): 616 (M+H)

Example 326

N-[(3R,4R)-1-[(1-acetylpiperidin-4-yl)carbonyl]-3-(3,4-dichlorophenyl)piperidin-4-yl]-N-methyl-4-(morpholin-4-ylmethyl)benzamide Using the compound obtained in Reference Example 78 and 4-(morpholin-4-ylmethyl)benzoic acid, and by the reaction and purification in the same manner as in Example 3, the title compound was obtained.

MS (ESI+): 615 (M+H)

Example 327

N-[(3R,4R)-1-[(1-acetylpiperidin-4-yl)carbonyl]-3-(3,4-dichlorophenyl)piperidin-4-yl]-2,2-difluoro-N-methyl-1,3-benzodioxole-5-carboxamide To a solution of the compound (200 mg) obtained in Reference Example 78, 2,2-difluoro-1,3-benzodioxole-5-carboxylic acid (147 mg) and triethylamine (138 μL) in acetonitrile (3 mL) were added WSC.HCl (186 mg) and HOBt (148 mg), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (NH Chromatorex) (solvent gradient; 15→100% ethyl acetate/hexane) to give the title compound (190 mg, 65%) as a white powder.

MS (ESI+): 596 (M+H)

Example 328

N-[(3R,4R)-1-[(1-acetylpiperidin-4-yl)carbonyl]-3-(3,4-dichlorophenyl)piperidin-4-yl]-N-methyl-4-piperidin-1-ylbenzamide Using the compound obtained in Reference Example 78 and 4-piperidin-1-ylbenzoic acid, and by the reaction and purification in the same manner as in Example 97, the title compound was obtained.

MS (ESI+): 599 (M+H)

Example 329

N-[(3R,4R)-1-[(1-acetylpiperidin-4-yl)carbonyl]-3-(3,4-dichlorophenyl)piperidin-4-yl]-4-(1,1-dioxidothiomorpholin-4-yl)-N-methylbenzamide Using the compound obtained in Reference Example 78 and 4-(1,1-dioxidothiomorpholin-4-yl)benzoic acid, and by the reaction and purification in the same manner as in Example 97, the title compound was obtained.

MS (ESI+): 649 (M+H)

Example 330

N-[(3R,4R)-1-[(1-acetylpiperidin-4-yl)carbonyl]-3-(3,4-dichlorophenyl)piperidin-4-yl]-N-methyl-1-benzothiophene-3-carboxamide Using the compound obtained in Reference Example 78 and 1-benzothiophene-3-carboxylic acid, and by the reaction and purification in the same manner as in Example 265, the title compound was obtained.

MS (ESI+): 572 (M+H)

Example 331

N-[(3R,4R)-1-[(1-acetylpiperidin-4-yl)carbonyl]-3-(3,4-dichlorophenyl)piperidin-4-yl]-N-methyl-5-pyridin-2-ylthiophene-2-carboxamide Using the compound obtained in Reference Example 78 and 5-pyridin-2-ylthiophene-2-carboxylic acid, and by the reaction and purification in the same manner as in Example 265, the title compound was obtained.

MS (ESI+): 599 (M+H)

Example 332

N-[(3R,4R)-1-[(1-acetylpiperidin-4-yl)carbonyl]-3-(3,4-dichlorophenyl)piperidin-4-yl]-4-(4-chlorophenyl)-N-methylthiophene-2-carboxamide Using the compound obtained in Reference Example 78 and 4-(4-chlorophenyl)thiophene-2-carboxylic acid, and by the reaction and purification in the same manner as in Example 265, the title compound was obtained.

MS (ESI+): 632 (M+H)

Example 333

N-[(3R,4R)-1-[(1-acetylpiperidin-4-yl)carbonyl]-3-(3,4-dichlorophenyl)piperidin-4-yl]-3-chloro-N-methyl-1-benzothiophene-2-carboxamide Using the compound obtained in Reference Example 78 and 3-chloro-1-benzothiophene-2-carboxylic acid, and by the reaction and purification in the same manner as in Example 265, the title compound was obtained.

MS (ESI+): 606 (M+H)

Example 334

N-[(3R,4R)-1-[(1-acetylpiperidin-4-yl)carbonyl]-3-(3,4-dichlorophenyl)piperidin-4-yl]-N-methyl-4-thiomorpholin-4-ylbenzamide Using the compound obtained in Reference Example 78 and 4-thiomorpholin-4-ylbenzoic acid, and by the reaction and purification in the same manner as in Example 265, the title compound was obtained.

MS (ESI+): 617 (M+H)

Example 335

N-[(3R,4R)-1-[(1-acetylpiperidin-4-yl)carbonyl]-3-(3,4-dichlorophenyl)piperidin-4-yl]-N-methyl-4-pyridin-4-ylbenzamide Using the compound obtained in Reference Example 78 and 4-pyridin-4-ylbenzoic acid, and by the reaction and purification in the same manner as in Example 3, the title compound was obtained.

MS (ESI+): 593 (M+H)

Example 336

N-[(3R,4R)-1-[(1-acetylpiperidin-4-yl)carbonyl]-3-(3,4-dichlorophenyl)piperidin-4-yl]-N-methyl-4-(1-oxidepyridin-4-yl)benzamide Using the compound obtained in Reference Example 78 and 4-(1-oxidepyridin-4-yl)benzoic acid, and by the reaction and purification in the same manner as in Example 3, the title compound was obtained.

MS (ESI+): 609 (M+H)

Example 337

N-[(3R,4R)-1-[(1-acetylpiperidin-4-yl)carbonyl]-3-(3,4-dichlorophenyl)piperidin-4-yl]-N-methyl-4'-(trifluoromethyl)biphenyl-4-carboxamide Using the compound obtained in Reference Example 78 and 4'-(trifluoromethyl)biphenyl-4-carboxylic acid, and by the reaction and purification in the same manner as in Example 3, the title compound was obtained.

MS (ESI+): 660 (M+H)

Example 338

N-[(3R,4R)-1-[(1-acetylpiperidin-4-yl)carbonyl]-3-(3,4-dichlorophenyl)piperidin-4-yl]-4'-cyano-N-methylbiphenyl-4-carboxamide Using the compound obtained in Reference Example 78 and 4'-cyanobiphenyl-4-carboxylic acid, and by the reaction and purification in the same manner as in Example 3, the title compound was obtained.

MS (ESI+): 617 (M+H)

Example 339

N-[(3R,4R)-1-[(1-acetylpiperidin-4-yl)carbonyl]-3-(3,4-dichlorophenyl)piperidin-4-yl]-4-chloro-N-ethylbenzamide To a solution of the compound (0.18 g) obtained in Example 137b, 1-acetylpiperidine-4-carboxylic acid (0.10 g) and triethylamine (0.12 g) in acetonitrile (3 mL) was added DEPC (0.10 g), and the mixture was stirred at room temperature for 18 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 10→25% ethyl acetate/hexane) to give the title compound (230 mg, 100%) as a pale brown powder.

MS (ESI+): 564 (M+H)

Example 340

N-[(3R,4S)-1-[(1-acetylpiperidin-4-yl)carbonyl]-4-(3,4-dichlorophenyl)pyrrolidin-3-yl]-4-chloro-N-methylbenzamide The compound obtained in Example 250 was optically resolved by chiral column chromatography. The collected fraction with a small retention time was concentrated to give the title compound as a white powder.
MS (ESI+): 536 (M+H)
$^1$H-NMR (CDCl$_3$) δ 1.60-1.91 (6H, m), 2.05-2.17 (3H, m), 2.44-4.36 (11H, m), 4.49-4.85 (1H, m), 6.69-7.68 (7H, m)
Purification Conditions by Chiral Column Chromatography
Column: CHIRALPAK AS-H 20 mmID×250 mL
Solvent: CO$_2$/2-propanol=600/400 (v/v)
Flow rate: 50 mL/min
Pressure: 100 bar
Temperature: 35° C.
Detection method: UV 220 nm

Example 341

N-[(3S,4R)-1-[(1-acetylpiperidin-4-yl)carbonyl]-4-(3,4-dichlorophenyl)pyrrolidin-3-yl]-4-chloro-N-methylbenzamide The collected fraction with a long retention time in Example 340 was concentrated to give the title compound as a white powder.
MS (ESI+): 536 (M+H)
$^1$H-NMR (CDCl$_3$) δ 1.60-1.91 (6H, m), 2.05-2.17 (3H, m), 2.44-4.36 (11H, m), 4.49-4.85 (1H, m), 6.69-7.68 (7H, m)
Purification Conditions by Chiral Column Chromatography
Same as the method described in Example 340.

Example 342

N-[(3R*,4R*)-1-[(1-acetylpiperidin-4-yl)carbonyl]-3-(3-fluoro-4-methylphenyl)piperidin-4-yl]-N-methyl-3,5-bis(trifluoromethyl)benzamide Using the compound obtained in Example 103 and 1-acetylpiperidine-4-carboxylic acid, and by the reaction and purification in the same manner as in Example 3, the title compound was obtained.
MS (ESI+): 616 (M+H)

Example 343

N-[(3R*,4R*)-1-[(1-acetylpiperidin-4-yl)carbonyl]-3-(4-fluoro-3-methylphenyl)piperidin-4-yl]-N-methyl-3,5-bis(trifluoromethyl)benzamide Using the compound obtained in Example 104 and 1-acetylpiperidine-4-carboxylic acid, and by the reaction and purification in the same manner as in Example 3, the title compound was obtained.
MS (ESI+): 616 (M+H)

Example 344

N-[(3R*,4R*)-1-[(1-acetylpiperidin-4-yl)carbonyl]-3-(3-fluoro-4-methylphenyl)piperidin-4-yl]-3-bromo-N-methyl-5-(trifluoromethyl)benzamide Using the compound obtained in Example 126c and 1-acetylpiperidine-4-carboxylic acid, and by the reaction and purification in the same manner as in Example 3, the title compound was obtained.
MS (ESI+): 626 (M+H)

Example 345

N-[(3R*,4R*)-1-[(1-acetylpiperidin-4-yl)carbonyl]-3-(4-fluoro-3-methylphenyl)piperidin-4-yl]-3-bromo-N-methyl-5-(trifluoromethyl)benzamide Using the compound obtained in Example 126d and 1-acetylpiperidine-4-carboxylic acid, and by the reaction and purification in the same manner as in Example 3, the title compound was obtained.
MS (ESI+): 626 (M+H)

Example 346

N-[(3R*,4R*)-1-[(1-acetylpiperidin-4-yl)carbonyl]-3-(4-fluorophenyl)piperidin-4-yl]-N-methyl-3,5-bis(trifluoromethyl)benzamide Using the compound obtained in Example 105 and 1-acetylpiperidine-4-carboxylic acid, and by the reaction and purification in the same manner as in Example 3, the title compound was obtained.
MS (ESI+): 602 (M+H)

Example 347

N-{(3R*,4R*)-1-[(1-acetylpiperidin-4-yl)carbonyl]-3-phenylpiperidin-4-yl}-N-methylthiophene-2-carboxamide Using the compound obtained in Example 115 and 1-acetylpiperidine-4-carboxylic acid, and by the reaction and purification in the same manner as in Example 3, the title compound was obtained.
MS (ESI+): 454 (M+H)

Example 348

N-[(3R*,4R*)-1-[(1-acetylpiperidin-4-yl)carbonyl]-3-(3,5-dichlorophenyl)piperidin-4-yl]-N-methyl-3,5-bis(trifluoromethyl)benzamide Using the compound obtained in Example 118, and by the reaction and purification in the same manner as in Example 3, the title compound was obtained.
MS (ESI+): 652 (M+H)

Example 349

N-[(3R*,4R*)-1-[(1-acetylpiperidin-4-yl)carbonyl]-3-(4-methylphenyl)piperidin-4-yl]-N-methyl-3,5-bis(trifluoromethyl)benzamide Using the compound obtained in Example 116 and 1-acetylpiperidine-4-carboxylic acid, and by the reaction and purification in the same manner as in Example 3, the title compound was obtained.
MS (ESI+): 598 (M+H)

Example 350

N-[(3R*,4R*)-1-[(1-acetylpiperidin-4-yl)carbonyl]-3-(4-methylphenyl)piperidin-4-yl]-3-bromo-N-methyl-5-(trifluoromethyl)benzamide Using the compound obtained in Example 117 and 1-acetylpiperidine-4-carboxylic acid, and by the reaction and purification in the same manner as in Example 3, the title compound was obtained.
MS (ESI+): 608 (M+H)

Example 351

N-[(3R*,4R*)-1-[(1-acetylpiperidin-4-yl)carbonyl]-3-(4-chlorophenyl)piperidin-4-yl]-N-methyl-3,5-bis(trifluoromethyl)benzamide Using the compound obtained in Example 120 and 1-acetylpiperidine-4-carboxylic acid, and by the reaction and purification in the same manner as in Example 3, the title compound was obtained.
MS (ESI+): 618 (M+H)

Example 352

N-[(3R*,4R*)-1-[(1-acetylpiperidin-4-yl)carbonyl]-3-(4-chlorophenyl)piperidin-4-yl]-3-bromo-N-methyl-5-(trifluoromethyl)benzamide Using the compound obtained in Example 121 and 1-acetylpiperidine-4-carboxylic acid, and by the reaction and purification in the same manner as in Example 3, the title compound was obtained.
MS (ESI+): 628 (M+H)

Example 353

N-[(3R*,4R*)-1-[(1-acetylpiperidin-4-yl)carbonyl]-3-phenylpiperidin-4-yl}-3-bromo-N-methyl-5-(trifluoromethyl)benzamide Using the compound obtained in Example 125 and 1-acetylpiperidine-4-carboxylic acid, and by the reaction and purification in the same manner as in Example 3, the title compound was obtained.
MS (ESI+): 594 (M+H)

Example 354

N-[(3R,4R)-1-[(1-acetylpiperidin-4-yl)carbonyl]-3-phenylpiperidin-4-yl}-N-methyl-3,5-bis(trifluoromethyl)benzamide Using the compound obtained in Example 135 and 1-acetylpiperidine-4-carboxylic acid, and by the reaction and purification in the same manner as in Example 3, the title compound was obtained.
MS (ESI+): 584 (M+H)

Example 355

N-[(3R*,4R*)-1-[(1-acetylpiperidin-4-yl)carbonyl]-3-(4-chloro-3-methylphenyl)piperidin-4-yl]-3-bromo-N-methyl-5-(trifluoromethyl)benzamide Using the compound obtained in Example 126a and 1-acetylpiperidine-4-carboxylic acid, and by the reaction and purification in the same manner as in Example 3, the title compound was obtained.
MS (ESI+): 642 (M+H)

Example 356

N-[(3R*,4R*)-1-[(1-acetylpiperidin-4-yl)carbonyl]-3-(4-fluorophenyl)piperidin-4-yl]-4-fluoro-N-methyl-3-(trifluoromethyl)benzamide Using the compound obtained in Example 127 and 1-acetylpiperidine-4-carboxylic acid, and by the reaction and purification in the same manner as in Example 3, the title compound was obtained.
MS (ESI+): 552 (M+H)

Example 357

N-[(3R*,4R*)-1-[(1-acetylpiperidin-4-yl)carbonyl]-3-(4-fluorophenyl)piperidin-4-yl]-4-chloro-N-methyl-3-(trifluoromethyl)benzamide Using the compound obtained in Example 130 and 1-acetylpiperidine-4-carboxylic acid, and by the reaction and purification in the same manner as in Example 3, the title compound was obtained.
MS (ESI+): 568 (M+H)

Example 358

N-[(3R*,4R*)-1-[(1-acetylpiperidin-4-yl)carbonyl]-3-(4-chlorophenyl)piperidin-4-yl]-4-fluoro-N-methyl-3-(trifluoromethyl)benzamide Using the compound obtained in Example 128 and 1-acetylpiperidine-4-carboxylic acid, and by the reaction and purification in the same manner as in Example 3, the title compound was obtained.
MS (ESI+): 568 (M+H)

Example 359

N-[(3R*,4R*)-1-[(1-acetylpiperidin-4-yl)carbonyl]-3-(4-chlorophenyl)piperidin-4-yl]-4-chloro-N-methyl-3-(trifluoromethyl)benzamide Using the compound obtained in Example 129 and 1-acetylpiperidine-4-carboxylic acid, and by the reaction and purification in the same manner as in Example 3, the title compound was obtained.
MS (ESI+): 584 (M+H)

Example 360

N-[(3R*,4S*)-1-[(1-acetylpiperidin-4-yl)carbonyl]-3-(3,4-dichlorophenyl)piperidin-4-yl]-4-chloro-N-methylbenzamide To a solution of the compound obtained in Reference Example 64 (200 mg) in DMF (3 mL) was added sodium tert-butoxide (72 mg) at 0° C., and the mixture was stirred for 5 min. Then, methyl iodide (115 µL) was added, and the mixture was stirred at room temperature for 14 hr. The reaction mixture was poured into water, and the resultant product was extracted with ethyl acetate. The organic layer was washed with water and dried, and the solvent was evaporated under reduced pressure. The obtained residue was purified by silica gel column chromatography (solvent gradient; 0→2% methanol/ethyl acetate) to give the title compound (129 mg, 61%) as a white powder.
MS (ESI+): 550 (M+H)

Example 361 tert-butyl (3R*,4R*)-4-[{[3,5-bis(trifluoromethyl) phenyl]carbonyl}(methyl)amino]-3-(3-fluoro-4-methylphenyl)-1,4'-bipiperidine-1'-carboxylate Using the compound obtained in Example 103, and by the reaction and purification in the same manner as in Example 37, the title compound was obtained.
MS (ESI+): 546 (M-Boc+2H)

Example 362 tert-butyl (3R*,4R*)-4-[{[3,5-bis(trifluoromethyl) phenyl]carbonyl}(methyl)amino]-3-(4-fluoro-3-methylphenyl)-1,4'-bipiperidine-1'-carboxylate Using the compound obtained in Example 104, and by the reaction and purification in the same manner as in Example 37, the title compound was obtained.
MS (ESI+): 546 (M-Boc+2H)

Example 363 tert-butyl (3R*,4R*)-4-[{[3,5-bis(trifluoromethyl) phenyl]carbonyl}(methyl)amino]-3-(4-fluorophenyl)-1,4'-bipiperidine-1'-carboxylate Using the compound obtained in Example 105, and by the reaction and purification in the same manner as in Example 37, the title compound was obtained.
MS (ESI+): 532 (M-Boc+2H)

Example 364 tert-butyl (3R*,4R*)-4-[{[3-bromo-5-(trifluoromethyl)phenyl]carbonyl}(methyl)amino]-3-(3,4-dichlorophenyl)-1,4'-bipiperidine-1'-carboxylate Using the compound obtained in Example 126b, and by the reaction and purification in the same manner as in Example 37, the title compound was obtained.
MS (ESI+): 592 (M-Boc+2H)

Example 365 tert-butyl (3R*,4R*)-4-[{[3,5-bis(trifluoromethyl) phenyl]carbonyl}(methyl)amino]-3-(4-methoxyphenyl)-1,4'-bipiperidine-1'-carboxylate Using the compound obtained in Example 108, and by the reaction and purification in the same manner as in Example 37, the title compound was obtained.
MS (ESI+): 644 (M+H)

Example 366 tert-butyl (3R*,4R*)-4-[{[3,5-bis(trifluoromethyl) phenyl]carbonyl}(methyl)amino]-3-(4-methylphenyl)-1,4'-bipiperidine-1'-carboxylate Using the compound obtained in Example 116, and by the reaction and purification in the same manner as in Example 37, the title compound was obtained.
MS (ESI+): 628 (M+H)

Example 367 tert-butyl (3R*,4R*)-4-[{[3,5-bis(trifluoromethyl) phenyl]carbonyl}(methyl)amino]-3-(4-chlorophenyl)-1,4'-bipiperidine-1'-carboxylate Using the compound obtained in Example 120, and by the reaction and purification in the same manner as in Example 37, the title compound was obtained.
MS (ESI+): 648 (M+H)

Example 368a tert-butyl (3R*,4R*)-4-[{[3,5-bis(trifluoromethyl) phenyl]carbonyl}(methyl)amino]-3-phenyl-1,4'-bipiperidine-1'-carboxylate Using the compound obtained in Example 74, and by the reaction and purification in the same manner as in Example 37, the title compound was obtained.
MS (ESI+): 614 (M+H)

Example 368b

N-methyl-N-[(3R*,4R*)-3-phenyl-1,4'-bipiperidin-4-yl]-3,5-bis(trifluoromethyl)benzamide dihydrochloride Using the compound obtained in Example 368a, and by the reaction and purification in the same manner as in Example 2, the title compound was obtained.
MS (ESI+): 514 (M-2HCl+H)

Example 369

N-[(3R*,4R*)-3-(3-chloro-4-fluorophenyl)-1,4'-bipiperidin-4-yl]-N-methyl-3,5-bis(trifluoromethyl)benzamide dihydrochloride Using the compound obtained in Example 78, and by the reaction and purification in the same manner as in Example 37 and Example 2, the title compound was obtained.
MS (ESI+): 566 (M-2HCl+H)

Example 370

N-[(3R*,4R*)-3-(3-fluoro-4-methylphenyl)-1,4'-bipiperidin-4-yl]-N-methyl-3,5-bis(trifluoromethyl)benzamide dihydrochloride Using the compound obtained in Example 361, and by the reaction and purification in the same manner as in Example 2, the title compound was obtained.
MS (ESI+): 546 (M-2HCl+H)

Example 371

N-[(3R*,4R*)-3-(4-fluoro-3-methylphenyl)-1,4-bipiperidin-4-yl]-N-methyl-3,5-bis(trifluoromethyl)benzamide dihydrochloride Using the compound obtained in Example 362, and by the reaction and purification in the same manner as in Example 2, the title compound was obtained.
MS (ESI+): 546 (M−2HCl+H)

Example 372

N-[(3R*,4R*)-3-(4-fluorophenyl)-1,4'-bipiperidin-4-yl]-N-methyl-3,5-bis(trifluoromethyl)benzamide dihydrochloride Using the compound obtained in Example 363, and by the reaction and purification in the same manner as in Example 2, the title compound was obtained.
MS (ESI+): 532 (M−2HCl+H)

Example 373

3-bromo-N-[(3R*,4R*)-3-(3,4-dichlorophenyl)-1,4'-bipiperidin-4-yl]-N-methyl-5-(trifluoromethyl)benzamide dihydrochloride Using the compound obtained in Example 364, and by the reaction and purification in the same manner as in Example 2, the title compound was obtained.
MS (ESI+): 592 (M−2HCl+H)

Example 374a

N-[(3R*,4R*)-3-(4-methoxyphenyl)-1,4'-bipiperidin-4-yl]-N-methyl-3,5-bis(trifluoromethyl)benzamide dihydrochloride Using the compound obtained in Example 365, and by the reaction and purification in the same manner as in Example 2, the title compound was obtained.
MS (ESI+): 544 (M−2HCl+H)

Example 374b

N-methyl-N-[(3R*,4R*)-3-(4-methylphenyl)-1,4'-bipiperidin-4-yl]-3,5-bis(trifluoromethyl)benzamide dihydrochloride Using the compound obtained in Example 366, and by the reaction and purification in the same manner as in Example 2, the title compound was obtained.
MS (ESI+): 528 (M−2HCl+H)

Example 374c

N-[(3R*,4R*)-3-(4-chlorophenyl)-1,4-bipiperidin-4-yl]-N-methyl-3,5-bis(trifluoromethyl)benzamide dihydrochloride Using the compound obtained in Example 367, and by the reaction and purification in the same manner as in Example 2, the title compound was obtained.
MS (ESI+): 548 (M−2HCl+H)

Example 375

N-[(3R*,4R*)-1'-acetyl-3-phenyl-1,4'-bipiperidin-4-yl]-N-methyl-3,5-bis(trifluoromethyl)benzamide monohydrochloride Using the compound obtained in Example 368b, and by the reaction and purification in the same manner as in Example 39, the title compound was obtained.
MS (ESI+): 556 (M−HCl+H)

Example 376

N-[(3R*,4R*)-1'-acetyl-3-(3-chloro-4-fluorophenyl)-1,4'-bipiperidin-4-yl]-N-methyl-3,5-bis(trifluoromethyl)benzamide monohydrochloride Using the compound obtained in Example 369, and by the reaction and purification in the same manner as in Example 39, the title compound was obtained.
MS (ESI+): 608 (M−HCl+H)

Example 377

N-[(3R*,4R*)-1'-acetyl-3-(3-fluoro-4-methylphenyl)-1,4'-bipiperidin-4-yl]-N-methyl-3,5-bis(trifluoromethyl)benzamide monohydrochloride Using the compound obtained in Example 370, and by the reaction and purification in the same manner as in Example 39, the title compound was obtained.
MS (ESI+): 588 (M−HCl+H)

Example 378

N-[(3R*,4R*)-1'-acetyl-3-(4-fluoro-3-methylphenyl)-1,4'-bipiperidin-4-yl]-N-methyl-3,5-bis(trifluoromethyl)benzamide monohydrochloride Using the compound obtained in Example 371, and by the reaction and purification in the same manner as in Example 39, the title compound was obtained.
MS (ESI+): 588 (M−HCl+H)

Example 379

N-[(3R*,4R*)-1'-acetyl-3-(3,4-dichlorophenyl)-1,4'-bipiperidin-4-yl]-3-bromo-N-methyl-5-(trifluoromethyl)benzamide monohydrochloride Using the compound obtained in Example 373, and by the reaction and purification in the same manner as in Example 39, the title compound was obtained.
MS (ESI+): 634 (M−HCl+H)

Example 380

N-[(3R*,4R*)-1-acetyl-3-(4-fluorophenyl)-1,4'-bipiperidin-4-yl]-N-methyl-3,5-bis(trifluoromethyl)benzamide monohydrochloride Using the compound obtained in Example 372, and by the reaction and purification in the same manner as in Example 39, the title compound was obtained.
MS (ESI+): 574 (M−HCl+H)

Example 381

N-[(3R*,4R*)-1'-acetyl-3-(4-methoxyphenyl)-1,4'-bipiperidin-4-yl]-N-methyl-3,5-bis(trifluoromethyl)benzamide monohydrochloride Using the compound obtained in Example 374a, and by the reaction and purification in the same manner as in Example 39, the title compound was obtained.
MS (ESI+): 586 (M−HCl+H)

Example 382

N-[(3R*,4R*)-1'-acetyl-3-(4-methylphenyl)-1,4-bipiperidin-4-yl]-N-methyl-3,5-bis(trifluoromethyl)benzamide monohydrochloride Using the compound obtained in Example 374b, and by the reaction and purification in the same manner as in Example 39, the title compound was obtained.
MS (ESI+): 570 (M−HCl+H)

Example 383

N-[(3R*,4R*)-1'-acetyl-3-(4-chlorophenyl)-1,4'-bipiperidin-4-yl]-N-methyl-3,5-bis(trifluoromethyl)benzamide monohydrochloride Using the compound obtained in Example 374c, and by the reaction and purification in the same manner as in Example 39, the title compound was obtained.
MS (ESI+): 590 (M−HCl+H)

Example 384

N-[(3R,4R)-3-(3,4-dichlorophenyl)-1-(1H-tetrazol-1-ylacetyl)piperidin-4-yl]-N-methyl-3,5-bis(trifluoromethyl)benzamide Using the compound obtained in Reference Example 78 and 1H-tetrazole-1-acetic acid, and by the reaction and purification in the same manner as in Example 178, the title compound was obtained.
MS (ESI+): 609 (M+H)

Example 385

N-{(3R,4R)-3-(3,4-dichlorophenyl)-1-[N-(phenylcarbonyl)glycyl]piperidin-4-yl}-N-methyl-3,5-bis(trifluoromethyl)benzamide Using the compound obtained in Reference Example 78 and N-(phenylcarbonyl)glycine, and by the reaction and purification in the same manner as in Example 178, the title compound was obtained.
MS (ESI+): 660 (M+H)

Example 386

N-[(3R,4R)-3-(3,4-dichlorophenyl)-1-(hydroxyacetyl)piperidin-4-yl]-N-methyl-3,5-bis(trifluoromethyl)benzamide Using the compound obtained in Reference Example 78 and glycol acid, and by the reaction and purification in the same manner as in Example 178, the title compound was obtained.
MS (ESI+): 557 (M+H)

Example 387

N-[(3R,4R)-1-[amino(oxo)acetyl]-3-(3,4-dichlorophenyl)piperidin-4-yl]-N-methyl-3,5-bis(trifluoromethyl)benzamide Using the compound obtained in Reference Example 78 and oxamic acid, and by the reaction and purification in the same manner as in Example 178, the title compound was obtained.
MS (ESI+): 570 (M+H)

Example 388

N-[(3R,4R)-3-(3,4-dichlorophenyl)-1-(2-hydroxy-2-methylpropanoyl)piperidin-4-yl]-N-methyl-3,5-bis(trifluoromethyl)benzamide Using the compound obtained in Reference Example 78 and 2-hydroxyisobutyric acid, and by the reaction and purification in the same manner as in Example 178, the title compound was obtained.
MS (ESI+): 585 (M+H)

Example 389

N-[(3R,4R)-3-(3,4-dichlorophenyl)-1-(tetrahydrofuran-3-ylcarbonyl)piperidin-4-yl]-N-methyl-3,5-bis(trifluoromethyl)benzamide Using the compound obtained in Reference Example 78 and tetrahydro-3-furoic acid, and by the reaction and purification in the same manner as in Example 178, the title compound was obtained.
MS (ESI+): 597 (M+H)

Example 390

N-[(3R,4R)-1-(cyclohexylcarbonyl)-3-(3,4-dichlorophenyl)piperidin-4-yl]-N-methyl-3,5-bis(trifluoromethyl)benzamide Using the compound obtained in Reference Example 78 and cyclohexanecarboxylic acid, and by the reaction and purification in the same manner as in Example 178, the title compound was obtained.
MS (ESI+): 609 (M+H)

Example 391

N-{(3R,4R)-3-(3,4-dichlorophenyl)-1-[(2,4-dioxo-1,2,3,4-tetrahydropyrimidin-5-yl)carbonyl]piperidin-4-yl}-N-methyl-3,5-bis(trifluoromethyl)benzamide Using the compound obtained in Reference Example 78 and 2,4-dihydroxypyrimidine-5-carboxylic acid, and by the reaction and purification in the same manner as in Example 178, the title compound was obtained.
MS (ESI+): 637 (M+H)

Example 392

N-[(3R,4R)-1-(N-acetylvalyl)-3-(3,4-dichlorophenyl)piperidin-4-yl]-N-methyl-3,5-bis(trifluoromethyl)benzamide Using the compound obtained in Reference Example 78 and N-acetyl-DL-valine, and by the reaction and purification in the same manner as in Example 178, the title compound was obtained.
MS (ESI+): 640 (M+H)

Example 393

N-{(3R,4R)-3-(3,4-dichlorophenyl)-1-[(2,6-dioxo-1,2,3,6-tetrahydropyrimidin-4-yl)carbonyl]piperidin-4-yl}-N-methyl-3,5-bis(trifluoromethyl)benzamide Using the compound obtained in Reference Example 78 and 2,6-dioxo-1,2,3,6-tetrahydropyrimidine-4-carboxylic acid monohydrate, and by the reaction and purification in the same manner as in Example 178, the title compound was obtained.
MS (ESI+): 637 (M+H)

Example 394

N-{(3R,4R)-3-(3,4-dichlorophenyl)-1-[(1,3-dioxo-1,3-dihydro-2H-isoindol-2-yl)acetyl]piperidin-4-yl}-N-methyl-3,5-bis(trifluoromethyl)benzamide Using the compound obtained in Reference Example 78 and N-phthaloylglycine, and by the reaction and purification in the same manner as in Example 178, the title compound was obtained.
MS (ESI+): 686 (M+H)

Example 395

N-[(3R,4R)-1-(cyclopropylcarbonyl)-3-(3,4-dichlorophenyl)piperidin-4-yl]-N-methyl-3,5-bis(trifluoromethyl)benzamide Using the compound obtained in Reference Example 78 and cyclopropanecarboxylic acid, and by the reaction and purification in the same manner as in Example 178, the title compound was obtained.
MS (ESI+): 567 (M+H)

Example 396

N-[(3R,4R)-3-(3,4-dichlorophenyl)-1-(2-methylpropanoyl)piperidin-4-yl]-N-methyl-3,5-bis(trifluoromethyl)benzamide Using the compound obtained in Reference Example 78 and isobutyric acid, and by the reaction and purification in the same manner as in Example 178, the title compound was obtained.
MS (ESI+): 569 (M+H)

Example 397

N-[(3R,4R)-1-(N-acetylalanyl)-3-(3,4-dichlorophenyl)piperidin-4-yl]-N-methyl-3,5-bis(trifluoromethyl)benzamide Using the compound obtained in Reference Example 78 and N-acetyl-DL-alanine, and by the reaction and purification in the same manner as in Example 178, the title compound was obtained.
MS (ESI+): 612 (M+H)

Example 398

N-[(3R,4R)-1-(1-benzofuran-2-ylcarbonyl)-3-(3,4-dichlorophenyl)piperidin-4-yl]-N-methyl-3,5-bis(trifluoromethyl)benzamide Using the compound obtained in Reference Example 78 and benzofuran-2-carboxylic acid, and by the reaction and purification in the same manner as in Example 178, the title compound was obtained.
MS (ESI+): 643 (M+H)

Example 399

N-[(3R,4R)-3-(3,4-dichlorophenyl)-1-(1H-indol-3-ylacetyl)piperidin-4-yl]-N-methyl-3,5-bis(trifluoromethyl)benzamide Using the compound obtained in Reference Example 78 and indole-3-acetic acid, and by the reaction and purification in the same manner as in Example 178, the title compound was obtained.
MS (ESI+): 656 (M+H)

Example 400

N-{(3R,4R)-3-(3,4-dichlorophenyl)-1-[(5-oxo-1-phenylpyrrolidin-3-yl)carbonyl]piperidin-4-yl}-N-methyl-3,5-bis(trifluoromethyl)benzamide Using the compound obtained in Reference Example 78 and 5-oxo-1-phenylpyrrolidine-3-carboxylic acid, and by the reaction and purification in the same manner as in Example 178, the title compound was obtained.
MS (ESI+): 686 (M+H)

Example 401

N-[(3R,4R)-3-(3,4-dichlorophenyl)-1-{[5-oxo-1-(pyridin-2-ylmethyl)pyrrolidin-3-yl]carbonyl}piperidin-4-yl]-N-methyl-3,5-bis(trifluoromethyl)benzamide trifluoroacetate Using the compound obtained in Reference Example 78 and 5-oxo-1-(pyridin-2-ylmethyl)pyrrolidine-3-carboxylic acid, and by the reaction and purification in the same manner as in Example 178, the title compound was obtained.
MS (ESI+): 701 (M-TFA+H)

Example 402

N-[(3R,4R)-3-(3,4-dichlorophenyl)-1-{[1-(1-methylpiperidin-4-yl)-5-oxopyrrolidin-3-yl]carbonyl}piperidin-4-yl]-N-methyl-3,5-bis(trifluoromethyl)benzamide trifluoroacetate Using the compound obtained in Reference Example 78 and 1-(1-methylpiperidin-4-yl)-5-oxopyrrolidine-3-carboxylic acid, and by the reaction and purification in the same manner as in Example 178, the title compound was obtained.
MS (ESI+): 707 (M-TFA+H)

Example 403

N-[(3R,4R)-3-(3,4-dichlorophenyl)-1-{1-[(4-methoxyphenyl)carbonyl]propyl}piperidin-4-yl]-N-methyl-3,5-bis(trifluoromethyl)benzamide Using the compound obtained in Reference Example 78 and 1-[(4-methoxyphenyl)carbonyl]proline, and by the reaction and purification in the same manner as in Example 178, the title compound was obtained.
MS (ESI+): 730 (M+H)

Example 404

N-[(3R,4R)-3-(3,4-dichlorophenyl)-1-({[1-(phenylcarbonyl)piperidin-4-yl]oxy}acetyl)piperidin-4-yl]-N-methyl-3,5-bis(trifluoromethyl)benzamide Using the compound obtained in Reference Example 78 and {[1-(phenylcarbonyl)piperidin-4-yl]oxy}acetic acid, and by the reaction and purification in the same manner as in Example 178, the title compound was obtained.
MS (ESI+): 744 (M+H)

Example 405

N-{(3R,4R)-3-(3,4-dichlorophenyl)-1-[(5,5-dimethyl-2,4-dioxo-3-phenylimidazolidin-1-yl)acetyl]piperidin-4-yl}-N-methyl-3,5-bis(trifluoromethyl)benzamide Using the compound obtained in Reference Example 78 and (5,5-dimethyl-2,4-dioxo-3-phenylimidazolidin-1-yl)acetic acid, and by the reaction and purification in the same manner as in Example 178, the title compound was obtained.
MS (ESI+): 743 (M+H)

Example 406

N-[(3R,4R)-1-{[3-(acetylamino)phenoxy]acetyl}-3-(3,4-dichlorophenyl)piperidin-4-yl]-N-methyl-3,5-bis(trifluoromethyl)benzamide Using the compound obtained in Reference Example 78 and [3-(acetylamino)phenoxy]acetic acid, and by the reaction and purification in the same manner as in Example 178, the title compound was obtained.
MS (ESI+): 690 (M+H)

Example 407

N-[(3R,4R)-3-(3,4-dichlorophenyl)-1-({cis-4-[(phenylcarbonyl)amino]cyclohexyl}carbonyl)piperidin-4-yl]-N-methyl-3,5-bis(trifluoromethyl)benzamide Using the compound obtained in Reference Example 78 and cis-4-[(phenylcarbonyl)amino]cyclohexanecarboxylic acid, and by the reaction and purification in the same manner as in Example 178, the title compound was obtained.
MS (ESI+): 728 (M+H)

Example 408

N-[(3R,4R)-1-(1,2-benzisoxazol-3-ylacetyl)-3-(3,4-dichlorophenyl)piperidin-4-yl]-N-methyl-3,5-bis(trifluoromethyl)benzamide Using the compound obtained in Reference Example 78 and 1,2-benzisoxazol-3-ylacetic acid, and by the reaction and purification in the same manner as in Example 178, the title compound was obtained.
MS (ESI+): 658 (M+H)

Example 409

N-[(3R,4R)-3-(3,4-dichlorophenyl)-1-(4-morpholin-4-ylbutanoyl)piperidin-4-yl]-N-methyl-3,5-bis(trifluoromethyl)benzamide trifluoroacetate Using the compound obtained in Reference Example 78 and 4-morpholin-4-ylbutanoic acid, and by the reaction and purification in the same manner as in Example 178, the title compound was obtained.
MS (ESI+): 654 (M-TFA+H)

Example 410

N-[(3R,4R)-1-[(4-benzylmorpholin-2-yl)carbonyl]-3-(3,4-dichlorophenyl)piperidin-4-yl]-N-methyl-3,5-bis(trifluoromethyl)benzamide trifluoroacetate Using the compound obtained in Reference Example 78 and 4-benzylmorpholine-2-carboxylic acid, and by the reaction and purification in the same manner as in Example 178, the title compound was obtained.
MS (ESI+): 702 (M-TFA+H)

Example 411

N-[(3R,4R)-1-{[1-(6-chloropyrimidin-4-yl)piperidin-3-yl]carbonyl}-3-(3,4-dichlorophenyl)piperidin-4-yl]-N-methyl-3,5-bis(trifluoromethyl)benzamide Using the compound obtained in Reference Example 78 and 1-(6-chloropyrimidin-4-yl)piperidine-3-carboxylic acid, and by the reaction and purification in the same manner as in Example 178, the title compound was obtained.
MS (ESI+): 722 (M+H)

Example 412

N-{(3R,4R)-3-(3,4-dichlorophenyl)-1-[3-(3-oxo-3,4-dihydroquinoxalin-2-yl)propanoyl]piperidin-4-yl}-N-methyl-3,5-bis(trifluoromethyl)benzamide Using the compound obtained in Reference Example 78 and 3-(3-oxo-3,4-dihydroquinoxalin-2-yl)propanoic acid, and by the reaction and purification in the same manner as in Example 178, the title compound was obtained.
MS (ESI+): 699 (M+H)

Example 413

N-{(3R,4R)-3-(3,4-dichlorophenyl)-1-[(5-oxo-4,5-dihydro-1H-1,2,4-triazol-3-yl)acetyl]piperidin-4-yl}-N-methyl-3,5-bis(trifluoromethyl)benzamide Using the compound obtained in Reference Example 78 and (5-oxo-4,5-dihydro-1H-1,2,4-triazol-3-yl)acetic acid, and by the reaction and purification in the same manner as in Example 178, the title compound was obtained.
MS (ESI+): 624 (M+H)

Example 414

N-{(3R,4R)-3-(3,4-dichlorophenyl)-1-[(1-methyl-1H-imidazol-5-yl)carbonyl]piperidin-4-yl}-N-methyl-3,5-bis(trifluoromethyl)benzamide Using the compound obtained in Reference Example 78 and 1-methyl-1H-imidazole-5-carboxylic acid, and by the reaction and purification in the same manner as in Example 178, the title compound was obtained.
MS (ESI+): 607 (M+H)

Example 415

N-{(3R,4R)-3-(3,4-dichlorophenyl)-1-[(2-oxopyrimidine-1(2H)-yl)acetyl]piperidin-4-yl}-N-methyl-3,5-bis(trifluoromethyl)benzamide Using the compound obtained in Reference Example 78 and (2-oxopyrimidin-1(2H)-yl)acetic acid, and by the reaction and purification in the same manner as in Example 178, the title compound was obtained.
MS (ESI+): 635 (M+H)

Example 416

N-[(3R,4R)-1-[(1-acetylpiperidin-3-yl)carbonyl]-3-(3,4-dichlorophenyl)piperidin-4-yl]-N-methyl-3,5-bis(trifluoromethyl)benzamide Using the compound obtained in Reference Example 78 and 1-acetylpiperidine-3-carboxylic acid, and by the reaction and purification in the same manner as in Example 178, the title compound was obtained.
MS (ESI+): 652 (M+H)

Example 417

N-{(3R,4R)-3-(3,4-dichlorophenyl)-1-[(1-methyl-1H-imidazol-4-yl)carbonyl]piperidin-4-yl}-N-methyl-3,5-bis(trifluoromethyl)benzamide Using the compound obtained in Reference Example 78 and 1-methyl-1H-imidazole-4-carboxylic acid, and by the reaction and purification in the same manner as in Example 178, the title compound was obtained.
MS (ESI+): 607 (M+H)

Example 418

N-{(3R,4R)-3-(3,4-dichlorophenyl)-1-[(3-ethyltricyclo[3.3.1.1$^{3,7}$]dec-1-yl)carbonyl]piperidin-4-yl}-N-methyl-3,5-bis(trifluoromethyl)benzamide Using the compound obtained in Reference Example 78 and 3-ethyltricyclo[3.3.1.1$^{3,7}$]decane-1-carboxylic acid, and by the reaction and purification in the same manner as in Example 178, the title compound was obtained.
MS (ESI+): 689 (M+H)

Example 419

N-{(3R,4R)-3-(3,4-dichlorophenyl)-1-[(3-methyl-5-phenylisoxazol-4-yl)carbonyl]piperidin-4-yl}-N-methyl-3,5-bis(trifluoromethyl)benzamide Using the compound obtained in Reference Example 78 and 3-methyl-5-phenylisoxazole-4-carboxylic acid, and by the reaction and purification in the same manner as in Example 178, the title compound was obtained.
MS (ESI+): 684 (M+H)

Example 420

N-[(3R,4R)-3-(3,4-dichlorophenyl)-1-{[4-(hydroxymethyl)tetrahydro-2H-pyran-4-yl]carbonyl}piperidin-4-yl]-N-methyl-3,5-bis(trifluoromethyl)benzamide Using the compound obtained in Reference Example 78 and 4-(hydroxymethyl)tetrahydro-2H-pyran-4-carboxylic acid, and by the reaction and purification in the same manner as in Example 178, the title compound was obtained.
MS (ESI+): 641 (M+H)

Example 421

N-[(3R,4R)-1-{[4-(acetylamino)phenyl]carbonyl}-3-(3,4-dichlorophenyl)piperidin-4-yl]-N-methyl-3,5-bis(trifluoromethyl)benzamide Using the compound obtained in Reference Example 78 and 4-acetamidebenzoic acid, and by the reaction and purification in the same manner as in Example 178, the title compound was obtained.
MS (ESI+): 660 (M+H)

Example 422

N-{(3R,4R)-3-(3,4-dichlorophenyl)-1-[(2E)-3-furan-2-ylprop-2-enoyl]piperidin-4-yl}-N-methyl-3,5-bis(trifluoromethyl)benzamide Using the compound obtained in Reference Example 78 and 3-(2-furyl)acrylic acid, and by the reaction and purification in the same manner as in Example 178, the title compound was obtained.
MS (ESI+): 619 (M+H)

Example 423

N-[(3R,4R)-1-[(4-acetylphenyl)carbonyl]-3-(3,4-dichlorophenyl)piperidin-4-yl]-N-methyl-3,5-bis(trifluoromethyl)benzamide Using the compound obtained in Reference Example 78 and 4-acetylbenzoic acid, and by the reaction and purification in the same manner as in Example 178, the title compound was obtained.
MS (ESI+): 645 (M+H)

Example 424

N-[(3R,4R)-1-(N-carbamoylglycyl)-3-(3,4-dichlorophenyl)piperidin-4-yl]-N-methyl-3,5-bis(trifluoromethyl)benzamide Using the compound obtained in Reference Example 78 and N-carbamoylglycine, and by the reaction and purification in the same manner as in Example 178, the title compound was obtained.
MS (ESI+): 599 (M+H)

Example 425

N-[(3R,4R)-3-(3,4-dichlorophenyl)-1-(3-piperidin-1-ylpropanoyl)piperidin-4-yl]-N-methyl-3,5-bis(trifluoromethyl)benzamide trifluoroacetate Using the compound obtained in Reference Example 78 and 1-piperidinepropionic acid, and by the reaction and purification in the same manner as in Example 178, the title compound was obtained.
MS (ESI+): 638 (M-TFA+H)

Example 426

N-{(3R,4R)-3-(3,4-dichlorophenyl)-1-[N-(phenylcarbonyl)-β-alanyl]piperidin-4-yl}-N-methyl-3,5-bis(trifluoromethyl)benzamide Using the compound obtained in Reference Example 78 and benzoyl-β-alanine, and by the reaction and purification in the same manner as in Example 178, the title compound was obtained.
MS (ESI+): 674 (M+H)

Example 427

N-[(3R,4R)-1-[4-(acetylamino)butanoyl]-3-(3,4-dichlorophenyl)piperidin-4-yl]-N-methyl-3,5-bis(trifluoromethyl)benzamide Using the compound obtained in Reference Example 78 and 4-acetamidebutyric acid, and by the reaction and purification in the same manner as in Example 178, the title compound was obtained.
MS (ESI+): 626 (M+H)

Example 428

N-{(3R,4R)-3-(3,4-dichlorophenyl)-1-[2-(1,3-dioxo-1,3-dihydro-2H-isoindol-2-yl)ethyl]piperidin-4-yl}-N-methyl-3,5-bis(trifluoromethyl)benzamide trifluoroacetate To a solution of the compound (32.1 mg) obtained in Reference Example 25 and potassium carbonate (16.6 mg) in DMF (1 mL) was added N-(2-bromoethyl)phthalimide (15.2 mg), and the mixture was stirred at 40° C. for 16 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by preparative HPLC, and the eluate was concentrated to give the title compound.
MS (ESI+): 672 (M-TFA+H)

Example 429

N-{(3R,4R)-3-(3,4-dichlorophenyl)-1-[3-(1,3-dioxo-1,3-dihydro-2H-isoindol-2-yl)propyl]piperidin-4-yl}-N-methyl-3,5-bis(trifluoromethyl)benzamide trifluoroacetate Using the compound obtained in Reference Example 78 and N-(3-bromopropyl)phthalimide, and by the reaction and purification in the same manner as in Example 428, the title compound was obtained.
MS (ESI+): 686 (M-TFA+H)

Example 430

N-[(3R,4R)-1-benzyl-3-(3,4-dichlorophenyl)piperidin-4-yl]-N-methyl-3,5-bis(trifluoromethyl)benzamide trifluoroacetate Using the compound obtained in Reference Example 78 and benzyl bromide, and by the reaction and purification in the same manner as in Example 428, the title compound was obtained.
MS (ESI+): 589 (M-TFA+H)

Example 431

N-{(3R,4R)-3-(3,4-dichlorophenyl)-1-[(1-methyl-5-oxopyrrolidin-3-yl)carbonyl]piperidin-4-yl}-N-methyl-3,5-bis(trifluoromethyl)benzamide Using the compound obtained in Reference Example 78 and 1-methyl-5-oxopyrrolidine-3-carboxylic acid, and by the reaction and purification in the same manner as in Example 178, the title compound was obtained.
MS (ESI+): 624 (M+H)

Example 432

N-[(3R,4R)-1-[(1-tert-butylazetidin-3-yl)carbonyl]-3-(3,4-dichlorophenyl)piperidin-4-yl]-N-methyl-3,5-bis(trifluoromethyl)benzamide trifluoroacetate Using the compound obtained in Reference Example 78 and 1-tert-butylazetidine-3-carboxylic acid, and by the reaction and purification in the same manner as in Example 178, the title compound was obtained.
MS (ESI+): 638 (M-TFA+H)

Example 433

N-[(3R,4R)-1-[2-(1H-benzimidazol-2-yl)propanoyl]-3-(3,4-dichlorophenyl)piperidin-4-yl]-N-methyl-3,5-bis(trifluoromethyl)benzamide Using the compound obtained in Reference Example 78 and 2-(1H-benzimidazol-2-yl)propanoic acid, and by the reaction and purification in the same manner as in Example 178, the title compound was obtained.
MS (ESI+): 671 (M+H)

Example 434

4-{[(3R,4R)-4-[{[3,5-bis(trifluoromethyl)phenyl]carbonyl}(methyl)amino]-3-(3,4-dichlorophenyl)piperidin-1-yl]carbonyl}piperidine-1-carboxamide Using the compound obtained in Reference Example 78 and 1-carbamoylpiperidine-4-carboxylic acid, and by the reaction and purification in the same manner as in Example 178, the title compound was obtained.

MS (ESI+): 653 (M+H)

Example 435

N-{(3R,4R)-3-(3,4-dichlorophenyl)-1-[2-(4-methylphenyl)propanoyl]piperidin-4-yl}-N-methyl-3,5-bis(trifluoromethyl)benzamide Using the compound obtained in Reference Example 78 and 2-(4-methylphenyl)propanoic acid, and by the reaction and purification in the same manner as in Example 178, the title compound was obtained.
MS (ESI+): 645 (M+H)

Example 436

N-{(3R,4R)-3-(3,4-dichlorophenyl)-1-[(2,2-dimethyl-5-oxotetrahydrofuran-3-yl)carbonyl]piperidin-4-yl}-N-methyl-3,5-bis(trifluoromethyl)benzamide Using the compound obtained in Reference Example 78 and 2,2-dimethyl-5-oxotetrahydrofuran-3-carboxylic acid, and by the reaction and purification in the same manner as in Example 178, the title compound was obtained.
MS (ESI+): 639 (M+H)

Example 437

N-{(3R,4R)-3-(3,4-dichlorophenyl)-1-[(5,5-dimethyl-2,4-dioxo-1,3-oxazolidin-3-yl)acetyl]piperidin-4-yl}-N-methyl-3,5-bis(trifluoromethyl)benzamide Using the compound obtained in Reference Example 78 and (5,5-dimethyl-2,4-dioxo-1,3-oxazolidin-3-yl)acetic acid, and by the reaction and purification in the same manner as in Example 178, the title compound was obtained.
MS (ESI+): 668 (M+H)

Example 438

N-{(3R,4R)-3-(3,4-dichlorophenyl)-1-[(3,3-dimethyl-2-oxoazetidin-1-yl)acetyl]piperidin-4-yl}-N-methyl-3,5-bis(trifluoromethyl)benzamide Using the compound obtained in Reference Example 78 and (3,3-dimethyl-2-oxoazetidin-1-yl)acetic acid, and by the reaction and purification in the same manner as in Example 178, the title compound was obtained.
MS (ESI+): 638 (M+H)

Example 439

N-{(3R,4R)-3-(3,4-dichlorophenyl)-1-[(3-oxo-2-azaspiro[4.5]dec-2-yl)acetyl]piperidin-4-yl}-N-methyl-3,5-bis(trifluoromethyl)benzamide Using the compound obtained in Reference Example 78 and (3-oxo-2-azaspiro[4.5]dec-2-yl)acetic acid, and by the reaction and purification in the same manner as in Example 178, the title compound was obtained.
MS (ESI+): 692 (M+H)

Example 440

N-{(3R,4R)-3-(3,4-dichlorophenyl)-1-[(2,4-dioxo-1,3-oxazolidin-3-yl)acetyl]piperidin-4-yl}-N-methyl-3,5-bis(trifluoromethyl)benzamide Using the compound obtained in Reference Example 78 and (2,4-dioxo-1,3-oxazolidin-3-yl)acetic acid, and by the reaction and purification in the same manner as in Example 178, the title compound was obtained.
MS (ESI+): 640 (M+H)

Example 441

N-[(3R,4R)-1-{[4-(acetylamino)phenyl]sulfonyl}-3-(3,4-dichlorophenyl)piperidin-4-yl]-N-methyl-3,5-bis(trifluoromethyl)benzamide To a solution of the compound obtained in Reference Example 25 (32.1 mg) and triethylamine (16.8 µL) in DMF (1 mL) was added 4-acetamidebenzenesulfonyl chloride (21.0 mg), and the mixture was stirred at 40° C. for 16 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by preparative HPLC, and the eluate was concentrated to give the title compound.
MS (ESI+): 696 (M+H)

Example 442

N-[(3R,4R)-3-(3,4-dichlorophenyl)-1-(N,N-dimethylglycyl)piperidin-4-yl]-N-methyl-3,5-bis(trifluoromethyl)benzamide trifluoroacetate Using the compound obtained in Reference Example 78 and N,N-dimethylglycine, and by the reaction and purification in the same manner as in Example 178, the title compound was obtained.
MS (ESI+): 584 (M-TFA+H)

Example 443

N-{(3R,4R)-3-(3,4-dichlorophenyl)-1-[(methylsulfonyl)acetyl]piperidin-4-yl}-N-methyl-3,5-bis(trifluoromethyl)benzamide Using the compound obtained in Reference Example 78 and methanesulfonylacetic acid, and by the reaction and purification in the same manner as in Example 178, the title compound was obtained.
MS (ESI+): 619 (M+H)

Example 444

N-{(3R,4R)-3-(3,4-dichlorophenyl)-1-[(1,1-dioxidothiomorpholin-4-yl)acetyl]piperidin-4-yl}-N-methyl-3,5-bis(trifluoromethyl)benzamide trifluoroacetate Using the compound obtained in Reference Example 78 and (1,1-dioxidothiomorpholin-4-yl)acetic acid, and by the reaction and purification in the same manner as in Example 178, the title compound was obtained.
MS (ESI+): 674 (M-TFA+H)

Example 445

N-[(3R,4R)-3-(3,4-dichlorophenyl)-1-(3-thiophen-2-ylpropanoyl)piperidin-4-yl]-N-methyl-3,5-bis(trifluoromethyl)benzamide Using the compound obtained in Reference Example 78 and 3-(2-thienyl)propionic acid, and by the reaction and purification in the same manner as in Example 178, the title compound was obtained.
MS (ESI+): 637 (M+H)

Example 446

N-{(3R,4R)-3-(3,4-dichlorophenyl)-1-[3-(2,5-dioxoimidazolidin-4-yl)propanoyl]piperidin-4-yl}-N-methyl-3,5-bis(trifluoromethyl)benzamide Using the compound obtained in Reference Example 78 and 3-(2,5-dioxo-imidazolidin-4-yl)propionic acid, and by the reaction and purification in the same manner as in Example 178, the title compound was obtained.
MS (ESI+): 653 (M+H)

Example 447

N-[(3R,4R)-3-(3,4-dichlorophenyl)-1-(2-hydroxyethyl)piperidin-4-yl]-N-methyl-3,5-bis(trifluoromethyl)benzamide trifluoroacetate Using the compound obtained in Reference Example 78 and 2-bromoethanol, and by the reaction and purification in the same manner as in Example 428, the title compound was obtained.
MS (ESI+): 543 (M-TFA+H)

Example 448

N-[(3R,4R)-3-(3,4-dichlorophenyl)-1-(3-oxocyclopent-1-en-1-yl)piperidin-4-yl]-N-methyl-3,5-bis(trifluoromethyl)benzamide (Step 1)
The compound obtained in Example 95 (214 mg) was dissolved in saturated aqueous sodium hydrogen carbonate solution and ethyl acetate and then the organic layer was separated, washed with brine and dried. The solvent was evaporated under reduced pressure to give a pale yellow oil (200 mg).
(Step 2)
The oil (200 mg) obtained in step 1 was dissolved in toluene (6 mL), p-toluenesulfonic acid monohydrate (7.6 mg) and 1,3-cyclopentanedione (58.9 mg) were added, and the mixture was stirred at 100° C. for 3 days. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (NH Chromatorex) (solvent gradient; 50→100% ethyl acetate/hexane) to give the title compound (193 mg, 83%) as a pale yellow powder.
MS (ESI+): 579 (M+H)

Example 449

N-[(3R,4R)-3-(3,4-dichlorophenyl)-1-(4,4-dimethyl-3-oxocyclohex-1-en-1-yl)piperidin-4-yl]-N-methyl-3,5-bis(trifluoromethyl)benzamide Using the compound obtained in Example 95 and 4,4-dimethyl-1,3-cyclohexanedione, and by the reaction and purification in the same manner as in Example 448, the title compound was obtained.
MS (ESI+): 621 (M+H)

Example 450

N-[(3R,4R)-1-(N-acetylglycyl)-3-(3,4-dichlorophenyl)piperidin-4-yl]-N-methyl-3,5-bis(trifluoromethyl)benzamide Using the compound obtained in Example 95 and N-acetylglycine, and by the reaction and purification in the same manner as in Example 3, the title compound was obtained.
MS (ESI+): 598 (M+H)

Example 451

N-[(3R,4R)-3-(3,4-dichlorophenyl)-1-{[1-(phenylcarbonyl)piperidin-4-yl]carbonyl}piperidin-4-yl]-N-methyl-3,5-bis(trifluoromethyl)benzamide Using the compound obtained in Example 95 and 1-(phenylcarbonyl)piperidine-4-carboxylic acid, and by the reaction and purification in the same manner as in Example 3, the title compound was obtained.
MS (ESI+): 714 (M+H)

Example 452

N-[(3R,4R)-3-(3,4-dichlorophenyl)-1-{[1-(hydroxyacetyl)piperidin-4-yl]carbonyl}piperidin-4-yl]-N-methyl-3,5-bis(trifluoromethyl)benzamide Using the compound obtained in Example 95 and 1-(hydroxyacetyl)piperidine-4-carboxylic acid, and by the reaction and purification in the same manner as in Example 3, the title compound was obtained.
MS (ESI+): 668 (M+H)

Example 453

N-[(3R,4R)-3-(3,4-dichlorophenyl)-1-{[5-oxo-1-(pyridin-2-ylmethyl)pyrrolidin-3-yl]carbonyl}piperidin-4-yl]-N-methyl-3,5-bis(trifluoromethyl)benzamide Using the compound obtained in Example 95 and 5-oxo-1-(pyridin-2-ylmethyl)pyrrolidine-3-carboxylic acid, and by the reaction and purification in the same manner as in Example 3, the title compound was obtained.
MS (ESI+): 701 (M+H)

Example 454

N-[(3R,4R)-1-[N-(1-acetylpiperidin-4-yl)glycyl]-3-(3,4-dichlorophenyl)piperidin-4-yl]-N-methyl-3,5-bis(trifluoromethyl)benzamide monohydrochloride (Step 1)
To a solution of the compound obtained in Example 95 (1.65 g) and triethylamine (140 µL) in acetonitrile (5 mL) was added bromoacetylbromide (48 µL) at 0° C., and the mixture was stirred at 0° C. for 30 min. Then, tert-butyl 4-aminopiperidine-1-carboxylate (0.13 g) and potassium carbonate (0.090 g) were added, and the mixture was stirred at room temperature for 2 hr. The reaction mixture was poured into water, and the resultant product was extracted with ethyl acetate. The organic layer was washed with saturated aqueous ammonium chloride solution and brine and dried, and the solvent was evaporated under reduced pressure. The obtained residue was purified by silica gel column chromatography (NH Chromatorex) (solvent gradient; 25→50% ethyl acetate/hexane) to give tert-butyl 4-({2-[(3R,4R)-4-[{[3,5-bis(trifluoromethyl)phenyl]carbonyl}(methyl)amino]-3-(3,4-dichlorophenyl)piperidin-1-yl]-2-oxoethyl}amino)piperidine-1-carboxylate (0.26 g, 70%) as a white powder.

MS (ESI+): 739 (M+H)

(Step 2)

A solution of the compound (0.23 g) obtained in step 1 in 2N hydrogen chloride/2-propanol (5 mL) was stirred at 50° C. for 2 hr. The reaction mixture was concentrated under reduced pressure to give N-[(3R,4R)-3-(3,4-dichlorophenyl)-1-(N-piperidin-4-ylglycyl)piperidin-4-yl]-N-methyl-3,5-bis(trifluoromethyl)benzamide dihydrochloride (0.14 g, 63%) as a white powder.

MS (ESI+): 639 (M-2HCl+H)

(Step 3)

Using the compound obtained in step 2 and acetic acid, and by the reaction and purification in the same manner as in Example 3, the title compound was obtained.

MS (ESI+): 681 (M−HCl+H)

Example 455

N-{(3S*,4*)-4-(3,4-dichlorophenyl)-1-[(2,6-dioxopiperidin-4-yl)carbonyl]pyrrolidin-3-yl}-N-methyl-3,5-bis(trifluoromethyl)benzamide Using the compound obtained in Example 81 and (2,6-dioxopiperidin-4-yl)carboxylic acid, and by the reaction and purification in the same manner as in Example 3, the title compound was obtained.

MS (ESI+): 624 (M+H)

Example 456

N-[(3S*,4R*)-1-(N-acetylglycyl)-4-(3,4-dichlorophenyl)pyrrolidin-3-yl]-N-methyl-3,5-bis(trifluoromethyl)benzamide Using the compound obtained in Example 81 and acetylglycine, and by the reaction and purification in the same manner as in Example 3, the title compound was obtained.

MS (ESI+): 584 (M+H)

Example 457

N-[(3S*,4R*)-1-(2-amino-2-oxoethyl)-4-(3,4-dichlorophenyl)pyrrolidin-3-yl]-N-methyl-3,5-bis(trifluoromethyl)benzamide monohydrochloride To a solution of the compound (0.21 g) obtained in Example 81 and potassium carbonate (0.14 g) in DMF (4 mL) was added 2-iodoacetamide (0.11 g), and the mixture was stirred overnight at room temperature. The reaction mixture was poured into water, and the resultant product was extracted with ethyl acetate. The organic layer was washed with water and brine and dried, and the solvent was evaporated under reduced pressure. The obtained residue was purified by silica gel column chromatography (NH Chromatorex) (solvent; 50→100% ethyl acetate/hexane). The obtained residue was treated with 1 equivalent of 4N hydrogen chloride/ethyl acetate to give the title compound (0.19 g, 87%) as a white powder.

MS (ESI+): 542 (M−HCl+H)

Example 458

4-chloro-N-[(3R,4R)-3-(3,4-dichlorophenyl)-1-{[1-(hydroxyacetyl)piperidin-4-yl]carbonyl}piperidin-4-yl]-N-methylbenzamide monohydrate To a solution of 4-chloro-N-[(3R,4R)-3-(3,4-dichlorophenyl)piperidin-4-yl]-N-methylbenzamide monohydrochloride (200 mg) obtained in Example 137a, 1-(hydroxyacetyl)piperidine-4-carboxylic acid (129 mg) and triethylamine (127 µL) in acetonitrile (5 mL) were added WSC.HCl (176 mg) and HOBt (140 mg), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was dissolved in methanol (5 mL), potassium carbonate (317 mg) was added, and the mixture was stirred at room temperature for 3 hr. The solution was concentrated and partitioned between ethyl acetate and water. The organic layer was washed with water and dried, and the solvent was evaporated under reduced pressure. The obtained residue was purified by silica gel column chromatography (NH Chromatorex) (solvent gradient; 15→100% ethyl acetate/hexane) to give 4-chloro-N-[(3R,4R)-3-(3,4-dichlorophenyl)-1-{[1-(hydroxyacetyl)piperidin-4-yl]carbonyl}piperidin-4-yl]-N-methylbenzamide (108 mg, 41%) as a white powder.

$^1$H-NMR (CDCl$_3$) δ 1.50-2.08 (9H, m), 2.45-4.27 (12H, m), 4.41-5.04 (1H, m), 6.83-7.23 (3H, m), 7.27-7.54 (4H, m)

$[α]_D^{25}$ +59.1° (c 0.25, MeOH)

The obtained compound (1.146 g) was recrystallized from ethyl acetate and hexane to give the title compound (502 mg, 43%) as a white crystal powder.

MS (ESI+): 566 (M−H$_2$O+H)

Elemental analysis: C$_{27}$H$_{30}$Cl$_3$N$_3$O$_4$.1.0H$_2$O

Found C, 55.58; H, 5.57; N, 7.01

Calcd. C, 55.44; H, 5.51; N, 7.18

Melting point: 128-131° C.

Example 459

(3R,4R)—N-(1-acetylpiperidin-4-yl)-4-{[(4-chlorophenyl)carbonyl](methyl)amino}-3-(3,4-dichlorophenyl)piperidine-1-carboxamide To a solution of 1-acetylpiperidine-4-carboxylic acid (236 mg) and triethylamine (191 µL) in toluene (3 mL) was added DPPA (296 µL), and the mixture was stirred at 100° C. for 1 hr. The reaction solution was cooled to room temperature, and then a mixture of the compound (300 mg) obtained in Example 137a and triethylamine (86 µL) in THF (1 mL)-DMF (1 mL) was added thereto, and the mixture was stirred for 14 hr. The reaction mixture was poured into water, and the resultant product was extracted with ethyl acetate. The organic layer was washed with water and dried, and the sol-

Example 460 tert-butyl 4-{[(3R,4R)-4-{[(4-chlorophenyl)carbonyl](methyl)amino}-3-(3,4-dichlorophenyl)piperidin-1-yl]carbonyl}piperidine-1-carboxylate Using the compound obtained in Example 137a and 1-(tert-butoxycarbonyl)piperidine-4-carboxylic acid, and by the reaction and purification in the same manner as in Example 231, the title compound was obtained.
MS (ESI+): 608 (M+H)

Example 461 tert-butyl 4-{[(3R,4R)-4-{[(4-chlorophenyl)carbonyl](methyl)amino}-3-(3,4-dichlorophenyl)piperidin-1-yl]methyl}piperidine-1-carboxylate To a mixture of 4-chloro-N-[(3R,4R)-3-(3,4-dichlorophenyl)piperidin-4-yl]-N-methylbenzamide monohydrochloride (300 mg) obtained in Example 137a, tert-butyl 4-formylpiperidine-1-carboxylate (735 mg) and triethylamine (105 μL) in acetic acid (0.69 mL)-ethyl acetate (10 mL) was added sodium triacetoxyborohydride (731 mg), and the mixture was stirred at room temperature for 14 hr. The reaction mixture was poured into water, and the resultant product was extracted with ethyl acetate. The organic layer was washed with water and dried, and the solvent was evaporated under reduced pressure. The obtained residue was purified by silica gel column chromatography (solvent gradient; 60→90% ethyl acetate/hexane, and then 0→30% methanol/ethyl acetate) to give the title compound (242 mg, 58%) as a white powder.
MS (ESI+): 594 (M+H)

Example 462

4-chloro-N-[(3R,4R)-3-(3,4-dichlorophenyl)-1-(piperidin-4-ylcarbonyl)piperidin-4-yl]-N-methylbenzamide monohydrochloride Using the compound obtained in Example 460, and by the reaction and purification in the same manner as in Example 2, the title compound was obtained.
MS (ESI+): 508 (M−HCl+H)

Example 463

4-chloro-N-[(3R,4R)-3-(3,4-dichlorophenyl)-1-(piperidin-4-ylmethyl)piperidin-4-yl]-N-methylbenzamide monohydrochloride To a solution of tert-butyl 4-{[(3R,4R)-4-{[(4-chlorophenyl)carbonyl] (methyl)amino}-3-(3,4-dichlorophenyl)piperidin-1-yl]methyl}piperidine-1-carboxylate (200 mg) obtained in Example 461 in ethyl acetate (4 mL) was added 4N hydrogen chloride/ethyl acetate (4 mL), and the mixture was stirred at room temperature for 2 hr. The reaction mixture was concentrated under reduced pressure to give the title compound (150 mg, 85%) as a white powder.
MS (ESI+); 494 (M−HCl+H)

Example 464

N-[(3R,4R)-1-[(1-acetylpiperidin-4-yl)methyl]-3-(3,4-dichlorophenyl)piperidin-4-yl]-4-chloro-N-methylbenzamide 2.45 hydrate To a solution of 4-chloro-N-[(3R,4R)-3-(3,4-dichlorophenyl)-1-(piperidin-4-ylmethyl)piperidin-4-yl]-N-methylbenzamide monohydrochloride (100 mg) obtained in Example 463 and triethylamine (78 μL) in THF (3 mL) was added acetyl chloride (40 μL) at room temperature, and the mixture was stirred for 14 hr. To the reaction mixture was added water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography to give the title compound (12.5 mg, 12%) as a white powder.
MS (ESI+): 536 (M-2.45H$_2$O+H)
$^1$H-NMR (CDCl$_3$) δ 0.88-1.17 (2H, m), 1.42-2.41 (12H, m), 2.43-3.19 (8H, m), 3.43-5.09 (3H, m), 6.46-7.70 (7H, m)
Elemental analysis: C$_{27}$H$_{32}$Cl$_3$N$_3$O$_2$.2.45H$_2$O
Found C, 55.88; H, 6.15; N, 6.94
Calcd. C, 55.81; H, 6.40; N, 7.23
$[\alpha]_D^{25}$ +70.9° (c 0.25, MeOH)

Example 465

(3R,4R)—N-(1-acetylpiperidin-4-yl)-4-{[(4-chlorophenyl)carbonyl](methyl)amino}-3-(3,4-dichlorophenyl)-N-methylpiperidine-1-carboxamide To a solution of the compound obtained in Example 459 (100 mg) in DMF (3 mL) was added sodium tert-butoxide (25.3 mg) at 0° C., and the mixture was stirred for 5 min. Then, methyl iodide (16.5 μL) was added, and the mixture was stirred at room temperature for 14 hr. The reaction mixture was poured into water, and the resultant product was extracted with ethyl acetate. The organic layer was washed with water and dried, and the solvent was evaporated under reduced pressure. The obtained residue was purified by silica gel column chromatography (solvent gradient; 0→12% methanol/ethyl acetate) to give the title compound (55 mg, 54%) as a white powder.
MS (ESI+): 579 (M+H)

Example 466

4-chloro-N-{(3R,4R)-3-(3,4-dichlorophenyl)-1-[(1-formylpiperidin-4-yl)carbonyl]piperidin-4-yl}-N-methylbenzamide Using the compound obtained in Example 137a and 1-formylpiperidine-4-carboxylic acid, and by the reaction and purification in the same manner as in Example 339, the title compound was obtained.
MS (ESI+): 536 (M+H)

Example 467 tert-butyl 4-{[(3R,4R)-4-{[(4-chlorophenyl)carbonyl](methyl)amino}-3-(3,4-dichlorophenyl)piperidin-1-yl]carbonyl}-4-methylpiperidine-1-carboxylate Using the compound obtained in Example 137a and 1-(tert-butoxycarbonyl)-4-methylpiperidine-4-carboxylic acid, and by the reaction in the same manner as in Example 339, the title compound was obtained.
MS (ESI+): 622 (M+H)

Example 468

N-[(3R,4R)-1-acetyl-3-(3,4-dichlorophenyl)piperidin-4-yl]-4-chloro-N-methylbenzamide Using the compound obtained in Example 137a and acetic acid, and by the reaction in the same manner as in Example 339, the title compound was obtained.
MS (ESI+): 439 (M+H)

Example 469 methyl 4-{[(3R,4R)-4-{[(4-chlorophenyl)carbonyl](methyl)amino}-3-(3,4-dichlorophenyl)piperidin-1-yl]carbonyl}piperidine-1-carboxylate Using the compound obtained in Example 137a and 1-(methoxycarbonyl)piperidine-4-carboxylic acid, and by the reaction and purification in the same manner as in Example 339, the title compound was obtained.
MS (ESI+): 566 (M+H)

Example 470 tert-butyl 4-{2-[(3R,4R)-4-{[(4-chlorophenyl)carbonyl](methyl)amino}-3-(3,4-dichlorophenyl)piperidin-1-yl]-2-oxoethyl}piperidine-1-carboxylate Using the compound obtained in Example 137a and [1-(tert-butoxycarbonyl)piperidin-4-yl]acetic acid, and by the reaction and purification in the same manner as in Example 339, the title compound was obtained.
MS (ESI+): 622 (M+H)

Example 471

4-chloro-N-[(3R,4R)-3-(3,4-dichlorophenyl)-1-{[1-(2-oxopropyl)piperidin-4-yl]carbonyl}piperidin-4-yl]-N-methylbenzamide To a solution of the compound obtained in Example 462 (100 mg) and potassium carbonate (75 mg) in acetonitrile (3 mL) was added chloroacetone (38 mg) at room temperature, and the mixture was stirred at 100° C. for 5 hr. The reaction mixture was poured into water, and the resultant product was extracted with ethyl acetate. The organic layer was washed with water and dried, and the solvent was evaporated under reduced pressure. The obtained residue was purified by silica gel column chromatography (solvent gradient; 0→40% methanol/ethyl acetate) to give the title compound (72 mg, 46%) as a white powder.
MS (ESI+): 564 (M+H)

Example 472

4-chloro-N-[(3R,4R)-1-{[1-(cyclopropylcarbonyl)piperidin-4-yl]carbonyl}-3-(3,4-dichlorophenyl)piperidin-4-yl]-N-methylbenzamide Using the compound obtained in Example 462 and cyclopropylcarbonyl chloride, and by the reaction and purification in the same manner as in Example 39, the title compound was obtained.

MS (ESI+): 576 (M+H)
$^1$H-NMR (CDCl$_3$) δ 0.56-1.16 (4H, m), 1.51-2.20 (8H, m), 2.52-5.32 (13H, m), 6.35-7.88 (7H, m)

Example 473

4-chloro-N-[(3R,4R)-3-(3,4-dichlorophenyl)-1-({1-[(1-hydroxycyclopropyl)carbonyl]piperidin-4-yl}carbonyl)piperidin-4-yl]-N-methylbenzamide Using the compound obtained in Example 462 and (1-hydroxycyclopropyl)carboxylic acid, and by the reaction and purification in the same manner as in Example 39, the title compound was obtained.
MS (ESI+): 592 (M+H)

Example 474

4-chloro-N-[(3R,4R)-3-(3,4-dichlorophenyl)-1-{[1-(methylsulfonyl)piperidin-4-yl]carbonyl}piperidin-4-yl]-N-methylbenzamide Using the compound obtained in Example 137a and 1-(methylsulfonyl)piperidine-4-carboxylic acid, and by the reaction and purification in the same manner as in Example 339, the title compound was obtained.
MS (ESI+): 586 (M+H)

Example 475

4-chloro-N-{(3R,4R)-3-(3,4-dichlorophenyl)-1-[(1-methylpiperidin-4-yl)carbonyl]piperidin-4-yl}-N-methylbenzamide monohydrochloride Using the compound obtained in Example 137a and 1-methylpiperidine-4-carboxylic acid, and by the reaction and purification in the same manner as in Reference Example 339 and a treatment with 1 equivalent of 4N hydrogen chloride/ethyl acetate, the title compound was obtained.
MS (ESI+): 522 (M−HCl+H)

Example 476

4-chloro-N-{(3R,4R)-3-(3,4-dichlorophenyl)-1-[(4-methylpiperidin-4-yl)carbonyl]piperidin-4-yl}-N-methylbenzamide monohydrochloride Using the compound obtained in Example 467, and by the reaction and purification in the same manner as in Reference Example 59, the title compound was obtained.
MS (ESI+): 522 (M−HCl+H)

Example 477

N-[(3R,4R)-1-(1H-benzotriazol-5-ylcarbonyl)-3-(3,4-dichlorophenyl)piperidin-4-yl]-4-chloro-N-methylbenzamide Using the compound obtained in Example 137a and 1H-benzotriazol-5-carboxylic acid, and by the reaction and purification in the same manner as in Example 265, the title compound was obtained.
MS (ESI+): 542 (M+H)

Example 478 ethyl 6-[(3R,4R)-4-{[(4-chlorophenyl)carbonyl](methyl)amino}-3-(3,4-dichlorophenyl)piperidin-1-yl]pyridine-3-carboxylate A solution of the compound (0.150 g) obtained in Example 137a, ethyl 6-chloropyridine-3-carboxylate (0.9 g) and potassium carbonate (0.144 g) in DMF (3 mL) was stirred at 100° C. for 10 hr. To the reaction mixture was added water, and the resultant product was extracted with ethyl acetate. The organic layer was washed with brine and dried, and the solvent was evaporated under reduced pressure. The obtained residue was purified by silica gel column chromatography (solvent gradient; 30→100% ethyl acetate/hexane) to give the title compound (0.139 g, 73%) as a white powder.
MS (ESI+): 546 (M+H)

Example 479

4-chloro-N-[(3R,4R)-3-(3,4-dichlorophenyl)-1-(piperidin-4-ylacetyl)piperidin-4-yl]-N-methylbenzamide monohydrochloride Using the compound obtained in Example 470, and by the reaction and purification in the same manner as in Reference Example 59, the title compound was obtained.
MS (ESI+): 522 (M−HCl+H)

Example 480 tert-butyl 3-{[(3R,4R)-4-{[(4-chlorophenyl)carbonyl](methyl)amino}-3-(3,4-dichlorophenyl)piperidin-1-yl]carbonyl}pyrrolidine-1-carboxylate Using the compound obtained in Example 137a and 1-(tert-butoxycarbonyl)pyrrolidine-3-carboxylic acid, and by the reaction and purification in the same manner as in Example 339, the title compound was obtained.
MS (ESI+): 594 (M+H)

Example 481

4-chloro-N-{(3R,4R)-3-(3,4-dichlorophenyl)-1-[(2-methyl-1H-benzimidazol-5-yl)carbonyl]piperidin-4-yl}-N-methylbenzamide Using the compound obtained in Example 137a and 2-methyl-1H-benzimidazol-5-carboxylic acid, and by the reaction and purification in the same manner as in Example 265, the title compound was obtained.
MS (ESI+): 555 (M+H)

Example 482

4-chloro-N-{(3R,4R)-3-(3,4-dichlorophenyl)-1-[(4,4-difluorocyclohexyl)carbonyl]piperidin-4-yl}-N-methylbenzamide Using the compound obtained in Example 137a and 4,4-difluorocyclohexanecarboxylic acid, and by the reaction and purification in the same manner as in Example 265, the title compound was obtained.
MS (ESI+): 543 (M+H)

Example 483 ethyl 2-[(3R,4R)-4-{[(4-chlorophenyl)carbonyl](methyl)amino}-3-(3,4-dichlorophenyl)piperidin-1-yl]pyridine-4-carboxylate Using the compound obtained in Example 137a and ethyl 2-chloropyridine-4-carboxylate, and by the reaction and purification in the same manner as in Example 478, the title compound was obtained.
MS (ESI+): 546 (M+H)

Example 484 tert-butyl 4-{[(3R,4R)-4-{[(4-chlorophenyl)carbonyl](methyl)amino}-3-(3,4-dichlorophenyl)piperidin-1-yl]carbonyl}-3-methylpiperidine-1-carboxylate Using the compound obtained in Example 137a and 1-(tert-butoxycarbonyl)-3-methylpiperidine-4-carboxylic acid, and by the reaction and purification in the same manner as in Example 339, the title compound was obtained.
MS (ESI+): 622 (M+H)

Example 485

N-[(3R,4R)-1-(N-acetyl-N-methyl-β-alanyl)-3-(3,4-dichlorophenyl)piperidin-4-yl]-4-chloro-N-methylbenzamide Using the compound obtained in Example 137a and N-acetyl-N-methyl-β-alanine, and by the reaction and purification in the same manner as in Example 339, the title compound was obtained.
MS (ESI+): 524 (M+H)

Example 486

N-[(3R,4R)-1-[(1-acetyl-4-methylpiperidin-4-yl)carbonyl]-3-(3,4-dichlorophenyl)piperidin-4-yl]-4-chloro-N-methylbenzamide To a solution of the compound (0.10 g) obtained in Example 476 and triethylamine (0.20 g) in THF (1 mL) was added acetic anhydride (0.10 g) at room temperature, and the mixture was stirred at room temperature for 18 hr. The reaction mixture was concentrated under reduced pressure, and the obtained residue was purified by silica gel column chromatography (solvent gradient; 20→30% methanol/ethyl acetate) to give the title compound (39 mg, 39%) as a pale brown powder.
MS (ESI+): 564 (M+H)

Example 487

4-chloro-N-[(3R,4R)-3-(3,4-dichlorophenyl)-1-(pyrrolidin-3-ylcarbonyl)piperidin-4-yl]-N-methylbenzamide monohydrochloride Using the compound obtained in Example 480, and by the reaction and purification in the same manner as in Reference Example 59, the title compound was obtained.
MS (ESI+): 494 (M−HCl+H)

Example 488

N-[(3R,4R)-1-[(1-acetylpiperidin-4-yl)acetyl]-3-(3,4-dichlorophenyl)piperidin-4-yl]-4-chloro-N-methylbenzamide Using the compound obtained in Example 479, and by the reaction and purification in the same manner as in Example 486, the title compound was obtained.
MS (ESI+): 564 (M+H)

Example 489

N-[(3R,4R)-1-[(1-acetylpyrrolidin-3-yl)carbonyl]-3-(3,4-dichlorophenyl)piperidin-4-yl]-4-chloro-N-methylbenzamide Using the compound obtained in Example 487, and by the reaction and purification in the same manner as in Example 486, the title compound was obtained.
MS (ESI+): 536 (M+H)

Example 490

4-chloro-N-{(3R,4R)-3-(3,4-dichlorophenyl)-1-[(3-methylpiperidin-4-yl)carbonyl]piperidin-4-yl}-N-methylbenzamide monohydrochloride Using the compound obtained in Example 484, and by the reaction and purification in the same manner as in Reference Example 59, the title compound was obtained.
MS (ESI+): 522 (M−HCl+H)

Example 491

N-[(3R,4R)-1-[(4-acetylphenyl)carbonyl]-3-(3,4-dichlorophenyl)piperidin-4-yl]-4-chloro-N-methylbenzamide Using the compound obtained in Example 137a and 4-acetylbenzoic acid, and by the reaction and purification in the same manner as in Example 3, the title compound was obtained.
MS (ESI+): 543 (M+H)

Example 492

4-{[(3R,4R)-4-{[(4-chlorophenyl)carbonyl](methyl)amino}-3-(3,4-dichlorophenyl)piperidin-1-yl]carbonyl}piperidine-1-carboxamide Using the compound obtained in Example 137a and 1-carbamoylpiperidine-4-carboxylic acid, and by the reaction and purification in the same manner as in Example 3, the title compound was obtained.
MS (ESI+): 551 (M+H)

Example 493

N-[(3R,4R)-1-[(4-acetylpiperazin-1-yl)carbonyl]-3-(3,4-dichlorophenyl)piperidin-4-yl]-4-chloro-N-methylbenzamide A solution of the compound (170 mg) obtained in Example 137a, 4-nitrophenyl 4-acetylpiperazine-1-carboxylate (170 mg) and potassium carbonate (106 mg) in DMF (3 mL) was stirred overnight at 120° C. The reaction mixture was poured into water, and the resultant product was extracted with ethyl acetate. The organic layer was washed with water and dried, and the solvent was evaporated under reduced pressure. The obtained residue was purified by silica gel column chromatography (solvent gradient; 0→15% methanol/ethyl acetate) to give the title compound (114 mg, 53%) as a white powder.
MS (ESI+): 551 (M+H)

Example 494

N-[(3R,4R)-1-{[4-(acetylamino)-4-phenylpiperidin-1-yl]carbonyl}-3-(3,4-dichlorophenyl)piperidin-4-yl]-4-chloro-N-methylbenzamide Using the compound obtained in Example 137a and 4-nitrophenyl 4-(acetylamino)-4-phenylpiperidine-1-carboxylate, and by the reaction and purification in the same manner as in Example 493, the title compound was obtained.
MS (ESI+): 641 (M+H)

Example 495

4-chloro-N-[(3R,4R)-3-(3,4-dichlorophenyl)-1-{[1-(phenylcarbonyl)piperidin-4-yl]carbonyl}piperidin-4-yl]-N-methylbenzamide Using the compound obtained in Example 137a and 1-(phenylcarbonyl)piperidine-4-carboxylic acid, and by the reaction and purification in the same manner as in Example 3, the title compound was obtained.
MS (ESI+): 612 (M+H)

Example 496 benzyl 4-{[(3R,4R)-4-{[(4-chlorophenyl)carbonyl](methyl)amino}-3-(3,4-dichlorophenyl)piperidin-1-yl]sulfonyl}piperidine-1-carboxylate To a solution of the compound (0.14 g) obtained in Example 137a and triethylamine (0.12 g) in THF (5 mL) was added benzyl 4-(chlorosulfonyl)piperidine-1-carboxylate (0.10 g), and the mixture was stirred at room temperature for 18 hr. The reaction mixture was concentrated under reduced pressure, and the obtained residue was purified by silica gel column chromatography (solvent gradient; 30→50% ethyl acetate/hexane) to give the title compound (90 mg, 43%) as a white powder.
MS (ESI+): 678 (M+H)

Example 497

N-[(3R,4R)-1-[3-(1-acetylpiperidin-4-yl)propanoyl]-3-(3,4-dichlorophenyl)piperidin-4-yl]-4-chloro-N-methylbenzamide Using the compound obtained in Example 137a and 3-(1-acetylpiperidin-4-yl)propanoic acid, and by the reaction and purification in the same manner as in Example 339, the title compound was obtained.
MS (ESI+): 578 (M+H)

Example 498

N-[(3R,4R)-1-[(1-acetyl-3-methylpiperidin-4-yl)carbonyl]-3-(3,4-dichlorophenyl)piperidin-4-yl]-4-chloro-N-methylbenzamide Using the compound obtained in Example 490, and by the reaction and purification in the same manner as in Example 486, the title compound was obtained.
MS (ESI+): 564 (M+H)

Example 499

4-chloro-N-{(3R,4R)-3-(3,4-dichlorophenyl)-1-[5-(trifluoromethyl)pyridin-2-yl]piperidin-4-yl}-N-methylbenzamide Using the compound obtained in Example 137a and 2-chloro-5-(trifluoromethyl)pyridine, and by the reaction and purification in the same manner as in Example 478, the title compound was obtained.
MS (ESI+): 542 (M+H)

Example 500

6-[(3R,4R)-4-{[(4-chlorophenyl)carbonyl](methyl)amino}-3-(3,4-dichlorophenyl)piperidin-1-yl]pyridine-3-carboxylic acid To a solution of the compound (0.500 g) obtained in Example 478 in methanol (6 mL) was added 1N aqueous sodium hydroxide solution (2.74 mL), and the mixture was stirred for 10 hr. The reaction mixture was concentrated, the residue was made neutral with 1N hydrochloric acid, and the resultant product was extracted with ethyl acetate. The organic layer was washed with brine and dried, and the solvent was evaporated under reduced pressure. The obtained residue was purified by silica gel column chromatography (solvent gradient; 30→100% ethyl acetate/hexane) to give the title compound (0.474 g, 100%) as a white powder.
MS (ESI+): 518 (M+H)

Example 501

4-chloro-N-[(3R,4R)-1-[(1-cyclopropylpiperidin-4-yl)carbonyl]-3-(3,4-dichlorophenyl)piperidin-4-yl]-N-methylbenzamide Using the compound obtained in Example 137a and 1-cyclopropylpiperidine-4-carboxylic acid, and by the reaction and purification in the same manner as in Example 339, the title compound was obtained.
MS (ESI+): 548 (M+H)

Example 502a tert-butyl 4-{2-[(3R,4R)-4-{[(4-chlorophenyl)carbonyl](methyl)amino}-3-(3,4-dichlorophenyl)piperidin-1-yl]-2-oxoethylidene}piperidine-1-carboxylate Using the compound obtained in Example 137a and [1-(tert-butoxycarbonyl)piperidin-4-ylidene]acetic acid, and by the reaction and purification in the same manner as in Example 339, the title compound was obtained.
MS (ESI+): 620 (M+H)

Example 502b 4-chloro-N-[(3R,4R)-3-(3,4-dichlorophenyl)-1-(piperidin-4-ylideneacetyl)piperidin-4-yl]-N-methylbenzamide monohydrochloride Using the compound obtained in Example 502a, and by the reaction and purification in the same manner as in Reference Example 59, the title compound was obtained.
MS (ESI+): 520 (M−HCl+H)

Example 503 tert-butyl 3-{[(3R,4R)-4-{[(4-chlorophenyl)carbonyl](methyl)amino}-3-(3,4-dichlorophenyl)piperidin-1-yl]carbonyl}azetidine-1-carboxylate Using the compound obtained in Example 137a and 1-(tert-butoxycarbonyl)azetidine-3-carboxylic acid, and by the reaction and purification in the same manner as in Example 339, the title compound was obtained.
MS (ESI+): 580 (M+H)

Example 504 tert-butyl (3R)-3-{[(3R,4R)-4-{[(4-chlorophenyl)carbonyl](methyl)amino}-3-(3,4-dichlorophenyl)piperidin-1-yl]carbonyl}pyrrolidine-1-carboxylate Using the compound obtained in Example 137a and (3R)-1-(tert-butoxycarbonyl)pyrrolidine-3-carboxylic acid, and by the reaction and purification in the same manner as in Example 339, the title compound was obtained.
MS (ESI+): 594 (M+H)

Example 505

4-chloro-N-{(3R,4R)-3-(3,4-dichlorophenyl)-1-[(4-hydroxy-4-phenylpiperidin-1-yl)carbonyl]piperidin-4-yl}-N-methylbenzamide Using the compound obtained in Example 137a and 4-nitrophenyl 4-hydroxy-4-phenylpiperidine-1-carboxylate, and by the reaction and purification in the same manner as in Example 493, the title compound was obtained.
MS (ESI+): 600 (M+H)

Example 506

N-[(3R,4R)-1-[(4-acetylpiperidin-1-yl)carbonyl]-3-(3,4-dichlorophenyl)piperidin-4-yl]-4-chloro-N-methylbenzamide Using the compound obtained in Example 137a and 4-nitrophenyl 4-acetylpiperidine-1-carboxylate, and by the reaction and purification in the same manner as in Example 493, the title compound was obtained.
MS (ESI+): 550 (M+H)

Example 507

N-[(3R,4R)-1-[(trans-4-acetylcyclohexyl)carbonyl]-3-(3,4-dichlorophenyl)piperidin-4-yl]-4-chloro-N-methylbenzamide Using the compound obtained in Example 137a and trans-4-acetylcyclohexanecarboxylic acid, and by the reaction and purification in the same manner as in Example 3, the title compound was obtained.
MS (ESI+): 549 (M+H)

Example 508

N-[(3R,4R)-1-(azetidin-3-ylcarbonyl)-3-(3,4-dichlorophenyl)piperidin-4-yl]-4-chloro-N-methylbenzamide monohydrochloride Using the compound obtained in Example 503, and by the reaction and purification in the same manner as in Reference Example 59, the title compound was obtained.
MS (ESI+): 480 (M−HCl+H)

Example 509

4-chloro-N-{(3R,4R)-3-(3,4-dichlorophenyl)-1-[(3R)-pyrrolidin-3-ylcarbonyl]piperidin-4-yl}-N-methylbenzamide monohydrochloride Using the compound obtained in Example 504, and by the reaction and purification in the same manner as in Reference Example 59, the title compound was obtained.
MS (ESI+): 494 (M–HCl+H)

Example 510

6-[(3R,4R)-4-{[(4-chlorophenyl)carbonyl](methyl)amino}-3-(3,4-dichlorophenyl)piperidin-1-yl]-N-methylpyridine-3-carboxamide To a solution of the compound (0.150 g) obtained in Example 500 in THF (5 mL) were added oxalyl chloride (38 μL) and DMF (3 μL), and the mixture was stirred at room temperature for 30 min. The reaction mixture was concentrated, and to a solution of the residue in THF (2 mL) was added a solution of methylamine (0.0269 g) in THF (5 mL), and the mixture was stirred for 10 min. To the reaction mixture was added water, and the resultant product was extracted with ethyl acetate. The organic layer was washed with brine and dried, and the solvent was evaporated under reduced pressure to give the title compound (0.039 g, 25%) as a white powder.
MS (ESI+): 531 (M+H)

Example 511

6-[(3R,4R)-4-{[(4-chlorophenyl)carbonyl](methyl)amino}-3-(3,4-dichlorophenyl)piperidin-1-yl]pyridine-3-carboxamide Using the compound obtained in Example 500 and aqueous ammonia, and by the reaction and purification in the same manner as in Example 510, the title compound was obtained.
MS (ESI+): 517 (M+H)

Example 512

N-[(3R,4R)-1-[(1-acetylpiperidin-4-ylidene)acetyl]-3-(3,4-dichlorophenyl)piperidin-4-yl]-4-chloro-N-methylbenzamide Using the compound obtained in Example 502b, and by the reaction and purification in the same manner as in Example 486, the title compound was obtained.
MS (ESI+): 562 (M+H)

Example 513

N-[(3R,4R)-1-[(1-acetylazetidin-3-yl)carbonyl]-3-(3,4-dichlorophenyl)piperidin-4-yl]-4-chloro-N-methylbenzamide Using the compound obtained in Example 508, and by the reaction and purification in the same manner as in Example 486, the title compound was obtained.
MS (ESI+): 522 (M+H)

Example 514

N-[(3R,4R)-1-{[(3R)-1-acetylpyrrolidin-3-yl]carbonyl}-3-(3,4-dichlorophenyl)piperidin-4-yl]-4-chloro-N-methylbenzamide Using the compound obtained in Example 509, and by the reaction and purification in the same manner as in Example 486, the title compound was obtained.
MS (ESI+): 536 (M+H)

Example 515

N-[(3R,4R)-1-(N-acetyl-N-methylglycyl)-3-(3,4-dichlorophenyl)piperidin-4-yl]-4-chloro-N-methylbenzamide Using the compound obtained in Example 137a and N-acetyl-N-methylglycine, and by the reaction and purification in the same manner as in Example 339, the title compound was obtained.
MS (ESI+): 510 (M+H)

Example 516

(3R,4R)-4-{[(4-chlorophenyl)carbonyl](methyl)amino}-3-(3,4-dichlorophenyl)-N-(6-fluoropyridin-3-yl)piperidine-1-carboxamide A solution of 6-fluoropyridin-3-amine (0.11 g), N,N'-carbonyldiimidazole (0.32 g) and triethylamine (0.70 g) in THF (5 mL) was stirred at room temperature for 5 hr, the compound (0.17 g) obtained in Example 137a was added, and the mixture was stirred at room temperature for 18 hr. The reaction mixture was poured into water, and the resultant product was extracted with ethyl acetate. The organic layer was washed with brine and dried, and the solvent was evaporated under reduced pressure. The obtained residue was purified by silica gel column chromatography (solvent gradient; 10→33% ethyl acetate/hexane) and recrystallized (ethyl acetate/hexane) to give the title compound (73 mg, 34%) as a white crystal powder.
MS (ESI+): 535 (M+H)
Melting point: 156-158° C.

Example 517 tert-butyl 4-{[(3R,4R)-4-{[(4-chlorophenyl)carbonyl](methyl)amino}-3-(3,4-dichlorophenyl)piperidin-1-yl]carbonyl}-3,6-dihydropyridine-1(2H)-carboxylate Using the compound obtained in Example 137a and 1-(tert-butoxycarbonyl)-1,2,3,6-tetrahydropyridine-4-carboxylic acid, and by the reaction and purification in the same manner as in Example 3, the title compound was obtained.
MS (ESI+): 506 (M-Boc+2H)

Example 518 trans-4-{[(3R,4R)-4-{[(4-chlorophenyl)carbonyl](methyl)amino}-3-(3,4-dichlorophenyl)piperidin-1-yl]carbonyl}cyclohexyl acetate Using the compound obtained in Example 137a and trans-4-(acetyloxy)cyclohexanecarboxylic acid, and by the reaction and purification in the same manner as in Example 231, the title compound was obtained.
MS (ESI+): 565 (M+H)

Example 519

4-chloro-N-[(3R,4R)-3-(3,4-dichlorophenyl)-1-(1,2,3,6-tetrahydropyridin-4-ylcarbonyl)piperidin-4-yl]-N-methylbenzamide monohydrochloride Using the compound obtained in Example 517, and by the reaction and purification in the same manner as in Example 2, the title compound was obtained.
MS (ESI+): 506 (M−HCl+H)

Example 520

N-[(3R,4R)-1-[(1-acetyl-1,2,3,6-tetrahydropyridin-4-yl)carbonyl]-3-(3,4-dichlorophenyl)piperidin-4-yl]-4-chloro-N-methylbenzamide Using the compound obtained in Example 519, and by the reaction and purification in the same manner as in Example 91, the title compound was obtained.
MS (ESI+): 548 (M+H)

Example 521

N-[(3R,4R)-1-({1-[amino(oxo)acetyl]piperidin-4-yl}carbonyl)-3-(3,4-dichlorophenyl)piperidin-4-yl]-4-chloro-N-methylbenzamide Using the compound obtained in Example 462 and amino(oxo)acetic acid, and by the reaction and purification in the same manner as in Example 3, the title compound was obtained.
MS (ESI+): 579 (M+H)

Example 522

4-chloro-N-[(3R,4R)-1-{[1-(cyanoacetyl)piperidin-4-yl]carbonyl}-3-(3,4-dichlorophenyl)piperidin-4-yl]-N-methylbenzamide Using the compound obtained in Example 462 and cyanoacetic acid, and by the reaction and purification in the same manner as in Example 3, the title compound was obtained.
MS (ESI+): 575 (M+H)

Example 523

4-chloro-N-{(3R,4R)-3-(3,4-dichlorophenyl)-1-[(2,6-dioxopiperidin-4-yl)carbonyl]piperidin-4-yl}-N-methylbenzamide Using the compound obtained in Example 137a and 2,6-dioxopiperidine-4-carboxylic acid, and by the reaction and purification in the same manner as in Example 3, the title compound was obtained.
MS (ESI+): 536 (M+H)

Example 524

4-chloro-N-[(3R,4R)-3-(3,4-dichlorophenyl)-1-pyrimidin-2-ylpiperidin-4-yl]-N-methylbenzamide Using the compound obtained in Example 137a and 2-chloropyrimidine, and by the reaction and purification in the same manner as in Example 478, the title compound was obtained.
MS (ESI+): 475 (M+H)

Example 525

N-[(3R,4R)-1-(1,3-benzothiazole-2-yl)-3-(3,4-dichlorophenyl)piperidin-4-yl]-4-chloro-N-methylbenzamide Using the compound obtained in Example 137a and 2-chloro-1,3-benzothiazole, and by the reaction and purification in the same manner as in Example 478, the title compound was obtained.
MS (ESI+): 530 (M+H)

Example 526

4-chloro-N-[(3R,4R)-1-(5-cyanopyridin-2-yl)-3-(3,4-dichlorophenyl)piperidin-4-yl]-N-methylbenzamide Using the compound obtained in Example 137a and 6-chloropyridine-3-carbonitrile, and by the reaction and purification in the same manner as in Example 478, the title compound was obtained.
MS (ESI+): 499 (M+H)

Example 527

4-chloro-N-[(3R,4R)-1-(5-chloropyridin-2-yl)-3-(3,4-dichlorophenyl)piperidin-4-yl]-N-methylbenzamide Using the compound obtained in Example 137a and 2,5-dichloropyridine, and by the reaction and purification in the same manner as in Example 478, the title compound was obtained.
MS (ESI+): 508 (M+H)

Example 528

4-chloro-N-[(3R,4R)-3-(3,4-dichlorophenyl)-1-{[1-(fluoroacetyl)piperidin-4-yl]carbonyl}piperidin-4-yl]-N-methylbenzamide Using the compound obtained in Example 462 and fluoroacetic acid, and by the reaction and purification in the same manner as in Example 3, the title compound was obtained.
MS (ESI+): 568 (M+H)

Example 529

(3R,4R)—N-(4-acetylphenyl)-4-{[(4-chlorophenyl)carbonyl](methyl)amino}-3-(3,4-dichlorophenyl)piperidine-1-carboxamide A solution of the compound (174 mg) obtained in Example 137a, (4-acetyl)phenyl isocyanate (64 mg) and triethylamine (0.112 mL) in DMF (2 mL) was stirred at room temperature for 1 hr. To the reaction mixture was added 1N hydrochloric acid, and the mixture was extracted with ethyl acetate. The organic layer was washed with saturated aqueous sodium hydrogen carbonate solution and brine and dried, and the solvent was evaporated under reduced pressure. The obtained residue was washed with a mixture of diethyl ether and hexane to give the title compound (191 mg, 85%) as a white powder.
MS (ESI+): 558 (M+H)

Example 530 tert-butyl [(1R,2S)-2-{[(3R,4R)-4-{[(4-chlorophenyl)carbonyl](methyl)amino}-3-(3,4-dichlorophenyl)piperidin-1-yl]carbonyl}cyclohexyl]carbamate Using the compound obtained in Example 137a and (1S,2R)-2-[(tert-butoxycarbonyl)amino]cyclohexanecarboxylic acid, and by the reaction and purification in the same manner as in Example 3, the title compound was obtained.
MS (ESI+): 522 (M-Boc+2H)

Example 531

N-[(3R,4R)-1-{[(1S,2R)-2-aminocyclohexyl]carbonyl}-3-(3,4-dichlorophenyl)piperidin-4-yl]-4-chloro-N-methylbenzamide monohydrochloride Using the compound obtained in Example 530, and by the reaction and purification in the same manner as in Example 2, the title compound was obtained.
MS (ESI+): 522 (M−HCl+H)

Example 532 tert-butyl 3-{[(3R,4R)-4-{[(4-chlorophenyl)carbonyl](methyl)amino}-3-(3,4-dichlorophenyl)piperidin-1-yl]carbonyl}piperidine-1-carboxylate Using the compound obtained in Example 137a and 1-(tert-butoxycarbonyl)piperidine-2-carboxylic acid, and by the reaction and purification in the same manner as in Example 3, the title compound was obtained.
MS (ESI+): 508 (M-Boc+2H)

Example 533

4-chloro-N-[(3R,4R)-3-(3,4-dichlorophenyl)-1-({(1S,2R)-2-[(phenylcarbonyl)amino]cyclohexyl}carbonyl)piperidin-4-yl]-N-methylbenzamide Using the compound obtained in Example 531 and benzoyl chloride, and by the reaction and purification in the same manner as in Example 39, the title compound was obtained.
MS (ESI+): 626 (M+H)

Example 534 tert-butyl (1-{[(3R,4R)-4-{[(4-chlorophenyl)carbonyl](methyl)amino}-3-(3,4-dichlorophenyl)piperidin-1-yl]carbonyl}cyclopropyl)carbamate Using the compound obtained in Example 137a and 1-[(tert-butoxycarbonyl)amino]cyclopropanecarboxylic acid, and by the reaction and purification in the same manner as in Example 3, the title compound was obtained.
MS (ESI+): 480 (M-Boc+2H)

Example 535

N-[(3R,4R)-1-[(1-carbamoylcyclopropyl)carbonyl]-3-(3,4-dichlorophenyl)piperidin-4-yl]-4-chloro-N-methylbenzamide Using the compound obtained in Example 137a and 1-carbamoylcyclopropanecarboxylic acid, and by the reaction and purification in the same manner as in Example 3, the title compound was obtained.
MS (ESI+): 508 (M+H)

Example 536

N-[(3R,4R)-1-{[(1S,2R)-2-(acetylamino)cyclohexyl]carbonyl}-3-(3,4-dichlorophenyl)piperidin-4-yl]-4-chloro-N-methylbenzamide Using the compound obtained in Example 531, and by the reaction and purification in the same manner as in Example 39, the title compound was obtained.
MS (ESI+): 397 (M-$C_9H_{14}NO_2$+2H)
(The above-mentioned $C_9H_{14}NO_2$ means a [2-(acetylamino)cyclohexyl]carbonyl group).
$^1$H-NMR (CDCl$_3$) δ 1.01-2.23 (15H, m), 2.41-3.43 (7H, m), 3.65-5.31 (3H, m), 5.89-7.84 (7H, m)

Example 537

N-[(3R,4R)-1-[(1-aminocyclopropyl)carbonyl]-3-(3,4-dichlorophenyl)piperidin-4-yl]-4-chloro-N-methylbenzamide monohydrochloride Using the compound obtained in Example 534, and by the reaction and purification in the same manner as in Example 2, the title compound was obtained.
MS (ESI+): 397 (M−HCl—$C_4H_6NO$+2H)
(The above-mentioned $C_4H_6NO$ means a (1-aminocyclopropyl)carbonyl group).
$^1$H-NMR (CDCl$_3$) δ 0.99-1.88 (10H, m), 2.41-3.05 (2H, m), 3.56-5.24 (3H, m), 6.64-7.73 (7H, m), 9.11 (2H, s)

Example 538

4-chloro-N-{(3R,4R)-3-(3,4-dichlorophenyl)-1-[(6-oxopiperidin-2-yl)carbonyl]piperidin-4-yl}-N-methylbenzamide Using the compound obtained in Example 137a and 6-oxopiperidine-2-carboxylic acid, and by the reaction and purification in the same manner as in Example 3, the title compound was obtained.
MS (ESI+): 522 (M+H)

Example 539

N-[(3R,4R)-1-[(1-acetylpiperidin-3-yl)carbonyl]-3-(3,4-dichlorophenyl)piperidin-4-yl]-4-chloro-N-methylbenzamide Using the compound obtained in Example 137a and 1-acetylpiperidine-3-carboxylic acid, and by the reaction and purification in the same manner as in Example 3, the title compound was obtained.
MS (ESI+): 550 (M+H)

Example 540

N-[(3R,4R)-1-{[1-(acetylamino)cyclopropyl]carbonyl}-3-(3,4-dichlorophenyl)piperidin-4-yl]-4-chloro-N-methylbenzamide Using the compound obtained in Example 537, and by the reaction and purification in the same manner as in Example 39, the title compound was obtained.
$^1$H-NMR (CDCl$_3$) δ 1.51-3.00 (15H, m), 3.06-4.22 (2H, m), 4.64-5.33 (2H, m), 6.58-7.60 (7H, m)

Example 541

4-chloro-N-[(3R,4R)-3-(3,4-dichlorophenyl)-1-({1-[(phenylcarbonyl)amino]cyclopropyl}carbonyl)piperidin-4-yl]-N-methylbenzamide Using the compound obtained in Example 537 and benzoyl chloride, and by the reaction and purification in the same manner as in Example 39, the title compound was obtained.
$^1$H-NMR (CDCl$_3$) δ 1.47-2.20 (4H, m), 2.56-5.66 (12H, m), 6.66-7.99 (12H, m)

Example 542

4-chloro-N-[(3R,4R)-3-(3,4-dichlorophenyl)-1-(piperidin-3-ylcarbonyl)piperidin-4-yl]-N-methylbenzamide monohydrochloride Using the compound obtained in Example 532, and by the reaction and purification in the same manner as in Example 2, the title compound was obtained.
$^1$H-NMR (CDCl$_3$) δ 1.66-2.28 (6H, m), 2.41-5.41 (14H, m), 6.69-7.64 (7H, m), 8.64-10.88 (2H, m)

Example 543 tert-butyl 2-{[(3R,4R)-4-{[(4-chlorophenyl)carbonyl](methyl)amino}-3-(3,4-dichlorophenyl)piperidin-1-yl]carbonyl}piperidine-1-carboxylate Using the compound obtained in Example 137a and 1-(tert-butoxycarbonyl)piperidine-2-carboxylic acid, and by the reaction and purification in the same manner as in Example 3, the title compound was obtained.
MS (ESI+): 508 (M-Boc+2H)

Example 544

4-chloro-N-[(3R,4R)-3-(3,4-dichlorophenyl)-1-{[1-(phenylcarbonyl)piperidin-3-yl]carbonyl}piperidin-4-yl]-N-methylbenzamide Using the compound obtained in Example 542 and benzoyl chloride, and by the reaction and purification in the same manner as in Example 39, the title compound was obtained.
MS (ESI+): 612 (M+H)

Example 545

4-chloro-N-[(3R,4R)-3-(3,4-dichlorophenyl)-1-(piperidin-2-ylcarbonyl)piperidin-4-yl]-N-methylbenzamide monohydrochloride Using the compound obtained in Example 543, and by the reaction and purification in the same manner as in Example 2, the title compound was obtained.
$^1$H-NMR (CDCl$_3$) δ 1.50-2.26 (7H, m), 2.38-5.39 (13H, m), 6.68-7.72 (7H, m), 10.23 (2H, m)

Example 546

N-[(3R,4R)-1-[(1-acetylpiperidin-2-yl)carbonyl]-3-(3,4-dichlorophenyl)piperidin-4-yl]-4-chloro-N-methylbenzamide Using the compound obtained in Example 545, and by the reaction and purification in the same manner as in Example 39, the title compound was obtained.
$^1$H-NMR (CDCl$_3$) δ1.15-2.26 (14H, m), 2.39-5.86 (9H, m), 6.60-7.79 (7H, m)

Example 547

4-chloro-N-[(3R,4R)-3-(3,4-dichlorophenyl)-1-{[1-(phenylcarbonyl)piperidin-2-yl]carbonyl}piperidin-4-yl]-N-methylbenzamide Using the compound obtained in Example 545 and benzoyl chloride, and by the reaction and purification in the same manner as in Example 39, the title compound was obtained.
$^1$H-NMR (CDCl$_3$) δ 1.15-2.15 (12H, m), 2.44-6.01 (8H, m), 6.52-7.86 (12H, m)

Example 548

4-chloro-N-[(3R,4R)-3-(3,4-dichlorophenyl)-1-nitrosopiperidin-4-yl]-N-methylbenzamide To a mixture of the compound (400 mg) obtained in Example 137a in acetic acid (2.5 mL) and water (0.5 mL) was added NaNO$_2$ (76 mg), and the mixture was stirred at room temperature for 2 hr. The reaction mixture was poured into water, and the resultant product was extracted with ethyl acetate. The organic layer was washed with water and brine and dried, and the solvent was evaporated under reduced pressure. The obtained residue was purified by silica gel column chromatography (solvent gradient; 30→60% ethyl acetate/hexane) to give the title compound (310 mg, 79%) as a white powder.
$^1$H-NMR (CDCl$_3$) δ 1.21-1.36 (1H, m), 1.54-2.26 (3H, m), 2.43-3.26 (4H, m), 3.67-4.21 (1H, m), 4.90-5.91 (2H, m), 6.81-7.61 (7H, m)

Example 549

N-[(3R,4R)-1-amino-3-(3,4-dichlorophenyl)piperidin-4-yl]-4-chloro-N-methylbenzamide monohydrochloride To a solution of the compound obtained in Example 548 (300 mg) in acetic acid (3 mL) was added Zn powder (229 mg), and the mixture was stirred overnight at room temperature. The reaction mixture was poured into water, and the resultant product was extracted with ethyl acetate. The organic layer was washed with water and dried, and the solvent was evaporated under reduced pressure. The obtained residue was treated with 1 equivalent of 4N hydrogen chloride/ethyl acetate to give the title compound (243 mg, 76%) as a white powder.
MS (ESI+): 412 (M−HCl+H)

Example 550

1-acetyl-N-[(3R,4R)-4-{[(4-chlorophenyl)carbonyl](methyl)amino}-3-(3,4-dichlorophenyl)piperidin-1-yl]piperidine-4-carboxamide Using the compound obtained in Example 549, and by the reaction and purification in the same manner as in Example 3, the title compound was obtained.
MS (ESI+): 565 (M+H)

Example 551

4-chloro-N-[(3R,4R)-3-(3,4-dichlorophenyl)-1-{[1-(trifluoroacetyl)piperidin-4-yl]carbonyl}piperidin-4-yl]-N-methylbenzamide To a mixture of the compound obtained in Example 462 (170 mg) in pyridine (75 μL) and THF (3 mL) was added trifluoroacetic anhydride (65 μL), and the mixture was stirred at room temperature for 14 hr. The reaction mixture was poured into water, and the resultant product was extracted with ethyl acetate. The organic layer was washed with water and dried, and the solvent was evaporated under reduced pressure. The obtained residue was purified by silica gel column chromatography (solvent gradient; 65→90% ethyl acetate/hexane) to give the title compound (90 mg, 47%) as a white powder.
$^1$H-NMR (CDCl$_3$) δ 1.17-2.20 (9H, m), 2.45-3.60 (7H, m), 3.74-5.43 (4H, m), 6.65-7.78 (7H, m)

Example 552

4-chloro-N-[(3R,4R)-3-(3,4-dichlorophenyl)-1-(methylsulfonyl)piperidin-4-yl]-N-methylbenzamide Using the compound obtained in Example 137a and methylsulfonyl chloride, and by the reaction and purification in the same manner as in Example 39, the title compound was obtained.
MS (ESI+): 475 (M+H)

Example 553

4-chloro-N-{(3R,4R)-3-(3,4-dichlorophenyl)-1-[(1-oxidepyridin-2-yl)carbonyl]piperidin-4-yl}-N-methylbenzamide Using the compound obtained in Example 137a and pyridine-2-carboxylic acid 1-oxide, and by the reaction and purification in the same manner as in Example 3, the title compound was obtained.
MS (ESI+): 518 (M+H)

Example 554

4-chloro-N-[(3R,4R)-3-(3,4-dichlorophenyl)-1-{[1-(2-hydroxypropanoyl)piperidin-4-yl]carbonyl}piperidin-4-yl]-N-methylbenzamide Using the compound obtained in Example 462 and 2-hydroxypropanoic acid, and by the reaction and purification in the same manner as in Example 265, the title compound was obtained.
MS (ESI+): 580 (M+H)

Example 555

4-chloro-N-[(3R,4R)-3-(3,4-dichlorophenyl)-1-{[1-(2-hydroxy-2-methylpropanoyl)piperidin-4-yl]carbonyl}piperidin-4-yl]-N-methylbenzamide Using the compound obtained in Example 462 and 2-hydroxy-2-methylpropanoic acid, and by the reaction and purification in the same manner as in Example 265, the title compound was obtained.
MS (ESI+): 594 (M+H)

Example 556

4-chloro-N-[(3R,4R)-3-(3,4-dichlorophenyl)-1-{[1-(2-hydroxy-3-methylbutanoyl)piperidin-4-yl]carbonyl}piperidin-4-yl]-N-methylbenzamide Using the compound obtained in Example 462 and 2-hydroxy-3-methylbutanoic acid, and by the reaction and purification in the same manner as in Example 265, the title compound was obtained.
MS (ESI+): 608 (M+H)

Example 557 ethyl 4-[(3R,4R)-4-{[(4-chlorophenyl)carbonyl](methyl)amino}-3-(3,4-dichlorophenyl)piperidin-1-yl]benzoate A solution of the compound (0.150 g) obtained in Example 137a, ethyl 4-iodobenzoate (0.069 mL), tris(dibenzylideneacetone)dipalladium (0.0691 g), 9,9-dimethyl-4,5-bis(diphenylphosphino)xanthene (0.0175 g) and sodium tert-butoxide (0.091 g) in toluene (3 mL) was stirred at room temperature for 2 days. To the reaction mixture was added water, and the resultant product was extracted with ethyl acetate. The organic layer was washed with brine and dried, and the solvent was evaporated under reduced pressure. The obtained residue was purified by silica gel column chromatography (solvent gradient; 30→70% ethyl acetate/hexane) to give the title compound (0.026 g, 13%) as a white powder.
MS (ESI+): 545 (M+H)

Example 558

4-chloro-N-[(3R,4R)-1-(3-cyanopyridin-2-yl)-3-(3,4-dichlorophenyl)piperidin-4-yl]-N-methylbenzamide Using the compound obtained in Example 137a and 2-chloropyridine-3-carbonitrile, and by the reaction and purification in the same manner as in Example 478, the title compound was obtained.
MS (ESI+): 499 (M+H)

Example 559

4-chloro-N-[(3R,4R)-1-(4-cyanopyridin-2-yl)-3-(3,4-dichlorophenyl)piperidin-4-yl]-N-methylbenzamide Using the compound obtained in Example 137a and 2-chloropyridine-4-carbonitrile, and by the reaction and purification in the same manner as in Example 478, the title compound was obtained.
MS (ESI+): 499 (M+H)

Example 560

4-chloro-N-[(3R,4R)-1-(6-cyanopyridin-2-yl)-3-(3,4-dichlorophenyl)piperidin-4-yl]-N-methylbenzamide Using the compound obtained in Example 137a and 6-chloropyridine-2-carbonitrile, and by the reaction and purification in the same manner as in Example 478, the title compound was obtained.
MS (ESI+): 499 (M+H)

Example 561 methyl 2-[(3R,4R)-4-{[(4-chlorophenyl)carbonyl](methyl)amino}-3-(3,4-dichlorophenyl)piperidin-1-yl]-1,3-thiazole-5-carboxylate Using the compound obtained in Example 137a and methyl 2-chloro-1,3-thiazole-5-carboxylate, and by the reaction and purification in the same manner as in Example 478, the title compound was obtained.
MS (ESI+): 538 (M+H)

Example 562 tert-butyl 3-{[(3R,4R)-4-{[(4-chlorophenyl)carbonyl](methyl)amino}-3-(3,4-dichlorophenyl)piperidin-1-yl]carbonyl}morpholine-4-carboxylate Using the compound obtained in Example 137a and 4-(tert-butoxycarbonyl)morpholine-3-carboxylic acid, and by the reaction and purification in the same manner as in Example 3, the title compound was obtained.
MS (ESI+): 510 (M-Boc+2H)

Example 563

4-chloro-N-{(3R,4R)-3-(3,4-dichlorophenyl)-1-[(2-nitrophenyl)carbonyl]piperidin-4-yl}-N-methylbenzamide Using the compound obtained in Example 137a and 2-nitrobenzoic acid, and by the reaction and purification in the same manner as in Example 3, the title compound was obtained.
MS (ESI+): 546 (M+H)

Example 564

N-[(3R,4R)-1-[(3-aminopyrazin-2-yl)carbonyl]-3-(3,4-dichlorophenyl)piperidin-4-yl]-4-chloro-N-methylbenzamide Using the compound obtained in Example 137a and 3-aminopyrazine-2-carboxylic acid, and by the reaction and purification in the same manner as in Example 3, the title compound was obtained.
MS (ESI+): 518 (M+H)

Example 565

4-chloro-N-[(3R,4R)-3-(3,4-dichlorophenyl)-1-{[2-nitro-4-(trifluoromethyl)phenyl]carbonyl}piperidin-4-yl]-N-methylbenzamide Using the compound obtained in Example 137a and 4-fluoro-2-nitrobenzoic acid, and by the reaction and purification in the same manner as in Example 3, the title compound was obtained.
MS (ESI+): 614 (M+H)

Example 566 tert-butyl (2R)-2-{[(3R,4R)-4-{[(4-chlorophenyl)carbonyl](methyl)amino}-3-(3,4-dichlorophenyl)piperidin-1-yl]carbonyl}piperidine-1-carboxylate Using the compound obtained in Example 137a and (2R)-1-(tert-butoxycarbonyl)piperidine-2-carboxylic acid, and by the reaction and purification in the same manner as in Example 3, the title compound was obtained.
MS (ESI+): 508 (M-Boc+2H)

Example 567 tert-butyl (2S)-2-{[(3R,4R)-4-{[(4-chlorophenyl)carbonyl](methyl)amino}-3-(3,4-dichlorophenyl)piperidin-1-yl]carbonyl}piperidine-1-carboxylate Using the compound obtained in Example 137a and (2S)-1-(tert-butoxycarbonyl)piperidine-2-carboxylic acid, and by the reaction and purification in the same manner as in Example 3, the title compound was obtained.
MS (ESI+): 508 (M-Boc+2H)

Example 568 tert-butyl 2-(2-{[(3R,4R)-4-{[(4-chlorophenyl)carbonyl](methyl)amino}-3-(3,4-dichlorophenyl)piperidin-1-yl]carbonyl}phenyl)hydrazinecarboxylate Using the compound obtained in Example 137a and 2-[2-(tert-butoxycarbonyl)hydrazino]benzoic acid, and by the reaction and purification in the same manner as in Example 3, the title compound was obtained.
MS (ESI+): 531 (M-Boc+2H)

Example 569

4-chloro-N-[(3R,4R)-3-(3,4-dichlorophenyl)-1-(morpholin-3-ylcarbonyl)piperidin-4-yl]-N-methylbenzamide monohydrochloride Using the compound obtained in Example 562, and by the reaction and purification in the same manner as in Example 2, the title compound was obtained.
MS (ESI+): 510 (M−HCl+H)

Example 570

4-chloro-N-{(3R,4R)-3-(3,4-dichlorophenyl)-1-[(2R)-piperidin-2-ylcarbonyl]piperidin-4-yl}-N-methylbenzamide monohydrochloride Using the compound obtained in Example 566, and by the reaction and purification in the same manner as in Example 2, the title compound was obtained.
MS (ESI+): 508 (M−HCl+H)

Example 571

4-chloro-N-{(3R,4R)-3-(3,4-dichlorophenyl)-1-[(2S)-piperidin-2-ylcarbonyl]piperidin-4-yl}-N-methylbenzamide monohydrochloride Using the compound obtained in Example 567, and by the reaction and purification in the same manner as in Example 2, the title compound was obtained.
MS (ESI+): 508 (M−HCl+H)

Example 572 tert-butyl [(3S,4S)-4-{[(3R,4R)-4-{[(4-chlorophenyl)carbonyl](methyl)amino}-3-(3,4-dichlorophenyl)piperidin-1-yl]carbonyl}tetrahydro-2H-pyran-3-yl]carbamate Using the compound obtained in Example 137a and (3S,4S)-3-[(tert-butoxycarbonyl)amino]tetrahydro-2H-pyran-4-carboxylic acid, and by the reaction and purification in the same manner as in Example 3, the title compound was obtained.
MS (ESI+): 524 (M-Boc+2H)

Example 573

N-[(3R,4R)-1-[(2-aminophenyl)carbonyl]-3-(3,4-dichlorophenyl)piperidin-4-yl]-4-chloro-N-methyl-benzamide Using the compound obtained in Example 137a and 2-aminobenzoic acid, and by the reaction and purification in the same manner as in Example 3, the title compound was obtained.
MS (ESI+): 516 (M+H)

Example 574

4-chloro-N-[(3R,4R)-3-(3,4-dichlorophenyl)-1-{[(2R)-1-methylpiperidin-2-yl]carbonyl}piperidin-4-yl]-N-methylbenzamide To a solution of the compound obtained in Example 570 (170 mg) and triethylamine (90 μL) in THF (3 mL) were added 35% formalin aqueous solution (40 mg) and NaBH(OAc)$_3$ (103 mg), and the mixture was stirred at room temperature for 14 hr. The reaction mixture was poured into water, and the resultant product was extracted with ethyl acetate. The organic layer was washed with water and dried, and the solvent was evaporated under reduced pressure. The obtained residue was purified by silica gel column chromatography (solvent gradient; 15→45% methanol/ethyl acetate) to give the title compound (86 mg, 53%) as a white powder.
MS (ESI+): 522 (M+H)

Example 575

N-[(3R,4R)-1-{[(3S,4S)-3-aminotetrahydro-2H-pyran-4-yl]carbonyl}-3-(3,4-dichlorophenyl)piperidin-4-yl]-4-chloro-N-methylbenzamide monohydrochloride Using the compound obtained in Example 572, and by the reaction and purification in the same manner as in Example 2, the title compound was obtained.
MS (ESI+): 524 (M−HCl+H)

Example 576

4-chloro-N-[(3R,4R)-3-(3,4-dichlorophenyl)-1-{[4-(phenylcarbonyl)morpholin-3-yl]carbonyl}piperidin-4-yl]-N-methylbenzamide Using the compound obtained in Example 569 and benzoyl chloride, and by the reaction and purification in the same manner as in Example 39, the title compound was obtained.
MS (ESI+): 614 (M+H)

Example 577

4-chloro-N-[(3R,4R)-3-(3,4-dichlorophenyl)-1-{[(2R)-1-(phenylcarbonyl)piperidin-2-yl]carbonyl}piperidin-4-yl]-N-methylbenzamide Using the compound obtained in Example 570 and benzoyl chloride, and by the reaction and purification in the same manner as in Example 39, the title compound was obtained.
MS (ESI+): 612 (M+H)

Example 578

4-chloro-N-[(3R,4R)-3-(3,4-dichlorophenyl)-1-{[(2S)-1-(phenylcarbonyl)piperidin-2-yl]carbonyl}piperidin-4-yl]-N-methylbenzamide Using the compound obtained in Example 571 and benzoyl chloride, and by the reaction and purification in the same manner as in Example 39, the title compound was obtained.
MS (ESI+): 612 (M+H)

Example 579

4-chloro-N-[(3R,4R)-3-(3,4-dichlorophenyl)-1-({(3S,4S)-3-[(phenylcarbonyl)amino]tetrahydro-2H-pyran-4-yl}carbonyl)piperidin-4-yl]-N-methylbenzamide Using the compound obtained in Example 575 and benzoyl chloride, and by the reaction and purification in the same manner as in Example 39, the title compound was obtained.
MS (ESI+): 628 (M+H)

Example 580

4-chloro-N-[(3R,4R)-1-({(2R)-1-[(4-chlorophenyl)carbonyl]piperidin-2-yl}carbonyl)-3-(3,4-dichlorophenyl)piperidin-4-yl]-N-methylbenzamide (Step 1)
Using the compound obtained in Example 137a and (R)-(+)-Boc-piperidinecarboxylic acid, and by the reaction and purification in the same manner as in Example 3, tert-butyl (2R)-2-{[(3R,4R)-4-{[(4-chlorophenyl)carbonyl](methyl)amino}-3-(3,4-dichlorophenyl)piperidin-1-yl]carbonyl}piperidine-1-carboxylate was obtained.
MS (ESI+): 508 (M-Boc+2H)

(Step 2)
Using the compound obtained in step 1, and by the reaction and purification in the same manner as in Example 2, 4-chloro-N-{(3R,4R)-3-(3,4-dichlorophenyl)-1-[(2R)-piperidin-2-ylcarbonyl]piperidin-4-yl}-N-methylbenzamide monohydrochloride was obtained.
MS (ESI+): 508 (M−HCl+H)

(Step 3)
Using the compound obtained in step 2 and 4-chlorobenzoyl chloride, and by the reaction and purification in the same manner as in Example 39, the title compound was obtained.
MS (ESI+): 646 (M+H)

Example 581

4-chloro-N-[(3R,4R)-1-({(2R)-1-[(3-chlorophenyl)carbonyl]piperidin-2-yl}carbonyl)-3-(3,4-dichlorophenyl)piperidin-4-yl]-N-methylbenzamide Using the compound obtained in Example 580, step 2 and 3-chlorobenzoyl chloride, and by the reaction and purification in the same manner as in Example 39, the title compound was obtained.

MS (ESI+): 646 (M+H)

Example 582

4-chloro-N-[(3R,4R)-1-({(2R)-1-[(2-chlorophenyl)carbonyl]piperidin-2-yl}carbonyl)-3-(3,4-dichlorophenyl)piperidin-4-yl]-N-methylbenzamide Using the compound obtained in Example 580, step 2 and 2-chlorobenzoyl chloride, and by the reaction and purification in the same manner as in Example 39, the title compound was obtained.

MS (ESI+): 646 (M+H)

Example 583

4-chloro-N-[(3R,4R)-3-(3,4-dichlorophenyl)-1-({(2R)-1-[(4-methoxyphenyl)carbonyl]piperidin-2-yl}carbonyl)piperidin-4-yl]-N-methylbenzamide Using the compound obtained in Example 580, step 2 and 4-methoxybenzoyl chloride, and by the reaction and purification in the same manner as in Example 39, the title compound was obtained.

MS (ESI+): 642 (M+H)

Example 584

4-chloro-N-[(3R,4R)-1-({(2R)-1-[(4-cyanophenyl)carbonyl]piperidin-2-yl}carbonyl)-3-(3,4-dichlorophenyl)piperidin-4-yl]-N-methylbenzamide Using the compound obtained in Example 580, step 2 and 4-cyanobenzoyl chloride, and by the reaction and purification in the same manner as in Example 39, the title compound was obtained.

MS (ESI+): 637 (M+H)

Example 585

N-[(3R,4R)-1-{[(2R)-1-(biphenyl-4-ylcarbonyl)piperidin-2-yl]carbonyl}-3-(3,4-dichlorophenyl)piperidin-4-yl]-4-chloro-N-methylbenzamide Using the compound obtained in Example 580, step 2 and biphenyl-4-carbonyl chloride, and by the reaction and purification in the same manner as in Example 39, the title compound was obtained.

MS (ESI+): 688 (M+H)

Example 586

4-chloro-N-[(3R,4R)-3-(3,4-dichlorophenyl)-1-(imidazo[1,2-a]pyridin-6-ylcarbonyl)piperidin-4-yl]-N-methylbenzamide Using the compound obtained in Example 137a and imidazo[1,2-a]pyridine-6-carboxylic acid, and by the reaction and purification in the same manner as in Example 97, the title compound was obtained.

MS (ESI+): 541 (M+H)

Example 587

4-chloro-N-[(3R,4R)-3-(3,4-dichlorophenyl)-1-{[3-(trifluoromethyl)-5,6-dihydro[1,2,4]triazolo[4,3-a]pyrazin-7(8H)-yl]carbonyl}piperidin-4-yl]-N-methylbenzamide To a solution of the compound (0.058 mg) obtained in Example 137a and 4-nitrophenyl 3-(trifluoromethyl)-5,6-dihydro[1,2,4]triazolo[4,3-a]pyrazine-7(8H)-carboxylate (0.052 mg) in DMF (1.5 mL) was added triethylamine (0.030 mL) and the mixture was heated to 110° C. The reaction mixture was concentrated under reduced pressure, and the obtained residue was purified by silica gel column chromatography (NH Chromatorex) (solvent gradient; 30→70% ethyl acetate/hexane) to give the title compound (0.059 mg, 61%) as a white powder.

MS (ESI+): 615 (M+H)

Example 588

N-[(3R,4R)-1-acryloyl-3-(3,4-dichlorophenyl)piperidin-4-yl]-4-chloro-N-methylbenzamide Using the compound obtained in Example 137a and prop-2-enoyl chloride, and by the reaction and purification in the same manner as in Example 98, the title compound was obtained.

MS (ESI+): 451 (M+H)

Example 589

4-chloro-N-{(3R,4R)-3-(3,4-dichlorophenyl)-1-[3-(2-oxopyrrolidin-1-yl)propanoyl]piperidin-4-yl}-N-methylbenzamide To a solution of the compound obtained in Example 588 (0.050 mg) in DMF (1 mL) were added potassium carbonate (0.0166 mg) and 2-pyrrolidinone (0.0093 mL), and the mixture was stirred at 110° C. for 1 hr. To the reaction mixture was added water, and the resultant product was extracted with ethyl acetate. The organic layer was washed with brine and dried, and the solvent was evaporated under reduced pressure. The obtained residue was purified by silica gel column chromatography (NH Chromatorex) (solvent gradient; 30→100% ethyl acetate/hexane) to give the title compound (37 mg, 63%) as a white powder.

MS (ESI+): 536 (M+H)

Example 590

4-chloro-N-{(3R,4R)-3-(3,4-dichlorophenyl)-1-[(4-sulfamoylphenyl)carbonyl]piperidin-4-yl}-N-methylbenzamide Using the compound obtained in Example 137a and 4-sulfamoylbenzoic acid, and by the reaction and purification in the same manner as in Example 97, the title compound was obtained.
MS (ESI+): 580 (M+H)

Example 591

N-[(3R,4R)-1-{[4-(acetylamino)phenyl]carbonyl}-3-(3,4-dichlorophenyl)piperidin-4-yl]-4-chloro-N-methylbenzamide Using the compound obtained in Example 137a and 4-(acetylamino)benzoic acid, and by the reaction and purification in the same manner as in Example 97, the title compound was obtained.
MS (ESI+): 558 (M+H)

Example 592

N-[(3R,4R)-1-{[3-(acetylamino)phenyl]carbonyl}-3-(3,4-dichlorophenyl)piperidin-4-yl]-4-chloro-N-methylbenzamide Using the compound obtained in Example 137a and 3-(acetylamino)benzoic acid, and by the reaction and purification in the same manner as in Example 97, the title compound was obtained.
MS (ESI+): 558 (M+H)

Example 593

4-chloro-N-[(3R,4R)-3-(3,4-dichlorophenyl)-1-{[4-(hydroxymethyl)tetrahydro-2H-pyran-4-yl]carbonyl}piperidin-4-yl]-N-methylbenzamide Using the compound obtained in Example 137a and 4-(hydroxymethyl)tetrahydro-2H-pyran-4-carboxylic acid, and by the reaction and purification in the same manner as in Example 97, the title compound was obtained.
MS (ESI+): 539 (M+H)

Example 594

N-[(3R,4R)-1-{[(2R)-1-benzylpiperidin-2-yl]carbonyl}-3-(3,4-dichlorophenyl)piperidin-4-yl]-4-chloro-N-methylbenzamide To a solution of the compound (170 mg) obtained in Example 580, step 2 and potassium carbonate (85 mg) in DMF (5 mL) was added benzylbromide (55 μL), and the mixture was stirred at 100° C. for 14 hr. The reaction mixture was poured into water, and the resultant product was extracted with ethyl acetate. The organic layer was washed with water and dried, and the solvent was evaporated under reduced pressure. The obtained residue was purified by silica gel column chromatography (solvent gradient; 0→55% methanol/ethyl acetate) to give the title compound (69 mg, 37%) as a white powder.
MS (ESI+): 598 (M+H)

Example 595

N-[(3R,4R)-1-(1-acetyl-D-prolyl)-3-(3,4-dichlorophenyl)piperidin-4-yl]-4-chloro-N-methylbenzamide Using the compound obtained in Example 137a and 1-acetyl-D-proline, and by the reaction and purification in the same manner as in Example 3, the title compound was obtained.
MS (ESI+): 536 (M+H)

Example 596 tert-butyl (2R)-2-{[(3R,4R)-4-{[(4-chlorophenyl)carbonyl](methyl)amino}-3-(3,4-dichlorophenyl)piperidin-1-yl]carbonyl}pyrrolidine-1-carboxylate Using the compound obtained in Example 137a and 1-(tert-butoxycarbonyl)-D-proline, and by the reaction and purification in the same manner as in Example 3, the title compound was obtained.
MS (ESI+): 494 (M-Boc+2H)

Example 597 tert-butyl (2R,4R)-2-{[(3R,4R)-4-{[(4-chlorophenyl)carbonyl](methyl)amino}-3-(3,4-dichlorophenyl)piperidin-1-yl]carbonyl}-4-hydroxypyrrolidine-1-carboxylate Using the compound obtained in Example 137a and (4R)-1-(tert-butoxycarbonyl)-4-hydroxy-D-proline, and by the reaction and purification in the same manner as in Example 3, the title compound was obtained.
MS (ESI+): 510 (M-Boc+2H)

Example 598 tert-butyl (2R)-2-{[(3R,4R)-4-{[(4-chlorophenyl)carbonyl](methyl)amino}-3-(3,4-dichlorophenyl)piperidin-1-yl]carbonyl}-4-oxopyrrolidine-1-carboxylate Using the compound obtained in Example 137a and 1-(tert-butoxycarbonyl)-4-oxo-D-proline, and by the reaction and purification in the same manner as in Example 3, the title compound was obtained.
MS (ESI+): 508 (M-Boc+2H)

Example 599

4-chloro-N-[(3R,4R)-3-(3,4-dichlorophenyl)-1-D-prolylpiperidin-4-yl]-N-methylbenzamide monohydrochloride Using the compound obtained in Example 596, and by the reaction and purification in the same manner as in Example 2, the title compound was obtained.
MS (ESI+): 494 (M−HCl+H)

Example 600

4-chloro-N-{(3R,4R)-3-(3,4-dichlorophenyl)-1-[(4R)-4-hydroxy-D-prolyl]piperidin-4-yl}-N-methylbenzamide monohydrochloride Using the compound obtained in Example 597, and by the reaction and purification in the same manner as in Example 2, the title compound was obtained.
MS (ESI+): 510 (M−HCl+H)

Example 601

4-chloro-N-[(3R,4R)-3-(3,4-dichlorophenyl)-1-(4-oxo-D-prolyl)piperidin-4-yl]-N-methylbenzamide monohydrochloride Using the compound obtained in Example 598, and by the reaction and purification in the same manner as in Example 2, the title compound was obtained.
MS (ESI+): 508 (M−HCl+H)

Example 602

4-chloro-N-[(3R,4R)-3-(3,4-dichlorophenyl)-1-{[(2R)-1-(pyridin-4-ylcarbonyl)piperidin-2-yl]carbonyl}piperidin-4-yl]-N-methylbenzamide Using the compound obtained in Example 580, step 2 and pyridine-4-carboxylic acid, and by the reaction and purification in the same manner as in Example 3, the title compound was obtained.
MS (ESI+): 613 (M+H)

Example 603

4-chloro-N-[(3R,4R)-3-(3,4-dichlorophenyl)-1-({(2R)-1-[(1-oxidepyridin-4-yl)carbonyl]piperidin-2-yl}carbonyl)piperidin-4-yl]-N-methylbenzamide Using the compound obtained in Example 580, step 2 and pyridine-4-carboxylic acid 1-oxide, and by the reaction and purification in the same manner as in Example 3, the title compound was obtained.
MS (ESI+): 629 (M+H)

Example 604

4-chloro-N-[(3R,4R)-3-(3,4-dichlorophenyl)-1-(3-hydroxy-2,2-dimethylpropanoyl)piperidin-4-yl]-N-methylbenzamide Using the compound obtained in Example 137a and 3-hydroxy-2,2-dimethylpropanoic acid, and by the reaction and purification in the same manner as in Example 265, the title compound was obtained.
MS (ESI+): 497 (M+H)

Example 605

4-chloro-N-[(3R,4R)-3-(3,4-dichlorophenyl)-1-(5H-pyrrolo[3,2-d]pyrimidin-4-yl)piperidin-4-yl]-N-methylbenzamide Using the compound obtained in Example 137a and 4-chloro-5H-pyrrolo[3,2-d]pyrimidine, and by the reaction and purification in the same manner as in Example 478, the title compound was obtained.
MS (ESI+): 514 (M+H)

Example 606

4-chloro-N-[(3R,4R)-3-(3,4-dichlorophenyl)-1-(3-hydroxy-3-methylbutanoyl)piperidin-4-yl]-N-methylbenzamide Using the compound obtained in Example 137a and 3-hydroxy-3-methylbutanoic acid, and by the reaction and purification in the same manner as in Example 265, the title compound was obtained.
MS (ESI+): 497 (M+H)

Example 607

4-chloro-N-{(3R,4R)-3-(3,4-dichlorophenyl)-1-[1-(phenylcarbonyl)-D-prolyl]piperidin-4-yl}-N-methylbenzamide Using the compound obtained in Example 599 and benzoyl chloride, and by the reaction and purification in the same manner as in Example 39, the title compound was obtained.
MS (ESI+): 598 (M+H)

Example 608

4-chloro-N-{(3R,4R)-3-(3,4-dichlorophenyl)-1-[(4R)-4-hydroxy-1-(phenylcarbonyl)-D-prolyl]piperidin-4-yl}-N-methylbenzamide Using the compound obtained in Example 600 and benzoyl chloride, and by the reaction and purification in the same manner as in Example 39, the title compound was obtained.
MS (ESI+): 614 (M+H)

Example 609

4-chloro-N-{(3R,4R)-3-(3,4-dichlorophenyl)-1-[4-oxo-1-(phenylcarbonyl)-D-prolyl]piperidin-4-yl}-N-methylbenzamide Using the compound obtained in Example 601 and benzoyl chloride, and by the reaction and purification in the same manner as in Example 39, the title compound was obtained.
MS (ESI+): 612 (M+H)

Example 610

4-chloro-N-[(3R,4R)-3-(3,4-dichlorophenyl)-1-{[(1E)-(2-methyl-1H-imidazol-4-yl)methylidene]amino}piperidin-4-yl]-N-methylbenzamide A solution of the compound obtained in Example 549 (845 mg) and 2-methyl-1H-imidazole-4-carbaldehyde (269 mg) in methanol (10 mL) was stirred at 80° C. for 14 hr. The reaction mixture was poured into water, and the resultant product was extracted with ethyl acetate. The organic layer was washed with water and dried, and the solvent was evaporated under reduced pressure. The obtained residue was purified by silica gel column chromatography (solvent gradient; 0→15% methanol/ethyl acetate) to give the title compound (950 mg, 92%) as a white powder.
MS (ESI+): 504 (M+H)

Example 611

4-{[(3R,4R)-4-{[(4-chlorophenyl)carbonyl](methyl)amino}-3-(3,4-dichlorophenyl)piperidin-1-yl]carbonyl}-N-ethylpiperidine-1-carboxamide To a solution of the compound (170 mg) obtained in Example 462 and triethylamine (86 μL) in acetonitrile (3 mL) was added ethyl isocyanate (376 μL), and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 0→25% methanol/ethyl acetate) to give the title compound (128 mg, 70%) as a white powder.
MS (ESI+): 579 (M+H)

Example 612

4-{[(3R,4R)-4-{[(4-chlorophenyl)carbonyl](methyl)amino}-3-(3,4-dichlorophenyl)piperidin-1-yl]carbonyl}-N-cyclopropylpiperidine-1-carboxamide A solution of cyclopropanecarboxylic acid (50 μL), triethylamine (86 μL) and DPPA (133 μL) in toluene (3 mL) was stirred at 80° C. for 1 hr. The reaction mixture was cooled to room temperature, and then the compound obtained in Example 462 (170 mg) was added, and the mixture was stirred at room temperature for 14 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 0→20% methanol/ethyl acetate) to give the title compound (97 mg, 53%) as a white powder.
MS (ESI+): 591 (M+H)

Example 613

4-chloro-N-{(3R,4R)-3-(3,4-dichlorophenyl)-1-[(1-propanoylpiperidin-4-yl)carbonyl]piperidin-4-yl}-N-methylbenzamide Using the compound obtained in Example 462 and propanoyl chloride, and by the reaction and purification in the same manner as in Example 39, the title compound was obtained.
MS (ESI+): 564 (M+H)

Example 614

N-[(3R,4R)-3-(3,4-dichlorophenyl)-1-(trifluoroacetyl)piperidin-4-yl]-N-methyl-4-morpholin-4-ylbenzamide (Step 1)
To a solution of tert-butyl (3R,4R)-4-amino-3-(3,4-dichlorophenyl)piperidine-1-carboxylate p-toluenesulfonate (2.00 g) obtained in Reference Example 23, step 4, 4-morpholin-4-ylbenzoic acid (1.20 g) and triethylamine (1.60 mL) in acetonitrile (10 mL) were added WSC.HCl (1.1 g) and HOBt (0.886 g), and the mixture was stirred at room temperature for 2 hr. To the reaction solution was added water, and the resultant product was extracted with ethyl acetate. The organic layer was washed with brine and dried, and the solvent was evaporated under reduced pressure. The obtained residue was purified by silica gel column chromatography to give tert-butyl (3R,4R)-3-(3,4-dichlorophenyl)-4-{[(4-morpholin-4-ylphenyl)carbonyl]amino}piperidine-1-carboxylate (2.18 g, 100%) as a white powder.
MS (ESI+): 434 (M-Boc+2H)

(Step 2)
To a solution of the compound (2.18 g) obtained in step 1 in DMF (10 mL) was added sodium hydride (60% in oil, 308 mg) at 0° C., and the mixture was stirred for 10 min. Then, methyl iodide (1.2 mL) was added, and the mixture was stirred at room temperature for 14 hr. To the reaction mixture was added water, and the resultant product was extracted with ethyl acetate. The organic layer was washed with water, saturated aqueous sodium hydrogen carbonate solution and brine and dried, and the solvent was evaporated under reduced pressure. The obtained residue was purified by silica gel column chromatography (solvent gradient; 10→90% ethyl acetate/hexane) to give tert-butyl (3R,4R)-3-(3,4-dichlorophenyl)-4-{methyl[(4-morpholin-4-ylphenyl)carbonyl]amino}piperidine-1-carboxylate (1.86 g, 87%).
MS (ESI+): 548 (M+H)

(Step 3)
To the compound (1.86 g) obtained in step 2 was added 2N hydrogen chloride/2-propanol (10 mL), and the mixture was stirred at 50° C. for 1.5 hr. The reaction mixture was concentrated under reduced pressure to give N-[(3R,4R)-3-(3,4-dichlorophenyl)piperidin-4-yl]-N-methyl-4-morpholin-4-ylbenzamide monohydrochloride (2.00 g, 100%) as a white powder.
MS (ESI+): 448 (M−HCl+H)

(Step 4)
Using the compound obtained in step 3, and by the reaction and purification in the same manner as in Example 551, the title compound was obtained as a white powder.
MS (ESI+): 544 (M+H)

Example 615

N-[(3R,4R)-3-(3,4-dichlorophenyl)-1-methylpiperidin-4-yl]-N-methyl-4-morpholin-4-ylbenzamide Using the compound obtained in Example 614, step 3, and by the reaction and purification in the same manner as in Example 574, the title compound was obtained as a white powder.
MS (ESI+): 462 (M+H)

Example 616

N-[(3R,4R)-3-(3,4-dichlorophenyl)-1-(methylsulfonyl)piperidin-4-yl]-N-methyl-4-morpholin-4-ylbenzamide Using the compound obtained in Example 614, step 3, and by the reaction and purification in the same manner as in Example 552, the title compound was obtained as a white powder.
MS (ESI+): 526 (M+H)

Example 617

N-[(3R,4R)-3-(3,4-dichlorophenyl)-1-(phenylcarbonyl)piperidin-4-yl]-N-methyl-4-morpholin-4-ylbenzamide Using the compound obtained in Example 614, step 3 and benzoyl chloride, and by the reaction and purification in the same manner as in Example 39, the title compound was obtained as a white powder.
MS (ESI+): 552 (M+H)

Example 618

N-[(3R,4R)-3-(3,4-dichlorophenyl)-1-(2,2,2-trifluoroethyl)piperidin-4-yl]-N-methyl-4-morpholin-4-ylbenzamide Using the compound obtained in Example 614, step 3 and 2,2,2-trifluoroethyl trifluoromethanesulfonate, and by the reaction and purification in the same manner as in Example 594, the title compound was obtained as a white powder.
MS (ESI+): 530 (M+H)

Example 619

N-{(3R,4R)-3-(3,4-dichlorophenyl)-1-[5-(trifluoromethyl)pyridin-2-yl]piperidin-4-yl}-N-methyl-4-morpholin-4-ylbenzamide Using the compound obtained in Example 614, step 3 and 2-chloro-5-(trifluoromethyl)pyridine, and by the reaction and purification in the same manner as in Example 478, the title compound was obtained as a white powder.
$^1$H-NMR (CDCl$_3$) δ 1.47-2.36 (3H, m), 2.45-3.42 (10H, m), 3.62-5.53 (6H, m), 6.41-8.65 (10H, m)

Example 620 tert-butyl 4-{[(3R,4R)-3-(3,4-dichlorophenyl)-4-{methyl[(4-morpholin-4-ylphenyl)carbonyl]amino}piperidin-1-yl]carbonyl}piperidine-1-carboxylate To a solution of N-[(3R,4R)-3-(3,4-dichlorophenyl)piperidin-4-yl]-N-methyl-4-morpholin-4-ylbenzamide monohydrochloride (800 mg) obtained in Example 614, step 3, 1-(tert-butoxycarbonyl)piperidine-4-carboxylic acid (566 mg) and triethylamine (684 µL) in acetonitrile (5 mL) were added WSC.HCl (473 mg) and HOBt (378 mg), and the mixture was stirred at room temperature for 14 hr. To the reaction solution was added water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography to give the title compound (855 mg, 79%) as a white powder.
MS (ESI+): 559 (M-Boc+2H)

Example 621

N-[(3R,4R)-3-(3,4-dichlorophenyl)-1-(piperidin-4-ylcarbonyl)piperidin-4-yl]-N-methyl-4-morpholin-4-ylbenzamide monohydrochloride To tert-butyl 4-{[(3R,4R)-3-(3,4-dichlorophenyl)-4-{methyl[(4-morpholin-4-ylphenyl)carbonyl]amino}piperidin-1-yl]carbonyl}piperidine-1-carboxylate (800 mg) obtained in Example 620 was added 2N hydrogen chloride/2-propanol (10 mL), and the mixture was stirred at 50° C. for 4 hr. The reaction mixture was concentrated under reduced pressure to give the title compound (771 mg, 100%) as a white powder.
MS (ESI+): 559 (M−HCl+H)

Example 622

N-[(3R,4R)-1-{[1-(cyclopropylcarbonyl)piperidin-4-yl]carbonyl}-3-(3,4-dichlorophenyl)piperidin-4-yl]-N-methyl-4-morpholin-4-ylbenzamide Using the compound obtained in Example 621 and cyclopropylcarbonyl chloride, and by the reaction and purification in the same manner as in Example 39, the title compound was obtained as a white powder.
MS (ESI+): 627 (M+H)

Example 623

N-[(3R,4R)-3-(3,4-dichlorophenyl)-1-({1-[(1-hydroxycyclopropyl)carbonyl]piperidin-4-yl}carbonyl)piperidin-4-yl]-N-methyl-4-morpholin-4-ylbenzamide 0.5 ethyl acetate To a solution of N-[(3R,4R)-3-(3,4-dichlorophenyl)-1-(piperidin-4-ylcarbonyl)piperidin-4-yl]-N-methyl-4-morpholin-4-ylbenzamide monohydrochloride (200 mg) obtained in Example 621, 1-hydroxycyclopropanecarboxylic acid (44.5 mg) and triethylamine (143 µL) in acetonitrile (5 mL) were added WSC.HCl (96 mg) and HOBt (76.8 mg), and the mixture was stirred at room temperature for 14 hr. To the reaction solution was added water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography to give the title compound (119 mg, 55%) as a white crystal powder.
MS (ESI+): 643 (M-0.5EtOAc+H)
$^1$H-NMR (CDCl$_3$) δ 0.79-1.39 (5H, m), 1.44-2.22 (9H, m), 2.40-3.53 (11H, m), 3.67-5.21 (8H, m), 6.51-7.58 (7H, m)
Elemental analysis: $C_{33}H_{40}Cl_2N_4O_4 \cdot 0.5EtOAc$
Found C, 62.45; H, 6.44; N, 8.73
Calcd. C, 62.59; H, 6.60; N, 8.34
Melting point: 151-153° C.
$[\alpha]_D^{25}$ +61.9° (c 0.25, MeOH)

Example 624

N-[(3R,4R)-3-(3,4-dichlorophenyl)-1-{[1-(phenylcarbonyl)piperidin-4-yl]carbonyl}piperidin-4-yl]-N-methyl-4-morpholin-4-ylbenzamide Using the compound obtained in Example 614, step 3 and 1-(phenylcarbonyl)piperidine-4-carboxylic acid, and by the reaction and purification in the same manner as in Example 3, the title compound was obtained as a white powder.
MS (ESI+): 663 (M+H)

Example 625

N-[(3R,4R)-3-(3,4-dichlorophenyl)-1-{[1-(methylsulfonyl)piperidin-4-yl]carbonyl}piperidin-4-yl]-N-methyl-4-morpholin-4-ylbenzamide Using the compound obtained in Example 621 and methylsulfonyl chloride, and by the reaction and purification in the same manner as in Example 39, the title compound was obtained.
MS (ESI+): 637 (M+H)

Example 626 tert-butyl [(1R,2S)-2-{[(3R,4R)-3-(3,4-dichlorophenyl)-4-{methyl[(4-morpholin-4-ylphenyl)carbonyl]amino}piperidin-1-yl]carbonyl}cyclohexyl]carbamate Using the compound obtained in Example 614, step 3 and (1S,2R)-2-[(tert-butoxycarbonyl)amino]cyclohexanecarboxylic acid, and by the reaction and purification in the same manner as in Example 3, the title compound was obtained.
MS (ESI+): 573 (M-Boc+2H)

Example 627 tert-butyl [(3S,4S)-4-{[(3R,4R)-3-(3,4-dichlorophenyl)-4-{methyl[(4-morpholin-4-ylphenyl)carbonyl]amino}piperidin-1-yl]carbonyl}tetrahydro-2H-pyran-3-yl]carbamate Using the compound obtained in Example 614, step 3 and (3S,4S)-3-[(tert-butoxycarbonyl)amino]tetrahydro-2H-pyran-4-carboxylic acid, and by the reaction and purification in the same manner as in Example 3, the title compound was obtained.
MS (ESI+): 575 (M-Boc+2H)

Example 628

N-[(3R,4R)-1-{[(1S,2R)-2-aminocyclohexyl]carbonyl}-3-(3,4-dichlorophenyl)piperidin-4-yl]-N-methyl-4-morpholin-4-ylbenzamide monohydrochloride Using the compound obtained in Example 626, and by the reaction and purification in the same manner as in Example 2, the title compound was obtained as a white powder.
MS (ESI+): 573 (M−HCl+H)

Example 629

N-[(3R,4R)-1-{[(3S,4S)-3-aminotetrahydro-2H-pyran-4-yl]carbonyl}-3-(3,4-dichlorophenyl)piperidin-4-yl]-N-methyl-4-morpholin-4-ylbenzamide monohydrochloride 2.75 hydrate A solution of tert-butyl [(3S,4S)-4-{[(3R,4R)-3-(3,4-dichlorophenyl)-4-{methyl[(4-morpholin-4-ylphenyl)carbonyl]amino}piperidin-1-yl]carbonyl}tetrahydro-2H-pyran-3-yl]carbamate (200 mg) obtained in Example 627 in 2N hydrogen chloride/2-propanol (5 mL) was stirred at 55° C. for 2 hr. The reaction mixture was concentrated under reduced pressure to give the title compound (226 mg, 100%) as a white powder.
MS (ESI+): 575 (M−HCl−2.75H$_2$O+H)

$^1$H-NMR (DMSO-d$_6$) δ0.93-1.27 (4H, m), 1.46-2.22 (3H, m), 2.62-4.32 (17H, m), 5.78-6.29 (5H, m), 6.64-8.57 (7H, m)
Elemental analysis: C$_{24}$H$_{37}$Cl$_3$N$_4$O$_4$.2.75H$_2$O
Found C, 52.95; H, 6.53; N, 8.31
Calcd. C, 52.65; H, 6.48; N, 8.47
Melting point: 201-203° C.
[α]$_D^{25}$ +19.2° (c 0.25, MeOH)

Example 630

N-[(3R,4R)-3-(3,4-dichlorophenyl)-1-({(1S,2R)-2-[(phenylcarbonyl)amino]cyclohexyl}carbonyl)piperidin-4-yl]-N-methyl-4-morpholin-4-ylbenzamide Using the compound obtained in Example 628 and benzoyl chloride, and by the reaction and purification in the same manner as in Example 39, the title compound was obtained as a white powder.
MS (ESI+): 677 (M+H)

Example 631

N-[(3R,4R)-3-(3,4-dichlorophenyl)-1-({(3S,4S)-3-[(phenylcarbonyl)amino]tetrahydro-2H-pyran-4-yl}carbonyl)piperidin-4-yl]-N-methyl-4-morpholin-4-ylbenzamide Using the compound obtained in Example 629 and benzoyl chloride, and by the reaction and purification in the same manner as in Example 39, the title compound was obtained as a white powder.
MS (ESI+): 679 (M+H)

Example 632

N-[(3R,4R)-3-(3,4-dichlorophenyl)-1-{[1-(hydroxyacetyl)piperidin-4-yl]carbonyl}piperidin-4-yl]-N-methyl-4-(trifluoromethyl)benzamide monohydrate (Step 1)
To a solution of tert-butyl (3R,4R)-4-amino-3-(3,4-dichlorophenyl)piperidine-1-carboxylate p-toluenesulfonate (1.50 g) obtained in Reference Example 23, step 4, 4-(trifluoromethyl)benzoic acid (0.688 g) and triethylamine (1.20 mL) in acetonitrile (20 mL) were added WSC.HCl (0.831 g) and HOBt (0.664 g), and the mixture was stirred at room temperature for 14 hr. To the reaction solution was added water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography to give tert-butyl (3R,4R)-3-(3,4-dichlorophenyl)-4-({[4-(trifluoromethyl)phenyl]carbonyl}amino)piperidine-1-carboxylate (1.67 g, 100%) as a white powder.
MS (ESI+): 417 (M-Boc+2H)
(Step 2)
To a solution of the compound (1.67 g) obtained in step 1 in DMF (10 mL) was added sodium hydride (60% in oil, 231 mg) at 0° C., and the mixture was stirred for 10 min. Then, methyl iodide (900 µL) was added, and the mixture was stirred overnight at room temperature. To the reaction mixture was added water, and the resultant product was extracted with ethyl acetate. The organic layer was washed with brine and dried, and the solvent was evaporated under reduced pressure. The obtained residue was purified by silica gel column chromatography (solvent gradient; 25→65% ethyl acetate/hexane) to give tert-butyl (3R,4R)-3-(3,4-dichlorophenyl)-4-(methyl{[4-(trifluoromethyl)phenyl]carbonyl}amino)piperidine-1-carboxylate (1.56 g, 100%) as a white powder.

MS (ESI+): 431 (M−Boc+2H)

(Step 3)

A solution of the compound (1.56 g) obtained in step 2 in 2N hydrogen chloride/2-propanol (10 mL) was stirred at 55° C. for 2 hr. The reaction mixture was concentrated under reduced pressure to give N-[(3R,4R)-3-(3,4-dichlorophenyl)piperidin-4-yl]-N-methyl-4-(trifluoromethyl)benzamide monohydrochloride (1.33 g, 98%) as a white powder.

MS (ESI+): 431 (M−HCl+2H)

(Step 4)

To a solution of the compound (1.0 g) obtained in step 3, 1-(hydroxyacetyl)piperidine-4-carboxylic acid (0.48 g) and triethylamine (954 μL) in DMF (10 mL) was added DEPC (502 μL) at 0° C., and the mixture was stirred at room temperature for 14 hr. To the reaction mixture was added water, and the resultant product was extracted with ethyl acetate. The organic layer was washed with brine and dried, and the solvent was evaporated under reduced pressure. The obtained residue was dissolved in methanol (10 mL), potassium carbonate (1.5 g) was added, and the mixture was stirred at room temperature for 2 hr. The solution was concentrated, and partitioned between ethyl acetate and water. The organic layer was washed with water and dried, and the solvent was evaporated under reduced pressure. The obtained residue was purified by silica gel column chromatography to give N-[(3R,4R)-3-(3,4-dichlorophenyl)-1-{[1-(hydroxyacetyl)piperidin-4-yl]carbonyl}piperidin-4-yl]-N-methyl-4-(trifluoromethyl)benzamide (0.936 g, 73%) as a white powder.

$^1$H-NMR (CDCl$_3$) δ 1.66-2.18 (7H, m), 2.42-5.20 (16H, m), 6.79-8.00 (7H, m)

The obtained compound (0.778 g) was recrystallized from ethyl acetate/hexane to give the title compound (0.731 g, 94%) as a white crystal powder.

MS (ESI+): 600 (M−H$_2$O+H)

Elemental analysis: C$_{28}$H$_{30}$Cl$_2$F$_3$N$_3$O$_4$·1.0H$_2$O

Found C, 54.48; H, 5.19; N, 6.72

Calcd. C, 54.38; H, 5.22; N, 6.79

$[α]_D^{25}$ +46.5° (c 0.25, MeOH)

Melting point: 124-127° C.

Example 633

4-bromo-N-[(3R,4R)-3-(3,4-dichlorophenyl)-1-{[1-(hydroxyacetyl)piperidin-4-yl]carbonyl}piperidin-4-yl]-N-methylbenzamide monohydrate (Step 1)

To a solution of tert-butyl (3R,4R)-4-amino-3-(3,4-dichlorophenyl)piperidine-1-carboxylate p-toluenesulfonate (1.50 g) obtained in Reference Example 23, step 4 and 4-bromobenzoyl chloride (0.825 g) in acetonitrile (15 mL) was added triethylamine (524 μL) at room temperature, and the mixture was stirred overnight. Furthermore, triethylamine (681 μL) was added to the reaction mixture, and the mixture was stirred overnight. To the reaction mixture was added water, and the resultant product was extracted with ethyl acetate. The organic layer was washed with 1N hydrochloric acid, saturated aqueous sodium hydrogen carbonate solution and brine and dried, and the solvent was evaporated under reduced pressure. The obtained residue was purified by silica gel column chromatography to give tert-butyl (3R,4R)-4-{[(4-bromophenyl)carbonyl]amino}-3-(3,4-dichlorophenyl)piperidine-1-carboxylate (1.15 g, 79%) as a white crystal powder.

(Step 2)

To a solution of the compound (1.16 g) obtained in step 1 in DMF (22 mL) was added sodium hydride (60% in oil, 175 mg) at 0° C., and the mixture was stirred for 10 min. Then, methyl iodide (681 μL) was added, and the mixture was stirred overnight at room temperature. To the reaction mixture was added water, and the resultant product was extracted with ethyl acetate. The organic layer was washed with brine and dried, and the solvent was evaporated under reduced pressure. The obtained residue was purified by silica gel column chromatography (solvent gradient; 10→90% ethyl acetate/hexane) to give tert-butyl (3R,4R)-4-{[(4-bromophenyl)carbonyl](methyl)amino}-3-(3,4-dichlorophenyl)piperidine-1-carboxylate (1.09 g, 92%) as a white powder.

(Step 3)

To a solution of the compound (1.09 g) obtained in step 2 in ethyl acetate (8 mL) was added 4N hydrogen chloride/ethyl acetate (8 mL), and the mixture was stirred at 50° C. for 2 hr. The reaction mixture was concentrated under reduced pressure, and the residue was dissolved in a mixture of ethyl acetate and acetonitrile. This solution was washed with 1N aqueous sodium hydroxide solution and dried, and the solvent was evaporated under reduced pressure to give 4-bromo-N-[(3R,4R)-3-(3,4-dichlorophenyl)piperidin-4-yl]-N-methylbenzamide (0.830 g, 93%) as a white powder.

(Step 4)

To a solution of the compound obtained in step 3 (200 mg), triethylamine (313 μL) and 1-(hydroxyacetyl)piperidine-4-carboxylic acid (101 mg) in DMF (4.5 mL) was added DEPC (87 mg), and the mixture was stirred overnight at room temperature. To the reaction mixture was added water, and the resultant product was extracted with ethyl acetate. The organic layer was washed with saturated aqueous sodium hydrogen carbonate solution, 1N hydrochloric acid and brine and dried, and the solvent was evaporated under reduced pressure. The obtained residue was purified by silica gel column chromatography (NH Chromatorex) (solvent gradient; 40→95% ethyl acetate/hexane) to give the title compound (135 mg, 49%) as a white crystal powder.

MS (ESI+): 610 (M−H$_2$O+H)

$^1$H-NMR (CDCl$_3$) δ 0.75-2.25 (7H, m), 2.40-5.30 (16H, m), 6.75-7.75 (7H, m)

Elemental analysis: C$_{27}$H$_{30}$BrCl$_2$N$_3$O$_4$·1.0H$_2$O

Found C, 51.66; H, 5.14; N, 6.60

Calcd. C, 51.53; H, 5.12; N, 6.68

$[α]_D^{25}$ +60.9° (c 0.25, MeOH)

Melting point: 130-132° C.

Example 634

N-[(3R,4R)-1-{[1-(cyclopropylcarbonyl)piperidin-4-yl]carbonyl}-3-(3,4-dichlorophenyl)piperidin-4-yl]-N-methyl-5-(trifluoromethyl)pyridine-2-carboxamide (Step 1)

To a solution of tert-butyl (3R,4R)-4-amino-3-(3,4-dichlorophenyl)piperidine-1-carboxylate p-toluenesulfonate (11.4 g) obtained in Reference Example 23, step 4, 5-(trifluoromethyl)pyridine-2-carboxylic acid (5.0 g) and triethylamine (6.15 mL) in acetonitrile (110 mL) were added WSC.HCl (6.39 g) and HOBt (5.06 g), and the mixture was stirred at room temperature for 14 hr. To the reaction mixture was added water, and the resultant product was extracted with ethyl acetate. The organic layer was washed with saturated aqueous sodium hydrogen carbonate solution, 1N hydrochloric acid and brine and dried, and the solvent was evaporated under reduced pressure. The obtained residue was purified by silica gel column chromatography (solvent gradient; 40→90% ethyl acetate/hexane) to give tert-butyl (3R,4R)-3-(3,4-dichlorophenyl)-4-({[5-(trifluoromethyl)pyridin-2-yl]carbonyl}amino)piperidine-1-carboxylate (12.15 g, 100%) as a pale yellow powder.

To a solution of the thus-obtained compound (12.15 g) in DMF (120 mL) was added sodium hydride (60% in oil, 1.88 g) at 0° C., and the mixture was stirred for 20 min. Then, methyl iodide (7.30 mL) was added, and the mixture was stirred overnight at room temperature. To the reaction mixture was added water, and the resultant product was extracted with ethyl acetate. The organic layer was washed with brine and dried, and the solvent was evaporated under reduced pressure. The obtained residue was purified by silica gel column chromatography (solvent gradient; 40→90% ethyl acetate/hexane) to give tert-butyl (3R,4R)-3-(3,4-dichlorophenyl)-4-(methyl{[5-(trifluoromethyl)pyridin-2-yl]carbonyl}amino)piperidine-1-carboxylate (11.6 g, 93%) as a pale yellow oil.

MS (ESI+): 432 (M−Boc+2H)

To a solution of the thus-obtained compound (11.6 g) in 2-propanol (50 mL) was added 2N hydrogen chloride/2-propanol (130 mL), and the mixture was stirred at 50° C. for 2 hr. The reaction mixture was concentrated under reduced pressure to give N-[(3R,4R)-3-(3,4-dichlorophenyl)piperidin-4-yl]-N-methyl-5-(trifluoromethyl)pyridine-2-carboxamide monohydrochloride (11.2 g, 100%).

MS (ESI+): 432 (M−HCl+H)
(Step 2)

Using the compound obtained in step 1 and 1-(cyclopropylcarbonyl)piperidine-4-carboxylic acid, and by the reaction and purification in the same manner as in Example 97, the title compound was obtained.

MS (ESI+): 611 (M+H)

Example 635

N-[(3R,4R)-3-(3,4-dichlorophenyl)-1-{[1-(hydroxyacetyl)piperidin-4-yl]carbonyl}piperidin-4-yl]-N-methyl-5-(trifluoromethyl)pyridine-2-carboxamide 0.5 hydrate To a solution of the compound (200 mg) obtained in Example 634, step 1, triethylamine (300 µL) and 1-(hydroxyacetyl)piperidine-4-carboxylic acid (96 mg) in DMF (4 mL) was added DEPC (89 mg), and the mixture was stirred overnight at room temperature. To the reaction mixture was added water, and the resultant product was extracted with ethyl acetate. The organic layer was washed with saturated aqueous sodium hydrogen carbonate solution, 1N hydrochloric acid and brine and dried, and the solvent was evaporated under reduced pressure. The obtained residue was purified by silica gel column chromatography (NH Chromatorex) (solvent gradient; 40→100% ethyl acetate/hexane) to give the title compound (69 mg, 28%) as a white crystal powder.

MS (ESI+): 601 (M-0.5H$_2$O+H)
$^1$H-NMR (CDCl$_3$) δ 0.80-2.25 (7H, m), 2.30-5.30 (16H, m), 6.75-7.00 (1H, m), 7.20-7.50 (3H, m), 7.90-8.20 (1H, m), 8.75-8.90 (1H, m)
Elemental analysis: C$_{27}$H$_{29}$Cl$_2$F$_3$N$_4$O$_4$·0.5H$_2$O
Found C, 52.96; H, 5.05; N, 8.98
Calcd. C, 53.12; H, 4.95; N, 9.18
$[\alpha]_D^{25}$ +73.3° (c 0.25, MeOH)
Melting point: 50-92° C.

Example 636

N-[(3R,4R)-1-[(1-carbamoylpiperidin-4-yl)carbonyl]-3-(3,4-dichlorophenyl)piperidin-4-yl]-N-methyl-5-(trifluoromethyl)pyridine-2-carboxamide Using the compound obtained in Example 634, step 1 and 1-carbamoylpiperidine-4-carboxylic acid, and by the reaction and purification in the same manner as in Example 97, the title compound was obtained.

MS (ESI+): 586 (M+H)

Example 637

N-{(3R,4R)-3-(3,4-dichlorophenyl)-1-[(1-formylpiperidin-4-yl)carbonyl]piperidin-4-yl}-N-methyl-5-(trifluoromethyl)pyridine-2-carboxamide Using the compound obtained in Example 634, step 1 and 1-formylpiperidine-4-carboxylic acid, and by the reaction and purification in the same manner as in Example 97, the title compound was obtained.

MS (ESI+): 571 (M+H)

Example 638 methyl 4-{[(3R,4R)-3-(3,4-dichlorophenyl)-4-(methyl{[5-(trifluoromethyl)pyridin-2-yl]carbonyl}amino)piperidin-1-yl]carbonyl}piperidine-1-carboxylate Using the compound obtained in Example 634, step 1 and 1-(methoxycarbonyl)piperidine-4-carboxylic acid, and by the reaction and purification in the same manner as in Example 97, the title compound was obtained.

MS (ESI+): 601 (M+H)

Example 639

N-[(3R,4R)-3-(3,4-dichlorophenyl)-1-{[1-(methylsulfonyl)piperidin-4-yl]carbonyl}piperidin-4-yl]-N-methyl-5-(trifluoromethyl)pyridine-2-carboxamide Using the compound obtained in Example 634, step 1 and 1-(methylsulfonyl)piperidine-4-carboxylic acid, and by the reaction and purification in the same manner as in Example 97, the title compound was obtained.

MS (ESI+): 621 (M+H)

Example 640

N-[(3R,4R)-3-(3,4-dichlorophenyl)-1-{[1-(2-hydroxy-2-methylpropanoyl)piperidin-4-yl]carbonyl}piperidin-4-yl]-N-methyl-5-(trifluoromethyl)pyridine-2-carboxamide Using the compound obtained in Example 634, step 1 and 2-hydroxy-2-methylpropanoic acid, and by the reaction and purification in the same manner as in Example 265, the title compound was obtained.

MS (ESI+): 629 (M+H)

Example 641

N-{(3R,4R)-3-(3,4-dichlorophenyl)-1-[(2-methyl-3-oxo-2,3,3a,4,5,7-hexahydro-6H-pyrazolo[3,4-c]pyridin-6-yl)carbonyl]piperidin-4-yl}-N-methyl-5-(trifluoromethyl)pyridine-2-carboxamide To a solution of 4-nitrophenyl chlorocarbonate (475 mg) in acetonitrile (20 mL) was added triethylamine (1.195 mL) at 0° C., a solution of the compound (1.00 g) obtained in Example 634, step 1 in acetonitrile (4 mL) was added, and the mixture was stirred at room temperature. The reaction mixture was concentrated under reduced pressure, and the residue was purified by silica gel column chromatography (solvent gradient; 30→70% ethyl acetate/hexane), and the solvent was evaporated under reduced pressure. To a solution of the obtained residue and 2-methyl-2,3a,4,5,6,7-hexahydro-3H-pyrazolo[3,4-c]pyridin-3-one (0.075 g) in ethyl acetate (1.5 mL) was added triethylamine (0.035 mL), and the mixture was stirred at 155° C. for 1 hr. The reaction mixture was poured into water, and the resultant product was extracted with ethyl acetate. The organic layer was washed with saturated aqueous sodium hydrogen carbonate solution and brine and dried, and the solvent was evaporated under reduced pressure. The obtained residue was purified by silica gel column chromatography (solvent gradient; 10→33% ethyl acetate/hexane) to give the title compound (0.055 g, 45%) as a white powder.
MS (ESI+): 611 (M+H)

Example 642

N-{(3R,4R)-3-(3,4-dichlorophenyl)-1-[(7-oxo-4,5,6,7-tetrahydro-1H-indol-2-yl)carbonyl]piperidin-4-yl}-N-methyl-5-(trifluoromethyl)pyridine-2-carboxamide Using the compound obtained in Example 634, step 1 and 7-oxo-4,5,6,7-tetrahydro-1H-indol-2-carboxylic acid, and by the reaction and purification in the same manner as in Example 97, the title compound was obtained.
MS (ESI+): 593 (M+H)

Example 643 methyl 5-{[(3R,4R)-3-(3,4-dichlorophenyl)-4-(methyl{[5-(trifluoromethyl)pyridin-2-yl]carbonyl}amino)piperidin-1-yl]carbonyl}-1H-pyrrole-2-carboxylate Using the compound obtained in Example 634, step 1 and 5-(methoxycarbonyl)-1H-pyrrole-2-carboxylic acid, and by the reaction and purification in the same manner as in Example 97, the title compound was obtained.
MS (ESI+): 583 (M+H)

Example 644

N-{(3R,4R)-3-(3,4-dichlorophenyl)-1-[(1-methyl-7-oxo-4,5,6,7-tetrahydro-1H-indol-2-yl)carbonyl]piperidin-4-yl}-N-methyl-5-(trifluoromethyl)pyridine-2-carboxamide To a solution of the compound (0.060 g) obtained in Example 642 in DMF (1 mL) was added sodium hydride (0.005 g) and the mixture was stirred for 10 min. Methyl iodide (0.020 mL) was added at 0° C. and the mixture was stirred at room temperature. To the reaction mixture was added water, and the resultant product was extracted with ethyl acetate. The organic layer was washed with brine and dried, and the solvent was evaporated under reduced pressure. The obtained residue was purified by silica gel column chromatography (NH Chromatorex) (solvent gradient; 30→70% ethyl acetate/hexane) to give the title compound (0.020 g, 33%) as a white powder.
MS (ESI+): 607 (M+H)

Example 645 methyl 5-{[(3R,4R)-3-(3,4-dichlorophenyl)-4-(methyl{[5-(trifluoromethyl)pyridin-2-yl]carbonyl}amino)piperidin-1-yl]carbonyl}-1-methyl-1H-pyrrole-2-carboxylate Using the compound obtained in Example 643, and by the reaction and purification in the same manner as in Example 644, the title compound was obtained.
MS (ESI+): 597 (M+H)

Example 646

N-[(3R,4R)-3-(3,4-dichlorophenyl)-1-{methyl[(5-methylisoxazol-3-yl)methyl]carbamoyl}piperidin-4-yl]-N-methyl-5-(trifluoromethyl)pyridine-2-carboxamide Using the compound obtained in Example 634, step 1 and N-methyl-1-(5-methylisoxazol-3-yl)methanamine, and by the reaction and purification in the same manner as in Example 641, the title compound was obtained.
MS (ESI+): 584 (M+H)

Example 647

N-[(3R,4R)-3-(3,4-dichlorophenyl)-1-(piperidin-1-ylcarbonyl)piperidin-4-yl]-N-methyl-5-(trifluoromethyl)pyridine-2-carboxamide Using the compound obtained in Example 634, step 1 and piperidine, and by the reaction and purification in the same manner as in Example 641, the title compound was obtained.
MS (ESI+): 543 (M+H)

Example 648

5-bromo-N-[(3R,4R)-3-(3,4-dichlorophenyl)-1-{[1-(hydroxyacetyl)piperidin-4-yl]carbonyl}piperidin-4-yl]-N-methylpyridine-2-carboxamide (Step 1)
Using the compound obtained in Reference Example 23, step 4 and 5-bromopyridine-2-carboxylic acid, and by the reaction and purification in the same manner as in Reference Example 1, step 5, Example 1 and Example 14, 5-bromo-N-[(3R,4R)-3-(3,4-dichlorophenyl)piperidin-4-yl]-N-methylpyridine-2-carboxamide was obtained.
MS (ESI+): 443 (M+H)
(Step 2)
Using the compound obtained in step 1 and 1-(hydroxyacetyl)piperidine-4-carboxylic acid, and by the reaction and purification in the same manner as in Example 265, the title compound was obtained.
MS (ESI+): 611 (M+H)

Example 649

4-cyclopropyl-N-[(3R,4R)-3-(3,4-dichlorophenyl)-1-{[1-(methylsulfonyl)piperidin-4-yl]carbonyl}piperidin-4-yl]-N-methylbenzamide (Step 1)
Using the compound obtained in Reference Example 23, step 4 and 4-cyclopropylbenzoic acid, and by the reaction and purification in the same manner as in Reference Example 1, step 5, Example 1 and Example 14, 4-cyclopropyl-N-[(3R,4R)-3-(3,4-dichlorophenyl)piperidin-4-yl]-N-methylbenzamide was obtained.
MS (ESI+): 403 (M+H)

(Step 2)
Using the compound obtained in step 1 and 1-(methylsulfonyl)piperidine-4-carboxylic acid, and by the reaction and purification in the same manner as in Example 97, the title compound was obtained.
MS (ESI+): 592 (M+H)

Example 650

N-[(3R,4R)-3-(3,4-dichlorophenyl)-1-{[4-(furan-2-ylcarbonyl)piperazin-1-yl]carbonyl}piperidin-4-yl]-N-methyl-5-(trifluoromethyl)pyridine-2-carboxamide Using the compound obtained in Example 634, step 1 and 4-(furan-2-ylcarbonyl)piperazine, and by the reaction and purification in the same manner as in Example 641, the title compound was obtained.
MS (ESI+): 638 (M+H)

Example 651

N-[(3R*,4R*)-1-{[trans-4-(acetylamino)cyclohexyl]carbonyl}-3-(4-fluorophenyl)piperidin-4-yl]-N-methyl-3,5-bis(trifluoromethyl)benzamide Using the compound obtained in Example 105 and trans-4-(acetylamino)cyclohexylcarboxylic acid, and by the reaction and purification in the same manner as in Example 3, the title compound was obtained.
MS (ESI+): 616 (M+H)

Example 652

N-[(3R*,4R*)-1-{[trans-4-(acetylamino)cyclohexyl]carbonyl}-3-(4-fluorophenyl)piperidin-4-yl]-3-bromo-N-methyl-5-(trifluoromethyl)benzamide Using the compound obtained in Example 106 and trans-4-(acetylamino)cyclohexylcarboxylic acid, and by the reaction and purification in the same manner as in Example 3, the title compound was obtained.
MS (ESI+): 626 (M+H)

Example 653

N-[(3R*,4R*)-1-{[trans-4-(acetylamino)cyclohexyl]carbonyl}-3-(4-chloro-3-methylphenyl)piperidin-4-yl]-N-methyl-3,5-bis(trifluoromethyl)benzamide Using the compound obtained in Example 68 and trans-4-(acetylamino)cyclohexylcarboxylic acid, and by the reaction and purification in the same manner as in Example 3, the title compound was obtained.
MS (ESI+): 646 (M+H)

Example 654a

N-[(3R*,4R*)-1-{[trans-4-(acetylamino)cyclohexyl]carbonyl}-3-phenylpiperidin-4-yl]-N-methyl-3,5-bis(trifluoromethyl)benzamide Using the compound obtained in Example 74 and trans-4-(acetylamino)cyclohexylcarboxylic acid, and by the reaction and purification in the same manner as in Example 3, the title compound was obtained.
MS (ESI+): 598 (M+H)

Example 654b

N-[(3R*,4R*)-1-{[trans-4-(acetylamino)cyclohexyl]carbonyl}-3-(4-methylphenyl)piperidin-4-yl]-N-methyl-3,5-bis(trifluoromethyl)benzamide Using the compound obtained in Example 116 and trans-4-(acetylamino)cyclohexylcarboxylic acid, and by the reaction and purification in the same manner as in Example 3, the title compound was obtained.
MS (ESI+): 612 (M+H)

Example 654c

N-[(3R*,4R*)-1-{[trans-4-(acetylamino)cyclohexyl]carbonyl}-3-(4-chlorophenyl)piperidin-4-yl]-N-methyl-3,5-bis(trifluoromethyl)benzamide Using the compound obtained in Example 120 and trans-4-(acetylamino)cyclohexylcarboxylic acid, and by the reaction and purification in the same manner as in Example 3, the title compound was obtained.
MS (ESI+): 632 (M+H)

Example 655

N-[(3R*,4R*)-1-{[trans-4-(acetylamino)cyclohexyl]carbonyl}-3-phenylpiperidin-4-yl]-3-bromo-N-methyl-5-(trifluoromethyl)benzamide Using the compound obtained in Example 125 and trans-4-(acetylamino)cyclohexylcarboxylic acid, and by the reaction and purification in the same manner as in Example 3, the title compound was obtained.
MS (ESI+): 608 (M+H)

Example 656

N-[(3R,4R)-1-{[trans-4-(acetylamino)cyclohexyl]carbonyl}-3-phenylpiperidin-4-yl]-3-bromo-N-methyl-5-(trifluoromethyl)benzamide Using the compound obtained in Example 136 and trans-4-(acetylamino)cyclohexylcarboxylic acid, and by the reaction and purification in the same manner as in Example 3, the title compound was obtained.
MS (ESI+): 608 (M+H)

Example 657

N-[(3R*,4R*)-1-{[trans-4-(acetylamino)cyclohexyl]
carbonyl}-3-(4-chloro-3-methylphenyl)piperidin-4-
yl]-3-bromo-N-methyl-5-(trifluoromethyl)benzamide Using the compound obtained in Example 126a and trans-4-(acetylamino)cyclohexylcarboxylic acid, and by the reaction and purification in the same manner as in Example 3, the title compound was obtained.
MS (ESI+): 656 (M+H)

Example 658

N-[(3R*,4R*)-1-{[trans-4-(acetylamino)cyclohexyl]
carbonyl}-3-(4-fluorophenyl)piperidin-4-yl]-4-
fluoro-N-methyl-3-(trifluoromethyl)benzamide Using the compound obtained in Example 127 and trans-4-(acetylamino)cyclohexylcarboxylic acid, and by the reaction and purification in the same manner as in Example 3, the title compound was obtained.
MS (ESI+): 566 (M+H)

Example 659

N-[(3R*,4R*)-1-{[trans-4-(acetylamino)cyclohexyl]
carbonyl}-3-(4-fluorophenyl)piperidin-4-yl]-4-
chloro-N-methyl-3-(trifluoromethyl)benzamide Using the compound obtained in Example 130 and trans-4-(acetylamino)cyclohexylcarboxylic acid, and by the reaction and purification in the same manner as in Example 3, the title compound was obtained.
MS (ESI+): 582 (M+H)

Example 660

4-chloro-N-[(3S,4R)-4-(3,4-dichlorophenyl)-1-{[1-
(hydroxyacetyl)piperidin-4-yl]carbonyl}pyrrolidin-
3-yl]-N-methylbenzamide Using the compound obtained in Example 114 and 1-(hydroxyacetyl)piperidine-4-carboxylic acid, and by the reaction and purification in the same manner as in Example 3, the title compound was obtained as a white powder.
MS (ESI+): 552 (M+H)

Example 661

4-{[(3R,4R)-3-(3,4-dichlorophenyl)-4-(methyl{[4-
(trifluoromethyl)phenyl]carbonyl}amino)piperidin-
1-yl]carbonyl}piperidine-1-carboxamide Using the compound obtained in Example 632, step 3 and 1-carbamoylpiperidine-4-carboxylic acid, and by the reaction and purification in the same manner as in Example 3, the title compound was obtained as a white powder.
MS (ESI+): 585 (M+H)

Example 662

N-[(3R,4R)-1-[(1-acetylpiperidin-4-yl)sulfonyl]-3-
(3,4-dichlorophenyl)piperidin-4-yl]-4-chloro-N-me-
thylbenzamide (Step 1)
A solution of the compound obtained in Example 496 (250 mg) and 6N hydrochloric acid (4 mL) in THF (4 mL) was stirred at 80° C. for 14 hr. The reaction mixture was made basic with 8N aqueous sodium hydroxide solution, and the resultant product was extracted with ethyl acetate. The organic layer was dried, and the solvent was evaporated under reduced pressure to give crude 4-chloro-N-[(3R,4R)-3-(3,4-dichlorophenyl)-1-(piperidin-4-ylsulfonyl)piperidin-4-yl]-N-methylbenzamide as a colorless oil.
MS (ESI+): 544 (M+H)
(Step 2)
Using the compound obtained in step 1 and acetyl chloride, and by the reaction and purification in the same manner as in Example 39, the title compound was obtained as a white powder.
MS (ESI+): 586 (M+H)

Example 663

N-[(3R,4R)-1-{[1-(cyclopropylcarbonyl)piperidin-4-
yl]carbonyl}-3-(3,4-dichlorophenyl)piperidin-4-yl]-
N-methyl-4-(trifluoromethyl)benzamide (Step 1)
Using the compound obtained in Reference Example 23, step 4 and 4-(trifluoromethyl)benzoic acid, and by the reaction and purification in the same manner as in Reference Example 1, step 5, Example 1 and Example 14, N-[(3R,4R)-3-(3,4-dichlorophenyl)piperidin-4-yl]-N-methyl-4-(trifluoromethyl)benzamide was obtained.
MS (ESI+): 431 (M+H)
(Step 2)
Using the compound obtained in step 1 and 1-(cyclopropylcarbonyl)piperidine-4-carboxylic acid, and by the reaction and purification in the same manner as in Example 97, the title compound was obtained.
MS (ESI+): 610 (M+H)

Example 664

4-cyclopropyl-N-[(3R,4R)-1-{[1-(cyclopropylcarbo-
nyl)piperidin-4-yl]carbonyl}-3-(3,4-dichlorophenyl)
piperidin-4-yl]-N-methylbenzamide Using the compound obtained in Example 649, step 1 and 1-(cyclopropylcarbonyl)piperidine-4-carboxylic acid, and by the reaction and purification in the same manner as in Example 97, the title compound was obtained.
MS (ESI+): 582 (M+H)

Example 665

5-bromo-N-[(3R,4R)-1-{[1-(cyclopropylcarbonyl)
piperidin-4-yl]carbonyl}-3-(3,4-dichlorophenyl)pip-
eridin-4-yl]-N-methylpyridine-2-carboxamide Using the compound obtained in Example 648, step 1 and 1-(cyclopropylcarbonyl)piperidine-4-carboxylic acid, and by the reaction and purification in the same manner as in Example 97, the title compound was obtained.
MS (ESI+): 621 (M+H)

Example 666

4-bromo-N-[(3R,4R)-1-{[1-(cyclopropylcarbonyl)
piperidin-4-yl]carbonyl}-3-(3,4-dichlorophenyl)pip-
eridin-4-yl]-N-methylbenzamide Using the compound obtained in Example 633, step 3 and 1-(cyclopropylcarbonyl)piperidine-4-carboxylic acid, and by the reaction and purification in the same manner as in Example 97, the title compound was obtained.

MS (ESI+): 620 (M+H)

Example 667

4-chloro-N-{(3R,4R)-3-(3,4-dichlorophenyl)-1-[(4-hydroxycyclohexyl)carbonyl]piperidin-4-yl}-N-methylbenzamide To a solution of the compound obtained in Example 518 (0.103 g) in methanol (1.8 mL) was added sodium carbonate (0.067 g) and the mixture was stirred at room temperature. The reaction mixture was poured into water, and the resultant product was extracted with ethyl acetate. The organic layer was washed with brine and dried, and the solvent was evaporated under reduced pressure to give the title compound (0.076 g, 80%) as a white powder.

MS (ESI+): 523 (M+H)

Example 668

N-[(3R,4R)-1-acetyl-3-(3,4-dichlorophenyl)piperidin-4-yl]-N-methyl-4-morpholin-4-ylbenzamide Using the compound obtained in Example 614, step 3 and acetyl chloride, and by the reaction and purification in the same manner as in Example 39, the title compound was obtained as a white powder.

MS (ESI+): 490 (M+H)

The compounds described in Examples 103-668 are as follows (Tables 20-71).

TABLE 20

TABLE 20-continued

| Ex. No. | A | B | C | R¹ | R² | salt/additive |
|---|---|---|---|---|---|---|
| 107 | (+)- 1-methyl-3,4-piperidine | 4-OCH₃-phenyl | 3-Br-5-CF₃-phenyl | H | CH₃ | HCl |
| 108 | (+)- 1-methyl-3,4-piperidine | 4-OCH₃-phenyl | 3,5-bis(CF₃)-phenyl | H | CH₃ | HCl |
| 109 | (+)- 1-methyl-3,4-piperidine | 3-Cl-4-CH₃-phenyl | 4-Cl-phenyl | H | CH₃ | HCl |
| 110 | (+)- 1-methyl-3,4-piperidine | 4-Cl-3-CH₃-phenyl | 4-Cl-phenyl | H | CH₃ | HCl |
| 111 | (+)- 1-methyl-3,4-piperidine | 2-CH₃-phenyl | 4-Cl-phenyl | H | CH₃ | HCl |
| 112 | (+)- 1-methyl-3,4-piperidine | 2-CH₃-5-F-phenyl | 4-Cl-phenyl | H | CH₃ | HCl |

TABLE 20-continued
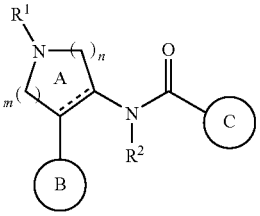
| Ex. No. | 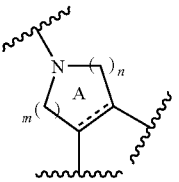 | B | C | R¹ | R² | salt/additive |
|---|---|---|---|---|---|---|
| 113 |  (±)- |  3,4-diCl-phenyl | 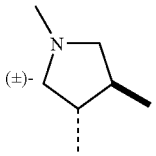 4-Cl-phenyl | H | CH₃ | HCl |
| 114 | 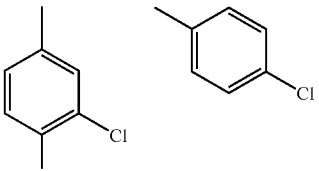 S,R | 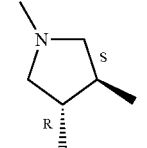 3,4-diCl-phenyl | 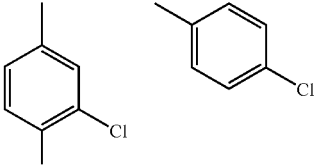 4-Cl-phenyl | H | CH₃ | HCl |
TABLE 21
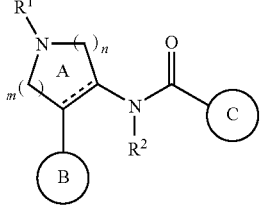
| Ex. No. | 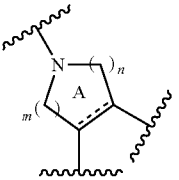 | B | C | R¹ | R² | salt/additive |
|---|---|---|---|---|---|---|
| 115 |  (+)- |  phenyl | 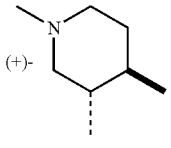 2-thienyl | H | CH₃ | HCl |

TABLE 21-continued

| Ex. No. | A | B | C | R¹ | R² | salt/additive |
|---|---|---|---|---|---|---|
| 116 | (+)- 1-methyl-piperidinyl (3,4-dimethyl) | 4-methylphenyl | 3,5-bis(CF₃)phenyl | H | CH₃ | HCl |
| 117 | (+)- 1-methyl-piperidinyl | 4-methylphenyl | 3-Br-5-CF₃-phenyl | H | CH₃ | HCl |
| 118 | (+)- 1-methyl-piperidinyl | 3,5-dichlorophenyl | 3,5-bis(CF₃)phenyl | H | CH₃ | HCl |
| 119 | (+)- 1-methyl-piperidinyl | 4-bromophenyl | 4-OCH₃-phenyl | H | CH₃ | HCl |
| 120 | (+)- 1-methyl-piperidinyl | 4-chlorophenyl | 3,5-bis(CF₃)phenyl | H | CH₃ | HCl |
| 121 | (+)- 1-methyl-piperidinyl | 4-chlorophenyl | 3-Br-5-CF₃-phenyl | H | CH₃ | HCl |

TABLE 21-continued

| Ex. No. | A | B | C | R¹ | R² | salt/additive |
|---|---|---|---|---|---|---|
| 122 | (+)- 1-methyl-3,4-dimethylpiperidine | 3-chlorophenyl | 3,5-bis(trifluoromethyl)phenyl | H | CH₃ | HCl |
| 123 | (+)- 1-methyl-3,4-dimethylpiperidine | 4-bromophenyl | 3,5-bis(trifluoromethyl)phenyl | H | CH₃ | HCl |
| 124 | (+)- 1-methyl-3,4-dimethylpiperidine | 3,4-dibromophenyl | 3-bromo-5-(trifluoromethyl)phenyl | H | CH₃ | HCl |
| 125 | (+)- 1-methyl-3,4-dimethylpiperidine | phenyl | 3-bromo-5-(trifluoromethyl)phenyl | H | CH₃ | HCl |
| 126a | (+)- 1-methyl-3,4-dimethylpiperidine | 4-chloro-2-methylphenyl | 3-bromo-5-(trifluoromethyl)phenyl | H | CH₃ | HCl |

TABLE 22
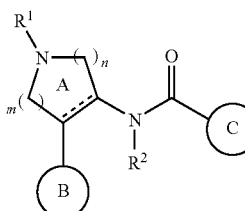
| Ex. No. | 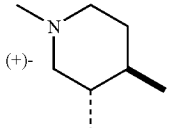 | B | C | R¹ | R² | salt/additive |
|---|---|---|---|---|---|---|
| 126b | (+)-  |  3,4-diCl | 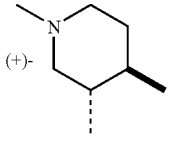 3-Br, 5-CF₃ | H | CH₃ | HCl |
| 126c | (+)-  | 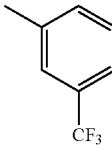 3-F, 4-CH₃ | 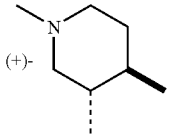 3-Br, 5-CF₃ | H | CH₃ | HCl |
| 126d | (+)- 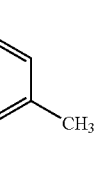 |  3-CH₃, 4-F | 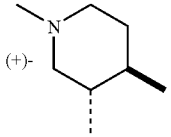 3-Br, 5-CF₃ | H | CH₃ | HCl |
| 127 | (+)- 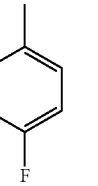 | 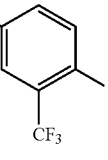 4-F | 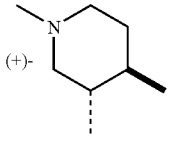 3-CF₃, 4-F | H | CH₃ | HCl |
| 128 | (+)- 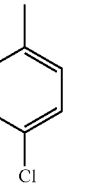 | 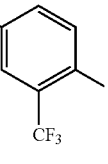 4-Cl | 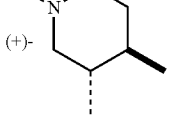 3-CF₃, 4-F | H | CH₃ | HCl |
| 129 | (+)- 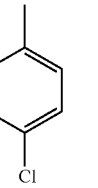 | 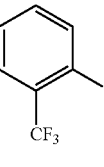 4-Cl | 3-CF₃, 4-Cl | H | CH₃ | HCl |

TABLE 22-continued
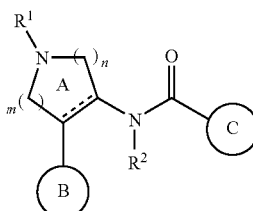
| Ex. No. | 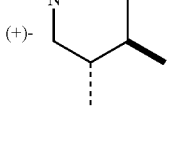 | B | C | R¹ | R² | salt/additive |
|---|---|---|---|---|---|---|
| 130 | 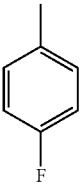 (+)- | 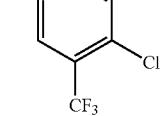 | 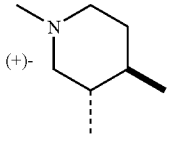 | H | CH₃ | HCl |
| 131 | 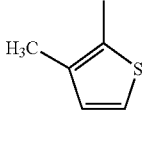 (+)- | 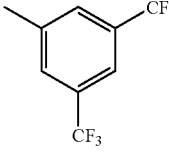 | 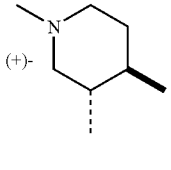 | H | CH₃ | HCl |
| 132 |  (+)- | 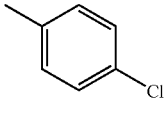 | 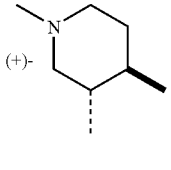 | H | CH₃ | HCl |
| 133 |  (+)- | 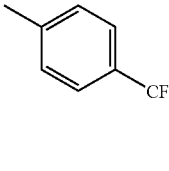 | 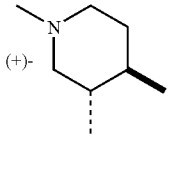 | H | CH₃ | HCl |
| 134 |  (+)- | 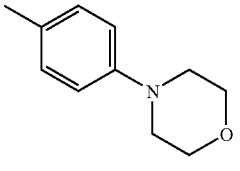 | 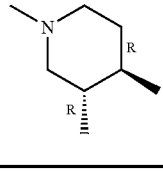 | H | CH₃ | HCl |
| 135 | 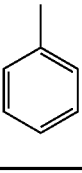 | 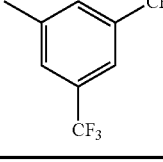 | | H | CH₃ | HCl |

TABLE 23

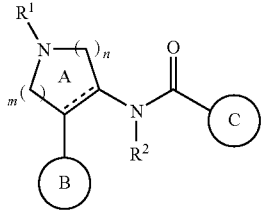

| Ex. No. | [A ring] | B | C | R¹ | R² | salt/additive |
|---|---|---|---|---|---|---|
| 136 | N-methylpiperidine (R,R) | phenyl | 3-Br-5-CF₃-phenyl | H | CH₃ | HCl |
| 137a | N-methylpiperidine (R,R) | 3,4-diCl-phenyl | 4-Cl-phenyl | H | CH₃ | HCl |
| 137b | N-methylpiperidine (R,R) | 3,4-diCl-phenyl | 4-Cl-phenyl | H | C₂H₅ | HCl |
| 138 | N-methylpiperidine (±) | 3,4-diCl-phenyl | 3-Br-5-CF₃-phenyl | C(CH₃)₃-O-C(O)- | CH₃ | |
| 139 | N-methylpiperidine (±) | 4-CH₃-3-F-phenyl | 3-Br-5-CF₃-phenyl | C(CH₃)₃-O-C(O)- | CH₃ | |
| 140 | N-methylpiperidine (±) | 3-CH₃-4-F-phenyl | 3-Br-5-CF₃-phenyl | C(CH₃)₃-O-C(O)- | CH₃ | |

TABLE 23-continued

| Ex. No. | A | B | C | R¹ | R² | salt/additive |
|---|---|---|---|---|---|---|
| 141 | (±)- N-methylpiperidine | 2-F-4-methylphenyl (with CH₃) | 3,5-bis(CF₃)phenyl | tert-butyl acetate | CH₃ | |
| 142 | (±)- N-methylpiperidine | 4-F-3-methylphenyl | 3,5-bis(CF₃)phenyl | tert-butyl acetate | CH₃ | |
| 143 | (±)- N-methylpiperidine | 4-F-phenyl | 3,5-bis(CF₃)phenyl | tert-butyl acetate | CH₃ | |
| 144 | (±)- N-methylpiperidine | 4-F-phenyl | 3-Br-5-CF₃-phenyl | tert-butyl acetate | CH₃ | |
| 145 | (±)- N-methylpiperidine | 4-OCH₃-phenyl | 3-Br-5-CF₃-phenyl | tert-butyl acetate | CH₃ | |
| 146 | (±)- N-methylpiperidine | 4-OCH₃-phenyl | 3,5-bis(CF₃)phenyl | tert-butyl acetate | CH₃ | |

TABLE 24
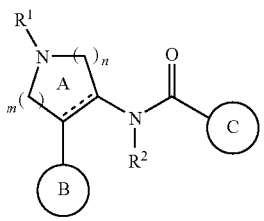
| Ex. No. | 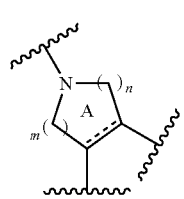 | B | C | R¹ | R² | salt/additive |
|---|---|---|---|---|---|---|
| 147 |  (±)- |  (4-CH₃-C₆H₄) | 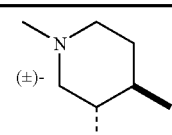 (3,5-bis-CF₃-C₆H₃) |  (OC(CH₃)₃) | CH₃ | |
| 148 |  (±)- | 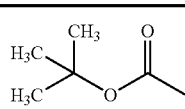 (4-CH₃-C₆H₄) | 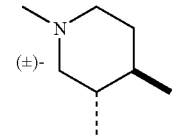 (3-Br-5-CF₃-C₆H₃) |  (OC(CH₃)₃) | CH₃ | |
| 149 |  (±)- | 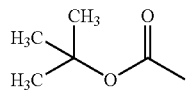 (3,5-Cl₂-C₆H₃) | 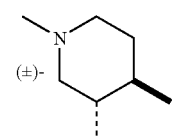 (3,5-bis-CF₃-C₆H₃) |  (OC(CH₃)₃) | CH₃ | |
| 150 |  (±)- | 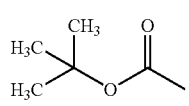 (4-Cl-C₆H₄) | 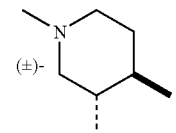 (3,5-bis-CF₃-C₆H₃) |  (OC(CH₃)₃) | CH₃ | |
| 151 |  (±)- | 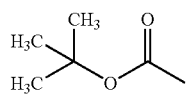 (3-Cl-C₆H₄) | 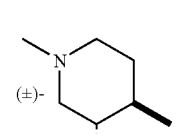 (3,5-bis-CF₃-C₆H₃) |  (OC(CH₃)₃) | CH₃ | |
| 152 |  (±)- | 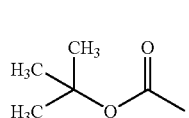 (4-Br-C₆H₄) | 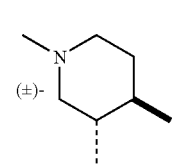 (3,5-bis-CF₃-C₆H₃) | 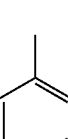 (OC(CH₃)₃) | CH₃ | |

US 8,470,816 B2
TABLE 24-continued
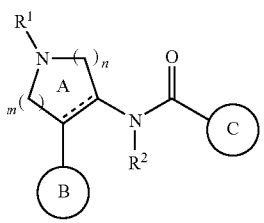
| Ex. No. | 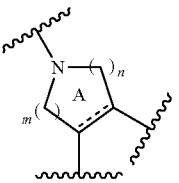 | B | C | R¹ | R² | salt/ additive |
|---|---|---|---|---|---|---|
| 153a |  (±)- |  | 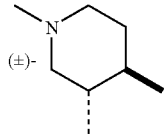 | 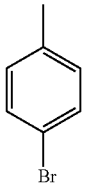 | CH₃ | |
| 153b | 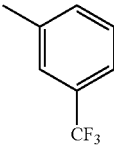 (±)- | 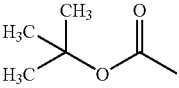 |  | 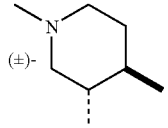 | CH₃ | |
| 154 | 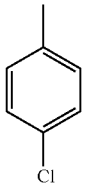 (±)- | 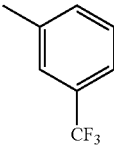 | 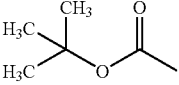 |  | CH₃ | |
| 155 | 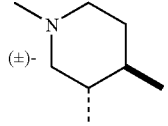 (±)- | 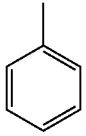 | 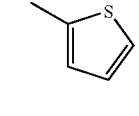 | 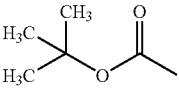 | CH₃ | |
| 156 |  (±)- | 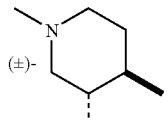 | 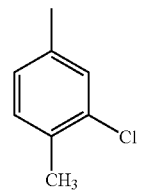 | 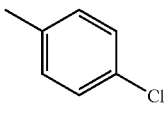 | CH₃ | |
| 157 | 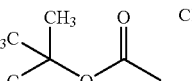 (±)- |  | 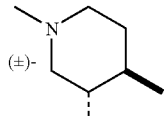 | 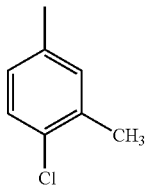 | CH₃ | |

TABLE 25

| Ex. No. | A ring | B | C | R¹ | R² | salt/additive |
|---|---|---|---|---|---|---|
| 158 | (±)- 1-methyl-piperidin-3,4-diyl | 2-methyl-4-fluorophenyl | 4-chlorophenyl | C(CH₃)₂-O-C(O)-CH₃ | CH₃ | |
| 159 | (±)- 1-methyl-piperidin-3,4-diyl | 4-bromophenyl | 4-methoxyphenyl | C(CH₃)₂-O-C(O)-CH₃ | CH₃ | |
| 160 | (±)- 1-methyl-piperidin-3,4-diyl | phenyl | 3-bromo-5-trifluoromethylphenyl | C(CH₃)₂-O-C(O)-CH₃ | CH₃ | |
| 161 | (±)- 1-methyl-piperidin-3,4-diyl | 4-chlorophenyl | 4-fluoro-3-trifluoromethylphenyl | C(CH₃)₂-O-C(O)-CH₃ | CH₃ | |
| 162 | (±)- 1-methyl-piperidin-3,4-diyl | 4-chlorophenyl | 4-chloro-3-trifluoromethylphenyl | C(CH₃)₂-O-C(O)-CH₃ | CH₃ | |
| 163 | (±)- 1-methyl-piperidin-3,4-diyl | 4-fluorophenyl | 4-chloro-3-trifluoromethylphenyl | C(CH₃)₂-O-C(O)-CH₃ | CH₃ | |

TABLE 25-continued

| Ex. No. | A | B | C | R¹ | R² | salt/additive |
|---|---|---|---|---|---|---|
| 164 | (±)- N-methyl piperidine (3,4-dimethyl) | 2,3-dimethylthiophene | 3,5-bis(CF₃)phenyl | tert-butyl acetate | CH₃ | |
| 165 | (±)- N-methyl piperidine (3,4-dimethyl) | 4-CF₃-phenyl | 4-Cl-phenyl | tert-butyl acetate | CH₃ | |
| 166 | (±)- N-methyl piperidine (3,4-dimethyl) | 4-CF₃-phenyl | 4-CF₃-phenyl | tert-butyl acetate | CH₃ | |
| 167 | (±)- N-methyl piperidine (3,4-dimethyl) | 4-CF₃-phenyl | 4-morpholinophenyl | tert-butyl acetate | CH₃ | |
| 168 | N-methyl piperidine (3R,4R) | 3,4-dichlorophenyl | 4-Cl-phenyl | tert-butyl acetate | CH₃ | |
| 169 | N-methyl piperidine (3R,4R) | 3,4-dichlorophenyl | 4-OCH₃-phenyl | tert-butyl acetate | CH₃ | |

TABLE 26
| Ex. No. | 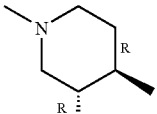 | B | C | R¹ | R² | salt/additive |
|---|---|---|---|---|---|---|
| 170 | 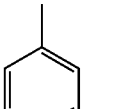 | 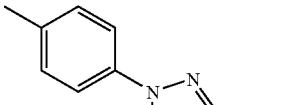 3,4-diCl | 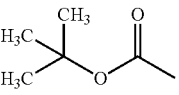 1-(p-tolyl)-3-methylpyrazol-5-yl | 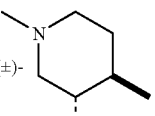 tert-butyl acetate | CH₃ | CH₃ |
| 171 | 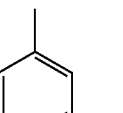 (±)- | 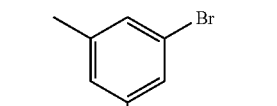 4-Cl-3-CH₃ | 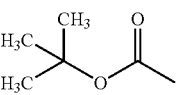 3-Br-5-CF₃ | 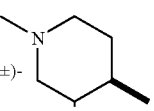 | CH₃ | CH₃ |
| 172 | 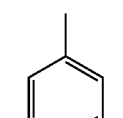 (±)- | 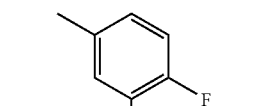 4-F | 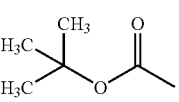 4-F-3-CF₃ | 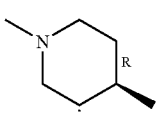 | CH₃ | CH₃ |
| 173 | 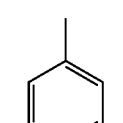 | 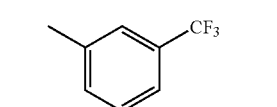 | 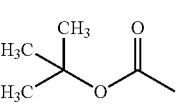 3,5-di-CF₃ | 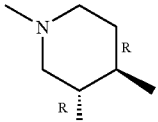 | CH₃ | CH₃ |
| 174 | 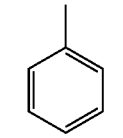 | 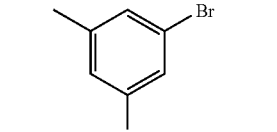 | 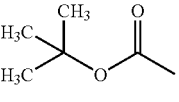 3-Br-5-CF₃ | 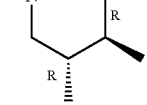 | CH₃ | CH₃ |
| 175 | 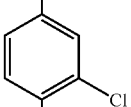 | 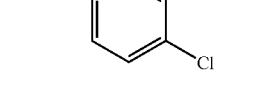 3,4-diCl | 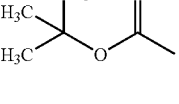 4-Cl | 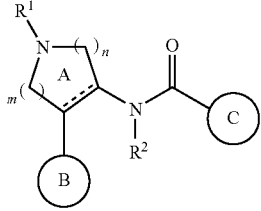 | CH₃ | C₂H₅ |

TABLE 26-continued
| Ex. No. | 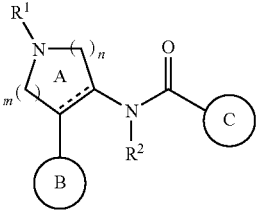 | B | C | R¹ | R² | salt/additive |
|---|---|---|---|---|---|---|
| 176 | 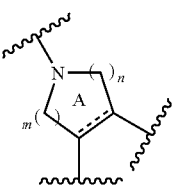 (±)- |  |  | 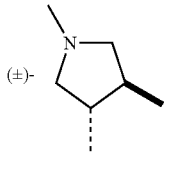 | CH₃ | |
| 177 | 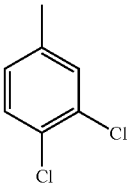 |  | 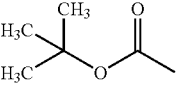 | 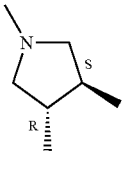 | CH₃ | |
| 178 | 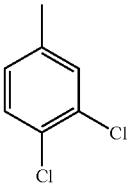 (±)- |  | 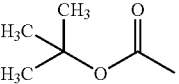 | 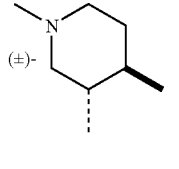 | CH₃ | |
| 179 |  (±)- |  | 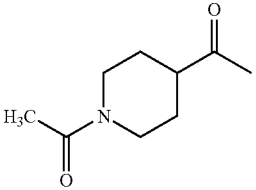 | 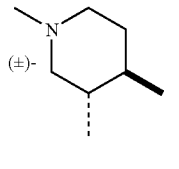 | CH₃ | |
| 180 | 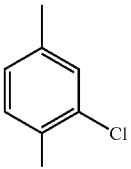 (±)- |  | 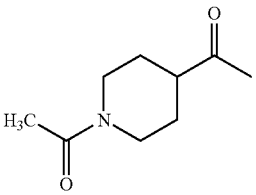 | 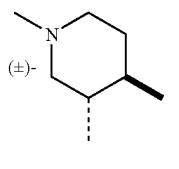 | CH₃ | |

TABLE 26-continued
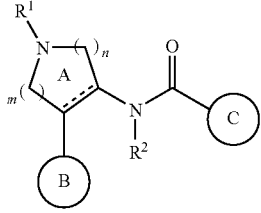
| Ex. No. | 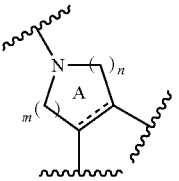 | B | C | R[1] | R[2] | salt/additive |
|---|---|---|---|---|---|---|
| 181 | 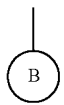 (±)- |  | 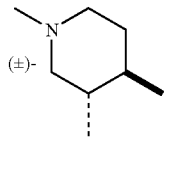 | 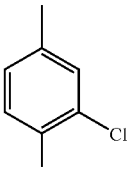 | CH$_3$ | |
TABLE 27
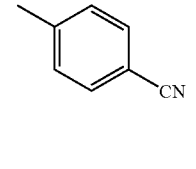
| Ex. No. | 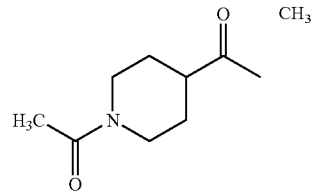 | B | C | R[1] | R[2] | salt/additive |
|---|---|---|---|---|---|---|
| 182 | 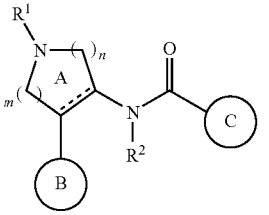 (±)- | 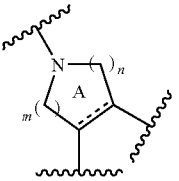 | 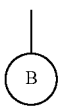 |  | CH$_3$ | |
| 183 | 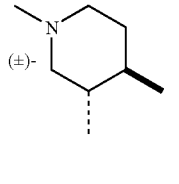 (±)- | 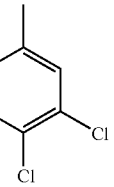 | 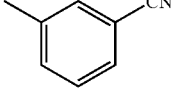 | 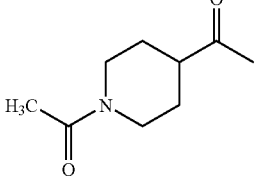 | CH$_3$ | |

TABLE 27-continued

| Ex. No. | A | B | C | R¹ | R² | salt/additive |
|---|---|---|---|---|---|---|
| 184 | (±)- 1-methyl-piperidinyl | 3,4-dichlorophenyl | 2-indolyl | 1-acetylpiperidin-4-yl | CH₃ | |
| 185 | (±)- 1-methyl-piperidinyl | 3,4-dichlorophenyl | 3-indolyl | 1-acetylpiperidin-4-yl | CH₃ | |
| 186 | (±)- 1-methyl-piperidinyl | 3,4-dichlorophenyl | 4-tert-butylphenyl | 1-acetylpiperidin-4-yl | CH₃ | |
| 187 | (±)- 1-methyl-piperidinyl | 3,4-dichlorophenyl | 4-acetamidophenyl | 1-acetylpiperidin-4-yl | CH₃ | |
| 188 | (±)- 1-methyl-piperidinyl | 3,4-dichlorophenyl | 4-(methoxycarbonyl)phenyl | 1-acetylpiperidin-4-yl | CH₃ | |

TABLE 27-continued
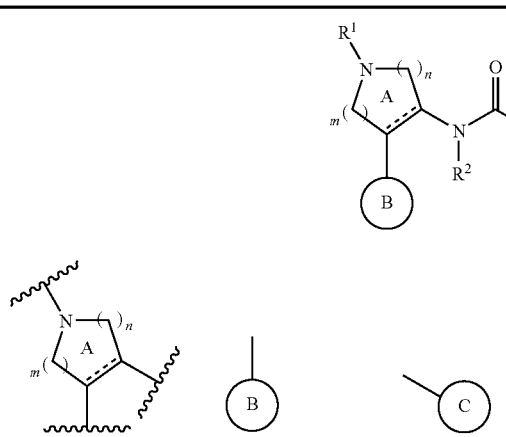
| Ex. No. | 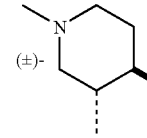 | B | C | R[1] | R[2] | salt/ additive |
|---|---|---|---|---|---|---|
| 189 |  (±)- |  | 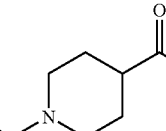 | 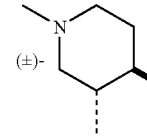 | CH$_3$ | |
| 190 |  (±)- |  | 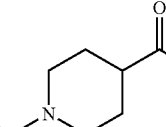 | 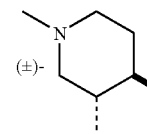 | CH$_3$ | |
| 191 | 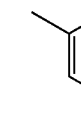 (±)- |  | 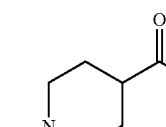 | 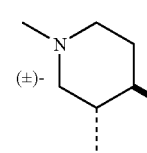 | CH$_3$ | |
| 192 | 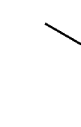 (±)- |  | 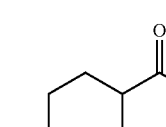 | 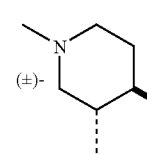 | CH$_3$ | |
| 193 | 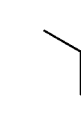 (±)- |  | 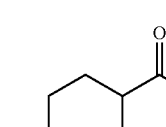 | | CH$_3$ | |

TABLE 28

| Ex. No. | A | B | C | R¹ | R² | salt/additive |
|---|---|---|---|---|---|---|
| 194 | (±)- N-methyl-piperidinyl | 3,4-dichlorophenyl | 2-fluorophenyl | 1-acetylpiperidin-4-yl | CH₃ | |
| 195 | (±)- N-methyl-piperidinyl | 3,4-dichlorophenyl | 3-cyanophenyl | 1-acetylpiperidin-4-yl | CH₃ | |
| 196 | (±)- N-methyl-piperidinyl | 3,4-dichlorophenyl | furan-3-yl | 1-acetylpiperidin-4-yl | CH₃ | |
| 197 | (±)- N-methyl-piperidinyl | 3,4-dichlorophenyl | 2-methylphenyl | 1-acetylpiperidin-4-yl | CH₃ | |
| 198 | (±)- N-methyl-piperidinyl | 3,4-dichlorophenyl | 3-methylphenyl | 1-acetylpiperidin-4-yl | CH₃ | |
| 199 | (±)- N-methyl-piperidinyl | 3,4-dichlorophenyl | imidazol-4-yl | 1-acetylpiperidin-4-yl | CH₃ | TFA |

TABLE 28-continued
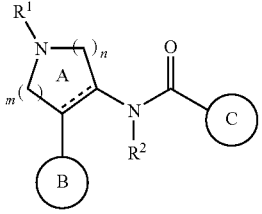
| Ex. No. | 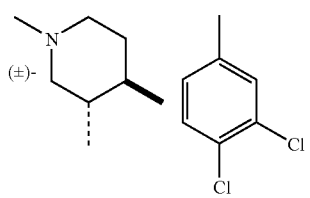 | B | C | R¹ | R² | salt/additive |
|---|---|---|---|---|---|---|
| 200 | 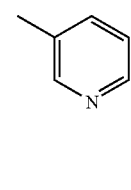 | 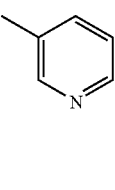 | 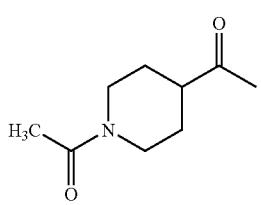 | 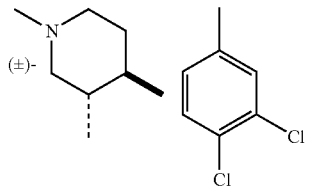 | CH₃ | TFA |
| 201 | 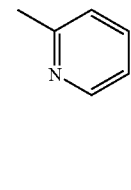 | 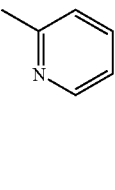 | 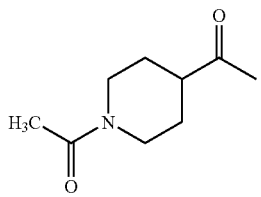 | 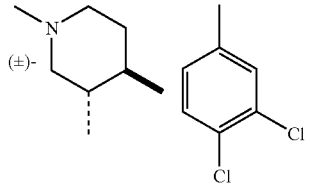 | CH₃ | TFA |
| 202 | 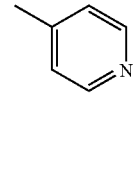 | 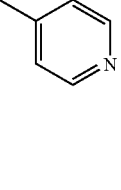 | 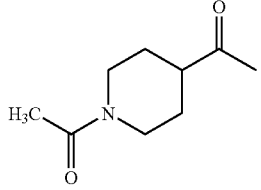 | 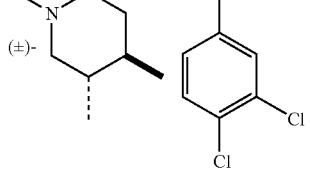 | CH₃ | TFA |
| 203 | 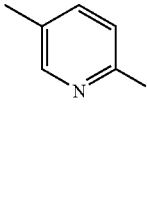 | 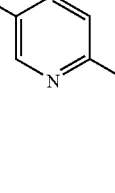 | 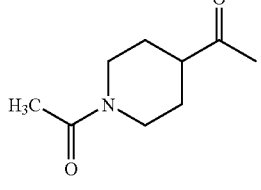 | 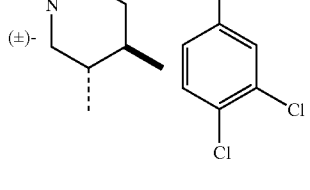 | CH₃ | TFA |
| 204 | 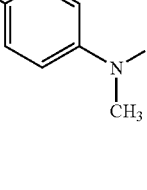 | 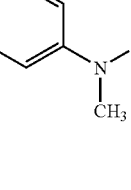 | 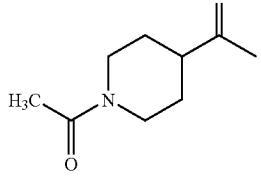 |  | CH₃ | TFA |

TABLE 28-continued

| Ex. No. | (structure A) | B | C | R¹ | R² | salt/additive |
|---|---|---|---|---|---|---|
| 205 | (±)- N-methylpiperidine | 3,4-dichlorophenyl | 2-methyl-5-chloropyridyl | 1-acetylpiperidin-4-yl-carbonyl | CH₃ | TFA |

TABLE 29

| Ex. No. | (structure A) | B | C | R¹ | R² | salt/additive |
|---|---|---|---|---|---|---|
| 206 | (±)- N-methylpiperidine | 3,4-dichlorophenyl | 3-cyano-5-fluorophenyl | 1-acetylpiperidin-4-yl-carbonyl | CH₃ | |
| 207 | (±)- N-methylpiperidine | 3,4-dichlorophenyl | 3-CF₃-5-chlorophenyl | 1-acetylpiperidin-4-yl-carbonyl | CH₃ | |

TABLE 29-continued
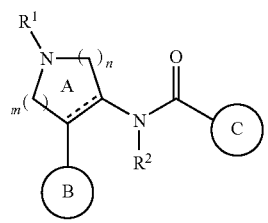
| Ex. No. | 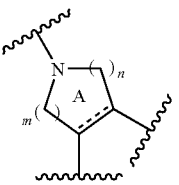 | B | C | R[1] | R[2] | salt/additive |
|---|---|---|---|---|---|---|
| 208 |  |  | 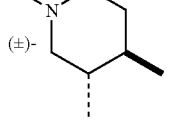 | 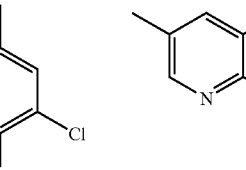 | CH₃ | TFA |
| 209 | 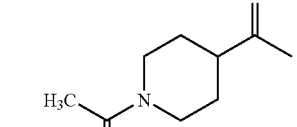 | 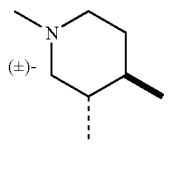 | 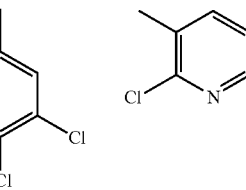 | 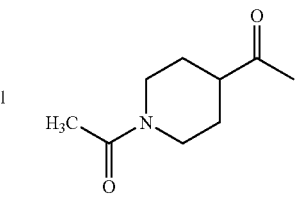 | CH₃ | TFA |
| 210 | 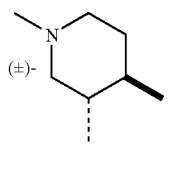 | 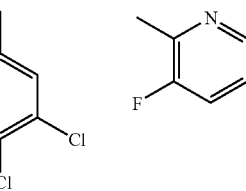 | 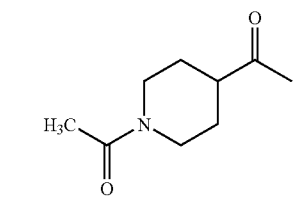 | 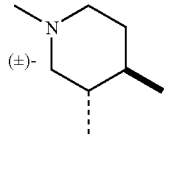 | CH₃ | TFA |
| 211 | 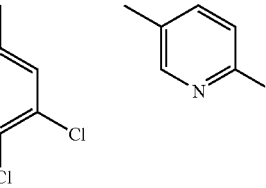 | 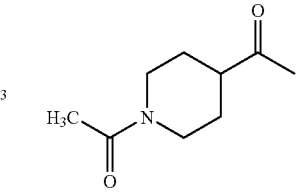 | 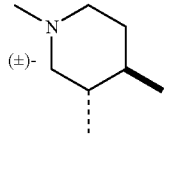 | 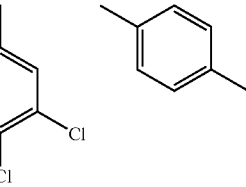 | CH₃ | TFA |
| 212 | 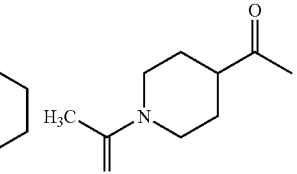 | | 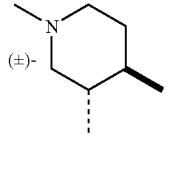 | | CH₃ | |
| 213 | 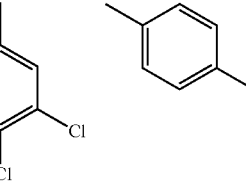 | | 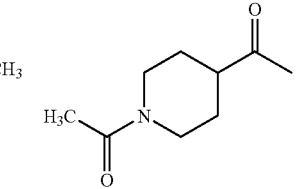 | | CH₃ | |

US 8,470,816 B2

357                                                                                      358

TABLE 29-continued

| Ex. No. | A | B | C | R¹ | R² | salt/additive |
|---|---|---|---|---|---|---|
| 214 | (±)- N-methylpiperidine | 3,4-dichlorophenyl | 3,4-dichlorophenyl | 1-acetylpiperidin-4-yl | CH₃ | |
| 215 | (±)- N-methylpiperidine | 3,4-dichlorophenyl | 3,5-dimethylphenyl | 1-acetylpiperidin-4-yl | CH₃ | |
| 216 | (±)- N-methylpiperidine | 3,4-dichlorophenyl | 1H-pyrrol-2-yl | 1-acetylpiperidin-4-yl | CH₃ | |
| 217 | (±)- N-methylpiperidine | 3,4-dichlorophenyl | 3-biphenyl | 1-acetylpiperidin-4-yl | CH₃ | |

TABLE 30

| Ex. No. | A | B | C | R¹ | R² | salt/additive |
|---|---|---|---|---|---|---|
| 218 | (±)- 1-methyl-piperidine | 3,4-dichlorophenyl | 2-methyl-5-benzimidazole | 1-acetylpiperidin-4-yl | CH₃ | TFA |
| 219 | (±)- 1-methyl-piperidine | 3,4-dichlorophenyl | 4-(difluoromethoxy)phenyl | 1-acetylpiperidin-4-yl | CH₃ | |
| 220 | (±)- 1-methyl-piperidine | 3,4-dichlorophenyl | 4-carbamoylphenyl | 1-acetylpiperidin-4-yl | CH₃ | |
| 221 | (±)- 1-methyl-piperidine | 3,4-dichlorophenyl | 1H-pyrazol-4-yl | 1-acetylpiperidin-4-yl | CH₃ | TFA |
| 222 | (±)- 1-methyl-piperidine | 3,4-dichlorophenyl | 1H-pyrrol-3-yl | 1-acetylpiperidin-4-yl | CH₃ | |

TABLE 30-continued
| Ex. No. | 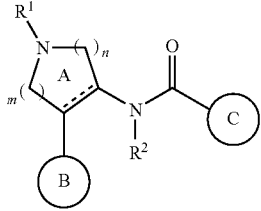 | B | C | R¹ | R² | salt/additive |
|---|---|---|---|---|---|---|
| 223 | 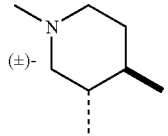 | 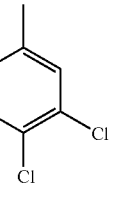 | 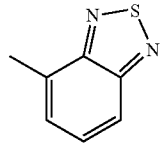 | 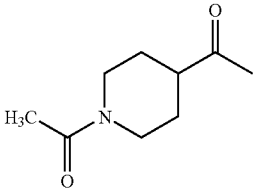 | CH₃ | |
| 224 | 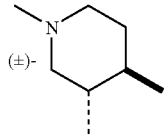 | 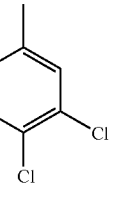 | 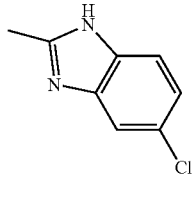 | 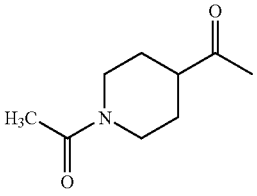 | CH₃ | |
| 225 | 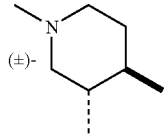 | 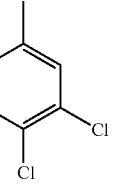 | 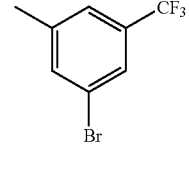 | 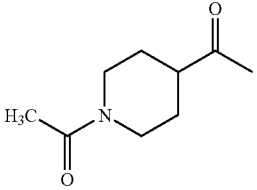 | CH₃ | |
| 226 | 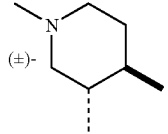 | 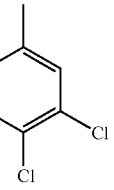 | 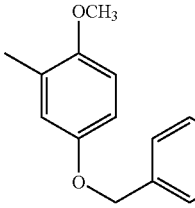 | 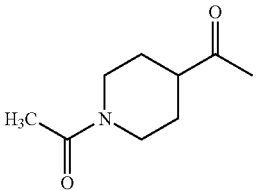 | CH₃ | |
| 227 | 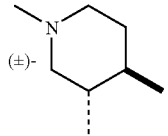 | 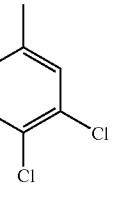 | 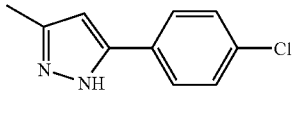 | 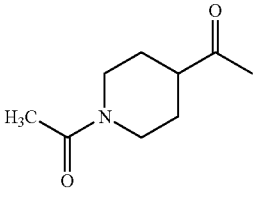 | CH₃ | TFA |

TABLE 30-continued
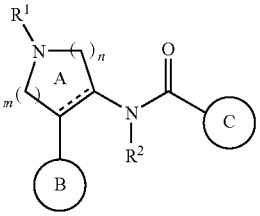
| Ex. No. | 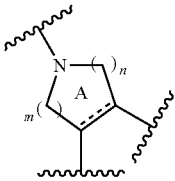 | B | C | R¹ | R² | salt/additive |
|---|---|---|---|---|---|---|
| 228 | (±)-  |  | 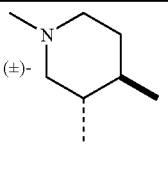 | 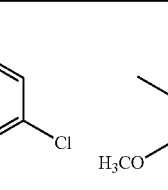 | CH₃ | |
| 229 | (±)- 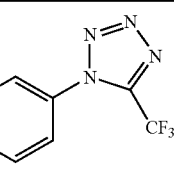 | 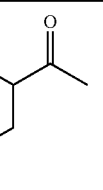 | 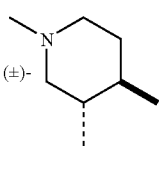 | 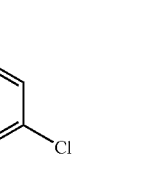 | CH₃ | |
TABLE 31
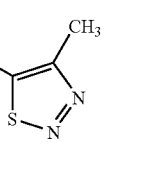
| Ex. No. | 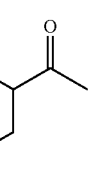 | B | C | R¹ | R² | salt/additive |
|---|---|---|---|---|---|---|
| 230 | (±)- 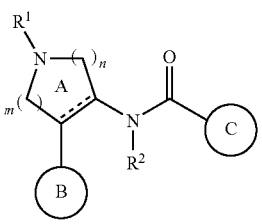 | 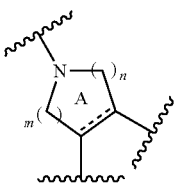 |  |  | CH₃ | TFA |

TABLE 31-continued

| Ex. No. | A | B | C | R¹ | R² | salt/additive |
|---|---|---|---|---|---|---|
| 231 | (±)- 1-methylpiperidin-3,4-diyl | 3,4-dichlorophenyl | 2-biphenyl | 1-acetylpiperidin-4-yl | CH₃ | |
| 232 | (±)- 1-methylpiperidin-3,4-diyl | 3-chloro-4-methylphenyl | 4-chlorophenyl | 1-acetylpiperidin-4-yl | CH₃ | |
| 233 | (±)- 1-methylpiperidin-3,4-diyl | 2-chloro-3-methylphenyl | 4-chlorophenyl | 1-acetylpiperidin-4-yl | CH₃ | |
| 234 | (±)- 1-methylpiperidin-3,4-diyl | 2-methylphenyl | 4-chlorophenyl | 1-acetylpiperidin-4-yl | CH₃ | |
| 235 | (±)- 1-methylpiperidin-3,4-diyl | 5-fluoro-2-methylphenyl | 4-chlorophenyl | 1-acetylpiperidin-4-yl | CH₃ | |

TABLE 31-continued
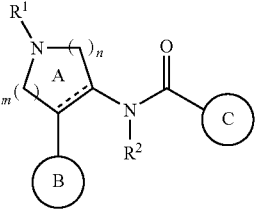
| Ex. No. | 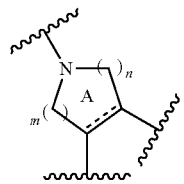 | B | C | R¹ | R² | salt/ additive |
|---|---|---|---|---|---|---|
| 236 | 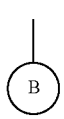 (±)- |  | 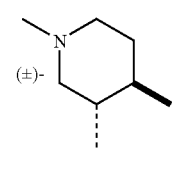 | 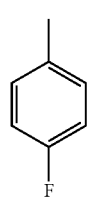 | CH₃ | |
| 237 | 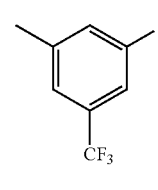 (±)- | 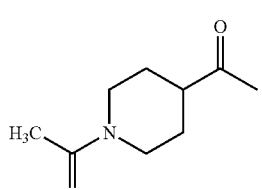 | 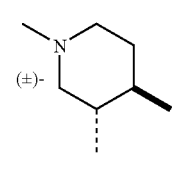 | 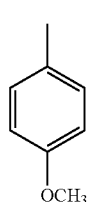 | CH₃ | |
| 238 | 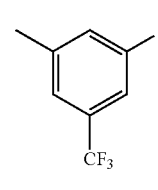 (±)- | 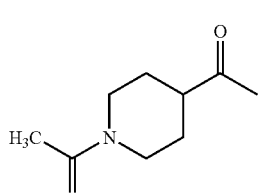 | 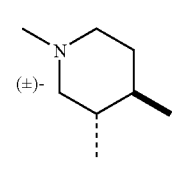 | 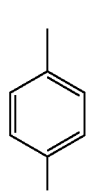 | CH₃ | |
| 239 | 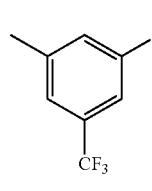 (±)- | 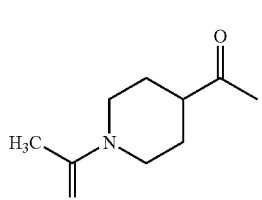 | 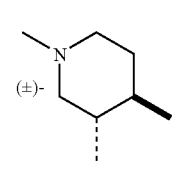 | 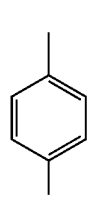 | CH₃ | |
| 240 | 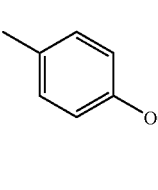 (±)- | 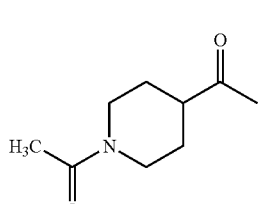 | 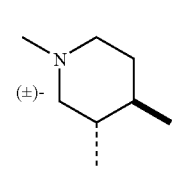 | 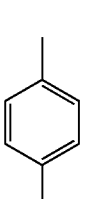 | CH₃ | |

TABLE 31-continued
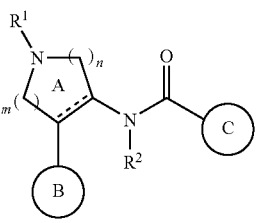
| Ex. No. | 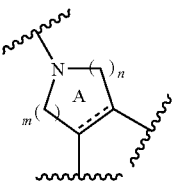 | B | C | R[1] | R[2] | salt/additive |
|---|---|---|---|---|---|---|
| 241 | 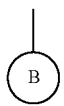 | 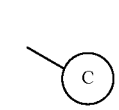 | 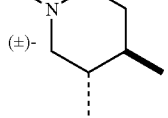 | 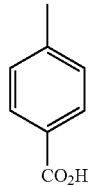 | CH[3] | |
TABLE 32
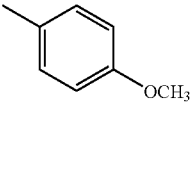
| Ex. No. | 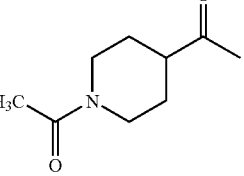 | B | C | R[1] | R[2] | salt/additive |
|---|---|---|---|---|---|---|
| 242 |  | 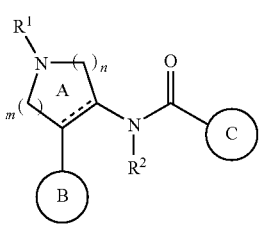 | 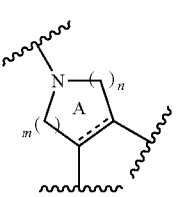 |  | CH[3] | |

US 8,470,816 B2
TABLE 32-continued
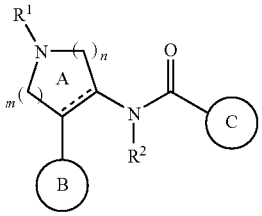
| Ex. No. | 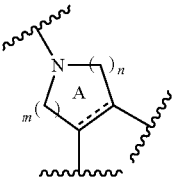 | B | C | R¹ | R² | salt/additive |
|---|---|---|---|---|---|---|
| 243 |  |  | 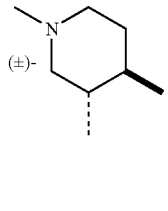 | 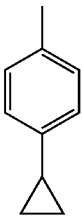 | CH₃ | |
| 244 | 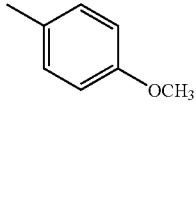 | 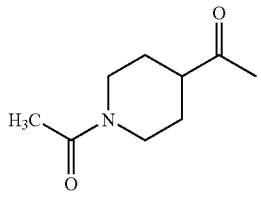 | 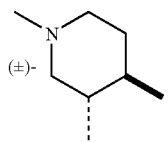 |  | CH₃ | |
| 245 | 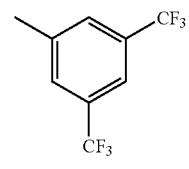 | 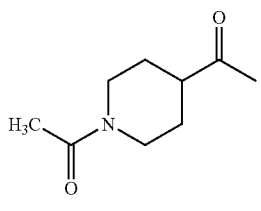 | 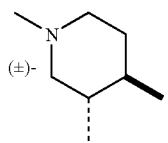 |  | CH₃ | |
| 246 | 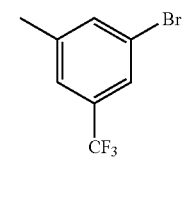 | 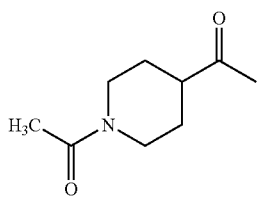 | 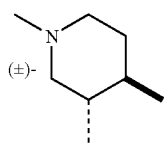 | 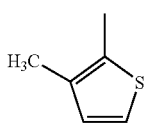 | CH₃ | |
| 247 | 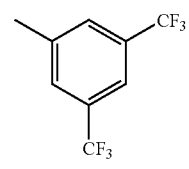 | 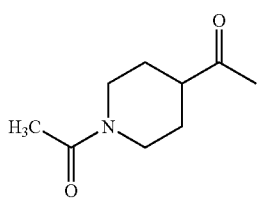 | 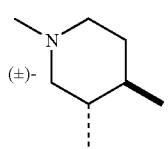 | 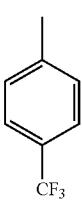 | CH₃ | |

TABLE 32-continued
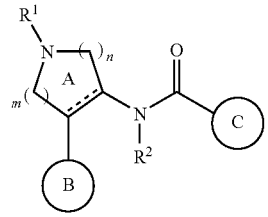
| Ex. No. | 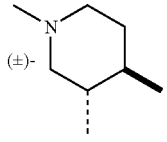 | B | C | R¹ | R² | salt/additive |
|---|---|---|---|---|---|---|
| 248 | 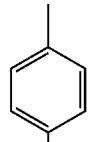 (±)- | 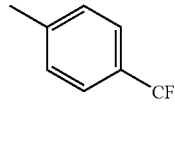 | 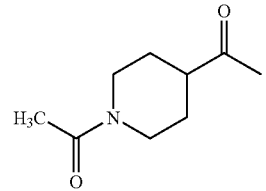 | 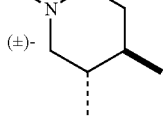 | CH₃ | |
| 249 | 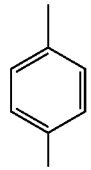 (±)- | 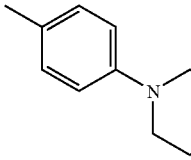 | 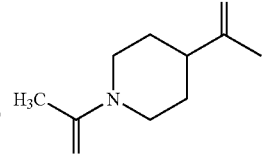 | 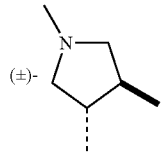 | CH₃ | |
| 250 | 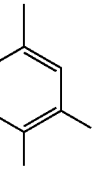 (±)- | 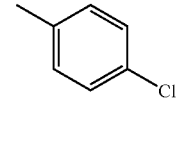 | 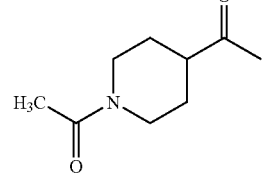 | 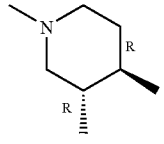 | CH₃ | |
| 251a | 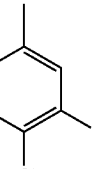 | 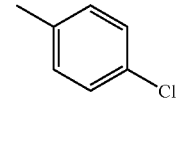 | 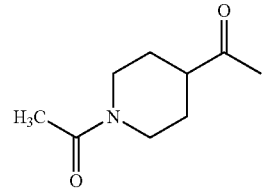 | 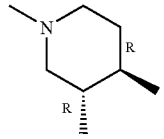 | CH₃ | |
| 251b | 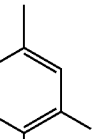 | 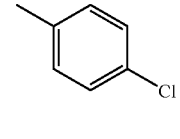 | 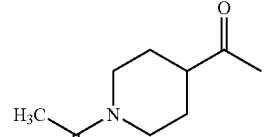 | | CH₃ | 0.5H₂O |

TABLE 33

| Ex. No. | A | B | C | R¹ | R² | salt/additive |
|---|---|---|---|---|---|---|
| 251c | 1-methyl piperidine (R,R) | 3,4-dichlorophenyl | 4-chlorophenyl | 1-acetylpiperidin-4-yl | CH₃ | H₂O |
| 252 | 1-methyl piperidine (R,R) | 3,4-dichlorophenyl | 4-methoxyphenyl | 1-acetylpiperidin-4-yl | CH₃ | |
| 253 | 1-methyl piperidine (R,R) | 3,4-dichlorophenyl | 1-(4-methylphenyl)-3-methyl-pyrazol-5-yl | 1-acetylpiperidin-4-yl | CH₃ | |
| 254 | 1-methyl piperidine (R,R) | 3,4-dichlorophenyl | 4-fluorophenyl | 1-acetylpiperidin-4-yl | CH₃ | |
| 255 | 1-methyl piperidine (R,R) | 3,4-dichlorophenyl | 4-bromophenyl | 1-acetylpiperidin-4-yl | CH₃ | |

TABLE 33-continued
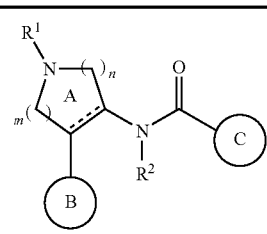

TABLE 34
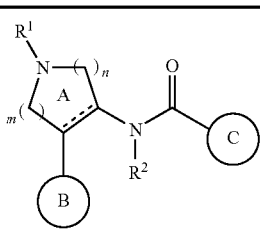
| Ex. No. | 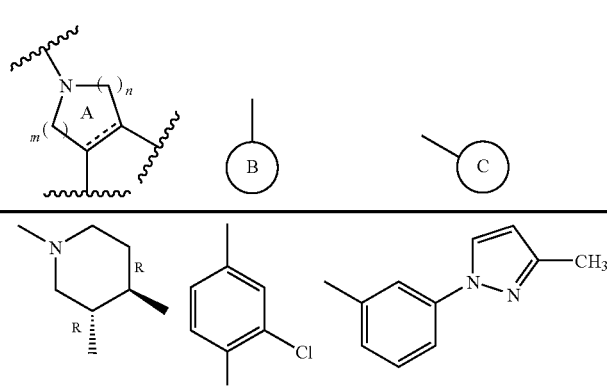 | B | C | R¹ | R² | salt/additive |
|---|---|---|---|---|---|---|
| 261 | 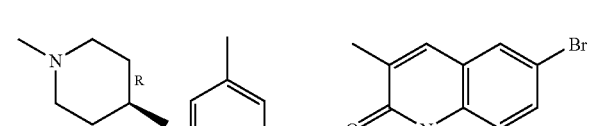 | 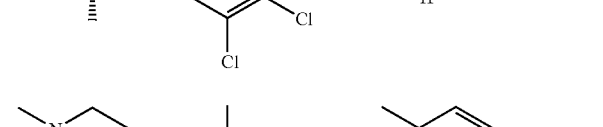 | 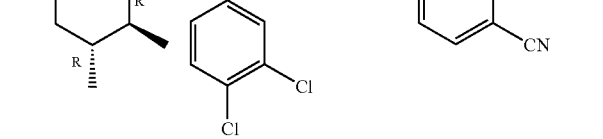 | 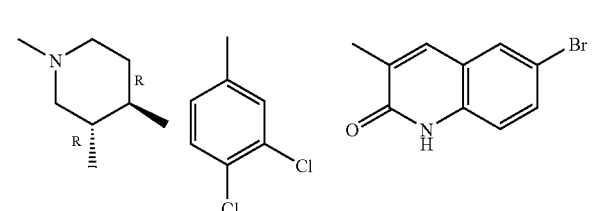 | CH₃ | |
| 262 | 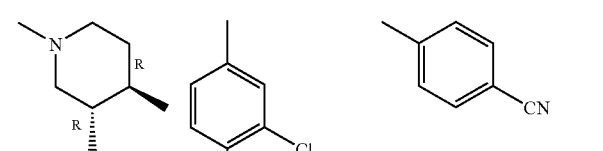 |  | 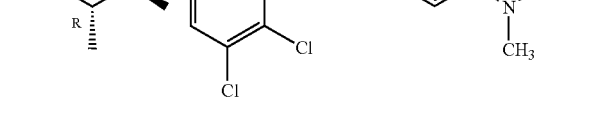 | 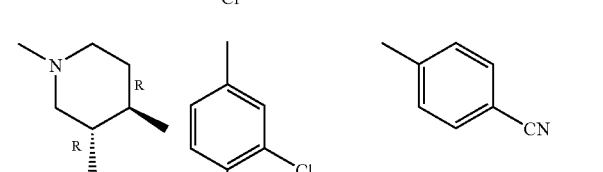 | CH₃ | |
| 263 |  | 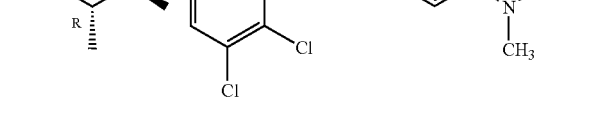 | 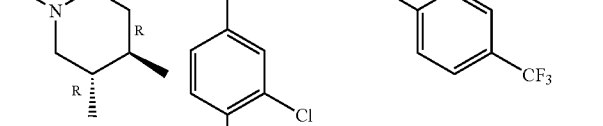 | 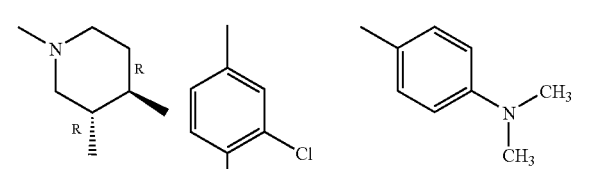 | CH₃ | |
| 264 | 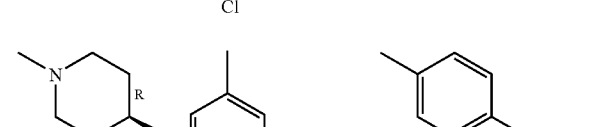 | 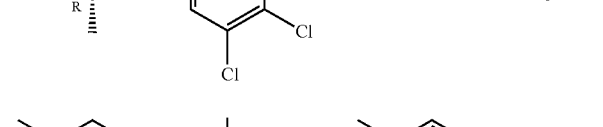 | 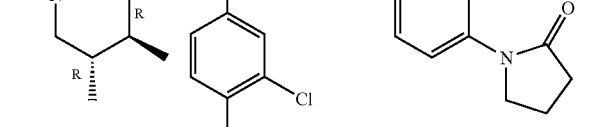 | 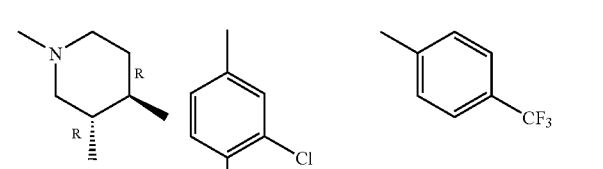 | CH₃ | |
| 265 | 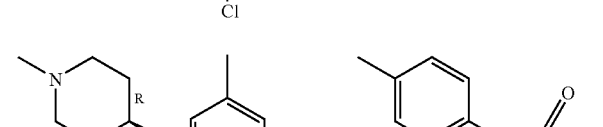 | 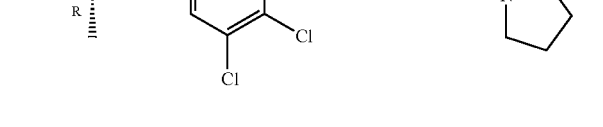 |  | 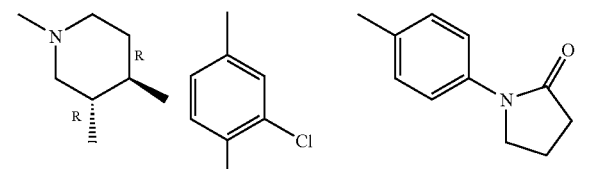 | CH₃ | 0.5H₂O |
| 266 |  | | | | CH₃ | |

TABLE 34-continued
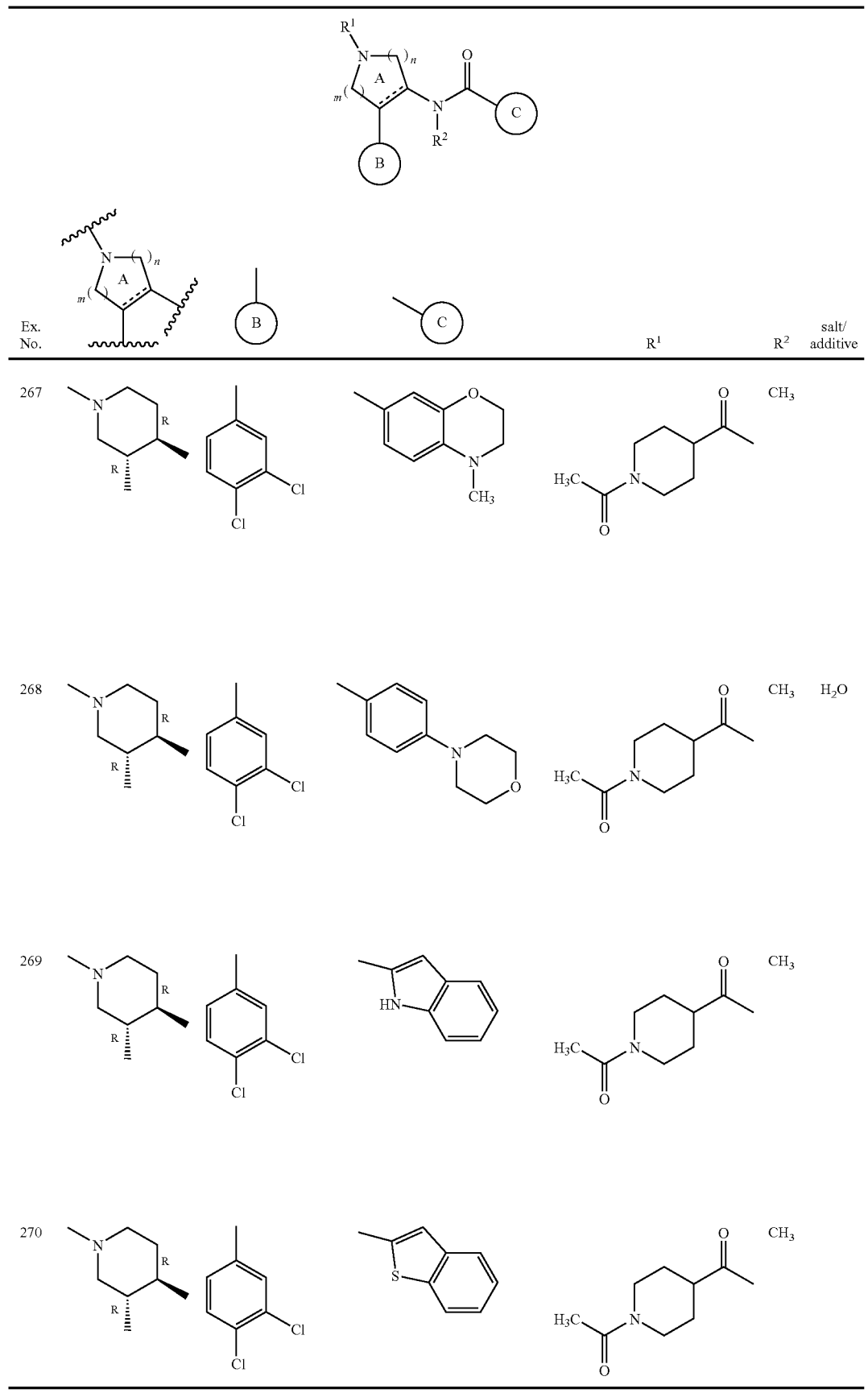

TABLE 35

| Ex. No. | [A ring] | B | C | R¹ | R² | salt/additive |
|---|---|---|---|---|---|---|
| 271 | N-methylpiperidine (R,R) | 3,4-dichlorophenyl | 4-(4-methylpiperazin-1-yl)phenyl | 1-acetylpiperidin-4-yl | CH₃ | |
| 272 | N-methylpiperidine (R,R) | 3,4-dichlorophenyl | 4-cyclohexylphenyl | 1-acetylpiperidin-4-yl | CH₃ | |
| 273 | N-methylpiperidine (R,R) | 3,4-dichlorophenyl | 4-(difluoromethoxy)phenyl | 1-acetylpiperidin-4-yl | CH₃ | |
| 274 | N-methylpiperidine (R,R) | 3,4-dichlorophenyl | 5-phenylthiophen-2-yl | 1-acetylpiperidin-4-yl | CH₃ | |
| 275 | N-methylpiperidine (R,R) | 3,4-dichlorophenyl | 4'-chloro-4-trifluoromethoxy-3-methylbiphenyl | 1-acetylpiperidin-4-yl | CH₃ | |
| 276 | N-methylpiperidine (R,R) | 3,4-dichlorophenyl | 4-methoxy-3-methyl-(5-trifluoromethyltetrazol-1-yl)phenyl | 1-acetylpiperidin-4-yl | CH₃ | |

TABLE 35-continued

| Ex. No. | A | B | C | R¹ | R² | salt/additive |
|---|---|---|---|---|---|---|
| 277 | N-methylpiperidine (R,R) | 3,4-dichlorophenyl | 3-bromo-5-(trifluoromethyl)phenyl | 1-acetylpiperidin-4-yl | CH₃ | |
| 278 | N-methylpiperidine (R,R) | 3,4-dichlorophenyl | 5-(morpholin-4-yl)pyridin-2-yl | 1-acetylpiperidin-4-yl | CH₃ | |
| 279 | N-methylpiperidine (R,R) | 3,4-dichlorophenyl | 2-methoxy-4-cyanophenyl | 1-acetylpiperidin-4-yl | CH₃ | |
| 280 | N-methylpiperidine (R,R) | 3,4-dichlorophenyl | 2-methyl-4-(4-methylphenyl)thiazol-5-yl | 1-acetylpiperidin-4-yl | CH₃ | |

TABLE 36
| Ex. No. | 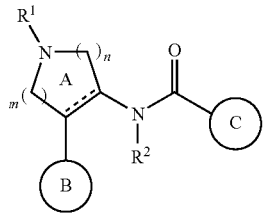 | B | C | R¹ | R² | salt/additive |
|---|---|---|---|---|---|---|
| 281 | 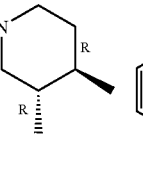 | 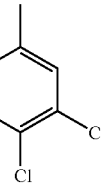 | 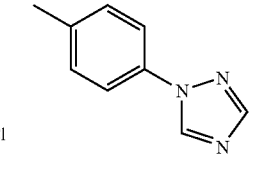 | 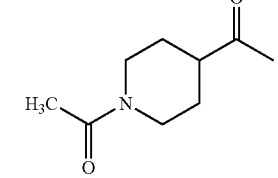 | CH₃ | |
| 282 | 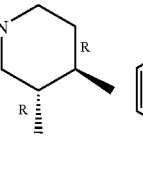 | 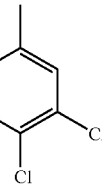 | 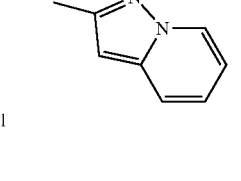 | 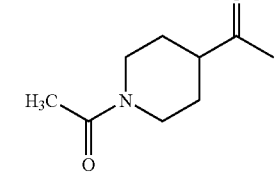 | CH₃ | |
| 283 | 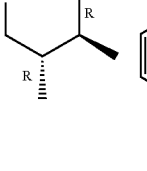 | 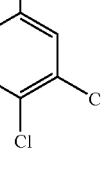 | 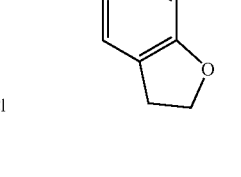 | 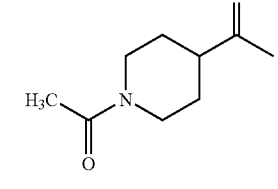 | CH₃ | |
| 284 | 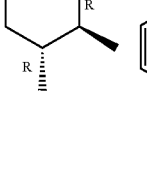 | 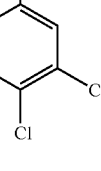 | 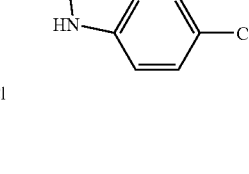 | 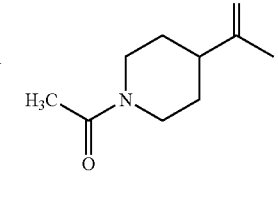 | CH₃ | |
| 285 | 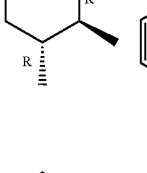 | 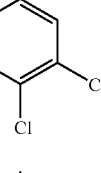 | 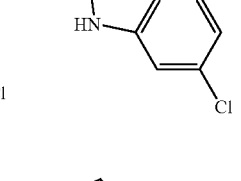 | 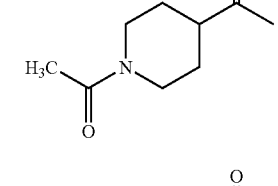 | CH₃ | |
| 286 | 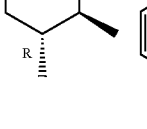 | 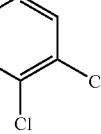 | 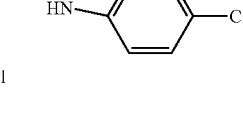 | 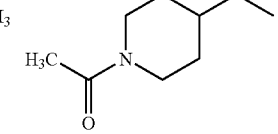 | CH₃ | |

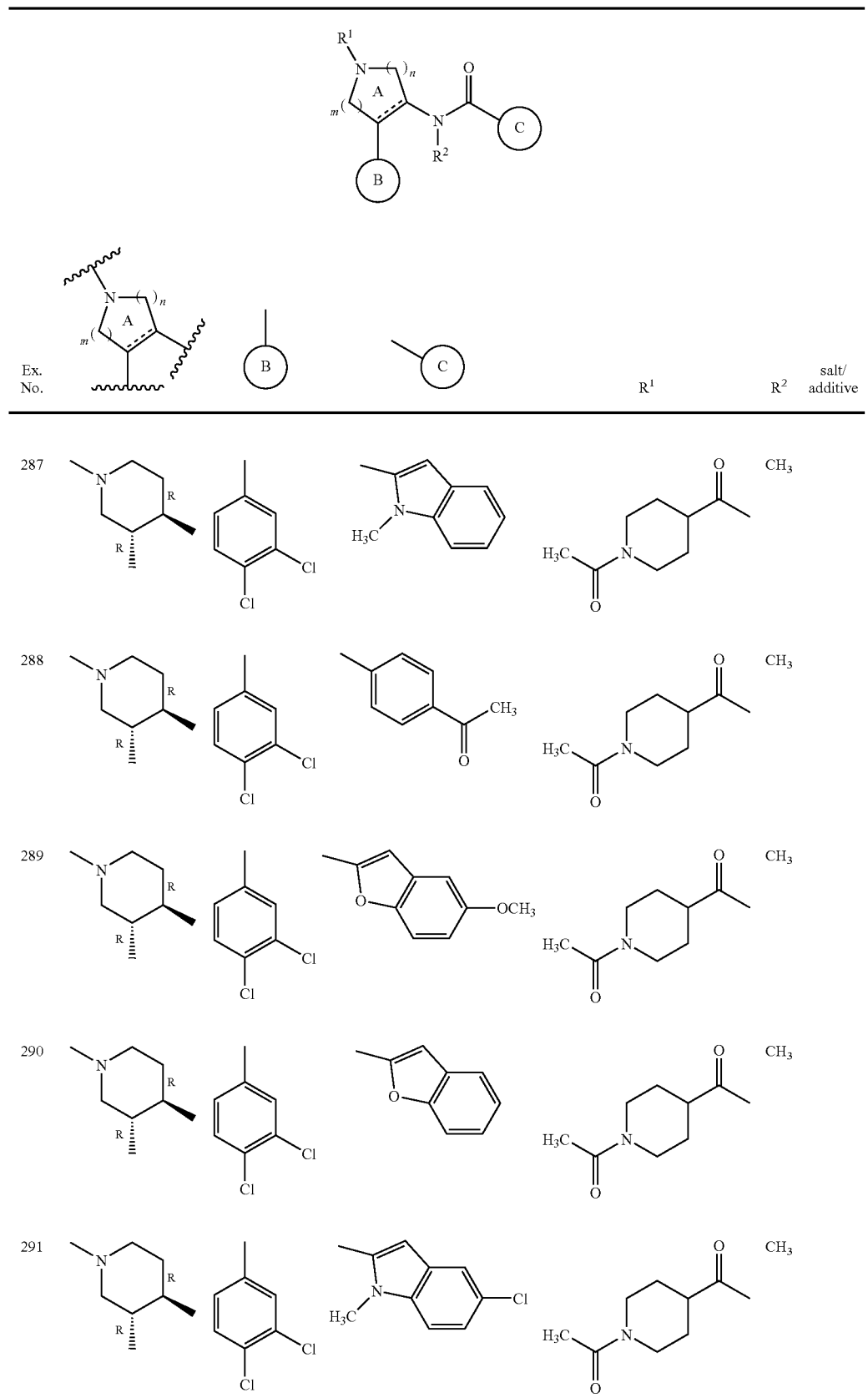

TABLE 36-continued
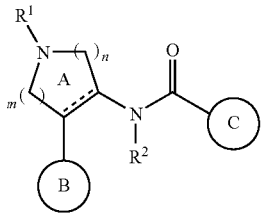
| Ex. No. | 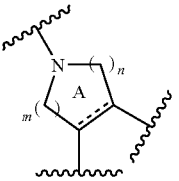 | B | C | R¹ | R² | salt/additive |
|---|---|---|---|---|---|---|
| 292 | 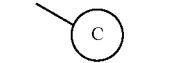 | 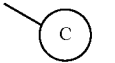 | 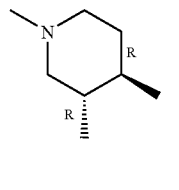 | 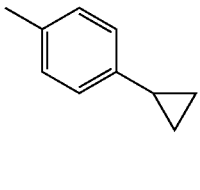 | CH₃ | 0.5 EtOAc |
TABLE 37
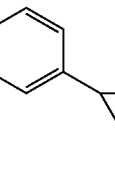
| Ex. No. | 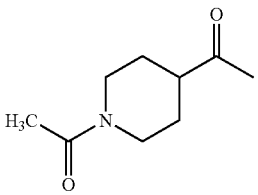 | B | C | R¹ | R² | salt/additive |
|---|---|---|---|---|---|---|
| 293 | 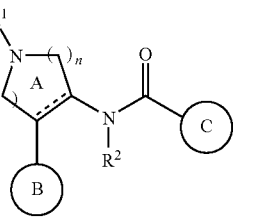 | 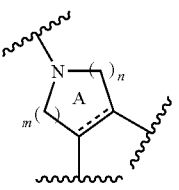 | 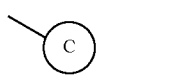 | 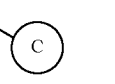 | CH₃ | |
| 294 | 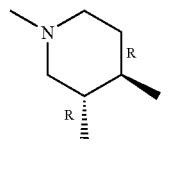 | 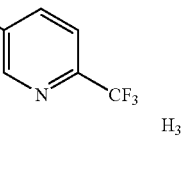 | 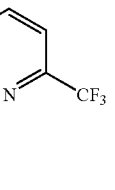 | 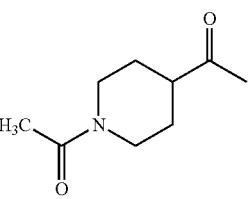 | CH₃ | |

TABLE 37-continued
| Ex. No. | 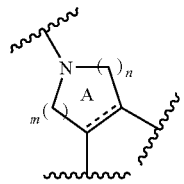 | B | C | R¹ | R² | salt/additive |
|---|---|---|---|---|---|---|
| 295 | 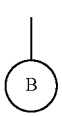 |  | 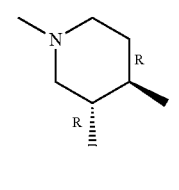 | 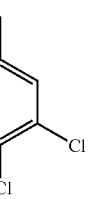 | CH₃ | |
| 296 | 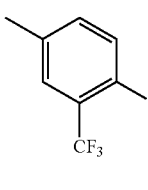 | 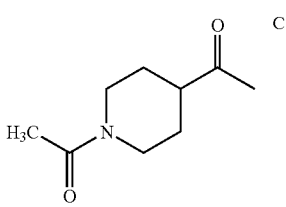 | 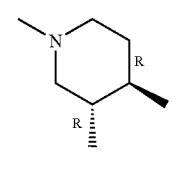 | 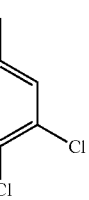 | CH₃ | |
| 297 | 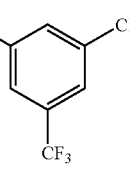 | 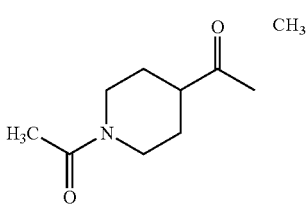 | 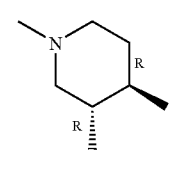 | 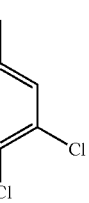 | CH₃ | |
| 298 | 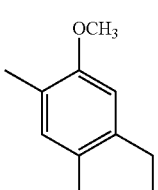 | 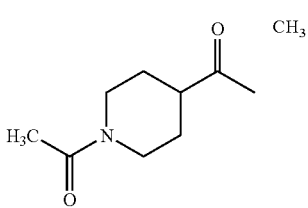 | 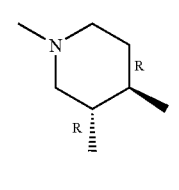 | 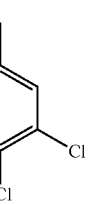 | CH₃ | |

TABLE 37-continued

| Ex. No. | A | B | C | R¹ | R² | salt/additive |
|---|---|---|---|---|---|---|
| 299 | 1-methylpiperidin-4,3-diyl | 3,4-dichlorophenyl | 1-(2-(trifluoromethyl)phenyl)-2-methyl-1H-imidazol-5-yl | 1-acetylpiperidine-4-carbonyl | CH₃ | |
| 300 | 1-methylpiperidin-4,3-diyl | 3,4-dichlorophenyl | 6-methoxy-1,7-dimethyl-2-oxo-1,1a,2,7b-tetrahydrocyclopropa[c]quinolin-5-yl | 1-acetylpiperidine-4-carbonyl | CH₃ | |
| 301 | 1-methylpiperidin-4,3-diyl | 3,4-dichlorophenyl | m-tolyl | 1-acetylpiperidine-4-carbonyl | CH₃ | |
| 302 | 1-methylpiperidin-4,3-diyl | 3,4-dichlorophenyl | p-tolyl | 1-acetylpiperidine-4-carbonyl | CH₃ | |

TABLE 38

| Ex. No. | A | B | C | R¹ | R² | salt/additive |
|---|---|---|---|---|---|---|
| 303 | N-methylpiperidine (R,R) | 3,4-dichlorophenyl | 4-(OCF₃)phenyl | 1-acetylpiperidin-4-yl | CH₃ | |
| 304 | N-methylpiperidine (R,R) | 3,4-dichlorophenyl | 4-ethylphenyl | 1-acetylpiperidin-4-yl | CH₃ | |
| 305 | N-methylpiperidine (R,R) | 3,4-dichlorophenyl | 1,5-dimethylindol-3-yl | 1-acetylpiperidin-4-yl | CH₃ | |
| 306 | N-methylpiperidine (R,R) | 3,4-dichlorophenyl | 2-fluoro-4-methyl-1-CF₃-phenyl | 1-acetylpiperidin-4-yl | CH₃ | |
| 307 | N-methylpiperidine (R,R) | 3,4-dichlorophenyl | 6-methyl-3-CF₃-pyridin-2-yl | 1-acetylpiperidin-4-yl | CH₃ | |
| 308 | N-methylpiperidine (R,R) | 3,4-dichlorophenyl | 3-fluoro-4-chlorophenyl | 1-acetylpiperidin-4-yl | CH₃ | |

TABLE 38-continued
| Ex. No. | 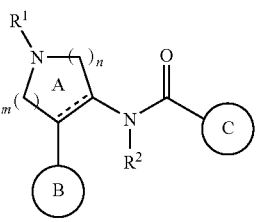 | B | C | R¹ | R² | salt/additive |
|---|---|---|---|---|---|---|
| 309 | 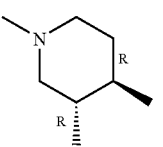 | 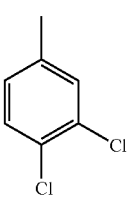 | 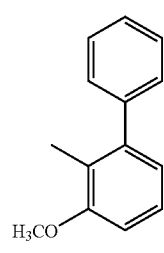 |  | CH₃ | |
| 310 | 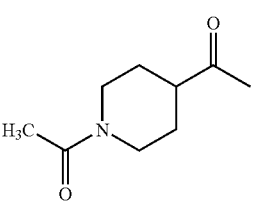 | 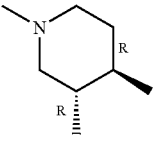 | 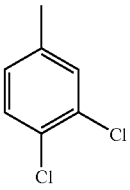 | 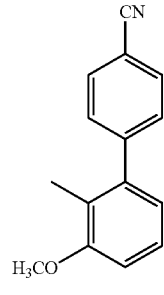 | CH₃ | |
| 311 |  | 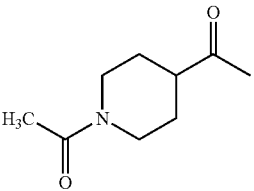 | 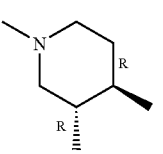 | 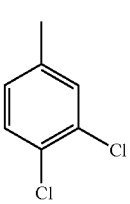 | CH₃ | |
| 312a | 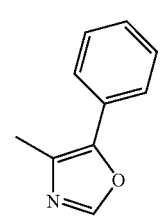 | 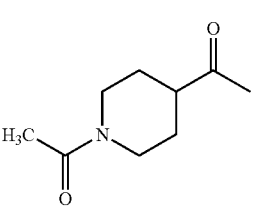 | 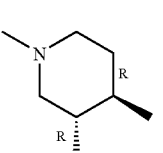 | 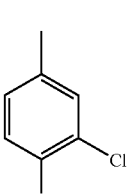 | CH₃ | |

TABLE 39
| Ex. No. | 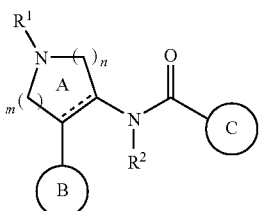 | B | C | R¹ | R² | salt/additive |
|---|---|---|---|---|---|---|
| 312b | 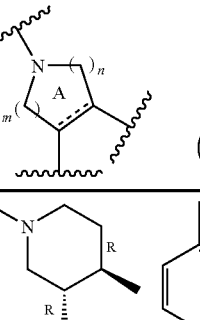 | 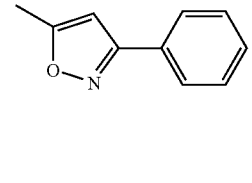 | 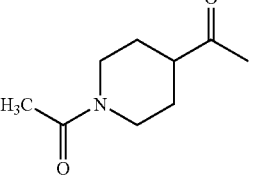 |  | CH₃ | |
| 313 | 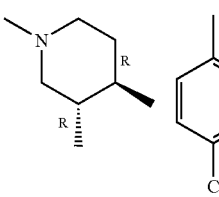 | 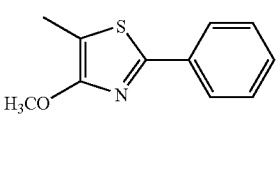 | 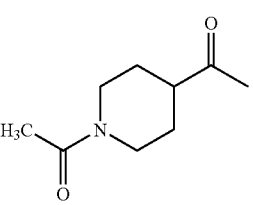 |  | CH₃ | |
| 314 | 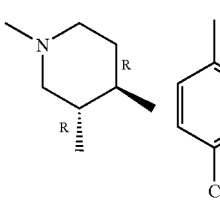 | 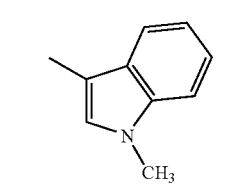 | 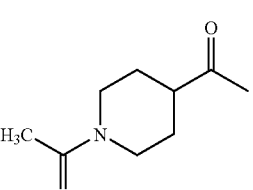 |  | CH₃ | |
| 315 | 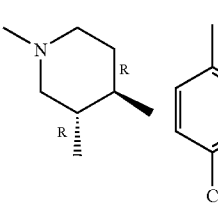 | 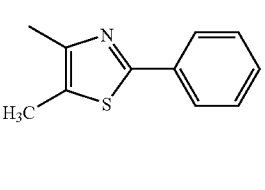 | 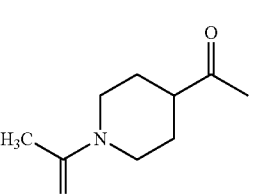 |  | CH₃ | |
| 316 | 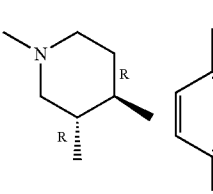 | 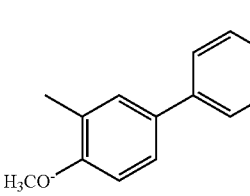 | 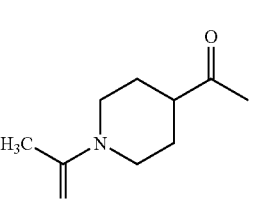 |  | CH₃ | |
| 317 | 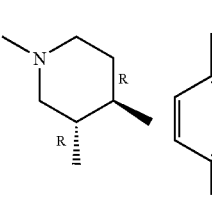 | 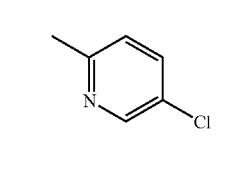 | 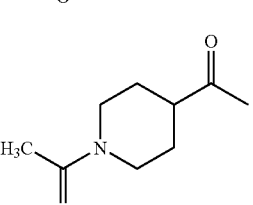 |  | CH₃ | |

TABLE 39-continued
| Ex. No. | A | B | C | R¹ | R² | salt/additive |
|---|---|---|---|---|---|---|
| 318 | 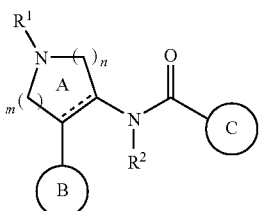 | 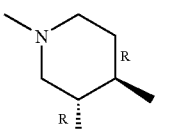 | 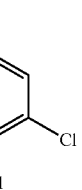 | 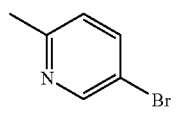 | CH₃ | |
| 319 | 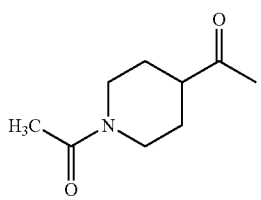 | 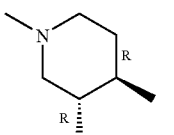 | 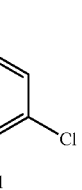 | 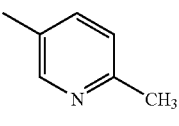 | CH₃ | |
| 320 | 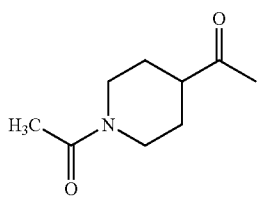 | 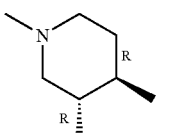 | 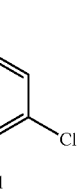 | 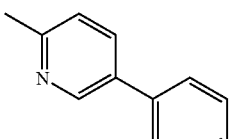 | CH₃ | |
| 321 | 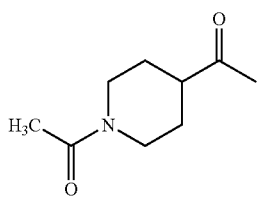 | 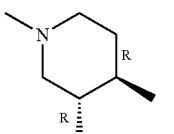 | 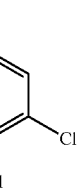 | 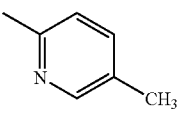 | CH₃ | |

TABLE 40

| Ex. No. | A | B | C | R¹ | R² | salt/additive |
|---|---|---|---|---|---|---|
| 322 | 1-methyl-3,4-dimethylpiperidine | 3,4-dichlorophenyl | 3-fluoro-4-cyanophenyl | 1-(cyclopropylcarbonyl)piperidin-4-yl-C(O)- | CH₃ | |
| 323 | 1-methyl-3,4-dimethylpiperidine | 3,4-dichlorophenyl | 4-[N-methyl-N-(2-methoxyethyl)amino]phenyl | 1-acetylpiperidin-4-yl | CH₃ | |
| 324 | 1-methyl-3,4-dimethylpiperidine | 3,4-dichlorophenyl | 4-(pyrrolidin-1-yl)phenyl | 1-acetylpiperidin-4-yl | CH₃ | |
| 325 | 1-methyl-3,4-dimethylpiperidine | 3,4-dichlorophenyl | 4-(morpholin-4-ylamino)phenyl | 1-acetylpiperidin-4-yl | CH₃ | |
| 326 | 1-methyl-3,4-dimethylpiperidine | 3,4-dichlorophenyl | 4-(morpholin-4-ylmethyl)phenyl | 1-acetylpiperidin-4-yl | CH₃ | |
| 327 | 1-methyl-3,4-dimethylpiperidine | 3,4-dichlorophenyl | 2,2-difluoro-1,3-benzodioxol-5-yl | 1-acetylpiperidin-4-yl | CH₃ | |

TABLE 40-continued

| Ex. No. | A | B | C | R¹ | R² | salt/additive |
|---|---|---|---|---|---|---|
| 328 | 1-methylpiperidin-4,3-diyl | 3,4-dichlorophenyl | 4-methylphenyl-piperidin-1-yl | 1-acetylpiperidin-4-yl | CH₃ | |
| 329 | 1-methylpiperidin-4,3-diyl | 3,4-dichlorophenyl | 4-(4-methylphenyl)-1,1-dioxothiomorpholin-4-yl | 1-acetylpiperidin-4-yl | CH₃ | |
| 330 | 1-methylpiperidin-4,3-diyl | 3,4-dichlorophenyl | 3-methylbenzothiophen-2-yl | 1-acetylpiperidin-4-yl | CH₃ | |
| 331 | 1-methylpiperidin-4,3-diyl | 3,4-dichlorophenyl | 5-methyl-2-(pyridin-2-yl)thiophen-2-yl | 1-acetylpiperidin-4-yl | CH₃ | |
| 332 | 1-methylpiperidin-4,3-diyl | 3,4-dichlorophenyl | 5-methyl-4-(4-chlorophenyl)thiophen-2-yl | 1-acetylpiperidin-4-yl | CH₃ | |

TABLE 40-continued
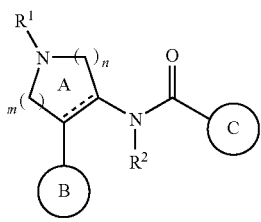
| Ex. No. | 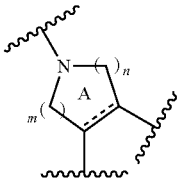 | B | C | R¹ | R² | salt/additive |
|---|---|---|---|---|---|---|
| 333 | 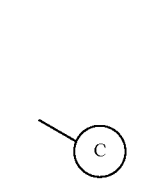 | 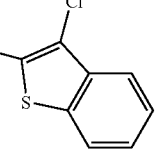 | 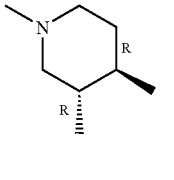 | 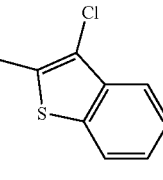 | CH₃ | |
TABLE 41
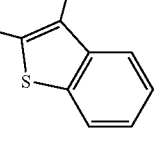
| Ex. No. | 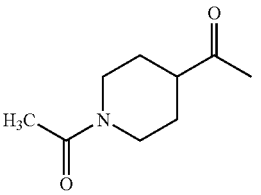 | B | C | R¹ | R² | salt/additive |
|---|---|---|---|---|---|---|
| 334 | 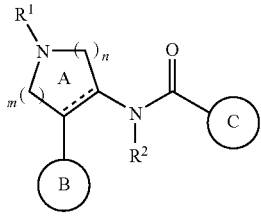 | 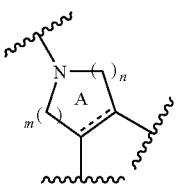 | 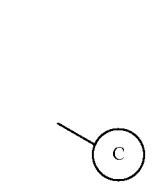 | 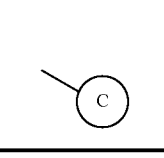 | CH₃ | |
| 335 | 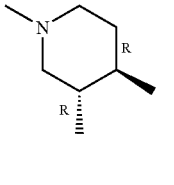 | 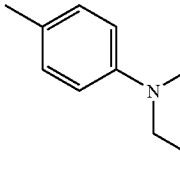 | 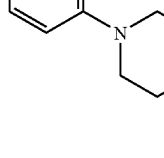 | 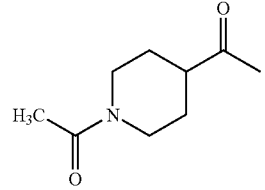 | CH₃ | |

TABLE 41-continued

| Ex. No. | A | B | C | R¹ | R² | salt/additive |
|---|---|---|---|---|---|---|
| 336 | 1-methylpiperidine (R,R) | 3,4-dichlorophenyl | 4-(pyridin-4-yl N-oxide)phenyl | 1-acetylpiperidin-4-yl | CH₃ | |
| 337 | 1-methylpiperidine (R,R) | 3,4-dichlorophenyl | 4'-(trifluoromethyl)biphenyl-4-yl | 1-acetylpiperidin-4-yl | CH₃ | |
| 338 | 1-methylpiperidine (R,R) | 3,4-dichlorophenyl | 4'-cyanobiphenyl-4-yl | 1-acetylpiperidin-4-yl | CH₃ | |
| 339 | 1-methylpiperidine (R,R) | 3,4-dichlorophenyl | 4-chlorophenyl | 1-acetylpiperidin-4-yl | C₂H₅ | |
| 340 | 1-methylpyrrolidine (R,S) | 3,4-dichlorophenyl | 4-chlorophenyl | 1-acetylpiperidin-4-yl | CH₃ | |
| 341 | 1-methylpyrrolidine (S,R) | 3,4-dichlorophenyl | 4-chlorophenyl | 1-acetylpiperidin-4-yl | CH₃ | |

TABLE 41-continued
| Ex. No. | 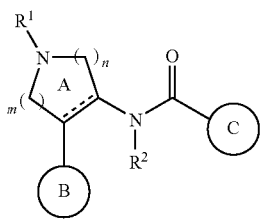 | B | C | R¹ | R² | salt/additive |
|---|---|---|---|---|---|---|
| 342 | 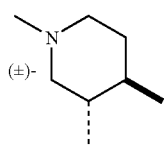 (±)- | 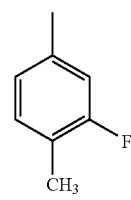 | 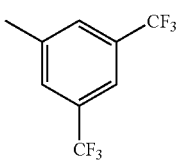 | 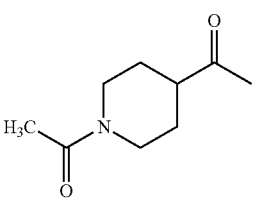 | CH₃ | |
| 343 | 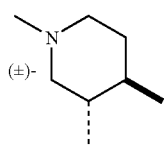 (±)- | 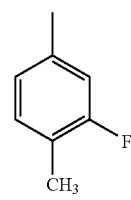 | 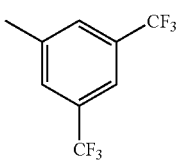 | 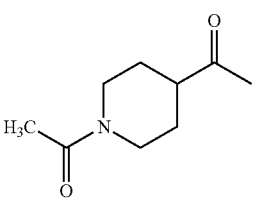 | CH₃ | |
| 344 | 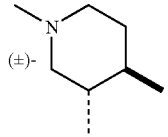 (±)- | 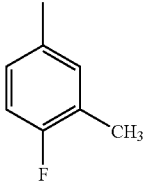 | 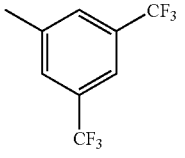 | 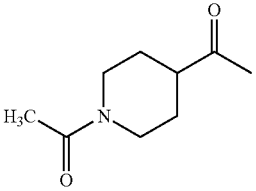 | CH₃ | |
| 345 | 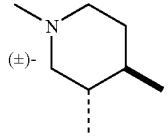 (±)- | 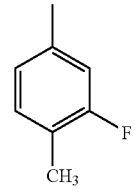 | 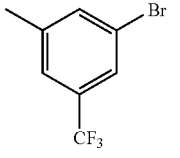 | 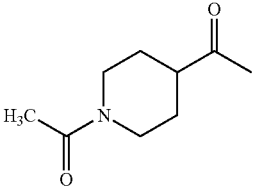 | CH₃ | |

TABLE 42

| Ex. No. | A | B | C | R¹ | R² | salt/additive |
|---|---|---|---|---|---|---|
| 346 | (±)- 1-methyl-3,4-dimethylpiperidine | 4-F-phenyl | 3,5-bis(CF₃)phenyl | 1-acetylpiperidin-4-yl | CH₃ | |
| 347 | (±)- 1-methyl-3,4-dimethylpiperidine | phenyl | 2-thienyl | 1-acetylpiperidin-4-yl | CH₃ | |
| 348 | (±)- 1-methyl-3,4-dimethylpiperidine | 3,5-dichlorophenyl | 3,5-bis(CF₃)phenyl | 1-acetylpiperidin-4-yl | CH₃ | |
| 349 | (±)- 1-methyl-3,4-dimethylpiperidine | 4-methylphenyl | 3,5-bis(CF₃)phenyl | 1-acetylpiperidin-4-yl | CH₃ | |
| 350 | (±)- 1-methyl-3,4-dimethylpiperidine | 4-methylphenyl | 3-Br-5-CF₃-phenyl | 1-acetylpiperidin-4-yl | CH₃ | |
| 351 | (±)- 1-methyl-3,4-dimethylpiperidine | 4-Cl-phenyl | 3,5-bis(CF₃)phenyl | 1-acetylpiperidin-4-yl | CH₃ | |

TABLE 42-continued
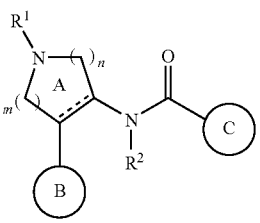
| Ex. No. | 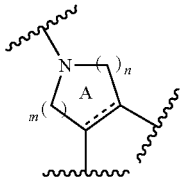 | B | C | R¹ | R² | salt/additive |
|---|---|---|---|---|---|---|
| 352 |  (±)- |  | 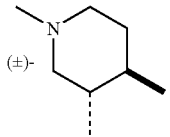 | 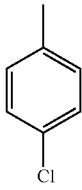 | CH₃ | |
| 353 | 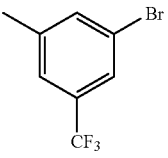 (±)- | 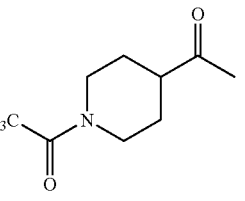 | 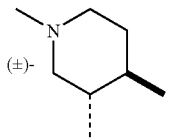 | 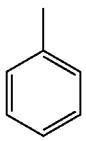 | CH₃ | |
| 354 | 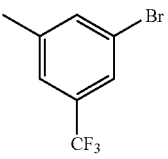 | 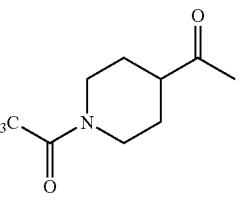 | 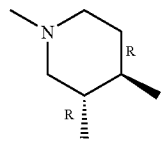 | 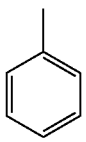 | CH₃ | |
| 355 | 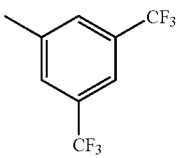 (±)- | 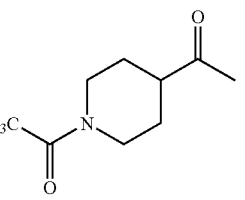 | 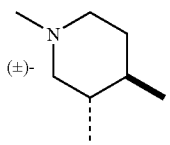 | 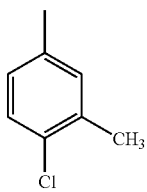 | CH₃ | |
| 356 | 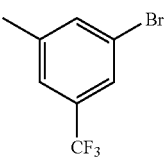 (±)- | 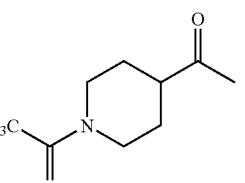 | 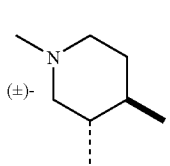 | 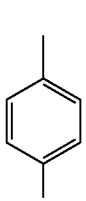 | CH₃ | |

TABLE 42-continued
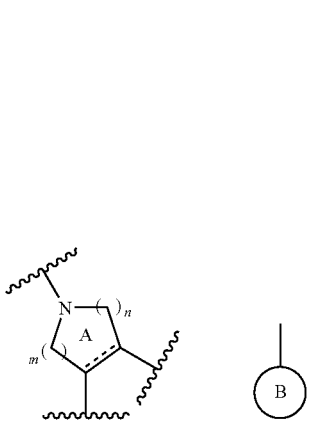
| Ex. No. | 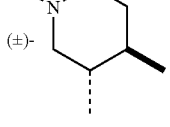 | B | C | R¹ | R² | salt/additive |
|---|---|---|---|---|---|---|
| 357 | 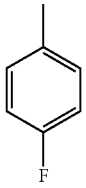 (±)- | 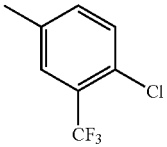 | 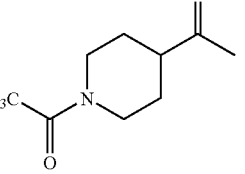 | 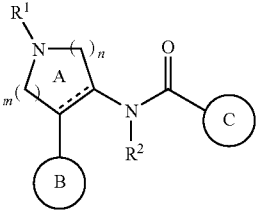 | CH₃ | |
TABLE 43
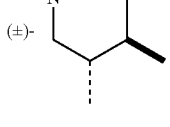
| Ex. No. | 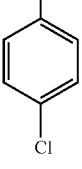 | B | C | R¹ | R² | salt/additive |
|---|---|---|---|---|---|---|
| 358 | 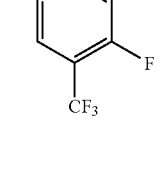 (±)- | 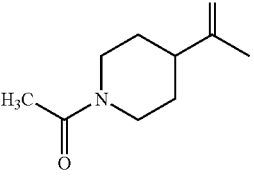 | 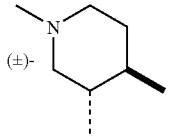 |  | CH₃ | |
| 359 | 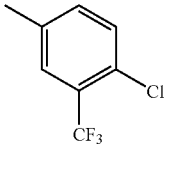 (±)- | 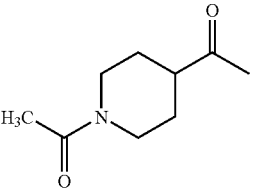 | | | CH₃ | |

TABLE 43-continued
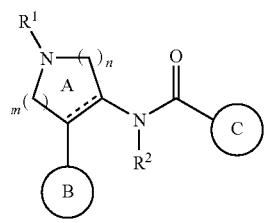
| Ex. No. | 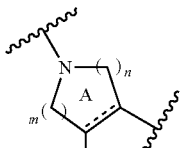 | B | C | R¹ | R² | salt/additive |
|---|---|---|---|---|---|---|
| 360 |  (±)- |  3,4-diCl | 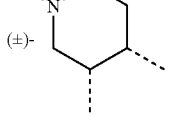 4-Cl | 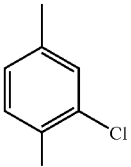 | CH₃ | |
| 361 | 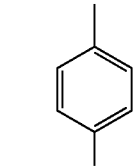 (±)- | 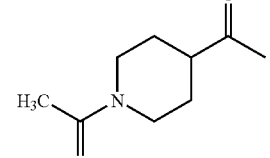 | 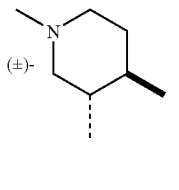 | 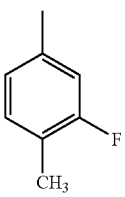 | CH₃ | |
| 362 | 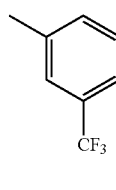 (±)- | 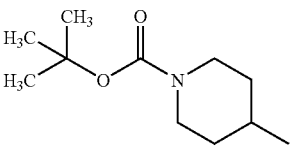 | 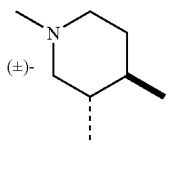 | 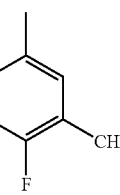 | CH₃ | |
| 363 | 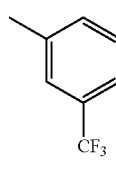 (±)- | 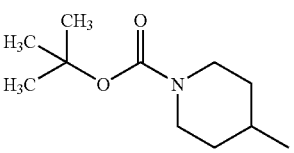 | 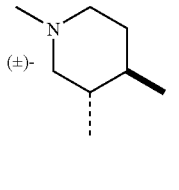 | 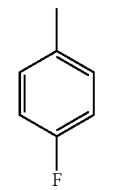 | CH₃ | |
| 364 | 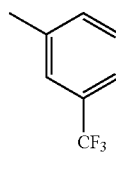 (±)- | 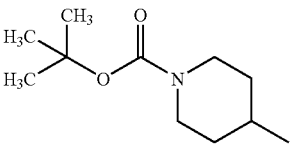 | 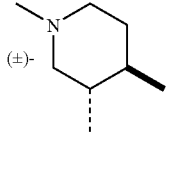 | 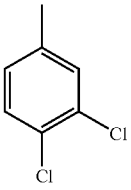 | CH₃ | |
| 365 | 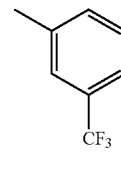 (±)- | 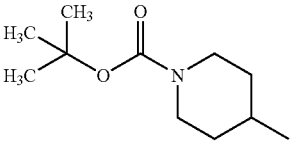 | 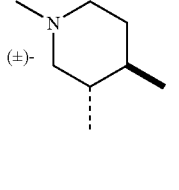 | 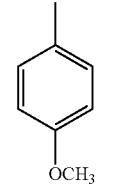 | CH₃ | |

TABLE 43-continued

| Ex. No. | A | B | C | R¹ | R² | salt/additive |
|---|---|---|---|---|---|---|
| 366 | (±)- 1-methyl-3,4-dimethylpiperidine | 4-methylphenyl | 3,5-bis(CF₃)phenyl | tert-butyl 4-methylpiperidine-1-carboxylate | CH₃ | |
| 367 | (±)- 1-methyl-3,4-dimethylpiperidine | 4-chlorophenyl | 3,5-bis(CF₃)phenyl | tert-butyl 4-methylpiperidine-1-carboxylate | CH₃ | |
| 368a | (±)- 1-methyl-3,4-dimethylpiperidine | phenyl | 3,5-bis(CF₃)phenyl | tert-butyl 4-methylpiperidine-1-carboxylate | CH₃ | |
| 368b | (±)- 1-methyl-3,4-dimethylpiperidine | phenyl | 3,5-bis(CF₃)phenyl | 4-methylpiperidine | CH₃ | 2HCl |

TABLE 44

| Ex. No. | A | B | C | R¹ | R² | salt/additive |
|---|---|---|---|---|---|---|
| 369 | (±)- N-methylpiperidine | 2-Cl-4-F-phenyl | 3,5-bis(CF₃)phenyl | 4-piperidinyl (HN) | CH₃ | 2HCl |
| 370 | (±)- N-methylpiperidine | 3-F-4-CH₃-phenyl | 3,5-bis(CF₃)phenyl | 4-piperidinyl (HN) | CH₃ | 2HCl |
| 371 | (±)- N-methylpiperidine | 3-CH₃-4-F-phenyl | 3,5-bis(CF₃)phenyl | 4-piperidinyl (HN) | CH₃ | 2HCl |
| 372 | (±)- N-methylpiperidine | 4-F-phenyl | 3,5-bis(CF₃)phenyl | 4-piperidinyl (HN) | CH₃ | 2HCl |
| 373 | (±)- N-methylpiperidine | 3,4-diCl-phenyl | 3-Br-5-CF₃-phenyl | 4-piperidinyl (HN) | CH₃ | 2HCl |
| 374a | (±)- N-methylpiperidine | 4-OCH₃-phenyl | 3,5-bis(CF₃)phenyl | 4-piperidinyl (HN) | CH₃ | 2HCl |

TABLE 44-continued

| Ex. No. | A | B | C | R¹ | R² | salt/additive |
|---|---|---|---|---|---|---|
| 374b | (±)- 1-methyl-3,4-dimethylpiperidine | 4-methylphenyl | 3,5-bis(CF₃)phenyl | 4-piperidinyl (HN) | CH₃ | 2HCl |
| 374c | (±)- 1-methyl-3,4-dimethylpiperidine | 4-chlorophenyl | 3,5-bis(CF₃)phenyl | 4-piperidinyl (HN) | CH₃ | 2HCl |
| 375 | (±)- 1-methyl-3,4-dimethylpiperidine | phenyl | 3,5-bis(CF₃)phenyl | 1-acetyl-4-piperidinyl | CH₃ | HCl |
| 376 | (±)- 1-methyl-3,4-dimethylpiperidine | 3-chloro-4-fluorophenyl | 3,5-bis(CF₃)phenyl | 1-acetyl-4-piperidinyl | CH₃ | HCl |
| 377 | (±)- 1-methyl-3,4-dimethylpiperidine | 3-fluoro-4-methylphenyl | 3,5-bis(CF₃)phenyl | 1-acetyl-4-piperidinyl | CH₃ | HCl |
| 378 | (±)- 1-methyl-3,4-dimethylpiperidine | 4-fluoro-3-methylphenyl | 3,5-bis(CF₃)phenyl | 1-acetyl-4-piperidinyl | CH₃ | HCl |

TABLE 45

| Ex. No. | A | B | C | R¹ | R² | salt/additive |
|---|---|---|---|---|---|---|
| 379 | (±)- N-methylpiperidine | 3,4-dichlorophenyl | 3-bromo-5-(trifluoromethyl)phenyl | 1-(4-methylpiperidin-1-yl)ethan-1-one | CH₃ | HCl |
| 380 | (±)- N-methylpiperidine | 4-fluorophenyl | 3,5-bis(trifluoromethyl)phenyl | 1-(4-methylpiperidin-1-yl)ethan-1-one | CH₃ | HCl |
| 381 | (±)- N-methylpiperidine | 4-methoxyphenyl | 3,5-bis(trifluoromethyl)phenyl | 1-(4-methylpiperidin-1-yl)ethan-1-one | CH₃ | HCl |
| 382 | (±)- N-methylpiperidine | 4-methylphenyl | 3,5-bis(trifluoromethyl)phenyl | 1-(4-methylpiperidin-1-yl)ethan-1-one | CH₃ | HCl |
| 383 | (±)- N-methylpiperidine | 4-chlorophenyl | 3,5-bis(trifluoromethyl)phenyl | 1-(4-methylpiperidin-1-yl)ethan-1-one | CH₃ | HCl |
| 384 | N-methylpiperidine (R,R) | 3,4-dichlorophenyl | 3,5-bis(trifluoromethyl)phenyl | 1-(1H-tetrazol-1-yl)propan-2-one | CH₃ | |

TABLE 45-continued
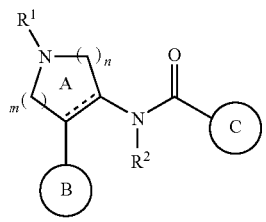
| Ex. No. | A | B | C | R¹ | R² | salt/additive |
|---|---|---|---|---|---|---|
| 385 | 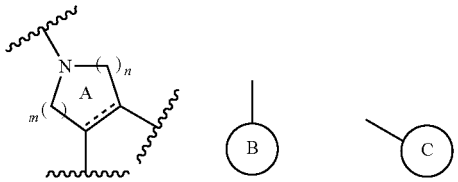 |  |  | 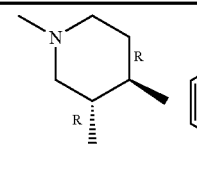 | CH₃ | |
| 386 | 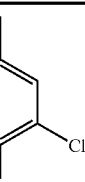 | 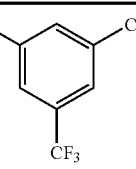 | 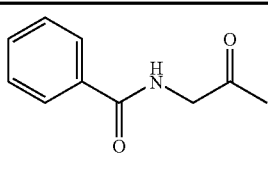 |  | CH₃ | |
| 387 | 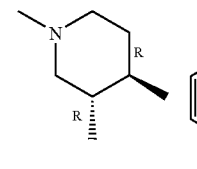 | 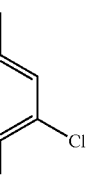 | 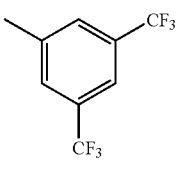 | 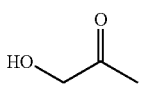 | CH₃ | |
| 388 |  | 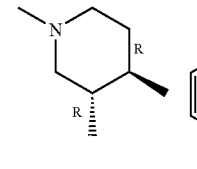 | 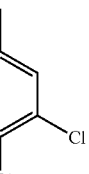 | 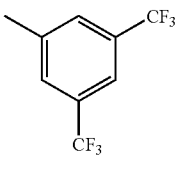 | CH₃ | |
| 389 | 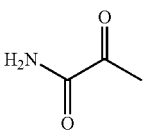 |  | 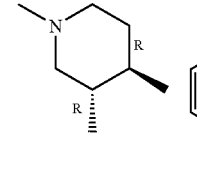 | 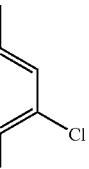 | CH₃ | |
| 390 | 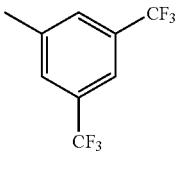 | 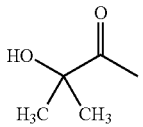 |  | 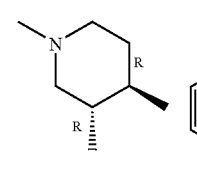 | CH₃ | |

TABLE 46
| Ex. No. | A | B | C | R¹ | R² | salt/additive |
|---|---|---|---|---|---|---|
| 391 | 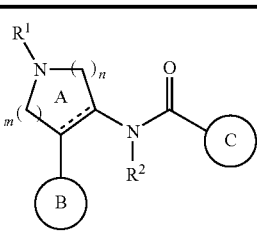 |  |  | 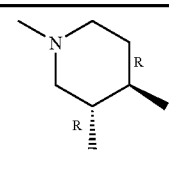 | CH₃ | |
| 392 | 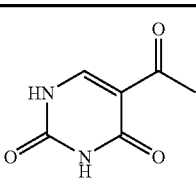 |  | 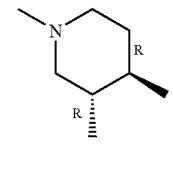 | 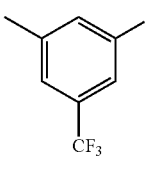 | CH₃ | |
| 393 | 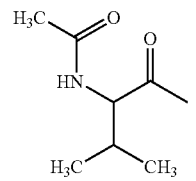 |  | 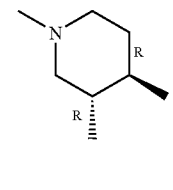 | 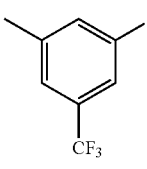 | CH₃ | |
| 394 | 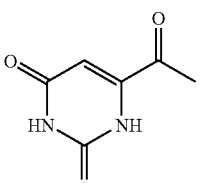 |  | 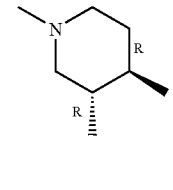 | 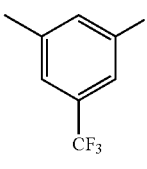 | CH₃ | |
| 395 | 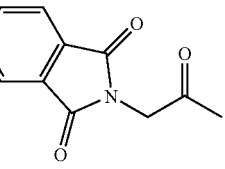 |  | 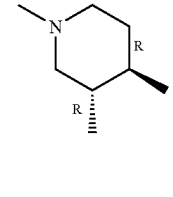 | 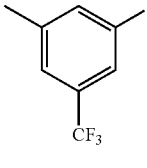 | CH₃ | |
| 396 | 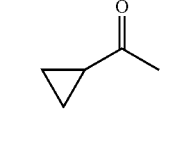 |  | 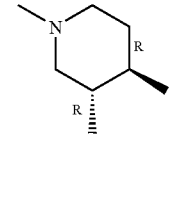 | 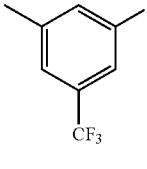 | CH₃ | |

TABLE 46-continued
| Ex. No. | 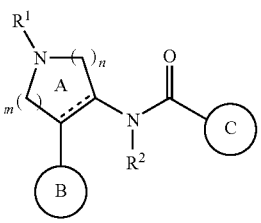 | B | C | R¹ | R² | salt/additive |
|---|---|---|---|---|---|---|
| 397 | 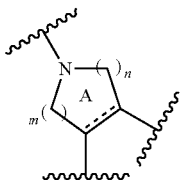 |  |  | 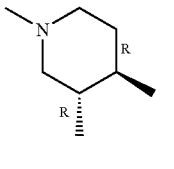 | CH₃ | |
| 398 | 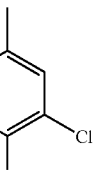 | 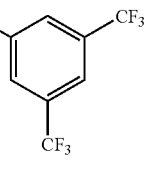 | 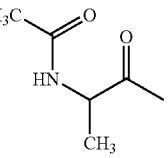 | 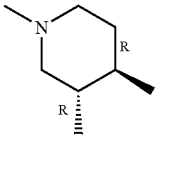 | CH₃ | |
| 399 | 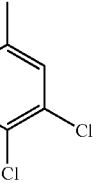 | 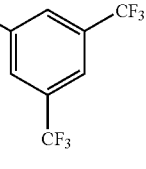 | 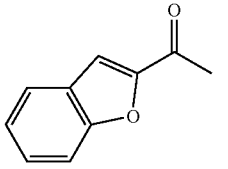 | 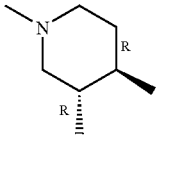 | CH₃ | |
| 400 | 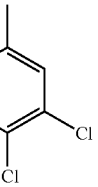 | 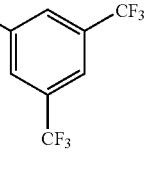 | 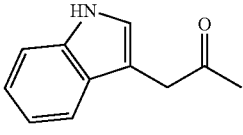 | 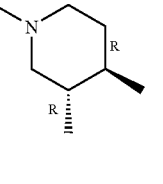 | CH₃ | |
| 401 | 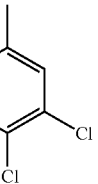 | 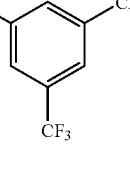 | 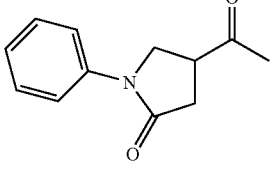 | 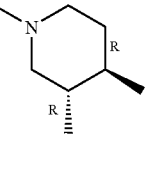 | CH₃ | TFA |
| 402 | 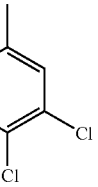 | 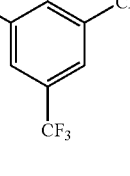 | 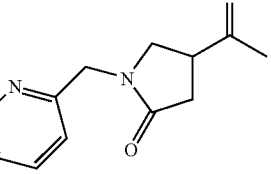 | 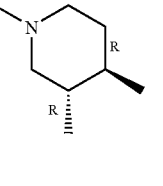 | CH₃ | TFA |

TABLE 47
| Ex. No. |  |  |  | R¹ | R² | salt/additive |
|---|---|---|---|---|---|---|
| 403 | 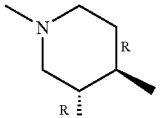 | 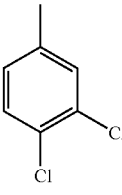 | 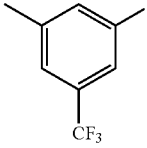 | 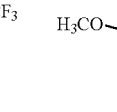 | CH₃ | |
| 404 | 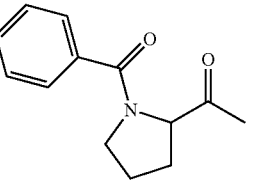 | 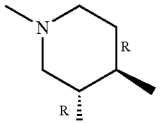 | 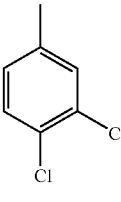 | 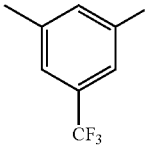 | CH₃ | |
| 405 | 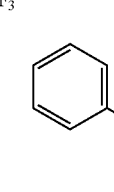 | 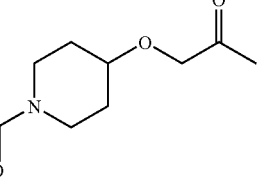 | 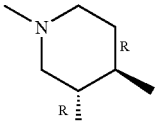 | 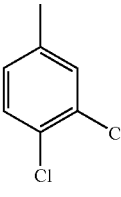 | CH₃ | |
| 406 | 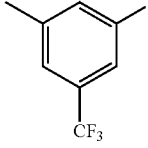 | 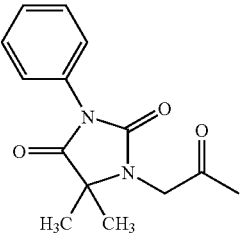 [SMILES: CC(=O)CN1C(=O)N(c2ccccc2)C(=O)C1(C)C] | 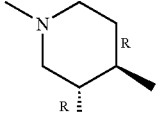 | 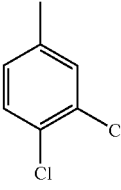 | CH₃ | |
| 407 | 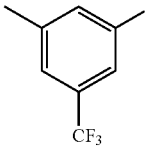 | 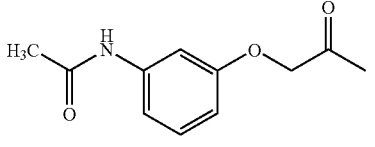 | 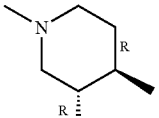 | 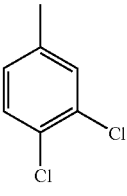 | CH₃ | |

TABLE 47-continued
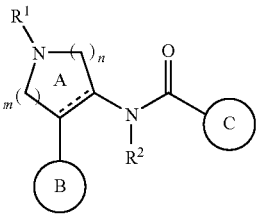
| Ex. No. | 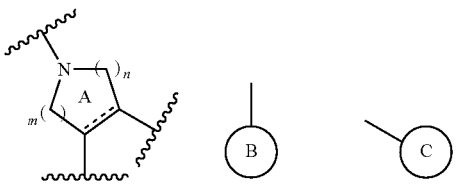 | B | C | R¹ | R² | salt/additive |
|---|---|---|---|---|---|---|
| 408 | 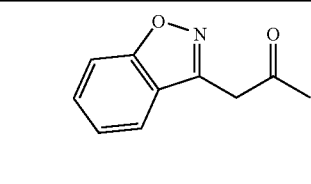 | 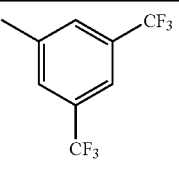 | 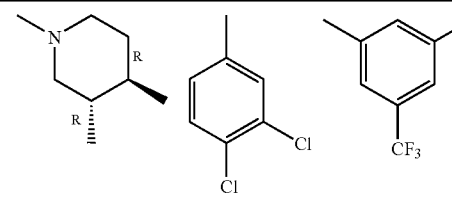 | 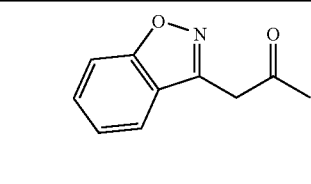 | CH₃ | |
| 409 | 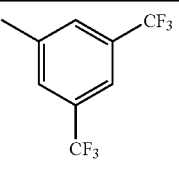 | 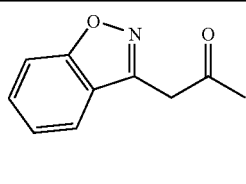 | 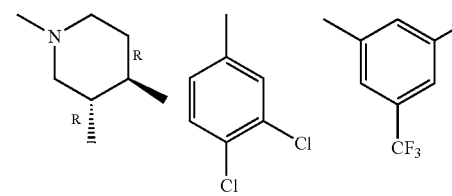 | 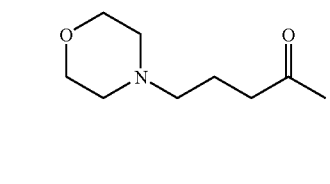 | CH₃ | TFA |
| 410 | 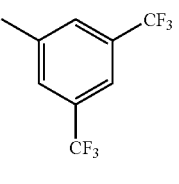 | 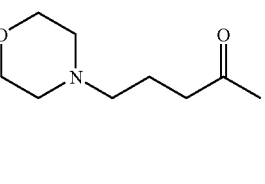 | 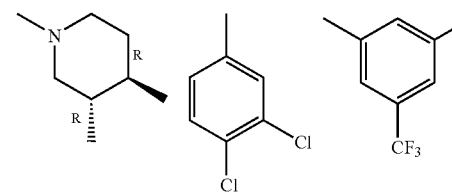 | 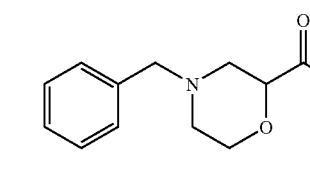 | CH₃ | TFA |
| 411 | 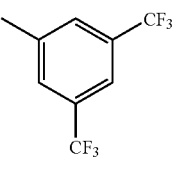 | 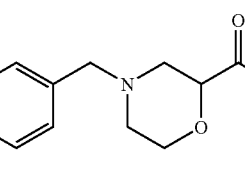 | 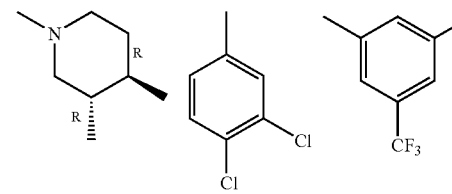 | 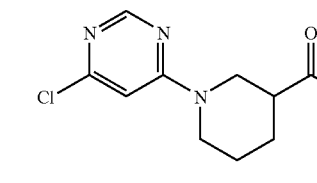 | CH₃ | |
| 412 | 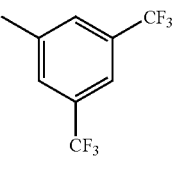 | 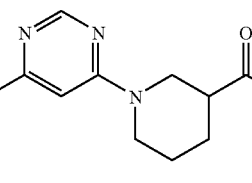 | 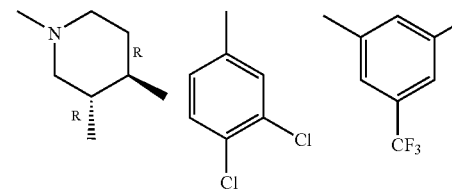 | 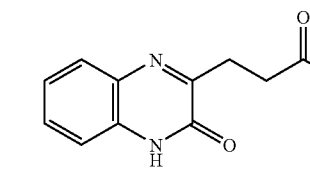 | CH₃ | |
| 413 | 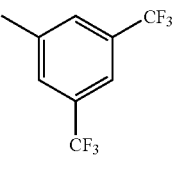 | 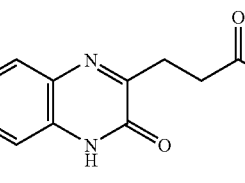 | 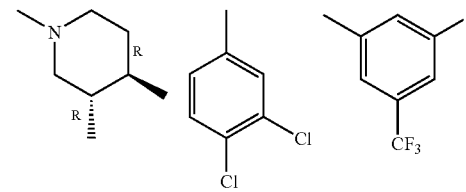 | 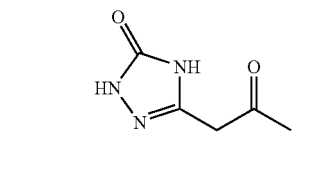 | CH₃ | |

TABLE 47-continued
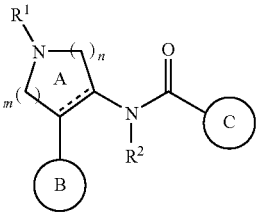
| Ex. No. | 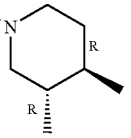 | B | C | R¹ | R² | salt/additive |
|---|---|---|---|---|---|---|
| 414 | 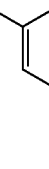 | 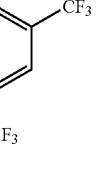 | 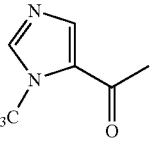 | 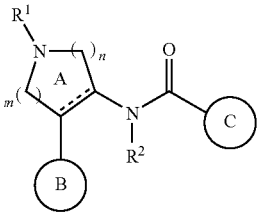 | CH₃ | |
TABLE 48
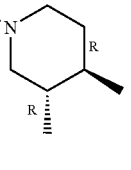
| Ex. No. |  | B | C | R¹ | R² | salt/additive |
|---|---|---|---|---|---|---|
| 415 | 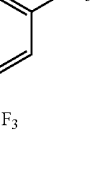 | 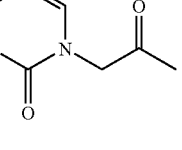 | 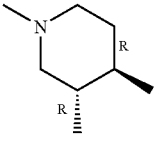 | 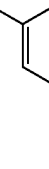 | CH₃ | |
| 416 | 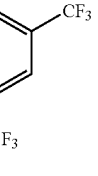 | | | 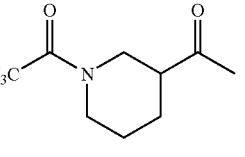 | CH₃ | |

US 8,470,816 B2
TABLE 48-continued
| Ex. No. | 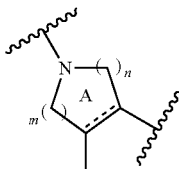 | B | C | R¹ | R² | salt/additive |
|---|---|---|---|---|---|---|
| 417 |  |  | 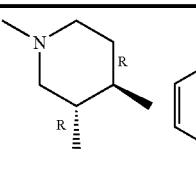 | 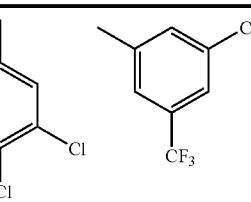 | CH₃ | |
| 418 | 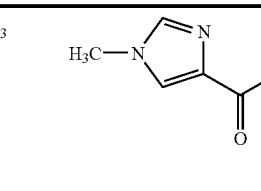 |  | 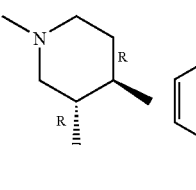 | 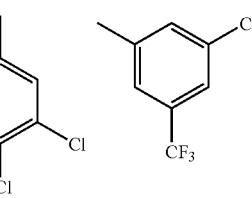 | CH₃ | |
| 419 | 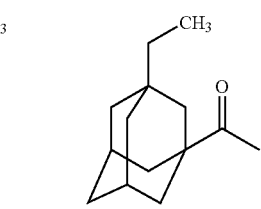 |  | 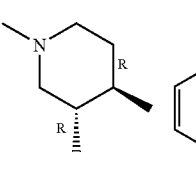 | 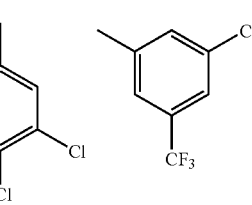 | CH₃ | |
| 420 | 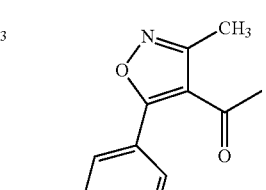 |  | 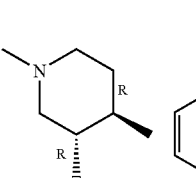 | 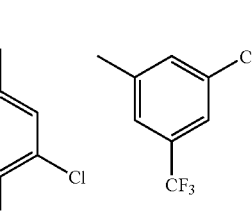 | CH₃ | |
| 421 | 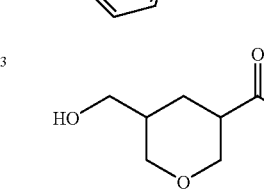 |  | 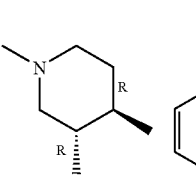 | 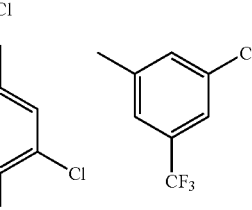 | CH₃ | |
| 422 | 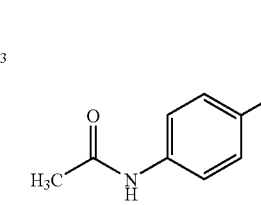 | 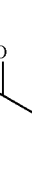 | 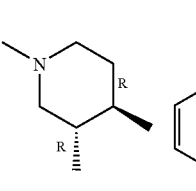 | 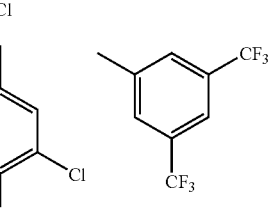 | CH₃ | |

TABLE 48-continued
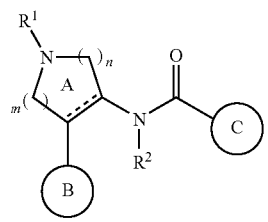
| Ex. No. | 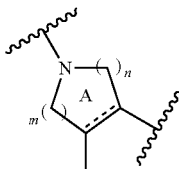 | B | C | R¹ | R² | salt/additive |
|---|---|---|---|---|---|---|
| 423 |  |  | 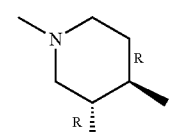 | 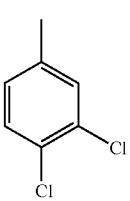 | CH₃ | |
| 424 | 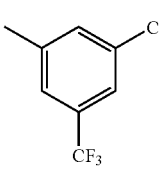 | 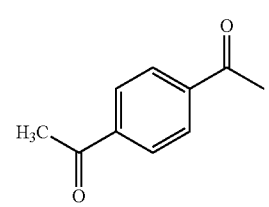 | 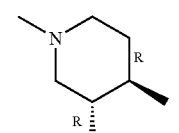 | 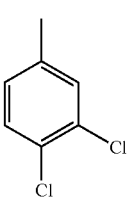 | CH₃ | |
| 425 | 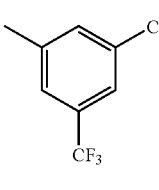 | 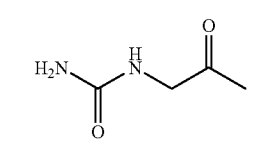 | 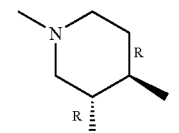 | 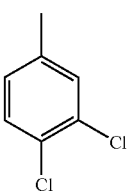 | CH₃ | TFA |
| 426 | 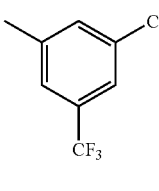 | 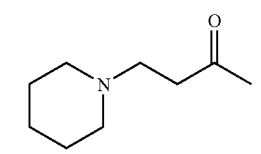 | 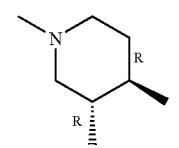 | 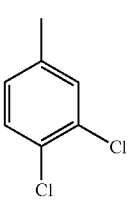 | CH₃ | |

TABLE 49

| Ex. No. | A | B | C | R¹ | R² | salt/additive |
|---|---|---|---|---|---|---|
| 427 | 1-methyl-3,4-disub piperidine | 3,4-diCl-phenyl | 3,5-(CF₃)₂-phenyl | H₃C-C(O)-NH-CH₂CH₂CH₂-C(O)-CH₃ | CH₃ | |
| 428 | 1-methyl-3,4-disub piperidine | 3,4-diCl-phenyl | 3,5-(CF₃)₂-phenyl | N-propyl-phthalimide | CH₃ | TFA |
| 429 | 1-methyl-3,4-disub piperidine | 3,4-diCl-phenyl | 3,5-(CF₃)₂-phenyl | N-butyl-phthalimide | CH₃ | TFA |
| 430 | 1-methyl-3,4-disub piperidine | 3,4-diCl-phenyl | 3,5-(CF₃)₂-phenyl | phenethyl | CH₃ | TFA |
| 431 | 1-methyl-3,4-disub piperidine | 3,4-diCl-phenyl | 3,5-(CF₃)₂-phenyl | 1-methyl-2-oxo-pyrrolidin-4-yl-C(O)CH₃ | CH₃ | |
| 432 | 1-methyl-3,4-disub piperidine | 3,4-diCl-phenyl | 3,5-(CF₃)₂-phenyl | 1-tert-butyl-azetidin-3-yl-C(O)CH₃ | CH₃ | TFA |

TABLE 49-continued

| Ex. No. | A | B | C | R¹ | R² | salt/additive |
|---|---|---|---|---|---|---|
| 433 | N-methyl piperidine (R,R) | 3,4-dichlorophenyl | 3,5-bis(CF₃)phenyl | 1-(1H-benzimidazol-2-yl)ethyl-C(O)CH₃ | CH₃ | |
| 434 | N-methyl piperidine (R,R) | 3,4-dichlorophenyl | 3,5-bis(CF₃)phenyl | 4-acetyl-1-(aminocarbonyl)piperidinyl | CH₃ | |
| 435 | N-methyl piperidine (R,R) | 3,4-dichlorophenyl | 3,5-bis(CF₃)phenyl | 1-(4-methylphenyl)-1-methyl-2-oxopropyl | CH₃ | |
| 436 | N-methyl piperidine (R,R) | 3,4-dichlorophenyl | 3,5-bis(CF₃)phenyl | 3-acetyl-5,5-dimethyl-2-oxotetrahydrofuran-4-yl | CH₃ | |
| 437 | N-methyl piperidine (R,R) | 3,4-dichlorophenyl | 3,5-bis(CF₃)phenyl | 3-(5,5-dimethyl-2,4-dioxooxazolidin-3-yl)-2-oxopropyl | CH₃ | |
| 438 | N-methyl piperidine (R,R) | 3,4-dichlorophenyl | 3,5-bis(CF₃)phenyl | 1-(3,3-dimethyl-2-oxoazetidin-1-yl)-2-oxopropyl | CH₃ | |

TABLE 50

| Ex. No. | A | B | C | R¹ | R² | salt/additive |
|---|---|---|---|---|---|---|
| 439 | 1-methyl-3,4-dimethylpiperidin-4-yl | 3,4-dichlorophenyl | 3,5-bis(trifluoromethyl)phenyl | 2-(3-oxo-2-azaspiro[4.5]decan-2-yl)...oxopropyl | CH₃ | |
| 440 | 1-methyl-3,4-dimethylpiperidin-4-yl | 3,4-dichlorophenyl | 3,5-bis(trifluoromethyl)phenyl | (2,4-dioxooxazolidin-3-yl)acetonyl | CH₃ | |
| 441 | 1-methyl-3,4-dimethylpiperidin-4-yl | 3,4-dichlorophenyl | 3,5-bis(trifluoromethyl)phenyl | N-(4-methylsulfonylphenyl)acetamide | CH₃ | |
| 442 | 1-methyl-3,4-dimethylpiperidin-4-yl | 3,4-dichlorophenyl | 3,5-bis(trifluoromethyl)phenyl | (dimethylamino)acetonyl | CH₃ | TFA |
| 443 | 1-methyl-3,4-dimethylpiperidin-4-yl | 3,4-dichlorophenyl | 3,5-bis(trifluoromethyl)phenyl | (methylsulfonyl)acetonyl | CH₃ | |
| 444 | 1-methyl-3,4-dimethylpiperidin-4-yl | 3,4-dichlorophenyl | 3,5-bis(trifluoromethyl)phenyl | (1,1-dioxothiomorpholin-4-yl)acetonyl | CH₃ | TFA |

TABLE 50-continued
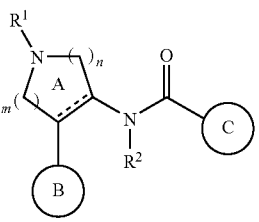
| Ex. No. | 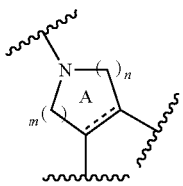 | B | C | R¹ | R² | salt/additive |
|---|---|---|---|---|---|---|
| 445 |  |  | 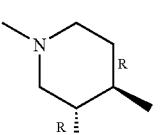 | 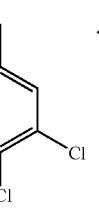 | CH₃ | |
| 446 | 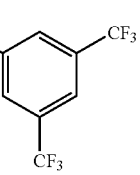 | 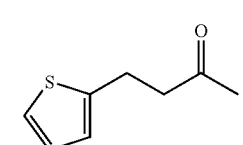 | 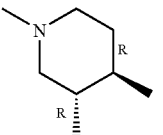 | 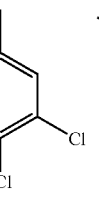 | CH₃ | |
| 447 | 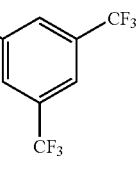 | 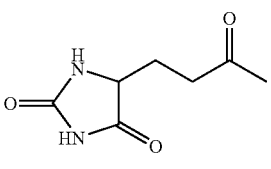 | 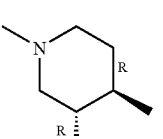 | 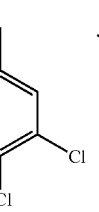 | CH₃ | TFA |
| 448 | 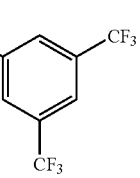 | 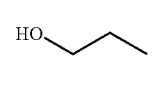 | 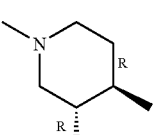 | 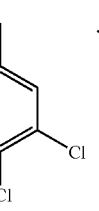 | CH₃ | |
| 449 | 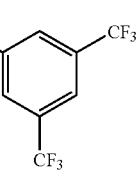 | 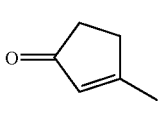 | 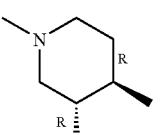 | 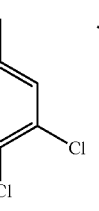 | CH₃ | |

TABLE 50-continued

| Ex. No. | ![A ring] | B | C | R¹ | R² | salt/additive |
|---|---|---|---|---|---|---|
| 450 | 1-methylpiperidine (R,R) | 3,4-dichlorophenyl | 3,5-bis(CF₃)phenyl | H₃C-C(O)-NH-CH₂-C(O)-CH₃ | CH₃ | |

TABLE 51

| Ex. No. | ![A ring] | B | C | R¹ | R² | salt/additive |
|---|---|---|---|---|---|---|
| 451 | 1-methylpiperidine (R,R) | 3,4-dichlorophenyl | 3,5-bis(CF₃)phenyl | 1-benzoyl-4-acetylpiperidine | CH₃ | |
| 452 | 1-methylpiperidine (R,R) | 3,4-dichlorophenyl | 3,5-bis(CF₃)phenyl | 1-(hydroxyacetyl)-4-acetylpiperidine | CH₃ | |

TABLE 51-continued
| Ex. No. | 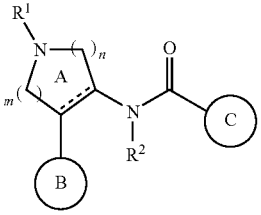 | B | C | R¹ | R² | salt/additive |
|---|---|---|---|---|---|---|
| 453 | 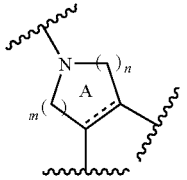 |  | 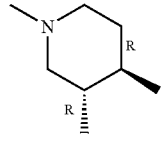 | 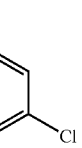 | CH₃ | |
| 454 | 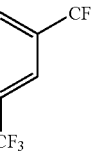 | 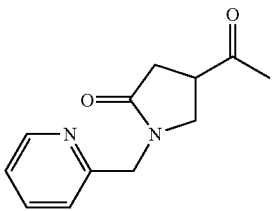 | 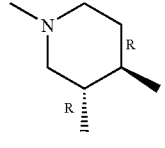 | 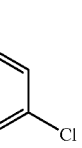 | CH₃ | HCl |
| 455 | 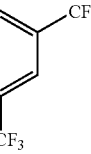 | 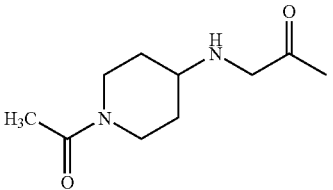 | 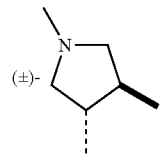 | 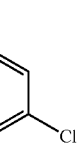 | CH₃ | |
| 456 | 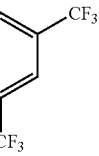 | 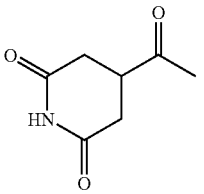 | 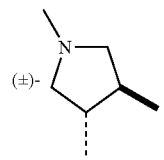 | 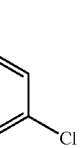 | CH₃ | |
| 457 | 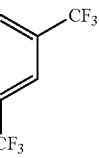 | 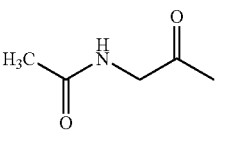 | 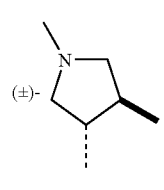 | 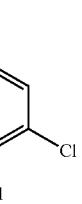 | CH₃ | HCl |

TABLE 51-continued
| Ex. No. | 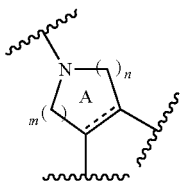 | B | C | R¹ | R² | salt/additive |
|---|---|---|---|---|---|---|
| 458 |  |  | 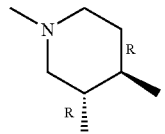 | 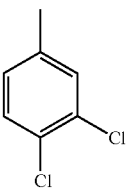 | CH₃ | H₂O |
| 459 | 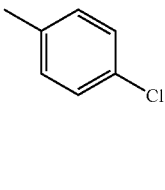 | 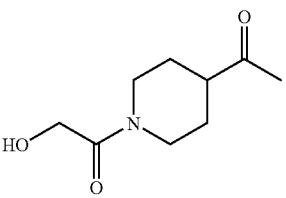 | 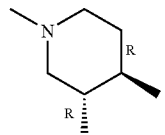 | 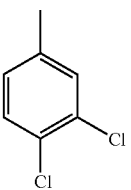 | CH₃ | |
| 460 | 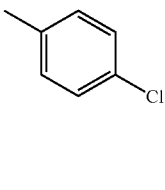 | 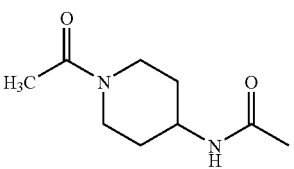 | 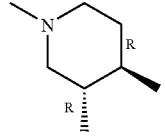 | 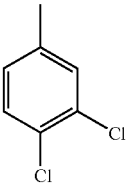 | CH₃ | |
| 461 | 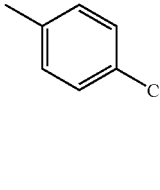 | 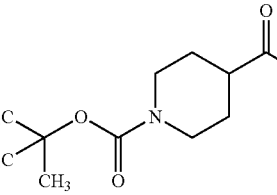 | 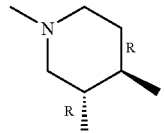 | 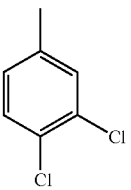 | CH₃ | |
| 462 | 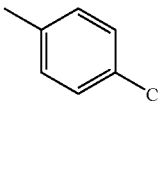 | 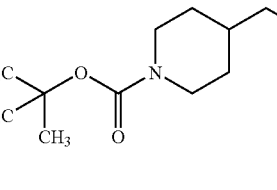 | 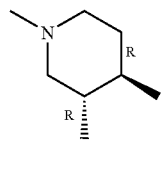 | 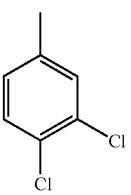 | CH₃ | HCl |

TABLE 52
| Ex. No. | 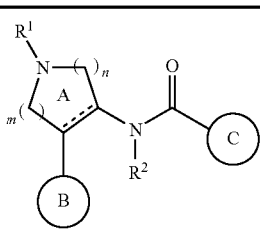 | B | C | R¹ | R² | salt/additive |
|---|---|---|---|---|---|---|
| 463 | 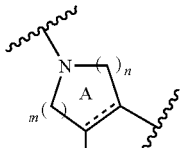 |  |  | 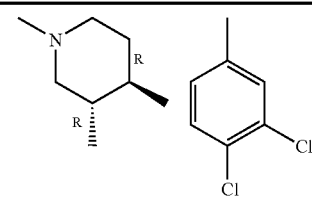 | CH₃ | HCl |
| 464 | 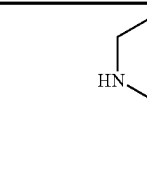 | 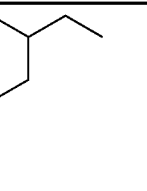 | 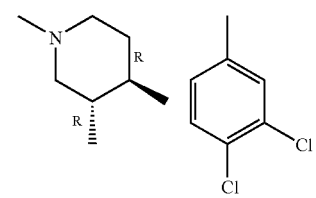 | 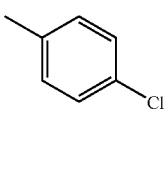 | CH₃ | 2.45H₂O |
| 465 | 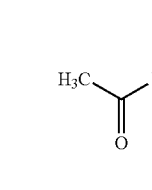 | 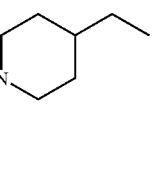 | 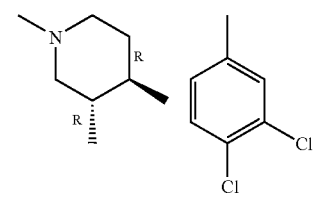 | 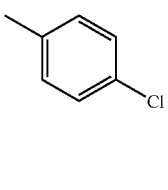 | CH₃ | |
| 466 | 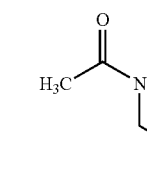 | 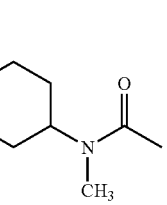 | 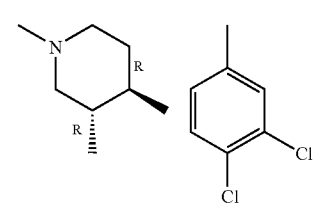 | 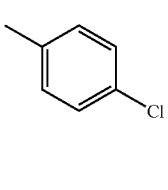 | CH₃ | |
| 467 | 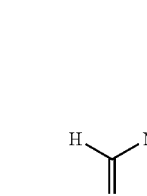 | 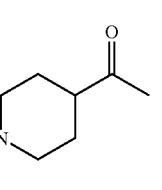 | 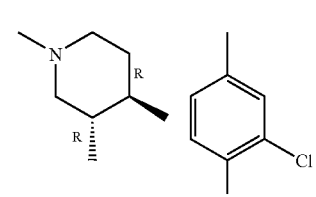 | 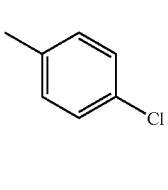 | CH₃ | |
| 468 | 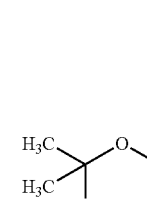 | 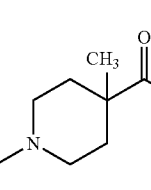 | 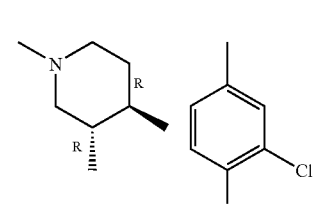 | 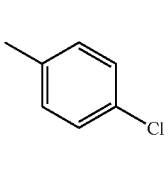 | CH₃ | |

TABLE 52-continued

| Ex. No. | A | B | C | R¹ | R² | salt/additive |
|---|---|---|---|---|---|---|
| 469 | 1-methyl-piperidine (trans 3,4) | 3,4-dichlorophenyl | 4-chlorophenyl | 1-(methoxycarbonyl)piperidin-4-yl carbonyl (acetyl at 4) | CH₃ | |
| 470 | 1-methyl-piperidine (trans 3,4) | 3,4-dichlorophenyl | 4-chlorophenyl | 1-(tert-butoxycarbonyl)piperidin-4-yl-CH₂-C(O)- | CH₃ | |
| 471 | 1-methyl-piperidine (trans 3,4) | 3,4-dichlorophenyl | 4-chlorophenyl | 1-(2-oxopropyl)-4-acetylpiperidine | CH₃ | |
| 472 | 1-methyl-piperidine (trans 3,4) | 3,4-dichlorophenyl | 4-chlorophenyl | 1-(cyclopropylcarbonyl)-4-acetylpiperidine | CH₃ | |
| 473 | 1-methyl-piperidine (trans 3,4) | 3,4-dichlorophenyl | 4-chlorophenyl | 1-(1-hydroxycyclopropylcarbonyl)-4-acetylpiperidine | CH₃ | |

TABLE 52-continued
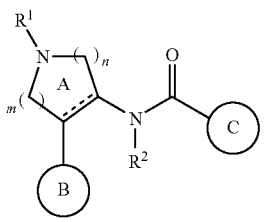
| Ex. No. | 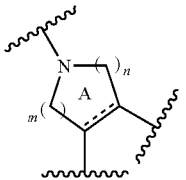 | B | C | R¹ | R² | salt/additive |
|---|---|---|---|---|---|---|
| 474 | 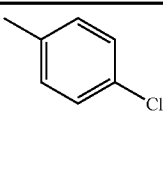 | 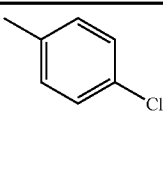 | 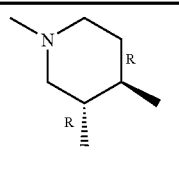 | 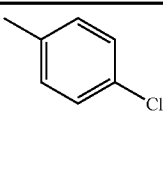 | CH₃ | |
TABLE 53
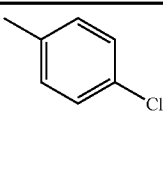
| Ex. No. | 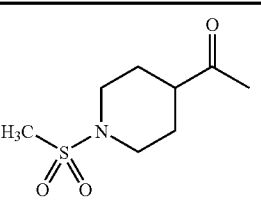 | B | C | R¹ | R² | salt/additive |
|---|---|---|---|---|---|---|
| 475 |  | 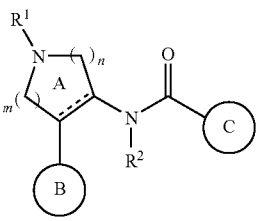 | 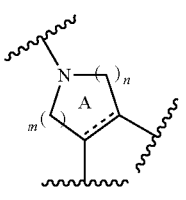 | 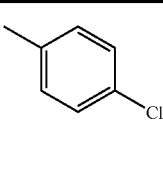 | CH₃ | HCl |
| 476 | 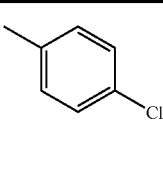 | 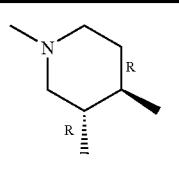 | 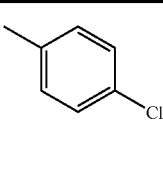 | 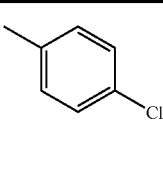 | CH₃ | HCl |

TABLE 53-continued

| Ex. No. | A | B | C | R¹ | R² | salt/additive |
|---|---|---|---|---|---|---|
| 477 | N-methyl piperidine | 3,4-dichlorophenyl | 4-chlorophenyl | 1H-benzotriazol-5-yl methyl ketone | CH₃ | |
| 478 | N-methyl piperidine | 3,4-dichlorophenyl | 4-chlorophenyl | ethyl 6-methylnicotinate | CH₃ | |
| 479 | N-methyl piperidine | 3,4-dichlorophenyl | 4-chlorophenyl | 1-(piperidin-4-yl)propan-2-one | CH₃ | HCl |
| 480 | N-methyl piperidine | 3,4-dichlorophenyl | 4-chlorophenyl | tert-butyl 3-acetylpyrrolidine-1-carboxylate | CH₃ | |
| 481 | N-methyl piperidine | 3,4-dichlorophenyl | 4-chlorophenyl | 2-methyl-1H-benzimidazol-5-yl methyl ketone | CH₃ | |
| 482 | N-methyl piperidine | 3,4-dichlorophenyl | 4-chlorophenyl | 1-(4,4-difluorocyclohexyl)ethanone | CH₃ | |

US 8,470,816 B2
TABLE 53-continued
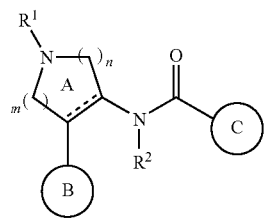
| Ex. No. | 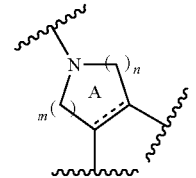 | B | C | R¹ | R² | salt/additive |
|---|---|---|---|---|---|---|
| 483 |  |  | 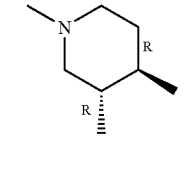 | 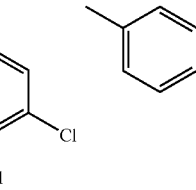 | CH₃ | |
| 484 | 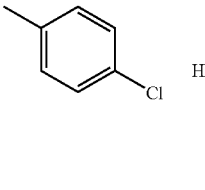 | 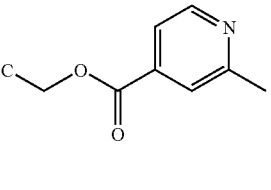 | 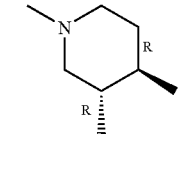 | 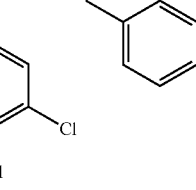 | CH₃ | |
| 485 | 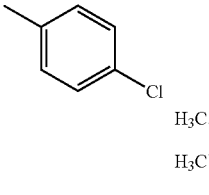 | 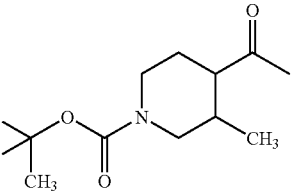 | 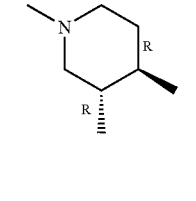 | 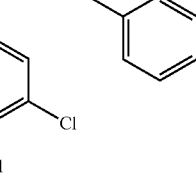 | CH₃ | |
| 486 | 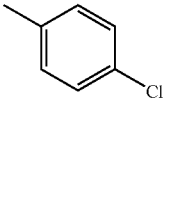 | 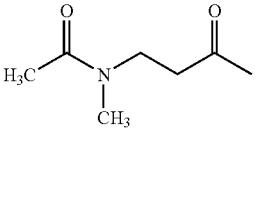 | 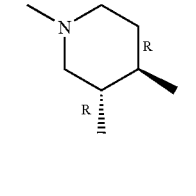 | 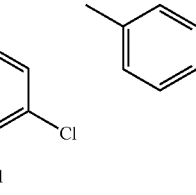 | CH₃ | |

TABLE 54
| Ex. No. | 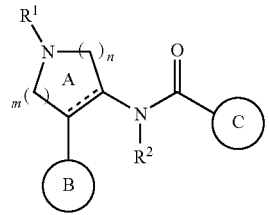 | B | C | R¹ | R² | salt/additive |
|---|---|---|---|---|---|---|
| 487 | 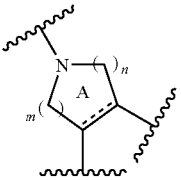 |  | 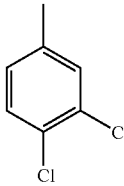 | 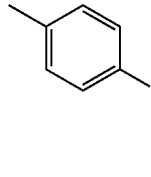 | CH₃ | HCl |
| 488 | 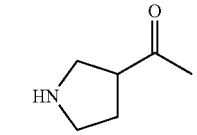 | 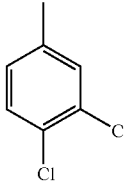 | 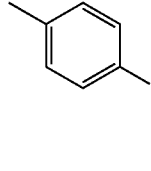 | 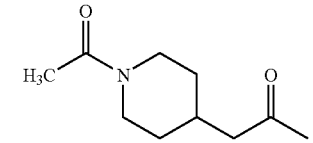 | CH₃ | |
| 489 | 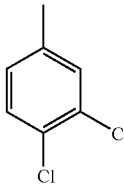 | 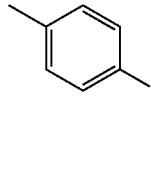 | 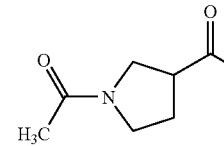 | 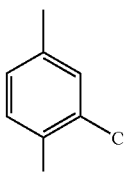 | CH₃ | |
| 490 | 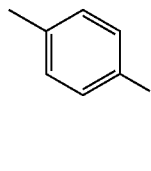 | 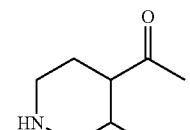 | 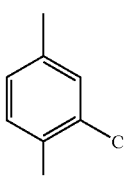 | 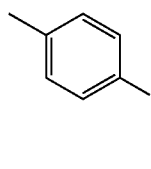 | CH₃ | HCl |
| 491 | 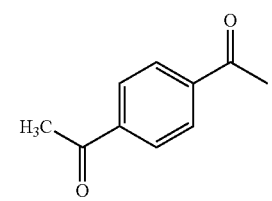 | | 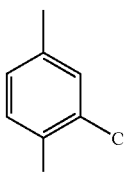 | 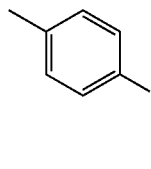 | CH₃ | |
| 492 | | | | 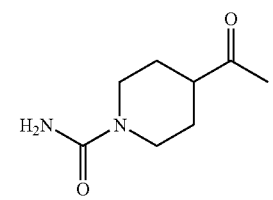 | CH₃ | |

TABLE 54-continued
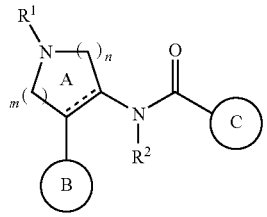

TABLE 55
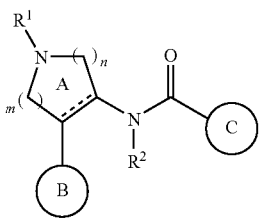
| Ex. No. | 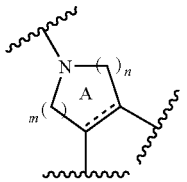 | B | C | R¹ | R² | salt/additive |
|---|---|---|---|---|---|---|
| 497 |  |  | 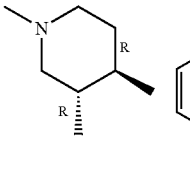 | 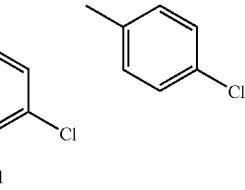 | CH₃ | |
| 498 | 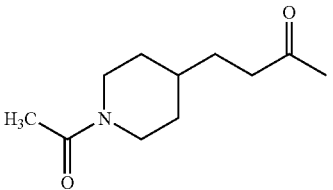 |  | 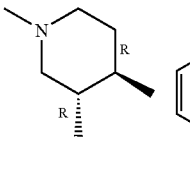 | 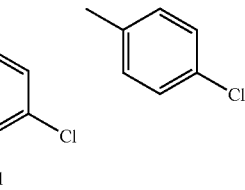 | CH₃ | |
| 499 | 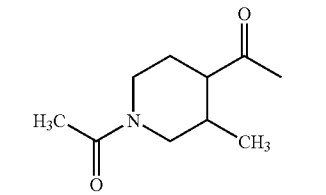 |  | 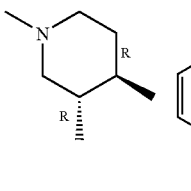 | 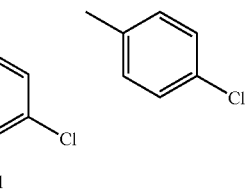 | CH₃ | |
| 500 |  |  | 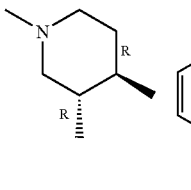 | 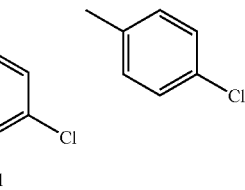 | CH₃ | |
| 501 | 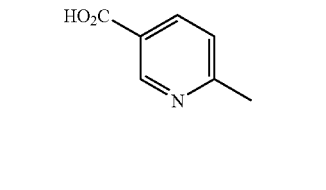 |  | 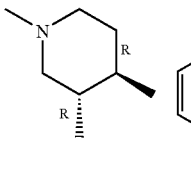 | 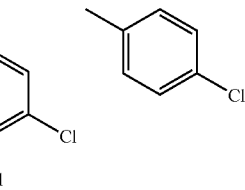 | CH₃ | |
| 502a | 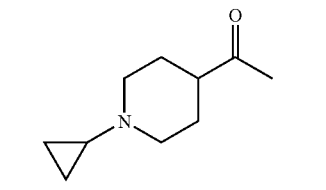 |  | 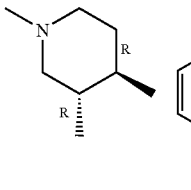 | 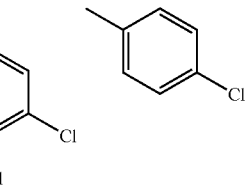 | CH₃ | |

TABLE 55-continued
| Ex. No. | 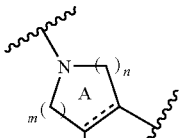 | B | C | R¹ | R² | salt/additive |
|---|---|---|---|---|---|---|
| 502b | 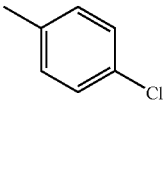 | 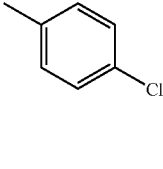 | 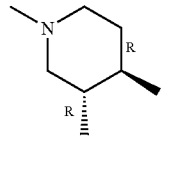 | 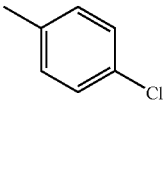 | CH₃ | HCl |
| 503 | 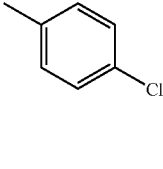 | 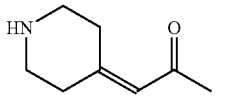 | 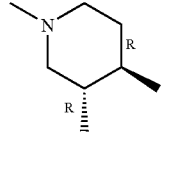 | 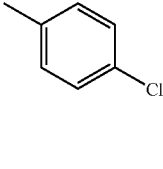 | CH₃ | |
| 504 | 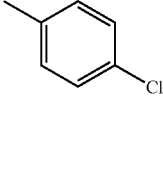 | 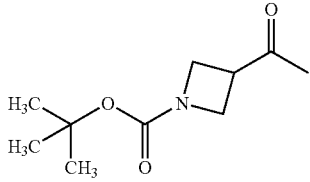 | 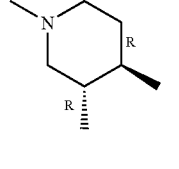 | 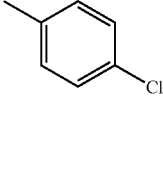 | CH₃ | |
| 505 | 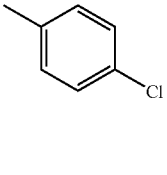 | 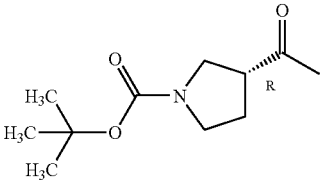 | 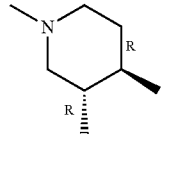 | 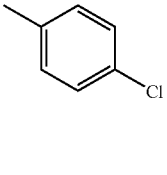 | CH₃ | |
| 506 | 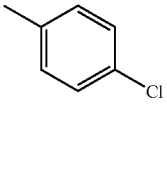 | 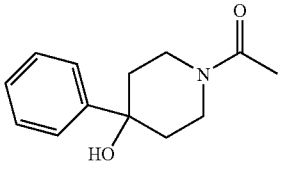 | 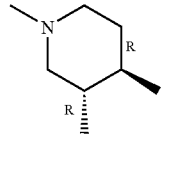 | 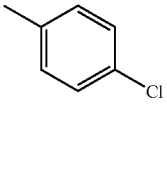 | CH₃ | |
| 507 | 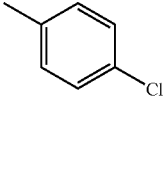 | 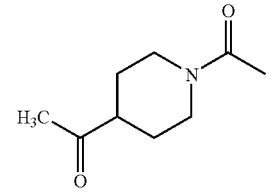 | 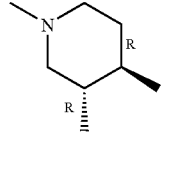 | 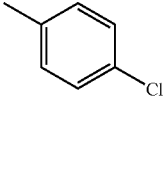 | CH₃ | |

TABLE 56
| Ex. No. | 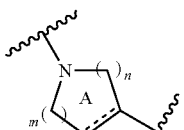 | B | C | R¹ | R² | salt/additive |
|---|---|---|---|---|---|---|
| 508 |  |  | 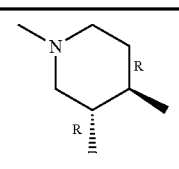 | 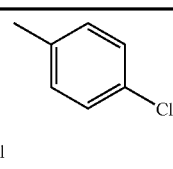 | CH₃ | HCl |
| 509 | 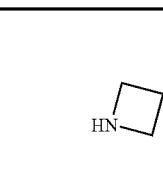 | 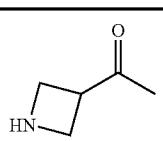 | 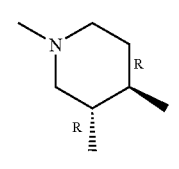 | 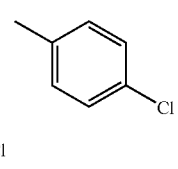 | CH₃ | HCl |
| 510 | 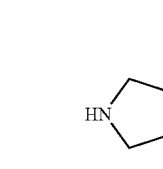 | 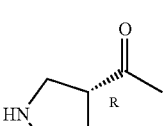 | 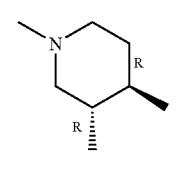 | 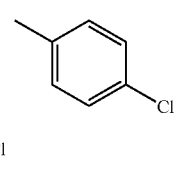 | CH₃ | |
| 511 | 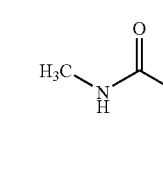 | 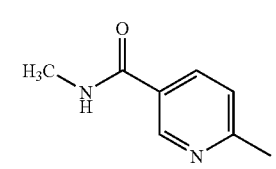 | 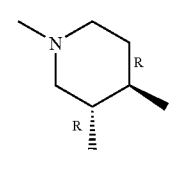 | 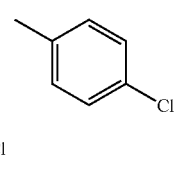 | CH₃ | |
| 512 | 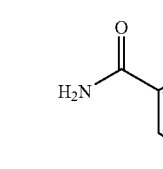 | 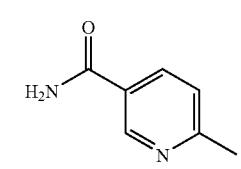 | 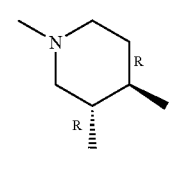 | 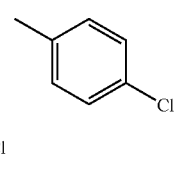 | CH₃ | |
| 513 | 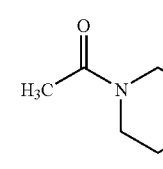 | 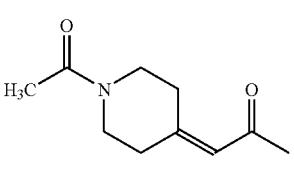 | 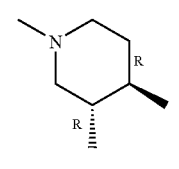 | 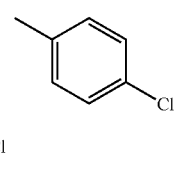 | CH₃ | |

TABLE 56-continued
| Ex. No. | 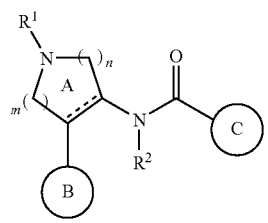 | B | C | R¹ | R² | salt/additive |
|---|---|---|---|---|---|---|
| 514 | 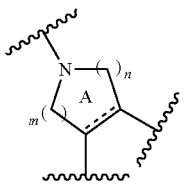 | 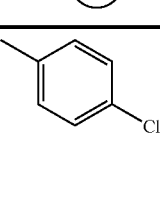 | 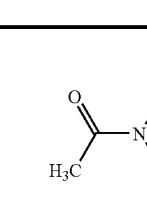 | 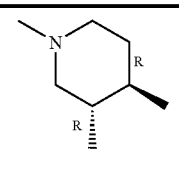 | CH₃ | |
| 515 | 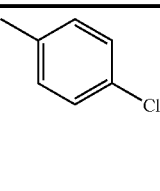 | 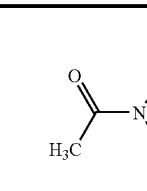 | 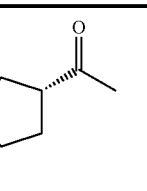 |  | CH₃ | |
| 516 | 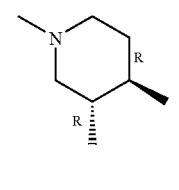 | 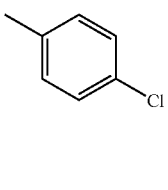 | 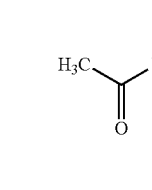 | 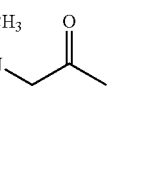 | CH₃ | |
| 517 |  | 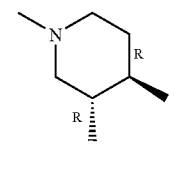 | 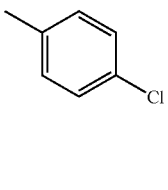 | 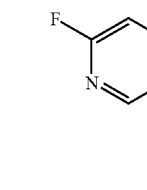 | CH₃ | |
| 518 | 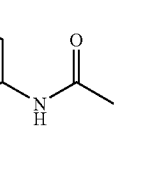 |  | 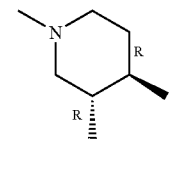 | 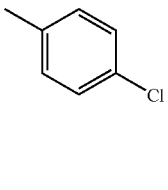 | CH₃ | |
| 519 | 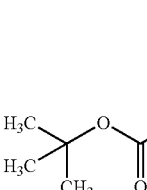 | 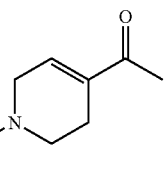 |  | 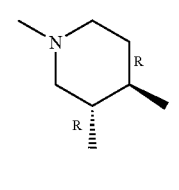 | CH₃ | HCl |

TABLE 57
| Ex. No. | A | B | C | R¹ | R² | salt/additive |
|---|---|---|---|---|---|---|
| 520 | 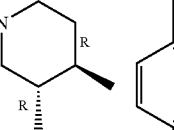 | 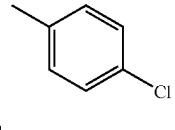 | 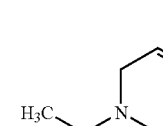 | 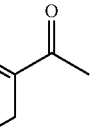 | CH₃ | |
| 521 | 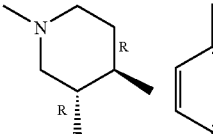 | 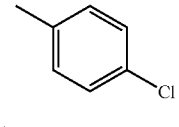 | 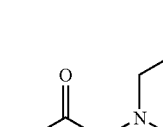 | 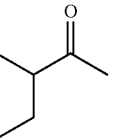 | CH₃ | |
| 522 | 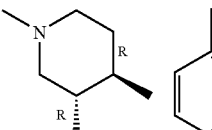 | 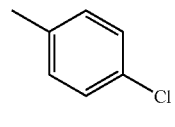 | 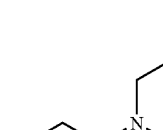 | 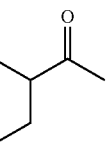 | CH₃ | |
| 523 | 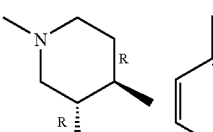 | 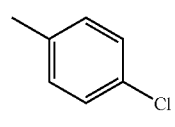 | 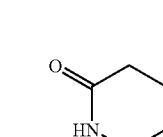 | 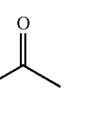 | CH₃ | |
| 524 | 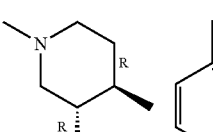 | 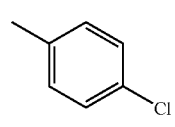 | 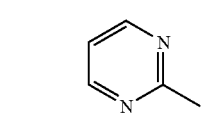 |  | CH₃ | |
| 525 | 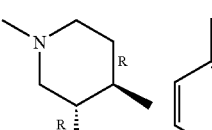 | 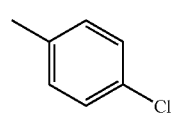 | 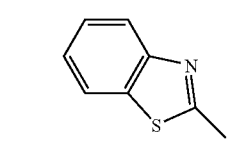 |  | CH₃ | |

TABLE 57-continued
| Ex. No. | 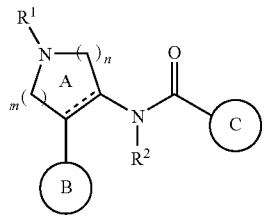 A | 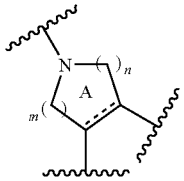 B | 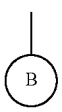 C | R¹ | R² | salt/additive |
|---|---|---|---|---|---|---|
| 526 |  | 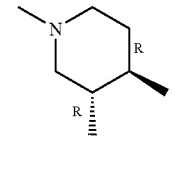 | 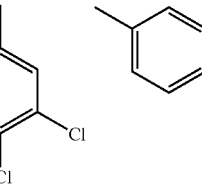 | 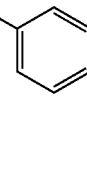 | CH₃ | |
| 527 | 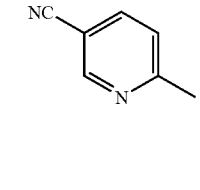 | 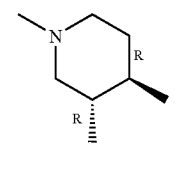 | 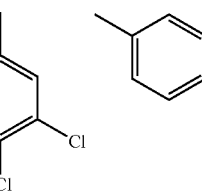 | 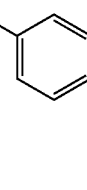 | CH₃ | |
| 528 | 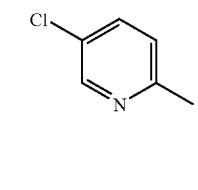 | 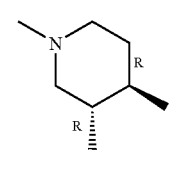 | 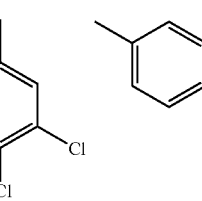 | 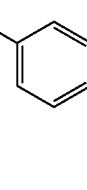 | CH₃ | |
| 529 | 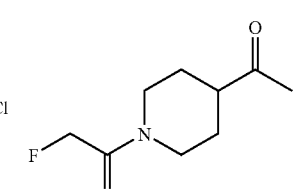 | 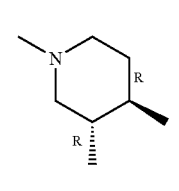 | 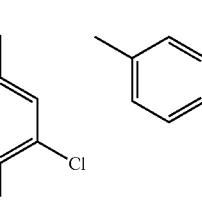 | 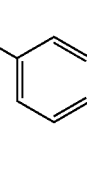 | CH₃ | |
| 530 | 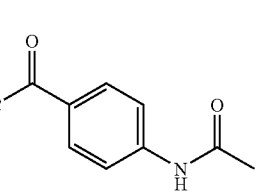 | 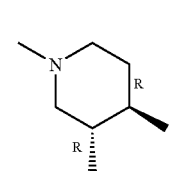 | 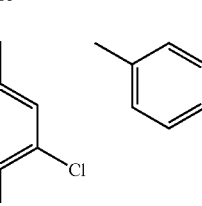 | 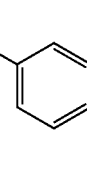 | CH₃ | |

TABLE 57-continued

| Ex. No. | A | B | C | R¹ | R² | salt/additive |
|---|---|---|---|---|---|---|
| 531 | N-methylpiperidine (4,3-disubst, R,R) | 3,4-dichlorophenyl | 4-chlorophenyl | (1S,2R)-2-aminocyclohexyl-C(O)- | CH₃ | HCl |

TABLE 58

| Ex. No. | A | B | C | R¹ | R² | salt/additive |
|---|---|---|---|---|---|---|
| 532 | N-methylpiperidine (4,3-disubst, R,R) | 3,4-dichlorophenyl | 4-chlorophenyl | 1-Boc-piperidin-3-yl-C(O)- | CH₃ | |
| 533 | N-methylpiperidine (4,3-disubst, R,R) | 3,4-dichlorophenyl | 4-chlorophenyl | (1S,2R)-2-benzamidocyclohexyl-C(O)- | CH₃ | |

US 8,470,816 B2
TABLE 58-continued
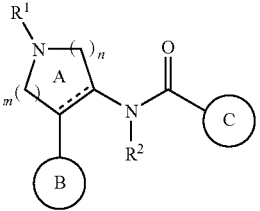
| Ex. No. | 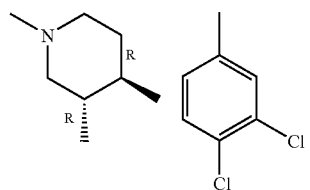 | B | C | R¹ | R² | salt/ additive |
|---|---|---|---|---|---|---|
| 534 | 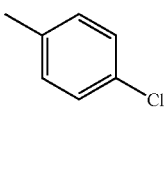 | 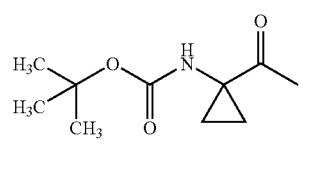 | 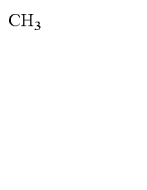 | 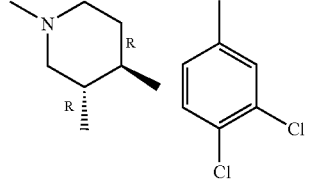 | CH₃ | |
| 535 | 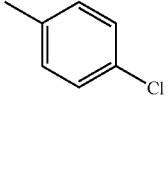 | 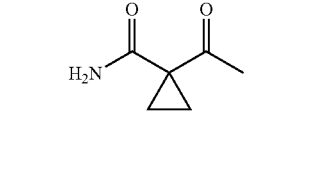 |  | 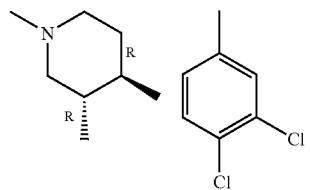 | CH₃ | |
| 536 | 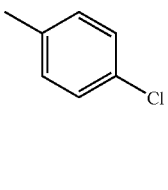 | 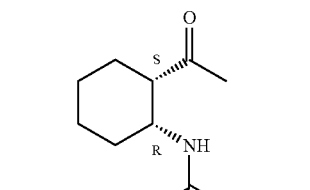 | 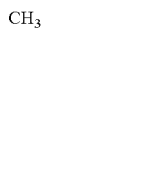 | 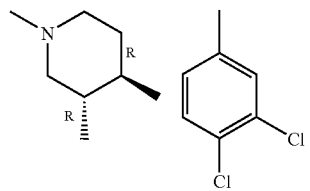 | CH₃ | |
| 537 | 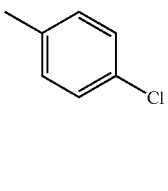 | 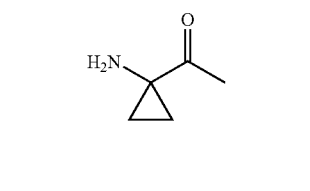 | | 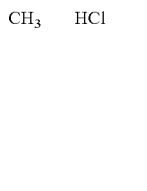 | CH₃ | HCl |

TABLE 58-continued
| Ex. No. | 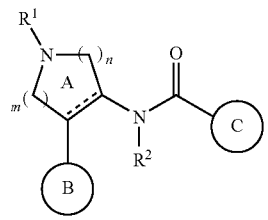 | B | C | R¹ | R² | salt/additive |
|---|---|---|---|---|---|---|
| 538 | 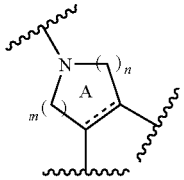 | 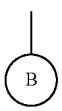 |  | 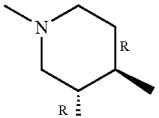 | CH₃ | |
| 539 | 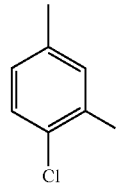 | 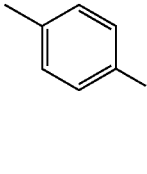 | 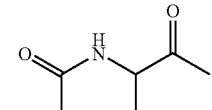 | 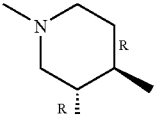 | CH | |
| 540 | 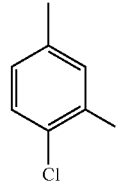 | 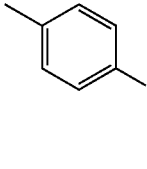 | 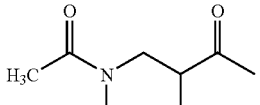 | 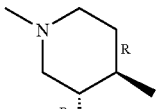 | CH₃ | |
| 541 | 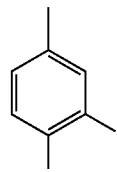 | 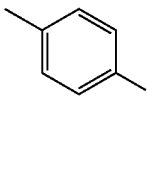 | 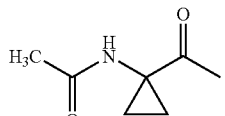 | 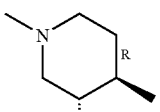 | CH₃ | |

TABLE 59

| Ex. No. | A | B | C | R¹ | R² | salt/additive |
|---|---|---|---|---|---|---|
| 542 | 1-methylpiperidine (4,3-substituted) | 3,4-dichlorophenyl | 4-chlorophenyl | piperidin-3-yl | CH₃ | HCl |
| 543 | 1-methylpiperidine (4,3-substituted) | 3,4-dichlorophenyl | 4-chlorophenyl | N-Boc-piperidin-2-yl | CH₃ | |
| 544 | 1-methylpiperidine (4,3-substituted) | 3,4-dichlorophenyl | 4-chlorophenyl | 1-benzoylpiperidin-3-yl | CH₃ | |
| 545 | 1-methylpiperidine (4,3-substituted) | 3,4-dichlorophenyl | 4-chlorophenyl | piperidin-2-yl | CH₃ | HCl |
| 546 | 1-methylpiperidine (4,3-substituted) | 3,4-dichlorophenyl | 4-chlorophenyl | 1-acetylpiperidin-2-yl | CH₃ | |

TABLE 59-continued

| Ex. No. | A ring | B | C | R¹ | R² | salt/additive |
|---|---|---|---|---|---|---|
| 547 | 1-methyl-3,4-dimethylpiperidine | 3,4-diCl-phenyl | 4-Cl-phenyl | 1-benzoyl-2-acetylpiperidine | CH₃ | |
| 548 | 1-methyl-3,4-dimethylpiperidine | 3,4-diCl-phenyl | 4-Cl-phenyl | O=N-CH₃ | CH₃ | |
| 549 | 1-methyl-3,4-dimethylpiperidine | 3,4-diCl-phenyl | 4-Cl-phenyl | H₂N-CH₃ | CH₃ | HCl |
| 550 | 1-methyl-3,4-dimethylpiperidine | 3,4-diCl-phenyl | 4-Cl-phenyl | 1-acetyl-piperidine-4-(N-methyl)carboxamide | CH₃ | |
| 551 | 1-methyl-3,4-dimethylpiperidine | 3,4-diCl-phenyl | 4-Cl-phenyl | 1-trifluoroacetyl-4-acetylpiperidine | CH₃ | |

TABLE 60

| Ex. No. | A | B | C | R¹ | R² | salt/additive |
|---|---|---|---|---|---|---|
| 552 | 1-methyl-piperidine (3,4-trans) | 3,4-dichlorophenyl | 4-chlorophenyl | methanesulfonyl (H₃C-SO₂-) | CH₃ | |
| 553 | 1-methyl-piperidine (3,4-trans) | 3,4-dichlorophenyl | 4-chlorophenyl | 2-acetylpyridine N-oxide | CH₃ | |
| 554 | 1-methyl-piperidine (3,4-trans) | 3,4-dichlorophenyl | 4-chlorophenyl | 4-acetyl-1-(2-hydroxypropanoyl)piperidine | CH₃ | |
| 555 | 1-methyl-piperidine (3,4-trans) | 3,4-dichlorophenyl | 4-chlorophenyl | 4-acetyl-1-(2-hydroxy-2-methylpropanoyl)piperidine | CH₃ | |
| 556 | 1-methyl-piperidine (3,4-trans) | 3,4-dichlorophenyl | 4-chlorophenyl | 4-acetyl-1-(2-hydroxy-3-methylbutanoyl)piperidine | CH₃ | |
| 557 | 1-methyl-piperidine (3,4-trans) | 3,4-dichlorophenyl | 4-chlorophenyl | ethyl 4-methylbenzoate | CH₃ | |

TABLE 60-continued

| Ex. No. | A | B | C | R[1] | R[2] | salt/additive |
|---|---|---|---|---|---|---|
| 558 | 1-methylpiperidin-4,3-diyl | 3,4-dichlorophenyl | 4-chlorophenyl | 3-cyano-2-methylpyridin-... | CH₃ | |
| 559 | 1-methylpiperidin-4,3-diyl | 3,4-dichlorophenyl | 4-chlorophenyl | 4-cyano-2-methylpyridin-... | CH₃ | |
| 560 | 1-methylpiperidin-4,3-diyl | 3,4-dichlorophenyl | 4-chlorophenyl | 6-cyano-2-methylpyridin-... | CH₃ | |
| 561 | 1-methylpiperidin-4,3-diyl | 3,4-dichlorophenyl | 4-chlorophenyl | methyl 2-methylthiazole-5-carboxylate | CH₃ | |
| 562 | 1-methylpiperidin-4,3-diyl | 3,4-dichlorophenyl | 4-chlorophenyl | 3-acetyl-4-Boc-morpholine | CH₃ | |
| 563 | 1-methylpiperidin-4,3-diyl | 3,4-dichlorophenyl | 4-chlorophenyl | 2'-nitroacetophenone | CH₃ | |

TABLE 61
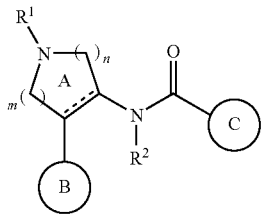
| Ex. No. | 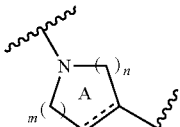 | B | C | R¹ | R² | salt/additive |
|---|---|---|---|---|---|---|
| 564 |  |  | 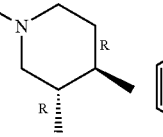 | 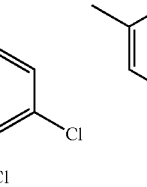 | CH₃ | |
| 565 | 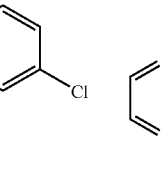 | 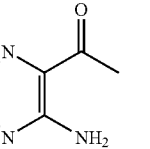 | 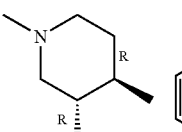 | 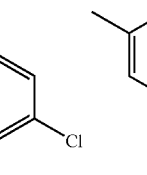 | CH₃ | |
| 566 | 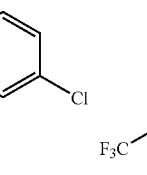 | 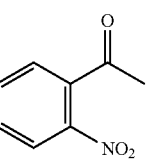 | 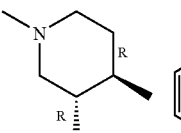 | 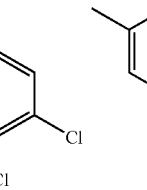 | CH₃ | |
| 567 | 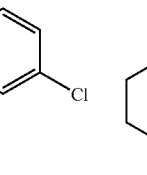 | 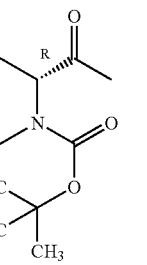 | 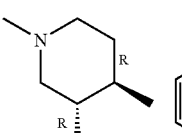 | 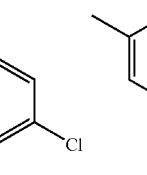 | CH₃ | |
| 568 | 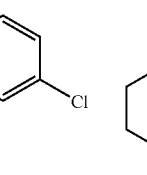 | 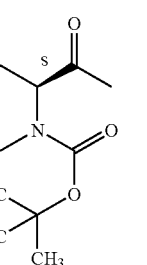 | 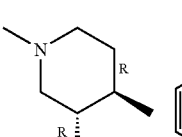 | 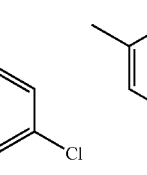 | CH₃ | |

TABLE 61-continued

| Ex. No. | A (ring) | B | C | R¹ | R² | salt/additive |
|---|---|---|---|---|---|---|
| 569 | N-methyl piperidine (3,4-diR) | 3,4-diCl-phenyl | 4-Cl-phenyl | morpholin-3-yl-carbonyl (NH) | CH₃ | HCl |
| 570 | N-methyl piperidine (3,4-diR) | 3,4-diCl-phenyl | 4-Cl-phenyl | (R)-piperidin-2-yl-carbonyl | CH₃ | HCl |
| 571 | N-methyl piperidine (3,4-diR) | 3,4-diCl-phenyl | 4-Cl-phenyl | (S)-piperidin-2-yl-carbonyl | CH₃ | HCl |
| 572 | N-methyl piperidine (3,4-diR) | 3,4-diCl-phenyl | 4-Cl-phenyl | (3S,4S)-3-(Boc-amino)-tetrahydropyran-4-yl-carbonyl | CH₃ | |
| 573 | N-methyl piperidine (3,4-diR) | 3,4-diCl-phenyl | 4-Cl-phenyl | 2-aminophenyl-carbonyl | CH₃ | |

TABLE 62

| Ex. No | A | B | C | R¹ | R² | salt/additive |
|---|---|---|---|---|---|---|
| 574 | 1-methyl-piperidine (3R,4R) | 3,4-dichlorophenyl | 4-chlorophenyl | (R)-1-methyl-2-acetyl-piperidine | CH₃ | |
| 575 | 1-methyl-piperidine (3R,4R) | 3,4-dichlorophenyl | 4-chlorophenyl | (3S,4S)-3-amino-tetrahydropyran-4-yl acetyl | CH₃ | HCl |
| 576 | 1-methyl-piperidine (3R,4R) | 3,4-dichlorophenyl | 4-chlorophenyl | 4-benzoyl-morpholin-2-yl acetyl | CH₃ | |
| 577 | 1-methyl-piperidine (3R,4R) | 3,4-dichlorophenyl | 4-chlorophenyl | (R)-1-benzoyl-2-acetyl-piperidine | CH₃ | |

TABLE 62-continued

| Ex. No | [A ring] | B | C | R¹ | R² | salt/additive |
|---|---|---|---|---|---|---|
| 578 | 1-methyl-piperidine (R,R) | 3,4-diCl-phenyl | 4-Cl-phenyl | (S)-1-benzoyl-piperidin-2-yl | CH₃ | |
| 579 | 1-methyl-piperidine (R,R) | 3,4-diCl-phenyl | 4-Cl-phenyl | (3S,4S)-3-benzamido-tetrahydropyran-4-yl | CH₃ | |
| 580 | 1-methyl-piperidine (R,R) | 3,4-diCl-phenyl | 4-Cl-phenyl | (R)-1-(4-chlorobenzoyl)-piperidin-2-yl | CH₃ | |
| 581 | 1-methyl-piperidine (R,R) | 3,4-diCl-phenyl | 4-Cl-phenyl | (R)-1-(3-chlorobenzoyl)-piperidin-2-yl | CH₃ | |

TABLE 63

| Ex. No. | A | B | C | R¹ | R² | salt/additive |
|---|---|---|---|---|---|---|
| 582 | 1-methylpiperidine (4,3-trans diMe) | 3,4-diCl-phenyl | 4-Cl-phenyl | (R)-1-(2-chlorobenzoyl)piperidin-2-yl acetyl | CH₃ | |
| 583 | 1-methylpiperidine (4,3-trans diMe) | 3,4-diCl-phenyl | 4-Cl-phenyl | (R)-1-(4-methoxybenzoyl)piperidin-2-yl acetyl | CH₃ | |
| 584 | 1-methylpiperidine (4,3-trans diMe) | 3,4-diCl-phenyl | 4-Cl-phenyl | (R)-1-(4-cyanobenzoyl)piperidin-2-yl acetyl | CH₃ | |

TABLE 63-continued

| Ex. No. | A | B | C | R¹ | R² | salt/additive |
|---|---|---|---|---|---|---|
| 585 | 1-methyl-piperidine (trans 3,4) | 3,4-dichlorophenyl | 4-chlorophenyl | 1-([1,1'-biphenyl]-4-carbonyl)piperidin-2-yl methyl ketone | CH₃ | |
| 586 | 1-methyl-piperidine (trans 3,4) | 3,4-dichlorophenyl | 4-chlorophenyl | 6-acetylimidazo[1,2-a]pyridine | CH₃ | |
| 587 | 1-methyl-piperidine (trans 3,4) | 3,4-dichlorophenyl | 4-chlorophenyl | 7-acetyl-3-(trifluoromethyl)-5,6,7,8-tetrahydro-[1,2,4]triazolo[4,3-a]pyrazine | CH₃ | |
| 588 | 1-methyl-piperidine (trans 3,4) | 3,4-dichlorophenyl | 4-chlorophenyl | methyl vinyl ketone (H₂C=CH-C(O)-CH₃) | CH₃ | |
| 589 | 1-methyl-piperidine (trans 3,4) | 3,4-dichlorophenyl | 4-chlorophenyl | 1-(3-oxobutyl)pyrrolidin-2-one | CH₃ | |

TABLE 63-continued

| Ex. No. | A | B | C | R¹ | R² | salt/additive |
|---|---|---|---|---|---|---|
| 590 | 1-methylpiperidin-4,3-diyl | 3,4-dichlorophenyl | 4-chlorophenyl | 4-sulfamoylbenzoyl | CH₃ | |
| 591 | 1-methylpiperidin-4,3-diyl | 3,4-dichlorophenyl | 4-chlorophenyl | 4-acetamidophenylcarbonyl (H₃C-C(O)NH-C₆H₄-C(O)-) | CH₃ | |

TABLE 64

| Ex. No. | A | B | C | R¹ | R² | salt/additive |
|---|---|---|---|---|---|---|
| 592 | 1-methylpiperidin-4,3-diyl | 3,4-dichlorophenyl | 4-chlorophenyl | 3-acetylphenyl-NHC(O)CH₃ | CH₃ | |

TABLE 64-continued

| Ex. No. | A | B | C | R¹ | R² | salt/additive |
|---|---|---|---|---|---|---|
| 593 | N-methyl piperidine (trans diMe) | 3,4-dichlorophenyl | 4-chlorophenyl | 4-(hydroxymethyl)tetrahydropyran-4-yl carbonyl | CH₃ | |
| 594 | N-methyl piperidine (trans diMe) | 3,4-dichlorophenyl | 4-chlorophenyl | 1-benzyl-piperidin-2-yl carbonyl | CH₃ | |
| 595 | N-methyl piperidine (trans diMe) | 3,4-dichlorophenyl | 4-chlorophenyl | 1-acetyl-pyrrolidin-2-yl carbonyl | CH₃ | |
| 596 | N-methyl piperidine (trans diMe) | 3,4-dichlorophenyl | 4-chlorophenyl | 1-Boc-pyrrolidin-2-yl carbonyl | CH₃ | |
| 597 | N-methyl piperidine (trans diMe) | 3,4-dichlorophenyl | 4-chlorophenyl | 1-Boc-4-hydroxy-pyrrolidin-2-yl carbonyl | CH₃ | |

TABLE 64-continued

| Ex. No. | A | B | C | R¹ | R² | salt/additive |
|---|---|---|---|---|---|---|
| 598 | | | | | CH₃ | |
| 599 | | | | | CH₃ | HCl |
| 600 | | | | | CH₃ | HCl |
| 601 | | | | | CH₃ | HCl |

TABLE 65

| Ex. No. | A | B | C | R¹ | R² | salt/additive |
|---|---|---|---|---|---|---|
| 602 | 1-methylpiperidine (trans-3,4-diR) | 3,4-dichlorophenyl | 4-chlorophenyl | (R)-1-(isonicotinoyl)piperidin-2-yl (acetyl) | CH₃ | |
| 603 | 1-methylpiperidine (trans-3,4-diR) | 3,4-dichlorophenyl | 4-chlorophenyl | (R)-1-(isonicotinoyl N-oxide)piperidin-2-yl (acetyl) | CH₃ | |
| 604 | 1-methylpiperidine (trans-3,4-diR) | 3,4-dichlorophenyl | 4-chlorophenyl | 1-hydroxy-2,2-dimethyl-3-oxobutyl | CH₃ | |
| 605 | 1-methylpiperidine (trans-3,4-diR) | 3,4-dichlorophenyl | 4-chlorophenyl | 7H-pyrrolo[2,3-d]pyrimidin-4-yl | CH₃ | |
| 606 | 1-methylpiperidine (trans-3,4-diR) | 3,4-dichlorophenyl | 4-chlorophenyl | 2-hydroxy-2-methyl-4-oxopentan-3-yl | CH₃ | |

TABLE 65-continued
| Ex. No. | 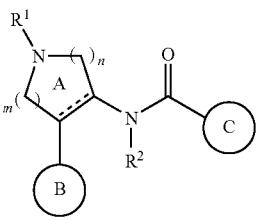 | B | C | R¹ | R² | salt/additive |
|---|---|---|---|---|---|---|
| 607 | 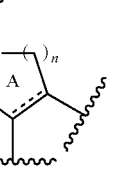 |  |  | 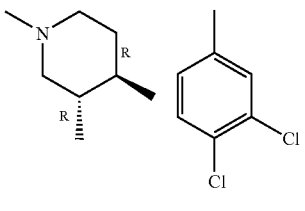 | CH₃ | |
| 608 | 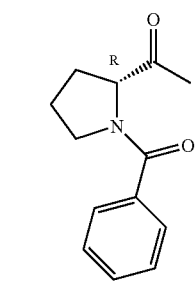 [SMILES: CC(=O)[C@H]1CCCN1C(=O)c1ccccc1] |  | 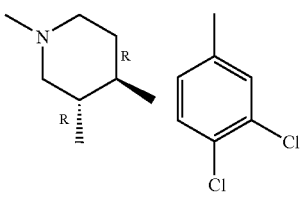 | 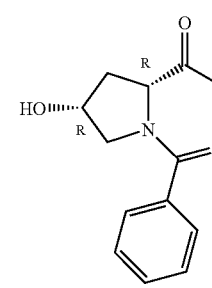 | CH₃ | |
| 609 |  | 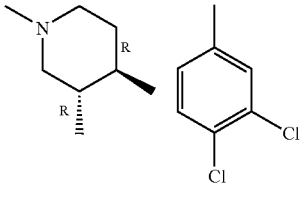 | 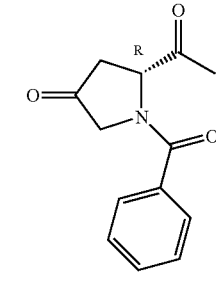 |  | CH₃ | |
| 610 | 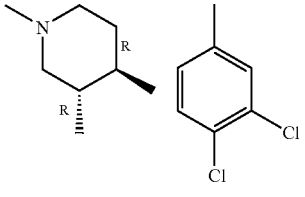 | 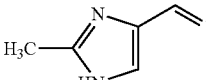 |  | | CH₃ | |

TABLE 65-continued
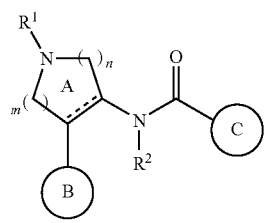
| Ex. No. | 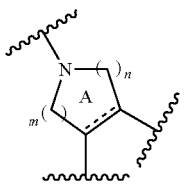 | B | C | R¹ | R² | salt/additive |
|---|---|---|---|---|---|---|
| 611 |  |  | 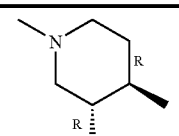 |  | CH₃ | |
TABLE 66
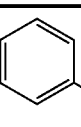
| Ex. No. | 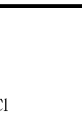 | B | C | R¹ | R² | salt/additive |
|---|---|---|---|---|---|---|
| 612 | 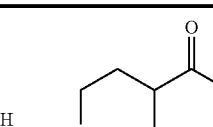 |  | 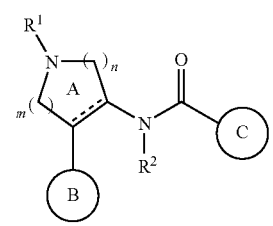 | 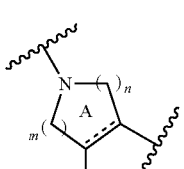 | CH₃ | |
| 613 |  |  | 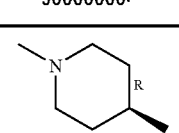 |  | CH₃ | |

TABLE 66-continued

| Ex. No. | A | B | C | R¹ | R² | salt/additive |
|---|---|---|---|---|---|---|
| 614 | N-methylpiperidine (R,R) | 3,4-dichlorophenyl | 4-morpholinophenyl | C(O)CF₃ | CH₃ | |
| 615 | N-methylpiperidine (R,R) | 3,4-dichlorophenyl | 4-morpholinophenyl | CH₃ | CH₃ | |
| 616 | N-methylpiperidine (R,R) | 3,4-dichlorophenyl | 4-morpholinophenyl | SO₂CH₃ | CH₃ | |
| 617 | N-methylpiperidine (R,R) | 3,4-dichlorophenyl | 4-morpholinophenyl | C(O)Ph | CH₃ | |
| 618 | N-methylpiperidine (R,R) | 3,4-dichlorophenyl | 4-morpholinophenyl | CH₂CF₃ | CH₃ | |
| 619 | N-methylpiperidine (R,R) | 3,4-dichlorophenyl | 4-morpholinophenyl | 5-(trifluoromethyl)-2-methylpyridinyl | CH₃ | |

TABLE 66-continued

| Ex. No. | [ring A] | B | C | R¹ | R² | salt/additive |
|---|---|---|---|---|---|---|
| 620 | 1-methyl-piperidine (trans-3,4-dimethyl) | 3,4-diCl-phenyl | 4-morpholinophenyl | N-Boc-piperidin-4-yl | CH₃ | |
| 621 | 1-methyl-piperidine (trans-3,4-dimethyl) | 3,4-diCl-phenyl | 4-morpholinophenyl | piperidin-4-yl | CH₃ | HCl |
| 622 | 1-methyl-piperidine (trans-3,4-dimethyl) | 3,4-diCl-phenyl | 4-morpholinophenyl | 1-(cyclopropanecarbonyl)piperidin-4-yl | CH₃ | |
| 623 | 1-methyl-piperidine (trans-3,4-dimethyl) | 3,4-diCl-phenyl | 4-morpholinophenyl | 1-(1-hydroxycyclopropanecarbonyl)piperidin-4-yl | CH₃ | 0.5 EtOAc |

TABLE 67
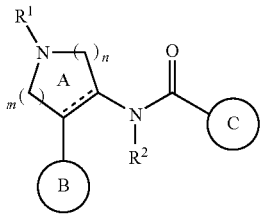
| Ex. No. | 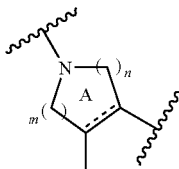 | B | C | R[1] | R[2] | salt/additive |
|---|---|---|---|---|---|---|
| 624 |  |  | 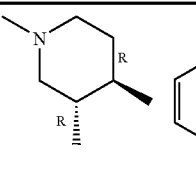 | 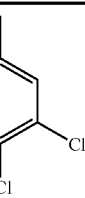 | CH₃ | |
| 625 | 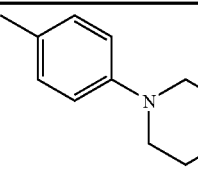 | 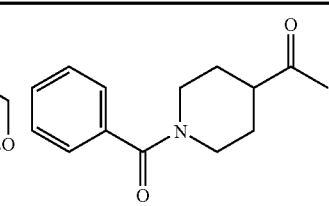 | 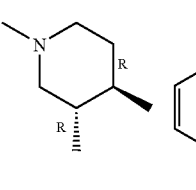 | 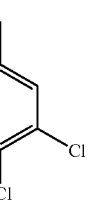 | CH₃ | |
| 626 | 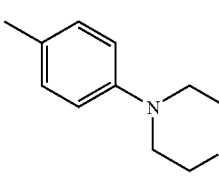 | 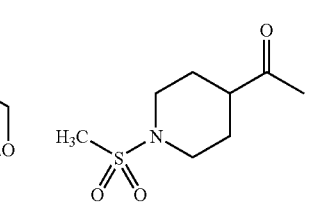 | 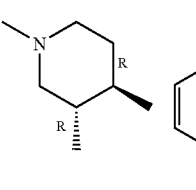 | 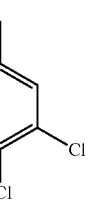 | CH₃ | |
| 627 | 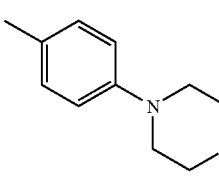 | 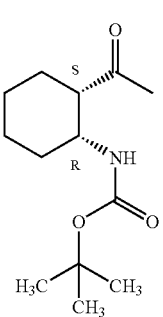 | 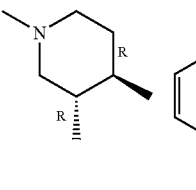 | 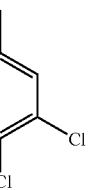 | CH₃ | |
| 628 | 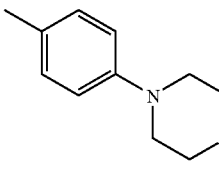 | 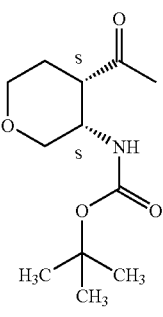 | 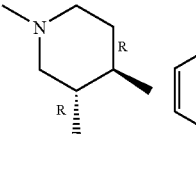 | 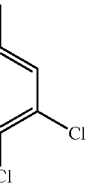 | CH₃ | HCl |

TABLE 67-continued
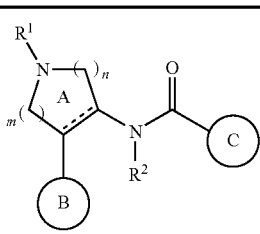
| Ex. No. | A | B | C | R¹ | R² | salt/additive |
|---|---|---|---|---|---|---|
| 629 | 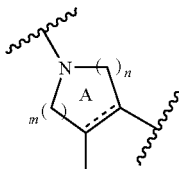 |  |  | 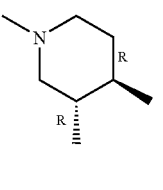 | CH₃ | HCl, 2.75 H₂O |
| 630 | 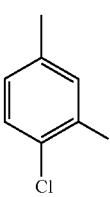 | 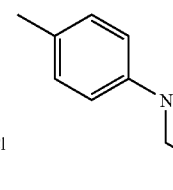 | 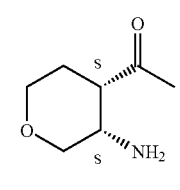 | 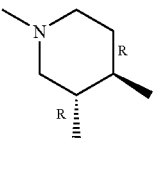 | CH₃ | |
| 631 | 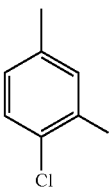 | 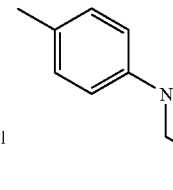 | 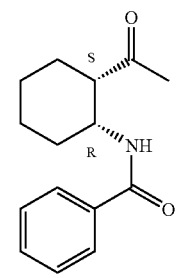 | 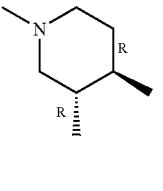 | CH₃ | |
| 632 | 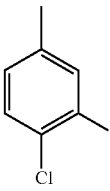 | 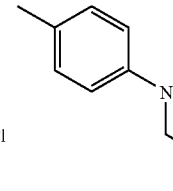 | 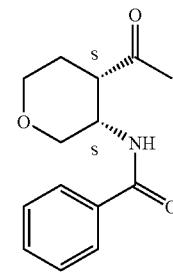 | 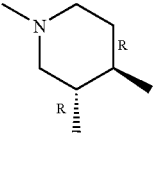 | CH₃ | H₂O |
| 633 | 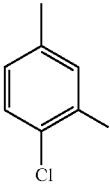 | 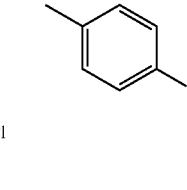 | 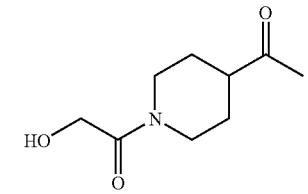 | 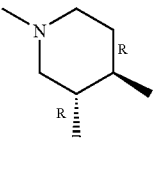 | CH₃ | H₂O |

TABLE 68
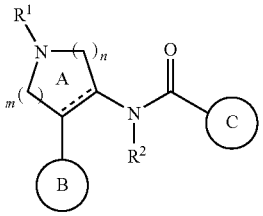
| Ex. No. | 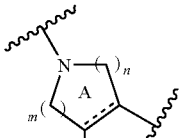 | B | C | R¹ | R² | salt/additive |
|---|---|---|---|---|---|---|
| 634 |  |  3,4-diCl | 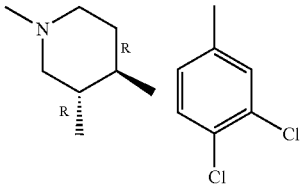 2-Me-5-CF₃-pyridyl | 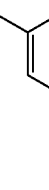 | CH₃ | |
| 635 | 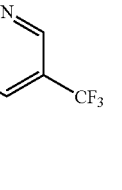 | 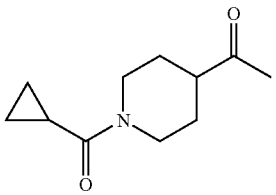 | 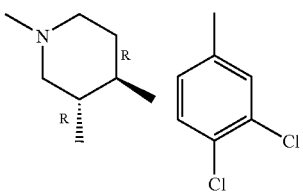 | 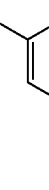 | CH₃ | 0.5H₂O |
| 636 | 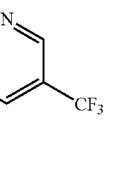 | 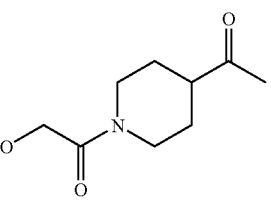 | 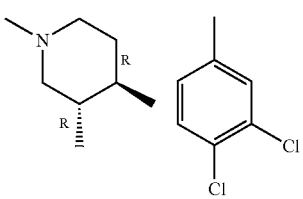 | 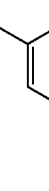 | CH₃ | |
| 637 | 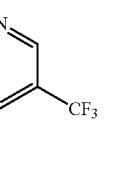 | 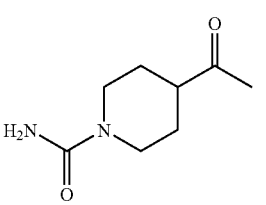 | 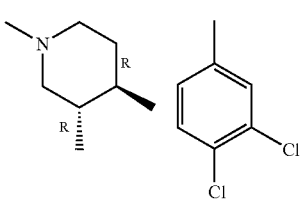 | 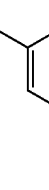 | CH₃ | |
| 638 | 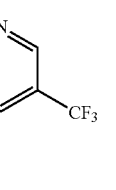 | 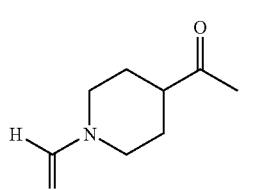 | 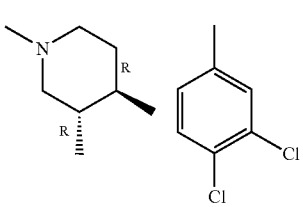 | 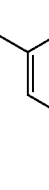 | CH₃ | |
| 639 | 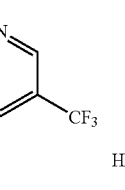 | 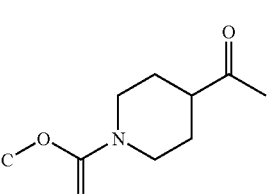 | 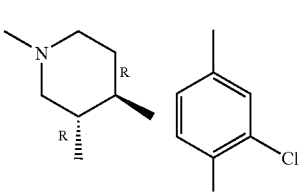 | 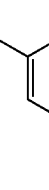 | CH₃ | |

TABLE 68-continued

| Ex. No. | A | B | C | R¹ | R² | salt/additive |
|---|---|---|---|---|---|---|
| 640 | piperidine | 3,4-dichlorophenyl | 6-CF₃-pyridin-3-yl | 1-(2-hydroxy-2-methylpropanoyl)piperidin-4-yl | CH₃ | |
| 641 | piperidine | 3,4-dichlorophenyl | 6-CF₃-pyridin-3-yl | 2-methyl-3-oxo-2,3,3a,4,5,6-hexahydropyrazolo[3,4-c]pyridin-5-yl acetyl | CH₃ | |
| 642 | piperidine | 3,4-dichlorophenyl | 6-CF₃-pyridin-3-yl | 7-oxo-4,5,6,7-tetrahydro-1H-indol-2-yl | CH₃ | |
| 643 | piperidine | 3,4-dichlorophenyl | 6-CF₃-pyridin-3-yl | 5-(methoxycarbonyl)-1H-pyrrol-2-yl | CH₃ | |
| 644 | piperidine | 3,4-dichlorophenyl | 6-CF₃-pyridin-3-yl | 1-methyl-7-oxo-4,5,6,7-tetrahydro-1H-indol-2-yl | CH₃ | |

TABLE 68-continued

| Ex. No. | A | B | C | R¹ | R² | salt/additive |
|---|---|---|---|---|---|---|
| 645 | | | | | CH₃ | |

TABLE 69

| Ex. No. | A | B | C | R¹ | R² | salt additive |
|---|---|---|---|---|---|---|
| 646 | | | | | CH₃ | |
| 647 | | | | | CH₃ | |

TABLE 69-continued

| Ex. No. | [A ring] | B | C | R¹ | R² | salt additive |
|---|---|---|---|---|---|---|
| 648 | N-methyl piperidine (R,R) | 3,4-diCl-phenyl | 2-methyl-5-Br-pyridine | HOCH₂C(O)-N-piperidin-4-yl acetyl | CH₃ | |
| 649 | N-methyl piperidine (R,R) | 3,4-diCl-phenyl | 4-cyclopropyl-phenyl | CH₃SO₂-N-piperidin-4-yl acetyl | CH₃ | |
| 650 | N-methyl piperidine (R,R) | 3,4-diCl-phenyl | 2-methyl-5-CF₃-pyridine | 2-furoyl-piperazin-4-yl acetyl | CH₃ | |
| 651 | N-methyl piperidine (±) | 4-F-phenyl | 3,5-bis(CF₃)-phenyl | 4-acetamido-cyclohexyl acetyl | CH₃ | |
| 652 | N-methyl piperidine (±) | 4-F-phenyl | 3-Br-5-CF₃-phenyl | 4-acetamido-cyclohexyl acetyl | CH₃ | |
| 653 | N-methyl piperidine (±) | 4-Cl-2-methyl-phenyl | 3,5-bis(CF₃)-phenyl | 4-acetamido-cyclohexyl acetyl | CH₃ | |

TABLE 69-continued
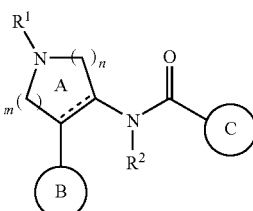
| Ex. No. | 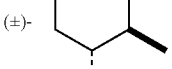 | B | C | R¹ | R² | salt additive |
|---|---|---|---|---|---|---|
| 654a |  (±)- | 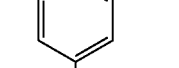 | 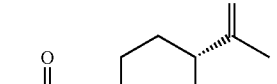 | 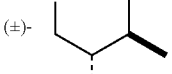 | CH₃ | |
| 654b |  (±)- | 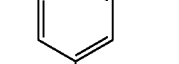 | 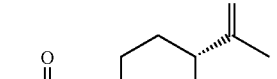 | 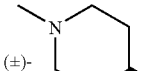 | CH₃ | |
| 654c |  (±)- | 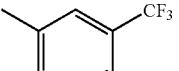 | 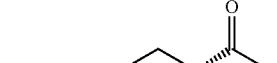 |  | CH₃ | |
| 655 |  (±)- | 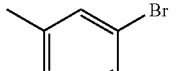 | 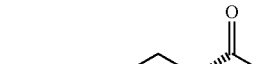 | | CH₃ | |

TABLE 70

TABLE 70-continued
| Ex. No. | 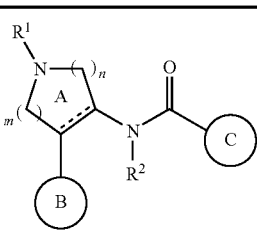 | B | C | R¹ | R² | salt/additive |
|---|---|---|---|---|---|---|
| 662 | 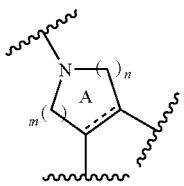 |  |  | 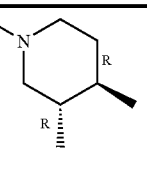 | CH₃ | |
| 663 | 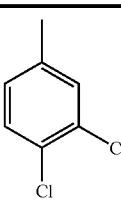 | 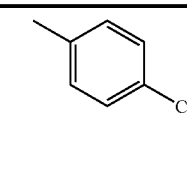 | 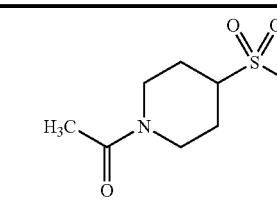 | 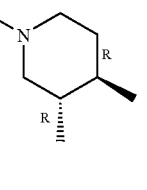 | CH₃ | |
| 664 | 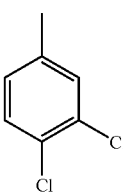 | 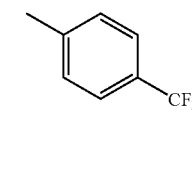 | 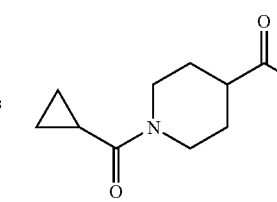 | 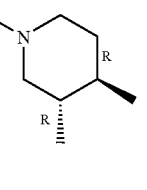 | CH₃ | |
| 665 | 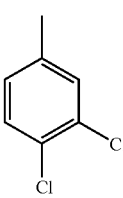 | 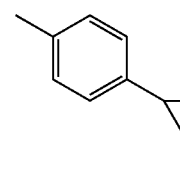 | 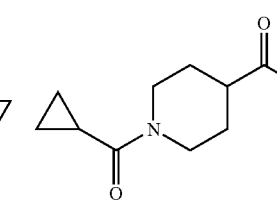 | 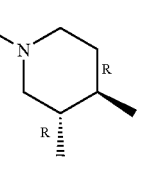 | CH₃ | |

TABLE 71

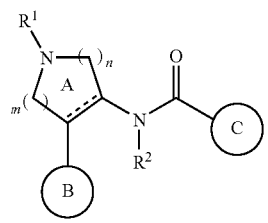

| Ex. No. | 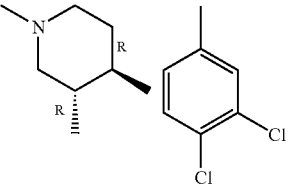 | B | C | R¹ | R² | salt/ additive |
|---|---|---|---|---|---|---|
| 666 | 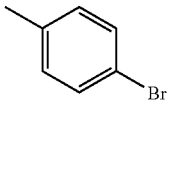 | 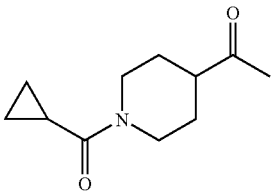 | 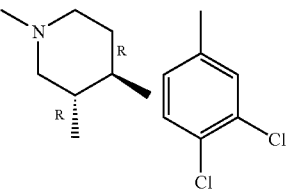 | 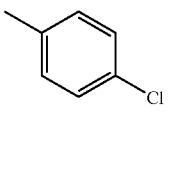 | CH₃ | |
| 667 | 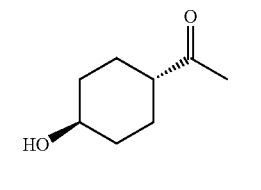 | (same) | 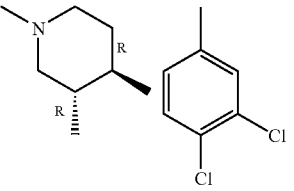 | 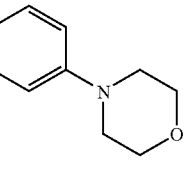 | CH₃ | |
| 668 | (same) | (same) | 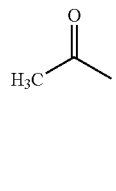 | H₃C—C(=O)— | CH₃ | |

Preparative Example 1

| | |
|---|---|
| (1) Compound of Example 1 | 10 mg |
| (2) Lactose | 60 mg |
| (3) Corn starch | 35 mg |
| (4) Hydroxypropylmethylcellulose | 3 mg |
| (5) Magnesium stearate | 2 mg |

A mixture of the compound obtained in Example 1 (10 mg), lactose (60 mg) and corn starch (35 mg) is granulated using an aqueous solution (0.03 mL) of 10 wt % hydroxypropylmethylcellulose (3 mg as hydroxypropylmethylcellulose), and then dried at 40° C. and sieved. The obtained granules are mixed with magnesium stearate (2 mg) and compressed. The obtained uncoated tablets are sugar-coated with an aqueous suspension of sucrose, titanium dioxide, talc and gum arabic. The thus-coated tablets are glazed with beeswax to obtain finally-coated tablets.

Preparative Example 2

| | |
|---|---|
| (1) Compound of Example 1 | 10 mg |
| (2) Lactose | 70 mg |
| (3) Corn starch | 50 mg |
| (4) Soluble starch | 7 mg |
| (5) Magnesium stearate | 3 mg |

The compound obtained in Example 1 (10 mg) and magnesium stearate (3 mg) are granulated with an aqueous soluble starch solution (0.07 mL, 7 mg as soluble starch), dried, and mixed with lactose (70 mg) and corn starch (50 mg). The mixture is compressed to obtain tablets.

Reference Preparative Example 1

| | |
|---|---|
| (1) Rofecoxib | 5.0 mg |
| (2) Sodium chloride | 20.0 mg |
| (3) Distilled water | to 2.0 mL of total volume |

Rofecoxib (5.0 mg) and sodium chloride (20.0 mg) are dissolved in distilled water, and water is added to make the total volume 2.0 mL. The solution is filtered, and filled into ampoule (2 mL) under sterile condition. The ampoule is sterilized, and then sealed to obtain a solution for injection.

Reference Preparative Example 2

| (1) Rofecoxib | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethylcellulose | 20 mg |
| Total | 120 mg |

The above-mentioned (1) to (6) are mixed according to a conventional method and tableted by a tablet machine to obtain tablets.

Preparative Example 3

The formulation prepared in Preparative Example 1 or 2, and the formulation prepared in Reference Preparative Example 1 or 2 are combined.

Experimental Example 1

Human $NK_1$ Receptor Binding Assay

Radioligand receptor binding inhibitory activity (Binding inhibitory activity using receptor from human lymphoblast cells (IM-9))

The method of M. A. Cascieri et al. [Molecular Pharmacology, vol. 42, p. 458 (1992)] was modified and used. The receptor was prepared from human lymphoblast cells (IM-9).

IM-9 cells ($2 \times 10^5$ cells/mL) were cultured for 3 days after inoculation, and centrifuged at 500×g for 10 min to give cell pellets. The obtained pellets were washed with PBS (Phosphate-Buffered saline) (GIBCO), disrupted in buffer A (50 mM Tris-hydrochloric acid buffer (Tris-HCl) (pH 7.4) containing 120 mM sodium chloride, 5 mM potassium chloride, 2 μg/mL chymostatin, 40 μg/mL bacitracin, 40 μg/mL APMSF (p-amidinophenylmethanesulfonyl fluoride hydrochloride) and 1 mM ethylenediaminetetraacetic acid (EDTA)) using a Polytron homogenizer (Kinematika, Germany), and centrifuged at 100,000×g for 40 min. The precipitation fraction was suspended in buffer B (50 mM Tris-HCl (pH 7.4), 0.02% bovine serum albumin, 2 μg/mL chymostatin, 40 μg/mL bacitracin, 40 μg/mL APMSF, 3 mM manganese dichloride ($MnCl_2$)) and cryopreserved (−80° C.) as a receptor reference standard.

Buffer B (50 μL) was added to a 96-well microassay plate (Corning Incorporated). The membrane reference standard suspended in buffer B at 250 μg/mL was added by 50 μL. A measurement buffer containing 2% dimethyl sulfoxide was added by 50 μL to examine the total binding, 4 μM non-labeled SP diluted with a measurement buffer containing 2% dimethyl sulfoxide was added by 50 μL to examine the non-specific binding, and a test compound diluted with a measurement buffer (containing 2% dimethyl sulfoxide) was added by 50 μL to examine the binding inhibitory activity of the test compound. Furthermore, 400 μM $^{125}$I-Bolton-Hunter-SP (BH-SP) solution was added to each well by 50 μL.

After reaction at room temperature for 30 min, the reaction was quenched using a cell harvester (PerkinElmer) by rapid filtration on a GF/C filter plate (PerkinElmer), and the cells were washed 10 times with 250 μL of a 50 mM Tris-hydrochloric acid buffer (pH 7.4) containing 0.02% bovine serum albumin. The GF/C filter plate was dried, MicroScinti-0 (PerkinElmer) was added by 20 μL, and the radioactivity was measured on a TopCount (PerkinElmer). The GF/C filter plate was immersed in 0.3% polyethyleneimine for one day before use.

The specific binding is a value obtained by subtracting non-specific binding from the total binding. The binding inhibitory activity of the test compound is shown by a ratio of the value obtained by subtracting the measurement value with addition of a test compound from the total binding, to the specific binding.

The antagonistic activity of each compound obtained in Examples was determined in terms of the drug concentration necessary to cause 50% inhibition ($IC_{50}$ value) under the above-described conditions, and the results are shown in Table (Table 72). Alternatively, it was determined in terms of the inhibitory rate (% inh.) when the drug concentration was 10 μM. The results are shown in Table (Table 72).

Experimental Example 2

Human $NK_2$ Receptor Binding Assay

Radioligand receptor binding inhibitory activity using membrane fraction of CHO cell expressing human $NK_2$ ($hNK_2$) receptor CHO cells expressing $hNK_2$ receptor were cultured in a HAM-F12 medium containing 400 μg/mL geneticin, 100 U/mL penicillin, 100 μg/mL streptomycin and 10% inactivated serum. The medium was removed, the adhered cells were washed with PBS, and PBS containing 5 mM EDTA was added to detach the cells from the flask. The cells were collected by centrifugation, suspended in suspension buffer A (15 mM Tris-HCl (pH 7.5), 2 mM $MgCl_2$, 0.3 mM ethylenediaminetetraacetic acid (EDTA), 1 mM O,O'-bis(2-aminoethyl)ethyleneglycol-N,N,N',N'-tetraacetic acid (EGTA)), disrupted by a Polytron homogenizer (Kinematika), and centrifuged at 800×g for 10 min. The supernatant was recovered and ultracentrifuged at 100,000×g for 25 min. The precipitation fraction was suspended in suspension buffer B (7.5 mM Tris-HCl (pH 7.5), 12.5 mM $MgCl_2$, 0.3 mM EDTA, 1 mM EGTA, 250 mM sucrose), and cryopreserved (−80° C.) as a receptor reference standard.

Measurement buffer (50 mM Tris-HCl (pH 7.4), 0.02% bovine serum albumin, 2 μg/mL chymostatin, 40 μg/mL bacitracin, 40 μg/mL APMSF, 3 mM $MnCl_2$) (50 μL) was added to a 96-well microassay plate. The membrane reference standard (20 μg/mL) suspended in a measurement buffer was added by 50 μL. A measurement buffer containing 2% dimethyl sulfoxide was added by 50 μL to examine the total binding level, 4 μM non-labeled NK-A (PEPTIDE INSTITUTE, INC.) solution diluted with a measurement buffer containing 2% dimethyl sulfoxide was added by 50 μL to examine the non-specific binding level, and a test compound diluted with a measurement buffer (containing 2% dimethyl sulfoxide) was added by 50 μL to examine the binding inhibitory activity of the test compound. Furthermore, 400 μM [$^{125}$I]-NK-A (GE Healthcare Bio-Sciences KK) solution was added to each well by 50 μL.

After reaction at 25° C. for 30 min, the reaction was quenched using a cell harvester (PerkinElmer) by rapid filtration on a GF/C filter plate, and the cells were washed 5 times with 250 μL of a 50 mM Tris-HCl buffer (pH 7.4) containing 0.02% bovine serum albumin. The GF/C filter plate was dried, MicroScinti-0 (PerkinElmer) was added by 20 μL, and the radioactivity was measured on a TopCount (PerkinElmer). The GF/C filter plate used had been immersed in 0.3% polyethyleneimine for one day.

The specific binding level is shown by a value obtained by subtracting non-specific binding level from the total binding level. The binding inhibitory activity of the test compound is shown by a ratio of the value obtained by subtracting the measurement value with addition of a test compound from the total binding level, to the value of the specific binding level.

The antagonistic activity of the compounds obtained in Examples was determined in terms of the drug concentration necessary to cause 50% inhibition ($IC_{50}$ value) under the above-described conditions, and the results are shown in Table (Table 72).

Experimental Example 3

Human $NK_3$ Receptor Binding Assay

Radioligand receptor binding inhibitory activity using membrane fraction of CHO cell expressing human $NK_3$ ($hNK_3$) receptor CHO cells expressing $hNK_3$ receptor were cultured in a MEMα medium (Nikken Seibutsu Igaku Kenkyusho, K.K.) containing 100 U/mL penicillin, 100 μg/mL streptomycin and 10% inactivated dialyzed serum. The medium was removed, the adhered cells were washed with PBS, and PBS containing 5 mM EDTA was added to detach the cells from the flask. The cells were collected by centrifugation, suspended in suspension buffer A (50 mM Tris-HCl (pH 7.4) containing 120 mM NaCl, 5 mM KCl, 2 μg/mL chymostatin, 40 μg/mL bacitracin, 40 μg/mL APMSF, 1 mM EDTA), disrupted by a Polytron homogenizer (Kinematika), and centrifuged at 800×g for 10 min. The supernatant was recovered and ultracentrifuged at 100,000×g for 25 min. The precipitation fraction was suspended in suspension buffer B (50 mM Tris-HCl (pH 7.4), 0.02% bovine serum albumin, 2 μg/mL chymostatin, 40 μg/mL bacitracin, 40 μg/mL APMSF, 3 mM $MnCl_2$), and cryopreserved (−80° C.) as a receptor reference standard.

Measurement buffer (50 mM Tris-HCl (pH 7.4), 0.02% bovine serum albumin, 2 μg/mL chymostatin, 40 μg/mL bacitracin, 40 μg/mL APMSF, 3 mM $MnCl_2$) (50 μL) was added to a 96-well microassay plate. The membrane reference standard (300 μg/mL) suspended in a measurement buffer was added by 50 μL. A measurement buffer containing 2% dimethyl sulfoxide was added by 50 μL to examine the total binding level, 16 μM non-labeled NK-B (PEPTIDE INSTITUTE, INC.) solution diluted with a measurement buffer containing 2% dimethyl sulfoxide was added by 50 μL to examine the non-specific binding level, and a test compound diluted with a measurement buffer (containing 2% dimethyl sulfoxide) was added by 50 μL to examine the binding inhibitory activity of the test compound. Furthermore, 400 μM [$^{125}$I]-NK-B (Neurokinin-B (N-Me-Phe$^7$), [$^{125}$I]His$^3$-) (PerkinElmer) solution was added to each well by 50 μL.

After reaction at 25° C. for 30 min, the reaction was quenched using a cell harvester (PerkinElmer) by rapid filtration on a GF/C filter plate, and the cells were washed 5 times with 250 μL of a 50 mM Tris-HCl buffer (pH 7.4) containing 0.02% bovine serum albumin. The GF/C filter plate was dried, MicroScinti-0 (Perkin Elmer) was added by 20 μL, and the radioactivity was measured on a TopCount (PerkinElmer). The GF/C filter plate used had been immersed in 0.3% polyethyleneimine for one day.

The specific binding level is shown by a value obtained by subtracting non-specific binding level from the total binding level. The binding inhibitory activity of the test compound is shown by a ratio of the value obtained by subtracting the measurement value with addition of a test compound from the total binding level, to the value of the specific binding level.

The antagonistic activity of the compounds obtained in Examples was determined in terms of the drug concentration necessary to cause 50% inhibition ($IC_{50}$ value) under the above-described conditions, and the results are shown in Table (Table 72).

TABLE 72

| Example No. | $IC_{50}$ (nM) or % inh. (10 μM) | | |
| --- | --- | --- | --- |
| | $hNK_1$ | $hNK_2$ | $hNK_3$ |
| 18 | 67 | 0.45 | 24 |
| 21 | 330 | 2.3 | 130 |
| 24 | 260 | 2.0 | 49 |
| 30 | 240 | 1.1 | 23 |
| 31 | 410 | 1.7 | 160 |
| 82 | 1.5 | 2.2 | N.T. |
| 91 | 0.092 | 0.79 | 330 |
| 251a | 78 | 0.31 | N.T. |
| 252 | 250 | 0.56 | N.T. |
| 265 | 80 | 0.23 | N.T. |
| 268 | 58.2% inh. | 0.42 | N.T. |
| 292 | 62 | 0.25 | N.T. |
| 318 | 520 | 0.82 | N.T. |
| 458 | 79 | 0.22 | N.T. |
| 464 | 220 | 0.22 | N.T. |
| 623 | 57.7% inh. | 0.31 | N.T. |
| 629 | 28.5% inh. | 0.55 | N.T. |
| 632 | 140 | 0.22 | N.T. |
| 633 | 84 | 0.24 | N.T. |
| 635 | 1100 | 0.36 | N.T. |

(N.T. = Not Tested)

From the results of Table 72, it was found that the compound of the present invention has a superior NK-1 receptor, NK-2 receptor and NK-3 receptor antagonistic action.

INDUSTRIAL APPLICABILITY

Compound (I) or a salt thereof or a prodrug thereof of the present invention shows a high tachykinin receptor antagonistic action, excellent in sustainability, low in toxicity, safe as a pharmaceutical agent and less influential to other agents. Therefore, compound (I) or a salt thereof or a prodrug thereof of the present invention is useful as a pharmaceutical agent, for example, a tachykinin receptor antagonist agent or an agent for the prophylaxis or treatment of lower urinary tract diseases, gastrointestinal diseases, central nervous system diseases and the like.

This application is based on a U.S. provisional patent application No. 60/996,734, the contents of which are incorporated in full herein by this reference.

The invention claimed is:
1. A compound represented by the formula

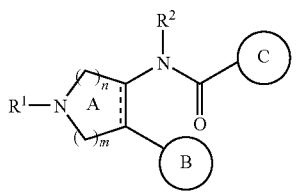

wherein ring A is a nitrogen-containing heterocycle optionally further having substituent(s), ring B is an aromatic ring optionally having substituent(s), ring C is an aromatic ring optionally having substituent(s), $R^1$ is a hydrogen atom, a hydrocarbon group optionally having substituent(s), an acyl group, or a heterocyclic group optionally having substituent(s), $R^2$ is an optionally halogenated $C_{1-6}$ alkyl group, m and n are each an integer of 0 to 5, m+n is an integer of 2 to 5, and

----- is a single bond or a double bond,
provided that N-[(rac.)-(3R,4R)-1-benzyl-4-phenylpiperidin-3-yl]-N-isopropyl-4-methoxy-3-(3-methoxypropoxy)benzamide, N-isopropyl-4-methoxy-3-(3-methoxypropoxy)-N-[(rac.)-(3R,4R)-4-phenylpiperidin-3-yl]benzamide, N-isopropyl-4-methoxy-3-(3-methoxypropoxy)-N-[(rac.)-(3R,4R)-4-(3-(methylsulfonyl)amino-phenyl)-piperidin-3-yl]benzamide, N-isopropyl-[(rac.)-(3R,4R)-4-[1,1'-biphenyl]-3-yl-3-piperidinyl]-4-methoxy-3-(3-methoxypropoxy)benzamide, N-ethyl-[(rac.)-(3R,4R)-4-[1,1'-biphenyl]-3-yl-3-piperidinyl]-4-methoxy-3-(3-methoxypropoxy)benzamide, N-propyl-[(rac.)-(3R,4R)-4-[1,1'-biphenyl]-3-yl-3-piperidinyl]-4-methoxy-3-(3-methoxypropoxy)benzamide, N-ethyl-[(rac.)-(3R,4R)-4-[3-[(3,5-dimethoxyphenyl)methoxy]phenyl]-3-piperidinyl]-4-methoxy-3-(3-methoxypropoxy) benzamide and 4-methoxy-3-(3-methoxypropoxy)-N-isopropyl-N-[(rac.)-4-(4-phenyl-2-oxazolyl)-3-piperidinyl]benzamide are excluded, or a salt thereof or a prodrug thereof.
2. The compound of claim 1, wherein ring A is a ring selected from the group consisting of

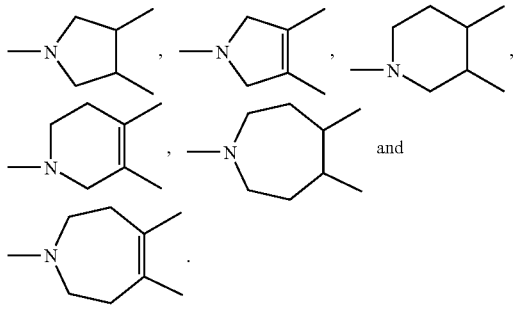

3. The compound of claim 1, wherein ring B is a phenyl group or a thienyl group each optionally having substituent(s).
4. The compound of claim 1, wherein ring C is a phenyl group, a pyrrolyl group, a thienyl group, a furyl group, a pyrazolyl group, an indolyl group, a benzimidazolyl group or a pyridyl group, each optionally having substituent(s).
5. The compound of claim 1, wherein ring C is a phenyl group, a pyridyl group, a benzothienyl group or a benzodioxolyl group, each optionally having substituent(s).
6. The compound of claim 1, wherein $R^1$ is a hydrogen atom, an acyl group, a piperidyl group optionally having substituent(s), a pyridyl group optionally having substituent(s), a pyrrolopyrimidinyl group optionally having substituent(s), an alkyl group optionally having substituent(s), a cycloalkenyl group optionally having substituent(s), or an aryl group optionally having substituent(s).
7. The compound of claim 1, wherein $R^2$ is a methyl group.
8. N-[(3R,4R)-1-[(1-Acetylpiperidin-4-yl)carbonyl]-3-(3,4-dichlorophenyl)piperidin-4-yl]-N-methyl-3,5-bis(trifluoromethyl)benzamide.
9. N-[(3R,4R)-1-[(1-Acetylpiperidin-4-yl)carbonyl]-3-(3,4-dichlorophenyl)piperidin-4-yl]-4-chloro-N-methylbenzamide.
10. N-[(3R,4R)-1-[(1-Acetylpiperidin-4-yl)carbonyl]-3-(3,4-dichlorophenyl)piperidin-4-yl]-4-methoxy-N-methylbenzamide.
11. N-[(3R,4R)-1-[(1-Acetylpiperidin-4-yl)carbonyl]-3-(3,4-dichlorophenyl)piperidin-4-yl]-N-methyl-4-(trifluoromethyl)benzamide.
12. N-[(3R,4R)-1-[(1-Acetylpiperidin-4-yl)carbonyl]-3-(3,4-dichlorophenyl)piperidin-4-yl]-N-methyl-4-morpholin-4-ylbenzamide or a salt thereof.
13. N-[(3R,4R)-1-[(1-Acetylpiperidin-4-yl)carbonyl]-3-(3,4-dichlorophenyl)piperidin-4-yl]-4-cyclopropyl-N-methylbenzamide.
14. N-[(3R,4R)-1-[(1-Acetylpiperidin-4-yl)carbonyl]-3-(3,4-dichlorophenyl)piperidin-4-yl]-5-bromo-N-methylpyridine-2-carboxamide.
15. 4-Chloro-N-[(3R,4R)-3-(3,4-dichlorophenyl)-1-{[1-(hydroxyacetyl)piperidin-4-yl]carbonyl}piperidin-4-yl]-N-methylbenzamide or a salt thereof.
16. N-[(3R,4R)-1-[(1-Acetylpiperidin-4-yl)methyl]-3-(3,4-dichlorophenyl)piperidin-4-yl]-4-chloro-N-methylbenzamide.
17. N-[(3R,4R)-3-(3,4-Dichlorophenyl)-1-({1-[(1-hydroxycyclopropyl)carbonyl]piperidin-4-yl}carbonyl)piperidin-4-yl]-N-methyl-4-morpholin-4-ylbenzamide or a salt thereof.
18. N-[(3R,4R)-1-{[(3S,4S)-3-Aminotetrahydro-2H-pyran-4-yl]carbonyl}-3-(3,4-dichlorophenyl)piperidin-4-yl]-N-methyl-4-morpholin-4-ylbenzamide or a salt thereof.
19. N-[(3R,4R)-3-(3,4-Dichlorophenyl)-1-{[1-(hydroxyacetyl)piperidin-4-yl]carbonyl}piperidin-4-yl]-N-methyl-4-(trifluoromethyl)benzamide or a salt thereof.
20. 4-Bromo-N-[(3R,4R)-3-(3,4-dichlorophenyl)-1-{[1-(hydroxyacetyl)piperidin-4-yl]carbonyl}piperidin-4-yl]-N-methylbenzamide or a salt thereof.
21. N-[(3R,4R)-3-(3,4-Dichlorophenyl)-1-{[1-(hydroxyacetyl)piperidin-4-yl]carbonyl}piperidin-4-yl]-N-methyl-5-(trifluoromethyl)pyridine-2-carboxamide or a salt thereof.
22. A prodrug of the compound of claim 1.
23. A pharmaceutical composition comprising the compound of claim 1 or a salt thereof or a prodrug thereof, and a pharmaceutically acceptable carrier.
24. A tachykinin receptor antagonist composition comprising a compound represented by the formula

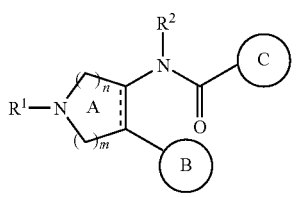

(I)

wherein ring A is a nitrogen-containing heterocycle optionally further having substituent(s), ring B is an aromatic ring optionally having substituent(s), ring C is an aromatic ring optionally having substituent(s), $R^1$ is a hydrogen atom, a hydrocarbon group optionally having substituent(s), an acyl group, or a heterocyclic group optionally having substituent(s), $R^2$ is an optionally halogenated $C_{1-6}$ alkyl group, m and n are each an integer of 0 to 5, m+n is an integer of 2 to 5, and

----- is a single bond or a double bond,
or a salt thereof or a prodrug thereof, and
a pharmaceutically acceptable carrier.

25. The composition of claim 24, which is an NK-2 receptor antagonist composition.

26. The composition of claim 25, concurrently having an NK-1 receptor antagonistic action and/or an NK-3 receptor antagonistic action.

27. The composition of claim 24, which is an NK-1 receptor antagonist composition.

28. The composition of claim 27, concurrently having an NK-2 receptor antagonistic action and/or an NK-3 receptor antagonistic action.

29. A pharmaceutical composition which is a composition for the treatment of overactive bladder, irritable bowel syndrome, functional dyspepsia, inflammatory bowel disease, gastroesophageal reflux disease, vomiting, nausea, depression, anxiety neurosis, anxiety symptom, pelvic visceral pain or interstitial cystitis, comprising a compound represented by the formula

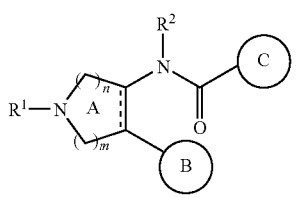

(I)

wherein ring A is a nitrogen-containing heterocycle optionally further having substituent(s), ring B is an aromatic ring optionally having substituent(s), ring C is an aromatic ring optionally having substituent(s), $R^1$ is a hydrogen atom, a hydrocarbon group optionally having substituent(s), an acyl group, or a heterocyclic group optionally having substituent(s), $R^2$ is an optionally halogenated $C_{1-6}$ alkyl group, m and n are each an integer of 0 to 5, m+n is an integer of 2 to 5, and

----- is a single bond or a double bond,
or a salt thereof or a prodrug thereof, and
a pharmaceutically acceptable carrier.

30. A method of treating overactive bladder, irritable bowel syndrome, functional dyspepsia, inflammatory bowel disease, gastroesophageal reflux disease, vomiting, nausea, depression, anxiety neurosis, anxiety symptom, pelvic visceral pain or interstitial cystitis, comprising administering, to a mammal, an effective amount of a compound represented by the formula

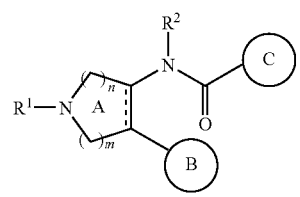

(I)

wherein ring A is a nitrogen-containing heterocycle optionally further having substituent(s), ring B is an aromatic ring optionally having substituent(s), ring C is a cyclic group optionally having substituent(s), $R^1$ is a hydrogen atom, a hydrocarbon group optionally having substituent(s), an acyl group, a heterocyclic group optionally having substituent(s) or an amino group optionally having substituent(s), $R^2$ is an optionally halogenated $C_{1-6}$ alkyl group, m and n are each an integer of 0 to 5, m+n is an integer of 2 to 5, and

----- is a single bond or a double bond,
or a salt thereof or a prodrug thereof.

31. A compound represented by the formula

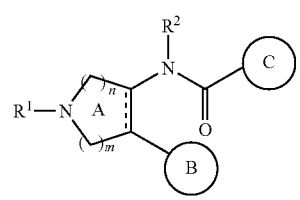

(I)

wherein ring A is a nitrogen-containing heterocycle optionally further having substituent(s), ring B is an aromatic ring optionally having substituent(s), ring C is an unsaturated nonaromatic ring optionally having substituent(s), $R^1$ is a hydrogen atom, a hydrocarbon group optionally having substituent(s), an acyl group, a heterocyclic group optionally having substituent(s) or an amino group optionally having substituent(s), $R^2$ is an optionally halogenated $C_{1-6}$ alkyl group, m and n are each an integer of 0 to 5, m+n is an integer of 2 to 5, and

- - - - - is a single bond or a double bond, or a salt thereof.

32. The compound of claim 31, wherein ring A is a ring selected from the group consisting of

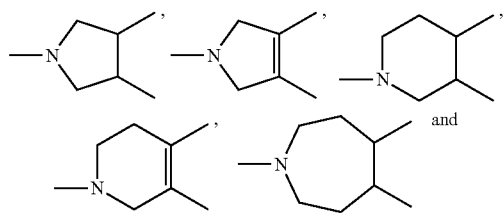

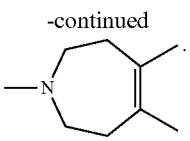

33. The compound of claim 31, wherein ring B is a phenyl group or a thienyl group each optionally having substituent(s).

34. The compound of claim 31, wherein $R^1$ is a hydrogen atom, an acyl group, a piperidyl group optionally having substituent(s), a pyridyl group optionally having substituent(s), a pyrrolopyrimidinyl group optionally having substituent(s), an alkyl group optionally having substituent(s), a cycloalkenyl group optionally having substituent(s), an aryl group optionally having substituent(s) or an amino group optionally having substituent(s).

35. The compound of claim 31, wherein $R^2$ is a $C_{1-6}$ alkyl group.

36. A pharmaceutical composition comprising the compound of claim 31 or a salt thereof, and a pharmaceutically acceptable carrier.

* * * * *